US006290960B1

(12) United States Patent
Kink et al.

(10) Patent No.: US 6,290,960 B1
(45) Date of Patent: *Sep. 18, 2001

(54) VACCINE AND ANTITOXIN FOR THE TREATMENT OF *C. DIFFICILE* DISEASE

(75) Inventors: John A. Kink; Bruce S. Thalley; Douglas C. Stafford, all of Madison, WI (US)

(73) Assignee: Ophidian Pharmaceuticals, Inc., Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/915,136

(22) Filed: Aug. 20, 1997

Related U.S. Application Data

(63) Continuation of application No. 08/480,604, filed on Jun. 7, 1995, now Pat. No. 5,736,139, which is a continuation-in-part of application No. 08/422,711, filed on Apr. 14, 1995, now abandoned, which is a continuation-in-part of application No. 08/405,496, filed on Mar. 16, 1995, now Pat. No. 5,919,665, which is a continuation-in-part of application No. 08/329,154, filed on Oct. 24, 1994, now abandoned, which is a continuation-in-part of application No. 08/161,907, filed on Dec. 2, 1993, now Pat. No. 5,601,823, which is a continuation-in-part of application No. 07/985,321, filed on Dec. 4, 1992, which is a continuation-in-part of application No. 07/429,791, filed on Oct. 31, 1989, now Pat. No. 5,196,193.

(51) Int. Cl.⁷ .................... A61K 39/395; A61K 39/40; C07K 16/00
(52) U.S. Cl. .................... 424/164.1; 424/130.1; 424/150.1; 424/167.1; 530/389.1; 530/389.5
(58) Field of Search .................... 424/130.1, 150.1, 424/167.1, 164.1; 530/389.1, 389.5

(56) References Cited

U.S. PATENT DOCUMENTS

| 4,550,019 | * | 10/1985 | Polson . |
|---|---|---|---|
| 5,080,895 | | 1/1992 | Tokoro . |
| 5,196,193 | | 3/1993 | Carroll . |
| 5,268,295 | | 12/1993 | Serrero . |
| 5,736,139 | * | 4/1998 | Kink et al. . |
| 5,762,934 | * | 6/1998 | Williams et al. . |

OTHER PUBLICATIONS

P.H.A. Sneath et al., "Clostridium," in *Bergey's Manual® of Systematic Bacteriology*, vol. 2, pp. 1141–1200, Williams & Wilkins (1986).
P.G. Engelkirk et al. "Classification", in *Principles and Practice of Clinical Anaerobic Bacteriology*, pp. 22–23, Star Publishing Co., Belmont, CA (1992).

J. Stephen and R.A. Petrowski, "Toxins Which Traverse Membranes and Deregulate Cells," in *Bacterial Toxins*, 2d ed., American Society for Microbiology (1986) pp. 66–67.
R. Berkow and A.J. Fletcher (eds.), "Bacterial Diseases," in *Merck Manual of Diagnosis and Therapy*, 16th ed., pp. 119–126, Merck Research Laboratories, Rahway, N.J. (1992).
O.H. Sigmund and C.M. Fraser (eds.), "Clostridial Infections," *Merck Veterinary Manual*, 5th ed., pp. 396–409, Merck & Co., Rahway, N.J. (1979).
C.L. Hatheway, "Toxigenic Clostridia," *Clin. Microbiol. Rev.* 3:66–98 (1990).
S. Arnon, "Infant Botulism: Anticipating the Second Decade," *J. Infect. Dis.* 154:201–206 (1986).
S. Arnon, "Infant Botulism," *Ann. Rev. Med.* 31:541–561 (1980).
K.L. MacDonald et al., "The Changing Epidemiology of Adult Botulism in the United States," *Am. J. Epidemiol.* 124:794–798 (1986).
C.O. Tacket et al., "Equine Antitoxin Use and Other Factors That Predict Outcome in Type A Foodborne Botulism," *Am. J. Med.* 76:794–798 (1984).
M.N. Swartz, "Anaerobic Spore–Forming Bacilli: The Clostridia," in *Microbiology*, B.D. Davis et al., eds., 4th edition, pp. 633–646, J.B. Lippincott Co. (1990).
V.E. Holzer, "Botulismus durch Inhalation," *Med. Klin.* 41:1735–1738 (1962).
D.R. Franz et al., "Efficacy of Prophylactic and Therapeutic Administration of Antitoxin for Inhalation Botulism," in *Botulinum and Tetanus Neurotoxins*, B.R. DasGupta, ed., pp. 473–476, Plenum Press, New York (1993).
S. Arnon, "Infant Botulism: Epidemiology and Relation to Sudden Infant Death Syndrome," *Epidemiol. Rev.* 3:45–66 (1981).
T.L. Frankovich and S. Arnon, "Clinical Trial of Botulism Immune Globulin for Infant Botulism," *West. J. Med.* 154:103 (1991).
H. Sugiyama, "*Clostridium botulinum* Neurotoxin," *Microbiol. Rev.* 44:419–448 (1980).
M. Balady, "Botulism Antitoxin Fielded for Operation Desert Storm," USAMRDC Newsletter, p. 6 (1991).
P.J. Schwarz and S.S. Arnon, "Botulism Immune Globulin for Infant Botulism Arrives—One Year and a Gulf War Later," *Western J. Med.* 156:197–198 (1992).
D.R. Peterson et al., "The Sudden Infant Death Syndrome and Infant Botulism," *Rev. Infect. Dis.* 1:630–634 (1979).

(List continued on next page.)

Primary Examiner—Albert Navarro
(74) Attorney, Agent, or Firm—Medlen & Carroll, LLP

(57) ABSTRACT

The present invention provides vaccines capable of protecting a vaccinated recipient from the morbidity and mortality associated with *C. difficile* infection. These vaccines are produced with portions of *C. difficile* Toxin A, or Toxin B, or both. These portions of Toxins A and B may be fusion proteins with at least one non-toxin protein sequence, and may also be soluble and substantially endotoxin-free. These vaccines are useful for administration to humans and other animals at risk of exposure to *C. difficile* toxins.

14 Claims, 54 Drawing Sheets

OTHER PUBLICATIONS

S. Arnon et al., "Intestinal Infection and Toxin Production by Clostridium Botulinum as One Cause of Sudden Infant Death Syndrome," *Lancet*, pp. 1273–1276, Jun. 17, 1978.

G.F. Brooks et al., (eds.) "Infection Caused by Anaerobic Bacteria," *Jawetz, Melnick, & Adelberg's Medical Microbiology*, 19th ed., pp. 257–262, Appleton & Lange, San Mateo, CA (1991).

Lyerly et al., "Characterization of a Toxin A–Negative, Toxin B–Positive Strain of Clostridium difficile," *Infect. Immun.* 60:4633–4639 (1992).

Borriello et al., "Virulence Factors of Clostridium difficile," *Rev. Infect. Dis.*, 12(suppl. 2):S185–S191 (1990).

Lyerly et al., "Effects of Clostridium difficile Toxins Given Intragastrically to Animals," *Infect. Immun.*, 47:349–352 (1985).

Rolfe, "Binding Kinetics of Clostridium difficile Toxins A and B to Intestinal Brush Border Membranes from Infant and Adult Hamsters," *Infect. Immun.*, 59:1223–1230 (1990).

Kim and Rolfe, "The Protective Role of antibody to Toxin A In Clostridium difficile—Induced Ileocecitis," *Abstr. Ann. Meet. Am. Soc. Microbiol.*, 69:62 (1987).

Banno et al., "Biochemical Characterization and Biologic Actions of Two Toxins (D–1 and D–2) from Clostridium dificile," *Rev. Infect. Dis.*, 6(Suppl. 1:S11–S20 (1984).

Rihn et al., "A New Purification Procedure for Clostridium difficile Enterotoxin," *Biochem. Biophys. Res. Comm.*, 124:690–695 (1984).

Justus et al., "Myoelectric Effects of Clostridium difficile: Motility–Altering Factors Distinct From Its Cytotoxin and Enterotoxin in Rabbits," *Gastroenterol.*, 83:836–843 (1982).

S.M. Finegold et al., "Antimicrobial–Associated Pseudomembranous Colitis," in *A Clinical Guide to Anaerobic Infections*, pp. 88–89, Star Publishing Co., Belmont, CA (1992).

United States Pharmacopeia, vol. XXII (1990) United States Pharmacopeial Convention, Rockville, MD, pp. 1515–1516.

FDA Guidelines for Parenteral Drugs (Dec. 1987); i.e., *Guideline on Validation of the Linulus Amebocyte Lysate Test as an End–Product Endotoxin Test for Human and Animal Parenteral Drugs, Biological Products and Medical Devices*, Maintained by: Division of Manufacturing and Product Quality (HFN–320), Office of Compliance, Center for Drug Evaluation and Research, Food and Drug Administration, Rockville, MD.

Code of Federal Regulation 21 C.F.R. §§ 660.100–105.

F.C. Perason, *Pyrogens: Endotoxins, LAL testing and Depyrogenation*, Marcel Dekker, pp. 150–158, New York (1985).

Lyerly et al., "Passive Immunization of Hamsters against Disease Caused by Clostridium difficile by Use of Bovine Immunoglobulin G Concentrate," *Infect. Immun.* 59:2215–2218 (1991).

H.N. Benson et al., "Requirement of Avian C'1 For Fixation of Guinea Pig Complement By Avian Antibody–Antigen Complexes," *J. Immunol.* 87:616–622 (1961).

A.A. Benedict and K. Yamaga, "Immunoglobulins and Antibody Production in Avian Species," in *Comparative Immunology*, J.J. Marchaloni, ed., pp. 335–375, Blackwell, Oxford (1966).

R. Patterson et al., "Antibody Production and Transfer to Egg Yolk in Chickens," *J. Immunol.* 89:272–278 (1962).

S.B. Carroll and B.D. Stollar, "Antibodies to Calf Thymus RNA Polymerase II From Egg Yolks of Immunized Hens," *J. Biol. Chem.* 258:24–26 (1983).

Polson et al., "Antibodies to Proteins From Yolk of Immunized Hens," *Immunol. Comm.* 9:495–514 (1980).

Delmée et al., "Characterization of Flagella of Clostridium difficile and Their Role in Serogrouping Reactions," *J. Clin. Microbiol.*, 28(10):2210–2214 (1990).

Delmée et al., "Virulence of Ten Serogroups of Clostridium difficile in Hamsters," *J. Med. Microbiol.*, 33:85–90 (1990).

Toma et al., "Serotyping of Clostridium difficile," *J. Clin. Microbiol.*, 26(3):426–428 (1988).

Delmeée et al., "Serogrouping of Clostridium difficile Strains by Slide Agglutination," *J. Clin. Microbiol.*, 21:323–327 (1985).

Davies et al., "Detection of Capsule in Stains of Clostridium difficile of Varying Virulence and Toxigenicity," *Microbial Path.*, 9:141–146 (1990).

M.A.C. Edelstein, "Processing Clinical Specimens for Anaerobic Bacteria: Isolation and Identification Procedures," in *Bailey and Scott's Diagnostic Microbiology*, S.M. Finegold et al (eds.), pp. 477–507, C.V. Mosby Co., (1990).

N.V. Padhye et al., "Production and Characterization of a Monoclonal Antibody Specific for Enterohemorrhagic Escherichia coli of Serotypes O157:H7 and O26:H11," *J. Clin. Microbiol.* 29:99–103 (1990).

B.R. DasGupta & V. Sathyamoorthy, "Purification and Amino Acid Composition of Type A Botulinum Neurotoxin," *Toxicon*, 22:415–424 (1984).

B.R. Singh & B.R. DasGupta, "Molecular Differences Between Type a Botulinum Neurotoxin and is Toxoid," *Toxicon*, 27:403 (1989).

H. Towbin et al., "Electrophoretic Transfer of Proteins from Polyacrylamide Gels to Nitrocellulose Sheets: Procedure and Some Applications," *Proc. Natl. Acad. Sci. USA*, 76:4350–4354 (1979).

K. Weber and M. Osborn, "Proteins and Sodium Dodecyl Sulfate: Molecular Weight Determination on Polyacrylamide Gels and Related Procedures," in *The Proteins*, 3d Edition (H. Neurath & R.L. Hill, eds), pp. 179–223, (Academic Press, NY, 1975).

S.B. Carroll and A. Laughon, "Production and Purification of Polyclonal Antibodies to the Foreign Segment of β–galactosidase Fusion Proteins," in *DNA Cloning: A Practical Approach*, vol. III, (D. Glover, ed.), pp. 89–111, IRL Press, Oxford, (1987).

Thalley and Carroll, "Rattlesnake and Scorpion Antivenoms From the Egg Yolks of Immunized Hens," *Bio/Technology*, 8:934–938 (1990).

I. Ohishi et al., "Oral Toxicities of Clostridium botulinum Toxins in Response to Molecular Size," *Infect. Immun.*, 16:107–109 (1977).

Wren et al., "Antigenic Cross–Reactivity and Functional Inhibition by antibodies to Clostridium difficile Toxin A, Streptococcus mutans Glucan–Binding Protein, and a Synthetic Peptide," *Infect. Immun.*, 59:3151–3155 (1991).

Ehrich et al., "Production of Clostridium difficile Antitoxin," *Infect. Immun.* 28:1041–1043 (1980).

McGee et al., "Local Induction of Tumor Necrosis Factor as a Molecular Mechanism of Mucosal Damage by Gonococci," *Microb. Path.* 12:333–341 (1992).

R. Fekety, "Animal Models of Antibiotic–Induced Colitis," in *Experimental Models In Antimicrobial Chemotherapy*, O. Zak and M. Sande (eds.), vol. 2, pp. 61–72, (1986).

Borriello et al., "Clostridium difficile—A Spectrum of Virulence and Analysis of Putative Virulence Determinants in the Hamster Model of Antibiotic–Associated Colitis," *J. Med. Microbiol.*, 24:53–64 (1987).

Kim et al., "Immunization of Adult Hamsters Against Clostridium diffile–Associated Ileocecitis and Transfer of Protection to Infant Hamsters," *Infect. Immun.*, 55:2984–2992 (1987).

Borriello et al., "Mucosal Association by *Clostridium difficile* in the Hamster Gastrointestinal Tract," *J. Med. Microbiol.*, 25:191–196 (1988).

Dove et al., "Molecular Characterization of the *Clsotrodium difficile* Toxin A Gene," *Infect. Immun.*, 58:480–488 (1990).

Williams et al., "Preparation and Purification of Antibodies to Foreign Proteins Produced in *E. coli* using Plasmid Expression Vectors," in *DNA Cloning: Expression Systems*, Chapter 4 (1994).

von Eichel–Streiber and Sauerborn, "*Clostridium difficile* Toxin A Carries a C–Terminal Repetitive Structure Homologous to the Carbohydrate Binding Region of Streptococcal Glycosyltransferases," *Gene* 96:107–113 (1990).

Wren and Tabaqchali, "Restriction Endonuclease DNA Analysis of *Clostridium difficile*," *J. Clin. Microbiol.*, 25:2402 (1987).

Sambrook et al., *Molecular Cloning, A Laboratory Manual*, Second Edition, Cold Spring Harbor Press, pp. 1.85–1.91 (1989).

Price et al., "Cloning of the Carbohydrate–Binding Portion of the Toxin A Gene of *Clostridium difficile*," *Curr. Microbiol.*, 16:55–60 (1987).

H.C. Krivan et al., "Cell Surface Binding Site for *Clostridium difficile* Enterotoxin: Evidence for a Glycoconjugate Containing the Sequence Ga1α1–3Ga1β1–4G1cNAc," *Infect. Immun.*, 53:573–581 (1986).

von Eichel–Streiber et al, "Cloning and Characterization of Overlapping DNA Fragments of the Toxin A Gene of *Clostridium difficile*," *J. Gen. Microbiol.*, 135:55–64 (1989).

Lyerly et al., "Nonspecific Binding of Mouse Monoclonal Antibodies to *Clostridium difficile* Toxins A and B," *Curr. Microbiol.*, 19:303–306 (1989).

Lyerly, D.M., et al., "Vaccination Against Lethal *Clostridium difficile* Enterocolitis with a Nontoxic Recombinant Peptide of Toxin A," Curr. *Microbiol.* 21:29–32 (1990).

Swanson et al., "In Vitro and In Vivo Evaluation of Tiacumicins B and C Against *Clostridium difficile*," *Antimicrobial Agents and Chemotherapy* 35:1108–1111 (1991).

Swanson, et al., "Phenefamycins, A Novel Complex of Elfamycin–Type Antibiotics. III. Activity in vitro and in a Hamster Colitis Model," *J. Antibiotics* 42:94–101 (1989).

Barroso et al., "Nucleotide Sequences of *Clostridium difficile* Toxin B Gene," *Nucl. Acids Res.* 18:4004 (1990).

Riggs, in *Current Protocols in Molecular Biology*, vol. 2, Ausubel, et al., Eds. (1989), Current Protocols, pp. 16.6.1–16.6.14.

Eichel–Streiber, et al., "Comparative Sequence Analysis of the *Clostridium difficile* Toxins A and B," *Molec. Gen. Genetics* 233:260–268 (1992).

Thompson, et al., "The Complete Amino Acid Sequence of the *Clostridium botulinum* Type A Neurotoxin, Deduced by Nucleotide Sequence Analysis of the Encoding Gene," *Eur. J. Biochem.* 189:73–81 (1990).

Sambrook et al., *Molecular Cloning, A Laboratory Manual*, 1.82–1.83 (1989).

H.F. LaPenotiere, et al., "Development of a Molecular Engineered Vaccine for *C. botulinum* Neurotoxins," in *Botulinum and Tetanus Neurotoxins*, B.R. DasGupta, ed., Plenum Press, New York, pp. 463–466, (1993).

E.J. Schantz and D.A. Kautter, "Microbiological Methods: Standardized Assay for *Clostridium botulinum* Toxins," *J. Assoc. Off. Anal. Chem.* 61:96–99 (1990).

Investigational New Drug (BB–IND–3703) Application by the Surgeon General of the Army to The Federal Food and Drug Administration.

F.C. Pearson, *Pyrogens: Endotoxins, LAL Testing and Depyrogenation*, Marcel Dekker, New York, pp. 23–56, (1985).

Smith and Corcoran in *Current Protocols in Molecular Biology*, Ausubel, et al., Eds. Supplement 28 (1994), pp. 16.7.1–16.7.7.

La Vallie, et al., "A Thioredoxin Gene Fusion Expression System That Circumvents Inclusion Inclusion Body Formation in the *E. coli* Cytoplasm," *Bio/Technology* 11:187–193 (1993).

Kim and Rolfe, "Characterisation of Protective Antibodies in Master Immunised Against *Clostridium difficile* Toxins A and B," *Microbial Ecology in Health and Disease*, 2:47–59 (1989).

Akita and Nakai, "Immunoglobulins From Egg Yolk: Isolation and Purification," *J. of Food Science*, 57:629–634 (1992).

T.A. Mietzner et al., "A Conjugated Synthetic Peptide Corresponding to the C–Terminal Region of *Clostridium perfringens* Type A Enterotoxin Elicits an Enterotoxin–Neutralizing Antibody Response in Mice," *Infect. Immun.*, 60:3947–3951 (1992).

C. von Eichel–Streiber et al., "Cloning and Characterization of Overlapping DNA Fragments of the Toxin A Gene of *Clostridium difficile*," *J. Gen. Microbiol.*, 135:55–64 (1989).

S. Kamiya et al., "Production of Monoclonal Antibody fo *Clostridium difficile* Toxin A Which Neutralizes Enterotoxicity but not Hemagglutination Activity," *FEMS Microbiology Lett.*, 81:311–316 (1991).

G.M. Thorne and S.L. Gorbach, "General Characteristics: Nomenclature of Microbial Toxins," in *Pharmacology of Bacterial Toxins, in International Encyclopedia of Pharmacology and Therapeutics*, pp. 5–16, (Dorner and Drews, Eds.) (Pergamon Press, Oxford) (1986).

C.J. Phelps, et al., "Construction and Expression of the Complete *Clostridium difficile* Toxin A Gene in *Escherichia coli*," *Infect. Immun.*, 59:150–153 (1991).

B.W. Wren, et al., "Molecular Cloning and Expression of *Clostridium difficile* Toxin A in *Escherichia coli* K12," *FEBS Lett.*, 225:82–86 (1987).

L.L. Muldrow, et al., "Molecular Cloning of *Clostridium difficile* Toxin A Gene Fragment in λgt11," *FEBS Lett.*, 213:249–253 (1987).

J.L. Johnson, et al., "Cloning and Expression of the Toxin B Gene of *Clostridium difficile*," *Curr. Microbiol.*, 20:397–401 (1990).

C. von Eichel–Streiber, et al., "Cloning of *Clostridium difficle* Toxin B Gene and Demonstration of High N–Terminal Homology Between Toxin A and B," *Med. Microbiol. Immunol.*, 179:271–279 (1990).

Beitle, et al., "One–Step Purification of a Model Periplasmic Protein From Inclusion Bodies By Its Fusion to an Efective Metal–Binding Peptide," *Biotechnol. Prog.* 9:64–69 (1993).

* cited by examiner

```
TOXIN A ┌─────────────────────────────────────────────┬//////////////┐
        Hincll   Pstl    EcoRI      Pstl     Stul   Spel Pstl        Pstl
        Hincll           EcoRI     (BamHI)                         (HindIII)
        ├─────────────────┤         ├─────────────────────────────────┤
        P1              P2          Pstl                              Pstl
            FRAGMENT 1                      FRAGMENT 3

EcoRI     Pstl
                 ├───────┼────────┼──────┤
                 P3                     P4
                      FRAGMENT 2
```

P1-P4 ARE PCR PRIMERS 1-4.
P1 = 5'GGAAATTTAGCTGCAGCATCTGAC3',
P2 = 5'TCTAGCAAATTCGCTTGTGTTGAA3',
P3 = 5'CTCGCATATAGCATTAGACC3',
P4 = 5'CTATCTAGGCCTAAAGTAT3'.
INDICATED RESTRICTION SITES IN FRAGMENTS 1 AND 2 ARE INTERNAL SITES USED TO CLONE INTO pGEX2T VECTOR (FRAGMENT 1; CONSTRUCT CALLED pGA30-660) OR pMALc VECTOR (FRAGMENT 2; CONSTRUCT CALLED pMA660-1100). BRACKETED RESTRICTION SITES AT ENDS OF FRAGMENT 3 ARE pUC9 POLYLINKER SITES UTILIZED TO CLONE FRAGMENT 3 INTO pET23 VECTOR (CONSTRUCT CALLED pPA1100-2680). NUMBERS IN THESE CONSTRUCTS REFER TO TOXIN A AMINO ACID INTERVAL THAT IS EXPRESSED. THE SHADED PORTION OF THE TOXIN A GENE CORRESPONDS TO THE REPEATING LIGAND BINDING DOMAIN.

FIG. 6 pP REFERS TO pET23 VECTOR, pM REFERS TO pMALc VECTOR, A REFERS TO TOXIN A, AND NUMBERS REFER TO AMINO ACID INTERVAL EXPRESSED IN CLONE. ENDPOINTS OF CLONES CORRESPOND TO INDICATED RESTRICTION SITES SHOWN OF TOXIN A MAP.

pP REFERS TO pET23 VECTOR, pM REFERS TO pMALc VECTOR, A REFERS TO TOXIN A, AND NUMBERS REFER TO AMINO ACID INTERVAL EXPRESSED IN CLONE. ENDPOINTS OF CLONES CORRESPOND TO INDICATED RESTRICTION SITES SHOWN OF TOXIN A MAP.

BINDING OF NEUTRALIZING CTB ANTIBODIES BY
RECOMBINANT TOXIN B PROTEIN

INTERVAL 3: SpeI (1750) — P14 (1850) — HindIII (1970) — PvuII (2070) — P8 (2360)

pMB1750-2360
pPB1750-2360 ...HHH
pMB1750-1970
pMB1970-2360
pPB1850-2360 HHH...
pMB1850-1970
pPB1850-2070 HHH...

FIG. 23

ANTI-CTB
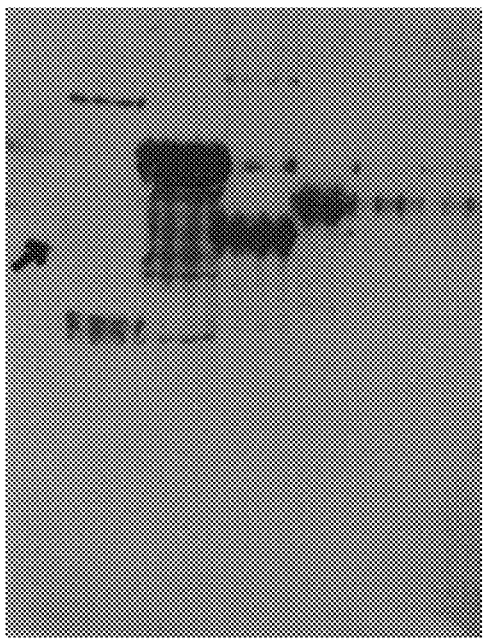
ANTI-pPB1750-2360
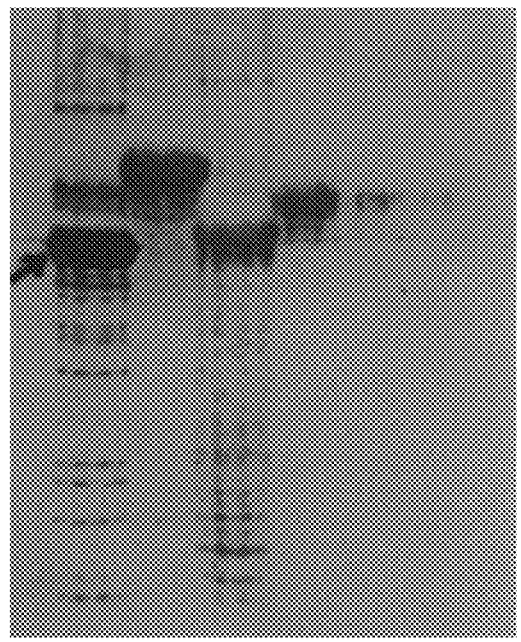
FIG. 24

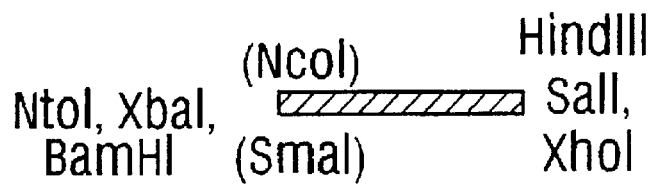
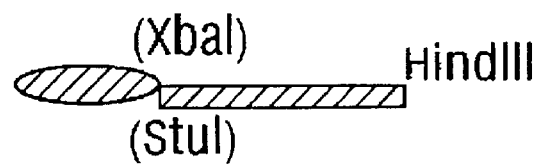
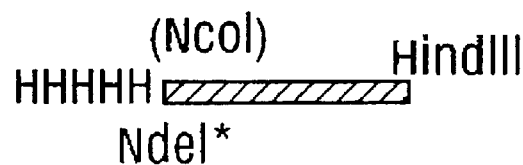
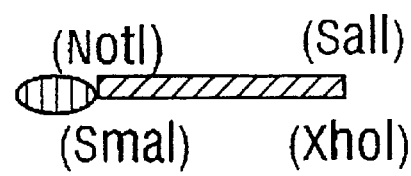
FIG. 27

```
                        SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:1:

GGAAATTTAG CTGCAGCATC TGAC                                              24

(2) INFORMATION FOR SEQ ID NO:2:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:2:

TCTAGCAAAT TCGCTTGTGT TGAA                                              24

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

CTCGCATATA GCATTAGACC                                                   20

(2) INFORMATION FOR SEQ ID NO:4:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

CTATCTAGGC CTAAAGTAT                                                    19

(2) INFORMATION FOR SEQ ID NO:5:
```

(i) SEQUENCE CHARACTERISTICS:
    (A) LENGTH: 8133 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..8130

(xi) SEQUENCE DESCRIPTION: SEQ ID NO:5:

```
ATG TCT TTA ATA TCT AAA GAA GAG TTA ATA AAA CTC GCA TAT AGC ATT        48
Met Ser Leu Ile Ser Lys Glu Glu Leu Ile Lys Leu Ala Tyr Ser Ile
 1               5                  10                  15

AGA CCA AGA GAA AAT GAG TAT AAA ACT ATA CTA ACT AAT TTA GAC GAA        96
Arg Pro Arg Glu Asn Glu Tyr Lys Thr Ile Leu Thr Asn Leu Asp Glu
                20                  25                  30

TAT AAT AAG TTA ACT ACA AAC AAT AAT GAA AAT AAA TAT TTG CAA TTA       144
Tyr Asn Lys Leu Thr Thr Asn Asn Asn Glu Asn Lys Tyr Leu Gln Leu
            35                  40                  45

AAA AAA CTA AAT GAA TCA ATT GAT GTT TTT ATG AAT AAA TAT AAA ACT       192
Lys Lys Leu Asn Glu Ser Ile Asp Val Phe Met Asn Lys Tyr Lys Thr
50                  55                  60

TCA AGC AGA AAT AGA GCA CTC TCT AAT CTA AAA AAA GAT ATA TTA AAA       240
Ser Ser Arg Asn Arg Ala Leu Ser Asn Leu Lys Lys Asp Ile Leu Lys
65                  70                  75                  80

GAA GTA ATT CTT ATT AAA AAT TCC AAT ACA AGC CCT GTA GAA AAA AAT       288
Glu Val Ile Leu Ile Lys Asn Ser Asn Thr Ser Pro Val Glu Lys Asn
                85                  90                  95

TTA CAT TTT GTA TGG ATA GGT GGA GAA GTC AGT GAT ATT GCT CTT GAA       336
Leu His Phe Val Trp Ile Gly Gly Glu Val Ser Asp Ile Ala Leu Glu
               100                 105                 110

TAC ATA AAA CAA TGG GCT GAT ATT AAT GCA GAA TAT AAT ATT AAA CTG       384
Tyr Ile Lys Gln Trp Ala Asp Ile Asn Ala Glu Tyr Asn Ile Lys Leu
           115                 120                 125

TGG TAT GAT AGT GAA GCA TTC TTA GTA AAT ACA CTA AAA AAG GCT ATA       432
Trp Tyr Asp Ser Glu Ala Phe Leu Val Asn Thr Leu Lys Lys Ala Ile
130                 135                 140

GTT GAA TCT TCT ACC ACT GAA GCA TTA CAG CTA CTA GAG GAA GAG ATT       480
Val Glu Ser Ser Thr Thr Glu Ala Leu Gln Leu Leu Glu Glu Glu Ile
145                 150                 155                 160

CAA AAT CCT CAA TTT GAT AAT ATG AAA TTT TAC AAA AAA AGG ATG GAA       528
Gln Asn Pro Gln Phe Asp Asn Met Lys Phe Tyr Lys Lys Arg Met Glu
                165                 170                 175

TTT ATA TAT GAT AGA CAA AAA AGG TTT ATA AAT TAT TAT AAA TCT CAA       576
Phe Ile Tyr Asp Arg Gln Lys Arg Phe Ile Asn Tyr Tyr Lys Ser Gln
            180                 185                 190

ATC AAT AAA CCT ACA GTA CCT ACA ATA GAT GAT ATT ATA AAG TCT CAT       624
Ile Asn Lys Pro Thr Val Pro Thr Ile Asp Asp Ile Ile Lys Ser His
        195                 200                 205

CTA GTA TCT GAA TAT AAT AGA GAT GAA ACT GTA TTA GAA TCA TAT AGA       672
Leu Val Ser Glu Tyr Asn Arg Asp Glu Thr Val Leu Glu Ser Tyr Arg
    210                 215                 220

ACA AAT TCT TTG AGA AAA ATA AAT AGT AAT CAT GGG ATA GAT ATC AGG       720
Thr Asn Ser Leu Arg Lys Ile Asn Ser Asn His Gly Ile Asp Ile Arg
225                 230                 235                 240

GCT AAT AGT TTG TTT ACA GAA CAA GAG TTA TTA AAT ATT TAT AGT CAG       768
Ala Asn Ser Leu Phe Thr Glu Gln Glu Leu Leu Asn Ile Tyr Ser Gln
                245                 250                 255

GAG TTG TTA AAT CGT GGA AAT TTA GCT GCA GCA TCT GAC ATA GTA AGA       816
```

```
                                                                -continued

Glu Leu Leu Asn Arg Gly Asn Leu Ala Ala Ala Ser Asp Ile Val Arg
            260                 265                 270

TTA TTA GCC CTA AAA AAT TTT GGC GGA GTA TAT TTA GAT GTT GAT ATG      864
Leu Leu Ala Leu Lys Asn Phe Gly Gly Val Tyr Leu Asp Val Asp Met
            275                 280                 285

CTT CCA GGT ATT CAC TCT GAT TTA TTT AAA ACA ATA TCT AGA CCT AGC      912
Leu Pro Gly Ile His Ser Asp Leu Phe Lys Thr Ile Ser Arg Pro Ser
            290                 295                 300

TCT ATT GGA CTA GAC CGT TGG GAA ATG ATA AAA TTA GAG GCT ATT ATG      960
Ser Ile Gly Leu Asp Arg Trp Glu Met Ile Lys Leu Glu Ala Ile Met
305             310                 315                 320

AAG TAT AAA AAA TAT ATA AAT AAT TAT ACA TCA GAA AAC TTT GAT AAA     1008
Lys Tyr Lys Lys Tyr Ile Asn Asn Tyr Thr Ser Glu Asn Phe Asp Lys
                325                 330                 335

CTT GAT CAA CAA TTA AAA GAT AAT TTT AAA CTC ATT ATA GAA AGT AAA     1056
Leu Asp Gln Gln Leu Lys Asp Asn Phe Lys Leu Ile Ile Glu Ser Lys
                340                 345                 350

AGT GAA AAA TCT GAG ATA TTT TCT AAA TTA GAA AAT TTA AAT GTA TCT     1104
Ser Glu Lys Ser Glu Ile Phe Ser Lys Leu Glu Asn Leu Asn Val Ser
                355                 360                 365

GAT CTT GAA ATT AAA ATA GCT TTC GCT TTA GGC AGT GTT ATA AAT CAA     1152
Asp Leu Glu Ile Lys Ile Ala Phe Ala Leu Gly Ser Val Ile Asn Gln
            370                 375                 380

GCC TTG ATA TCA AAA CAA GGT TCA TAT CTT ACT AAC CTA GTA ATA GAA     1200
Ala Leu Ile Ser Lys Gln Gly Ser Tyr Leu Thr Asn Leu Val Ile Glu
385             390                 395                 400

CAA GTA AAA AAT AGA TAT CAA TTT TTA AAC CAA CAC CTT AAC CCA GCC     1248
Gln Val Lys Asn Arg Tyr Gln Phe Leu Asn Gln His Leu Asn Pro Ala
                405                 410                 415

ATA GAG TCT GAT AAT AAC TTC ACA GAT ACT ACT AAA ATT TTT CAT GAT     1296
Ile Glu Ser Asp Asn Asn Phe Thr Asp Thr Thr Lys Ile Phe His Asp
                420                 425                 430

TCA TTA TTT AAT TCA GCT ACC GCA GAA AAC TCT ATG TTT TTA ACA AAA     1344
Ser Leu Phe Asn Ser Ala Thr Ala Glu Asn Ser Met Phe Leu Thr Lys
            435                 440                 445

ATA GCA CCA TAC TTA CAA GTA GGT TTT ATG CCA GAA GCT CGC TCC ACA     1392
Ile Ala Pro Tyr Leu Gln Val Gly Phe Met Pro Glu Ala Arg Ser Thr
            450                 455                 460

ATA AGT TTA AGT GGT CCA GGA GCT TAT GCG TCA GCT TAC TAT GAT TTC     1440
Ile Ser Leu Ser Gly Pro Gly Ala Tyr Ala Ser Ala Tyr Tyr Asp Phe
465             470                 475                 480

ATA AAT TTA CAA GAA AAT ACT ATA GAA AAA ACT TTA AAA GCA TCA GAT     1488
Ile Asn Leu Gln Glu Asn Thr Ile Glu Lys Thr Leu Lys Ala Ser Asp
                485                 490                 495

TTA ATA GAA TTT AAA TTC CCA GAA AAT AAT CTA TCT CAA TTG ACA GAA     1536
Leu Ile Glu Phe Lys Phe Pro Glu Asn Asn Leu Ser Gln Leu Thr Glu
                500                 505                 510

CAA GAA ATA AAT AGT CTA TGG AGC TTT GAT CAA GCA AGT GCA AAA TAT     1584
Gln Glu Ile Asn Ser Leu Trp Ser Phe Asp Gln Ala Ser Ala Lys Tyr
                515                 520                 525

CAA TTT GAG AAA TAT GTA AGA GAT TAT ACT GGT GGA TCT CTT TCT GAA     1632
Gln Phe Glu Lys Tyr Val Arg Asp Tyr Thr Gly Gly Ser Leu Ser Glu
            530                 535                 540

GAC AAT GGG GTA GAC TTT AAT AAA AAT ACT GCC CTC GAC AAA AAC TAT     1680
Asp Asn Gly Val Asp Phe Asn Lys Asn Thr Ala Leu Asp Lys Asn Tyr
545             550                 555                 560

TTA TTA AAT AAT AAA ATT CCA TCA AAC AAT GTA GAA GAA GCT GGA AGT     1728
Leu Leu Asn Asn Lys Ile Pro Ser Asn Asn Val Glu Glu Ala Gly Ser
                565                 570                 575
```

| | |
|---|---|
| AAA AAT TAT GTT CAT TAT ATC ATA CAG TTA CAA GGA GAT GAT ATA AGT<br>Lys Asn Tyr Val His Tyr Ile Ile Gln Leu Gln Gly Asp Asp Ile Ser<br>580 585 590 | 1776 |
| TAT GAA GCA ACA TGC AAT TTA TTT TCT AAA AAT CCT AAA AAT AGT ATT<br>Tyr Glu Ala Thr Cys Asn Leu Phe Ser Lys Asn Pro Lys Asn Ser Ile<br>595 600 605 | 1824 |
| ATT ATA CAA CGA AAT ATG AAT GAA AGT GCA AAA AGC TAC TTT TTA AGT<br>Ile Ile Gln Arg Asn Met Asn Glu Ser Ala Lys Ser Tyr Phe Leu Ser<br>610 615 620 | 1872 |
| GAT GAT GGA GAA TCT ATT TTA GAA TTA AAT AAA TAT AGG ATA CCT GAA<br>Asp Asp Gly Glu Ser Ile Leu Glu Leu Asn Lys Tyr Arg Ile Pro Glu<br>625 630 635 640 | 1920 |
| AGA TTA AAA AAT AAG GAA AAA GTA AAA GTA ACC TTT ATT GGA CAT GGT<br>Arg Leu Lys Asn Lys Glu Lys Val Lys Val Thr Phe Ile Gly His Gly<br>645 650 655 | 1968 |
| AAA GAT GAA TTC AAC ACA AGC GAA TTT GCT AGA TTA AGT GTA GAT TCA<br>Lys Asp Glu Phe Asn Thr Ser Glu Phe Ala Arg Leu Ser Val Asp Ser<br>660 665 670 | 2016 |
| CTT TCC AAT GAG ATA AGT TCA TTT TTA GAT ACC ATA AAA TTA GAT ATA<br>Leu Ser Asn Glu Ile Ser Ser Phe Leu Asp Thr Ile Lys Leu Asp Ile<br>675 680 685 | 2064 |
| TCA CCT AAA AAT GTA GAA GTA AAC TTA CTT GGA TGT AAT ATG TTT AGT<br>Ser Pro Lys Asn Val Glu Val Asn Leu Leu Gly Cys Asn Met Phe Ser<br>690 695 700 | 2112 |
| TAT GAT TTT AAT GTT GAA GAA ACT TAT CCT GGG AAG TTG CTA TTA AGT<br>Tyr Asp Phe Asn Val Glu Glu Thr Tyr Pro Gly Lys Leu Leu Leu Ser<br>705 710 715 720 | 2160 |
| ATT ATG GAC AAA ATT ACT TCC ACT TTA CCT GAT GTA AAT AAA AAT TCT<br>Ile Met Asp Lys Ile Thr Ser Thr Leu Pro Asp Val Asn Lys Asn Ser<br>725 730 735 | 2208 |
| ATT ACT ATA GGA GCA AAT CAA TAT GAA GTA AGA ATT AAT AGT GAG GGA<br>Ile Thr Ile Gly Ala Asn Gln Tyr Glu Val Arg Ile Asn Ser Glu Gly<br>740 745 750 | 2256 |
| AGA AAA GAA CTT CTG GCT CAC TCA GGT AAA TGG ATA AAT AAA GAA GAA<br>Arg Lys Glu Leu Leu Ala His Ser Gly Lys Trp Ile Asn Lys Glu Glu<br>755 760 765 | 2304 |
| GCT ATT ATG AGC GAT TTA TCT AGT AAA GAA TAC ATT TTT TTT GAT TCT<br>Ala Ile Met Ser Asp Leu Ser Ser Lys Glu Tyr Ile Phe Phe Asp Ser<br>770 775 780 | 2352 |
| ATA GAT AAT AAG CTA AAA GCA AAG TCC AAG AAT ATT CCA GGA TTA GCA<br>Ile Asp Asn Lys Leu Lys Ala Lys Ser Lys Asn Ile Pro Gly Leu Ala<br>785 790 795 800 | 2400 |
| TCA ATA TCA GAA GAT ATA AAA ACA TTA TTA CTT GAT GCA AGT GTT AGT<br>Ser Ile Ser Glu Asp Ile Lys Thr Leu Leu Leu Asp Ala Ser Val Ser<br>805 810 815 | 2448 |
| CCT GAT ACA AAA TTT ATT TTA AAT AAT CTT AAG CTT AAT ATT GAA TCT<br>Pro Asp Thr Lys Phe Ile Leu Asn Asn Leu Lys Leu Asn Ile Glu Ser<br>820 825 830 | 2496 |
| TCT ATT GGG GAT TAC ATT TAT TAT GAA AAA TTA GAG CCT GTT AAA AAT<br>Ser Ile Gly Asp Tyr Ile Tyr Tyr Glu Lys Leu Glu Pro Val Lys Asn<br>835 840 845 | 2544 |
| ATA ATT CAC AAT TCT ATA GAT GAT TTA ATA GAT GAG TTC AAT CTA CTT<br>Ile Ile His Asn Ser Ile Asp Asp Leu Ile Asp Glu Phe Asn Leu Leu<br>850 855 860 | 2592 |
| GAA AAT GTA TCT GAT GAA TTA TAT GAA TTA AAA AAA TTA AAT AAT CTA<br>Glu Asn Val Ser Asp Glu Leu Tyr Glu Leu Lys Lys Leu Asn Asn Leu<br>865 870 875 880 | 2640 |
| GAT GAG AAG TAT TTA ATA TCT TTT GAA GAT ATC TCA AAA AAT AAT TCA<br>Asp Glu Lys Tyr Leu Ile Ser Phe Glu Asp Ile Ser Lys Asn Asn Ser<br>885 890 895 | 2688 |

```
ACT TAC TCT GTA AGA TTT ATT AAC AAA AGT AAT GGT GAG TCA GTT TAT       2736
Thr Tyr Ser Val Arg Phe Ile Asn Lys Ser Asn Gly Glu Ser Val Tyr
            900                 905                 910

GTA GAA ACA GAA AAA GAA ATT TTT TCA AAA TAT AGC GAA CAT ATT ACA       2784
Val Glu Thr Glu Lys Glu Ile Phe Ser Lys Tyr Ser Glu His Ile Thr
                915                 920                 925

AAA GAA ATA AGT ACT ATA AAG AAT AGT ATA ATT ACA GAT GTT AAT GGT       2832
Lys Glu Ile Ser Thr Ile Lys Asn Ser Ile Ile Thr Asp Val Asn Gly
        930                 935                 940

AAT TTA TTG GAT AAT ATA CAG TTA GAT CAT ACT TCT CAA GTT AAT ACA       2880
Asn Leu Leu Asp Asn Ile Gln Leu Asp His Thr Ser Gln Val Asn Thr
945                 950                 955                 960

TTA AAC GCA GCA TTC TTT ATT CAA TCA TTA ATA GAT TAT AGT AGC AAT       2928
Leu Asn Ala Ala Phe Phe Ile Gln Ser Leu Ile Asp Tyr Ser Ser Asn
                965                 970                 975

AAA GAT GTA CTG AAT GAT TTA AGT ACC TCA GTT AAG GTT CAA CTT TAT       2976
Lys Asp Val Leu Asn Asp Leu Ser Thr Ser Val Lys Val Gln Leu Tyr
            980                 985                 990

GCT CAA CTA TTT AGT ACA GGT TTA AAT ACT ATA TAT GAC TCT ATC CAA       3024
Ala Gln Leu Phe Ser Thr Gly Leu Asn Thr Ile Tyr Asp Ser Ile Gln
                995                 1000                1005

TTA GTA AAT TTA ATA TCA AAT GCA GTA AAT GAT ACT ATA AAT GTA CTA       3072
Leu Val Asn Leu Ile Ser Asn Ala Val Asn Asp Thr Ile Asn Val Leu
        1010                1015                1020

CCT ACA ATA ACA GAG GGG ATA CCT ATT GTA TCT ACT ATA TTA GAC GGA       3120
Pro Thr Ile Thr Glu Gly Ile Pro Ile Val Ser Thr Ile Leu Asp Gly
1025                1030                1035                1040

ATA AAC TTA GGT GCA GCA ATT AAG GAA TTA CTA GAC GAA CAT GAC CCA       3168
Ile Asn Leu Gly Ala Ala Ile Lys Glu Leu Leu Asp Glu His Asp Pro
                1045                1050                1055

TTA CTA AAA AAA GAA TTA GAA GCT AAG GTG GGT GTT TTA GCA ATA AAT       3216
Leu Leu Lys Lys Glu Leu Glu Ala Lys Val Gly Val Leu Ala Ile Asn
            1060                1065                1070

ATG TCA TTA TCT ATA GCT GCA ACT GTA GCT TCA ATT GTT GGA ATA GGT       3264
Met Ser Leu Ser Ile Ala Ala Thr Val Ala Ser Ile Val Gly Ile Gly
                1075                1080                1085

GCT GAA GTT ACT ATT TTC TTA TTA CCT ATA GCT GGT ATA TCT GCA GGA       3312
Ala Glu Val Thr Ile Phe Leu Leu Pro Ile Ala Gly Ile Ser Ala Gly
        1090                1095                1100

ATA CCT TCA TTA GTT AAT AAT GAA TTA ATA TTG CAT GAT AAG GCA ACT       3360
Ile Pro Ser Leu Val Asn Asn Glu Leu Ile Leu His Asp Lys Ala Thr
1105                1110                1115                1120

TCA GTG GTA AAC TAT TTT AAT CAT TTG TCT GAA TCT AAA AAA TAT GGC       3408
Ser Val Val Asn Tyr Phe Asn His Leu Ser Glu Ser Lys Lys Tyr Gly
                1125                1130                1135

CCT CTT AAA ACA GAA GAT GAT AAA ATT TTA GTT CCT ATT GAT GAT TTA       3456
Pro Leu Lys Thr Glu Asp Asp Lys Ile Leu Val Pro Ile Asp Asp Leu
            1140                1145                1150

GTA ATA TCA GAA ATA GAT TTT AAT AAT AAT TCG ATA AAA CTA GGA ACA       3504
Val Ile Ser Glu Ile Asp Phe Asn Asn Asn Ser Ile Lys Leu Gly Thr
                1155                1160                1165

TGT AAT ATA TTA GCA ATG GAG GGG GGA TCA GGA CAC ACA GTG ACT GGT       3552
Cys Asn Ile Leu Ala Met Glu Gly Gly Ser Gly His Thr Val Thr Gly
        1170                1175                1180

AAT ATA GAT CAC TTT TTC TCA TCT CCA TCT ATA AGT TCT CAT ATT CCT       3600
Asn Ile Asp His Phe Phe Ser Ser Pro Ser Ile Ser Ser His Ile Pro
1185                1190                1195                1200

TCA TTA TCA ATT TAT TCT GCA ATA GGT ATA GAA ACA GAA AAT CTA GAT       3648
Ser Leu Ser Ile Tyr Ser Ala Ile Gly Ile Glu Thr Glu Asn Leu Asp
```

```
                        1205                 1210                 1215
TTT TCA AAA AAA ATA ATG ATG TTA CCT AAT GCT CCT TCA AGA GTG TTT             3696
Phe Ser Lys Lys Ile Met Met Leu Pro Asn Ala Pro Ser Arg Val Phe
            1220                 1225                 1230

TGG TGG GAA ACT GGA GCA GTT CCA GGT TTA AGA TCA TTG GAA AAT GAC             3744
Trp Trp Glu Thr Gly Ala Val Pro Gly Leu Arg Ser Leu Glu Asn Asp
            1235                 1240                 1245

GGA ACT AGA TTA CTT GAT TCA ATA AGA GAT TTA TAC CCA GGT AAA TTT             3792
Gly Thr Arg Leu Leu Asp Ser Ile Arg Asp Leu Tyr Pro Gly Lys Phe
            1250                 1255                 1260

TAC TGG AGA TTC TAT GCT TTT TTC GAT TAT GCA ATA ACT ACA TTA AAA             3840
Tyr Trp Arg Phe Tyr Ala Phe Phe Asp Tyr Ala Ile Thr Thr Leu Lys
1265                 1270                 1275                 1280

CCA GTT TAT GAA GAC ACT AAT ATT AAA ATT AAA CTA GAT AAA GAT ACT             3888
Pro Val Tyr Glu Asp Thr Asn Ile Lys Ile Lys Leu Asp Lys Asp Thr
                1285                 1290                 1295

AGA AAC TTC ATA ATG CCA ACT ATA ACT ACT AAC GAA ATT AGA AAC AAA             3936
Arg Asn Phe Ile Met Pro Thr Ile Thr Thr Asn Glu Ile Arg Asn Lys
            1300                 1305                 1310

TTA TCT TAT TCA TTT GAT GGA GCA GGA GGA ACT TAC TCT TTA TTA TTA             3984
Leu Ser Tyr Ser Phe Asp Gly Ala Gly Gly Thr Tyr Ser Leu Leu Leu
            1315                 1320                 1325

TCT TCA TAT CCA ATA TCA ACG AAT ATA AAT TTA TCT AAA GAT GAT TTA             4032
Ser Ser Tyr Pro Ile Ser Thr Asn Ile Asn Leu Ser Lys Asp Asp Leu
            1330                 1335                 1340

TGG ATA TTT AAT ATT GAT AAT GAA GTA AGA GAA ATA TCT ATA GAA AAT             4080
Trp Ile Phe Asn Ile Asp Asn Glu Val Arg Glu Ile Ser Ile Glu Asn
1345                 1350                 1355                 1360

GGT ACT ATT AAA AAA GGA AAG TTA ATA AAA GAT GTT TTA AGT AAA ATT             4128
Gly Thr Ile Lys Lys Gly Lys Leu Ile Lys Asp Val Leu Ser Lys Ile
                1365                 1370                 1375

GAT ATA AAT AAA AAT AAA CTT ATT ATA GGC AAT CAA ACA ATA GAT TTT             4176
Asp Ile Asn Lys Asn Lys Leu Ile Ile Gly Asn Gln Thr Ile Asp Phe
            1380                 1385                 1390

TCA GGC GAT ATA GAT AAT AAA GAT AGA TAT ATA TTC TTG ACT TGT GAG             4224
Ser Gly Asp Ile Asp Asn Lys Asp Arg Tyr Ile Phe Leu Thr Cys Glu
            1395                 1400                 1405

TTA GAT GAT AAA ATT AGT TTA ATA ATA GAA ATA AAT CTT GTT GCA AAA             4272
Leu Asp Asp Lys Ile Ser Leu Ile Ile Glu Ile Asn Leu Val Ala Lys
            1410                 1415                 1420

TCT TAT AGT TTG TTA TTG TCT GGG GAT AAA AAT TAT TTG ATA TCC AAT             4320
Ser Tyr Ser Leu Leu Leu Ser Gly Asp Lys Asn Tyr Leu Ile Ser Asn
1425                 1430                 1435                 1440

TTA TCT AAT ACT ATT GAG AAA ATC AAT ACT TTA GGC CTA GAT AGT AAA             4368
Leu Ser Asn Thr Ile Glu Lys Ile Asn Thr Leu Gly Leu Asp Ser Lys
                1445                 1450                 1455

AAT ATA GCG TAC AAT TAC ACT GAT GAA TCT AAT AAT AAA TAT TTT GGA             4416
Asn Ile Ala Tyr Asn Tyr Thr Asp Glu Ser Asn Asn Lys Tyr Phe Gly
            1460                 1465                 1470

GCT ATA TCT AAA ACA AGT CAA AAA AGC ATA ATA CAT TAT AAA AAA GAC             4464
Ala Ile Ser Lys Thr Ser Gln Lys Ser Ile Ile His Tyr Lys Lys Asp
            1475                 1480                 1485

AGT AAA AAT ATA TTA GAA TTT TAT AAT GAC AGT ACA TTA GAA TTT AAC             4512
Ser Lys Asn Ile Leu Glu Phe Tyr Asn Asp Ser Thr Leu Glu Phe Asn
            1490                 1495                 1500

AGT AAA GAT TTT ATT GCT GAA GAT ATA AAT GTA TTT ATG AAA GAT GAT             4560
Ser Lys Asp Phe Ile Ala Glu Asp Ile Asn Val Phe Met Lys Asp Asp
1505                 1510                 1515                 1520

ATT AAT ACT ATA ACA GGA AAA TAC TAT GTT GAT AAT AAT ACT GAT AAA             4608
```

-continued

```
Ile Asn Thr Ile Thr Gly Lys Tyr Tyr Val Asp Asn Asn Thr Asp Lys
            1525                1530                1535

AGT ATA GAT TTC TCT ATT TCT TTA GTT AGT AAA AAT CAA GTA AAA GTA      4656
Ser Ile Asp Phe Ser Ile Ser Leu Val Ser Lys Asn Gln Val Lys Val
            1540                1545                1550

AAT GGA TTA TAT TTA AAT GAA TCC GTA TAC TCA TCT TAC CTT GAT TTT      4704
Asn Gly Leu Tyr Leu Asn Glu Ser Val Tyr Ser Ser Tyr Leu Asp Phe
            1555                1560                1565

GTG AAA AAT TCA GAT GGA CAC CAT AAT ACT TCT AAT TTT ATG AAT TTA      4752
Val Lys Asn Ser Asp Gly His His Asn Thr Ser Asn Phe Met Asn Leu
            1570                1575                1580

TTT TTG GAC AAT ATA AGT TTC TGG AAA TTG TTT GGG TTT GAA AAT ATA      4800
Phe Leu Asp Asn Ile Ser Phe Trp Lys Leu Phe Gly Phe Glu Asn Ile
1585                1590                1595                1600

AAT TTT GTA ATC GAT AAA TAC TTT ACC CTT GTT GGT AAA ACT AAT CTT      4848
Asn Phe Val Ile Asp Lys Tyr Phe Thr Leu Val Gly Lys Thr Asn Leu
            1605                1610                1615

GGA TAT GTA GAA TTT ATT TGT GAC AAT AAT AAA AAT ATA GAT ATA TAT      4896
Gly Tyr Val Glu Phe Ile Cys Asp Asn Asn Lys Asn Ile Asp Ile Tyr
            1620                1625                1630

TTT GGT GAA TGG AAA ACA TCG TCA TCT AAA AGC ACT ATA TTT AGC GGA      4944
Phe Gly Glu Trp Lys Thr Ser Ser Ser Lys Ser Thr Ile Phe Ser Gly
            1635                1640                1645

AAT GGT AGA AAT GTT GTA GTA GAG CCT ATA TAT AAT CCT GAT ACG GGT      4992
Asn Gly Arg Asn Val Val Val Glu Pro Ile Tyr Asn Pro Asp Thr Gly
            1650                1655                1660

GAA GAT ATA TCT ACT TCA CTA GAT TTT TCC TAT GAA CCT CTC TAT GGA      5040
Glu Asp Ile Ser Thr Ser Leu Asp Phe Ser Tyr Glu Pro Leu Tyr Gly
1665                1670                1675                1680

ATA GAT AGA TAT ATA AAT AAA GTA TTG ATA GCA CCT GAT TTA TAT ACA      5088
Ile Asp Arg Tyr Ile Asn Lys Val Leu Ile Ala Pro Asp Leu Tyr Thr
            1685                1690                1695

AGT TTA ATA AAT ATT AAT ACC AAT TAT TAT TCA AAT GAG TAC TAC CCT      5136
Ser Leu Ile Asn Ile Asn Thr Asn Tyr Tyr Ser Asn Glu Tyr Tyr Pro
            1700                1705                1710

GAG ATT ATA GTT CTT AAC CCA AAT ACA TTC CAC AAA AAA GTA AAT ATA      5184
Glu Ile Ile Val Leu Asn Pro Asn Thr Phe His Lys Lys Val Asn Ile
            1715                1720                1725

AAT TTA GAT AGT TCT TCT TTT GAG TAT AAA TGG TCT ACA GAA GGA AGT      5232
Asn Leu Asp Ser Ser Ser Phe Glu Tyr Lys Trp Ser Thr Glu Gly Ser
            1730                1735                1740

GAC TTT ATT TTA GTT AGA TAC TTA GAA GAA AGT AAT AAA AAA ATA TTA      5280
Asp Phe Ile Leu Val Arg Tyr Leu Glu Glu Ser Asn Lys Lys Ile Leu
1745                1750                1755                1760

CAA AAA ATA AGA ATC AAA GGT ATC TTA TCT AAT ACT CAA TCA TTT AAT      5328
Gln Lys Ile Arg Ile Lys Gly Ile Leu Ser Asn Thr Gln Ser Phe Asn
            1765                1770                1775

AAA ATG AGT ATA GAT TTT AAA GAT ATT AAA AAA CTA TCA TTA GGA TAT      5376
Lys Met Ser Ile Asp Phe Lys Asp Ile Lys Lys Leu Ser Leu Gly Tyr
            1780                1785                1790

ATA ATG AGT AAT TTT AAA TCA TTT AAT TCT GAA AAT GAA TTA GAT AGA      5424
Ile Met Ser Asn Phe Lys Ser Phe Asn Ser Glu Asn Glu Leu Asp Arg
            1795                1800                1805

GAT CAT TTA GGA TTT AAA ATA ATA GAT AAT AAA ACT TAT TAC TAT GAT      5472
Asp His Leu Gly Phe Lys Ile Ile Asp Asn Lys Thr Tyr Tyr Tyr Asp
            1810                1815                1820

GAA GAT AGT AAA TTA GTT AAA GGA TTA ATC AAT ATA AAT AAT TCA TTA      5520
Glu Asp Ser Lys Leu Val Lys Gly Leu Ile Asn Ile Asn Asn Ser Leu
1825                1830                1835                1840
```

```
TTC TAT TTT GAT CCT ATA GAA TTT AAC TTA GTA ACT GGA TGG CAA ACT     5568
Phe Tyr Phe Asp Pro Ile Glu Phe Asn Leu Val Thr Gly Trp Gln Thr
                1845                1850                1855

ATC AAT GGT AAA AAA TAT TAT TTT GAT ATA AAT ACT GGA GCA GCT TTA     5616
Ile Asn Gly Lys Lys Tyr Tyr Phe Asp Ile Asn Thr Gly Ala Ala Leu
                1860                1865                1870

ACT AGT TAT AAA ATT ATT AAT GGT AAA CAC TTT TAT TTT AAT AAT GAT     5664
Thr Ser Tyr Lys Ile Ile Asn Gly Lys His Phe Tyr Phe Asn Asn Asp
                1875                1880                1885

GGT GTG ATG CAG TTG GGA GTA TTT AAA GGA CCT GAT GGA TTT GAA TAT     5712
Gly Val Met Gln Leu Gly Val Phe Lys Gly Pro Asp Gly Phe Glu Tyr
                1890                1895                1900

TTT GCA CCT GCC AAT ACT CAA AAT AAT AAC ATA GAA GGT CAG GCT ATA     5760
Phe Ala Pro Ala Asn Thr Gln Asn Asn Asn Ile Glu Gly Gln Ala Ile
1905                1910                1915                1920

GTT TAT CAA AGT AAA TTC TTA ACT TTG AAT GGC AAA AAA TAT TAT TTT     5808
Val Tyr Gln Ser Lys Phe Leu Thr Leu Asn Gly Lys Lys Tyr Tyr Phe
                1925                1930                1935

GAT AAT AAC TCA AAA GCA GTC ACT GGA TGG AGA ATT ATT AAC AAT GAG     5856
Asp Asn Asn Ser Lys Ala Val Thr Gly Trp Arg Ile Ile Asn Asn Glu
                1940                1945                1950

AAA TAT TAC TTT AAT CCT AAT AAT GCT ATT GCT GCA GTC GGA TTG CAA     5904
Lys Tyr Tyr Phe Asn Pro Asn Asn Ala Ile Ala Ala Val Gly Leu Gln
                1955                1960                1965

GTA ATT GAC AAT AAT AAG TAT TAT TTC AAT CCT GAC ACT GCT ATC ATC     5952
Val Ile Asp Asn Asn Lys Tyr Tyr Phe Asn Pro Asp Thr Ala Ile Ile
                1970                1975                1980

TCA AAA GGT TGG CAG ACT GTT AAT GGT AGT AGA TAC TAC TTT GAT ACT     6000
Ser Lys Gly Trp Gln Thr Val Asn Gly Ser Arg Tyr Tyr Phe Asp Thr
1985                1990                1995                2000

GAT ACC GCT ATT GCC TTT AAT GGT TAT AAA ACT ATT GAT GGT AAA CAC     6048
Asp Thr Ala Ile Ala Phe Asn Gly Tyr Lys Thr Ile Asp Gly Lys His
                2005                2010                2015

TTT TAT TTT GAT AGT GAT TGT GTA GTG AAA ATA GGT GTG TTT AGT ACC     6096
Phe Tyr Phe Asp Ser Asp Cys Val Val Lys Ile Gly Val Phe Ser Thr
                2020                2025                2030

TCT AAT GGA TTT GAA TAT TTT GCA CCT GCT AAT ACT TAT AAT AAT AAC     6144
Ser Asn Gly Phe Glu Tyr Phe Ala Pro Ala Asn Thr Tyr Asn Asn Asn
                2035                2040                2045

ATA GAA GGT CAG GCT ATA GTT TAT CAA AGT AAA TTC TTA ACT TTG AAT     6192
Ile Glu Gly Gln Ala Ile Val Tyr Gln Ser Lys Phe Leu Thr Leu Asn
                2050                2055                2060

GGT AAA AAA TAT TAC TTT GAT AAT AAC TCA AAA GCA GTT ACC GGA TTG     6240
Gly Lys Lys Tyr Tyr Phe Asp Asn Asn Ser Lys Ala Val Thr Gly Leu
2065                2070                2075                2080

CAA ACT ATT GAT AGT AAA AAA TAT TAC TTT AAT ACT AAC ACT GCT GAA     6288
Gln Thr Ile Asp Ser Lys Lys Tyr Tyr Phe Asn Thr Asn Thr Ala Glu
                2085                2090                2095

GCA GCT ACT GGA TGG CAA ACT ATT GAT GGT AAA AAA TAT TAC TTT AAT     6336
Ala Ala Thr Gly Trp Gln Thr Ile Asp Gly Lys Lys Tyr Tyr Phe Asn
                2100                2105                2110

ACT AAC ACT GCT GAA GCA GCT ACT GGA TGG CAA ACT ATT GAT GGT AAA     6384
Thr Asn Thr Ala Glu Ala Ala Thr Gly Trp Gln Thr Ile Asp Gly Lys
                2115                2120                2125

AAA TAT TAC TTT AAT ACT AAC ACT GCT ATA GCT TCA ACT GGT TAT ACA     6432
Lys Tyr Tyr Phe Asn Thr Asn Thr Ala Ile Ala Ser Thr Gly Tyr Thr
                2130                2135                2140

ATT ATT AAT GGT AAA CAT TTT TAT TTT AAT ACT GAT GGT ATT ATG CAG     6480
Ile Ile Asn Gly Lys His Phe Tyr Phe Asn Thr Asp Gly Ile Met Gln
2145                2150                2155                2160
```

```
ATA GGA GTG TTT AAA GGA CCT AAT GGA TTT GAA TAT TTT GCA CCT GCT        6528
Ile Gly Val Phe Lys Gly Pro Asn Gly Phe Glu Tyr Phe Ala Pro Ala
             2165                2170                2175

AAT ACG GAT GCT AAC AAC ATA GAA GGT CAA GCT ATA CTT TAC CAA AAT        6576
Asn Thr Asp Ala Asn Asn Ile Glu Gly Gln Ala Ile Leu Tyr Gln Asn
         2180                2185                2190

GAA TTC TTA ACT TTG AAT GGT AAA AAA TAT TAC TTT GGT AGT GAC TCA        6624
Glu Phe Leu Thr Leu Asn Gly Lys Lys Tyr Tyr Phe Gly Ser Asp Ser
     2195                2200                2205

AAA GCA GTT ACT GGA TGG AGA ATT ATT AAC AAT AAG AAA TAT TAC TTT        6672
Lys Ala Val Thr Gly Trp Arg Ile Ile Asn Asn Lys Lys Tyr Tyr Phe
     2210                2215                2220

AAT CCT AAT AAT GCT ATT GCT GCA ATT CAT CTA TGC ACT ATA AAT AAT        6720
Asn Pro Asn Asn Ala Ile Ala Ala Ile His Leu Cys Thr Ile Asn Asn
2225                2230                2235                2240

GAC AAG TAT TAC TTT AGT TAT GAT GGA ATT CTT CAA AAT GGA TAT ATT        6768
Asp Lys Tyr Tyr Phe Ser Tyr Asp Gly Ile Leu Gln Asn Gly Tyr Ile
             2245                2250                2255

ACT ATT GAA AGA AAT AAT TTC TAT TTT GAT GCT AAT AAT GAA TCT AAA        6816
Thr Ile Glu Arg Asn Asn Phe Tyr Phe Asp Ala Asn Asn Glu Ser Lys
             2260                2265                2270

ATG GTA ACA GGA GTA TTT AAA GGA CCT AAT GGA TTT GAG TAT TTT GCA        6864
Met Val Thr Gly Val Phe Lys Gly Pro Asn Gly Phe Glu Tyr Phe Ala
     2275                2280                2285

CCT GCT AAT ACT CAC AAT AAT AAC ATA GAA GGT CAG GCT ATA GTT TAC        6912
Pro Ala Asn Thr His Asn Asn Asn Ile Glu Gly Gln Ala Ile Val Tyr
         2290                2295                2300

CAG AAC AAA TTC TTA ACT TTG AAT GGC AAA AAA TAT TAT TTT GAT AAT        6960
Gln Asn Lys Phe Leu Thr Leu Asn Gly Lys Lys Tyr Tyr Phe Asp Asn
2305                2310                2315                2320

GAC TCA AAA GCA GTT ACT GGA TGG CAA ACC ATT GAT GGT AAA AAA TAT        7008
Asp Ser Lys Ala Val Thr Gly Trp Gln Thr Ile Asp Gly Lys Lys Tyr
             2325                2330                2335

TAC TTT AAT CTT AAC ACT GCT GAA GCA GCT ACT GGA TGG CAA ACT ATT        7056
Tyr Phe Asn Leu Asn Thr Ala Glu Ala Ala Thr Gly Trp Gln Thr Ile
             2340                2345                2350

GAT GGT AAA AAA TAT TAC TTT AAT CTT AAC ACT GCT GAA GCA GCT ACT        7104
Asp Gly Lys Lys Tyr Tyr Phe Asn Leu Asn Thr Ala Glu Ala Ala Thr
             2355                2360                2365

GGA TGG CAA ACT ATT GAT GGT AAA AAA TAT TAC TTT AAT ACT AAC ACT        7152
Gly Trp Gln Thr Ile Asp Gly Lys Lys Tyr Tyr Phe Asn Thr Asn Thr
     2370                2375                2380

TTC ATA GCC TCA ACT GGT TAT ACA AGT ATT AAT GGT AAA CAT TTT TAT        7200
Phe Ile Ala Ser Thr Gly Tyr Thr Ser Ile Asn Gly Lys His Phe Tyr
2385                2390                2395                2400

TTT AAT ACT GAT GGT ATT ATG CAG ATA GGA GTG TTT AAA GGA CCT AAT        7248
Phe Asn Thr Asp Gly Ile Met Gln Ile Gly Val Phe Lys Gly Pro Asn
         2405                2410                2415

GGA TTT GAA TAC TTT GCA CCT GCT AAT ACG GAT GCT AAC AAC ATA GAA        7296
Gly Phe Glu Tyr Phe Ala Pro Ala Asn Thr Asp Ala Asn Asn Ile Glu
             2420                2425                2430

GGT CAA GCT ATA CTT TAC CAA AAT AAA TTC TTA ACT TTG AAT GGT AAA        7344
Gly Gln Ala Ile Leu Tyr Gln Asn Lys Phe Leu Thr Leu Asn Gly Lys
         2435                2440                2445

AAA TAT TAC TTT GGT AGT GAC TCA AAA GCA GTT ACC GGA CTG CGA ACT        7392
Lys Tyr Tyr Phe Gly Ser Asp Ser Lys Ala Val Thr Gly Leu Arg Thr
     2450                2455                2460

ATT GAT GGT AAA AAA TAT TAC TTT AAT ACT AAC ACT GCT GTT GCA GTT        7440
Ile Asp Gly Lys Lys Tyr Tyr Phe Asn Thr Asn Thr Ala Val Ala Val
```

```
                2465                2470                2475                2480
ACT GGA TGG CAA ACT ATT AAT GGT AAA AAA TAC TAC TTT AAT ACT AAC        7488
Thr Gly Trp Gln Thr Ile Asn Gly Lys Lys Tyr Tyr Phe Asn Thr Asn
                    2485                2490                2495

ACT TCT ATA GCT TCA ACT GGT TAT ACA ATT ATT AGT GGT AAA CAT TTT        7536
Thr Ser Ile Ala Ser Thr Gly Tyr Thr Ile Ile Ser Gly Lys His Phe
                2500                2505                2510

TAT TTT AAT ACT GAT GGT ATT ATG CAG ATA GGA GTG TTT AAA GGA CCT        7584
Tyr Phe Asn Thr Asp Gly Ile Met Gln Ile Gly Val Phe Lys Gly Pro
            2515                2520                2525

GAT GGA TTT GAA TAC TTT GCA CCT GCT AAT ACA GAT GCT AAC AAT ATA        7632
Asp Gly Phe Glu Tyr Phe Ala Pro Ala Asn Thr Asp Ala Asn Asn Ile
        2530                2535                2540

GAA GGT CAA GCT ATA CGT TAT CAA AAT AGA TTC CTA TAT TTA CAT GAC        7680
Glu Gly Gln Ala Ile Arg Tyr Gln Asn Arg Phe Leu Tyr Leu His Asp
2545                2550                2555                2560

AAT ATA TAT TAT TTT GGT AAT AAT TCA AAA GCG GCT ACT GGT TGG GTA        7728
Asn Ile Tyr Tyr Phe Gly Asn Asn Ser Lys Ala Ala Thr Gly Trp Val
                2565                2570                2575

ACT ATT GAT GGT AAT AGA TAT TAC TTC GAG CCT AAT ACA GCT ATG GGT        7776
Thr Ile Asp Gly Asn Arg Tyr Tyr Phe Glu Pro Asn Thr Ala Met Gly
            2580                2585                2590

GCG AAT GGT TAT AAA ACT ATT GAT AAT AAA AAT TTT TAC TTT AGA AAT        7824
Ala Asn Gly Tyr Lys Thr Ile Asp Asn Lys Asn Phe Tyr Phe Arg Asn
        2595                2600                2605

GGT TTA CCT CAG ATA GGA GTG TTT AAA GGG TCT AAT GGA TTT GAA TAC        7872
Gly Leu Pro Gln Ile Gly Val Phe Lys Gly Ser Asn Gly Phe Glu Tyr
            2610                2615                2620

TTT GCA CCT GCT AAT ACG GAT GCT AAC AAT ATA GAA GGT CAA GCT ATA        7920
Phe Ala Pro Ala Asn Thr Asp Ala Asn Asn Ile Glu Gly Gln Ala Ile
2625                2630                2635                2640

CGT TAT CAA AAT AGA TTC CTA CAT TTA CTT GGA AAA ATA TAT TAC TTT        7968
Arg Tyr Gln Asn Arg Phe Leu His Leu Leu Gly Lys Ile Tyr Tyr Phe
                2645                2650                2655

GGT AAT AAT TCA AAA GCA GTT ACT GGA TGG CAA ACT ATT AAT GGT AAA        8016
Gly Asn Asn Ser Lys Ala Val Thr Gly Trp Gln Thr Ile Asn Gly Lys
            2660                2665                2670

GTA TAT TAC TTT ATG CCT GAT ACT GCT ATG GCT GCA GCT GGT GGA CTT        8064
Val Tyr Tyr Phe Met Pro Asp Thr Ala Met Ala Ala Ala Gly Gly Leu
        2675                2680                2685

TTC GAG ATT GAT GGT GTT ATA TAT TTC TTT GGT GTT GAT GGA GTA AAA        8112
Phe Glu Ile Asp Gly Val Ile Tyr Phe Phe Gly Val Asp Gly Val Lys
    2690                2695                2700

GCC CCT GGG ATA TAT GGC TAA                                            8133
Ala Pro Gly Ile Tyr Gly
2705                2710
```

(2) INFORMATION FOR SEQ ID NO:6:

(i) SEQUENCE CHARACTERISTICS:
        (A) LENGTH: 2710 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30
```

-continued

```
Tyr Asn Lys Leu Thr Thr Asn Asn Glu Asn Lys Tyr Leu Gln Leu
         35                  40                  45

Lys Lys Leu Asn Glu Ser Ile Asp Val Phe Met Asn Lys Tyr Lys Thr
 50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Glu Lys Asn
                 85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
                115                 120                 125

Trp Tyr Asp Ser Glu Ala Phe Leu Val Asn Thr Leu Lys Lys Ala Ile
                130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
                180                 185                 190

Ile Asn Lys Pro Thr Val Pro Thr Ile Asp Asp Ile Ile Lys Ser His
                195                 200                 205

Leu Val Ser Glu Tyr Asn Arg Asp Glu Thr Val Leu Glu Ser Tyr Arg
                210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ser Asp Ile Val Arg
                260                 265                 270

Leu Leu Ala Leu Lys Asn Phe Gly Gly Val Tyr Leu Asp Val Asp Met
                275                 280                 285

Leu Pro Gly Ile His Ser Asp Leu Phe Lys Thr Ile Ser Arg Pro Ser
                290                 295                 300

Ser Ile Gly Leu Asp Arg Trp Glu Met Ile Lys Leu Glu Ala Ile Met
305                 310                 315                 320

Lys Tyr Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
                340                 345                 350

Ser Glu Lys Ser Glu Ile Phe Ser Lys Leu Glu Asn Leu Asn Val Ser
                355                 360                 365

Asp Leu Glu Ile Lys Ile Ala Phe Ala Leu Gly Ser Val Ile Asn Gln
                370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
                420                 425                 430

Ser Leu Phe Asn Ser Ala Thr Ala Glu Asn Ser Met Phe Leu Thr Lys
                435                 440                 445
```

```
Ile Ala Pro Tyr Leu Gln Val Gly Phe Met Pro Glu Ala Arg Ser Thr
450                 455                 460
Ile Ser Leu Ser Gly Pro Gly Ala Tyr Ala Ser Ala Tyr Tyr Asp Phe
465             470                 475                 480
Ile Asn Leu Gln Glu Asn Thr Ile Glu Lys Thr Leu Lys Ala Ser Asp
                485                 490                 495
Leu Ile Glu Phe Lys Phe Pro Glu Asn Asn Leu Ser Gln Leu Thr Glu
            500                 505                 510
Gln Glu Ile Asn Ser Leu Trp Ser Phe Asp Gln Ala Ser Ala Lys Tyr
        515                 520                 525
Gln Phe Glu Lys Tyr Val Arg Asp Tyr Thr Gly Gly Ser Leu Ser Glu
    530                 535                 540
Asp Asn Gly Val Asp Phe Asn Lys Asn Thr Ala Leu Asp Lys Asn Tyr
545                 550                 555                 560
Leu Leu Asn Asn Lys Ile Pro Ser Asn Val Glu Glu Ala Gly Ser
                565                 570                 575
Lys Asn Tyr Val His Tyr Ile Ile Gln Leu Gln Gly Asp Asp Ile Ser
            580                 585                 590
Tyr Glu Ala Thr Cys Asn Leu Phe Ser Lys Asn Pro Lys Asn Ser Ile
        595                 600                 605
Ile Ile Gln Arg Asn Met Asn Glu Ser Ala Lys Ser Tyr Phe Leu Ser
    610                 615                 620
Asp Asp Gly Glu Ser Ile Leu Glu Leu Asn Lys Tyr Arg Ile Pro Glu
625                 630                 635                 640
Arg Leu Lys Asn Lys Glu Lys Val Lys Val Thr Phe Ile Gly His Gly
                645                 650                 655
Lys Asp Glu Phe Asn Thr Ser Glu Phe Ala Arg Leu Ser Val Asp Ser
            660                 665                 670
Leu Ser Asn Glu Ile Ser Ser Phe Leu Asp Thr Ile Lys Leu Asp Ile
        675                 680                 685
Ser Pro Lys Asn Val Glu Val Asn Leu Leu Gly Cys Asn Met Phe Ser
    690                 695                 700
Tyr Asp Phe Asn Val Glu Glu Thr Tyr Pro Gly Lys Leu Leu Leu Ser
705                 710                 715                 720
Ile Met Asp Lys Ile Thr Ser Thr Leu Pro Asp Val Asn Lys Asn Ser
                725                 730                 735
Ile Thr Ile Gly Ala Asn Gln Tyr Glu Val Arg Ile Asn Ser Glu Gly
            740                 745                 750
Arg Lys Glu Leu Leu Ala His Ser Gly Lys Trp Ile Asn Lys Glu Glu
        755                 760                 765
Ala Ile Met Ser Asp Leu Ser Ser Lys Glu Tyr Ile Phe Phe Asp Ser
    770                 775                 780
Ile Asp Asn Lys Leu Lys Ala Lys Ser Lys Asn Ile Pro Gly Leu Ala
785                 790                 795                 800
Ser Ile Ser Glu Asp Ile Lys Thr Leu Leu Asp Ala Ser Val Ser
                805                 810                 815
Pro Asp Thr Lys Phe Ile Leu Asn Asn Leu Lys Leu Asn Ile Glu Ser
            820                 825                 830
Ser Ile Gly Asp Tyr Ile Tyr Tyr Glu Lys Leu Glu Pro Val Lys Asn
        835                 840                 845
Ile Ile His Asn Ser Ile Asp Asp Leu Ile Asp Glu Phe Asn Leu Leu
    850                 855                 860
Glu Asn Val Ser Asp Glu Leu Tyr Glu Leu Lys Lys Leu Asn Asn Leu
```

```
                865                 870                 875                 880
Asp Glu Lys Tyr Leu Ile Ser Phe Glu Asp Ile Ser Lys Asn Asn Ser
                    885                 890                 895
Thr Tyr Ser Val Arg Phe Ile Asn Lys Ser Asn Gly Glu Ser Val Tyr
                    900                 905                 910
Val Glu Thr Glu Lys Glu Ile Phe Ser Lys Tyr Ser Glu His Ile Thr
                    915                 920                 925
Lys Glu Ile Ser Thr Ile Lys Asn Ser Ile Ile Thr Asp Val Asn Gly
                    930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                    965                 970                 975
Lys Asp Val Leu Asn Asp Leu Ser Thr Ser Val Lys Val Gln Leu Tyr
                    980                 985                 990
Ala Gln Leu Phe Ser Thr Gly Leu Asn Thr Ile Tyr Asp Ser Ile Gln
                    995                 1000                1005
Leu Val Asn Leu Ile Ser Asn Ala Val Asn Asp Thr Ile Asn Val Leu
                    1010                1015                1020
Pro Thr Ile Thr Glu Gly Ile Pro Ile Val Ser Thr Ile Leu Asp Gly
1025                1030                1035                1040
Ile Asn Leu Gly Ala Ala Ile Lys Glu Leu Leu Asp Glu His Asp Pro
                    1045                1050                1055
Leu Leu Lys Lys Glu Leu Glu Ala Lys Val Gly Val Leu Ala Ile Asn
                    1060                1065                1070
Met Ser Leu Ser Ile Ala Ala Thr Val Ala Ser Ile Val Gly Ile Gly
                    1075                1080                1085
Ala Glu Val Thr Ile Phe Leu Leu Pro Ile Ala Gly Ile Ser Ala Gly
                    1090                1095                1100
Ile Pro Ser Leu Val Asn Asn Glu Leu Ile Leu His Asp Lys Ala Thr
1105                1110                1115                1120
Ser Val Val Asn Tyr Phe Asn His Leu Ser Glu Ser Lys Lys Tyr Gly
                    1125                1130                1135
Pro Leu Lys Thr Glu Asp Asp Lys Ile Leu Val Pro Ile Asp Asp Leu
                    1140                1145                1150
Val Ile Ser Glu Ile Asp Phe Asn Asn Asn Ser Ile Lys Leu Gly Thr
                    1155                1160                1165
Cys Asn Ile Leu Ala Met Glu Gly Gly Ser Gly His Thr Val Thr Gly
                    1170                1175                1180
Asn Ile Asp His Phe Phe Ser Ser Pro Ser Ile Ser Ser His Ile Pro
1185                1190                1195                1200
Ser Leu Ser Ile Tyr Ser Ala Ile Gly Ile Glu Thr Glu Asn Leu Asp
                    1205                1210                1215
Phe Ser Lys Lys Ile Met Met Leu Pro Asn Ala Pro Ser Arg Val Phe
                    1220                1225                1230
Trp Trp Glu Thr Gly Ala Val Pro Gly Leu Arg Ser Leu Glu Asn Asp
                    1235                1240                1245
Gly Thr Arg Leu Leu Asp Ser Ile Arg Asp Leu Tyr Pro Gly Lys Phe
                    1250                1255                1260
Tyr Trp Arg Phe Tyr Ala Phe Phe Asp Tyr Ala Ile Thr Thr Leu Lys
1265                1270                1275                1280
Pro Val Tyr Glu Asp Thr Asn Ile Lys Ile Lys Leu Asp Lys Asp Thr
                    1285                1290                1295
```

-continued

```
Arg Asn Phe Ile Met Pro Thr Ile Thr Thr Asn Glu Ile Arg Asn Lys
            1300                1305                1310
Leu Ser Tyr Ser Phe Asp Gly Ala Gly Gly Thr Tyr Ser Leu Leu Leu
            1315                1320                1325
Ser Ser Tyr Pro Ile Ser Thr Asn Ile Asn Leu Ser Lys Asp Asp Leu
            1330                1335                1340
Trp Ile Phe Asn Ile Asp Asn Glu Val Arg Glu Ile Ser Ile Glu Asn
1345                1350                1355                1360
Gly Thr Ile Lys Lys Gly Lys Leu Ile Lys Asp Val Leu Ser Lys Ile
            1365                1370                1375
Asp Ile Asn Lys Asn Lys Leu Ile Ile Gly Asn Gln Thr Ile Asp Phe
            1380                1385                1390
Ser Gly Asp Ile Asp Asn Lys Asp Arg Tyr Ile Phe Leu Thr Cys Glu
            1395                1400                1405
Leu Asp Asp Lys Ile Ser Leu Ile Ile Glu Ile Asn Leu Val Ala Lys
            1410                1415                1420
Ser Tyr Ser Leu Leu Leu Ser Gly Asp Lys Asn Tyr Leu Ile Ser Asn
1425                1430                1435                1440
Leu Ser Asn Thr Ile Glu Lys Ile Asn Thr Leu Gly Leu Asp Ser Lys
            1445                1450                1455
Asn Ile Ala Tyr Asn Tyr Thr Asp Glu Ser Asn Asn Lys Tyr Phe Gly
            1460                1465                1470
Ala Ile Ser Lys Thr Ser Gln Lys Ser Ile Ile His Tyr Lys Lys Asp
            1475                1480                1485
Ser Lys Asn Ile Leu Glu Phe Tyr Asn Asp Ser Thr Leu Glu Phe Asn
            1490                1495                1500
Ser Lys Asp Phe Ile Ala Glu Asp Ile Asn Val Phe Met Lys Asp Asp
1505                1510                1515                1520
Ile Asn Thr Ile Thr Gly Lys Tyr Tyr Val Asp Asn Thr Asp Lys
            1525                1530                1535
Ser Ile Asp Phe Ser Ile Ser Leu Val Ser Lys Asn Gln Val Lys Val
            1540                1545                1550
Asn Gly Leu Tyr Leu Asn Glu Ser Val Tyr Ser Ser Tyr Leu Asp Phe
            1555                1560                1565
Val Lys Asn Ser Asp Gly His His Asn Thr Ser Asn Phe Met Asn Leu
1570                1575                1580
Phe Leu Asp Asn Ile Ser Phe Trp Lys Leu Phe Gly Phe Glu Asn Ile
1585                1590                1595                1600
Asn Phe Val Ile Asp Lys Tyr Phe Thr Leu Val Gly Lys Thr Asn Leu
            1605                1610                1615
Gly Tyr Val Glu Phe Ile Cys Asp Asn Asn Lys Asn Ile Asp Ile Tyr
            1620                1625                1630
Phe Gly Glu Trp Lys Thr Ser Ser Ser Lys Ser Thr Ile Phe Ser Gly
            1635                1640                1645
Asn Gly Arg Asn Val Val Val Glu Pro Ile Tyr Asn Pro Asp Thr Gly
            1650                1655                1660
Glu Asp Ile Ser Thr Ser Leu Asp Phe Ser Tyr Glu Pro Leu Tyr Gly
1665                1670                1675                1680
Ile Asp Arg Tyr Ile Asn Lys Val Leu Ile Ala Pro Asp Leu Tyr Thr
            1685                1690                1695
Ser Leu Ile Asn Ile Asn Thr Asn Tyr Tyr Ser Asn Glu Tyr Tyr Pro
            1700                1705                1710
```

-continued

```
Glu Ile Ile Val Leu Asn Pro Asn Thr Phe His Lys Lys Val Asn Ile
        1715                1720                1725
Asn Leu Asp Ser Ser Ser Phe Glu Tyr Lys Trp Ser Thr Glu Gly Ser
    1730                1735                1740
Asp Phe Ile Leu Val Arg Tyr Leu Glu Glu Ser Asn Lys Lys Ile Leu
1745                1750                1755                1760
Gln Lys Ile Arg Ile Lys Gly Ile Leu Ser Asn Thr Gln Ser Phe Asn
            1765                1770                1775
Lys Met Ser Ile Asp Phe Lys Asp Ile Lys Lys Leu Ser Leu Gly Tyr
        1780                1785                1790
Ile Met Ser Asn Phe Lys Ser Phe Asn Ser Glu Asn Glu Leu Asp Arg
        1795                1800                1805
Asp His Leu Gly Phe Lys Ile Ile Asp Asn Lys Thr Tyr Tyr Tyr Asp
    1810                1815                1820
Glu Asp Ser Lys Leu Val Lys Gly Leu Ile Asn Ile Asn Asn Ser Leu
1825                1830                1835                1840
Phe Tyr Phe Asp Pro Ile Glu Phe Asn Leu Val Thr Gly Trp Gln Thr
                1845                1850                1855
Ile Asn Gly Lys Lys Tyr Tyr Phe Asp Ile Asn Thr Gly Ala Ala Leu
            1860                1865                1870
Thr Ser Tyr Lys Ile Ile Asn Gly Lys His Phe Tyr Phe Asn Asn Asp
        1875                1880                1885
Gly Val Met Gln Leu Gly Val Phe Lys Gly Pro Asp Gly Phe Glu Tyr
        1890                1895                1900
Phe Ala Pro Ala Asn Thr Gln Asn Asn Asn Ile Glu Gly Gln Ala Ile
1905                1910                1915                1920
Val Tyr Gln Ser Lys Phe Leu Thr Leu Asn Gly Lys Lys Tyr Tyr Phe
            1925                1930                1935
Asp Asn Asn Ser Lys Ala Val Thr Gly Trp Arg Ile Ile Asn Asn Glu
        1940                1945                1950
Lys Tyr Tyr Phe Asn Pro Asn Asn Ala Ile Ala Ala Val Gly Leu Gln
        1955                1960                1965
Val Ile Asp Asn Asn Lys Tyr Tyr Phe Asn Pro Asp Thr Ala Ile Ile
    1970                1975                1980
Ser Lys Gly Trp Gln Thr Val Asn Gly Ser Arg Tyr Tyr Phe Asp Thr
1985                1990                1995                2000
Asp Thr Ala Ile Ala Phe Asn Gly Tyr Lys Thr Ile Asp Gly Lys His
            2005                2010                2015
Phe Tyr Phe Asp Ser Asp Cys Val Val Lys Ile Gly Val Phe Ser Thr
        2020                2025                2030
Ser Asn Gly Phe Glu Tyr Phe Ala Pro Ala Asn Thr Tyr Asn Asn Asn
        2035                2040                2045
Ile Glu Gly Gln Ala Ile Val Tyr Gln Ser Lys Phe Leu Thr Leu Asn
    2050                2055                2060
Gly Lys Lys Tyr Tyr Phe Asp Asn Asn Ser Lys Ala Val Thr Gly Leu
2065                2070                2075                2080
Gln Thr Ile Asp Ser Lys Lys Tyr Tyr Phe Asn Thr Asn Thr Ala Glu
            2085                2090                2095
Ala Ala Thr Gly Trp Gln Thr Ile Asp Gly Lys Lys Tyr Tyr Phe Asn
        2100                2105                2110
Thr Asn Thr Ala Glu Ala Ala Thr Gly Trp Gln Thr Ile Asp Gly Lys
        2115                2120                2125
Lys Tyr Tyr Phe Asn Thr Asn Thr Ala Ile Ala Ser Thr Gly Tyr Thr
```

```
                 2130                2135                2140
Ile Ile Asn Gly Lys His Phe Tyr Phe Asn Thr Asp Gly Ile Met Gln
2145                2150                2155                2160
Ile Gly Val Phe Lys Gly Pro Asn Gly Phe Glu Tyr Phe Ala Pro Ala
                2165                2170                2175
Asn Thr Asp Ala Asn Asn Ile Glu Gly Gln Ala Ile Leu Tyr Gln Asn
    2180                2185                2190
Glu Phe Leu Thr Leu Asn Gly Lys Lys Tyr Tyr Phe Gly Ser Asp Ser
        2195                2200                2205
Lys Ala Val Thr Gly Trp Arg Ile Ile Asn Asn Lys Lys Tyr Tyr Phe
            2210                2215                2220
Asn Pro Asn Asn Ala Ile Ala Ala Ile His Leu Cys Thr Ile Asn Asn
2225                2230                2235                2240
Asp Lys Tyr Tyr Phe Ser Tyr Asp Gly Ile Leu Gln Asn Gly Tyr Ile
                2245                2250                2255
Thr Ile Glu Arg Asn Asn Phe Tyr Phe Asp Ala Asn Asn Glu Ser Lys
    2260                2265                2270
Met Val Thr Gly Val Phe Lys Gly Pro Asn Gly Phe Glu Tyr Phe Ala
        2275                2280                2285
Pro Ala Asn Thr His Asn Asn Asn Ile Glu Gly Gln Ala Ile Val Tyr
            2290                2295                2300
Gln Asn Lys Phe Leu Thr Leu Asn Gly Lys Lys Tyr Tyr Phe Asp Asn
2305                2310                2315                2320
Asp Ser Lys Ala Val Thr Gly Trp Gln Thr Ile Asp Gly Lys Lys Tyr
                2325                2330                2335
Tyr Phe Asn Leu Asn Thr Ala Glu Ala Ala Thr Gly Trp Gln Thr Ile
    2340                2345                2350
Asp Gly Lys Lys Tyr Tyr Phe Asn Leu Asn Thr Ala Glu Ala Ala Thr
        2355                2360                2365
Gly Trp Gln Thr Ile Asp Gly Lys Lys Tyr Tyr Phe Asn Thr Asn Thr
            2370                2375                2380
Phe Ile Ala Ser Thr Gly Tyr Thr Ser Ile Asn Gly Lys His Phe Tyr
2385                2390                2395                2400
Phe Asn Thr Asp Gly Ile Met Gln Ile Gly Val Phe Lys Gly Pro Asn
                2405                2410                2415
Gly Phe Glu Tyr Phe Ala Pro Ala Asn Thr Asp Ala Asn Asn Ile Glu
    2420                2425                2430
Gly Gln Ala Ile Leu Tyr Gln Asn Lys Phe Leu Thr Leu Asn Gly Lys
        2435                2440                2445
Lys Tyr Tyr Phe Gly Ser Asp Ser Lys Ala Val Thr Gly Leu Arg Thr
            2450                2455                2460
Ile Asp Gly Lys Lys Tyr Tyr Phe Asn Thr Asn Thr Ala Val Ala Val
2465                2470                2475                2480
Thr Gly Trp Gln Thr Ile Asn Gly Lys Lys Tyr Tyr Phe Asn Thr Asn
                2485                2490                2495
Thr Ser Ile Ala Ser Thr Gly Tyr Thr Ile Ile Ser Gly Lys His Phe
    2500                2505                2510
Tyr Phe Asn Thr Asp Gly Ile Met Gln Ile Gly Val Phe Lys Gly Pro
        2515                2520                2525
Asp Gly Phe Glu Tyr Phe Ala Pro Ala Asn Thr Asp Ala Asn Asn Ile
            2530                2535                2540
Glu Gly Gln Ala Ile Arg Tyr Gln Asn Arg Phe Leu Tyr Leu His Asp
2545                2550                2555                2560
```

```
Asn Ile Tyr Tyr Phe Gly Asn Asn Ser Lys Ala Ala Thr Gly Trp Val
                2565                2570                2575

Thr Ile Asp Gly Asn Arg Tyr Tyr Phe Glu Pro Asn Thr Ala Met Gly
                2580                2585                2590

Ala Asn Gly Tyr Lys Thr Ile Asp Asn Lys Asn Phe Tyr Phe Arg Asn
                2595                2600                2605

Gly Leu Pro Gln Ile Gly Val Phe Lys Gly Ser Asn Gly Phe Glu Tyr
                2610                2615                2620

Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
                2645                2650                2655

Gly Asn Asn Ser Lys Ala Val Thr Gly Trp Gln Thr Ile Asn Gly Lys
                2660                2665                2670

Val Tyr Tyr Phe Met Pro Asp Thr Ala Met Ala Ala Gly Gly Leu
                2675                2680                2685

Phe Glu Ile Asp Gly Val Ile Tyr Phe Phe Gly Val Asp Gly Val Lys
                2690                2695                2700

Ala Pro Gly Ile Tyr Gly
2705                2710

(2) INFORMATION FOR SEQ ID NO:7:

(i) SEQUENCE CHARACTERISTICS:
        (A) LENGTH: 811 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:7:

Ser Tyr Lys Ile Ile Asn Gly Lys His Phe Tyr Phe Asn Asn Asp Gly
1               5                   10                  15

Val Met Gln Leu Gly Val Phe Lys Gly Pro Asp Gly Phe Glu Tyr Phe
                20                  25                  30

Ala Pro Ala Asn Thr Gln Asn Asn Ile Glu Gly Gln Ala Ile Val
                35                  40                  45

Tyr Gln Ser Lys Phe Leu Thr Leu Asn Gly Lys Lys Tyr Tyr Phe Asp
50                  55                  60

Asn Asn Ser Lys Ala Val Thr Gly Trp Arg Ile Ile Asn Asn Glu Lys
65                  70                  75                  80

Tyr Tyr Phe Asn Pro Asn Asn Ala Ile Ala Ala Val Gly Leu Gln Val
                85                  90                  95

Ile Asp Asn Asn Lys Tyr Tyr Phe Asn Pro Asp Thr Ala Ile Ile Ser
                100                 105                 110

Lys Gly Trp Gln Thr Val Asn Gly Ser Arg Tyr Tyr Phe Asp Thr Asp
                115                 120                 125

Thr Ala Ile Ala Phe Asn Gly Tyr Lys Thr Ile Asp Gly Lys His Phe
                130                 135                 140

Tyr Phe Asp Ser Asp Cys Val Val Lys Ile Gly Val Phe Ser Thr Ser
145                 150                 155                 160

Asn Gly Phe Glu Tyr Phe Ala Pro Ala Asn Thr Tyr Asn Asn Asn Ile
                165                 170                 175

Glu Gly Gln Ala Ile Val Tyr Gln Ser Lys Phe Leu Thr Leu Asn Gly
                180                 185                 190
```

-continued

```
Lys Lys Tyr Tyr Phe Asp Asn Asn Ser Lys Ala Val Thr Gly Leu Gln
            195                 200                 205

Thr Ile Asp Ser Lys Lys Tyr Tyr Phe Asn Thr Asn Thr Ala Glu Ala
210                 215                 220

Ala Thr Gly Trp Gln Thr Ile Asp Gly Lys Lys Tyr Tyr Phe Asn Thr
225                 230                 235                 240

Asn Thr Ala Glu Ala Ala Thr Gly Trp Gln Thr Ile Asp Gly Lys Lys
                245                 250                 255

Tyr Tyr Phe Asn Thr Asn Thr Ala Ile Ala Ser Thr Gly Tyr Thr Ile
            260                 265                 270

Ile Asn Gly Lys His Phe Tyr Phe Asn Thr Asp Gly Ile Met Gln Ile
            275                 280                 285

Gly Val Phe Lys Gly Pro Asn Gly Phe Glu Tyr Phe Ala Pro Ala Asn
            290                 295                 300

Thr Asp Ala Asn Asn Ile Glu Gly Gln Ala Ile Leu Tyr Gln Asn Glu
305                 310                 315                 320

Phe Leu Thr Leu Asn Gly Lys Lys Tyr Tyr Phe Gly Ser Asp Ser Lys
                325                 330                 335

Ala Val Thr Gly Trp Arg Ile Ile Asn Asn Lys Lys Tyr Tyr Phe Asn
            340                 345                 350

Pro Asn Asn Ala Ile Ala Ala Ile His Leu Cys Thr Ile Asn Asn Asp
            355                 360                 365

Lys Tyr Tyr Phe Ser Tyr Asp Gly Ile Leu Gln Asn Gly Tyr Ile Thr
            370                 375                 380

Ile Glu Arg Asn Asn Phe Tyr Phe Asp Ala Asn Asn Glu Ser Lys Met
385                 390                 395                 400

Val Thr Gly Val Phe Lys Gly Pro Asn Gly Phe Glu Tyr Phe Ala Pro
                405                 410                 415

Ala Asn Thr His Asn Asn Asn Ile Glu Gly Gln Ala Ile Val Tyr Gln
            420                 425                 430

Asn Lys Phe Leu Thr Leu Asn Gly Lys Lys Tyr Tyr Phe Asp Asn Asp
            435                 440                 445

Ser Lys Ala Val Thr Gly Trp Gln Thr Ile Asp Gly Lys Lys Tyr Tyr
450                 455                 460

Phe Asn Leu Asn Thr Ala Glu Ala Ala Thr Gly Trp Gln Thr Ile Asp
465                 470                 475                 480

Gly Lys Lys Tyr Tyr Phe Asn Leu Asn Thr Ala Glu Ala Ala Thr Gly
                485                 490                 495

Trp Gln Thr Ile Asp Gly Lys Lys Tyr Tyr Phe Asn Thr Asn Thr Phe
            500                 505                 510

Ile Ala Ser Thr Gly Tyr Thr Ser Ile Asn Gly Lys His Phe Tyr Phe
            515                 520                 525

Asn Thr Asp Gly Ile Met Gln Ile Gly Val Phe Lys Gly Pro Asn Gly
            530                 535                 540

Phe Glu Tyr Phe Ala Pro Ala Asn Thr Asp Ala Asn Asn Ile Glu Gly
545                 550                 555                 560

Gln Ala Ile Leu Tyr Gln Asn Lys Phe Leu Thr Leu Asn Gly Lys Lys
                565                 570                 575

Tyr Tyr Phe Gly Ser Asp Ser Lys Ala Val Thr Gly Leu Arg Thr Ile
            580                 585                 590

Asp Gly Lys Lys Tyr Tyr Phe Asn Thr Asn Thr Ala Val Ala Val Thr
            595                 600                 605
```

```
Gly Trp Gln Thr Ile Asn Gly Lys Lys Tyr Tyr Phe Asn Thr Asn Thr
    610                 615                 620

Ser Ile Ala Ser Thr Gly Tyr Thr Ile Ile Ser Gly Lys His Phe Tyr
625                 630                 635                 640

Phe Asn Thr Asp Gly Ile Met Gln Ile Gly Val Phe Lys Gly Pro Asp
                645                 650                 655

Gly Phe Glu Tyr Phe Ala Pro Ala Asn Thr Asp Ala Asn Asn Ile Glu
            660                 665                 670

Gly Gln Ala Ile Arg Tyr Gln Asn Arg Phe Leu Tyr Leu His Asp Asn
            675                 680                 685

Ile Tyr Tyr Phe Gly Asn Asn Ser Lys Ala Ala Thr Gly Trp Val Thr
    690                 695                 700

Ile Asp Gly Asn Arg Tyr Tyr Phe Glu Pro Asn Thr Ala Met Gly Ala
705                 710                 715                 720

Asn Gly Tyr Lys Thr Ile Asp Asn Lys Asn Phe Tyr Phe Arg Asn Gly
                725                 730                 735

Leu Pro Gln Ile Gly Val Phe Lys Gly Ser Asn Gly Phe Glu Tyr Phe
            740                 745                 750

Ala Pro Ala Asn Thr Asp Ala Asn Asn Ile Glu Gly Gln Ala Ile Arg
            755                 760                 765

Tyr Gln Asn Arg Phe Leu His Leu Leu Gly Lys Ile Tyr Tyr Phe Gly
    770                 775                 780

Asn Asn Ser Lys Ala Val Thr Gly Trp Gln Thr Ile Asn Gly Lys Val
785                 790                 795                 800

Tyr Tyr Phe Met Pro Asp Thr Ala Met Ala Ala
                805                 810

(2) INFORMATION FOR SEQ ID NO:8:

(i) SEQUENCE CHARACTERISTICS:
        (A) LENGTH: 91 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:8:

Ser Tyr Lys Ile Ile Asn Gly Lys His Phe Tyr Phe Asn Asn Asp Gly
1               5                   10                  15

Val Met Gln Leu Gly Val Phe Lys Gly Pro Asp Gly Phe Glu Tyr Phe
            20                  25                  30

Ala Pro Ala Asn Thr Gln Asn Asn Asn Ile Glu Gly Gln Ala Ile Val
            35                  40                  45

Tyr Gln Ser Lys Phe Leu Thr Leu Asn Gly Lys Lys Tyr Tyr Phe Asp
    50                  55                  60

Asn Asn Ser Lys Ala Val Thr Gly Trp Arg Ile Ile Asn Asn Glu Lys
65                  70                  75                  80

Tyr Tyr Phe Asn Pro Asn Asn Ala Ile Ala Ala
                85                  90

(2) INFORMATION FOR SEQ ID NO:9:

(i) SEQUENCE CHARACTERISTICS:
        (A) LENGTH: 7101 base pairs
        (B) TYPE: nucleic acid
        (C) STRANDEDNESS: single
        (D) TOPOLOGY: linear
```

(ii) MOLECULE TYPE: DNA (genomic)

(ix) FEATURE:
    (A) NAME/KEY: CDS
    (B) LOCATION: 1..7098

(xi) SEQUENCE DESCRIPTION: SEQ ID NO:9:

```
ATG AGT TTA GTT AAT AGA AAA CAG TTA GAA AAA ATG GCA AAT GTA AGA        48
Met Ser Leu Val Asn Arg Lys Gln Leu Glu Lys Met Ala Asn Val Arg
 1               5                  10                  15

TTT CGT ACT CAA GAA GAT GAA TAT GTT GCA ATA TTG GAT GCT TTA GAA        96
Phe Arg Thr Gln Glu Asp Glu Tyr Val Ala Ile Leu Asp Ala Leu Glu
                 20                  25                  30

GAA TAT CAT AAT ATG TCA GAG AAT ACT GTA GTC GAA AAA TAT TTA AAA       144
Glu Tyr His Asn Met Ser Glu Asn Thr Val Val Glu Lys Tyr Leu Lys
             35                  40                  45

TTA AAA GAT ATA AAT AGT TTA ACA GAT ATT TAT ATA GAT ACA TAT AAA       192
Leu Lys Asp Ile Asn Ser Leu Thr Asp Ile Tyr Ile Asp Thr Tyr Lys
         50                  55                  60

AAA TCT GGT AGA AAT AAA GCC TTA AAA AAA TTT AAG GAA TAT CTA GTT       240
Lys Ser Gly Arg Asn Lys Ala Leu Lys Lys Phe Lys Glu Tyr Leu Val
 65                  70                  75                  80

ACA GAA GTA TTA GAG CTA AAG AAT AAT AAT TTA ACT CCA GTT GAG AAA       288
Thr Glu Val Leu Glu Leu Lys Asn Asn Asn Leu Thr Pro Val Glu Lys
                 85                  90                  95

AAT TTA CAT TTT GTT TGG ATT GGA GGT CAA ATA AAT GAC ACT GCT ATT       336
Asn Leu His Phe Val Trp Ile Gly Gly Gln Ile Asn Asp Thr Ala Ile
                100                 105                 110

AAT TAT ATA AAT CAA TGG AAA GAT GTA AAT AGT GAT TAT AAT GTT AAT       384
Asn Tyr Ile Asn Gln Trp Lys Asp Val Asn Ser Asp Tyr Asn Val Asn
            115                 120                 125

GTT TTT TAT GAT AGT AAT GCA TTT TTG ATA AAC ACA TTG AAA AAA ACT       432
Val Phe Tyr Asp Ser Asn Ala Phe Leu Ile Asn Thr Leu Lys Lys Thr
130                 135                 140

GTA GTA GAA TCA GCA ATA AAT GAT ACA CTT GAA TCA TTT AGA GAA AAC       480
Val Val Glu Ser Ala Ile Asn Asp Thr Leu Glu Ser Phe Arg Glu Asn
145                 150                 155                 160

TTA AAT GAC CCT AGA TTT GAC TAT AAT AAA TTC TTC AGA AAA CGT ATG       528
Leu Asn Asp Pro Arg Phe Asp Tyr Asn Lys Phe Phe Arg Lys Arg Met
                165                 170                 175

GAA ATA ATT TAT GAT AAA CAG AAA AAT TTC ATA AAC TAC TAT AAA GCT       576
Glu Ile Ile Tyr Asp Lys Gln Lys Asn Phe Ile Asn Tyr Tyr Lys Ala
                180                 185                 190

CAA AGA GAA GAA AAT CCT GAA CTT ATA ATT GAT GAT ATT GTA AAG ACA       624
Gln Arg Glu Glu Asn Pro Glu Leu Ile Ile Asp Asp Ile Val Lys Thr
            195                 200                 205

TAT CTT TCA AAT GAG TAT TCA AAG GAG ATA GAT GAA CTT AAT ACC TAT       672
Tyr Leu Ser Asn Glu Tyr Ser Lys Glu Ile Asp Glu Leu Asn Thr Tyr
        210                 215                 220

ATT GAA GAA TCC TTA AAT AAA ATT ACA CAG AAT AGT GGA AAT GAT GTT       720
Ile Glu Glu Ser Leu Asn Lys Ile Thr Gln Asn Ser Gly Asn Asp Val
225                 230                 235                 240

AGA AAC TTT GAA GAA TTT AAA AAT GGA GAG TCA TTC AAC TTA TAT GAA       768
Arg Asn Phe Glu Glu Phe Lys Asn Gly Glu Ser Phe Asn Leu Tyr Glu
                245                 250                 255

CAA GAG TTG GTA GAA AGG TGG AAT TTA GCT GCT GCT TCT GAC ATA TTA       816
Gln Glu Leu Val Glu Arg Trp Asn Leu Ala Ala Ala Ser Asp Ile Leu
                260                 265                 270

AGA ATA TCT GCA TTA AAA GAA ATT GGT GGT ATG TAT TTA GAT GTT GAT       864
Arg Ile Ser Ala Leu Lys Glu Ile Gly Gly Met Tyr Leu Asp Val Asp
            275                 280                 285
```

```
ATG TTA CCA GGA ATA CAA CCA GAC TTA TTT GAG TCT ATA GAG AAA CCT        912
Met Leu Pro Gly Ile Gln Pro Asp Leu Phe Glu Ser Ile Glu Lys Pro
        290                 295                 300

AGT TCA GTA ACA GTG GAT TTT TGG GAA ATG ACA AAG TTA GAA GCT ATA        960
Ser Ser Val Thr Val Asp Phe Trp Glu Met Thr Lys Leu Glu Ala Ile
305                 310                 315                 320

ATG AAA TAC AAA GAA TAT ATA CCA GAA TAT ACC TCA GAA CAT TTT GAC       1008
Met Lys Tyr Lys Glu Tyr Ile Pro Glu Tyr Thr Ser Glu His Phe Asp
                325                 330                 335

ATG TTA GAC GAA GAA GTT CAA AGT AGT TTT GAA TCT GTT CTA GCT TCT       1056
Met Leu Asp Glu Glu Val Gln Ser Ser Phe Glu Ser Val Leu Ala Ser
        340                 345                 350

AAG TCA GAT AAA TCA GAA ATA TTC TCA TCA CTT GGT GAT ATG GAG GCA       1104
Lys Ser Asp Lys Ser Glu Ile Phe Ser Ser Leu Gly Asp Met Glu Ala
355                 360                 365

TCA CCA CTA GAA GTT AAA ATT GCA TTT AAT AGT AAG GGT ATT ATA AAT       1152
Ser Pro Leu Glu Val Lys Ile Ala Phe Asn Ser Lys Gly Ile Ile Asn
        370                 375                 380

CAA GGG CTA ATT TCT GTG AAA GAC TCA TAT TGT AGC AAT TTA ATA GTA       1200
Gln Gly Leu Ile Ser Val Lys Asp Ser Tyr Cys Ser Asn Leu Ile Val
385                 390                 395                 400

AAA CAA ATC GAG AAT AGA TAT AAA ATA TTG AAT AAT AGT TTA AAT CCA       1248
Lys Gln Ile Glu Asn Arg Tyr Lys Ile Leu Asn Asn Ser Leu Asn Pro
                405                 410                 415

GCT ATT AGC GAG GAT AAT GAT TTT AAT ACT ACA ACG AAT ACC TTT ATT       1296
Ala Ile Ser Glu Asp Asn Asp Phe Asn Thr Thr Thr Asn Thr Phe Ile
        420                 425                 430

GAT AGT ATA ATG GCT GAA GCT AAT GCA GAT AAT GGT AGA TTT ATG ATG       1344
Asp Ser Ile Met Ala Glu Ala Asn Ala Asp Asn Gly Arg Phe Met Met
435                 440                 445

GAA CTA GGA AAG TAT TTA AGA GTT GGT TTC TTC CCA GAT GTT AAA ACT       1392
Glu Leu Gly Lys Tyr Leu Arg Val Gly Phe Phe Pro Asp Val Lys Thr
        450                 455                 460

ACT ATT AAC TTA AGT GGC CCT GAA GCA TAT GCG GCA GCT TAT CAA GAT       1440
Thr Ile Asn Leu Ser Gly Pro Glu Ala Tyr Ala Ala Ala Tyr Gln Asp
465                 470                 475                 480

TTA TTA ATG TTT AAA GAA GGC AGT ATG AAT ATC CAT TTG ATA GAA GCT       1488
Leu Leu Met Phe Lys Glu Gly Ser Met Asn Ile His Leu Ile Glu Ala
                485                 490                 495

GAT TTA AGA AAC TTT GAA ATC TCT AAA ACT AAT ATT TCT CAA TCA ACT       1536
Asp Leu Arg Asn Phe Glu Ile Ser Lys Thr Asn Ile Ser Gln Ser Thr
        500                 505                 510

GAA CAA GAA ATG GCT AGC TTA TGG TCA TTT GAC GAT GCA AGA GCT AAA       1584
Glu Gln Glu Met Ala Ser Leu Trp Ser Phe Asp Asp Ala Arg Ala Lys
515                 520                 525

GCT CAA TTT GAA GAA TAT AAA AGG AAT TAT TTT GAA GGT TCT CTT GGT       1632
Ala Gln Phe Glu Glu Tyr Lys Arg Asn Tyr Phe Glu Gly Ser Leu Gly
        530                 535                 540

GAA GAT GAT AAT CTT GAT TTT TCT CAA AAT ATA GTA GTT GAC AAG GAG       1680
Glu Asp Asp Asn Leu Asp Phe Ser Gln Asn Ile Val Val Asp Lys Glu
545                 550                 555                 560

TAT CTT TTA GAA AAA ATA TCT TCA TTA GCA AGA AGT TCA GAG AGA GGA       1728
Tyr Leu Leu Glu Lys Ile Ser Ser Leu Ala Arg Ser Ser Glu Arg Gly
                565                 570                 575

TAT ATA CAC TAT ATT GTT CAG TTA CAA GGA GAT AAA ATT AGT TAT GAA       1776
Tyr Ile His Tyr Ile Val Gln Leu Gln Gly Asp Lys Ile Ser Tyr Glu
        580                 585                 590

GCA GCA TGT AAC TTA TTT GCA AAG ACT CCT TAT GAT AGT GTA CTG TTT       1824
Ala Ala Cys Asn Leu Phe Ala Lys Thr Pro Tyr Asp Ser Val Leu Phe
```

```
              595                 600                 605
CAG AAA AAT ATA GAA GAT TCA GAA ATT GCA TAT TAT TAT AAT CCT GGA    1872
Gln Lys Asn Ile Glu Asp Ser Glu Ile Ala Tyr Tyr Tyr Asn Pro Gly
        610                 615                 620

GAT GGT GAA ATA CAA GAA ATA GAC AAG TAT AAA ATT CCA AGT ATA ATT    1920
Asp Gly Glu Ile Gln Glu Ile Asp Lys Tyr Lys Ile Pro Ser Ile Ile
625                 630                 635                 640

TCT GAT AGA CCT AAG ATT AAA TTA ACA TTT ATT GGT CAT GGT AAA GAT    1968
Ser Asp Arg Pro Lys Ile Lys Leu Thr Phe Ile Gly His Gly Lys Asp
                645                 650                 655

GAA TTT AAT ACT GAT ATA TTT GCA GGT TTT GAT GTA GAT TCA TTA TCC    2016
Glu Phe Asn Thr Asp Ile Phe Ala Gly Phe Asp Val Asp Ser Leu Ser
            660                 665                 670

ACA GAA ATA GAA GCA GCA ATA GAT TTA GCT AAA GAG GAT ATT TCT CCT    2064
Thr Glu Ile Glu Ala Ala Ile Asp Leu Ala Lys Glu Asp Ile Ser Pro
        675                 680                 685

AAG TCA ATA GAA ATA AAT TTA TTA GGA TGT AAT ATG TTT AGC TAC TCT    2112
Lys Ser Ile Glu Ile Asn Leu Leu Gly Cys Asn Met Phe Ser Tyr Ser
        690                 695                 700

ATC AAC GTA GAG GAG ACT TAT CCT GGA AAA TTA TTA CTT AAA GTT AAA    2160
Ile Asn Val Glu Glu Thr Tyr Pro Gly Lys Leu Leu Leu Lys Val Lys
705                 710                 715                 720

GAT AAA ATA TCA GAA TTA ATG CCA TCT ATA AGT CAA GAC TCT ATT ATA    2208
Asp Lys Ile Ser Glu Leu Met Pro Ser Ile Ser Gln Asp Ser Ile Ile
                725                 730                 735

GTA AGT GCA AAT CAA TAT GAA GTT AGA ATA AAT AGT GAA GGA AGA AGA    2256
Val Ser Ala Asn Gln Tyr Glu Val Arg Ile Asn Ser Glu Gly Arg Arg
            740                 745                 750

GAA TTA TTG GAT CAT TCT GGT GAA TGG ATA AAT AAA GAA GAA AGT ATT    2304
Glu Leu Leu Asp His Ser Gly Glu Trp Ile Asn Lys Glu Glu Ser Ile
        755                 760                 765

ATA AAG GAT ATT TCA TCA AAA GAA TAT ATA TCA TTT AAT CCT AAA GAA    2352
Ile Lys Asp Ile Ser Ser Lys Glu Tyr Ile Ser Phe Asn Pro Lys Glu
        770                 775                 780

AAT AAA ATT ACA GTA AAA TCT AAA AAT TTA CCT GAG CTA TCT ACA TTA    2400
Asn Lys Ile Thr Val Lys Ser Lys Asn Leu Pro Glu Leu Ser Thr Leu
785                 790                 795                 800

TTA CAA GAA ATT AGA AAT AAT TCT AAT TCA AGT GAT ATT GAA CTA GAA    2448
Leu Gln Glu Ile Arg Asn Asn Ser Asn Ser Ser Asp Ile Glu Leu Glu
                805                 810                 815

GAA AAA GTA ATG TTA ACA GAA TGT GAG ATA AAT GTT ATT TCA AAT ATA    2496
Glu Lys Val Met Leu Thr Glu Cys Glu Ile Asn Val Ile Ser Asn Ile
            820                 825                 830

GAT ACG CAA ATT GTT GAG GAA AGG ATT GAA GAA GCT AAG AAT TTA ACT    2544
Asp Thr Gln Ile Val Glu Glu Arg Ile Glu Glu Ala Lys Asn Leu Thr
        835                 840                 845

TCT GAC TCT ATT AAT TAT ATA AAA GAT GAA TTT AAA CTA ATA GAA TCT    2592
Ser Asp Ser Ile Asn Tyr Ile Lys Asp Glu Phe Lys Leu Ile Glu Ser
        850                 855                 860

ATT TCT GAT GCA CTA TGT GAC TTA AAA CAA CAG AAT GAA TTA GAA GAT    2640
Ile Ser Asp Ala Leu Cys Asp Leu Lys Gln Gln Asn Glu Leu Glu Asp
865                 870                 875                 880

TCT CAT TTT ATA TCT TTT GAG GAC ATA TCA GAG ACT GAT GAG GGA TTT    2688
Ser His Phe Ile Ser Phe Glu Asp Ile Ser Glu Thr Asp Glu Gly Phe
                885                 890                 895

AGT ATA AGA TTT ATT AAT AAA GAA ACT GGA GAA TCT ATA TTT GTA GAA    2736
Ser Ile Arg Phe Ile Asn Lys Glu Thr Gly Glu Ser Ile Phe Val Glu
            900                 905                 910

ACT GAA AAA ACA ATA TTC TCT GAA TAT GCT AAT CAT ATA ACT GAA GAG    2784
```

-continued

```
Thr Glu Lys Thr Ile Phe Ser Glu Tyr Ala Asn His Ile Thr Glu Glu
        915                 920                 925
ATT TCT AAG ATA AAA GGT ACT ATA TTT GAT ACT GTA AAT GGT AAG TTA        2832
Ile Ser Lys Ile Lys Gly Thr Ile Phe Asp Thr Val Asn Gly Lys Leu
930                 935                 940
GTA AAA AAA GTA AAT TTA GAT ACT ACA CAC GAA GTA AAT ACT TTA AAT        2880
Val Lys Lys Val Asn Leu Asp Thr Thr His Glu Val Asn Thr Leu Asn
945                 950                 955                 960
GCT GCA TTT TTT ATA CAA TCA TTA ATA GAA TAT AAT AGT TCT AAA GAA        2928
Ala Ala Phe Phe Ile Gln Ser Leu Ile Glu Tyr Asn Ser Ser Lys Glu
                965                 970                 975
TCT CTT AGT AAT TTA AGT GTA GCA ATG AAA GTC CAA GTT TAC GCT CAA        2976
Ser Leu Ser Asn Leu Ser Val Ala Met Lys Val Gln Val Tyr Ala Gln
            980                 985                 990
TTA TTT AGT ACT GGT TTA AAT ACT ATT ACA GAT GCA GCC AAA GTT GTT        3024
Leu Phe Ser Thr Gly Leu Asn Thr Ile Thr Asp Ala Ala Lys Val Val
        995                 1000                1005
GAA TTA GTA TCA ACT GCA TTA GAT GAA ACT ATA GAC TTA CTT CCT ACA        3072
Glu Leu Val Ser Thr Ala Leu Asp Glu Thr Ile Asp Leu Leu Pro Thr
    1010                1015                1020
TTA TCT GAA GGA TTA CCT ATA ATT GCA ACT ATT ATA GAT GGT GTA AGT        3120
Leu Ser Glu Gly Leu Pro Ile Ile Ala Thr Ile Ile Asp Gly Val Ser
1025                1030                1035                1040
TTA GGT GCA GCA ATC AAA GAG CTA AGT GAA ACG AGT GAC CCA TTA TTA        3168
Leu Gly Ala Ala Ile Lys Glu Leu Ser Glu Thr Ser Asp Pro Leu Leu
                1045                1050                1055
AGA CAA GAA ATA GAA GCT AAG ATA GGT ATA ATG GCA GTA AAT TTA ACA        3216
Arg Gln Glu Ile Glu Ala Lys Ile Gly Ile Met Ala Val Asn Leu Thr
            1060                1065                1070
ACA GCT ACA ACT GCA ATC ATT ACT TCA TCT TTG GGG ATA GCT AGT GGA        3264
Thr Ala Thr Thr Ala Ile Ile Thr Ser Ser Leu Gly Ile Ala Ser Gly
        1075                1080                1085
TTT AGT ATA CTT TTA GTT CCT TTA GCA GGA ATT TCA GCA GGT ATA CCA        3312
Phe Ser Ile Leu Leu Val Pro Leu Ala Gly Ile Ser Ala Gly Ile Pro
    1090                1095                1100
AGC TTA GTA AAC AAT GAA CTT GTA CTT CGA GAT AAG GCA ACA AAG GTT        3360
Ser Leu Val Asn Asn Glu Leu Val Leu Arg Asp Lys Ala Thr Lys Val
1105                1110                1115                1120
GTA GAT TAT TTT AAA CAT GTT TCA TTA GTT GAA ACT GAA GGA GTA TTT        3408
Val Asp Tyr Phe Lys His Val Ser Leu Val Glu Thr Glu Gly Val Phe
                1125                1130                1135
ACT TTA TTA GAT GAT AAA ATA ATG ATG CCA CAA GAT GAT TTA GTG ATA        3456
Thr Leu Leu Asp Asp Lys Ile Met Met Pro Gln Asp Asp Leu Val Ile
            1140                1145                1150
TCA GAA ATA GAT TTT AAT AAT AAT TCA ATA GTT TTA GGT AAA TGT GAA        3504
Ser Glu Ile Asp Phe Asn Asn Asn Ser Ile Val Leu Gly Lys Cys Glu
        1155                1160                1165
ATC TGG AGA ATG GAA GGT GGT TCA GGT CAT ACT GTA ACT GAT GAT ATA        3552
Ile Trp Arg Met Glu Gly Gly Ser Gly His Thr Val Thr Asp Asp Ile
    1170                1175                1180
GAT CAC TTC TTT TCA GCA CCA TCA ATA ACA TAT AGA GAG CCA CAC TTA        3600
Asp His Phe Phe Ser Ala Pro Ser Ile Thr Tyr Arg Glu Pro His Leu
1185                1190                1195                1200
TCT ATA TAT GAC GTA TTG GAA GTA CAA AAA GAA GAA CTT GAT TTG TCA        3648
Ser Ile Tyr Asp Val Leu Glu Val Gln Lys Glu Glu Leu Asp Leu Ser
                1205                1210                1215
AAA GAT TTA ATG GTA TTA CCT AAT GCT CCA AAT AGA GTA TTT GCT TGG        3696
Lys Asp Leu Met Val Leu Pro Asn Ala Pro Asn Arg Val Phe Ala Trp
            1220                1225                1230
```

```
GAA ACA GGA TGG ACA CCA GGT TTA AGA AGC TTA GAA AAT GAT GGC ACA      3744
Glu Thr Gly Trp Thr Pro Gly Leu Arg Ser Leu Glu Asn Asp Gly Thr
        1235                1240                1245

AAA CTG TTA GAC CGT ATA AGA GAT AAC TAT GAA GGT GAG TTT TAT TGG      3792
Lys Leu Leu Asp Arg Ile Arg Asp Asn Tyr Glu Gly Glu Phe Tyr Trp
1250                1255                1260

AGA TAT TTT GCT TTT ATA GCT GAT GCT TTA ATA ACA ACA TTA AAA CCA      3840
Arg Tyr Phe Ala Phe Ile Ala Asp Ala Leu Ile Thr Thr Leu Lys Pro
1265                1270                1275                1280

AGA TAT GAA GAT ACT AAT ATA AGA ATA AAT TTA GAT AGT AAT ACT AGA      3888
Arg Tyr Glu Asp Thr Asn Ile Arg Ile Asn Leu Asp Ser Asn Thr Arg
                1285                1290                1295

AGT TTT ATA GTT CCA ATA ATA ACT ACA GAA TAT ATA AGA GAA AAA TTA      3936
Ser Phe Ile Val Pro Ile Ile Thr Thr Glu Tyr Ile Arg Glu Lys Leu
            1300                1305                1310

TCA TAT TCT TTC TAT GGT TCA GGA GGA ACT TAT GCA TTG TCT CTT TCT      3984
Ser Tyr Ser Phe Tyr Gly Ser Gly Gly Thr Tyr Ala Leu Ser Leu Ser
                1315                1320                1325

CAA TAT AAT ATG GGT ATA AAT ATA GAA TTA AGT GAA AGT GAT GTT TGG      4032
Gln Tyr Asn Met Gly Ile Asn Ile Glu Leu Ser Glu Ser Asp Val Trp
            1330                1335                1340

ATT ATA GAT GTT GAT AAT GTT GTG AGA GAT GTA ACT ATA GAA TCT GAT      4080
Ile Ile Asp Val Asp Asn Val Val Arg Asp Val Thr Ile Glu Ser Asp
1345                1350                1355                1360

AAA ATT AAA AAA GGT GAT TTA ATA GAA GGT ATT TTA TCT ACA CTA AGT      4128
Lys Ile Lys Lys Gly Asp Leu Ile Glu Gly Ile Leu Ser Thr Leu Ser
                1365                1370                1375

ATT GAA GAG AAT AAA ATT ATC TTA AAT AGC CAT GAG ATT AAT TTT TCT      4176
Ile Glu Glu Asn Lys Ile Ile Leu Asn Ser His Glu Ile Asn Phe Ser
            1380                1385                1390

GGT GAG GTA AAT GGA AGT AAT GGA TTT GTT TCT TTA ACA TTT TCA ATT      4224
Gly Glu Val Asn Gly Ser Asn Gly Phe Val Ser Leu Thr Phe Ser Ile
            1395                1400                1405

TTA GAA GGA ATA AAT GCA ATT ATA GAA GTT GAT TTA TTA TCT AAA TCA      4272
Leu Glu Gly Ile Asn Ala Ile Ile Glu Val Asp Leu Leu Ser Lys Ser
        1410                1415                1420

TAT AAA TTA CTT ATT TCT GGC GAA TTA AAA ATA TTG ATG TTA AAT TCA      4320
Tyr Lys Leu Leu Ile Ser Gly Glu Leu Lys Ile Leu Met Leu Asn Ser
1425                1430                1435                1440

AAT CAT ATT CAA CAG AAA ATA GAT TAT ATA GGA TTC AAT AGC GAA TTA      4368
Asn His Ile Gln Gln Lys Ile Asp Tyr Ile Gly Phe Asn Ser Glu Leu
                1445                1450                1455

CAG AAA AAT ATA CCA TAT AGC TTT GTA GAT AGT GAA GGA AAA GAG AAT      4416
Gln Lys Asn Ile Pro Tyr Ser Phe Val Asp Ser Glu Gly Lys Glu Asn
            1460                1465                1470

GGT TTT ATT AAT GGT TCA ACA AAA GAA GGT TTA TTT GTA TCT GAA TTA      4464
Gly Phe Ile Asn Gly Ser Thr Lys Glu Gly Leu Phe Val Ser Glu Leu
        1475                1480                1485

CCT GAT GTA GTT CTT ATA AGT AAG GTT TAT ATG GAT GAT AGT AAG CCT      4512
Pro Asp Val Val Leu Ile Ser Lys Val Tyr Met Asp Asp Ser Lys Pro
        1490                1495                1500

TCA TTT GGA TAT TAT AGT AAT AAT TTG AAA GAT GTC AAA GTT ATA ACT      4560
Ser Phe Gly Tyr Tyr Ser Asn Asn Leu Lys Asp Val Lys Val Ile Thr
1505                1510                1515                1520

AAA GAT AAT GTT AAT ATA TTA ACA GGT TAT TAT CTT AAG GAT GAT ATA      4608
Lys Asp Asn Val Asn Ile Leu Thr Gly Tyr Tyr Leu Lys Asp Asp Ile
                1525                1530                1535

AAA ATC TCT CTT TCT TTG ACT CTA CAA GAT GAA AAA ACT ATA AAG TTA      4656
Lys Ile Ser Leu Ser Leu Thr Leu Gln Asp Glu Lys Thr Ile Lys Leu
            1540                1545                1550
```

```
AAT AGT GTG CAT TTA GAT GAA AGT GGA GTA GCT GAG ATT TTG AAG TTC    4704
Asn Ser Val His Leu Asp Glu Ser Gly Val Ala Glu Ile Leu Lys Phe
            1555                1560                1565

ATG AAT AGA AAA GGT AAT ACA AAT ACT TCA GAT TCT TTA ATG AGC TTT    4752
Met Asn Arg Lys Gly Asn Thr Asn Thr Ser Asp Ser Leu Met Ser Phe
1570                1575                1580

TTA GAA AGT ATG AAT ATA AAA AGT ATT TTC GTT AAT TTC TTA CAA TCT    4800
Leu Glu Ser Met Asn Ile Lys Ser Ile Phe Val Asn Phe Leu Gln Ser
1585                1590                1595                1600

AAT ATT AAG TTT ATA TTA GAT GCT AAT TTT ATA ATA AGT GGT ACT ACT    4848
Asn Ile Lys Phe Ile Leu Asp Ala Asn Phe Ile Ile Ser Gly Thr Thr
                1605                1610                1615

TCT ATT GGC CAA TTT GAG TTT ATT TGT GAT GAA AAT GAT AAT ATA CAA    4896
Ser Ile Gly Gln Phe Glu Phe Ile Cys Asp Glu Asn Asp Asn Ile Gln
            1620                1625                1630

CCA TAT TTC ATT AAG TTT AAT ACA CTA GAA ACT AAT TAT ACT TTA TAT    4944
Pro Tyr Phe Ile Lys Phe Asn Thr Leu Glu Thr Asn Tyr Thr Leu Tyr
            1635                1640                1645

GTA GGA AAT AGA CAA AAT ATG ATA GTG GAA CCA AAT TAT GAT TTA GAT    4992
Val Gly Asn Arg Gln Asn Met Ile Val Glu Pro Asn Tyr Asp Leu Asp
        1650                1655                1660

GAT TCT GGA GAT ATA TCT TCA ACT GTT ATC AAT TTC TCT CAA AAG TAT    5040
Asp Ser Gly Asp Ile Ser Ser Thr Val Ile Asn Phe Ser Gln Lys Tyr
1665                1670                1675                1680

CTT TAT GGA ATA GAC AGT TGT GTT AAT AAA GTT GTA ATT TCA CCA AAT    5088
Leu Tyr Gly Ile Asp Ser Cys Val Asn Lys Val Val Ile Ser Pro Asn
                1685                1690                1695

ATT TAT ACA GAT GAA ATA AAT ATA ACG CCT GTA TAT GAA ACA AAT AAT    5136
Ile Tyr Thr Asp Glu Ile Asn Ile Thr Pro Val Tyr Glu Thr Asn Asn
            1700                1705                1710

ACT TAT CCA GAA GTT ATT GTA TTA GAT GCA AAT TAT ATA AAT GAA AAA    5184
Thr Tyr Pro Glu Val Ile Val Leu Asp Ala Asn Tyr Ile Asn Glu Lys
            1715                1720                1725

ATA AAT GTT AAT ATC AAT GAT CTA TCT ATA CGA TAT GTA TGG AGT AAT    5232
Ile Asn Val Asn Ile Asn Asp Leu Ser Ile Arg Tyr Val Trp Ser Asn
        1730                1735                1740

GAT GGT AAT GAT TTT ATT CTT ATG TCA ACT AGT GAA GAA AAT AAG GTG    5280
Asp Gly Asn Asp Phe Ile Leu Met Ser Thr Ser Glu Glu Asn Lys Val
1745                1750                1755                1760

TCA CAA GTT AAA ATA AGA TTC GTT AAT GTT TTT AAA GAT AAG ACT TTG    5328
Ser Gln Val Lys Ile Arg Phe Val Asn Val Phe Lys Asp Lys Thr Leu
                1765                1770                1775

GCA AAT AAG CTA TCT TTT AAC TTT AGT GAT AAA CAA GAT GTA CCT GTA    5376
Ala Asn Lys Leu Ser Phe Asn Phe Ser Asp Lys Gln Asp Val Pro Val
            1780                1785                1790

AGT GAA ATA ATC TTA TCA TTT ACA CCT TCA TAT TAT GAG GAT GGA TTG    5424
Ser Glu Ile Ile Leu Ser Phe Thr Pro Ser Tyr Tyr Glu Asp Gly Leu
            1795                1800                1805

ATT GGC TAT GAT TTG GGT CTA GTT TCT TTA TAT AAT GAG AAA TTT TAT    5472
Ile Gly Tyr Asp Leu Gly Leu Val Ser Leu Tyr Asn Glu Lys Phe Tyr
        1810                1815                1820

ATT AAT AAC TTT GGA ATG ATG GTA TCT GGA TTA ATA TAT ATT AAT GAT    5520
Ile Asn Asn Phe Gly Met Met Val Ser Gly Leu Ile Tyr Ile Asn Asp
1825                1830                1835                1840

TCA TTA TAT TAT TTT AAA CCA CCA GTA AAT AAT TTG ATA ACT GGA TTT    5568
Ser Leu Tyr Tyr Phe Lys Pro Pro Val Asn Asn Leu Ile Thr Gly Phe
                1845                1850                1855

GTG ACT GTA GGC GAT GAT AAA TAC TAC TTT AAT CCA ATT AAT GGT GGA    5616
Val Thr Val Gly Asp Asp Lys Tyr Tyr Phe Asn Pro Ile Asn Gly Gly
```

```
                 -continued
         1860           1865            1870
GCT GCT TCA ATT GGA GAG ACA ATA ATT GAT GAC AAA AAT TAT TAT TTC      5664
Ala Ala Ser Ile Gly Glu Thr Ile Ile Asp Asp Lys Asn Tyr Tyr Phe
        1875            1880            1885

AAC CAA AGT GGA GTG TTA CAA ACA GGT GTA TTT AGT ACA GAA GAT GGA      5712
Asn Gln Ser Gly Val Leu Gln Thr Gly Val Phe Ser Thr Glu Asp Gly
    1890            1895            1900

TTT AAA TAT TTT GCC CCA GCT AAT ACA CTT GAT GAA AAC CTA GAA GGA      5760
Phe Lys Tyr Phe Ala Pro Ala Asn Thr Leu Asp Glu Asn Leu Glu Gly
1905            1910            1915            1920

GAA GCA ATT GAT TTT ACT GGA AAA TTA ATT ATT GAC GAA AAT ATT TAT      5808
Glu Ala Ile Asp Phe Thr Gly Lys Leu Ile Ile Asp Glu Asn Ile Tyr
            1925            1930            1935

TAT TTT GAT GAT AAT TAT AGA GGA GCT GTA GAA TGG AAA GAA TTA GAT      5856
Tyr Phe Asp Asp Asn Tyr Arg Gly Ala Val Glu Trp Lys Glu Leu Asp
        1940            1945            1950

GGT GAA ATG CAC TAT TTT AGC CCA GAA ACA GGT AAA GCT TTT AAA GGT      5904
Gly Glu Met His Tyr Phe Ser Pro Glu Thr Gly Lys Ala Phe Lys Gly
    1955            1960            1965

CTA AAT CAA ATA GGT GAT TAT AAA TAC TAT TTC AAT TCT GAT GGA GTT      5952
Leu Asn Gln Ile Gly Asp Tyr Lys Tyr Tyr Phe Asn Ser Asp Gly Val
    1970            1975            1980

ATG CAA AAA GGA TTT GTT AGT ATA AAT GAT AAT AAA CAC TAT TTT GAT      6000
Met Gln Lys Gly Phe Val Ser Ile Asn Asp Asn Lys His Tyr Phe Asp
1985            1990            1995            2000

GAT TCT GGT GTT ATG AAA GTA GGT TAC ACT GAA ATA GAT GGC AAG CAT      6048
Asp Ser Gly Val Met Lys Val Gly Tyr Thr Glu Ile Asp Gly Lys His
            2005            2010            2015

TTC TAC TTT GCT GAA AAC GGA GAA ATG CAA ATA GGA GTA TTT AAT ACA      6096
Phe Tyr Phe Ala Glu Asn Gly Glu Met Gln Ile Gly Val Phe Asn Thr
        2020            2025            2030

GAA GAT GGA TTT AAA TAT TTT GCT CAT CAT AAT GAA GAT TTA GGA AAT      6144
Glu Asp Gly Phe Lys Tyr Phe Ala His His Asn Glu Asp Leu Gly Asn
    2035            2040            2045

GAA GAA GGT GAA GAA ATC TCA TAT TCT GGT ATA TTA AAT TTC AAT AAT      6192
Glu Glu Gly Glu Glu Ile Ser Tyr Ser Gly Ile Leu Asn Phe Asn Asn
    2050            2055            2060

AAA ATT TAC TAT TTT GAT GAT TCA TTT ACA GCT GTA GTT GGA TGG AAA      6240
Lys Ile Tyr Tyr Phe Asp Asp Ser Phe Thr Ala Val Val Gly Trp Lys
2065            2070            2075            2080

GAT TTA GAG GAT GGT TCA AAG TAT TAT TTT GAT GAA GAT ACA GCA GAA      6288
Asp Leu Glu Asp Gly Ser Lys Tyr Tyr Phe Asp Glu Asp Thr Ala Glu
            2085            2090            2095

GCA TAT ATA GGT TTG TCA TTA ATA AAT GAT GGT CAA TAT TAT TTT AAT      6336
Ala Tyr Ile Gly Leu Ser Leu Ile Asn Asp Gly Gln Tyr Tyr Phe Asn
        2100            2105            2110

GAT GAT GGA ATT ATG CAA GTT GGA TTT GTC ACT ATA AAT GAT AAA GTC      6384
Asp Asp Gly Ile Met Gln Val Gly Phe Val Thr Ile Asn Asp Lys Val
            2115            2120            2125

TTC TAC TTC TCT GAC TCT GGA ATT ATA GAA TCT GGA GTA CAA AAC ATA      6432
Phe Tyr Phe Ser Asp Ser Gly Ile Ile Glu Ser Gly Val Gln Asn Ile
        2130            2135            2140

GAT GAC AAT TAT TTC TAT ATA GAT GAT AAT GGT ATA GTT CAA ATT GGT      6480
Asp Asp Asn Tyr Phe Tyr Ile Asp Asp Asn Gly Ile Val Gln Ile Gly
2145            2150            2155            2160

GTA TTT GAT ACT TCA GAT GGA TAT AAA TAT TTT GCA CCT GCT AAT ACT      6528
Val Phe Asp Thr Ser Asp Gly Tyr Lys Tyr Phe Ala Pro Ala Asn Thr
            2165            2170            2175

GTA AAT GAT AAT ATT TAC GGA CAA GCA GTT GAA TAT AGT GGT TTA GTT      6576
```

```
Val Asn Asp Asn Ile Tyr Gly Gln Ala Val Glu Tyr Ser Gly Leu Val
            2180                2185                2190

AGA GTT GGG GAA GAT GTA TAT TAT TTT GGA GAA ACA TAT ACA ATT GAG    6624
Arg Val Gly Glu Asp Val Tyr Tyr Phe Gly Glu Thr Tyr Thr Ile Glu
        2195                2200                2205

ACT GGA TGG ATA TAT GAT ATG GAA AAT GAA AGT GAT AAA TAT TAT TTC    6672
Thr Gly Trp Ile Tyr Asp Met Glu Asn Glu Ser Asp Lys Tyr Tyr Phe
        2210                2215                2220

AAT CCA GAA ACT AAA AAA GCA TGC AAA GGT ATT AAT TTA ATT GAT GAT    6720
Asn Pro Glu Thr Lys Lys Ala Cys Lys Gly Ile Asn Leu Ile Asp Asp
2225            2230                2235                2240

ATA AAA TAT TAT TTT GAT GAG AAG GGC ATA ATG AGA ACG GGT CTT ATA    6768
Ile Lys Tyr Tyr Phe Asp Glu Lys Gly Ile Met Arg Thr Gly Leu Ile
            2245                2250                2255

TCA TTT GAA AAT AAT AAT TAT TAC TTT AAT GAG AAT GGT GAA ATG CAA    6816
Ser Phe Glu Asn Asn Asn Tyr Tyr Phe Asn Glu Asn Gly Glu Met Gln
            2260                2265                2270

TTT GGT TAT ATA AAT ATA GAA GAT AAG ATG TTC TAT TTT GGT GAA GAT    6864
Phe Gly Tyr Ile Asn Ile Glu Asp Lys Met Phe Tyr Phe Gly Glu Asp
            2275                2280                2285

GGT GTC ATG CAG ATT GGA GTA TTT AAT ACA CCA GAT GGA TTT AAA TAC    6912
Gly Val Met Gln Ile Gly Val Phe Asn Thr Pro Asp Gly Phe Lys Tyr
            2290                2295                2300

TTT GCA CAT CAA AAT ACT TTG GAT GAG AAT TTT GAG GGA GAA TCA ATA    6960
Phe Ala His Gln Asn Thr Leu Asp Glu Asn Phe Glu Gly Glu Ser Ile
2305            2310                2315                2320

AAC TAT ACT GGT TGG TTA GAT TTA GAT GAA AAG AGA TAT TAT TTT ACA    7008
Asn Tyr Thr Gly Trp Leu Asp Leu Asp Glu Lys Arg Tyr Tyr Phe Thr
            2325                2330                2335

GAT GAA TAT ATT GCA GCA ACT GGT TCA GTT ATT ATT GAT GGT GAG GAG    7056
Asp Glu Tyr Ile Ala Ala Thr Gly Ser Val Ile Ile Asp Gly Glu Glu
            2340                2345                2350

TAT TAT TTT GAT CCT GAT ACA GCT CAA TTA GTG ATT AGT GAA             7098
Tyr Tyr Phe Asp Pro Asp Thr Ala Gln Leu Val Ile Ser Glu
            2355                2360                2365

TAG                                                                 7101
```

(2) INFORMATION FOR SEQ ID NO:10:

(i) SEQUENCE CHARACTERISTICS:
        (A) LENGTH: 2366 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65              70                  75                  80

Thr Glu Val Leu Glu Leu Lys Asn Asn Asn Leu Thr Pro Val Glu Lys
                85                  90                  95
```

```
Asn Leu His Phe Val Trp Ile Gly Gly Gln Ile Asn Asp Thr Ala Ile
            100                 105                 110
Asn Tyr Ile Asn Gln Trp Lys Asp Val Asn Ser Asp Tyr Asn Val Asn
            115                 120                 125
Val Phe Tyr Asp Ser Asn Ala Phe Leu Ile Asn Thr Leu Lys Lys Thr
            130                 135                 140
Val Val Glu Ser Ala Ile Asn Asp Thr Leu Glu Ser Phe Arg Glu Asn
145                 150                 155                 160
Leu Asn Asp Pro Arg Phe Asp Tyr Asn Lys Phe Phe Arg Lys Arg Met
                165                 170                 175
Glu Ile Ile Tyr Asp Lys Gln Lys Asn Phe Ile Asn Tyr Tyr Lys Ala
                180                 185                 190
Gln Arg Glu Glu Asn Pro Glu Leu Ile Ile Asp Asp Ile Val Lys Thr
            195                 200                 205
Tyr Leu Ser Asn Glu Tyr Ser Lys Glu Ile Asp Glu Leu Asn Thr Tyr
            210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
            260                 265                 270
Arg Ile Ser Ala Leu Lys Glu Ile Gly Gly Met Tyr Leu Asp Val Asp
            275                 280                 285
Met Leu Pro Gly Ile Gln Pro Asp Leu Phe Glu Ser Ile Glu Lys Pro
            290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
            340                 345                 350
Lys Ser Asp Lys Ser Glu Ile Phe Ser Ser Leu Gly Asp Met Glu Ala
            355                 360                 365
Ser Pro Leu Glu Val Lys Ile Ala Phe Asn Ser Lys Gly Ile Ile Asn
            370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
            435                 440                 445
Glu Leu Gly Lys Tyr Leu Arg Val Gly Phe Phe Pro Asp Val Lys Thr
            450                 455                 460
Thr Ile Asn Leu Ser Gly Pro Glu Ala Tyr Ala Ala Ala Tyr Gln Asp
465                 470                 475                 480
Leu Leu Met Phe Lys Glu Gly Ser Met Asn Ile His Leu Ile Glu Ala
                485                 490                 495
Asp Leu Arg Asn Phe Glu Ile Ser Lys Thr Asn Ile Ser Gln Ser Thr
            500                 505                 510
Glu Gln Glu Met Ala Ser Leu Trp Ser Phe Asp Asp Ala Arg Ala Lys
```

```
                515                 520                 525
Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Ser Ile
    755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
            885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
    930                 935                 940
```

-continued

```
Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
            965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro Thr
            1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
            1045                1050                1055

Arg Gln Glu Ile Glu Ala Lys Ile Gly Ile Met Ala Val Asn Leu Thr
            1060                1065                1070

Thr Ala Thr Thr Ala Ile Ile Thr Ser Ser Leu Gly Ile Ala Ser Gly
            1075                1080                1085

Phe Ser Ile Leu Leu Val Pro Leu Ala Gly Ile Ser Ala Gly Ile Pro
            1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
            1125                1130                1135

Thr Leu Leu Asp Asp Lys Ile Met Met Pro Gln Asp Asp Leu Val Ile
            1140                1145                1150

Ser Glu Ile Asp Phe Asn Asn Asn Ser Ile Val Leu Gly Lys Cys Glu
            1155                1160                1165

Ile Trp Arg Met Glu Gly Gly Ser Gly His Thr Val Thr Asp Asp Ile
            1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
            1205                1210                1215

Lys Asp Leu Met Val Leu Pro Asn Ala Pro Asn Arg Val Phe Ala Trp
            1220                1225                1230

Glu Thr Gly Trp Thr Pro Gly Leu Arg Ser Leu Glu Asn Asp Gly Thr
            1235                1240                1245

Lys Leu Leu Asp Arg Ile Arg Asp Asn Tyr Glu Gly Glu Phe Tyr Trp
1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
            1285                1290                1295

Ser Phe Ile Val Pro Ile Ile Thr Thr Glu Tyr Ile Arg Glu Lys Leu
            1300                1305                1310

Ser Tyr Ser Phe Tyr Gly Ser Gly Thr Tyr Ala Leu Ser Leu Ser
            1315                1320                1325

Gln Tyr Asn Met Gly Ile Asn Ile Glu Leu Ser Glu Ser Asp Val Trp
            1330                1335                1340

Ile Ile Asp Val Asp Asn Val Val Arg Asp Val Thr Ile Glu Ser Asp
1345                1350                1355                1360
```

```
Lys Ile Lys Lys Gly Asp Leu Ile Glu Gly Ile Leu Ser Thr Leu Ser
            1365                1370                1375

Ile Glu Glu Asn Lys Ile Ile Leu Asn Ser His Glu Ile Asn Phe Ser
        1380                1385                1390

Gly Glu Val Asn Gly Ser Asn Gly Phe Val Ser Leu Thr Phe Ser Ile
        1395                1400                1405

Leu Glu Gly Ile Asn Ala Ile Ile Glu Val Asp Leu Leu Ser Lys Ser
        1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
            1445                1450                1455

Gln Lys Asn Ile Pro Tyr Ser Phe Val Asp Ser Glu Gly Lys Glu Asn
            1460                1465                1470

Gly Phe Ile Asn Gly Ser Thr Lys Glu Gly Leu Phe Val Ser Glu Leu
            1475                1480                1485

Pro Asp Val Val Leu Ile Ser Lys Val Tyr Met Asp Asp Ser Lys Pro
        1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
            1525                1530                1535

Lys Ile Ser Leu Ser Leu Thr Leu Gln Asp Glu Lys Thr Ile Lys Leu
            1540                1545                1550

Asn Ser Val His Leu Asp Glu Ser Gly Val Ala Glu Ile Leu Lys Phe
        1555                1560                1565

Met Asn Arg Lys Gly Asn Thr Asn Thr Ser Asp Ser Leu Met Ser Phe
        1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
            1605                1610                1615

Ser Ile Gly Gln Phe Glu Phe Ile Cys Asp Glu Asn Asp Asn Ile Gln
            1620                1625                1630

Pro Tyr Phe Ile Lys Phe Asn Thr Leu Glu Thr Asn Tyr Thr Leu Tyr
            1635                1640                1645

Val Gly Asn Arg Gln Asn Met Ile Val Glu Pro Asn Tyr Asp Leu Asp
        1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Val Ile Ser Pro Asn
            1685                1690                1695

Ile Tyr Thr Asp Glu Ile Asn Ile Thr Pro Val Tyr Glu Thr Asn Asn
            1700                1705                1710

Thr Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser Asn
        1730                1735                1740

Asp Gly Asn Asp Phe Ile Leu Met Ser Thr Ser Glu Glu Asn Lys Val
1745                1750                1755                1760

Ser Gln Val Lys Ile Arg Phe Val Asn Val Phe Lys Asp Lys Thr Leu
            1765                1770                1775

Ala Asn Lys Leu Ser Phe Asn Phe Ser Asp Lys Gln Asp Val Pro Val
```

-continued

```
                1780                1785                1790
Ser Glu Ile Ile Leu Ser Phe Thr Pro Ser Tyr Tyr Glu Asp Gly Leu
            1795                1800                1805
Ile Gly Tyr Asp Leu Gly Leu Val Ser Leu Tyr Asn Glu Lys Phe Tyr
    1810                1815                1820
Ile Asn Asn Phe Gly Met Met Val Ser Gly Leu Ile Tyr Ile Asn Asp
1825                1830                1835                1840
Ser Leu Tyr Tyr Phe Lys Pro Pro Val Asn Asn Leu Ile Thr Gly Phe
                1845                1850                1855
Val Thr Val Gly Asp Asp Lys Tyr Tyr Phe Asn Pro Ile Asn Gly Gly
            1860                1865                1870
Ala Ala Ser Ile Gly Glu Thr Ile Ile Asp Asp Lys Asn Tyr Tyr Phe
    1875                1880                1885
Asn Gln Ser Gly Val Leu Gln Thr Gly Val Phe Ser Thr Glu Asp Gly
1890                1895                1900
Phe Lys Tyr Phe Ala Pro Ala Asn Thr Leu Asp Glu Asn Leu Glu Gly
1905                1910                1915                1920
Glu Ala Ile Asp Phe Thr Gly Lys Leu Ile Ile Asp Glu Asn Ile Tyr
            1925                1930                1935
Tyr Phe Asp Asp Asn Tyr Arg Gly Ala Val Glu Trp Lys Glu Leu Asp
        1940                1945                1950
Gly Glu Met His Tyr Phe Ser Pro Glu Thr Gly Lys Ala Phe Lys Gly
            1955                1960                1965
Leu Asn Gln Ile Gly Asp Tyr Lys Tyr Tyr Phe Asn Ser Asp Gly Val
    1970                1975                1980
Met Gln Lys Gly Phe Val Ser Ile Asn Asp Asn Lys His Tyr Phe Asp
1985                1990                1995                2000
Asp Ser Gly Val Met Lys Val Gly Tyr Thr Glu Ile Asp Gly Lys His
            2005                2010                2015
Phe Tyr Phe Ala Glu Asn Gly Glu Met Gln Ile Gly Val Phe Asn Thr
        2020                2025                2030
Glu Asp Gly Phe Lys Tyr Phe Ala His His Asn Glu Asp Leu Gly Asn
        2035                2040                2045
Glu Glu Gly Glu Glu Ile Ser Tyr Ser Gly Ile Leu Asn Phe Asn Asn
2050                2055                2060
Lys Ile Tyr Tyr Phe Asp Asp Ser Phe Thr Ala Val Val Gly Trp Lys
2065                2070                2075                2080
Asp Leu Glu Asp Gly Ser Lys Tyr Tyr Phe Asp Glu Asp Thr Ala Glu
            2085                2090                2095
Ala Tyr Ile Gly Leu Ser Leu Ile Asn Asp Gly Gln Tyr Tyr Phe Asn
        2100                2105                2110
Asp Asp Gly Ile Met Gln Val Gly Phe Val Thr Ile Asn Asp Lys Val
            2115                2120                2125
Phe Tyr Phe Ser Asp Ser Gly Ile Ile Glu Ser Gly Val Gln Asn Ile
        2130                2135                2140
Asp Asp Asn Tyr Phe Tyr Ile Asp Asp Asn Gly Ile Val Gln Ile Gly
2145                2150                2155                2160
Val Phe Asp Thr Ser Asp Gly Tyr Lys Tyr Phe Ala Pro Ala Asn Thr
            2165                2170                2175
Val Asn Asp Asn Ile Tyr Gly Gln Ala Val Glu Tyr Ser Gly Leu Val
        2180                2185                2190
Arg Val Gly Glu Asp Val Tyr Tyr Phe Gly Glu Thr Tyr Thr Ile Glu
        2195                2200                2205
```

```
Thr Gly Trp Ile Tyr Asp Met Glu Asn Glu Ser Asp Lys Tyr Tyr Phe
    2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
        2245                2250                2255

Ser Phe Glu Asn Asn Asn Tyr Tyr Phe Asn Glu Asn Gly Glu Met Gln
            2260                2265                2270

Phe Gly Tyr Ile Asn Ile Glu Asp Lys Met Phe Tyr Phe Gly Glu Asp
        2275                2280                2285

Gly Val Met Gln Ile Gly Val Phe Asn Thr Pro Asp Gly Phe Lys Tyr
    2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
            2325                2330                2335

Asp Glu Tyr Ile Ala Ala Thr Gly Ser Val Ile Ile Asp Gly Glu Glu
        2340                2345                2350

Tyr Tyr Phe Asp Pro Asp Thr Ala Gln Leu Val Ile Ser Glu
        2355                2360                2365
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TAGAAAAAAT GGCAAATGT                                        19

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTTCATCTTG TAGAGTCAAA G                                  21

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GATGCCACAA GATGATTTAG TG                               22

(2) INFORMATION FOR SEQ ID NO:14:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:14:

CTAATTGAGC TGTATCAGGA TC                                           22

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGGAATTCCT AGAAAAAATG GCAAATG                                      27

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GCTCTAGAAT GACCATAAGC TAGCCA                                       26

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGGAATTCGA GTTGGTAGAA AGGTGGA                                      27

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGGAATTCGG TTATTATCTT AAGGATG                                      27

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single -continued

```
            (D) TOPOLOGY: linear (ii) MOLECULE TYPE: DNA (genomic)

(xi) SEQUENCE DESCRIPTION: SEQ ID NO:19:

CGGAATTCTT GATAACTGGA TTTGTGAC                                          28

(2) INFORMATION FOR SEQ ID NO:20:

(i) SEQUENCE CHARACTERISTICS:
        (A) LENGTH: 511 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:20:
```

Leu Ile Thr Gly Phe Val Thr Val Gly Asp Asp Lys Tyr Tyr Phe Asn
1               5                   10                  15

Pro Ile Asn Gly Gly Ala Ala Ser Ile Gly Glu Thr Ile Ile Asp Asp
            20                  25                  30

Lys Asn Tyr Tyr Phe Asn Gln Ser Gly Val Leu Gln Thr Gly Val Phe
        35                  40                  45

Ser Thr Glu Asp Gly Phe Lys Tyr Phe Ala Pro Ala Asn Thr Leu Asp
50                  55                  60

Glu Asn Leu Glu Gly Glu Ala Ile Asp Phe Thr Gly Lys Leu Ile Ile
65                  70                  75                  80

Asp Glu Asn Ile Tyr Tyr Phe Asp Asp Asn Tyr Arg Gly Ala Val Glu
                85                  90                  95

Trp Lys Glu Leu Asp Gly Glu Met His Tyr Phe Ser Pro Glu Thr Gly
            100                 105                 110

Lys Ala Phe Lys Gly Leu Asn Gln Ile Gly Asp Tyr Lys Tyr Tyr Phe
        115                 120                 125

Asn Ser Asp Gly Val Met Gln Lys Gly Phe Val Ser Ile Asn Asp Asn
    130                 135                 140

Lys His Tyr Phe Asp Asp Ser Gly Val Met Lys Val Gly Tyr Thr Glu
145                 150                 155                 160

Ile Asp Gly Lys His Phe Tyr Phe Ala Glu Asn Gly Glu Met Gln Ile
                165                 170                 175

Gly Val Phe Asn Thr Glu Asp Gly Phe Lys Tyr Phe Ala His His Asn
            180                 185                 190

Glu Asp Leu Gly Asn Glu Glu Gly Glu Glu Ile Ser Tyr Ser Gly Ile
        195                 200                 205

Leu Asn Phe Asn Asn Lys Ile Tyr Tyr Phe Asp Asp Ser Phe Thr Ala
    210                 215                 220

Val Val Gly Trp Lys Asp Leu Glu Asp Gly Ser Lys Tyr Tyr Phe Asp
225                 230                 235                 240

Glu Asp Thr Ala Glu Ala Tyr Ile Gly Leu Ser Leu Ile Asn Asp Gly
                245                 250                 255

Gln Tyr Tyr Phe Asn Asp Asp Gly Ile Met Gln Val Gly Phe Val Thr
            260                 265                 270

Ile Asn Asp Lys Val Phe Tyr Phe Ser Asp Ser Gly Ile Ile Glu Ser
        275                 280                 285

Gly Val Gln Asn Ile Asp Asp Asn Tyr Phe Tyr Ile Asp Asp Asn Gly
    290                 295                 300

Ile Val Gln Ile Gly Val Phe Asp Thr Ser Asp Gly Tyr Lys Tyr Phe

-continued

```
305                 310                 315                 320
Ala Pro Ala Asn Thr Val Asn Asp Asn Ile Tyr Gly Gln Ala Val Glu
                325                 330                 335

Tyr Ser Gly Leu Val Arg Val Gly Glu Asp Val Tyr Tyr Phe Gly Glu
                340                 345                 350

Thr Tyr Thr Ile Glu Thr Gly Trp Ile Tyr Asp Met Glu Asn Glu Ser
                355                 360                 365

Asp Lys Tyr Tyr Phe Asn Pro Glu Thr Lys Lys Ala Cys Lys Gly Ile
                370                 375                 380

Asn Leu Ile Asp Asp Ile Lys Tyr Tyr Phe Asp Glu Lys Gly Ile Met
385                 390                 395                 400

Arg Thr Gly Leu Ile Ser Phe Glu Asn Asn Asn Tyr Tyr Phe Asn Glu
                405                 410                 415

Asn Gly Glu Met Gln Phe Gly Tyr Ile Asn Ile Glu Asp Lys Met Phe
                420                 425                 430

Tyr Phe Gly Glu Asp Gly Val Met Gln Ile Gly Val Phe Asn Thr Pro
                435                 440                 445

Asp Gly Phe Lys Tyr Phe Ala His Gln Asn Thr Leu Asp Glu Asn Phe
                450                 455                 460

Glu Gly Glu Ser Ile Asn Tyr Thr Gly Trp Leu Asp Leu Asp Glu Lys
465                 470                 475                 480

Arg Tyr Tyr Phe Thr Asp Glu Tyr Ile Ala Ala Thr Gly Ser Val Ile
                485                 490                 495

Ile Asp Gly Glu Glu Tyr Tyr Phe Asp Pro Asp Thr Ala Gln Leu
                500                 505                 510

(2) INFORMATION FOR SEQ ID NO:21:

(i) SEQUENCE CHARACTERISTICS:
        (A) LENGTH: 608 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:21:

Ser Glu Glu Asn Lys Val Ser Gln Val Lys Ile Arg Phe Val Asn Val
1               5                   10                  15

Phe Lys Asp Lys Thr Leu Ala Asn Lys Leu Ser Phe Asn Phe Ser Asp
                20                  25                  30

Lys Gln Asp Val Pro Val Ser Glu Ile Ile Leu Ser Phe Thr Pro Ser
                35                  40                  45

Tyr Tyr Glu Asp Gly Leu Ile Gly Tyr Asp Leu Gly Leu Val Ser Leu
                50                  55                  60

Tyr Asn Glu Lys Phe Tyr Ile Asn Asn Phe Gly Met Met Val Ser Gly
65                  70                  75                  80

Leu Ile Tyr Ile Asn Asp Ser Leu Tyr Tyr Phe Lys Pro Pro Val Asn
                85                  90                  95

Asn Leu Ile Thr Gly Phe Val Thr Val Gly Asp Asp Lys Tyr Tyr Phe
                100                 105                 110

Asn Pro Ile Asn Gly Gly Ala Ala Ser Ile Gly Glu Thr Ile Ile Asp
                115                 120                 125

Asp Lys Asn Tyr Tyr Phe Asn Gln Ser Gly Val Leu Gln Thr Gly Val
                130                 135                 140

Phe Ser Thr Glu Asp Gly Phe Lys Tyr Phe Ala Pro Ala Asn Thr Leu
```

```
145                 150                 155                 160
Asp Glu Asn Leu Glu Gly Glu Ala Ile Asp Phe Thr Gly Lys Leu Ile
                165                 170                 175
Ile Asp Glu Asn Ile Tyr Tyr Phe Asp Asp Asn Tyr Arg Gly Ala Val
            180                 185                 190
Glu Trp Lys Glu Leu Asp Gly Glu Met His Tyr Phe Ser Pro Glu Thr
        195                 200                 205
Gly Lys Ala Phe Lys Gly Leu Asn Gln Ile Gly Asp Tyr Lys Tyr Tyr
        210                 215                 220
Phe Asn Ser Asp Gly Val Met Gln Lys Gly Phe Val Ser Ile Asn Asp
225                 230                 235                 240
Asn Lys His Tyr Phe Asp Asp Ser Gly Val Met Lys Val Gly Tyr Thr
                245                 250                 255
Glu Ile Asp Gly Lys His Phe Tyr Phe Ala Glu Asn Gly Glu Met Gln
                260                 265                 270
Ile Gly Val Phe Asn Thr Glu Asp Gly Phe Lys Tyr Phe Ala His His
            275                 280                 285
Asn Glu Asp Leu Gly Asn Glu Glu Gly Glu Glu Ile Ser Tyr Ser Gly
        290                 295                 300
Ile Leu Asn Phe Asn Asn Lys Ile Tyr Tyr Phe Asp Asp Ser Phe Thr
305                 310                 315                 320
Ala Val Val Gly Trp Lys Asp Leu Glu Asp Gly Ser Lys Tyr Tyr Phe
                325                 330                 335
Asp Glu Asp Thr Ala Glu Ala Tyr Ile Gly Leu Ser Leu Ile Asn Asp
                340                 345                 350
Gly Gln Tyr Tyr Phe Asn Asp Asp Gly Ile Met Gln Val Gly Phe Val
            355                 360                 365
Thr Ile Asn Asp Lys Val Phe Tyr Phe Ser Asp Ser Gly Ile Ile Glu
370                 375                 380
Ser Gly Val Gln Asn Ile Asp Asp Asn Tyr Phe Tyr Ile Asp Asp Asn
385                 390                 395                 400
Gly Ile Val Gln Ile Gly Val Phe Asp Thr Ser Asp Gly Tyr Lys Tyr
                405                 410                 415
Phe Ala Pro Ala Asn Thr Val Asn Asp Asn Ile Tyr Gly Gln Ala Val
                420                 425                 430
Glu Tyr Ser Gly Leu Val Arg Val Gly Glu Asp Val Tyr Tyr Phe Gly
            435                 440                 445
Glu Thr Tyr Thr Ile Glu Thr Gly Trp Ile Tyr Asp Met Glu Asn Glu
        450                 455                 460
Ser Asp Lys Tyr Tyr Phe Asn Pro Glu Thr Lys Lys Ala Cys Lys Gly
465                 470                 475                 480
Ile Asn Leu Ile Asp Asp Ile Lys Tyr Tyr Phe Asp Glu Lys Gly Ile
                485                 490                 495
Met Arg Thr Gly Leu Ile Ser Phe Glu Asn Asn Asn Tyr Tyr Phe Asn
            500                 505                 510
Glu Asn Gly Glu Met Gln Phe Gly Tyr Ile Asn Ile Glu Asp Lys Met
        515                 520                 525
Phe Tyr Phe Gly Glu Asp Gly Val Met Gln Ile Gly Val Phe Asn Thr
        530                 535                 540
Pro Asp Gly Phe Lys Tyr Phe Ala His Gln Asn Thr Leu Asp Glu Asn
545                 550                 555                 560
Phe Glu Gly Glu Ser Ile Asn Tyr Thr Gly Trp Leu Asp Leu Asp Glu
                565                 570                 575
```

```
                          -continued

Lys Arg Tyr Tyr Phe Thr Asp Glu Tyr Ile Ala Ala Thr Gly Ser Val
            580                 585                 590

Ile Ile Asp Gly Glu Glu Tyr Tyr Phe Asp Pro Asp Thr Ala Gln Leu
            595                 600                 605

(2) INFORMATION FOR SEQ ID NO:22:

(i) SEQUENCE CHARACTERISTICS:
        (A) LENGTH: 1330 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1314

(xi) SEQUENCE DESCRIPTION: SEQ ID NO:22:

ATG GCT CGT CTG CTG TCT ACC TTC ACT GAA TAC ATC AAG AAC ATC ATC        48
Met Ala Arg Leu Leu Ser Thr Phe Thr Glu Tyr Ile Lys Asn Ile Ile
 1               5                  10                  15

AAT ACC TCC ATC CTG AAC CTG CGC TAC GAA TCC AAT CAC CTG ATC GAC        96
Asn Thr Ser Ile Leu Asn Leu Arg Tyr Glu Ser Asn His Leu Ile Asp
                20                  25                  30

CTG TCT CGC TAC GCT TCC AAA ATC AAC ATC GGT TCT AAA GTT AAC TTC       144
Leu Ser Arg Tyr Ala Ser Lys Ile Asn Ile Gly Ser Lys Val Asn Phe
            35                  40                  45

GAT CCG ATC GAC AAG AAT CAG ATC CAG CTG TTC AAT CTG GAA TCT TCC       192
Asp Pro Ile Asp Lys Asn Gln Ile Gln Leu Phe Asn Leu Glu Ser Ser
        50                  55                  60

AAA ATC GAA GTT ATC CTG AAG AAT GCT ATC GTA TAC AAC TCT ATG TAC       240
Lys Ile Glu Val Ile Leu Lys Asn Ala Ile Val Tyr Asn Ser Met Tyr
 65                  70                  75                  80

GAA AAC TTC TCC ACC TCC TTC TGG ATC CGT ATC CCG AAA TAC TTC AAC       288
Glu Asn Phe Ser Thr Ser Phe Trp Ile Arg Ile Pro Lys Tyr Phe Asn
                85                  90                  95

TCC ATC TCT CTG AAC AAT GAA TAC ACC ATC ATC AAC TGC ATG GAA AAC       336
Ser Ile Ser Leu Asn Asn Glu Tyr Thr Ile Ile Asn Cys Met Glu Asn
            100                 105                 110

AAT TCT GGT TGG AAA GTA TCT CTG AAC TAC GGT GAA ATC ATC TGG ACT       384
Asn Ser Gly Trp Lys Val Ser Leu Asn Tyr Gly Glu Ile Ile Trp Thr
        115                 120                 125

CTG CAG GAC ACT CAG GAA ATC AAA CAG CGT GTT GTA TTC AAA TAC TCT       432
Leu Gln Asp Thr Gln Glu Ile Lys Gln Arg Val Val Phe Lys Tyr Ser
130                 135                 140

CAG ATG ATC AAC ATC TCT GAC TAC ATC AAT CGC TGG ATC TTC GTT ACC       480
Gln Met Ile Asn Ile Ser Asp Tyr Ile Asn Arg Trp Ile Phe Val Thr
145                 150                 155                 160

ATC ACC AAC AAT CGT CTG AAT AAC TCC AAA ATC TAC ATC AAC GGC CGT       528
Ile Thr Asn Asn Arg Leu Asn Asn Ser Lys Ile Tyr Ile Asn Gly Arg
                165                 170                 175

CTG ATC GAC CAG AAA CCG ATC TCC AAT CTG GGT AAC ATC CAC GCT TCT       576
Leu Ile Asp Gln Lys Pro Ile Ser Asn Leu Gly Asn Ile His Ala Ser
            180                 185                 190

AAT AAC ATC ATG TTC AAA CTG GAC GGT TGT CGT GAC ACT CAC CGC TAC       624
Asn Asn Ile Met Phe Lys Leu Asp Gly Cys Arg Asp Thr His Arg Tyr
        195                 200                 205

ATC TGG ATC AAA TAC TTC AAT CTG TTC GAC AAA GAA CTG AAC GAA AAA       672
Ile Trp Ile Lys Tyr Phe Asn Leu Phe Asp Lys Glu Leu Asn Glu Lys
210                 215                 220
```

```
GAA ATC AAA GAC CTG TAC GAC AAC CAG TCC AAT TCT GGT ATC CTG AAA       720
Glu Ile Lys Asp Leu Tyr Asp Asn Gln Ser Asn Ser Gly Ile Leu Lys
225                 230                 235                 240

GAC TTC TGG GGT GAC TAC CTG CAG TAC GAC AAA CCG TAC TAC ATG CTG       768
Asp Phe Trp Gly Asp Tyr Leu Gln Tyr Asp Lys Pro Tyr Tyr Met Leu
                245                 250                 255

AAT CTG TAC GAT CCG AAC AAA TAC GTT GAC GTC AAC AAT GTA GGT ATC       816
Asn Leu Tyr Asp Pro Asn Lys Tyr Val Asp Val Asn Asn Val Gly Ile
            260                 265                 270

CGC GGT TAC ATG TAC CTG AAA GGT CCG CGT GGT TCT GTT ATG ACT ACC       864
Arg Gly Tyr Met Tyr Leu Lys Gly Pro Arg Gly Ser Val Met Thr Thr
        275                 280                 285

AAC ATC TAC CTG AAC TCT TCC CTG TAC CGT GGT ACC AAA TTC ATC ATC       912
Asn Ile Tyr Leu Asn Ser Ser Leu Tyr Arg Gly Thr Lys Phe Ile Ile
    290                 295                 300

AAG AAA TAC GCG TCT GGT AAC AAG GAC AAT ATC GTT CGC AAC AAT GAT       960
Lys Lys Tyr Ala Ser Gly Asn Lys Asp Asn Ile Val Arg Asn Asn Asp
305                 310                 315                 320

CGT GTA TAC ATC AAT GTT GTA GTT AAG AAC AAA GAA TAC CGT CTG GCT      1008
Arg Val Tyr Ile Asn Val Val Val Lys Asn Lys Glu Tyr Arg Leu Ala
                325                 330                 335

ACC AAT GCT TCT CAG GCT GGT GTA GAA AAG ATC TTG TCT GCT CTG GAA      1056
Thr Asn Ala Ser Gln Ala Gly Val Glu Lys Ile Leu Ser Ala Leu Glu
                340                 345                 350

ATC CCG GAC GTT GGT AAT CTG TCT CAG GTA GTT GTA ATG AAA TCC AAG      1104
Ile Pro Asp Val Gly Asn Leu Ser Gln Val Val Val Met Lys Ser Lys
            355                 360                 365

AAC GAC CAG GGT ATC ACT AAC AAA TGC AAA ATG AAT CTG CAG GAC AAC      1152
Asn Asp Gln Gly Ile Thr Asn Lys Cys Lys Met Asn Leu Gln Asp Asn
        370                 375                 380

AAT GGT AAC GAT ATC GGT TTC ATC GGT TTC CAC CAG TTC AAC AAT ATC      1200
Asn Gly Asn Asp Ile Gly Phe Ile Gly Phe His Gln Phe Asn Asn Ile
385                 390                 395                 400

GCT AAA CTG GTT GCT TCC AAC TGG TAC AAT CGT CAG ATC GAA CGT TCC      1248
Ala Lys Leu Val Ala Ser Asn Trp Tyr Asn Arg Gln Ile Glu Arg Ser
                405                 410                 415

TCT CGC ACT CTG GGT TGC TCT TGG GAG TTC ATC CCG GTT GAT GAC GGT      1296
Ser Arg Thr Leu Gly Cys Ser Trp Glu Phe Ile Pro Val Asp Asp Gly
                420                 425                 430

TGG GGT GAA CGT CCG CTG TAACCCGGGA AAGCTT                            1330
Trp Gly Glu Arg Pro Leu
            435

(2) INFORMATION FOR SEQ ID NO:23:

(i) SEQUENCE CHARACTERISTICS:
        (A) LENGTH: 438 amino acids
        (B) TYPE: amino acid
        (D) TOPOLOGY: linear (ii) MOLECULE TYPE: protein (xi) SEQUENCE DESCRIPTION: SEQ ID NO:23:

Met Ala Arg Leu Leu Ser Thr Phe Thr Glu Tyr Ile Lys Asn Ile Ile
 1               5                  10                  15

Asn Thr Ser Ile Leu Asn Leu Arg Tyr Glu Ser Asn His Leu Ile Asp
            20                  25                  30

Leu Ser Arg Tyr Ala Ser Lys Ile Asn Ile Gly Ser Lys Val Asn Phe
        35                  40                  45

Asp Pro Ile Asp Lys Asn Gln Ile Gln Leu Phe Asn Leu Glu Ser Ser
```

-continued

```
                50                  55                  60
Lys Ile Glu Val Ile Leu Lys Asn Ala Ile Val Tyr Asn Ser Met Tyr
 65                  70                  75                  80
Glu Asn Phe Ser Thr Ser Phe Trp Ile Arg Ile Pro Lys Tyr Phe Asn
                    85                  90                  95
Ser Ile Ser Leu Asn Asn Glu Tyr Thr Ile Ile Asn Cys Met Glu Asn
                   100                 105                 110
Asn Ser Gly Trp Lys Val Ser Leu Asn Tyr Gly Glu Ile Ile Trp Thr
                   115                 120                 125
Leu Gln Asp Thr Gln Glu Ile Lys Gln Arg Val Val Phe Lys Tyr Ser
                   130                 135                 140
Gln Met Ile Asn Ile Ser Asp Tyr Ile Asn Arg Trp Ile Phe Val Thr
145                 150                 155                 160
Ile Thr Asn Asn Arg Leu Asn Asn Ser Lys Ile Tyr Ile Asn Gly Arg
                   165                 170                 175
Leu Ile Asp Gln Lys Pro Ile Ser Asn Leu Gly Asn Ile His Ala Ser
                   180                 185                 190
Asn Asn Ile Met Phe Lys Leu Asp Gly Cys Arg Asp Thr His Arg Tyr
                   195                 200                 205
Ile Trp Ile Lys Tyr Phe Asn Leu Phe Asp Lys Glu Leu Asn Glu Lys
                   210                 215                 220
Glu Ile Lys Asp Leu Tyr Asp Asn Gln Ser Asn Ser Gly Ile Leu Lys
225                 230                 235                 240
Asp Phe Trp Gly Asp Tyr Leu Gln Tyr Asp Lys Pro Tyr Tyr Met Leu
                   245                 250                 255
Asn Leu Tyr Asp Pro Asn Lys Tyr Val Asp Val Asn Asn Val Gly Ile
                   260                 265                 270
Arg Gly Tyr Met Tyr Leu Lys Gly Pro Arg Gly Ser Val Met Thr Thr
                   275                 280                 285
Asn Ile Tyr Leu Asn Ser Ser Leu Tyr Arg Gly Thr Lys Phe Ile Ile
                   290                 295                 300
Lys Lys Tyr Ala Ser Gly Asn Lys Asp Asn Ile Val Arg Asn Asn Asp
305                 310                 315                 320
Arg Val Tyr Ile Asn Val Val Lys Asn Lys Glu Tyr Arg Leu Ala
                   325                 330                 335
Thr Asn Ala Ser Gln Ala Gly Val Glu Lys Ile Leu Ser Ala Leu Glu
                   340                 345                 350
Ile Pro Asp Val Gly Asn Leu Ser Gln Val Val Met Lys Ser Lys
                   355                 360                 365
Asn Asp Gln Gly Ile Thr Asn Lys Cys Lys Met Asn Leu Gln Asp Asn
                   370                 375                 380
Asn Gly Asn Asp Ile Gly Phe Ile Gly Phe His Gln Phe Asn Asn Ile
385                 390                 395                 400
Ala Lys Leu Val Ala Ser Asn Trp Tyr Asn Arg Gln Ile Glu Arg Ser
                   405                 410                 415
Ser Arg Thr Leu Gly Cys Ser Trp Glu Phe Ile Pro Val Asp Asp Gly
                   420                 425                 430
Trp Gly Glu Arg Pro Leu
                   435
```

(2) INFORMATION FOR SEQ ID NO:24:

(i) SEQUENCE CHARACTERISTICS:
        (A) LENGTH: 23 amino acids (B) TYPE: amino acid
                (C) STRANDEDNESS: unknown
                (D) TOPOLOGY: linear (ii) MOLECULE TYPE: protein (xi) SEQUENCE DESCRIPTION: SEQ ID NO:24:

Met Gly His His His His His His His His Ser Ser Gly His
1               5                   10                  15

Ile Glu Gly Arg His Met Ala
            20

(2) INFORMATION FOR SEQ ID NO:25:

(i) SEQUENCE CHARACTERISTICS:
                (A) LENGTH: 1402 base pairs
                (B) TYPE: nucleic acid
                (C) STRANDEDNESS: double
                (D) TOPOLOGY: linear (ii) MOLECULE TYPE: DNA (genomic)

(ix) FEATURE:
                (A) NAME/KEY: CDS
                (B) LOCATION: 1..1386

(xi) SEQUENCE DESCRIPTION: SEQ ID NO:25:

```
ATG GGC CAT CAT CAT CAT CAT CAT CAT CAT CAC AGC AGC GGC CAT          48
Met Gly His His His His His His His His His Ser Ser Gly His
1               5                   10                  15

ATC GAA GGT CGT CAT ATG GCT AGC ATG GCT CGT CTG CTG TCT ACC TTC      96
Ile Glu Gly Arg His Met Ala Ser Met Ala Arg Leu Leu Ser Thr Phe
            20                  25                  30

ACT GAA TAC ATC AAG AAC ATC ATC AAT ACC TCC ATC CTG AAC CTG CGC     144
Thr Glu Tyr Ile Lys Asn Ile Ile Asn Thr Ser Ile Leu Asn Leu Arg
        35                  40                  45

TAC GAA TCC AAT CAC CTG ATC GAC CTG TCT CGC TAC GCT TCC AAA ATC     192
Tyr Glu Ser Asn His Leu Ile Asp Leu Ser Arg Tyr Ala Ser Lys Ile
    50                  55                  60

AAC ATC GGT TCT AAA GTT AAC TTC GAT CCG ATC GAC AAG AAT CAG ATC     240
Asn Ile Gly Ser Lys Val Asn Phe Asp Pro Ile Asp Lys Asn Gln Ile
65                  70                  75                  80

CAG CTG TTC AAT CTG GAA TCT TCC AAA ATC GAA GTT ATC CTG AAG AAT     288
Gln Leu Phe Asn Leu Glu Ser Ser Lys Ile Glu Val Ile Leu Lys Asn
                85                  90                  95

GCT ATC GTA TAC AAC TCT ATG TAC GAA AAC TTC TCC ACC TCC TTC TGG     336
Ala Ile Val Tyr Asn Ser Met Tyr Glu Asn Phe Ser Thr Ser Phe Trp
            100                 105                 110

ATC CGT ATC CCG AAA TAC TTC AAC TCC ATC TCT CTG AAC AAT GAA TAC     384
Ile Arg Ile Pro Lys Tyr Phe Asn Ser Ile Ser Leu Asn Asn Glu Tyr
        115                 120                 125

ACC ATC ATC AAC TGC ATG GAA AAC AAT TCT GGT TGG AAA GTA TCT CTG     432
Thr Ile Ile Asn Cys Met Glu Asn Asn Ser Gly Trp Lys Val Ser Leu
    130                 135                 140

AAC TAC GGT GAA ATC ATC TGG ACT CTG CAG GAC ACT CAG GAA ATC AAA     480
Asn Tyr Gly Glu Ile Ile Trp Thr Leu Gln Asp Thr Gln Glu Ile Lys
145                 150                 155                 160

CAG CGT GTT GTA TTC AAA TAC TCT CAG ATG ATC AAC ATC TCT GAC TAC     528
Gln Arg Val Val Phe Lys Tyr Ser Gln Met Ile Asn Ile Ser Asp Tyr
                165                 170                 175

ATC AAT CGC TGG ATC TTC GTT ACC ATC ACC AAC AAT CGT CTG AAT AAC     576
Ile Asn Arg Trp Ile Phe Val Thr Ile Thr Asn Asn Arg Leu Asn Asn
            180                 185                 190
```

```
TCC AAA ATC TAC ATC AAC GGC CGT CTG ATC GAC CAG AAA CCG ATC TCC        624
Ser Lys Ile Tyr Ile Asn Gly Arg Leu Ile Asp Gln Lys Pro Ile Ser
        195                 200                 205

AAT CTG GGT AAC ATC CAC GCT TCT AAT AAC ATC ATG TTC AAA CTG GAC        672
Asn Leu Gly Asn Ile His Ala Ser Asn Asn Ile Met Phe Lys Leu Asp
    210                 215                 220

GGT TGT CGT GAC ACT CAC CGC TAC ATC TGG ATC AAA TAC TTC AAT CTG        720
Gly Cys Arg Asp Thr His Arg Tyr Ile Trp Ile Lys Tyr Phe Asn Leu
225                 230                 235                 240

TTC GAC AAA GAA CTG AAC GAA AAA GAA ATC AAA GAC CTG TAC GAC AAC        768
Phe Asp Lys Glu Leu Asn Glu Lys Glu Ile Lys Asp Leu Tyr Asp Asn
                245                 250                 255

CAG TCC AAT TCT GGT ATC CTG AAA GAC TTC TGG GGT GAC TAC CTG CAG        816
Gln Ser Asn Ser Gly Ile Leu Lys Asp Phe Trp Gly Asp Tyr Leu Gln
            260                 265                 270

TAC GAC AAA CCG TAC TAC ATG CTG AAT CTG TAC GAT CCG AAC AAA TAC        864
Tyr Asp Lys Pro Tyr Tyr Met Leu Asn Leu Tyr Asp Pro Asn Lys Tyr
        275                 280                 285

GTT GAC GTC AAC AAT GTA GGT ATC CGC GGT TAC ATG TAC CTG AAA GGT        912
Val Asp Val Asn Asn Val Gly Ile Arg Gly Tyr Met Tyr Leu Lys Gly
    290                 295                 300

CCG CGT GGT TCT GTT ATG ACT ACC AAC ATC TAC CTG AAC TCT TCC CTG        960
Pro Arg Gly Ser Val Met Thr Thr Asn Ile Tyr Leu Asn Ser Ser Leu
305                 310                 315                 320

TAC CGT GGT ACC AAA TTC ATC ATC AAG AAA TAC GCG TCT GGT AAC AAG       1008
Tyr Arg Gly Thr Lys Phe Ile Ile Lys Lys Tyr Ala Ser Gly Asn Lys
                325                 330                 335

GAC AAT ATC GTT CGC AAC AAT GAT CGT GTA TAC ATC AAT GTT GTA GTT       1056
Asp Asn Ile Val Arg Asn Asn Asp Arg Val Tyr Ile Asn Val Val Val
            340                 345                 350

AAG AAC AAA GAA TAC CGT CTG GCT ACC AAT GCT TCT CAG GCT GGT GTA       1104
Lys Asn Lys Glu Tyr Arg Leu Ala Thr Asn Ala Ser Gln Ala Gly Val
        355                 360                 365

GAA AAG ATC TTG TCT GCT CTG GAA ATC CCG GAC GTT GGT AAT CTG TCT       1152
Glu Lys Ile Leu Ser Ala Leu Glu Ile Pro Asp Val Gly Asn Leu Ser
    370                 375                 380

CAG GTA GTT GTA ATG AAA TCC AAG AAC GAC CAG GGT ATC ACT AAC AAA       1200
Gln Val Val Val Met Lys Ser Lys Asn Asp Gln Gly Ile Thr Asn Lys
385                 390                 395                 400

TGC AAA ATG AAT CTG CAG GAC AAC AAT GGT AAC GAT ATC GGT TTC ATC       1248
Cys Lys Met Asn Leu Gln Asp Asn Asn Gly Asn Asp Ile Gly Phe Ile
                405                 410                 415

GGT TTC CAC CAG TTC AAC AAT ATC GCT AAA CTG GTT GCT TCC AAC TGG       1296
Gly Phe His Gln Phe Asn Asn Ile Ala Lys Leu Val Ala Ser Asn Trp
            420                 425                 430

TAC AAT CGT CAG ATC GAA CGT TCC TCT CGC ACT CTG GGT TGC TCT TGG       1344
Tyr Asn Arg Gln Ile Glu Arg Ser Ser Arg Thr Leu Gly Cys Ser Trp
        435                 440                 445

GAG TTC ATC CCG GTT GAT GAC GGT TGG GGT GAA CGT CCG CTG                1386
Glu Phe Ile Pro Val Asp Asp Gly Trp Gly Glu Arg Pro Leu
450                 455                 460

TAACCCGGGA AAGCTT                                                      1402
```

(2) INFORMATION FOR SEQ ID NO:26:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO:26:

```
Met Gly His His His His His His His His Ser Ser Gly His
 1               5                  10                  15

Ile Glu Gly Arg His Met Ala Ser Met Ala Arg Leu Leu Ser Thr Phe
            20                  25                  30

Thr Glu Tyr Ile Lys Asn Ile Ile Asn Thr Ser Ile Leu Asn Leu Arg
        35                  40                  45

Tyr Glu Ser Asn His Leu Ile Asp Leu Ser Arg Tyr Ala Ser Lys Ile
    50                  55                  60

Asn Ile Gly Ser Lys Val Asn Phe Asp Pro Ile Asp Lys Asn Gln Ile
65                  70                  75                  80

Gln Leu Phe Asn Leu Glu Ser Ser Lys Ile Glu Val Ile Leu Lys Asn
                85                  90                  95

Ala Ile Val Tyr Asn Ser Met Tyr Glu Asn Phe Ser Thr Ser Phe Trp
            100                 105                 110

Ile Arg Ile Pro Lys Tyr Phe Asn Ser Ile Ser Leu Asn Asn Glu Tyr
        115                 120                 125

Thr Ile Ile Asn Cys Met Glu Asn Asn Ser Gly Trp Lys Val Ser Leu
    130                 135                 140

Asn Tyr Gly Glu Ile Ile Trp Thr Leu Gln Asp Thr Gln Glu Ile Lys
145                 150                 155                 160

Gln Arg Val Val Phe Lys Tyr Ser Gln Met Ile Asn Ile Ser Asp Tyr
                165                 170                 175

Ile Asn Arg Trp Ile Phe Val Thr Ile Thr Asn Asn Arg Leu Asn Asn
            180                 185                 190

Ser Lys Ile Tyr Ile Asn Gly Arg Leu Ile Asp Gln Lys Pro Ile Ser
        195                 200                 205

Asn Leu Gly Asn Ile His Ala Ser Asn Asn Ile Met Phe Lys Leu Asp
    210                 215                 220

Gly Cys Arg Asp Thr His Arg Tyr Ile Trp Ile Lys Tyr Phe Asn Leu
225                 230                 235                 240

Phe Asp Lys Glu Leu Asn Glu Lys Glu Ile Lys Asp Leu Tyr Asp Asn
                245                 250                 255

Gln Ser Asn Ser Gly Ile Leu Lys Asp Phe Trp Gly Asp Tyr Leu Gln
            260                 265                 270

Tyr Asp Lys Pro Tyr Tyr Met Leu Asn Leu Tyr Asp Pro Asn Lys Tyr
        275                 280                 285

Val Asp Val Asn Asn Val Gly Ile Arg Gly Tyr Met Tyr Leu Lys Gly
    290                 295                 300

Pro Arg Gly Ser Val Met Thr Thr Asn Ile Tyr Leu Asn Ser Ser Leu
305                 310                 315                 320

Tyr Arg Gly Thr Lys Phe Ile Ile Lys Lys Tyr Ala Ser Gly Asn Lys
                325                 330                 335

Asp Asn Ile Val Arg Asn Asn Asp Arg Val Tyr Ile Asn Val Val Val
            340                 345                 350

Lys Asn Lys Glu Tyr Arg Leu Ala Thr Asn Ala Ser Gln Ala Gly Val
        355                 360                 365

Glu Lys Ile Leu Ser Ala Leu Glu Ile Pro Asp Val Gly Asn Leu Ser
    370                 375                 380

Gln Val Val Val Met Lys Ser Lys Asn Asp Gln Gly Ile Thr Asn Lys
385                 390                 395                 400

Cys Lys Met Asn Leu Gln Asp Asn Asn Gly Asn Asp Ile Gly Phe Ile
```

```
                       405                 410                 415
Gly Phe His Gln Phe Asn Asn Ile Ala Lys Leu Val Ala Ser Asn Trp
                420                 425                 430

Tyr Asn Arg Gln Ile Glu Arg Ser Ser Arg Thr Leu Gly Cys Ser Trp
            435                 440                 445

Glu Phe Ile Pro Val Asp Asp Gly Trp Gly Glu Arg Pro Leu
       450                 455                 460

(2) INFORMATION FOR SEQ ID NO:27:

(i) SEQUENCE CHARACTERISTICS:
        (A) LENGTH: 3891 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..3888

(xi) SEQUENCE DESCRIPTION: SEQ ID NO:27:

ATG CAA TTT GTT AAT AAA CAA TTT AAT TAT AAA GAT CCT GTA AAT GGT      48
Met Gln Phe Val Asn Lys Gln Phe Asn Tyr Lys Asp Pro Val Asn Gly
  1               5                  10                  15

GTT GAT ATT GCT TAT ATA AAA ATT CCA AAT GTA GGA CAA ATG CAA CCA      96
Val Asp Ile Ala Tyr Ile Lys Ile Pro Asn Val Gly Gln Met Gln Pro
             20                  25                  30

GTA AAA GCT TTT AAA ATT CAT AAT AAA ATA TGG GTT ATT CCA GAA AGA     144
Val Lys Ala Phe Lys Ile His Asn Lys Ile Trp Val Ile Pro Glu Arg
         35                  40                  45

GAT ACA TTT ACA AAT CCT GAA GAA GGA GAT TTA AAT CCA CCA CCA GAA     192
Asp Thr Phe Thr Asn Pro Glu Glu Gly Asp Leu Asn Pro Pro Pro Glu
     50                  55                  60

GCA AAA CAA GTT CCA GTT TCA TAT TAT GAT TCA ACA TAT TTA AGT ACA     240
Ala Lys Gln Val Pro Val Ser Tyr Tyr Asp Ser Thr Tyr Leu Ser Thr
 65                  70                  75                  80

GAT AAT GAA AAA GAT AAT TAT TTA AAG GGA GTT ACA AAA TTA TTT GAG     288
Asp Asn Glu Lys Asp Asn Tyr Leu Lys Gly Val Thr Lys Leu Phe Glu
                 85                  90                  95

AGA ATT TAT TCA ACT GAT CTT GGA AGA ATG TTG TTA ACA TCA ATA GTA     336
Arg Ile Tyr Ser Thr Asp Leu Gly Arg Met Leu Leu Thr Ser Ile Val
            100                 105                 110

AGG GGA ATA CCA TTT TGG GGT GGA AGT ACA ATA GAT ACA GAA TTA AAA     384
Arg Gly Ile Pro Phe Trp Gly Gly Ser Thr Ile Asp Thr Glu Leu Lys
        115                 120                 125

GTT ATT GAT ACT AAT TGT ATT AAT GTG ATA CAA CCA GAT GGT AGT TAT     432
Val Ile Asp Thr Asn Cys Ile Asn Val Ile Gln Pro Asp Gly Ser Tyr
    130                 135                 140

AGA TCA GAA GAA CTT AAT CTA GTA ATA ATA GGA CCC TCA GCT GAT ATT     480
Arg Ser Glu Glu Leu Asn Leu Val Ile Ile Gly Pro Ser Ala Asp Ile
145                 150                 155                 160

ATA CAG TTT GAA TGT AAA AGC TTT GGA CAT GAA GTT TTG AAT CTT ACG     528
Ile Gln Phe Glu Cys Lys Ser Phe Gly His Glu Val Leu Asn Leu Thr
                165                 170                 175

CGA AAT GGT TAT GGC TCT ACT CAA TAC ATT AGA TTT AGC CCA GAT TTT     576
Arg Asn Gly Tyr Gly Ser Thr Gln Tyr Ile Arg Phe Ser Pro Asp Phe
            180                 185                 190

ACA TTT GGT TTT GAG GAG TCA CTT GAA GTT GAT ACA AAT CCT CTT TTA     624
Thr Phe Gly Phe Glu Glu Ser Leu Glu Val Asp Thr Asn Pro Leu Leu
        195                 200                 205
```

```
GGT GCA GGC AAA TTT GCT ACA GAT CCA GCA GTA ACA TTA GCA CAT GAA      672
Gly Ala Gly Lys Phe Ala Thr Asp Pro Ala Val Thr Leu Ala His Glu
        210                 215                 220

CTT ATA CAT GCT GGA CAT AGA TTA TAT GGA ATA GCA ATT AAT CCA AAT      720
Leu Ile His Ala Gly His Arg Leu Tyr Gly Ile Ala Ile Asn Pro Asn
225                 230                 235                 240

AGG GTT TTT AAA GTA AAT ACT AAT GCC TAT TAT GAA ATG AGT GGG TTA      768
Arg Val Phe Lys Val Asn Thr Asn Ala Tyr Tyr Glu Met Ser Gly Leu
                    245                 250                 255

GAA GTA AGC TTT GAG GAA CTT AGA ACA TTT GGG GGA CAT GAT GCA AAG      816
Glu Val Ser Phe Glu Glu Leu Arg Thr Phe Gly Gly His Asp Ala Lys
                260                 265                 270

TTT ATA GAT AGT TTA CAG GAA AAC GAA TTT CGT CTA TAT TAT TAT AAT      864
Phe Ile Asp Ser Leu Gln Glu Asn Glu Phe Arg Leu Tyr Tyr Tyr Asn
            275                 280                 285

AAG TTT AAA GAT ATA GCA AGT ACA CTT AAT AAA GCT AAA TCA ATA GTA      912
Lys Phe Lys Asp Ile Ala Ser Thr Leu Asn Lys Ala Lys Ser Ile Val
290                 295                 300

GGT ACT ACT GCT TCA TTA CAG TAT ATG AAA AAT GTT TTT AAA GAG AAA      960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA     1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT     1056
Lys Phe Asp Lys Leu Tyr Lys Met Leu Thr Glu Ile Tyr Thr Glu Asp
                340                 345                 350

AAT TTT GTT AAG TTT TTT AAA GTA CTT AAC AGA AAA ACA TAT TTG AAT     1104
Asn Phe Val Lys Phe Phe Lys Val Leu Asn Arg Lys Thr Tyr Leu Asn
            355                 360                 365

TTT GAT AAA GCC GTA TTT AAG ATA AAT ATA GTA CCT AAG GTA AAT TAC     1152
Phe Asp Lys Ala Val Phe Lys Ile Asn Ile Val Pro Lys Val Asn Tyr
370                 375                 380

ACA ATA TAT GAT GGA TTT AAT TTA AGA AAT ACA AAT TTA GCA GCA AAC     1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA     1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA     1296
Lys Asn Phe Thr Gly Leu Phe Glu Phe Tyr Lys Leu Leu Cys Val Arg
                420                 425                 430

GGG ATA ATA ACT TCT AAA ACT AAA TCA TTA GAT AAA GGA TAC AAT AAG     1344
Gly Ile Ile Thr Ser Lys Thr Lys Ser Leu Asp Lys Gly Tyr Asn Lys
            435                 440                 445

GCA TTA AAT GAT TTA TGT ATC AAA GTT AAT AAT TGG GAC TTG TTT TTT     1392
Ala Leu Asn Asp Leu Cys Ile Lys Val Asn Asn Trp Asp Leu Phe Phe
450                 455                 460

AGT CCT TCA GAA GAT AAT TTT ACT AAT GAT CTA AAT AAA GGA GAA GAA     1440
Ser Pro Ser Glu Asp Asn Phe Thr Asn Asp Leu Asn Lys Gly Glu Glu
465                 470                 475                 480

ATT ACA TCT GAT ACT AAT ATA GAA GCA GCA GAA GAA AAT ATT AGT TTA     1488
Ile Thr Ser Asp Thr Asn Ile Glu Ala Ala Glu Glu Asn Ile Ser Leu
                485                 490                 495

GAT TTA ATA CAA CAA TAT TAT TTA ACC TTT AAT TTT GAT AAT GAA CCT     1536
Asp Leu Ile Gln Gln Tyr Tyr Leu Thr Phe Asn Phe Asp Asn Glu Pro
            500                 505                 510

GAA AAT ATT TCA ATA GAA AAT CTT TCA AGT GAC ATT ATA GGC CAA TTA     1584
Glu Asn Ile Ser Ile Glu Asn Leu Ser Ser Asp Ile Ile Gly Gln Leu
```

```
                515                      520                      525
GAA CTT ATG CCT AAT ATA GAA AGA TTT CCT AAT GGA AAA AAG TAT GAG         1632
Glu Leu Met Pro Asn Ile Glu Arg Phe Pro Asn Gly Lys Lys Tyr Glu
        530                     535                     540

TTA GAT AAA TAT ACT ATG TTC CAT TAT CTT CGT GCT CAA GAA TTT GAA         1680
Leu Asp Lys Tyr Thr Met Phe His Tyr Leu Arg Ala Gln Glu Phe Glu
545                     550                     555                 560

CAT GGT AAA TCT AGG ATT GCT TTA ACA AAT TCT GTT AAC GAA GCA TTA         1728
His Gly Lys Ser Arg Ile Ala Leu Thr Asn Ser Val Asn Glu Ala Leu
                565                     570                     575

TTA AAT CCT AGT CGT GTT TAT ACA TTT TTT TCT TCA GAC TAT GTA AAG         1776
Leu Asn Pro Ser Arg Val Tyr Thr Phe Phe Ser Ser Asp Tyr Val Lys
            580                     585                     590

AAA GTT AAT AAA GCT ACG GAG GCA GCT ATG TTT TTA GGC TGG GTA GAA         1824
Lys Val Asn Lys Ala Thr Glu Ala Ala Met Phe Leu Gly Trp Val Glu
                595                     600                     605

CAA TTA GTA TAT GAT TTT ACC GAT GAA ACT AGC GAA GTA AGT ACT ACG         1872
Gln Leu Val Tyr Asp Phe Thr Asp Glu Thr Ser Glu Val Ser Thr Thr
        610                     615                     620

GAT AAA ATT GCG GAT ATA ACT ATA ATT ATT CCA TAT ATA GGA CCT GCT         1920
Asp Lys Ile Ala Asp Ile Thr Ile Ile Ile Pro Tyr Ile Gly Pro Ala
625                     630                     635                 640

TTA AAT ATA GGT AAT ATG TTA TAT AAA GAT GAT TTT GTA GGT GCT TTA         1968
Leu Asn Ile Gly Asn Met Leu Tyr Lys Asp Asp Phe Val Gly Ala Leu
                645                     650                     655

ATA TTT TCA GGA GCT GTT ATT CTG TTA GAA TTT ATA CCA GAG ATT GCA         2016
Ile Phe Ser Gly Ala Val Ile Leu Leu Glu Phe Ile Pro Glu Ile Ala
            660                     665                     670

ATA CCT GTA TTA GGT ACT TTT GCA CTT GTA TCA TAT ATT GCG AAT AAG         2064
Ile Pro Val Leu Gly Thr Phe Ala Leu Val Ser Tyr Ile Ala Asn Lys
        675                     680                     685

GTT CTA ACC GTT CAA ACA ATA GAT AAT GCT TTA AGT AAA AGA AAT GAA         2112
Val Leu Thr Val Gln Thr Ile Asp Asn Ala Leu Ser Lys Arg Asn Glu
        690                     695                     700

AAA TGG GAT GAG GTC TAT AAA TAT ATA GTA ACA AAT TGG TTA GCA AAG         2160
Lys Trp Asp Glu Val Tyr Lys Tyr Ile Val Thr Asn Trp Leu Ala Lys
705                     710                     715                 720

GTT AAT ACA CAG ATT GAT CTA ATA AGA AAA AAA ATG AAA GAA GCT TTA         2208
Val Asn Thr Gln Ile Asp Leu Ile Arg Lys Lys Met Lys Glu Ala Leu
                725                     730                     735

GAA AAT CAA GCA GAA GCA ACA AAG GCT ATA ATA AAC TAT CAG TAT AAT         2256
Glu Asn Gln Ala Glu Ala Thr Lys Ala Ile Ile Asn Tyr Gln Tyr Asn
            740                     745                     750

CAA TAT ACT GAG GAA GAG AAA AAT AAT ATT AAT TTT AAT ATT GAT GAT         2304
Gln Tyr Thr Glu Glu Glu Lys Asn Asn Ile Asn Phe Asn Ile Asp Asp
        755                     760                     765

TTA AGT TCG AAA CTT AAT GAG TCT ATA AAT AAA GCT ATG ATT AAT ATA         2352
Leu Ser Ser Lys Leu Asn Glu Ser Ile Asn Lys Ala Met Ile Asn Ile
        770                     775                     780

AAT AAA TTT TTG AAT CAA TGC TCT GTT TCA TAT TTA ATG AAT TCT ATG         2400
Asn Lys Phe Leu Asn Gln Cys Ser Val Ser Tyr Leu Met Asn Ser Met
785                     790                     795                 800

ATC CCT TAT GGT GTT AAA CGG TTA GAA GAT TTT GAT GCT AGT CTT AAA         2448
Ile Pro Tyr Gly Val Lys Arg Leu Glu Asp Phe Asp Ala Ser Leu Lys
                805                     810                     815

GAT GCA TTA TTA AAG TAT ATA TAT GAT AAT AGA GGA ACT TTA ATT GGT         2496
Asp Ala Leu Leu Lys Tyr Ile Tyr Asp Asn Arg Gly Thr Leu Ile Gly
            820                     825                     830

CAA GTA GAT AGA TTA AAA GAT AAA GTT AAT AAT ACA CTT AGT ACA GAT         2544
```

-continued

```
                Gln Val Asp Arg Leu Lys Asp Lys Val Asn Asn Thr Leu Ser Thr Asp
                            835                 840                 845

ATA CCT TTT CAG CTT TCC AAA TAC GTA GAT AAT CAA AGA TTA TTA TCT                 2592
Ile Pro Phe Gln Leu Ser Lys Tyr Val Asp Asn Gln Arg Leu Leu Ser
850                 855                 860

ACA TTT ACT GAA TAT ATT AAG AAT ATT ATT AAT ACT TCT ATA TTG AAT                 2640
Thr Phe Thr Glu Tyr Ile Lys Asn Ile Ile Asn Thr Ser Ile Leu Asn
865                 870                 875                 880

TTA AGA TAT GAA AGT AAT CAT TTA ATA GAC TTA TCT AGG TAT GCA TCA                 2688
Leu Arg Tyr Glu Ser Asn His Leu Ile Asp Leu Ser Arg Tyr Ala Ser
                            885                 890                 895

AAA ATA AAT ATT GGT AGT AAA GTA AAT TTT GAT CCA ATA GAT AAA AAT                 2736
Lys Ile Asn Ile Gly Ser Lys Val Asn Phe Asp Pro Ile Asp Lys Asn
                900                 905                 910

CAA ATT CAA TTA TTT AAT TTA GAA AGT AGT AAA ATT GAG GTA ATT TTA                 2784
Gln Ile Gln Leu Phe Asn Leu Glu Ser Ser Lys Ile Glu Val Ile Leu
            915                 920                 925

AAA AAT GCT ATT GTA TAT AAT AGT ATG TAT GAA AAT TTT AGT ACT AGC                 2832
Lys Asn Ala Ile Val Tyr Asn Ser Met Tyr Glu Asn Phe Ser Thr Ser
930                 935                 940

TTT TGG ATA AGA ATT CCT AAG TAT TTT AAC AGT ATA AGT CTA AAT AAT                 2880
Phe Trp Ile Arg Ile Pro Lys Tyr Phe Asn Ser Ile Ser Leu Asn Asn
945                 950                 955                 960

GAA TAT ACA ATA ATA AAT TGT ATG GAA AAT AAT TCA GGA TGG AAA GTA                 2928
Glu Tyr Thr Ile Ile Asn Cys Met Glu Asn Asn Ser Gly Trp Lys Val
                            965                 970                 975

TCA CTT AAT TAT GGT GAA ATA ATC TGG ACT TTA CAG GAT ACT CAG GAA                 2976
Ser Leu Asn Tyr Gly Glu Ile Ile Trp Thr Leu Gln Asp Thr Gln Glu
                980                 985                 990

ATA AAA CAA AGA GTA GTT TTT AAA TAC AGT CAA ATG ATT AAT ATA TCA                 3024
Ile Lys Gln Arg Val Val Phe Lys Tyr Ser Gln Met Ile Asn Ile Ser
            995                 1000                1005

GAT TAT ATA AAC AGA TGG ATT TTT GTA ACT ATC ACT AAT AAT AGA TTA                 3072
Asp Tyr Ile Asn Arg Trp Ile Phe Val Thr Ile Thr Asn Asn Arg Leu
       1010                1015                1020

AAT AAC TCT AAA ATT TAT ATA AAT GGA AGA TTA ATA GAT CAA AAA CCA                 3120
Asn Asn Ser Lys Ile Tyr Ile Asn Gly Arg Leu Ile Asp Gln Lys Pro
1025                1030                1035                1040

ATT TCA AAT TTA GGT AAT ATT CAT GCT AGT AAT AAT ATA ATG TTT AAA                 3168
Ile Ser Asn Leu Gly Asn Ile His Ala Ser Asn Asn Ile Met Phe Lys
                1045                1050                1055

TTA GAT GGT TGT AGA GAT ACA CAT AGA TAT ATT TGG ATA AAA TAT TTT                 3216
Leu Asp Gly Cys Arg Asp Thr His Arg Tyr Ile Trp Ile Lys Tyr Phe
            1060                1065                1070

AAT CTT TTT GAT AAG GAA TTA AAT GAA AAA GAA ATC AAA GAT TTA TAT                 3264
Asn Leu Phe Asp Lys Glu Leu Asn Glu Lys Glu Ile Lys Asp Leu Tyr
       1075                1080                1085

GAT AAT CAA TCA AAT TCA GGT ATT TTA AAA GAC TTT TGG GGT GAT TAT                 3312
Asp Asn Gln Ser Asn Ser Gly Ile Leu Lys Asp Phe Trp Gly Asp Tyr
1090                1095                1100

TTA CAA TAT GAT AAA CCA TAC TAT ATG TTA AAT TTA TAT GAT CCA AAT                 3360
Leu Gln Tyr Asp Lys Pro Tyr Tyr Met Leu Asn Leu Tyr Asp Pro Asn
1105                1110                1115                1120

AAA TAT GTC GAT GTA AAT AAT GTA GGT ATT AGA GGT TAT ATG TAT CTT                 3408
Lys Tyr Val Asp Val Asn Asn Val Gly Ile Arg Gly Tyr Met Tyr Leu
                1125                1130                1135

AAA GGG CCT AGA GGT AGC GTA ATG ACT ACA AAC ATT TAT TTA AAT TCA                 3456
Lys Gly Pro Arg Gly Ser Val Met Thr Thr Asn Ile Tyr Leu Asn Ser
            1140                1145                1150
```

```
AGT TTG TAT AGG GGG ACA AAA TTT ATT ATA AAA AAA TAT GCT TCT GGA       3504
Ser Leu Tyr Arg Gly Thr Lys Phe Ile Ile Lys Lys Tyr Ala Ser Gly
        1155                1160                1165

AAT AAA GAT AAT ATT GTT AGA AAT AAT GAT CGT GTA TAT ATT AAT GTA       3552
Asn Lys Asp Asn Ile Val Arg Asn Asn Asp Arg Val Tyr Ile Asn Val
        1170                1175                1180

GTA GTT AAA AAT AAA GAA TAT AGG TTA GCT ACT AAT GCA TCA CAG GCA       3600
Val Val Lys Asn Lys Glu Tyr Arg Leu Ala Thr Asn Ala Ser Gln Ala
1185                1190                1195                1200

GGC GTA GAA AAA ATA CTA AGT GCA TTA GAA ATA CCT GAT GTA GGA AAT       3648
Gly Val Glu Lys Ile Leu Ser Ala Leu Glu Ile Pro Asp Val Gly Asn
                1205                1210                1215

CTA AGT CAA GTA GTA GTA ATG AAG TCA AAA AAT GAT CAA GGA ATA ACA       3696
Leu Ser Gln Val Val Val Met Lys Ser Lys Asn Asp Gln Gly Ile Thr
                1220                1225                1230

AAT AAA TGC AAA ATG AAT TTA CAA GAT AAT AAT GGG AAT GAT ATA GGC       3744
Asn Lys Cys Lys Met Asn Leu Gln Asp Asn Asn Gly Asn Asp Ile Gly
        1235                1240                1245

TTT ATA GGA TTT CAT CAG TTT AAT AAT ATA GCT AAA CTA GTA GCA AGT       3792
Phe Ile Gly Phe His Gln Phe Asn Asn Ile Ala Lys Leu Val Ala Ser
        1250                1255                1260

AAT TGG TAT AAT AGA CAA ATA GAA AGA TCT AGT AGG ACT TTG GGT TGC       3840
Asn Trp Tyr Asn Arg Gln Ile Glu Arg Ser Ser Arg Thr Leu Gly Cys
1265                1270                1275                1280

TCA TGG GAA TTT ATT CCT GTA GAT GAT GGA TGG GGA GAA AGG CCA CTG       3888
Ser Trp Glu Phe Ile Pro Val Asp Asp Gly Trp Gly Glu Arg Pro Leu
                1285                1290                1295

TAA                                                                   3891

(2) INFORMATION FOR SEQ ID NO:28:

(i) SEQUENCE CHARACTERISTICS:
        (A) LENGTH: 1296 amino acids
        (B) TYPE: amino acid
        (D) TOPOLOGY: linear (ii) MOLECULE TYPE: protein (xi) SEQUENCE DESCRIPTION: SEQ ID NO:28:

Met Gln Phe Val Asn Lys Gln Phe Asn Tyr Lys Asp Pro Val Asn Gly
 1               5                  10                  15

Val Asp Ile Ala Tyr Ile Lys Ile Pro Asn Val Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
        50                  55                  60

Ala Lys Gln Val Pro Val Ser Tyr Tyr Asp Ser Thr Tyr Leu Ser Thr
 65                 70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160
```

-continued

```
Ile Gln Phe Glu Cys Lys Ser Phe Gly His Glu Val Leu Asn Leu Thr
            165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
            245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
            325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
            405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
            485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
```

-continued

```
Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
            595                 600             605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
            770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
```

-continued

```
                   995                 1000                     1005
Asp Tyr Ile Asn Arg Trp Ile Phe Val Thr Ile Thr Asn Asn Arg Leu
            1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
            1075                1080                1085

Asp Asn Gln Ser Asn Ser Gly Ile Leu Lys Asp Phe Trp Gly Asp Tyr
            1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Tyr Ala Ser Gly
            1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
                1220                1225                1230

Asn Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala Ser
            1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

(2) INFORMATION FOR SEQ ID NO:29:

(i) SEQUENCE CHARACTERISTICS:
        (A) LENGTH: 812 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:29:

Thr Ser Tyr Lys Ile Ile Asn Gly Lys His Phe Tyr Phe Asn Asn Asp
1               5                   10                  15

Gly Val Met Gln Leu Gly Val Phe Lys Gly Pro Asp Gly Phe Glu Tyr
            20                  25                  30

Phe Ala Pro Ala Asn Thr Gln Asn Asn Asn Ile Glu Gly Gln Ala Ile
        35                  40                  45

Val Tyr Gln Ser Lys Phe Leu Thr Leu Asn Gly Lys Lys Tyr Tyr Phe
```

-continued

```
                50                  55                  60
Asp Asn Asn Ser Lys Ala Val Thr Gly Trp Arg Ile Ile Asn Asn Glu
65                  70                  75                  80

Lys Tyr Tyr Phe Asn Pro Asn Ala Ile Ala Val Gly Leu Gln
                85                  90                  95

Val Ile Asp Asn Asn Lys Tyr Tyr Phe Asn Pro Asp Thr Ala Ile Ile
                100                 105                 110

Ser Lys Gly Trp Gln Thr Val Asn Gly Ser Arg Tyr Tyr Phe Asp Thr
                115                 120                 125

Asp Thr Ala Ile Ala Phe Asn Gly Tyr Lys Thr Ile Asp Gly Lys His
                130                 135                 140

Phe Tyr Phe Asp Ser Asp Cys Val Val Lys Ile Gly Val Phe Ser Thr
145                 150                 155                 160

Ser Asn Gly Phe Glu Tyr Phe Ala Pro Ala Asn Thr Tyr Asn Asn Asn
                165                 170                 175

Ile Glu Gly Gln Ala Ile Val Tyr Gln Ser Lys Phe Leu Thr Leu Asn
                180                 185                 190

Gly Lys Lys Tyr Tyr Phe Asp Asn Asn Ser Lys Ala Val Thr Gly Leu
                195                 200                 205

Gln Thr Ile Asp Ser Lys Lys Tyr Tyr Phe Asn Thr Asn Thr Ala Glu
210                 215                 220

Ala Ala Thr Gly Trp Gln Thr Ile Asp Gly Lys Lys Tyr Tyr Phe Asn
225                 230                 235                 240

Thr Asn Thr Ala Glu Ala Ala Thr Gly Trp Gln Thr Ile Asp Gly Lys
                245                 250                 255

Lys Tyr Tyr Phe Asn Thr Asn Thr Ala Ile Ala Ser Thr Gly Tyr Thr
                260                 265                 270

Ile Ile Asn Gly Lys His Phe Tyr Phe Asn Thr Asp Gly Ile Met Gln
                275                 280                 285

Ile Gly Val Phe Lys Gly Pro Asn Gly Phe Glu Tyr Phe Ala Pro Ala
                290                 295                 300

Asn Thr Asp Ala Asn Asn Ile Glu Gly Gln Ala Ile Leu Tyr Gln Asn
305                 310                 315                 320

Glu Phe Leu Thr Leu Asn Gly Lys Lys Tyr Tyr Phe Gly Ser Asp Ser
                325                 330                 335

Lys Ala Val Thr Gly Trp Arg Ile Ile Asn Asn Lys Lys Tyr Tyr Phe
                340                 345                 350

Asn Pro Asn Asn Ala Ile Ala Ala Ile His Leu Cys Thr Ile Asn Asn
                355                 360                 365

Asp Lys Tyr Tyr Phe Ser Tyr Asp Gly Ile Leu Gln Asn Gly Tyr Ile
                370                 375                 380

Thr Ile Glu Arg Asn Asn Phe Tyr Phe Asp Ala Asn Asn Glu Ser Lys
385                 390                 395                 400

Met Val Thr Gly Val Phe Lys Gly Pro Asn Gly Phe Glu Tyr Phe Ala
                405                 410                 415

Pro Ala Asn Thr His Asn Asn Asn Ile Glu Gly Gln Ala Ile Val Tyr
                420                 425                 430

Gln Asn Lys Phe Leu Thr Leu Asn Gly Lys Lys Tyr Tyr Phe Asp Asn
                435                 440                 445

Asp Ser Lys Ala Val Thr Gly Trp Gln Thr Ile Asp Gly Lys Lys Tyr
                450                 455                 460

Tyr Phe Asn Leu Asn Thr Ala Glu Ala Ala Thr Gly Trp Gln Thr Ile
465                 470                 475                 480
```

```
Asp Gly Lys Lys Tyr Tyr Phe Asn Leu Asn Thr Ala Glu Ala Ala Thr
                485                 490                 495
Gly Trp Gln Thr Ile Asp Gly Lys Lys Tyr Tyr Phe Asn Thr Asn Thr
            500                 505                 510
Phe Ile Ala Ser Thr Gly Tyr Thr Ser Ile Asn Gly Lys His Phe Tyr
            515                 520                 525
Phe Asn Thr Asp Gly Ile Met Gln Ile Gly Val Phe Lys Gly Pro Asn
            530                 535                 540
Gly Phe Glu Tyr Phe Ala Pro Ala Asn Thr Asp Ala Asn Asn Ile Glu
545                 550                 555                 560
Gly Gln Ala Ile Leu Tyr Gln Asn Lys Phe Leu Thr Leu Asn Gly Lys
                565                 570                 575
Lys Tyr Tyr Phe Gly Ser Asp Ser Lys Ala Val Thr Gly Leu Arg Thr
                580                 585                 590
Ile Asp Gly Lys Lys Tyr Tyr Phe Asn Thr Asn Thr Ala Val Ala Val
            595                 600                 605
Thr Gly Trp Gln Thr Ile Asn Gly Lys Lys Tyr Tyr Phe Asn Thr Asn
            610                 615                 620
Thr Ser Ile Ala Ser Thr Gly Tyr Thr Ile Ile Ser Gly Lys His Phe
625                 630                 635                 640
Tyr Phe Asn Thr Asp Gly Ile Met Gln Ile Gly Val Phe Lys Gly Pro
                645                 650                 655
Asp Gly Phe Glu Tyr Phe Ala Pro Ala Asn Thr Asp Ala Asn Asn Ile
                660                 665                 670
Glu Gly Gln Ala Ile Arg Tyr Gln Asn Arg Phe Leu Tyr Leu His Asp
            675                 680                 685
Asn Ile Tyr Tyr Phe Gly Asn Asn Ser Lys Ala Ala Thr Gly Trp Val
            690                 695                 700
Thr Ile Asp Gly Asn Arg Tyr Tyr Phe Glu Pro Asn Thr Ala Met Gly
705                 710                 715                 720
Ala Asn Gly Tyr Lys Thr Ile Asp Asn Lys Asn Phe Tyr Phe Arg Asn
                725                 730                 735
Gly Leu Pro Gln Ile Gly Val Phe Lys Gly Ser Asn Gly Phe Glu Tyr
            740                 745                 750
Phe Ala Pro Ala Asn Thr Asp Ala Asn Asn Ile Glu Gly Gln Ala Ile
            755                 760                 765
Arg Tyr Gln Asn Arg Phe Leu His Leu Leu Gly Lys Ile Tyr Tyr Phe
            770                 775                 780
Gly Asn Asn Ser Lys Ala Val Thr Gly Trp Gln Thr Ile Asn Gly Lys
785                 790                 795                 800
Val Tyr Tyr Phe Met Pro Asp Thr Ala Met Ala Ala
                805                 810
```

(2) INFORMATION FOR SEQ ID NO:30:

(i) SEQUENCE CHARACTERISTICS:
        (A) LENGTH: 609 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:30:

```
Thr Ser Glu Glu Asn Lys Val Ser Gln Val Lys Ile Arg Phe Val Asn
1               5                   10                  15
```

-continued

```
Val Phe Lys Asp Lys Thr Leu Ala Asn Lys Leu Ser Phe Asn Phe Ser
            20                  25                  30

Asp Lys Gln Asp Val Pro Val Ser Glu Ile Ile Leu Ser Phe Thr Pro
            35                  40                  45

Ser Tyr Tyr Glu Asp Gly Leu Ile Gly Tyr Asp Leu Gly Leu Val Ser
 50                  55                  60

Leu Tyr Asn Glu Lys Phe Tyr Ile Asn Asn Phe Gly Met Met Val Ser
 65                  70                  75                  80

Gly Leu Ile Tyr Ile Asn Asp Ser Leu Tyr Tyr Phe Lys Pro Pro Val
                 85                  90                  95

Asn Asn Leu Ile Thr Gly Phe Val Thr Val Gly Asp Asp Lys Tyr Tyr
                100                 105                 110

Phe Asn Pro Ile Asn Gly Gly Ala Ala Ser Ile Gly Glu Thr Ile Ile
            115                 120                 125

Asp Asp Lys Asn Tyr Tyr Phe Asn Gln Ser Gly Val Leu Gln Thr Gly
            130                 135                 140

Val Phe Ser Thr Glu Asp Gly Phe Lys Tyr Phe Ala Pro Ala Asn Thr
145                 150                 155                 160

Leu Asp Glu Asn Leu Glu Gly Glu Ala Ile Asp Phe Thr Gly Lys Leu
                165                 170                 175

Ile Ile Asp Glu Asn Ile Tyr Tyr Phe Asp Asp Asn Tyr Arg Gly Ala
                180                 185                 190

Val Glu Trp Lys Glu Leu Asp Gly Glu Met His Tyr Phe Ser Pro Glu
            195                 200                 205

Thr Gly Lys Ala Phe Lys Gly Leu Asn Gln Ile Gly Asp Tyr Lys Tyr
            210                 215                 220

Tyr Phe Asn Ser Asp Gly Val Met Gln Lys Gly Phe Val Ser Ile Asn
225                 230                 235                 240

Asp Asn Lys His Tyr Phe Asp Asp Ser Gly Val Met Lys Val Gly Tyr
                245                 250                 255

Thr Glu Ile Asp Gly Lys His Phe Tyr Phe Ala Glu Asn Gly Glu Met
            260                 265                 270

Gln Ile Gly Val Phe Asn Thr Glu Asp Gly Phe Lys Tyr Phe Ala His
            275                 280                 285

His Asn Glu Asp Leu Gly Asn Glu Glu Gly Glu Glu Ile Ser Tyr Ser
            290                 295                 300

Gly Ile Leu Asn Phe Asn Asn Lys Ile Tyr Tyr Phe Asp Asp Ser Phe
305                 310                 315                 320

Thr Ala Val Val Gly Trp Lys Asp Leu Glu Asp Gly Ser Lys Tyr Tyr
            325                 330                 335

Phe Asp Glu Asp Thr Ala Glu Ala Tyr Ile Gly Leu Ser Leu Ile Asn
            340                 345                 350

Asp Gly Gln Tyr Tyr Phe Asn Asp Asp Gly Ile Met Gln Val Gly Phe
            355                 360                 365

Val Thr Ile Asn Asp Lys Val Phe Tyr Phe Ser Asp Ser Gly Ile Ile
            370                 375                 380

Glu Ser Gly Val Gln Asn Ile Asp Asp Asn Tyr Phe Tyr Ile Asp Asp
385                 390                 395                 400

Asn Gly Ile Val Gln Ile Gly Val Phe Asp Thr Ser Asp Gly Tyr Lys
                405                 410                 415

Tyr Phe Ala Pro Ala Asn Thr Val Asn Asp Asn Ile Tyr Gly Gln Ala
            420                 425                 430
```

```
Val Glu Tyr Ser Gly Leu Val Arg Val Gly Glu Asp Val Tyr Tyr Phe
            435                 440                 445

Gly Glu Thr Tyr Thr Ile Glu Thr Gly Trp Ile Tyr Asp Met Glu Asn
        450                 455                 460

Glu Ser Asp Lys Tyr Tyr Phe Asn Pro Glu Thr Lys Lys Ala Cys Lys
465                 470                 475                 480

Gly Ile Asn Leu Ile Asp Asp Ile Lys Tyr Tyr Phe Asp Glu Lys Gly
                485                 490                 495

Ile Met Arg Thr Gly Leu Ile Ser Phe Glu Asn Asn Asn Tyr Tyr Phe
            500                 505                 510

Asn Glu Asn Gly Glu Met Gln Phe Gly Tyr Ile Asn Ile Glu Asp Lys
        515                 520                 525

Met Phe Tyr Phe Gly Glu Asp Gly Val Met Gln Ile Gly Val Phe Asn
    530                 535                 540

Thr Pro Asp Gly Phe Lys Tyr Phe Ala His Gln Asn Thr Leu Asp Glu
545                 550                 555                 560

Asn Phe Glu Gly Glu Ser Ile Asn Tyr Thr Gly Trp Leu Asp Leu Asp
                565                 570                 575

Glu Lys Arg Tyr Tyr Phe Thr Asp Glu Tyr Ile Ala Ala Thr Gly Ser
            580                 585                 590

Val Ile Ile Asp Gly Glu Glu Tyr Tyr Phe Asp Pro Asp Thr Ala Gln
                595                 600                 605

Leu (2) INFORMATION FOR SEQ ID NO:31:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Modified-site
        (B) LOCATION: 12
        (D) OTHER INFORMATION: /note= "The asparagine residue at
            this position contains an amide group."

(xi) SEQUENCE DESCRIPTION: SEQ ID NO:31:

Cys Gln Thr Ile Asp Gly Lys Lys Tyr Tyr Phe Asn
1               5                   10

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:32:

His His His His His
1               5
```

VACCINE AND ANTITOXIN FOR THE TREATMENT OF *C. DIFFICILE* DISEASE

This application is a Continuation of application Ser. No. 08/480,604 filed Jun. 7, 1995, now U.S. Pat. No. 5,736,139, which is a Continuation-in-Part of application Ser. No. 08/422,711 filed Apr. 14, 1995, now abandoned which is a Continuation-in-Part of application Ser. No. 08/405,496 filed Mar. 16, 1995, now U.S. Pat. No. 5,919,665, which is a Continuation-in-Part of application Ser. No. 08/329,154 filed, Oct. 24, 1994, now abandoned which is a Continuation-in-Part of application Ser. No. 08/161,907, filed on Dec. 2, 1993, now U.S. Pat. No. 5,601,823, which is a Continuation-in-Part of application Ser. No. 07/985,321, filed Dec. 4, 1992, which is a Continuation-in-Part of application Ser. No. 07/429,791, filed Oct. 31, 1989, now U.S. Pat. No. 5,196,193, all herein incorporated by reference.

FIELD OF THE INVENTION

The present invention relates to clostridial antitoxin and vaccine therapy for humans and other animals. Antitoxins which neutralize the pathologic effects of clostridial toxins are provided. Vaccines which prevent the morbidity and mortality associated with clostridial diseases are provided.

BACKGROUND OF THE INVENTION

The genus Clostridium is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. [See e.g., P. H. A. Sneath et al., "*Clostridium,*" *Bergey's Manual® of Systematic Bacteriology*, Vol. 2, pp. 1141–1200, Williams & Wilkins (1986).] Despite the identification of approximately 100 species of Clostridium, only a small number have been recognized as etiologic agents of medical and veterinary importance. Nonetheless, these species are associated with very serious diseases, including botulism, tetanus, anaerobic cellulitis, gas gangrene, bacteremia, pseudomembranous colitis, and clostridial gastroenteritis. Table 1 lists some of the species of medical and veterinary importance and the diseases with which they are associated. As virtually all of these species have been isolated from fecal samples of apparently healthy persons, some of these isolates may be transient, rather than permanent residents of the colonic flora.

TABLE 1

Clostridium Species of Medical and Veterinary Importance*

| Species | Disease |
| --- | --- |
| C. aminovalericum | Bacteriuria (pregnant women) |
| C. argentinense | Infected wounds; Bacteremia; Botulism; Infections of amniotic fluid |
| C. baratii | Infected war wounds; Peritonitis; Infectious processes of the eye, ear and prostate |
| C. beijerinckikii | Infected wounds |
| C. bifermentans | Infected wounds; Abscesses; Gas Gangrene; Bacteremia |
| C. botulinum | Food poisoning; Botulism (wound, food, infant) |
| C. butyricum | Urinary tract, lower respiratory tract, pleural cavity, and abdominal infections; Infected wounds; Abscesses; Bacteremia |
| C. cadaveris | Abscesses; Infected wounds |
| C. carnis | Soft tissue infections; Bacteremia |
| C. chauvoei | Blackleg |
| C. clostridioforme | Abdominal, cervical, scrotal, pleural, and other infections; Septicemia; Peritonitis; Appendicitis |
| C. cochlearium | Isolated from human disease processes, but role in disease unknown. |
| C. difficile | Antimicrobial-associated diarrhea; Pseudomembranous enterocolitis; Bacteremia; Pyogenic infections |
| C. fallax | Soft tissue infections |
| C. ghnoii | Soft tissue infections |
| C. glycolicum | Wound infections; Abscesses; Peritonitis |
| C. hastiforme | Infected war wounds; Bacteremia; Abscesses |
| C. histolyticum | Infected war wounds; Gas gangrene; Gingival plaque isolate |
| C. indolis | Gastrointestinal tract infections |
| C. innocuum | Gastrointestinal tract infections; Empyema |
| C. irregulare | Penile lesions |
| C. leptum | Isolated from human disease processes, but role in disease unknown. |
| C. limosum | Bacteremia; Peritonitis; Pulmonary infections |
| C. malenominatum | Various infectious processes |
| C. novyi | Infected wounds; Gas gangrene; Blackleg, Big head (ovine); Redwater disease (bovine) |
| C. oroticum | Urinary tract infections; Rectal abscesses |
| C. paraputrificum | Bacteremia; Peritonitis; Infected wounds; Appendicitis |
| C. perfringens | Gas gangrene; Anaerobic cellulitis; Intra-abdominal abscesses; Soft tissue infections; Food poisoning; Necrotizing pneumonia; Empyema; Meningitis; Bacteremia; Uterine Infections; Enteritis necrotans; Lamb dysentery; Struck; Ovine Enterotoxemia; |

TABLE 1-continued

Clostridium Species of Medical and Veterinary Importance*

| Species | Disease |
| --- | --- |
| C. putrefaciens | Bacteriuria (Pregnant women with bacteremia) |
| C. putrificum | Abscesses; Infected wounds; Bacteremia |
| C. ramosum | Infections of the abdominal cavity, genital tract, lung, and biliary tract; Bacteremia |
| C. sartagoforme | Isolated from human disease processes, but role in disease unknown. |
| C. septicum | Gas gangrene; Bacteremia; Suppurative infections; Necrotizing enterocolitis; Braxy |
| C. sordellii | Gas gangrene; Wound infections; Penile lesions; Bacteremia; Abscesses; Abdominal and vaginal infections |
| C. sphenoides | Appendicitis; Bacteremia; Bone and soft tissue infections; Intraperitoneal infections; Infected war wounds; Visceral gas gangrene; Renal abscesses |
| C. sporogenes | Gas gangrene; Bacteremia; Endocarditis; central nervous system and pleuropulmonary infections; Penile lesions; Infected war wounds; Other pyogenic infections |
| C. subterminale | Bacteremia; Empyema; Biliary tract, soft tissue and bone infections |
| C. symbiosum | Liver abscesses; Bacteremia; Infections resulting due to bowel flora |
| C. tertium | Gas gangrene; Appendicitis; Brain abscesses; Intestinal tract and soft tissue infections; Infected war wounds; Periodontitis; Bacteremia |
| C. tetani | Tetanus; Infected gums and teeth; Corneal ulcerations; Mastoid and middle ear infections; Intraperitoneal infections; Tetanus neonatorum; Postpartum uterine infections; Soft tissue infections, especially related to trauma (including abrasions and lacerations); Infections related to use of contaminated needles |
| C. thermosaccharolyticum | Isolated from human disease processes, but role in disease unknown. |

*Compiled from P.G. Engelkirk et al. "Classification", Principles and Practice of Clinical Anaerobic Bacteriology, pp. 22–23, Star Publishing Co., Belmont, CA (1992); J. Stephen and R.A. Petrowski, "Toxins Which Traverse Membranes and Deregulate Cells," in Bacterial Toxins, 2d ed., pp. 66–67, American Society for Microbiology (1986); R. Berkow and A.J. Fletcher (eds.), "Bacterial Diseases," Merck Manual of Diagnosis and Therapy, 16th ed., pp. 116–126, Merck Research Laboratories, Rahway, N.J. (1992); and O.H. Sigmund and C.M. Fraser (eds.), "Clostridial Infections," Merck Veterinary Manual, 5th ed., pp. 396–409, Merck & Co., Rahway, N.J. (1979).

In most cases, the pathogenicity of these organisms is related to the release of powerful exotoxins or highly destructive enzymes. Indeed, several species of the genus Clostridium produce toxins and other enzymes of great medical and veterinary significance. [C. L. Hatheway, Clin. Microbiol. Rev. 3:66–98 (1990).]

Perhaps because of their significance for human and veterinary medicine, much research has been conducted on these toxins, in particular those of *C. botulinum* and *C. difficile*.

C. botulinum

Several strains of *Clostridium botulinum* produce toxins of significance to human and animal health. [C. L. Hatheway, Clin. Microbiol. Rev. 3:66–98 (1990).] The effects of these toxins range from diarrheal diseases that can cause destruction of the colon, to paralytic effects that can cause death. Particularly at risk for developing clostridial diseases are neonates and humans and animals in poor health (e.g., those suffering from diseases associated with old age or immunodeficiency diseases).

*Clostridium botulinum* produces the most poisonous biological toxin known. The lethal human dose is a mere $10^{-9}$ mg/kg bodyweight for toxin in the bloodstream. Botulinal toxin blocks nerve transmission to the muscles, resulting in flaccid paralysis. When the toxin reaches airway and respiratory muscles, it results in respiratory failure that can cause death. [S. Arnon, J. Infect. Dis. 154:201–206 (1986).]

*C. botulinum* spores are carried by dust and are found on vegetables taken from the soil, on fresh fruits, and on agricultural products such as honey. Under conditions favorable to the organism, the spores germinate to vegetative cells which produces toxin. [S. Arnon, Ann. Rev. Med. 31:541 (1980).]

Botulism disease may be grouped into four types, based on the method of introduction of toxin into the bloodstream. Food-borne botulism results from ingesting improperly preserved and inadequately heated food that contains botulinal toxin. There were 355 cases of food-borne botulism in the United States between 1976 and 1984. [K. L. MacDonald et al., Am. J. Epidemiol. 124:794 (1986).] The death rate due to botulinal toxin is 12% and can be higher in particular risk groups. [C. O. Tacket et al., Am. J. Med. 76:794 (1984).] Wound-induced botulism results from *C. botulinum* penetrating traumatized tissue and producing toxin that is absorbed into the bloodstream. Since 1950, thirty cases of wound botulism have been reported. [M. N. Swartz, "Anaerobic Spore-Forming Bacilli: The Clostridia," pp. 633–646, in B. D. Davis et al.,(eds.), *Microbiology*, 4th edition, J. B. Lippincott Co. (1990).] Inhalation botulism results when the toxin is inhaled. Inhalation botulism has been reported as the result of accidental exposure in the laboratory [E. Holzer, Med. Klin. 41:1735 (1962)] and could arise if the toxin is used as an agent of biological warfare [D. R. Franz et al., in *Botulinum and Tetanus Neurotoxins*, B. R.

DasGupta, ed., Plenum Press, New York (1993), pp. 473–476]. Infectious infant botulism results from *C. botulinum* colonization of the infant intestine with production of toxin and its absorption into the bloodstream. It is likely that the bacterium gains entry when spores are ingested and subsequently germinate. [S. Arnon, J. Infect. Dis. 154:201 (1986).] There have been 500 cases reported since it was first recognized in 1976. [M. N. Swartz, supra.]

Infant botulism strikes infants who are three weeks to eleven months old (greater than 90% of the cases are infants less than six months). [S. Arnon, J. Infect. Dis. 154:201 (1986).] It is believed that infants are susceptible, due, in large part, to the absence of the full adult complement of intestinal microflora. The benign microflora present in the adult intestine provide an acidic environment that is not favorable to colonization by *C. botulinum*. Infants begin life with a sterile intestine which is gradually colonized by microflora. Because of the limited microflora present in early infancy, the intestinal environment is not as acidic, allowing for *C. botulinum* spore germination, growth, and toxin production. In this regard, some adults who have undergone antibiotic therapy which alters intestinal microflora become more susceptible to botulism.

An additional factor accounting for infant susceptibility to infectious botulism is the immaturity of the infant immune system. The mature immune system is sensitized to bacterial antigens and produces protective antibodies. Secretory IgA produced in the adult intestine has the ability to agglutinate vegetative cells of *C. botulinum*. [S. Arnon, J. Infect. Dis. 154:201 (1986).] Secretory IgA may also act by preventing intestinal bacteria and their products from crossing the cells of the intestine. [S. Arnon, Epidemiol. Rev. 3:45 (1981).] The infant immune system is not primed to do this.

Clinical symptoms of infant botulism range from mild paralysis, to moderate and severe paralysis requiring hospitalization, to fulminant paralysis, leading to sudden death. [S. Arnon, Epidemiol. Rev. 3:45 (1981).]

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment. [T. L. Frankovich and S. Arnon, West. J. Med. 154:103 (1991).]

Different strains of *Clostridium botulinum* each produce antigenically distinct toxin designated by the letters A–G. Serotype A toxin has been implicated in 26% of the cases of food botulism; types B, E and F have also been implicated in a smaller percentage of the food botulism cases [H. Sugiyama, Microbiol. Rev. 44:419 (1980)]. Wound botulism has been reportedly caused by only types A or B toxins [H. Sugiyama, supra]. Nearly all cases of infant botulism have been caused by bacteria producing either type A or type B toxin. (Exceptionally, one New Mexico case was caused by *Clostridium botulinum* producing type F toxin and another by *Clostridium botulinum* producing a type B-type F hybrid.) [S. Arnon, Epidemiol. Rev. 3:45 (1981).] Type C toxin affects waterfowl, cattle, horses and mink. Type D toxin affects cattle, and type E toxin affects both humans and birds.

A trivalent antitoxin derived from horse plasma is commercially available from Connaught Industries Ltd. as a therapy for toxin types A, B, and E. However, the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly. [C. O. Tacket et al., Am. J. Med. 76:794 (1984).]

A heptavalent equine botulinal antitoxin which uses only the F(ab')2 portion of the antibody molecule has been tested by the United States Military. [M. Balady, USAMRDC Newsletter, p. 6 (1991).] This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens. [P. J. Schwarz and S. S. Arnon, Western J. Med. 156:197 (1992).]

Infant botulism has been implicated as the cause of mortality in some cases of Sudden Infant Death Syndrome (SIDS, also known as crib death). SIDS is officially recognized as infant death that is sudden and unexpected and that remained unexplained despite complete post-mortem examination. The link of SIDS to infant botulism came when fecal or blood specimens taken at autopsy from SIDS infants were found to contain *C. botulinum* organisms and/or toxin in 3–4% of cases analyzed. [D. R. Peterson et al., Rev. Infect. Dis. 1:630 (1979).] In contrast, only 1 of 160 healthy infants (0.6%) had *C. botulinum* organisms in the feces and no botulinal toxin. (S. Arnon et al., Lancet, pp. 1273–76, Jun. 17, 1978.)

In developed countries, SIDS is the number one cause of death in children between one month and one year old. (S. Arnon et al., Lancet, pp. 1273–77, Jun. 17, 1978.) More children die from SIDS in the first year than from any other single cause of death in the first fourteen years of life. In the United States, there are 8,000–10,000 SIDS victims annually. Id.

What is needed is an effective therapy against infant botulism that is free of dangerous side effects, is available in large supply at a reasonable price, and can be safely and gently delivered so that prophylactic application to infants is feasible.

Immunization of subjects with toxin preparations has been done in an attempt to induce immunity against botulinal toxins. A *C. botulinum* vaccine comprising chemically inactivated (i.e., formaldehyde-treated) type A, B,C, D and E toxin is commercially available for human usage. However, this vaccine preparation has several disadvantages. First, the efficacy of this vaccine is variable (in particular, only 78% of recipients produce protective levels of anti-type B antibodies following administration of the primary series). Second, immunization is painful (deep subcutaneous inoculation is required for administration), with adverse reactions being common (moderate to severe local reactions occur in approximately 6% of recipients upon initial injection; this number rises to approximately 11% of individuals who receive booster injections) [Informational Brochure for the Pentavalent (ABCDE) Botulinum Toxoid, Centers for Disease Control]. Third, preparation of the vaccine is dangerous as active toxin must be handled by laboratory workers.

What is needed are safe and effective vaccine preparations for administration to those at risk of exposure to *C. botulinum* toxins.

*C. difficile*

*C. difficile*, an organism which gained its name due to difficulties encountered in its isolation, has recently been proven to be an etiologic agent of diarrheal disease. (Sneath et al., p. 1165.). *C. difficile* is present in the gastrointestinal tract of approximately 3% of healthy adults, and 10–30% of neonates without adverse effect (Swartz, at p. 644); by other estimates, *C. difficile* is a part of the normal gastrointestinal flora of 2–10% of humans. [G. F. Brooks et al., (eds.) "*Infections Caused by Anaerobic Bacteria,*" Jawetz, Melnick, & Adelberg's Medical Microbiology, 19th ed., pp. 257–262, Appleton & Lange, San Mateo, Calif. (1991).] As these organisms are relatively resistant to most commonly used antimicrobials, when a patient is treated with antibiotics, the other members of the normal gastrointestinal flora are suppressed and *C. difficile* flourishes, producing cytopathic toxins and enterotoxins. It has been found in 25% of cases of moderate diarrhea resulting from treatment with antibiotics, especially the cephalosporins, clindamycin, and ampicillin. [M.N. Swartz at 644.]

Importantly, *C. difficile* is commonly associated with nosocomial infections. The organism is often present in the hospital and nursing home environments and may be carried on the hands and clothing of hospital personnel who care for debilitated and immunocompromised patients. As many of these patients are being treated with antimicrobials or other chemotherapeutic agents, such transmission of *C. difficile* represents a significant risk factor for disease. (Engelkirk et al., pp. 64–67.)

*C. difficile* is associated with a range of diarrhetic illness, ranging from diarrhea alone to marked diarrhea and necrosis of the gastrointestinal mucosa with the accumulation of inflammatory cells and fibrin, which forms a pseudomembrane in the affected area. (Brooks et al.) It has been found in over 95% of pseudomembranous enterocolitis cases. (Swartz, at p. 644.) This occasionally fatal disease is characterized by diarrhea, multiple small colonic plaques, and toxic megacolon. (Swartz, at p. 644.) Although stool cultures are sometimes used for diagnosis, diagnosis is best made by detection of the heat labile toxins present in fecal filtrates from patients with enterocolitis due to *C. difficile*. (Swartz, at p. 644–645; and Brooks et al., at p. 260.) *C. difficile* toxins are cytotoxic for tissue/cell cultures and cause enterocolitis when injected intracecally into hamsters. (Swartz, at p. 644.)

The enterotoxicity of *C. difficile* is primarily due to the action of two toxins, designated A and B, each of approximately 300,000 in molecular weight. Both are potent cytotoxins, with toxin A possessing direct enterocytotoxic activity. [Lyerly et al., Infect. Immun. 60:4633 (1992).] Unlike toxin A of *C. perfringens*, an organism rarely associated with antimicrobial-associated diarrhea, the toxin of *C. difficile* is not a spore coat constituent and is not produced during sporulation. (Swartz, at p. 644.) *C. difficile* toxin A causes hemorrhage, fluid accumulation and mucosal damage in rabbit ileal loops and appears to increase the uptake of toxin B by the intestinal mucosa. Toxin B does not cause intestinal fluid accumulation, but it is 1000 times more toxic than toxin A to tissue culture cells and causes membrane damage. Although both toxins induce similar cellular effects such as actin disaggregation, differences in cell specificity occurs.

Both toxins are important in disease. [Borriello et al., Rev. Infect. Dis., 12(suppl. 2):S185 (1990); Lyerly et al., Infect. Immun., 47:349 (1985); and Rolfe, Infect. Immun., 59:1223 (1990).] Toxin A is thought to act first by binding to brush border receptors, destroying the outer mucosal layer, then allowing toxin B to gain access to the underlying tissue. These steps in pathogenesis would indicate that the production of neutralizing antibodies against toxin A may be sufficient in the prophylactic therapy of CDAD. However, antibodies against toxin B may be a necessary additional component for an effective therapeutic against later stage colonic disease. Indeed, it has been reported that animals require antibodies to both toxin A and toxin B to be completely protected against the disease. [Kim and Rolfe, Abstr. Ann. Meet. Am. Soc. Microbiol., 69:62 (1987).]

*C. difficile* has also been reported to produce other toxins such as an enterotoxin different from toxins A and B [Banno et al., Rev. Infect. Dis., 6(Suppl. 1:S11–S20 (1984)], a low molecular weight toxin [Rihn et al., Biochem. Biophys. Res. Comm., 124:690–695 (1984)], a motility altering factor [Justus et al., Gastroenterol., 83:836–843 (1982)], and perhaps other toxins. Regardless, *C. difficile* gastrointestinal disease is of primary concern.

It is significant that due to its resistance to most commonly used antimicrobials, *C. difficile* is associated with antimicrobial therapy with virtually all antimicrobial agents (although most commonly ampicillin, clindamycin and cephalosporins). It is also associated with disease in patients undergoing chemotherapy with such compounds as methotrexate, 5-fluorouracil, cyclophosphamide, and doxorubicin. [S. M. Finegold et al., *Clinical Guide to Anaerobic Infections*, pp. 88–89, Star Publishing Co., Belmont, Calif. (1992).]

Treatment of *C. difficile* disease is problematic, given the high resistance of the organism. Oral metronidazole, bacitracin and vancomycin have been reported to be effective. (Finegold et al., p. 89.) However there are problems associated with treatment utilizing these compounds. Vancomycin is very expensive, some patients are unable to take oral medication, and the relapse rate is high (20–25%), although it may not occur for several weeks. Id.

*C. difficile* disease would be prevented or treated by neutralizing the effects of these toxins in the gastrointestinal tract. Thus, what is needed is an effective therapy against *C. difficile* toxin that is free of dangerous side effects, is available in large supply at a reasonable price, and can be safely delivered so that prophylactic application to patients at risk of developing pseudomembranous enterocolitis can be effectively treated.

DESCRIPTION OF THE DRAWINGS

FIG. 6 is a restriction map of *C. difficile* toxin A gene, showing sequences of primers 1–4 (SEQ ID NOS:1–4).

FIG. 23 shows *C. difficile* toxin B expression constructs.

FIG. 24 is a Western blot of *C. difficile* toxin B reactive protein.

FIG. 27 shows *C. botulinum* type A toxin expression constructs; constructs used to provide *C. botulinum* sequences are also shown.

DEFINITIONS

Figure 1:
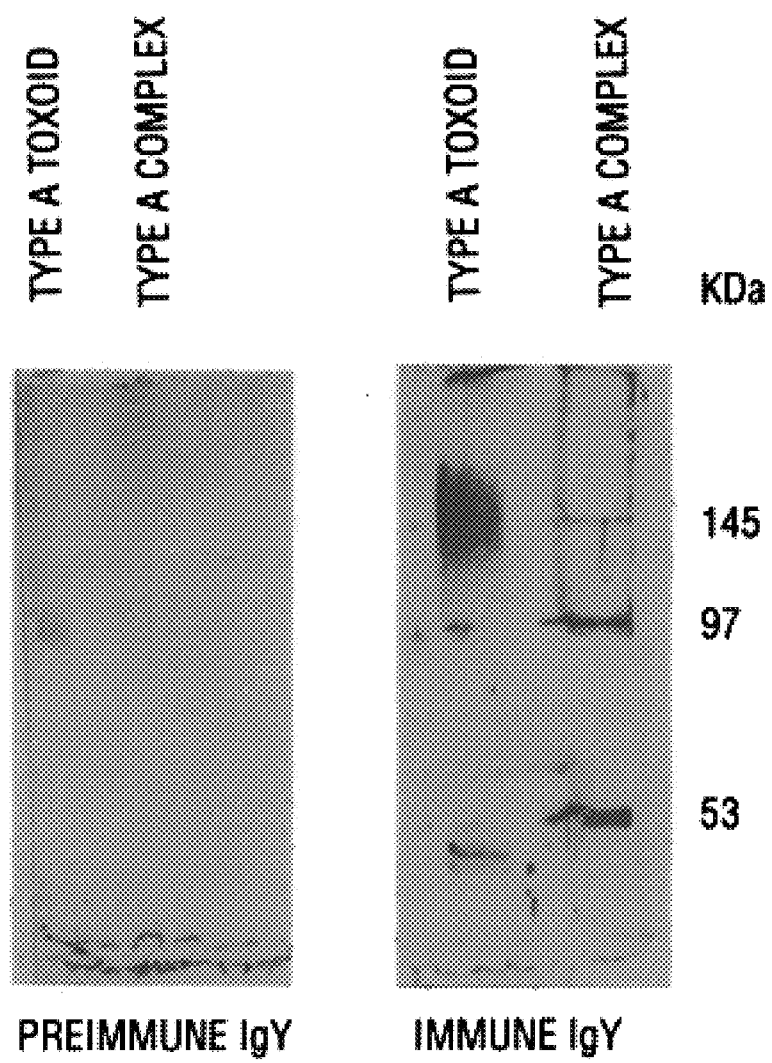
FIG. 1 shows the reactivity of anti-*C. botulinum* IgY by Western blot.

To facilitate understanding of the invention, a number of terms are defined below.

As used herein, the term "neutralizing" is used in reference to antitoxins, particularly antitoxins comprising antibodies, which have the ability to prevent the pathological actions of the toxin against which the antitoxin is directed.

As used herein, the term "overproducing" is used in reference to the production of clostridial toxin polypeptides in a host cell and indicates that the host cell is producing more of the clostridial toxin by virtue of the introduction of nucleic acid sequences encoding said clostridial toxin polypeptide than would be expressed by said host cell absent the introduction of said nucleic acid sequences. To allow ease of purification of toxin polypeptides produced in a host cell it is preferred that the host cell express or overproduce said toxin polypeptide at a level greater than 1 mg/liter of host cell culture.

As used herein, the term "fusion protein" refers to a chimeric protein containing the protein of interest (i.e., *C.*

*difficile* toxin A or B and fragments thereof) joined to an exogenous protein fragment (the fusion partner which consists of a non-toxin protein). The fusion partner may enhance solubility of the *C. difficile* protein as expressed in a host cell, may provide an affinity tag to allow purification of the recombinant fusion protein from the host cell or culture supernatant, or both. If desired, the fusion protein may be removed from the protein of interest (i.e., toxin protein or fragments thereof) prior to immunization by a variety of enzymatic or chemical means known to the art.

As used herein the term "non-toxin protein" or "non-toxin protein sequence" refers to that portion of a fusion protein which comprises a protein or protein sequence which is not derived from a bacterial toxin protein.

The term "protein of interest" as used herein refers to the protein whose expression is desired within the fusion protein. In a fusion protein the protein of interest will be joined or fused with another protein or protein domain, the fusion partner, to allow for enhanced stability of the protein of interest and/or ease of purification of the fusion protein.

As used herein, the term "maltose binding protein" refers to the maltose binding protein of *E. coli*. A portion of the maltose binding protein may be added to a protein of interest to generate a fusion protein; a portion of the maltose binding protein may merely enhance the solubility of the resulting fusion protein when expressed in a bacterial host. On the other hand, a portion of the maltose binding protein may allow affinity purification of the fusion protein on an amylose resin.

As used herein, the term "poly-histidine tract" when used in reference to a fusion protein refers to the presence of two to ten histidine residues at either the amino- or carboxy-terminus or both termini of a protein of interest or a fusion partner. A poly-histidine tract of six to ten residues is preferred. The poly-histidine tract is also defined functionally as being a number of consecutive histidine residues added to the protein of interest which allows the affinity purification of the resulting fusion protein on a nickel-chelate column.

The term "thioredoxin protein" when used in reference to a fusion protein refers to a the thioredoxin protein of *E. coli*. It is noted that the invention is not limited by the source of the thioredoxin protein, while the *E. coli* thioredoxin protein is particularly preferred, thioredoxin proteins may be obtained from several sources. A portion of the thioredoxin protein may be added to a protein of interest to generate a fusion protein; a portion of the thioredoxin protein may enhance the solubility of the resulting fusion protein when expressed in a bacterial host.

As used herein, the term "purified" or "to purify" refers to the removal of contaminants from a sample. For example, antitoxins are purified by removal of contaminating non-immunoglobulin proteins; they are also purified by the removal of immunoglobulin that does not bind toxin. The removal of non-immunoglobulin proteins and/or the removal of immunoglobulins that do not bind toxin results in an increase in the percent of toxin-reactive immunoglobulins in the sample. The purification of antitoxin may be accomplished by a variety of means including the extraction and precipitation of avian antitoxin from eggs using polyethylene glycol. Purification of anticlostridal antitoxin may also be accomplished by affinity chromatography on a resin comprising a portion of a clostridial toxin protein. In another example, recombinant toxin polypeptides are expressed in bacterial host cells and the toxin polypeptides are purified by the removal of host cell proteins; the percent of recombinant toxin polypeptides is thereby increased in the sample. Additionally, the recombinant toxin polypeptides are purified by the removal of host cell components such as lipopolysaccharide (e.g., endotoxin).

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein refers to a protein which is isolated from a natural source as opposed to the production of a protein by recombinant means.

As used herein the term "portion" when in reference to a protein (as in "a portion of a given protein") refers to fragments of that protein. The fragments may range in size from four amino acid residues to the entire amino acid sequence minus one amino acid.

As used herein "soluble" when in reference to a protein produced by recombinant DNA technology in a host cell is a protein which exists in solution in the cytoplasm of the host cell; if the protein contains a signal sequence the soluble protein is exported to the periplasmic space in bacteria hosts and is secreted into the culture medium in eucaryotic cells capable of secretion or by bacterial host possessing the appropriate genes (i.e., the kil gene). In contrast, an insoluble protein is one which exists in denatured form inside cytoplasmic granules (called an inclusion bodies) in the host cell. High level expression (i.e., greater than 10–20 mg recombinant protein/liter of bacterial culture) of recombinant proteins often results in the expressed protein being found in inclusion bodies in the bacterial host cells. A soluble protein is a protein which is not found in an inclusion body inside the host cell or is found both in the cytoplasm and in inclusion bodies and in this case the protein may be present at high or low levels in the cytoplasm.

A distinction is drawn between a soluble protein (i.e., a protein which when expressed in a host cell is produced in a soluble form) and a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (refold). Not all proteins will refold into an active conformation after solubilization in a denaturant and removal of the denaturant. Many proteins precipitate upon removal of the denaturant. SDS may be used to solubilize inclusion bodies and will maintain the proteins in solution at low concentration. However, dialysis will not always remove all of the SDS (SDS can form micelles which do not dialyze out); therefore, SDS-solubilized inclusion body protein is soluble but not refolded.

A distinction is drawn between proteins which are soluble (i.e., dissolved) in a solution devoid of significant amounts of ionic detergents (e.g., SDS) or denaturants (e.g., urea, guanidine hydrochloride) and proteins which exist as a suspension of insoluble protein molecules dispersed within the solution. A soluble protein will not be removed from a solution containing the protein by centrifugation using conditions sufficient to remove bacteria present in a liquid medium (i.e., centrifugation at 5,000×g for 4–5 minutes). For example, to test whether two proteins, protein A and protein B, are soluble in solution, the two proteins are placed into a solution selected from the group consisting of PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP-40, PBS-C containing either 0.1 or 0.5% Triton X-100, PBS-C containing 0.1% sodium deoxycholate. The mixture containing proteins A and B is then centrifuged at 5000×g for 5 minutes. The supernatant and pellet formed by centrifugation are then assayed for the presence of protein A and B. If protein A is found in the supernatant and not in the pellet [except for minor amounts (i.e., less than 10%) as a result of trapping], protein is said to be soluble in the solution tested. If the majority of protein B is found in the pellet (i.e., greater than 90%), then protein B is said to exist as a suspension in the solution tested.

As used herein, the term "therapeutic amount" refers to that amount of antitoxin required to neutralize the pathologic effects of one or more clostridial toxins in a subject.

The term "therapeutic mixture" when used in reference to a mixture of antitoxins refers to that amount of antitoxin required neutralize the pathologic effects of one or more clostridial toxins in a subject.

The term "therapeutic vaccine" when used in reference to a vaccine comprising one or more recombinant clostridial toxin fusion proteins means that the vaccine contains an irnmunologically-effective amount of the fusion proteins (i.e., the immunogens.

As used herein the term "immunogenically-effective amount" refers to that amount of an immunogen required to invoke the production of protective levels of antibodies in a host (i.e., a subject) upon vaccination.

The term "pyrogen" as used herein refers to a fever-producing substance. Pyrogens may be endogenous to the host (e.g., prostaglandins) or may be exogenous compounds (e.g., bacterial endo- and exotoxins, nonbacterial compounds such as antigens and certain steroid compounds, etc.). The presence of pyrogen in a pharmaceutical solution may be detected using the U.S. Pharmacopeia (USP) rabbit fever test (United States Pharmacopeia, Vol. XXII (1990) United States Pharmacopeial Convention, Rockville, Md., p. 151).

The term "endotoxin" as used herein refers to the high molecular weight complexes associated with the outer membrane of gram-negative bacteria. Unpurified endotoxin contains lipids, proteins and carbohydrates. Highly purified endotoxin does not contain protein and is referred to as lipopolysaccharide (LPS). Because unpurified endotoxin is of concern in the production of pharmaceutical compounds (e.g., proteins produced in E. coli using recombinant DNA technology), the term endotoxin as used herein refers to unpurified endotoxin. Bacterial endotoxin is a well known pyrogen.

As used herein, the term "endotoxin-free" when used in reference to a composition to be administered parenterally (with the exception of intrathecal administration) to a host means that the dose to be delivered contains less than 5 EU/kg body weight [FDA Guidelines for Parenteral Drugs (December 1987)]. Assuming a weight of 70 kg for an adult human, the dose must contain less than 350 EU to meet FDA Guidelines for parenteral administration. Endotoxin levels are measured herein using the Limulus Amebocyte Lysate (LAL) test (Limulus Amebocyte Lysate Pyrochrome™, Associates of Cape Cod, Inc. Woods Hole, Mass.). To measure endotoxin levels in preparations of recombinant proteins, 0.5 ml of a solution comprising 0.5 mg of purified recombinant protein in 50 mM $NaPO_4$, pH 7.0, 0.3M NaCl and 10% glycerol is used in the LAL assay according to the manufacturer's instructions for the endpoint chromogenic without diazo-coupling method. Compositions containing less than or equal to 450 endotoxin units (EU)/mg of purified recombinant protein are herein defined as "substantially endotoxin-free." Typically, administration of bacterial toxins or toxoids to adult humans for the purpose of vaccination involves doses of about 10–500 µg protein/dose. Therefore, administration of 10–500 µg of a purified recombinant protein to a 70 kg human, wherein said purified recombinant protein preparation contains 450 EU/mg protein, results in the introduction of only 4.5 to 225 EU (i.e., 1.3 to 64.5% of the maximum allowable endotoxin burden per parenteral dose).

The LAL test is accepted by the U.S. FDA as a means of detecting bacterial endotoxins (21 C.F.R. §§660.100–105). Studies have shown that the LAL test is equivalent or superior to the USP rabbit pyrogen test for the detection of endotoxin and thus the LAL test can be used as a surrogate for pyrogenicity studies in animals [F. C. Perason, *Pyrogens: endotoxins, LAL testing and depyrogenation*, Marcel Dekker, New York (1985), pp.150–155]. The FDA Bureau of Biologics accepts the LAL assay in place of the USP rabbit pyrogen test so long as the LAL assay utilized is shown to be as sensitive as, or more sensitive as the rabbit test [Fed. Reg., 38, 26130 (1980)].

The term "monovalent" when used in reference to a clostridial vaccine refers to a vaccine which is capable of provoking an immune response in a host (i.e., a subject) animal directed against a single type of clostridial toxin. For example, if immunization of a host with C. difficile type A toxin vaccine induces antibodies in the immunized host which protect against a challenge with type A toxin but not against challenge with type B toxin, then the type A vaccine is said to be monovalent. In contrast, a "multivalent" vaccine provokes an immune response in a host animal directed against several (i.e., more than one) clostridial toxins. For example, if immunization of a host with a vaccine comprising C. difficile type A and B toxins induces the production of antibodies which protect the host against a challenge with both type A and B toxin, the vaccine is said to be multivalent (in particular, this hypothetical vaccine is bivalent).

As used herein, the terms "aggregate" and "aggregation" refer to the production of clumps, groupings, or masses of materials. It is not intended that the terms be limited to a particular type of clumping. Rather, it is intended that the term be used in its broadest sense to encompass any situation where multiple items are brought together into close contact. Thus, the term encompasses agglutination of any type (including, but not limited to latex agglutination, hemagglutination, or any other method in which an immunological reaction is used to produce agglutination). The terms also apply to non-immunological methods, and also encompass non-specific relationships between multiple components; all that is required is that the individual components be clumped together.

The term "subject" when used in reference to administration of compositions comprising antitoxins or vaccines refers to the recipient animal to whom said antitoxins or vaccines are administered. The subject may be any animal, including mammals and more particularly, humans, in which it is desirable to administer said compositions. The subject may have been previously exposed to one or more C. difficile toxins prior to administration of said compositions (this constitutes therapeutic administration to the subject). Alternatively, the subject may not have been previously exposed to *C. difficile* toxins prior to administration of said compositions (this constitutes prophylactic administration to the subject).

The term "sample" in the present specification and claims is used in its broadest sense. On the one hand it is meant to include a specimen or culture (e.g., microbiological cultures). On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as eral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "culture" is used in reference to the in vivo or in vitro growth of organisms, including, but not limited to bacteria. It is intended that the term encompass any form of microbial culture. It is intended that the term encompass the propagation of micoorganisms or other living cells in media and in an environment that is conducive to their growth. Such cultures may be grown in any format, including but not limited to agar plates, broths, and semi-solid media, and may be grown in any environment suitable for the organisms cultured (i.e., aerobic, anaerobic, microaerophilic, etc.).

As used herein, the term "supernatant" is used in reference to any liquid or fluid solution. This liquid or fluid may or may not contain soluble particles such as proteins (e.g., antibodies or toxin molecules). The term encompasses any liquid lying above precipitated insoluble material, as well as liquids such as liquid culture media collected from a microbial or cell culture. It also encompasses the liquid portion of a sample which has been centrifuged to separate insoluble particles which are incapable of remaining in solution during centrifugation, from particles which are capable of remaining in solution during centrifugation. However, it is not intended that the term be limited to the situation in which centrifugation is utilized.

The term "protective level", when used in reference to the level of antibodies induced upon immunization of the host with an immunogen which comprises a bacterial toxin, means a level of circulating antibodies sufficient to protect the host from challenge with a lethal dose of the toxin.

As used herein the terms "protein" and "polypeptide" refer to compounds comprising amino acids joined via peptide bonds and are used interchangeably.

The term "toxin" when used in reference to toxins produced by members (i.e., species and strains) of the genus Clostridium refers to the proteins which are poisonous to tissue(s). For example, the toxins produced by *C. dfficile* are poisonous to intestinal tissues; the toxins produced by *C. botulinum* are poisonous to nerve tissue.

The terms "encapsulation" or "encapsulating" refers to the covering of a solid (e.g., lyophilized) form of antitoxin. The covering may comprise an enteric coating or a capsule. The terms "enteric coating" or "enteric film" are used interchangeably and refer to a material or compound which is resistant to acid pH (i.e., an acid-resistant compound), such as that found in the stomach. An enteric coating when applied to a solid inhibits the dissolution of the solid in the stomach.

Standard techniques are known to the art for the encapsulation of solid compositions. These techniques include microencapsulation of a solid composition wherein an enteric coating is applied to the solid composition. The coated material may be delivered orally to a subject by suspending the microencapsulated particles in pharmaceutical suspension solutions known to the art.

When a solid antitoxin is to be encapsulated using an enteric coating, the enteric coating may be applied using a one step coating process in which the enteric film is directly applied to the solid antitoxin; the coated antitoxin is said to be overcoated with the enteric film. Alternatively, a two step coating process may be employed wherein the solid antitoxin is first used to overcoat a non-pariel (i.e., a sugar particle of about 40–60 mesh size) and then the antitoxin-coated non-pariel is overcoated with the enteric film. Desirable enteric coatings for the delivery of antitoxins include polymethacrylates such as Eudragit® L30D (Röhm Tech, Inc.) Solid antitoxin may formulated for oral delivery by insertion of the desired qunatity of antitoxin into a capsule; the capsule would preferable have the characteristic of being resistant to dissolution in the stomach and being capable of dissolving in the intestines. Numerous suitable capsule formulations are available to the art; in addition standard techniques are available for the filling of capsules including the use of inert filler materials to provide sufficient bulk of the filling of a capsule with a therapeutic composition in a solid form. In addition to the use of microencapsulated antitoxin and antitoxin contained within a capsule, the solid antitoxin may be delivered orally in tablet or pill form. The solid antitoxin may be combined with inert materials to provide sufficient bulk for the pressing of the tablet or pill. Once formed, the tablet or pill may then be coated with an enteric film to prevent dissolution in the stomach and to enhance dissolution in the intestines.

The term "oral administration" refers to the delivery of a composition, such as a composition comprising antitoxin, via the mouth.

The term "parenteral administration" refers to the delivery of a composition, such as a composition comprising an antitoxin or vaccine, by a route other than through the gastrointestinal tract (e.g., oral delivery) or the lungs. In particular, parenteral administration may be via intravenous, subcutaneous, intramuscular or intramedullary (i.e., intrathecal) injection. The terms "symptoms" and "symptoms of intoxication" when used in reference to a subject exposed to or at risk of exposure to *C. difficile* toxins refers to presence of any of the following phenomenon: diarrhea, enterocolitis, pseudomembranous colitis, hemorrhage, ulceration and/or inflammation of the intestinal mucosa, cecitis (i.e., inflammation of the cecum).

As used herein, the term "ceases to exhibit symptoms" refers to the situation in which a subject has stopped exhibiting the signs and/or symptoms associated with *C. difficile* disease and/or infection.

The term "substantial elimination" of the symptoms of intoxication with *C. difficile* disease means that in subject exposed to and suffering from the symptoms of intoxication, the symptoms are abated, attenuated or eliminated. For example, if an intoxicated subject presents with severe diarrhea (i.e., voluminous, watery diarrhea), a return to an at least loosely formed stool would constitute a substantial elimination of this symptom.

The term "beyond the treatment period" when used in reference to a method of treating a subject exposed to a *C. difficile* toxin means a period of time following the cessation of administration of a therapeutic compound (e.g., antitoxin) to the subject for at least 7 days and more preferably at least 14 days. A therapeutic compound which results in the substantial elimination of the symptoms of intoxication beyond the treatment period will prevent the reappearance (when symptoms are eliminated) or the increase in severity (when symptoms are abated) of these symptoms for at least 7 days following the withdrawal of administration of the therapeutic compound. In other words, no relapse (i.e., reappearance or increase in severity) of the symptoms is seen in the majority [i.e., a statistically significant number (e.g.,75%)] of subjects for a period of at least 7 days following the cessation of therapy.

In contrast to the antitoxins of the present invention, existing therapeutic compounds for established *C. difficile* infections [i.e., antibiotics such as vancomycin or metronidazole or bovine IgG concentrate from cows immunized with *C. difficile* toxoids A and B [Lyerly et al. (1991) Infect. Immun. 59:2215] do not prevent relapse in a significant number of treated subjects. For example, about 25% of humans and up to 100% of hamsters suffering from *C. difficile* associated disease treated with either vancomycin or metronidazole relapse (i.e., symptoms of intoxication reappear).

Hamsters administered bovine IgG concentrate (BIC) from cows immunized with *C. difficile* toxoids A and B prior to infection with *C. difficile* (i.e., prophylactic treatment) invariably relapse (i.e., diarrheas returns) and die when the BIC is withdrawn [Lyerly et al. (1991), supra]. No therapeutic effect is observed when hamsters having established *C. difficile* infections are treated with the BIC (i.e., the administration of the BIC does not eliminate the diarrhea or prevent death) [Lyerly et al. (1991), supra].

In contrast, the antitoxins of the present invention, when used to treat established *C. difficile* infection (therapeutic regimen), substantially eliminate the symptoms of intoxication, including diarrhea and prevent death. The majority of animals treated with the anti-*C. difficile* toxin proteins do not relapse and remain healthy following cessation of antitoxin therapy for a period of at least 14 days [the animals remain healthy for long periods of time (e.g., about 5 months)].

SUMMARY OF THE INVENTION

The present invention provides compositions comprising an avian neutralizing antitoxin directed against a portion of *C. difficile* toxin A and a portion of *C. difficile* toxin B. The antitoxins find use in humans and other animals exposed to or at risk of exposure to *C. difficile*. In one embodiment, the component of the avian neutralizing antitoxin directed against a portion *C. difficile* toxin A is directed against a first fusion protein comprising a portion of *C. difficile* toxin A and a second fusion protein comprising a portion of *C. difficile* toxin B. In yet another embodiment, both first and second fusion proteins further comprise at least one non-toxin protein sequence. In a still further embodiment, the antitoxin is directed against a portion of *C. difficile* toxin A comprising a portion of SEQ ID NO:6. In another embodiment, the antitoxin is directed against a portion of *C. difficile* toxin A, wherein the portion of SEQ ID NO:6 comprises a sequence selected from the group comprising SEQ ID NOS:7, 8 and 29. In yet another embodiment, the first and second fusion proteins comprise at least one non-toxin protein sequence. It is not intended that the present invention be limited by the nature of the non-toxin protein sequence. In one embodiment, the non-toxin protein sequence comprises a poly-histidine tract. In yet another embodiment, the non-toxin protein sequence comprises the maltose binding protein. In yet another embodiment, the non-toxin protein sequence comprises a thioredoxin protein. In a still further embodiment, the antitoxin is directed against a portion of *C. difficile* toxin B comprising a portion of SEQ ID NO:10. In another embodiment, the antitoxin is directed against a portion of *C. difficile* toxin B, wherein the portion of SEQ ID NO:10 comprises a sequence selected from the group comprising SEQ ID NOS:11, 12, 20, 21 and 30. In still another embodiment, the compositions comprising the avian antitoxins further comprise an enteric coating.

The invention also contemplates a method of treatment comprising: a) providing: i) a subject, ii) a first avian neutralizing antitoxin directed against a portion of *Clostridium difficile* toxin A sequence SEQ ID NO:6, and iii) a second avian neutralizing antitoxin directed against a portion of *Clostridium difficile* toxin B sequence SEQ ID NO:10; b) mixing the first and second antitoxins to create a therapeutic mixture; and c) administering the therapeutic mixture to a subject for a treatment period. The invention further contemplates a method of treatment which further comprises the step of, prior to step c), processing the therapeutic mixture to improve its enteric stability. In a preferred embodiment, this treating comprises encapsulating the antitoxins of the therapeutic mixture. In a particularly preferred embodiment the encapsulating step comprises overcoating the antitoxins in the therapeutic mixture with an enteric film.

The invention further contemplates the method of treatment wherein the subject has been exposed to at least one *Clostridium difficile* toxin prior to administration of antitoxin. In one embodiment, the exposed subject is suffering from the symptoms of intoxication and administering antitoxin results in the substantial elimination of symptoms beyond the treatment period. In another embodiment, the symptoms of intoxication comprise diarrhea.

The invention also contemplates the method of treatment wherein the subject has not been exposed to *Clostridium difficile* toxin prior to administration of antitoxin.

In one embodiment, the method of treatment provides a first avian antitoxin directed against a portion of *Clostridium difficile* toxin A comprising a protein sequence selected from the group comprising SEQ ID NOS:7, 8 and 29. In another embodiment, the method of treatment provides a second avian antitoxin directed against a portion of *Clostridium difficile* toxin B comprising a protein sequence selected from the group comprising SEQ ID NOS:11, 12, 20, 21 and 30.

The method of treatment is not limited by the method of administration of the antitoxin. In one embodiment, the method of treatment comprises administration of the antitoxins by oral administration. In another embodiment, the method of treatment comprises administration of the antitoxins by parenteral administration.

The invention further contemplates a method of vaccinating a subject to produce neutralizing antitoxin directed against *C. difficile* toxin comprising: a) providing in any order: i) a subject, ii) a first purified soluble and substantially endotoxin-free protein comprising a portion of *Clostridium difficile* toxin A sequence SEQ ID NO:6, and iii) a second purified soluble and substantially endotoxin-free protein comprising a portion of *Clostridium difficile* toxin B sequence SEQ ID NO:10;b) mixing the first and second proteins to create a therapeutic vaccine; and c) vaccinating the subject with the therapeutic vaccine so as to generate neutralizing antitoxin. The method of vaccination is not limited by the nature or species of the subject. In one embodiment the subject is a bird. In another embodiment the subject is a mammal. In yet another embodiment the subject is a human. In a still further embodiment, the method of vaccination the first and second toxin proteins further comprise at least one non-toxin protein sequence. The invention is not limited by the nature of the non-toxin protein sequence. In one embodiment, the non-toxin protein sequence comprises a poly-histidine tract. In another embodiment, the non-toxin protein sequence comprises the maltose binding protein. In yet another embodiment, the non-toxin protein sequence comprises a thioredoxin protein.

In one embodiment, the method of vaccinating uses a first purified and substantially endotoxin-free protein comprising SEQ ID NO:29. In another embodiment, the method of vaccinating uses a second purified and substantially endotoxin-free protein comprising SEQ ID NO:30.

The invention further provides a fusion protein comprising at least one non-toxin protein sequence and a portion of the Clostridium difficile toxin A sequence consisting of SEQ ID NO:29. In one embodiment, the non-toxin protein sequence comprises a thioredoxin protein. In yet another embodiment, the non-toxin protein sequence further comprises a poly-histidine tract.

The present invention provides a method for the detection of Clostridium difficile antigens in a sample, comprising providing, in any order a sample suspected of containing Clostridium difficile antigens, solid support conjugates comprising antibodies reactive with Clostridium difficile antigens bound to a solid support; mixing the sample and solid support conjugates under conditions such that the conjugates are capable of binding to Clostridium difficile antigens; and detecting binding. In one embodiment, the antibodies reactive with Clostridium difficile antigens are avian antibodies. In a preferred embodiment, the avian antibodies reacts with Toxin A of Clostridium difficile. In a particularly preferred embodiment, the avian antibodies reacts with the A-6 interval of Toxin A. In an alternative preferred embodiment the avian antibodies react with Toxin B of Clostridium difficile. In another preferred embodiment, the avian antibodies react with the B-3 interval of Toxin B. In yet another preferred embodiment, the avian antibodies react with Toxin A and Toxin B. It is also contemplated that the solid support used in the method comprises polystyrene particles. In one preferred embodiment, the mixing of step results in the formation of visible aggregates. In a preferred embodiment, the sample is human feces.

In an alternative embodiment, the present invention comprises a method of treatment comprising providing a subject exposed to Clostridium difficile exhibiting symptoms comprising diarrhea, and antibody reactive with Clostridium difficile, wherein the antibody is present in a therapeutic amount that is administrable, and administering the antibody to the subject under conditions such that the subject ceases to exhibit symptoms and treatment can be terminated. In a particularly preferred embodiment, the subject exhibits long-term survival beyond the treatment period. In one preferred embodiment, the antibodies reactive with Clostridium difficile antigens are avian antibodies. It is contemplated that the antibodies will be reactive against various moieties or antigens, including, but not limited to Toxin A of Clostridium difficile, the A-6 interval of Toxin A, Toxin B of Clostridium difficile, the B-3 interval of Toxin B, and a combination of Toxin A and Toxin B.

The present invention also provides a method of purifying Clostridium difficile toxins from a culture, comprising providing in any order, a culture comprising Clostridium difficile organisms and a supernatant comprising toxins in solution, antibodies reactive with Clostridium difficile toxins immobiled on a solid support, collecting the supernatant from the culture comprising toxins, adding the supernatant to immobilized antibody under conditions such that antibodies are capable of binding to the toxins, eluting the toxins from the immobilized antibodies; and detecting any eluted toxins. In one preferred embodiment, the antibodies reactive with Clostridium difficile antigens are avian antibodies. It is contemplated that various antibodies will be used in this method, including antibodies reactive against various antigens or moieties, including, but not limited to Toxin A of Clostridium difficile, the A-6 interval of Toxin A, Toxin B of Clostridium difficile, the B-3 interval of Toxin B, and a combination of Toxin A and Toxin B.

DESCRIPTION OF THE INVENTION

The present invention contemplates vaccinating humans and other animals polypeptides derived from C. botulinum neurotoxin which are substantially endotoxin-free. These botulinal peptides are also useful for the production of antitoxin. Anti-botulinal toxin antitoxin is useful for the treatment of patients effected by or at risk of symptoms due to the action of C. botulinum toxins. The organisms, toxins and individual steps of the present invention are described separately below.

I. Clostridium Species, Clostridial Diseases And Associated Toxins

A preferred embodiment of the method of the present invention is directed toward obtaining antibodies against Clostridium species, their toxins, enzymes or other metabolic by-products, cell wall components, or synthetic or recombinant versions of any of these compounds. It is contemplated that these antibodies will be produced by immunization of humans or other animals. It is not intended that the present invention be limited to any particular toxin or any species of organism. In one embodiment,

TABLE 2

| | Clostridial Toxins |
|---|---|
| Organism | Toxins and Disease-Associated Antigens |
| C. botulinum | A, B, $C_1$, $C_2$, D, E, F, G |
| C. butyricum | Neuraminidase |
| C. difficile | A, B, Enterotoxin (not A nor B), Motility Altering Factor, Low Molecular Weight Toxin, Others |
| C. perfringens | $\alpha, \beta, \epsilon, \iota, \gamma, \delta, \nu, \theta, \kappa, \lambda, \mu, \upsilon$ |
| C. sordelli/ C. bifermentans | HT, LT, $\alpha, \beta, \gamma$ |
| C. novyi | $\alpha, \beta, \gamma, \delta, \epsilon, \zeta, \nu, \theta$ |
| C. septicum | $\alpha, \beta, \gamma, \delta$ |
| C. histolyticum | $\alpha, \beta, \gamma, \delta, \epsilon$ plus additional enzymes |
| C. chauvoei | $\alpha, \beta, \gamma, \delta$ | toxins from all Clostridium species are contemplated as immunogens. Examples of these toxins include the neuraminidase toxin of C. butyricum, C. sordellii toxins HT and LT, toxins A, B, C, D, E, F, and G of C. botulinum and the numerous C. perftingens toxins. In one preferred embodiment, toxins A and B of C. difficile are contemplated as immunogens. Table 2 above lists various Clostridium species, their toxins and some antigens associated with disease.

It is not intended that antibodies produced against one toxin will only be used against that toxin. It is contemplated that antibodies directed against one toxin (e.g., *C. perfringens* type A enterotoxin) may be used as an effective therapeutic against one or more toxin(s) produced by other members of the genus Clostridium or other toxin producing organisms (e.g., *Bacillus cereus, Staphylococcus aureus, Streptococcus mutans, Acinetobacter calcoaceticus, Pseudomonas aeruginosa*, other Pseudomonas species, etc.). It is further contemplated that antibodies directed against the portion of the toxin which binds to mammalian membranes (e.g., *C. perfringens* enterotoxin A) can also be used against other organisms. It is contemplated that these membrane binding domains are produced synthetically and used as immunogens.

II. Obtaining Antibodies In Non-Mammals

A preferred embodiment of the method of the present invention for obtaining antibodies involves immunization. However, it is also contemplated that antibodies could be obtained from non-mammals without immunization. In the case where no immunization is contemplated, the present invention may use non-mammals with preexisting antibodies to toxins as well as non-mammals that have antibodies to whole organisms by virtue of reactions with the administered antigen. An example of the latter involves immunization with synthetic peptides or recombinant proteins sharing epitopes with whole organism components.

In a preferred embodiment, the method of the present invention contemplates immunizing non-mammals with bacterial toxin(s). It is not intended that the present invention be limited to any particular toxin. In one embodiment, toxin from all clostridial bacteria sources (see Table 2) are contemplated as immunogens. Examples of these toxins are *C. butyricum* neuraminidase toxin, toxins A, B, C, D, E, F, and G from *C. botulinum, C. perfringens* toxins α, β, ϵ, and ι, and *C. sordellii* toxins HT and LT. In a preferred embodiment, *C. difficile* toxins A and B are contemplated as immunogens.

A particularly preferred embodiment involves the use of bacterial toxin protein or fragments of toxin proteins produced by molecular biological means (i.e., recombinant toxin proteins). In a preferred embodiment, the immunogen comprises interval 6 of *C. difficile* toxin A produced by recombinant DNA technology. In yet another preferred embodiment, the immunogen comprises interval 3 of *C. difficile* toxin B produced by recombinant DNA technology. The recombinant *C. difficile* toxin proteins may be used as immunogens separately or in combination to produce antibodies specific for either *C. difficile* toxin A, *C. difficile* toxin B or both *C. difficile* toxins A and B. Specifically, the recombinant *C. difficile* toxins A and B proteins may be mixed together and used as a single immunogen. Alternatively, *C. difficile* toxin A proteins may be used separately as an immunogen in a first subject. iSimilarly, *C. difficile* toxin B proteins may be used separately as an immunogen in a second subject. The antitoxin produced by separate immunization of two separate subjects with *C. difficile* toxin A proteins or *C. difficile* toxin B proteins may be combined to yield an antitoxin directed against both *C. difficile* toxins A and B.

The recombinant *C. difficile* toxin proteins provided herein enables the production of antibodies which are specific for a single *C. difficile* toxin (i.e., mono-specific antibodies). This is in contrast to the biochemical purification of *C. difficile* toxin A from natural sources results invariably in the isolation of a toxin A preparation contaminated with immunologically significant amounts of toxin B; similarly the biochemical purification of *C. difficile* toxin B from natural sources results in the isolation of a toxin B preparation contaminated with immunologically significant amounts of toxin A. Because, these preparations of non-recombinant toxin A and or toxin B are cross-contaminated with either toxin B or A, immunization of an animal will result in the production of polyclonal antibodies reactive against both toxins A and B.

As discussed below in section VI, accurate detection of the presence of *C. difficile* toxin A and/or B in a sample requires the availability of both pure preparations of toxin A and B and the availability of mono-specific antibodies. The use of recombinant *C. difficile* toxin proteins thus allows for the production of a polyclonal antibody preparation that can be used for accurate detection of individual *C. difficile* toxins as well as *C. difficile* organisms.

When immunization is used, the preferred non-mammal is from the class Aves. All birds are contemplated (e.g., duck, ostrich, emu, turkey, etc.). A preferred bird is a chicken. Importantly, chicken antibody does not fix mammalian complement. [See H. N. Benson et al., J. Immunol. 87:616 (1961).] Thus, chicken antibody will normally not cause a complement-dependent reaction. [A. A. Benedict and K. Yamaga, "*Immunoglobulins and Antibody Production in Avian Species,* " *in Comparative Immunology* (J. J. Marchaloni, ed.), pp. 335–375, Blackwell, Oxford (1966).] Thus, the preferred antitoxins of the present invention will not exhibit complement-related side effects observed with antitoxins known presently.

When birds are used, it is contemplated that the antibody will be obtained from either the bird serum or the egg. A preferred embodiment involves collection of the antibody from the egg. Laying hens transport immunoglobulin to the egg yolk ("IgY") in concentrations equal to or exceeding that found in serum. [See R. Patterson et al., J. Immunol. 89:272 (1962); and S. B. Carroll and B. D. Stollar, J. Biol. Chem. 258:24 (1983).] In addition, the large volume of egg yolk produced vastly exceeds the volume of serum that can be safely obtained from the bird over any given time period. Finally, the antibody from eggs is purer and more homogeneous; there is far less non-immunoglobulin protein (as compared to serum) and only one class of immunoglobulin is transported to the yolk.

When considering immunization with toxins, one may consider modification of the toxins to reduce the toxicity. In this regard, it is not intended that the present invention be limited by immunization with modified toxin. Unmodified ("native") toxin is also contemplated as an immunogen.

It is also not intended that the present invention be limited by the type of modification—if modification is used. The present invention contemplates all types of toxin modification, including chemical and heat treatment of the toxin. The preferred modification, however, is formaldehyde treatment.

It is not intended that the present invention be limited to a particular mode of immunization; the present invention contemplates all modes of immunization, including subcutaneous, intramuscular, intraperitoneal, and intravenous or intravascular injection, as well as per os administration of immunogen.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant. Another preferred use of adjuvant is the use of Gerbu Adjuvant. The invention also contemplates the use of RIBI fowl adjuvant and Quil A adjuvant.

When immunization is used, the present invention contemplates a wide variety of immunization schedules. In one embodiment, a chicken is administered toxin(s) on day zero and subsequently receives toxin(s) in intervals thereafter. It is not intended that the present invention be limited by the particular intervals or doses. Similarly, it is not intended that the present invention be limited to any particular schedule for collecting antibody. The preferred collection time is sometime after day 100.

Where birds are used and collection of antibody is performed by collecting eggs, the eggs may be stored prior to processing for antibody. It is preferred that eggs be stored at 4° C. for less than one year.

It is contemplated that chicken antibody produced in this manner can be buffer-extracted and used analytically. While unpurified, this preparation can serve as a reference for activity of the antibody prior to further manipulations (erg., immunoaffinity purification).

III. Increasing The Effectiveness Of Antibodies

When purification is used, the present invention contemplates purifying to increase the effectiveness of both non-mammalian antitoxins and mammalian antitoxins. Specifically, the present invention contemplates increasing the percent of toxin-reactive immunoglobulin. The preferred purification approach for avian antibody is polyethylene glycol (PEG) separation.

The present invention contemplates that avian antibody be initially purified using simple, inexpensive procedures. In one embodiment, chicken antibody from eggs is purified by extraction and precipitation with PEG. PEG purification exploits the differential solubility of lipids (which are abundant in egg yolks) and yolk proteins in high concentrations of PEG 8000. [Polson et al., Immunol. Comm. 9:495 (1980).] The technique is rapid, simple, and relatively inexpensive and yields an immunoglobulin fraction that is significantly purer in terms of contaminating non-immunoglobulin proteins than the comparable ammonium sulfate fractions of mammalian sera and horse antibodies. The majority of the PEG is removed from the precipitated chicken immunoglobulin by treatment with ethanol. Indeed, PEG-purified antibody is sufficiently pure that the present invention contemplates the use of PEG-purified antitoxins in the passive immunization of intoxicated humans and animals.

The invention further contemplates increasing the effectiveness of compositions comprising antitoxins by enterically-coating a solid form of the antitoxin to improve the survival of the antitoxin in the gastrointestinal tract (i.e., enteric stability) as discussed further below in section IV(C).

IV. Treatment

The present invention contemplates antitoxin therapy for humans and other animals intoxicated by bacterial toxins. A preferred method of treatment is by oral administration of antitoxin. Another preferred method of treatment is by parenteral administration of antitoxin.

A. Therapeutic Preparations and Combinations

The present invention contemplates using therapeutic compositions of antitoxins. The antitoxin compositions may comprise antitoxin in a solid or liquid form.

It is not intended that the present invention be limited by the particular nature of the therapeutic preparation. For example, such compositions can be provided together with physiologically tolerable liquid, gel or solid carriers, diluents, adjuvants and excipients. In addition, the antitoxins may be used together with other therapeutic agents, including antibiotics.

As noted above, these therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

With respect to the mode of administration, the antitoxins may be employed for oral, intravenous, intraperitoneal, intramuscular or intrathecal administration. Formulations for such administrations may comprise an effective amount of antitoxin in sterile water or physiological saline.

On the other hand, formulations may contain such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared for oral administration, either as liquid solutions or suspensions; solid forms, including solid forms suitable for solution in, or suspension in, liquid prior to administration, may also be prepared. Solid forms of the antitoxins may further comprise an enteric coating. The compositions are also preferably prepared as injectables, either as liquid solutions or suspensions; solid forms suitable for solution in, or suspension in, liquid prior to administration may also be prepared.

The antitoxins of the present invention are often mixed with diluents or excipients which are physiological tolerable and compatible. Suitable diluents and excipients are, for example, water, saline, nutritional formulations (e.g., Ensure®, Enfamil®, etc.) dextrose, glycerol, or the like, and combinations thereof. In addition, if desired the compositions may contain minor amounts of auxiliary substances such as wetting or emulsifying agents, stabilizing or pH buffering agents.

B. Dosage Of Antitoxin

It is noted by way of background that a balance must be struck when administering currently available antitoxin which is usually produced in large animals such as horses; sufficient antitoxin must be administered to neutralize the toxin, but not so much antitoxin as to increase the risk of untoward side effects. These side effects are caused by: i) patient sensitivity to foreign (e.g, horse) proteins; ii) anaphylactic or immunogenic properties of non-immunoglobulin proteins; iii) the complement fixing properties of mammalian antibodies; and/or iv) the overall burden of foreign protein administered. It is extremely difficult to strike this balance when, as noted above, the degree of intoxication (and hence the level of antitoxin therapy needed) can only be approximated.

The present invention contemplates significantly reducing side effects so that this balance is more easily achieved. Treatment according to the present invention contemplates reducing side effects by using PEG-purified antitoxin from birds.

In one embodiment, the treatment of the present invention contemplates the use of PEG-purified antitoxin from birds. The use of yolk-derived, PEG-purified antibody as antitoxin allows for the administration of: 1) non(mammalian)-complement-fixing, avian antibody; 2) a less heterogeneous mixture of non-immunoglobulin proteins; and 3) less total protein to deliver the equivalent weight of active antibody present in currently available antitoxins. The non-mammalian source of the antitoxin makes it useful for treating patients who are sensitive to horse or other mammalian sera.

As is true in cases of botulism, the degree of an individual's exposure to *C. difficile* toxin and the prognosis are often difficult to assess, and depend upon a number of factors (e.g., the quantity of the inoculum, the toxigenicity and serotype of *C. difficile* strain involved, etc.). Thus, the clinical presentation of a patient is usually a more important consideration than a quantitative diagnostic test, for determination of dosage in antitoxin administration. Indeed, for many toxin-associated diseases (e.g., botulism, tetanus, diphtheria, etc.), there is no rapid, quantitative test to detect the presence of the toxin or organism. Rather, these toxin-associated diseases are medical emergencies which mandate immediate treatment. Confirmation of the etiologic agent must not delay the institution of therapy, as the condition of an affected patient may rapidly deteriorate. In addition to the initial treatment with antitoxin, subsequent doses may be indicated, as the patient's disease progresses. The dosage and timing of these subsequent doses is dependent upon the signs and symptoms of disease in each individual patient.

It is contemplated that when antitoxin is to be administered parentally, the administration of antitoxin to an affected individual would involve an initial injection of an approximately 10 ml dose of immune globulin (with less than approximately 1 gram of total protein). In one preferred embodiment, it is contemplated that at least 50% of the initial injection comprises immune globulin. It is also contemplated that more purified immune globulin be used for treatment, wherein approximately 90% of the initial injection comprises immune globulin. When more purified immune globulin (e.g., purified IgY) is used, it is contemplated that the total protein will be less than approximately 100 milligrams. It is also contemplated that additional doses be given, depending upon the signs and symptoms associated with *C. difficile* associated disease progression.

It is contemplated that when antitoxin is to be administered orally, the administration of antitoxin to an affected individual would involve a treatment course (i.e., initial and subsequent doses) comprising the administration of a therapeutic composition comprising about 50 gm of antitoxin and more preferably about 4–5 gm of antitoxin.

C. Delivery Of Antitoxin

Although it is not intended to limit the route of delivery, the present invention contemplates a method for antitoxin treatment of bacterial intoxication in which delivery of antitoxin is parenteral or oral.

In one embodiment, antitoxin is parenterally administered to a subject in an aqueous solution. It is not intended that the parenteral administration be limited to a particular route. Indeed, it is contemplated that all routes of parenteral administration will be used. In one embodiment, parenteral administration is accomplished via intramuscular injection. In an alternative embodiment, parenteral administration is accomplished via intravenous injection.

In one embodiment, antitoxin is delivered in a solid form (e.g., tablets, capsules). In an alternative embodiment antitoxin is delivered in an aqueous solution. When an aqueous solution is used, the solution has sufficient ionic strength to solubilize antibody protein, yet is made palatable for oral administration. The delivery solution may also be buffered (e.g., carbonate buffer pH 9.5) which can neutralize stomach acids and stabilize the antibodies when the antibodies are administered orally. In one embodiment the delivery solution is an aqueous solution. In another embodiment the delivery solution is a nutritional formula. Preferably, the delivery solution is infant formula. Yet another embodiment contemplates the delivery of lyophilized antibody encapsulated or microencapsulated inside acid-resistant compounds.

Methods of applying enteric coatings to pharmaceutical compounds are well known to the art [companies specializing in the coating of pharmaceutical compounds are available; for example, The Coating Place (Verona, Wis.) and AAI (Wilmington, N.C.)]. Enteric coatings which are resistant to gastric fluid and whose release (i.e., dissolution of the coating to release the pharmaceutical compound) is pH dependent are commercially available [for example, the polymethacrylates Eudragit® L and Eudragit® S (Röhm GmbH)]. Eudragit® S is soluble in intestinal fluid from pH 7.0; this coating can be used to microencapsulate lyophilized antitoxin antibodies and the particles are suspended in a solution having a pH above or below pH 7.0 for oral administration. The microparticles remain intact and undissolved until they reach the intestines where the intestinal pH causes them to dissolve thereby releasing the antitoxin.

The invention is directed to the improvement of the enteric stability of the therapeutic antitoxin [Enteric stability is defined as the stability of the antitoxin during passage through the gastrointestinal tract; the enteric stability is improved by increasing the amount of the orally administered antitoxin which is delivered to the desired site (i.e., the intestines) in a functional or active form]. Antibodies, and avian antibodies in particular, are known to be significantly denatured when exposed to acidic solutions (e.g., gastric fluid). Denaturation of the antibody results in the loss of functionality (i.e., loss of the ability to bind to the specific target). In addition to the denaturation of antibodies due to the low pH found in portions of the gastrointestinal tract, proteolytic degradation of the antitoxin may occur due to digestion with enzymes. The invention improves the enteric stability of the therapeutic antitoxins by coating the antitoxins with an enteric coating. The enteric coating prevents the acid-induced denaturation of the antitoxin and prevents exposure of the antitoxin to enzymes present in the upper portions of the gastrointestinal tract.

Application of acid resistant enteric coatings are shown herein to prevent release of microencapsulated antitoxin (e.g., enterically-coated antitoxin) into simulated gastric solution while permitting release of the antitoxin in simulated intestinal solution. The enteric survival of the therapeutic antitoxins may also be improved through the use of excipients (more or less inert substances added to a therapeutic compound as a diluent or to give form or consistency when the compound is provided in tablet form). Excipients, such as carbonate buffers of about pH 9.5 or nutritional formulations (e.g., Ensure®, Enfamil®, etc.) may indirectly reduce the denaturation of the antitoxin in the stomach by raising the stomach pH or by providing additional protein to compete for degradation by gastric enzymes. In contrast, the use of enteric coatings on the antitoxin composition directly prevents the denaturation or digestion of the antitoxin in the stomach by preventing the release of the antitoxin from the enterically-coated particle until the particle reaches the intestinal fluid which has a basic pH. The use of enteric coatings is a particularly preferred means of improving the acid stability of the therapeutic antitoxins of the invention.

The invention contemplates a method of treatment which can be administered for treatment of acute intoxication. In one embodiment, antitoxin is administered orally in either a delivery solution or in tablet form, in therapeutic dosage, to a subject intoxicated by the bacterial toxin which served as immunogen for the antitoxin.

The invention also contemplates a method of treatment which can be administered prophylactically. In one embodiment, antitoxin is administered orally, in a delivery solution, in therapeutic dosage, to a subject, to prevent intoxication of the subject by the bacterial toxin which served as immunogen for the production of antitoxin. In another embodiment, antitoxin is administered orally in solid form such as tablets or as microencapsulated particles. Microencapsulation of lyophilized antibody using compounds such as Eudragit® (Röhm Tech, Inc.) or polyethylene glycol, which dissolve at a wide range of pH units, allows the oral administration of solid antitoxin in a liquid form (i.e., a suspension) to recipients unable to tolerate administration of tablets (e.g., children or patients on feeding tubes). In a preferred embodiment, the lyophilized antibody is coated with Eudragit® L30D (Röhm Tech, Inc.). In one preferred embodiment the subject is an child. In another embodiment, antibody raised against whole bacterial organism is administered orally to a subject, in a delivery solution, in therapeutic dosage.

V. Vaccines Against Clostridial Species

The invention contemplates the generation of mono- and multivalent vaccines for the protection of an animal (particularly humans) against several clostridial species. Of particular interest are vaccines which stimulate the production of a humoral immune response to *C. difficile, C. tetani* and *C. botulinum* in humans. The antigens comprising the vaccine preparation may be native or recombinantly produced toxin proteins from the clostridial species listed above. When toxin proteins are used as immunogens they are generally modified to reduce the toxicity. This modification may be by chemical or genetic (i.e., recombinant DNA technology) means. In general genetic detoxification (ie., the expression of nontoxic fragments in a host cell) is preferred as the expression of nontoxic fragments in a host cell precludes the presence of intact, active toxin in the final preparation. However, when chemical modification is desired, the preferred toxin modification is formaldehyde treatment.

The invention contemplates that recombinant *C. difficile* toxin proteins be used as antigens in mono- and multivalent vaccine preparations. Soluble, substantially endotoxin-free recombinant *C. difficile* toxin A and or toxin B proteins may be used alone or in conjunction with either recombinant or native toxins or toxoids from *C. botulinum, C. difficile* and *C. tetani* as antigens for the preparation of these mono- and multivalent vaccines. It is contemplated that, due to the structural similarity of *C. botulinum* and *C. tetani* toxin proteins, a vaccine comprising *C. difficile* and botulinum toxin proteins (native or recombinant or a mixture thereof) be used to stimulate an immune response against *C. botulinum, C. tetani* and *C. difficile*.

The adverse consequences of exposure to *C. difficile* toxins would be avoided by immunization of subjects at risk of exposure to the toxin with nontoxic preparations which confer immunity such as chemically or genetically detoxified toxin.

Vaccines which confer immunity against one or more of the toxin types A and B would be useful as a means of protecting animals, including humans, from the deleterious effects of *C. difficile* toxins. A subject may be immunized with compositions comprising one or more *C. difficile* toxin proteins to generate neutralizing antibodies in the subject. A subject may be immunized with a first immunogen comprising *C. difficile* toxin A proteins followed by a separate immunization with a second immunogen comprising *C. difficile* B toxin proteins to produce neutralizing antibodies directed against *C. difficile* toxins A and B. Alternatively, the subject may be immunized with a single immunogen comprising *C. difficile* toxin A and B proteins.

In general, chemical detoxification of bacterial toxins using agents such as formaldehyde, glutaraldehyde or hydrogen peroxide is not optimal for the generation of vaccines or antitoxins. A delicate balance must be struck between too much and too little chemical modification. If the treatment is insufficient, the vaccine may retain residual toxicity. If the treatment is too excessive, the vaccine may lose potency due to destruction of native immunogenic determinants. Another major limitation of using botulinal toxoids for the generation of antitoxins or vaccines is the high production expense. For the above reasons, the development of methods for the production of nontoxic but immunogenic *C. difficile* toxin proteins is desirable.

Recombinant *C. difficile* toxin proteins have be produced in a host cell such as *E. coli* in either a soluble or insoluble form. Insoluble recombinant proteins are found in inclusion bodies. Inclusion body protein must be solubilized prior to purification and/or administration to a host. The harsh treatment of inclusion body protein needed to accomplish this solubilization may reduce the immunogenicity of the purified protein. Ideally, recombinant proteins to be used as vaccines are expressed as soluble proteins at high levels (i.e., greater than or equal to about 0.75% of total cellular protein) in *E. coli* or other host cells. This facilitates the production and isolation of sufficient quantities of the immunogen in a highly purified form (i.e., substantially free of endotoxin or other pyrogen contamination). The ability to express recombinant toxin proteins as soluble proteins in *E. coli* is advantageous due to the low cost of growth compared to insect or mammalian tissue culture cells.

The subject invention provides soluble *C. difficile* toxin proteins produced in economical host cells (e.g., *E. coli*). Further, methods for the isolation of purified soluble *C. difficile* toxin proteins which are suitable for immunization of humans and other animals are provided. These soluble, purified preparations of *C. difficile* toxin proteins provide the basis for improved vaccine preparations and facilitate the production of antitoxin.

When recombinant clostridial toxin proteins produced in gram-negative bacteria (e.g., *E. coli*) are used as vaccines, they are purified to remove endotoxin prior to administration to a host animal. In order to vaccinate a host, an immunogenically-effective amount of purified substantially endotoxin-free recombinant clostridial toxin protein is administered in any of a number of physiologically acceptable carriers known to the art. When administered for the purpose of vaccination, the purified substantially endotoxin-free recombinant clostridial toxin protein may be used alone or in conjunction with known adjutants, including potassium alum, aluminum phosphate, aluminum hydroxide, Gerbu adjuvant (GMDP; C.C. Biotech Corp.), RIBI adjuvant (MPL; RIBI Immunochemical Research, Inc.), QS21 (Cambridge Biotech). The alum and aluminum-based adjutants are particularly preferred when vaccines are to be administered to humans. The route of immunization may be nasal, oral, intramuscular, intraperitoneal or subcutaneous.

The invention contemplates the use of soluble, substantially endotoxin-free preparations of fusion proteins comprising portions of *C. difficile* toxins A and B as vaccines. In one embodiment, the vaccine comprises a portion of a *C. difficile* toxin and a poly-histidine tract (also called a histidine tag). In a particularly preferred embodiment, a fusion protein comprising a portion of a *C. difficile* toxin protein and a poly-histidine tract is expressed using the pET series of expression vectors (Novagen). The pET expression system utilizes a vector containing the T7 promoter which encodes the fusion protein and a host cell which can be induced to express the T7 DNA polymerase (i.e., a DE3 host strain). The production of *C. difficile* toxin fusion proteins containing a histidine tract is not limited to the use of a particular expression vector and host strain. Several commercially available expression vectors and host strains can be used to express the *C. difficile* protein sequences as a fusion protein containing a histidine tract (For example, the pQE series (pQE-8, 12, 16, 17, 18, 30, 31, 32, 40, 41, 42, 50, 51, 52, 60 and 70) of expression vectors (Qiagen) which are used with the host strains M15[pREP4] (Qiagen) and SG13009[pREP4] (Qiagen) can be used to express fusion proteins containing six histidine residues at the amino-terminus of the fusion protein).

VI. Detection Of Toxin

The invention contemplates detecting bacterial toxin in a sample. The term "sample" in the present specification and claims is used in its broadest sense. On the one hand it is meant to include a specimen or culture. On the other hand, it is meant to include both biological and environmental samples.

Biological samples may be animal, including human, fluid, solid (e.g., stool) or tissue; liquid and solid food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

As discussed above in section IV, toxin-associated diseases are medical emergencies which mandate immediate treatment. Because existing methodologies do not provide rapid, quantitative tests for the presence of *C. difficile* toxins or organisms, treatment of subjects suspected of having *C. difficile* associated disease is begun prior to a determination of the amount or nature of the toxin or organism present. If a rapid and quantitative test for *C. difficile* toxins or organisms were available, the dosage of therapeutic compounds could be adjusted to provide maximum benefit to the intoxicated subject. The specific anti-*C. difficile* toxin A and B antibodies of the invention and the purified recombinant *C. difficile* toxin A and B proteins enable rapid and quantitative tests for *C. difficile* toxins or organisms.

The invention contemplates detecting bacterial toxin by a competitive immunoassay method that utilizes recombinant toxin A and toxin B proteins, antibodies raised against recombinant bacterial toxin proteins. A fixed amount of the recombinant toxin proteins are immobilized to a solid support (e.g., a microtiter plate) followed by the addition of a biological sample suspected of containing a bacterial toxin. The biological sample is first mixed with affinity-purified or PEG fractionated antibodies directed against the recombinant toxin protein. A reporter reagent is then added which is capable of detecting the presence of antibody bound to the immobilized toxin protein. The reporter substance may comprise an antibody with binding specificity for the antitoxin attached to a molecule which is used to identify the presence of the reporter substance. If toxin is present in the sample, this toxin will compete with the immobilized recombinant toxin protein for binding to the anti-recombinant antibody thereby reducing the signal obtained following the addition of the reporter reagent. A control is employed where the antibody is not mixed with the sample. This gives the highest (or reference) signal.

The invention also contemplates detecting bacterial toxin by a "sandwich" immunoassay method that utilizes antibodies directed against recombinant bacterial toxin proteins. Affinity-purified antibodies directed against recombinant bacterial toxin proteins are immobilized to a solid support (e.g., microtiter plates). Biological samples suspected of containing bacterial toxins are then added followed by a washing step to remove substantially all unbound antitoxin. The biological sample is next exposed to the reporter substance, which binds to antitoxin and is then washed free of substantially all unbound reporter substance. The reporter substance may comprise an antibody with binding specificity for the antitoxin attached to a molecule which is used to identify the presence of the reporter substance. Identification of the reporter substance in the biological tissue indicates the presence of the bacterial toxin.

It is also contemplated that bacterial toxin be detected by pouring liquids (e.g. soups and other fluid foods and feeds including nutritional supplements for humans and other animals) over immobilized antibody which is directed against the bacterial toxin. It is contemplated that the immobilized antibody will be present in or on such supports as cartridges, colunms, beads, or any other solid support medium. In one embodiment, following the exposure of the liquid to the immobilized antibody, unbound toxin is substantially removed by washing. The exposure of the liquid is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will be developed as necessary (e.g., the addition of enzyme substrate in enzyme systems; observation using fluorescent light for fluorescent dye systems; and quantitation of radioactivity for radioactive systems).

EXPERIMENTAL

The following examples serve to illustrate certain preferred embodiments and aspects of the present invention and are not to be construed as limiting the scope thereof.

In the disclosure which follows, the following abbreviations apply: ° C. (degrees Centigrade); rpm (revolutions per minute); BBS-Tween (borate buffered saline containing Tween); BSA (bovine serum albumin); ELISA (enzyme-linked inimmunosorbent assay); CFA (complete Freund's adjuvant); IFA (incomplete Freund's adjuvant); IgG (immunoglobulin G); IgY (immunoglobulin Y); IM (intramuscular); IP (intraperitoneal); IV (intravenous or intravascular); SC (subcutaneous); $H_2O$ (water); HCl (hydrochloric acid); $LD_{100}$ (lethal dose for 100% of experimental animals); aa (amino acid); HPLC (high performance liquid chromatography); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); MW (molecular weight); sec (seconds); min(s) (minute/minutes); hr(s) (hour/hours); $MgCl_2$ (magnesium chloride); NaCl (sodium chloride); Na$_2$CO$_3$ (sodium carbonate); OD$_{280}$ (optical density at 280 nm); OD$_{600}$ (optical density at 600 nm); PAGE (polyacrylamide gel electrophoresis); PBS [phosphate buffered saline (150 mM NaCl, 10 mM sodium phosphate buffer, pH 7.2)]; PEG (polyethylene glycol); PMSF (phenylmethylsulfonyl fluoride); SDS (sodium dodecyl sulfate); Tris (tris (hydroxymethyl)aminomethane); Ensure® (Ensure®, Ross Laboratories, Columbus Ohio); Enfamil® (Enfamil®, Mead Johnson); w/v (weight to volume); v/v (volume to volume); Accurate Chemical (Accurate Chemical & Scientific Corp., Westbury, N.Y.); Amicon (Amicon, Inc., Beverly, Mass.); Amresco (Amresco, Inc., Solon, Ohio); ATCC (American Type Culture Collection, Rockville, Md.); BBL (Baltimore Biologics Laboratory, (a division of Becton Dickinson), Cockeysville, Md.); Becton Dickinson (Becton Dickinson Labware, Lincoln Park, N.J.); BioRad (BioRad, Richmond, Calif.); Biotech (C-C Biotech Corp., Poway, Calif.); Charles River (Charles River Laboratories, Wilmington, Mass.); Cocalico (Cocalico Biologicals Inc., Reamstown, Pa.); CytRx (CytRx Corp., Norcross, Ga.); Falcon (e.g. Baxter Healthcare Corp., McGaw Park, Ill. and Becton Dickinson); FDA (Federal Food and Drug Administration); Fisher Biotech (Fisher Biotech, Springfield, N.J.); GIBCO (Grand Island Biologic Company/BRL, Grand Island, N.Y.); Gibco-BRL (Life Technologies, Inc., Gaithersburg, Md.); Harlan Sprague Dawley (Harlan Sprague Dawley, Inc., Madison, Wis.); Mallinckrodt (a division of Baxter Healthcare Corp., McGaw Park, Ill.); Millipore (Millipore Corp., Marlborough, Mass.); New England Biolabs (New England Biolabs, Inc., Beverly, Mass.); Novagen (Novagen, Inc., Madison, Wis.); Pharmacia (Pharmacia, Inc., Piscataway, N.J.); Qiagen (Qiagen, Chatsworth, Calif.); RIBI (RIBI Immunochemical Research, Inc., Hamilton, Mont.); Sasco (Sasco, Omaha, Nebr.); Showdex (Showa Denko America, Inc., New York, N.Y.); Sigma (Sigma Chemical Co., St. Louis, Mo.); Sterogene (Sterogene, Inc., Arcadia, Calif.); Tech Lab (Tech Lab, Inc., Blacksburg, Va.); and Vaxcell (Vaxcell, Inc., a subsidiary of CytRX Corp., Norcross, Ga.

When a recombinant protein is described in the specification it is referred to in a short-hand manner by the amino acids in the toxin sequence present in the recombinant protein rounded to the nearest 10. For example, the recombinant protein pMB1850–2360 contains amino acids 1852 through 2362 of the *C. difficile* toxin B protein. The specification gives detailed construction details for all recombinant proteins such that one skilled in the art will know precisely which amino acids are present in a given recombinant protein.

EXAMPLE 1

Production Of High-Titer Antibodies To *Clostridium difficile* Organisms In A Hen Antibodies to certain pathogenic organisms have been shown to be effective in treating diseases caused by those organisms. It has not been shown whether antibodies can be raised, against *Clostridium difficile*, which would be effective in treating infection by this organism. Accordingly, *C. difficile* was tested as immunogen for production of hen antibodies.

To determine the best course for raising high-titer egg antibodies against whole *C. difficile* organisms, different immunizing strains and different immunizing concentrations were examined. The example involved (a) preparation of the bacterial immunogen, (b) immunization, (c) purification of anti-bacterial chicken antibodies, and (d) detection of anti-bacterial antibodies in the purified IgY preparations.

a) Preparation Of Bacterial Immunogen

*C. difficile* strains 43594 (serogroup A) and 43596 (serogroup C) were originally obtained from the ATCC. These two strains were selected because they represent two of the most commonly-occurring serogroups isolated from patients with antibiotic-associated pseudomembranous colitis. [Delmee et al., J. Clin. Microbiol., 28(10):2210 (1990).] Additionally, both of these strains have been previously characterized with respect to their virulence in the Syrian hamster model for *C. difficile* infection. [Delmee et al., J. Med Microbiol., 33:85 (1990).]

The bacterial strains were separately cultured on brain heart infusion agar for 48 hours at 37° C. in a Gas Pack 100 Jar (BBL, Cockeysville, Md.) equipped with a Gas Pack Plus anaerobic envelope (BBL). Forty-eight hour cultures were used because they produce better growth and the organisms have been found to be more cross-reactive with respect to their surface antigen presentation. The greater the degree of cross-reactivity of our IgY preparations, the better the probability of a broad range of activity against different strains/serogroups. [Toma et al., J. Clin. Microbiol., 26(3):426 (1988).]

The resulting organisms were removed from the agar surface using a sterile dacron-tip swab, and were suspended in a solution containing 0.4% formaldehyde in PBS, pH 7.2. This concentration of formaldehyde has been reported as producing good results for the purpose of preparing whole-organism immunogen suspensions for the generation of polyclonal anti-*C. difficile* antisera in rabbits. [Delmee et al., J. Clin. Microbiol., 21:323 (1985); Davies et al., Microbial Path., 9:141 (1990).] In this manner, two separate bacterial suspensions were prepared, one for each strain. The two suspensions were then incubated at 4° C. for 1 hour. Following this period of formalin-treatment, the suspensions were centrifuged at 4,200×g for 20 min., and the resulting pellets were washed twice in normal saline. The washed pellets, which contained formalin-treated whole organisms, were resuspended in fresh normal saline such that the visual turbidity of each suspension corresponded to a #7 McFarland standard. [M. A. C. Edelstein, "*Processing Clinical Specimens for Anaerobic Bacteria: Isolation and Identification Procedures*," in S. M. Finegold et al (eds.)., *Bailey and Scott's Diagnostic Microbiology*, pp. 477–507, C. V. Mosby Co., (1990). The preparation of McFarland nephelometer standards and the corresponding approximate number of organisms for each tube are described in detail at pp. 172–173 of this volume.] Each of the two #7 suspensions was then split into two separate volumes. One volume of each suspension was volumetrically adjusted, by the addition of saline, to correspond to the visual turbidity of a #1 McFarland standard. [Id.] The #1 suspensions contained approximately $3\times10^8$ organisms/ml, and the #7 suspensions contained approximately $2\times10^9$ organisms/ml. [Id.] The four resulting concentration-adjusted suspensions of formalin-treated *C. difficile* organisms were considered to be "bacterial immunogen suspensions." These suspensions were used immediately after preparation for the initial immunization. [See section (b).]

The formalin-treatment procedure did not result in 100% non-viable bacteria in the immunogen suspensions. In order to increase the level of killing, the formalin concentration and length of treatment were both increased for subsequent immunogen preparations, as described below in Table 3. (Although viability was decreased with the stronger formalin treatment, 100% inviability of the bacterial immunogen suspensions was not reached.) Also, in subsequent immunogen preparations, the formalin solutions were prepared in normal saline instead of PBS. At day 49, the day of the fifth immunization, the excess volumes of the four previous bacterial immunogen suspensions were stored frozen at −70° C. for use during all subsequent immunizations.

b) Immunization

For the initial immunization, 1.0 ml volumes of each of the four bacterial immunogen suspensions described above were separately emulsified in 1.2 ml volumes of CFA (GIBCO). For each of the four emulsified immunogen suspensions, two four-month old White Leghorn hens (pre-laying) were immunized. (It is not necessary to use pre-laying hens; actively-laying hens can also be utilized.) Each hen received a total volume of approximately 1.0 ml of a single emulsified immunogen suspension via four injections (two subcutaneous and two intramuscular) of approximately 250 μl per site. In this manner, a total of four different immunization combinations, using two hens per combination, were initiated for the purpose of evaluating both the effect of immunizing concentration on egg yolk antibody (IgY) production, and interstrain cross-reactivity of IgY raised against heterologous strains. The four immunization groups are summarized in Table 3.

The time point for the first series of immunizations was designated as "day zero." All subsequent immunizations were performed as described above except that the bacterial immunogen suspensions were emulsified using IFA (GIBCO) instead of

TABLE 3

Immunization Groups

| GROUP DESIGNATION | IMMUNIZING STRAIN | APPROXIMATE IMMUNIZING DOSE |
|---|---|---|
| CD 43594, #1 | C. difficile strain 43594 | $1.5 \times 10^8$ organisms/hen |
| CD 43594, #7 | C. difficile strain 43594 | $1.0 \times 10^9$ organisms/hen |
| CD 43596, #1 | C. difficile strain 43596 | $1.5 \times 10^8$ organisms/hen |
| CD 43596, #7 | C. difficile strain 43596 | $1.0 \times 10^9$ organisms/hen |

CFA, and for the later time point immunization, the stored frozen suspensions were used instead of freshly-prepared suspensions. The immunization schedule used is listed in Table 4.

c) Purification Of Anti-Bacterial Chicken Antibodies

Groups of four eggs were collected per immunization group between days 80 and 84 post-initial immunization, and chicken immunoglobulin (IgY) was extracted according to a modification of the procedure of A. Polson et al., Immunol. Comm., 9:495 (1980). A gentle stream of distilled water from a squirt bottle was used to separate the yolks from the whites, and the yolks were broken by dropping them through a funnel into a graduated cylinder. The four individual yolks were pooled for each group. The pooled, broken yolks were blended with 4 volumes of egg extraction buffer to improve antibody yield (egg extraction buffer is 0.01 M sodium phosphate, 0.1 M NaCl, pH 7.5, containing 0.005% thimerosal), and PEG 8000 (Amresco) was

TABLE 4

Immunization Schedule

| DAY OF IMMUNIZATION | FORMALIN-TREATMENT | IMMUNOGEN PREPARATION USED |
|---|---|---|
| 0 | 1%, 1 hr. | freshly-prepared |
| 14 | 1%, overnight | freshly-prepared |
| 21 | 1%, overnight | freshly-prepared |
| 35 | 1%, 48 hrs. | freshly-prepared |
| 49 | 1%, 72 hrs. | freshly-prepared |
| 70 | 1%, 72 hrs. | stored frozen |
| 85 | 1%, 72 hrs. | stored frozen |
| 105 | 1%, 72 hrs. | stored frozen | added to a concentration of 3.5%. When all the PEG dissolved, the protein precipitates that formed were pelleted by centrifugation at 13,000×g for 10 minutes. The supernatants were decanted and filtered through cheesecloth to remove the lipid layer, and the PEG was added to the supernatants to a final concentration of 12% (the supernatants were assumed to contain 3.5% PEG). After a second centrifugation, the supernatants were discarded and the pellets were centrifuged a final time to extrude the remaining PEG. These crude IgY pellets were then dissolved in the original yolk volume of egg extraction buffer and stored at 4° C. As an additional control, a preimmune IgY solution was prepared as described above, using eggs collected from unimmunized hens.

d) Detection Of Anti-Bacterial Antibodies In The Purified IgY Preparations

In order to evaluate the relative levels of specific anti-C. difficile activity in the IgY preparations described above, a modified version of the whole-organism ELISA procedure of N. V. Padhye et al., J. Clin. Microbiol. 29:99–103 (1990) was used. Frozen organisms of both C. difficile strains described above were thawed and diluted to a concentration of approximately $1 \times 10^7$ organisms/ml using PBS, pH 7.2. In this way, two separate coating suspensions were prepared, one for each immunizing strain. Into the wells of 96-well microtiter plates (Falcon, Pro-Bind Assay Plates) were placed 100 μl volumes of the coating suspensions. In this manner, each plate well received a total of approximately $1 \times 10^6$ organisms of one strain or the other. The plates were then incubated at 4° C. overnight. The next morning, the coating suspensions were decanted, and all wells were washed three times using PBS. In order to block non-specific binding sites, 100 μl of 0.5% BSA (Sigma) in PBS was then added to each well, and the plates were incubated for 2 hours at room temperature. The blocking solution was decanted, and 100 μl volumes of the IgY preparations described above were initially diluted 1:500 with a solution of 0.1% BSA in PBS, and then serially diluted in 1:5 steps. The following dilutions were placed in the wells: 1:500, 1:2,500, 1:62, 5000, 1:312,500, and 1:1,562,500. The plates were again incubated for 2 hours at room temperature. Following this incubation, the IgY-containing solutions were decanted, and the wells were washed three times using BBS-Tween (0.1 M boric acid, 0.025 M sodium borate, 1.0 M NaCl, 0.1% Tween-20), followed by two washes using PBS-Tween (0.1% Tween-20), and finally, two washes using PBS only. To each well, 100 μl of a 1:750 dilution of rabbit anti-chicken IgG (whole-molecule)-alkaline phosphatase conjugate (Sigma) (diluted in 0.1% BSA in PBS) was added. The plates were again incubated for 2 hours at room temperature. The conjugate solutions were decanted and the plates were washed as described above, substituting 50 mM $Na_2CO_3$, pH 9.5 for the PBS in the final wash. The plates were developed by the addition of 100 μl of a solution containing 1 mg/ml para-nitrophenyl phosphate (Sigma) dissolved in 50 mM $Na_2CO_3$, 10 mM $MgCl_2$, pH 9.5 to each well, and incubating the plates at

TABLE 5

Results Of The Anti-C. difficile Whole-Organism ELISA

| IgY PREPARATION | DILUTION OF IgY PREP | 43594-COATED WELLS | 43596-COATED WELLS |
|---|---|---|---|
| CD 43594, #1 | 1:500 | 1.746 | 1.801 |
| | 1:2,500 | 1.092 | 1.670 |
| | 1:12,500 | 0.202 | 0.812 |
| | 1:62,500 | 0.136 | 0.179 |
| | 1:312,500 | 0.012 | 0.080 |
| | 1:1,562,500 | 0.002 | 0.020 |
| CD 43594, #7 | 1:500 | 1.780 | 1.771 |
| | 1:2,500 | 1.025 | 1.078 |
| | 1:12,500 | 0.188 | 0.382 |
| | 1:62,500 | 0.052 | 0.132 |
| | 1:312,500 | 0.022 | 0.043 |
| | 1:1,562,500 | 0.005 | 0.024 |
| CD 43596, #1 | 1:500 | 1.526 | 1.790 |
| | 1:2,500 | 0.832 | 1.477 |
| | 1:12,500 | 0.247 | 0.452 |
| | 1:62,500 | 0.050 | 0.242 |
| | 1:312,500 | 0.010 | 0.067 |
| | 1:1,562,500 | 0.000 | 0.036 |
| CD 43596, #7 | 1:500 | 1.702 | 1.505 |
| | 1:2,500 | 0.706 | 0.866 |
| | 1:12,500 | 0.250 | 0.282 |
| | 1:62,500 | 0.039 | 0.078 |
| | 1:312,500 | 0.002 | 0.017 |
| | 1:1,562,500 | 0.000 | 0.010 |
| Preimmune IgY | 1:500 | 0.142 | 0.309 |
| | 1:2,500 | 0.032 | 0.077 |
| | 1:12,500 | 0.006 | 0.024 |
| | 1:62,500 | 0.002 | 0.012 |
| | 1:312,500 | 0.004 | 0.010 |
| | 1:1,562,500 | 0.002 | 0.014 | room temperature in the dark for 45 minutes. The absorbance of each well was measured at 410 nm using a Dynatech MR 700 plate reader. In this manner, each of the four IgY preparations described above was tested for reactivity against both of the immunizing C. difficile strains; strain-specific, as well as cross-reactive activity was determined.

Table 5 shows the results of the whole-organism ELISA. All four IgY preparations demonstrated significant levels of activity, to a dilution of 1:62,500 or greater against both of the immunizing organism strains. Therefore, antibodies raised against one strain were highly cross-reactive with the other strain, and vice versa. The immunizing concentration of organisms did not have a significant effect on organism-specific IgY production, as both concentrations produced approximately equivalent responses. Therefore, the lower immunizing concentration of approximately $1.5 \times 10^8$ organisms/hen is the preferred immunizing concentration of the two tested. The preimmune IgY preparation appeared to possess relatively low levels of C. difficile—reactive activity to a dilution of 1:500, probably due to prior exposure of the animals to environmental clostridia.

An initial whole-organism ELISA was performed using IgY preparations made from single CD 43594, #1 and CD 43596, #1 eggs collected around day 50 (data not shown). Specific titers were found to be 5 to 10-fold lower than those reported in Table 5. These results demonstrate that it is possible to begin immunizing hens prior to the time that they begin to lay eggs, and to obtain high titer specific IgY from the first eggs that are laid. In other words, it is not necessary to wait for the hens to begin laying before the immunization schedule is started.

EXAMPLE 2

Treatment Of C. difficile Infection With Anti-C. difficile Antibody

In order to determine whether the immune IgY antibodies raised against whole C. difficile organisms were capable of inhibiting the infection of hamsters by C. difficile, hamsters infected by these bacteria were utilized. [Lyerly et al., Infect. Immun., 59:2215–2218 (1991).] This example involved: (a) determination of the lethal dose of C. difficile organisms; and (b) treatment of infected animals with immune antibody or control antibody in nutritional solution.

a) Determination Of The Lethal Dose Of C. difficile Organisms

Determination of the lethal dose of C. difficile organisms was carried out according to the model described by D. M. Lyerly et al., Infect. Immun., 59:2215–2218 (1991). C. difficile strain ATCC 43596 (serogroup C, ATCC) was plated on BHI agar and grown anaerobically (BBL Gas Pak 100 system) at 37° C. for 42 hours. Organisms were removed from the agar surface using a sterile dacron-tip swab and suspended in sterile 0.9% NaCl solution to a density of $10^8$ organisms/ml.

In order to determine the lethal dose of C. difficile in the presence of control antibody and nutritional formula, non-immune eggs were obtained from unimmunized hens and a 12% PEG preparation made as described in Example 1(c). This preparation was redissolved in one fourth the original yolk volume of vanilla flavor Ensure®.

Starting on day one, groups of female Golden Syrian hamsters (Harlan Sprague Dawley), 8–9 weeks old and weighing approximately 100 gm, were orally administered 1 ml of the preimmune/Ensure® formula at time zero, 2 hours, 6 hours, and 10 hours. At 1 hour, animals were orally administered 3.0 mg clindamycin HCl (Sigma) in 1 ml of water. This drug predisposes hamsters to C. difficile infection by altering the normal intestinal flora. On day two, the animals were given 1 ml of the preimmune IgY/Ensure® formula at time zero, 2 hours, 6 hours, and 10 hours. At 1 hour on day two, different groups of animals were inoculated orally with saline (control), or $10^2$, $10^4$, $10^6$, or $10^8$ C. difficile organisms in 1 ml of saline. From days 3–12, animals were given 1 ml of the preimmune IgY/Ensure® formula three times daily and observed for the onset of diarrhea and death. Each animal was housed in an individual cage and was offered food and water ad libitum.

Administration of $10^6$–$10^8$ organisms resulted in death in 3–4 days while the lower doses of $10^2$–$10^4$ organisms caused death in 5 days. Cecal swabs taken from dead animals indicated the presence of C. difficile. Given the effectiveness of the $10^2$ dose, this number of organisms was chosen for the following experiment to see if hyperimmune anti-C. difficile antibody could block infection.

b) Treatment Of Infected Animals With Immune Antibody Or Control Antibody In Nutritional Formula The experiment in (a) was repeated using three groups of seven hamsters each. Group A received no clindamycin or C. difficile and was the survival control. Group B received clindamycin, $10^2$ C. difficile organisms and preimmune IgY on the same schedule as the animals in (a) above. Group C received clindamycin, $10^2$ C. difficile organisms, and hyper-immune anti-C. difficile IgY on the same schedule as Group B. The anti-C. difficile IgY was prepared as described in Example 1 except that the 12% PEG preparation was dissolved in one fourth the original yolk volume of Ensure®.

All animals were observed for the onset of diarrhea or other disease symptoms and death. Each animal was housed in an individual cage and was offered food and water ad libitum. The results are shown in Table 6.

Hamsters in the control group A did not develop diarrhea and remained healthy during the experimental period. Hamsters in groups B and C developed diarrheal disease. Anti-*C. difficile* IgY did not protect the animals from diarrhea or death, all animals succumbed in the same time interval as the animals treated with preimmune

TABLE 6

The Effect Of Oral Feeding Of Hyperimmune IgY Antibody on *C. difficile* Infection

| ANIMAL GROUP | | TIME TO DIARRHEA[a] | TIME TO DEATH[a] |
|---|---|---|---|
| A | pre-immune IgY only | no diarrhea | no deaths |
| B | Clindamycin, *C. difficile*, preimmune IgY | 30 hrs. | 49 hrs. |
| C | Clindamycin, *C. difficile*, immune IgY | 33 hrs. | 56 hrs. |

[a]Mean of seven animals.

IgY. Thus, while immunization with whole organisms apparently can improve sub-lethal symptoms with particular bacteria (see U.S. Pat. No. 5,080,895 to H. Tokoro), such an approach does not prove to be productive to protect against the lethal effects of *C. difficile*.

EXAMPLE 3

Production of *C. botulinum* Type A Antitoxin in Hens

In order to determine whether antibodies could be raised against the toxin produced by clostridial pathogens, which would be effective in treating clostridial diseases, antitoxin to *C. botulinum* type A toxin was produced. This example involves: (a) toxin modification; (b) immunization; (c) antitoxin collection; (d) antigenicity assessment; and (e) assay of antitoxin titer.

a) Toxin Modification

*C. botulinum* type A toxoid was obtained from B. R. DasGupta. From this, the active type A neurotoxin (M.W. approximately 150 kD) was purified to greater than 99% purity, according to published methods. [B. R. DasGupta & V. Sathyamoorthy, Toxicon, 22:415 (1984).] The neurotoxin was detoxified with formaldehyde according to published methods. [B. R. Singh & B. R. DasGupta, Toxicon, 27:403 (1989).]

b) Immunization

*C. botulinum* toxoid for immunization was dissolved in PBS (1 mg/ml) and was emulsified with an approximately equal volume of CFA (GIBCO) for initial immunization or IFA for booster immunization. On day zero, two white leghorn hens, obtained from local breeders, were each injected at multiple sites (intramuscular and subcutaneous) with 1 ml inactivated toxoid emulsified in 1 ml CFA. Subsequent booster immunizations were made according to the following schedule for day of injection and toxoid amount: days 14 and 21—0.5 mg; day 171—0.75 mg; days 394, 401, 409—0.25 mg. One hen received an additional booster of 0.150 mg on day 544.

c) Antitoxin Collection

Total yolk immunoglobulin (IgY) was extracted as described in Example 1(c) and the IgY pellet was dissolved in the original yolk volume of PBS with thimerosal.

d) Antigenicity Assessment

Eggs were collected from day 409 through day 423 to assess whether the toxoid was sufficiently immunogenic to raise antibody. Eggs from the two hens were pooled and antibody was collected as described in the standard PEG protocol. [Example 1(c).] Antigenicity of the botulinal toxin was assessed on Western blots. The 150 kD detoxified type A neurotoxin and unmodified, toxic, 300 kD botulinal type A complex (toxin used for intragastric route administration for animal gut neutralization experiments; see Example 6) were separated on a SDS-polyacrylamide reducing gel. The Western blot technique was performed according to the method of Towbin. [H. Towbin et al., Proc. Natl. Acad. Sci. USA, 76:4350 (1979).] Ten µg samples of *C. botulinum* complex and toxoid were dissolved in SDS reducing sample buffer (1% SDS, 0.5% 2-mercaptoethanol, 50 mM Tris, pH 6.8, 10% glycerol, 0.025% w/v bromphenol blue, 10% P-mercaptoethanol), heated at 95° C. for 10 min and separated on a 1 mm thick 5% SDS-polyacrylamide gel. [K. Weber and M. Osborn,"Proteins and Sodium Dodecyl Sulfate: Molecular Weight Determination on Polyacrylamide Gels and Related Procedures," in *The Proteins*, 3d Edition (H. Neurath & R. L. Hill, eds), pp. 179–223, (Academic Press, N.Y., 1975).] Part of the gel was cut off and the proteins were stained with Coomassie Blue. The proteins in the remainder of the gel were transferred to nitrocellulose using the Milliblot-SDE electro-blotting system (Millipore) according to manufacturer's directions. The nitrocellulose was temporarily stained with 10% Ponceau S [S. B. Carroll and A. Laughon, *"Production and Purification of Polyclonal Antibodies to the Foreign Segment of β-galactosidase Fusion Proteins,"* in *DNA Cloning: A Practical Approach*, Vol.III, (D. Glover, ed.), pp. 89–111, IRL Press, Oxford, (1987)] to visualize the lanes, then destained by running a gentle stream of distilled water over the blot for several minutes. The nitrocellulose was immersed in PBS containing 3% BSA overnight at 4° C. to block any remaining protein binding sites.

The blot was cut into strips and each strip was incubated with the appropriate primary antibody. The avian anti-*C. botulinum* antibodies [described in (c)] and pre-immune chicken antibody (as control) were diluted 1:125 in PBS containing 1 mg/ml BSA for 2 hours at room temperature. The blots were washed with two changes each of large volumes of PBS, BBS-Tween and PBS, successively (10 min/wash). Goat anti-chicken IgG alkaline phosphatase conjugated secondary antibody (Fisher Biotech) was diluted 1:500 in PBS containing 1 mg/ml BSA and incubated with the blot for 2 hours at room temperature. The blots were washed with two changes each of large volumes of PBS and BBS-Tween, followed by one change of PBS and 0.1 M Tris-HCl, pH 9.5. Blots were developed in freshly prepared alkaline phosphatase substrate buffer (100 µg/ml nitroblue tetrazolium (Sigma), 50 µg/ml 5-bromo-4-chloro-3-indolyl phosphate (Sigma), 5 mM $MgCl_2$ in 50 mM $Na_2CO_3$, pH 9.5).

The Western blots are shown in FIG. 1. The anti-*C. botulinum* IgY reacted to the toxoid to give a broad immunoreactive band at about 145–150 kD on the reducing gel. This toxoid is refractive to disulfide cleavage by reducing agents due to formalin crosslinking. The immune IgY reacted with the active toxin complex, a 97 kD *C. botulinum* type A heavy chain and a 53 kD light chain. The preimmune IgY was unreactive to the *C. botulinum* complex or toxoid in the Western blot.

e) Antitoxin Antibody Titer

The IgY antibody titer to *C. botulinum* type A toxoid of eggs harvested between day 409 and 423 was evaluated by ELISA, prepared as follows. Ninety-six-well Falcon Probind plates were coated overnight at 4° C. with 100 µl/well toxoid [B. R. Singh & B. R. Das Gupta, Toxicon 27:403 (1989)] at 2.5 µg/ml in PBS, pH 7.5 containing 0.005% thimerosal. The following day the wells were blocked with PBS containing 1% BSA for 1 hour at 37° C. The IgY from immune or preimmune eggs was diluted in PBS containing 1% BSA and 0.05% Tween 20 and the plates were incubated for 1 hour at 37° C. The plates were washed three times with PBS containing 0.05% Tween 20 and three times with PBS alone. Alkaline phosphatase-conjugated goat-anti-chicken IgG (Fisher Biotech) was diluted 1:750 in PBS containing 1% BSA and 0.05% Tween 20, added to the plates, and incubated 1 hour at 37° C. The plates were washed as before, and p-nitrophenyl phosphate (Sigma) at 1 mg/ml in 0.05 M $Na_2CO_3$, pH 9.5, 10 mM $MgCl_2$ was added.

Figure 2:
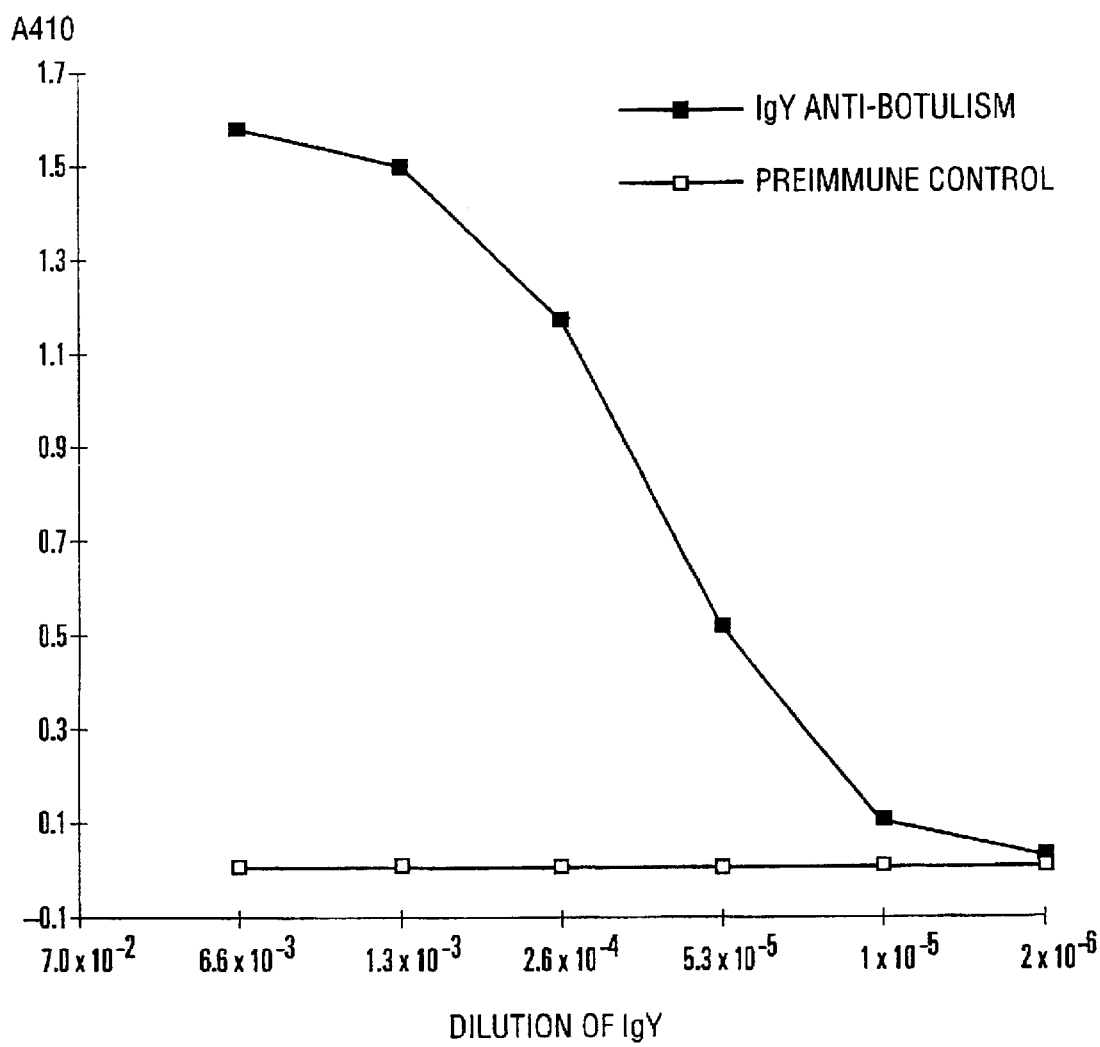
FIG. 2 shows the IgY antibody titer to *C. botulinum* type A toxoid in eggs, measured by ELISA.

The results are shown in FIG. 2. Chickens immunized with the toxoid generated high titers of antibody to the immunogen. Importantly, eggs from both immunized hens had significant anti-immunogen antibody titers as compared to preimmune control eggs. The anti-*C. botulinum* IgY possessed significant activity, to a dilution of 1:93,750 or greater.

EXAMPLE 4

Preparation Of Avian Egg Yolk Immunoglobulin In An Orally Administrable Form

In order to administer avian IgY antibodies orally to experimental mice, an effective delivery formula for the IgY had to be determined. The concern was that if the crude IgY was dissolved in PBS, the saline in PBS would dehydrate the mice, which might prove harmful over the duration of the study. Therefore, alternative methods of oral administration of IgY were tested. The example involved: (a) isolation of immune IgY; (b) solubilization of IgY in water or PBS, including subsequent dialysis of the IgY-PBS solution with water to eliminate or reduce the salts (salt and phosphate) in the buffer; and (c) comparison of the quantity and activity of recovered IgY by absorbance at 280 nm and PAGE, and enzyme-linked immunoassay (ELISA).

a) Isolation Of Immune IgY

In order to investigate the most effective delivery formula for IgY, we used IgY which was raised against *Crotalus durissus terrificus* venom. Three eggs were collected from hens immunized with the *C. durissus terrificus* venom and IgY was extracted from the yolks using the modified Polson procedure described by Thalley and Carroll [Bio/Technology, 8:934–938 (1990)] as described in Example 1(c).

The egg yolks were separated from the whites, pooled, and blended with four volumes of PBS. Powdered PEG 8000 was added to a concentration of 3.5%. The mixture was centrifuged at 10,000 rpm for 10 minutes to pellet the precipitated protein, and the supernatant was filtered through cheesecloth to remove the lipid layer. Powdered PEG 8000 was added to the supernatant to bring the final PEG concentration to 12% (assuming a PEG concentration of 3.5% in the supernatant). The 12% PEG/IgY mixture was divided into two equal volumes and centrifuged to pellet the IgY.

b) Solubilization Of The IgY In Water Or PBS

One pellet was resuspended in ½ the original yolk volume of PBS, and the other pellet was resuspended in ½ the original yolk volume of water. The pellets were then centrifuged to remove any particles or insoluble material. The IgY in PBS solution dissolved readily but the fraction resuspended in water remained cloudy.

In order to satisfy anticipated sterility requirements for orally administered antibodies, the antibody solution needs to be filter-sterilized (as an alternative to heat sterilization which would destroy the antibodies). The preparation of IgY resuspended in water was too cloudy to pass through either a 0.2 or 0.45 µm membrane filter, so 10 ml of the PBS resuspended fraction was dialyzed overnight at room temperature against 250 ml of water. The following morning the dialysis chamber was emptied and refilled with 250 ml of fresh $H_2O$ for a second dialysis. Thereafter, the yields of soluble antibody were determined at $OD_{280}$ and are compared in Table 7.

TABLE 7

Dependence Of IgY Yield On Solvents

| FRACTION | ABSORBANCE OF 1:10 DILUTION AT 280 nm | PERCENT RECOVERY |
|---|---|---|
| PBS dissolved | 1.149 | 100% |
| $H_2O$ dissolved | 0.706 | 61% |
| PBS dissolved/$H_2O$ dialyzed | 0.885 | 77% |

Resuspending the pellets in PBS followed by dialysis against water recovered more antibody than directly resuspending the pellets in water (77% versus 61%). Equivalent volumes of the IgY preparation in PBS or water were compared by PAGE, and these results were in accordance with the absorbance values (data not shown).

c) Activity Of IgY Prepared With Different Solvents

An ELISA was performed to compare the binding activity of the IgY extracted by each procedure described above. *C. durissus terrificus* (C.d.t.) venom at 2.5 µg/ml in PBS was used to coat each well of a 96-well microtiter plate. The remaining protein binding sites were blocked with PBS containing 5 mg/ml BSA. Primary antibody dilutions (in PBS containing 1 mg/ml BSA) were added in duplicate. After 2 hours of incubation at room temperature, the unbound primary antibodies were removed by washing the wells with PBS, BBS-Tween, and PBS. The species specific secondary antibody (goat anti-chicken immunoglobulin alkaline-phosphatase conjugate (Sigma) was diluted 1:750 in PBS containing 1 mg/ml BSA and added to each well of the microtiter plate. After 2 hours of incubation at room temperature, the unbound secondary antibody was removed by washing the plate as before, and freshly prepared alkaline phosphatase substrate (Sigma) at 1 mg/ml in 50 mM $Na_2CO_3$, 10 mM $MgCl_2$, pH 9.5 was added to each well. The color development was measured on a Dynatech MR 700 microplate reader using a 412 nm filter. The results are shown in Table 8.

The binding assay results parallel the recovery values in Table 7, with PBS-dissolved IgY showing slightly more activity than the PBS-dissolved/$H_2O$ dialyzed antibody. The water-dissolved antibody had considerably less binding activity than the other preparations.

EXAMPLE 5

Survival Of Antibody Activity After Passage Through The Gastrointestinal Tract

In order to determine the feasibility of oral administration of antibody, it was of interest to determine whether orally administered IgY survived passage through the gastrointestinal tract. The example involved: (a) oral administration of specific immune antibody mixed with a nutritional formula; and (b) assay of antibody activity extracted from feces.

TABLE 8

Antigen-Binding Activity of IgY Prepared with Different Solvents

| DILUTION | PRE-IMMUNE | PBS DISSOLVED | $H_2O$ DISSOLVED | PBS/$H_2O$ |
|---|---|---|---|---|
| 1:500 | 0.005 | 1.748 | 1.577 | 1.742 |
| 1:2,500 | 0.004 | 0.644 | 0.349 | 0.606 |
| 1:12,500 | 0.001 | 0.144 | 0.054 | 0.090 |
| 1:62,500 | 0.001 | 0.025 | 0.007 | 0.016 |
| 1:312,500 | 0.010 | 0.000 | 0.000 | 0.002 | a) Oral Administration Of Antibody

The IgY preparations used in this example are the same PBS-dissolved/$H_2O$ dialyzed antivenom materials obtained in Example 4 above, mixed with an equal volume of Enfamil®. Two mice were used in this experiment, each receiving a different diet as follows:
1) water and food as usual;
2) immune IgY preparation dialyzed against water and mixed 1:1 with Enfamil®. (The mice were given the corresponding mixture as their only source of food and water).

b) Antibody Activity After Ingestion

After both mice had ingested their respective fluids, each tube was refilled with approximately 10 ml of the appropriate fluid first thing in the morning. By mid-morning there was about 4 to 5 ml of liquid left in each tube. At this point stool samples were collected from each mouse, weighed, and dissolved in approximately 500 µl PBS per 100 mg stool sample. One hundred and sixty mg of control stools (no antibody) and 99 mg of experimental stools (specific antibody) in 1.5 ml microfuge tubes were dissolved in 800 and 500 µl PBS, respectively. The samples were heated at 37° C. for 10 minutes and vortexed vigorously. The experimental stools were also broken up with a narrow spatula. Each sample was centrifuged for 5 minutes in a microfuge and the supernatants, presumably containing the antibody extracts, were collected. The pellets were saved at 2–8° C. in case future extracts were needed. Because the supernatants were tinted, they were diluted five-fold in PBS containing 1 mg/ml BSA for the initial dilution in the enzyme immunoassay (ELISA). The primary extracts were then diluted five-fold serially from this initial dilution. The volume of primary extract added to each well was 190 µl. The ELISA was performed exactly as described in Example 4.

TABLE 9

Specific Antibody Activity After Passage Through the Gastrointestinal Tract

| DILUTION | PREIMMUNE IgY | CONTROL FECAL EXTRACT | EXP. FECAL EXTRACT |
|---|---|---|---|
| 1:5 | <0 | 0.000 | 0.032 |
| 1:25 | 0.016 | <0 | 0.016 |
| 1:125 | <0 | <0 | 0.009 |
| 1:625 | <0 | 0.003 | 0.001 |
| 1:3125 | <0 | <0 | 0.000 |

There was some active antibody in the fecal extract from the mouse given the specific antibody in Enfamil® formula, but it was present at a very low level. Since the samples were assayed at an initial 1:5 dilution, the binding observed could have been higher with less dilute samples. Consequently, the mice were allowed to continue ingesting either regular food and water or the specific IgY in Enfamil® formula, as appropriate, so the assay could be repeated. Another ELISA plate was coated overnight with 5 µg/ml of C.d.t. venom in PBS.

The following morning the ELISA plate was blocked with 5 mg/ml BSA, and the fecal samples were extracted as before, except that instead of heating the extracts at 37° C., the samples were kept on ice to limit proteolysis. The samples were assayed undiluted initially, and in 5× serial dilutions thereafter. Otherwise the assay was carried out as before.

TABLE 10

Specific Antibody Survives Passage Through the Gastrointestinal Tract

| DILUTION | PREIMMUNE IgY | CONTROL EXTRACT | EXP. EXTRACT |
|---|---|---|---|
| undiluted | 0.003 | <0 | 0.379 |
| 1:5 | <0 | <0 | 0.071 |
| 1:25 | 0.000 | <0 | 0.027 |
| 1:125 | 0.003 | <0 | 0.017 |
| 1:625 | 0.000 | <0 | 0.008 |
| 1:3125 | 0.002 | <0 | 0.002 |

The experiment confirmed the previous results, with the antibody activity markedly higher. The control fecal extract showed no anti-C.d.t. activity, even undiluted, while the fecal extract from the anti-C.d.t. IgY/Enfamil®-fed mouse showed considerable anti-C.d.t. activity. This experiment (and the previous experiment) clearly demonstrate that active IgY antibody survives passage through the mouse digestive tract, a finding with favorable implications for the success of IgY antibodies administered orally as a therapeutic or prophylactic.

EXAMPLE 6

In Vivo Neutralization Of Type C. botulinum Type A Neurotoxin By Avian Antitoxin Antibody This example demonstrated the ability of PEG-purified antitoxin, collected as described in Example 3, to neutralize the lethal effect of C. botulinum neurotoxin type A in mice. To determine the oral lethal dose ($LD_{100}$) of toxin A, groups of BALB/c mice were given different doses of toxin per unit body weight (average body weight of 24 grams). For oral administration, toxin A complex, which contains the neurotoxin associated with other non-toxin proteins was used. This complex is markedly more toxic than purified neurotoxin when given by the oral route. [I. Ohishi et al., Infect. Immun., 16:106 (1977).] C. botulinum toxin type A complex, obtained from Eric Johnson (University Of Wisconsin, Madison) was 250 µg/ml in 50 mM sodium citrate, pH 5.5, specific toxicity $3 \times 10^7$ mouse $LD_{50}$/mg with parenteral administration. Approximately 40–50 ng/gm body weight was usually fatal within 48 hours in mice maintained on conventional food and water. When mice were given a diet ad libitum of only Enfamil® the concentration needed to produce lethality was approximately 2.5 times higher (125 ng/gm body weight). Botulinal toxin concentrations of approximately 200 ng/gm body weight were fatal in mice fed Enfamil® containing preimmune IgY (resuspended in Enfamil® at the original yolk volume).

The oral $LD_{100}$ of C. botulinum toxin was also determined in mice that received known amounts of a mixture of preimmune IgY-Ensure® delivered orally through feeding needles. Using a 22 gauge feeding needle, mice were given 250 µl each of a preimmune IgY-Ensure® mixture (preimmune IgY dissolved in ¼ original yolk volume) 1 hour before and ½ hour and 5 hours after administering botulinal toxin. Toxin concentrations given orally ranged from approximately 12 to 312 ng/gm body weight (0.3 to 7.5 μg per mouse). Botulinal toxin complex concentration of approximately 40 ng/gm body weight (1 μg per mouse) was lethal in all mice in less than 36 hours.

Two groups of BALB/c mice, 10 per group, were each given orally a single dose of 1 μg each of botulinal toxin complex in 100 μl of 50 mM sodium citrate pH 5.5. The mice received 250 μl treatments of a mixture of either preimmune or immune IgY in Ensureg (¼ original yolk volume) 1 hour before and ½ hour, 4 hours, and 8 hours after botulinal toxin administration. The mice received three treatments per day for two more days. The mice were observed for 96 hours. The survival and mortality are shown in Table 11.

TABLE 11

Neutralization Of Botulinal Toxin A in Vivo

| TOXIN DOSE ng/gm | ANTIBODY TYPE | NUMBER OF MICE ALIVE | NUMBER OF MICE DEAD |
|---|---|---|---|
| 41.6 | non-immune | 0 | 10 |
| 41.6 | anti-botulinal toxin | 10 | 0 |

All mice treated with the preimmune IgY-Ensure® mixture died within 46 hours post-toxin administration. The average time of death in the mice was 32 hours post toxin administration. Treatments of preimmune IgY-Ensure® mixture did not continue beyond 24 hours due to extensive paralysis of the mouth in mice of this group. In contrast, all ten mice treated with the immune anti-botulinal toxin IgY-Ensure® mixture survived past 96 hours. Only 4 mice in this group exhibited symptoms of botulism toxicity (two mice about 2 days after and two mice 4 days after toxin administration). These mice eventually died 5 and 6 days later. Six of the mice in this immune group displayed no adverse effects to the toxin and remained alive and healthy long term. Thus, the avian anti-botulinal toxin antibody demonstrated very good protection from the lethal effects of the toxin in the experimental mice.

EXAMPLE 7

Production Of An Avian Antitoxin Against Clostridium difficile Toxin A

Toxin A is a potent cytotoxin secreted by pathogenic strains of C. difficile, that plays a direct role in damaging gastrointestinal tissues. In more severe cases of C. difficile intoxication, pseudomembranous colitis can develop which may be fatal. This would be prevented by neutralizing the effects of this toxin in the gastrointestinal tract. As a first step, antibodies were produced against a portion of the toxin. The example involved: (a) conjugation of a synthetic peptide of toxin A to bovine serum albumin; (b) immunization of hens with the peptide-BSA conjugate; and (c) detection of antitoxin peptide antibodies by ELISA.

a) Conjugation Of A Synthetic Peptide Of Toxin A To Bovine Serum Albumin

The synthetic peptide CQTIDGKKYYFN-NH$_2$ was prepared commercially (Multiple Peptide Systems, San Diego, Calif.) and validated to be >80% pure by high-pressure liquid chromatography. The eleven amino acids following the cysteine residue represent a consensus sequence of a repeated amino acid sequence found in Toxin A. [Wren et al., Infect. Immun., 59:3151–3155 (1991).] The cysteine was added to facilitate conjugation to carrier protein.

In order to prepare the carrier for conjugation, BSA (Sigma) was dissolved in 0.01 M NaPO$_4$, pH 7.0 to a final concentration of 20 mg/ml and n-maleimidobenzoyl-N-hydroxysuccinimide ester (MBS; Pierce) was dissolved in N,N-dimethyl formamide to a concentration of 5 mg/ml. MBS solution, 0.51 ml, was added to 3.25 ml of the BSA solution and incubated for 30 minutes at room temperature with stirring every 5 minutes. The MBS-activated BSA was then purified by chromatography on a Bio-Gel P-10 column (Bio-Rad; 40 ml bed volume) equilibrated with 50 mM NaPO$_4$, pH 7.0 buffer. Peak fractions were pooled (6.0 ml).

Lyophilized toxin A peptide (20 mg) was added to the activated BSA mixture, stirred until the peptide dissolved and incubated 3 hours at room temperature. Within 20 minutes, the reaction mixture became cloudy and precipitates formed. After 3 hours, the reaction mixture was centrifuged at 10,000×g for 10 min and the supernatant analyzed for protein content. No significant protein could be detected at 280 nm. The conjugate precipitate was washed three times with PBS and stored at 4° C. A second conjugation was performed with 15 mg of activated BSA and 5 mg of peptide and the conjugates pooled and suspended at a peptide concentration of 10 mg/ml in 10 mM NaPO$_4$, pH 7.2.

b) Immunization Of Hens With Peptide Conjugate

Two hens were each initially immunized on day zero by injection into two subcutaneous and two intramuscular sites with 1 mg of peptide conjugate that was emulsified in CFA (GIBCO). The hens were boosted on day 14 and day 21 with 1 mg of peptide conjugate emulsified in IFA (GIBCO).

c) Detection Of Antitoxin Peptide Antibodies By ELISA

IgY was purified from two eggs obtained before immunization (pre-immune) and two eggs obtained 31 and 32 days after the initial immunization using PEG fractionation as described in Example 1.

Wells of a 96-well microtiter plate (Falcon Pro-Bind Assay Plate) were coated overnight at 4° C. with 100 μg/ml solution of the toxin A synthetic peptide in PBS, pH 7.2 prepared by dissolving 1 mg of the peptide in 1.0 ml of H$_2$O and dilution of PBS. The pre-immune and immune IgY preparations were diluted in a five-fold series in a buffer containing 1% PEG 8000 and 0.1% Tween-20 (v/v) in PBS, pH 7.2. The wells were blocked for 2 hours at room temperature with 150 μl of a solution containing 5% (v/v) Carnation® nonfat dry milk and 1% PEG 8000 in PBS, pH 7.2. After incubation for 2 hours at room temperature, the wells were washed, secondary rabbit anti-chicken IgG-alkaline phosphatase (1:750) added, the wells washed again and the color development obtained as described in Example 1. The results are shown in Table 12.

TABLE 12

Reactivity Of IgY With Toxin Peptide

| | ABSORBANCE AT 410 nm | |
|---|---|---|
| DILUTION OF PEG PREP | PREIMMUNE | IMMUNE ANTI-PEPTIDE |
| 1:100 | 0.013 | 0.253 |
| 1:500 | 0.004 | 0.039 |
| 1:2500 | 0.004 | 0.005 |

Clearly, the immune antibodies contain titers against this repeated epitope of toxin A.

EXAMPLE 8

Production Of Avian Antitoxins Against Clostridium difficile Native Toxins A And B To determine whether avian antibodies are effective for the neutralization of C. difficile toxins, hens were immunized using native *C. difficile* toxins A and B. The resulting egg yolk antibodies were then extracted and assessed for their ability to neutralize toxins A and B in vitro. The Example involved (a) preparation of the toxin immunogens, (b) immunization, (c) purification of the antitoxins, and (d) assay of toxin neutralization activity.

a) Preparation Of The Toxin Immunogens

Both *C. difficile* native toxins A and B, and *C. difficile* toxoids, prepared by the treatment of the native toxins with formaldehyde, were employed as immunogens. *C. difficile* toxoids A and B were prepared by a procedure which was modified from published methods (Ehrich et al., Infect. Immun. 28:1041 (1980). Separate solutions (in PBS) of native *C. difficile* toxin A and toxin B (Tech Lab) were each adjusted to a concentration of 0.20 mg/ml, and formaldehyde was added to a final concentration of 0.4%. The toxin/formaldehyde solutions were then incubated at 37° C. for 40 hrs. Free formaldehyde was then removed from the resulting toxoid solutions by dialysis against PBS at 4° C. In previously published reports, this dialysis step was not performed. Therefore, free formaldehyde must have been present in their toxoid preparations. The toxoid solutions were concentrated, using a Centriprep concentrator unit (Amicon), to a final toxoid concentration of 4.0 mg/ml. The two resulting preparations were designated as toxoid A and toxoid B.

*C. difficile* native toxins were prepared by concentrating stock solutions of toxin A and toxin B (Tech Lab, Inc), using Centriprep concentrator units (Amicon), to a final concentration of 4.0 mg/ml.

b) Immunization

The first two immunizations were performed using the toxoid A and toxoid B immunogens described above. A total of 3 different immunization combinations were employed. For the first immunization group, 0.2 ml of toxoid A was emulsified in an equal volume of Titer Max adjuvant (CytRx). Titer Max was used in order to conserve the amount of immunogen used, and to simplify the immunization procedure. This immunization group was designated "CTA." For the second immunization group, 0.1 ml of toxoid B was emulsified in an equal volume of Titer Max adjuvant. This group was designated "CTB." For the third immunization group, 0.2 ml of toxoid A was first mixed with 0.2 ml of toxoid B, and the resulting mixture was emulsified in 0.4 ml of Titer Max adjuvant. This group was designated "CTAB." In this way, three separate immunogen emulsions were prepared, with each emulsion containing a final concentration of 2.0 mg/ml of toxoid A (CTA) or toxoid B (CTB) or a mixture of 2.0 mg/ml toxoid A and 2.0 mg/ml toxoid B (CTAB).

On day 0, White Leghorn hens, obtained from a local breeder, were immunized as follows: Group CTA. Four hens were immunized, with each hen receiving 200 μg of toxoid A, via two intramuscular (I.M.) injections of 50 μl of CTA emulsion in the breast area. Group CTB. One hen was immunized with 200 μg of toxoid B, via two I.M. injections of 50 μl of CTB emulsion in the breast area. Group CTAB. Four hens were immunized, with each hen receiving a mixture containing 200 μg of toxoid A and 200 μg of toxoid B, via two I.M. injections of 100 μl of CTAB emulsion in the breast area. The second immunization was performed 5 weeks later, on day 35, exactly as described for the first immunization above.

In order to determine whether hens previously immunized with *C. difficile* toxoids could tolerate subsequent booster immunizations using native toxins, a single hen from group CTAB was immunized for a third time, this time using a mixture of the native toxin A and native toxin B described in section (a) above (these toxins were not formaldehyde-treated, and were used in their active form). This was done in order to increase the amount (titer) and affinity of specific antitoxin antibody produced by the hen over that achieved by immunizing with toxoids only. On day 62, 0.1 ml of a toxin mixture was prepared which contained 200 μg of native toxin A and 200 μg of native toxin B. This toxin mixture was then emulsified in 0.1 ml of Titer Max adjuvant. A single CTAB hen was then immunized with the resulting immunogen emulsion, via two I.M. injections of 100 μl each, into the breast area. This hen was marked with a wing band, and observed for adverse effects for a period of approximately 1 week, after which time the hen appeared to be in good health.

Because the CTAB hen described above tolerated the booster immunization with native toxins A and B with no adverse effects, it was decided to boost the remaining hens with native toxin as well. On day 70, booster immunizations were performed as follows: Group CTA. A 0.2 ml volume of the 4 mg/ml native toxin A solution was emulsified in an equal volume of Titer Max adjuvant. Each of the 4 hens was then immunized with 200 μg of native toxin A, as described for the toxoid A immunizations above. Group CTB. A 50 μl volume of the 4 mg/ml native toxin B solution was emulsified in an equal volume of Titer Max adjuvant. The hen was then immunized with 200 μg of native toxin B, as described for the toxoid B immunizations above. Group CTAB. A 0.15 ml volume of the 4 mg/ml native toxin A solution was first mixed with a 0.15 ml volume the 4 mg/ml native toxin B solution. The resulting toxin mixture was then emulsified in 0.3 ml of Titer Max adjuvant. The 3 remaining hens (the hen with the wing band was not immunized this time) were then immunized with 200 μg of native toxin A and 200 μg of native toxin B as described for the toxoid A+ toxoid B immunizations (CTAB) above. On day 85, all hens received a second booster immunization using native toxins, done exactly as described for the first boost with native toxins above.

All hens tolerated both booster immunizations with native toxins with no adverse effects. As previous literature references describe the use of formaldehyde-treated toxoids, this is apparently the first time that any immunizations have been performed using native *C. difficile* toxins.

c) Purification Of Antitoxins

Eggs were collected from the hen in group CTB 10–12 days following the second immunization with toxoid (day 35 immunization described in section (b) above), and from the hens in groups CTA and CTAB 20–21 days following the second immunization with toxoid. To be used as a pre-immune (negative) control, eggs were also collected from unimmunized hens from the same flock. Egg yolk immunoglobulin (IgY) was extracted from the 4 groups of eggs as described in Example 1 (c), and the final IgY pellets were solubilized in the original yolk volume of PBS without thimerosal. Importantly, thimerosal was excluded because it would have been toxic to the CHO cells used in the toxin neutralization assays described in section (d) below.

d) Assay Of Toxin Neutralization Activity

The toxin neutralization activity of the IgY solutions prepared in section (c) above was determined using an assay system that was modified from published methods. [Ehrich et al., Infect. Immun. 28:1041–1043 (1992); and McGee et al. Microb. Path. 12:333–341 (1992).] As additional controls, affinity-purified goat anti-*C. difficile* toxin A (Tech Lab) and affinity-purified goat anti-*C. difficile* toxin B (Tech Lab) were also assayed for toxin neutralization activity.

The IgY solutions and goat antibodies were serially diluted using F 12 medium (GIBCO) which was supplemented with 2% FCS (GIBCO)(this solution will be referred to as "medium" for the remainder of this Example). The resulting antibody solutions were then mixed with a standardized concentration of either native *C. difficile* toxin A (Tech Lab), or native *C. difficile* toxin B (Tech Lab), at the concentrations indicated below. Following incubation at 37° C. for 60 min., 100 µl volumes of the toxin+antibody mixtures were added to the wells of 96-well microtiter plates (Falcon Microtest III) which contained $2.5 \times 10^4$ Chinese Hamster Ovary (CHO) cells per well (the CHO cells were plated on the previous day to allow them to adhere to the plate wells). The final concentration of toxin, or dilution of a antibody indicated below refers to the final test concentration of each reagent present in the respective microtiter plate wells. Toxin reference wells were prepared which contained CHO cells and toxin A or toxin B at the same concentration used for the toxin plus antibody mixtures (these wells contained no antibody). Separate control wells were also prepared which contained CHO cells and medium only. The assay plates were then incubated for 18–24 hrs. in a 37° C., humidified, 5% $CO_2$ incubator. On the following day, the remaining adherent (viable) cells in the plate wells were stained using 0.2% crystal violet (Mallinckrodt) dissolved in 2% ethanol, for 10 min. Excess stain was then removed by rinsing with water, and the stained cells were solubilized by adding 100 µl of 1% SDS (dissolved in water) to each well. The absorbance of each well was then measured at 570 nm, and the percent cytotoxicity of each test sample or mixture was calculated using the following formula:

$$\% \text{ CHO Cell Cytotoxicity} = \left[1 - \left(\frac{\text{Abs. Sample}}{\text{Abs. Control}}\right)\right] \times 100$$

Figure 3:
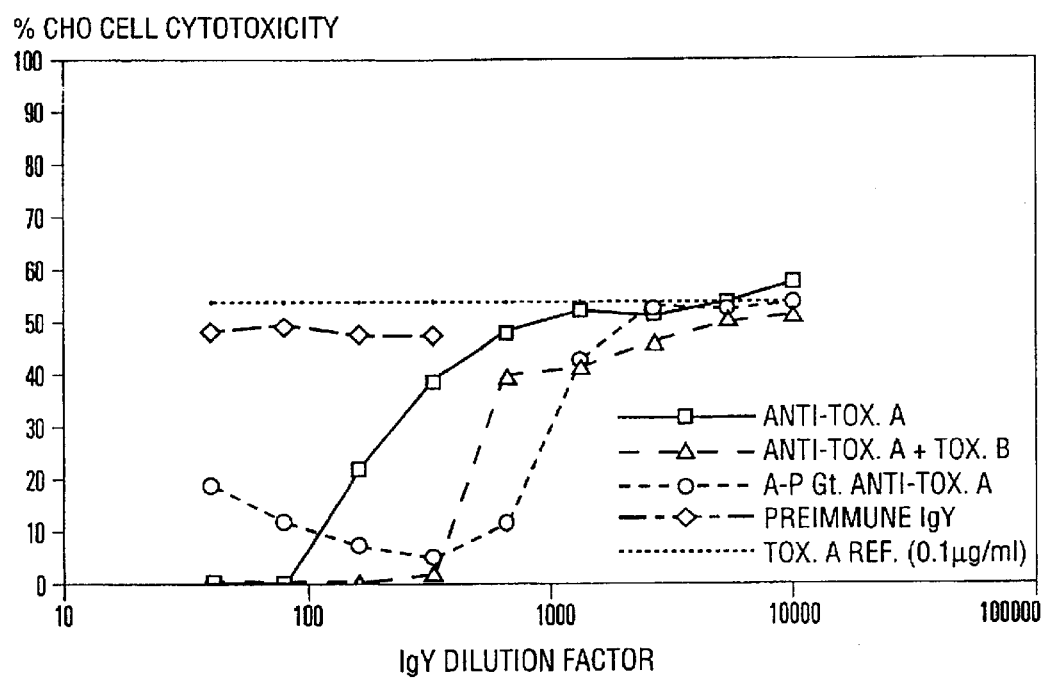
FIG. 3 shows the results of *C. difficile* toxin A neutralization assays.

Unlike previous reports which quantitate results visually by counting cell rounding by microscopy, this Example utilized spectrophotometric methods to quantitate the *C. difficile* toxin bioassay. In order to determine the toxin A neutralizing activity of the CTA, CTAB, and pre-immune IgY preparations, as well as the affinity-purified goat antitoxin A control, dilutions of these antibodies were reacted against a 0.1 µg/ml concentration of native toxin A (this is the approx. 50% cytotoxic dose of toxin A in this assay system). The results are shown in FIG. 3.

Complete neutralization of toxin A occurred with the CTA IgY (antitoxin A, above) at dilutions of 1:80 and lower, while significant neutralization occurred out to the 1:320 dilution. The CTAB IgY (antitoxin A+toxin B, above) demonstrated complete neutralization at the 1:320–1:160 and lower dilutions, and significant neutralization occurred out to the 1:1280 dilution. The commercially available affinity-purified goat antitoxin A did not completely neutralize toxin A at any of the dilutions tested, but demonstrated significant neutralization out to a dilution of 1:1,280. The preimmune IgY did not show any toxin A neutralizing activity at any of the concentrations tested. These results demonstrate that IgY purified from eggs laid by hens immunized with toxin A alone, or simultaneously with toxin A and toxin B, is an effective toxin A antitoxin.

Figure 4:
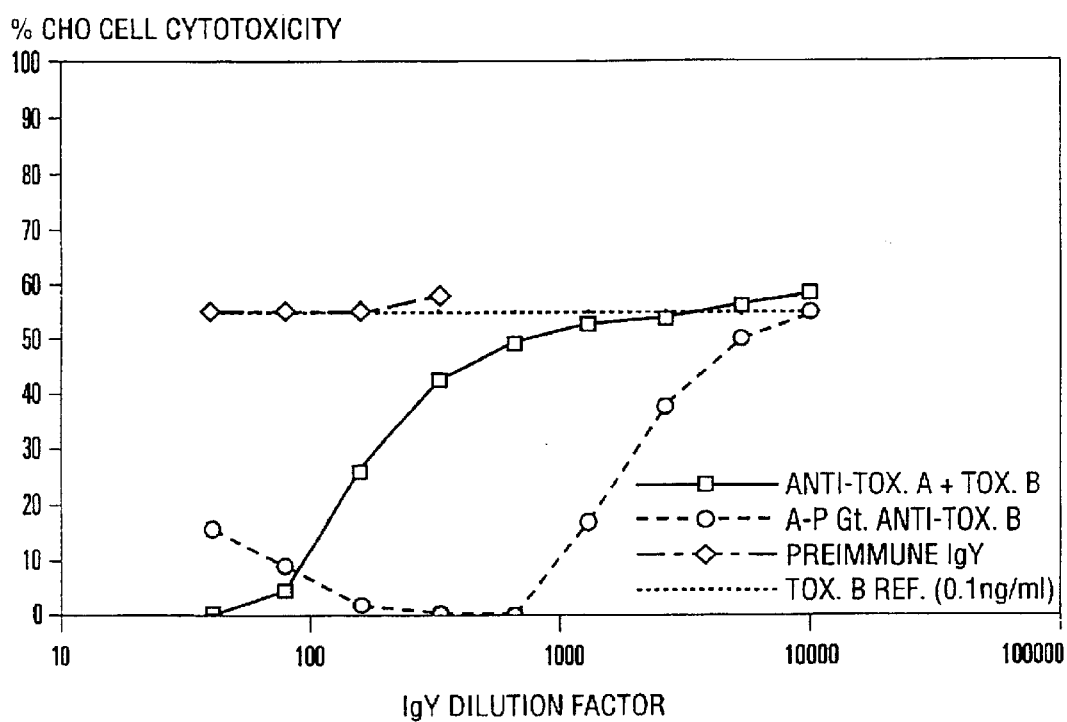
FIG. 4 shows the results of *C. difficile* toxin B neutralization assays.

The toxin B neutralizing activity of the CTAB and pre-immune IgY preparations, and also the affmity-purified goat antitoxin B control was determined by reacting dilutions of these antibodies against a concentration of native toxin B of 0.1 ng/ml (approximately the 50% cytotoxic dose of toxin B in the assay system). The results are shown in FIG. 4.

Complete neutralization of toxin B occurred with the CTAB IgY (antitoxin A+toxin B, above) at the 1:40 and lower dilutions, and significant neutralization occurred out to the 1:320 dilution. The affinity-purified goat antitoxin B demonstrated complete neutralization at dilutions of 1:640 and lower, and significant neutralization occurred out to a dilution of 1:2,560. The preimmune IgY did not show any toxin B neutralizing activity at any of the concentrations tested. These results demonstrate that IgY purified from eggs laid by hens immunized simultaneously with toxin A and toxin B is an effective toxin B antitoxin.

Figure 5:
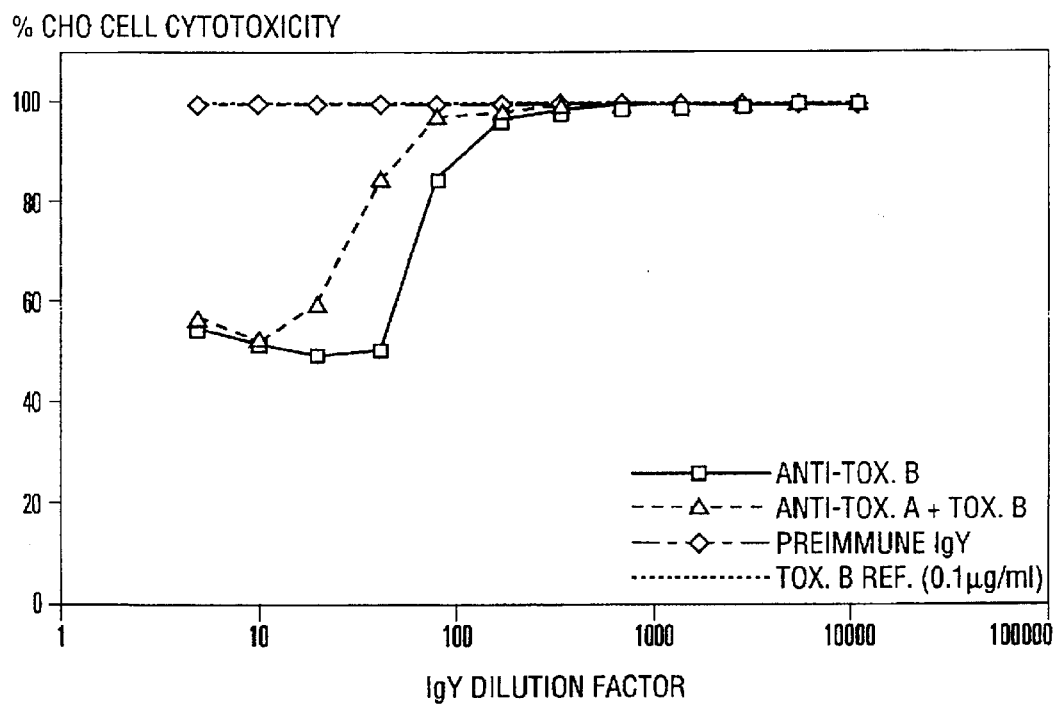
FIG. 5 shows the results of *C. difficile* toxin B neutralization assays.

In a separate study, the toxin B neutralizing activity of CTB, CTAB, and pre-immune IgY preparations was determined by reacting dilutions of these antibodies against a native toxin B concentration of 0.1 µg/ml (approximately 100% cytotoxic dose of toxin B in this assay system). The results are shown in FIG. 5.

Significant neutralization of toxin B occurred with the CTB IgY (antitoxin B, above) at dilutions of 1:80 and lower, while the CTAB IgY (antitoxin A+toxin B, above) was found to have significant neutralizing activity at dilutions of 1:40 and lower. The preimmune IgY did not show any toxin B neutralizing activity at any of the concentrations tested. These results demonstrate that IgY purified from eggs laid by hens immunized with toxin B alone, or simultaneously with toxin A and toxin B, is an effective toxin B antitoxin.

EXAMPLE 9

In vivo Protection Of Golden Syrian Hamsters From *C. difficile* Disease By Avian Antitoxins Against *C. difficile* Toxins A And B The most extensively used animal model to study *C. difficile* disease is the hamster. [Lyerly et al., Infect. Immun. 47:349–352 (1992).] Several other animal models for antibiotic-induced diarrhea exist, but none mimic the human form of the disease as closely as the hamster model. [R. Fekety, "Animal Models of Antibiotic-Induced Colitis," in O. Zak and M. Sande (eds.), *Experimental Models in Antimicrobial Chemotherapy*, Vol. 2, pp.61–72, (1986).] In this model, the animals are first predisposed to the disease by the oral administration of an antibiotic, such as clindamycin, which alters the population of normally-occurring gastrointestinal flora (Fekety, at 61–72). Following the oral challenge of these animals with viable *C. difficile* organisms, the hamsters develop cecitis, and hemorrhage, ulceration, and inflammation are evident in the intestinal mucosa. [Lyerly et al., Infect. Immun. 47:349–352 (1985).] The animals become lethargic, develop severe diarrhea, and a high percentage of them die from the disease. [Lyerly et al., Infect. Immun. 47:349–352 (1985).] This model is therefore ideally suited for the evaluation of therapeutic agents designed for the treatment or prophylaxis of *C. difficile* disease.

The ability of the avian *C. difficile* antitoxins, described in Example 1 above, to protect hamsters from *C. difficile* disease was evaluated using the Golden Syrian hamster model of *C. difficile* infection. The Example involved (a) preparation of the avian *C. difficile* antitoxins, (b) in vivo protection of hamsters from *C. difficile* disease by treatment with avian antitoxins, and (c) long-term survival of treated hamsters.

a) Preparation Of The Avian *C. difficile* Antitoxins

Eggs were collected from hens in groups CTA and CTAB described in Example 1 (b) above. To be used as a pre-immune (negative) control, eggs were also purchased from a local supermarket. Egg yolk immunoglobulin (IgY) was extracted from the 3 groups of eggs as described in Example 1 (c), and the final IgY pellets were solubilized in one fourth the original yolk volume of Ensure® nutritional formula.

b) In vivo Protection Of Hamsters Against *C. difficile* Disease By Treatment With Avian Antitoxins The avian *C. difficile* antitoxins prepared in section (a) above were evaluated for their ability to protect hamsters from *C. difficile* disease using an animal model system which was modified from published procedures. [Fekety, at 61–72; Borriello et al., J. Med. Microbiol., 24:53–64 (1987); Kim et al., Infect. Immun., 55:2984–2992 (1987); Borriello et al., J. Med. Microbiol., 25:191–196 (1988); Delmee and Avesani, J. Med. Microbiol., 33:85–90 (1990); and Lyerly et al., Infect. Immun., 59:2215–2218 (1991).] For the study, three separate experimental groups were used, with each group consisting of 7 female Golden Syrian hamsters (Charles River), approximately 10 weeks old and weighing approximately 100 gms. each. The three groups were designated "CTA," "CTAB" and "Pre-immune." These designations corresponded to the antitoxin preparations with which the animals in each group were treated. Each animal was housed in an individual cage, and was offered food and water ad libitum through the entire length of the study. On day 1, each animal was orally administered 1.0 ml of one of the three antitoxin preparations (prepared in section (a) above) at the following timepoints: 0 hrs., 4 hrs., and 8 hrs. On day 2, the day 1 treatment was repeated. On day 3, at the 0 hr. timepoint, each animal was again administered antitoxin, as described above. At 1 hr., each animal was orally administered 3.0 mg of clindamycin-HCl (Sigma) in 1 ml of water. This treatment predisposed the animals to infection with *C. difficile*. As a control for possible endogenous *C. difficile* colonization, an additional animal from the same shipment (untreated) was also administered 3.0 mg of clindamycin-HCl in the same manner. This clindamycin control animal was left untreated (and uninfected) for the remainder of the study. At the 4 hr. and 8 hr. timepoints, the animals were administered antitoxin as described above. On day 4, at the 0 hr. timepoint, each animal was again administered antitoxin as described above. At 1 hr., each animal was orally challenged with 1 ml of *C. difficile* inoculum, which contained approx. 100 *C. difficile* strain 43596 organisms in sterile saline. *C. difficile* strain 43596, which is a serogroup C strain, was chosen because it is representative of one of the most frequently-occurring serogroups isolated from patients with antibiotic-associated pseudomembranous colitis. [Delmee et al., J. Clin. Microbiol., 28:2210–2214 (1985).] In addition, this strain has been previously demonstrated to be virulent in the hamster model of infection. [Delmee and Avesani, J. Med. Microbiol., 33:85–90 (1990).] At the 4 hr. and 8 hr. timepoints, the animals were administered antitoxin as described above. On days 5 through 13, the animals were administered antitoxin 3x per day as described for day 1 above, and observed for the onset of diarrhea and death. On the morning of day 14, the final results of the study were tabulated. These results are shown in Table 13.

Representative animals from those that died in the Pre-Immune and CTA groups were necropsied. Viable *C. difficile* organisms were cultured from the ceca of these animals, and the gross pathology of the gastrointestinal tracts of these animals was consistent with that expected for *C. difficile* disease (inflamed, distended, hemorrhagic cecum, filled with watery diarrhea-like material). In addition, the

TABLE 13

| Treatment Group | Treatment Results | |
|---|---|---|
| | No. Animals Surviving | No. Animals Dead |
| Pre-Immune | 1 | 6 |
| CTA (Antitoxin A only) | 5 | 2 |
| CTAB (Antitoxin A + Antitoxin B) | 7 | 0 | clindamycin control animal remained healthy throughout the entire study period, therefore indicating that the hamsters used in the study had not previously been colonized with endogenous *C. difficile* organisms prior to the start of the study. Following the final antitoxin treatment on day 13, a single surviving animal from the CTA group, and also from the CTAB group, was sacrificed and necropsied. No pathology was noted in either animal.

Treatment of hamsters with orally-administered toxin A and toxin B antitoxin (group CTAB) successfully protected 7 out of 7 (100%) of the animals from *C. difficile* disease. Treatment of hamsters with orally-administered toxin A antitoxin (group CTA) protected 5 out of 7 (71%) of these animals from *C. difficile* disease. Treatment using pre-immune IgY was not protective against *C. difficile* disease, as only 1 out of 7 (14%) of these animals survived. These results demonstrate that the avian toxin A antitoxin and the avian toxin A+toxin B antitoxin effectively protected the hamsters from *C. difficile* disease. These results also suggest that although the neutralization of toxin A alone confers some degree of protection against *C. difficile* disease, in order to achieve maximal protection, simultaneous antitoxin A and antitoxin B activity is necessary.

c) Long-Term Survival Of Treated Hamsters

It has been previously reported in the literature that hamsters treated with orally-administered bovine antitoxin IgG concentrate are protected from *C. difficile* disease as long as the treatment is continued, but when the treatment is stopped, the animals develop diarrhea and subsequently die within 72 hrs. [Lyerly et al., Infect. Immun., 59(6) :2215–2218 (1991).]

In order to determine whether treatment of *C. difficile* disease using avian antitoxins promotes long-term survival following the discontinuation of treatment, the 4 surviving animals in group CTA, and the 6 surviving animals in group CTAB were observed for a period of 11 days (264 hrs.) following the discontinuation of antitoxin treatment described in section (b) above. All hamsters remained healthy through the entire post-treatment period. This result demonstrates that not only does treatment with avian antitoxin protect against the onset of *C. difficile* disease (i.e., it is effective as a prophylactic), it also promotes long-term survival beyond the treatment period, and thus provides a lasting cure.

EXAMPLE 10

In vivo Treatment Of Established *C. difficile* Infection In Golden Syrian Hamsters With Avian Antitoxins Against *C. difficile* Toxins A And B The ability of the avian *C. difficile* antitoxins, described in Example 8 above, to treat an established *C. difficile* infection was evaluated using the Golden Syrian hamster model. The Example involved (a) preparation of the avian *C. difficile* antitoxins, (b) in vivo treatment of hamsters with established *C. difficile* infection, and (c) histologic evaluation of cecal tissue.

a) Preparation Of The Avian C. difficile Antitoxins

Eggs were collected from hens in group CTAB described in Example 8 (b) above, which were immunized with C. difficile toxoids and native toxins A and B. Eggs purchased from a local supermarket were used as a pre-immune (negative) control. Egg yolk immunoglobulin (IgY) was extracted from the 2 groups of eggs as described in Example 1 (c), and the final IgY pellets were solubilized in one-fourth the original yolk volume of Ensure® nutritional formula.

b) In vivo Treatment Of Hamsters With Established C. difficile Infection

The avian C. difficile antitoxins prepared in section (a) above were evaluated for the ability to treat established C. difficile infection in hamsters using an animal model system which was modified from the procedure which was described for the hamster protection study in Example 8(b) above.

For the study, four separate experimental groups were used, with each group consisting of 7 female Golden Syrian hamsters (Charles River), approx. 10 weeks old, weighing approximately 100 gms. each. Each animal was housed separately, and was offered food and water ad libitum through the entire length of the study.

On day 1 of the study, the animals in all four groups were each predisposed to C. difficile infection by the oral administration of 3.0 mg of clindamycin-HCl (Sigma) in 1 ml of water.

On day 2, each animal in all four groups was orally challenged with 1 ml of C. difficile inoculum, which contained approximately 100 C. difficile strain 43596 organisms in sterile saline. C. difficile strain 43596 was chosen because it is representative of one of the most frequently-occurring serogroups isolated from patients with antibiotic-associated pseudomembranous colitis. [Delmee et al., J. Clin. Microbiol., 28:2210–2214 (1990).] In addition, as this was the same C. difficile strain used in all of the previous Examples above, it was again used in order to provide experimental continuity.

On day 3 of the study (24 hrs. post-infection), treatment was started for two of the four groups of animals. Each animal of one group was orally administered 1.0 ml of the CTAB IgY preparation (prepared in section (a) above) at the following timepoints: 0 hrs., 4 hrs., and 8 hrs. The animals in this group were designated "CTAB-24." The animals in the second group were each orally administered 1.0 ml of the pre-immune IgY preparation (also prepared in section (a) above) at the same timepoints as for the CTAB group. These animals were designated "Pre-24." Nothing was done to the remaining two groups of animals on day 3.

On day 4, 48 hrs. post-infection, the treatment described for day 3 above was repeated for the CTAB-24 and Pre-24 groups, and was initiated for the remaining two groups at the same timepoints. The final two groups of animals were designated "CTAB-48" and "Pre-48" respectively.

On days 5 through 9, the animals in all four groups were administered antitoxin or pre-immune IgY, 3× per day, as described for day 4 above. The four experimental groups are summarized in Table 14.

TABLE 14

Experimental Treatment Groups

| Group Designation | Experimental Treatment |
|---|---|
| CTAB-24 | Infected, treatment w/antitoxin IgY started @ 24 hrs. post-infection. |
| Pre-24 | Infected, treatment w/pre-immune IgY started @ 24 hrs. post-infection. |
| CTAB-48 | Infected, treatment w/antitoxin IgY started # 48 hrs. post-infection. |
| Pre-48 | Infected, treatment w/pre-immune IgY started @ 48 hrs. post-infection. |

All animals were observed for the onset of diarrhea and death through the conclusion of the study on the morning of day 10. The results of this study are displayed in Table 15.

Eighty-six percent of the animals which began receiving treatment with antitoxin IgY at 24 hrs. post-infection (CTAB-24 above) survived, while 57% of the animals treated with antitoxin IgY starting 48 hrs. post-infection (CTAB-48 above) survived. In contrast, none of the animals receiving pre-immune IgY starting 24 hrs. post-infection (Pre-24 above) survived, and only 29% of the animals which began receiving treatment with pre-immune IgY at 48 hrs. post-infection (Pre-48 above) survived through the conclusion of the study. These results demonstrate that avian antitoxins raised against C. difficile toxins A and B are capable of successfully treating established C. difficile infections in vivo.

TABLE 15

Experimental Outcome-Day 10

| Treatment Group | No. Animals Surviving | No. Animals Dead |
|---|---|---|
| CTAB-24 | 6 | 1 |
| Pre-24 | 0 | 7 |
| CTAB-48 | 4 | 3 |
| Pre-48 | 2 | 5 | c) Histologic Evaluation Of Cecal Tissue

In order to further evaluate the ability of the IgY preparations tested in this study to treat established C. difficile infection, histologic evaluations were performed on cecal tissue specimens obtained from representative animals from the study described in section (b) above.

Immediately following death, cecal tissue specimens were removed from animals which died in the Pre-24 and Pre-48 groups. Following the completion of the study, a representative surviving animal was sacrificed and cecal tissue specimens were removed from the CTAB-24 and CTAB-48 groups. A single untreated animal from the same shipment as those used in the study was also sacrificed and a cecal tissue specimen was removed as a normal control. All tissue specimens were fixed overnight at 4° C. in 10% buffered formalin. The fixed tissues were paraffin-embedded, sectioned, and mounted on glass microscope slides. The tissue sections were then stained using hematoxylin and eosin (H and E stain), and were examined by light microscopy.

Upon examination, the tissues obtained from the CTAB-24 and CTAB-48 animals showed no pathology, and were indistinguishable from the normal control. This observation provides further evidence for the ability of avian antitoxins raised against C. difficile toxins A and B to effectively treat established C. difficile infection, and to prevent the pathologic consequences which normally occur as a result of C. difficile disease.

In contrast, characteristic substantial mucosal damage and destruction was observed in the tissues of the animals from the Pre-24 and Pre-48 groups which died from *C. difficile* disease. Normal tissue architecture was obliterated in these two preparations, as most of the mucosal layer was observed to have sloughed away, and there were numerous large hemorrhagic areas containing massive numbers of erythrocytes.

EXAMPLE 11

Cloning And Expression Of *C. difficile* Toxin A Fragments

The toxin A gene has been cloned and sequenced, and shown to encode a protein of predicted MW of 308 kd. [Dove et al., Infect. Immun., 58:480–488 (1990).] Given the expense and difficulty of isolating native toxin A protein, it would be advantageous to use simple and inexpensive procaryotic expression systems to produce and purify high levels of recombinant toxin A protein for immunization purposes. Ideally, the isolated recombinant protein would be soluble in order to preserve native antigenicity, since solubilized inclusion body proteins often do not fold into native conformations. To allow ease of purification, the recombinant protein should be expressed to levels greater than 1 mg/liter of *E. coli* culture.

To determine whether high levels of recombinant toxin A protein can be produced in *E. coli*, fragments of the toxin A gene were cloned into various prokaryotic expression vectors, and assessed for the ability to express recombinant toxin A protein in *E. coli*. Three prokaryotic expression systems were utilized. These systems were chosen because they drive expression of either fusion (pMALc and pGEX2T) or native (pET23a–c) protein to high levels in *E. coli*, and allow affinity purification of the expressed protein on a ligand containing column. Fusion proteins expressed from pGEX vectors bind glutathione agarose beads, and are eluted with reduced glutathione. pMAL fusion proteins bind amylose resin, and are eluted with maltose. A poly-histidine tag is present at either the N-terminal (pET16b) or C-terminal (pET23a–c) end of pET fusion proteins. This sequence specifically binds $Ni_2^+$ chelate columns, and is eluted with imidazole salts. Extensive descriptions of these vectors are available (Williams et al. (1994) *DNA Cloning: Expression Systems*, in press), and will not be discussed in detail here. The Example involved (a) cloning of the toxin A gene, (b) expression of large fragments of toxin A in various prokaryotic expression systems, (c) identification of smaller toxin A gene fragments that express efficiently in *E. coli*, (d) purification of recombinant toxin A protein by affinity chromatography, and (e) demonstration of functional activity of a recombinant fragment of the toxin A gene.

a) Cloning Of The Toxin A Gene

A restriction map of the toxin A gene is shown in FIG. 6. The encoded protein contains a carboxy terminal ligand binding region, containing multiple repeats of a carbohydrate binding domain. [von Eichel-Streiber and Sauerborn, Gene 96:107–113 (1990).] The toxin A gene was cloned in three pieces, by using either the polymerase chain reaction (PCR) to amplify specific regions, (regions 1 and 2, FIG. 6) or by screening a constructed genomic library for a specific toxin A gene fragment (region 3, FIG. 6). The sequences of the utilized PCR primers are P1: 5' GGAAATT TAGCTGCAGCATCTGAC 3' (SEQ ID NO:1); P2: 5' TCTAGCAAATTCGCTTGT GTTGAA 3' (SEQ ID NO:2); P3: 5' CTCGCATATAGCATTAGACC 3' (SEQ ID NO:3); and P4: 5' CTATCTAGGCCTAAAGTAT 3' (SEQ ID NO:4). These regions were cloned into prokaryotic expression vectors that express either fusion (pMALc and pGEX2T) or native (pET23a–c) protein to high levels in *E. coli*, and allow affinity purification of the expressed protein on a ligand containing column.

*Clostridium difficile* VPI strain 10463 was obtained from the ATCC (ATCC #43255) and grown under anaerobic conditions in brain-heart infusion medium (BBL). High molecular-weight *C. difficile* DNA was isolated essentially as described by Wren and Tabaqchali (1987) J. Clin. Microbiol., 25:2402, except proteinase K and sodium dodecyl sulfate (SDS) was used to disrupt the bacteria, and cetyltrimethylammonium bromide precipitation [as described in Ausubel et al., *Current Protocols in Molecular Biology* (1989)] was used to remove carbohydrates from the cleared lysate. The integrity and yield of genomic DNA was assessed by comparison with a serial dilution of uncut lambda DNA after electrophoresis on an agarose gel.

Fragments 1 and 2 were cloned by PCR, utilizing a proofreading thermostable DNA polymerase (native pfu polymerase; Stratagene). The high fidelity of this polymerase reduces the mutation problems associated with amplification by error prone polymerases (e.g., Taq polymerase). PCR amplification was performed using the indicated PCR primers (FIG. 6) in 50 $\mu$l reactions containing 10 mM Tris-HCl(8.3), 50 mM KCl, 1.5 mM $MgCl_2$, 200 $\mu$M each dNTP, 0.2 $\mu$M each primer, and 50 ng *C. difficile* genomic DNA. Reactions were overlaid with 100 $\mu$l mineral oil, heated to 94° C. for 4 min, 0.5 $\mu$l native pfu polymerase (Stratagene) added, and the reaction cycled 30× at 94° C. for 1 min, 50° C. for 1 min, 72° C. for 4 min, followed by 10 min at 72° C. Duplicate reactions were pooled, chloroform extracted, and ethanol precipitated. After washing in 70% ethanol, the pellets were resuspended in 50 $\mu$l TE buffer [10 mM Tris-HCL, 1 mM EDTA pH 8.0]. Aliquots of 10 $\mu$l each were restriction digested with either EcoRI/HincII (fragment 1) or EcoRI/PstI (fragment 2), and the appropriate restriction fragments were gel purified using the Prep-A-Gene kit (BioRad), and ligated to either EcoRI/SmaI-restricted pGEX2T (Pharmacia) vector (fragment 1), or the EcoRI/PstI pMAlc (New England Biolabs) vector (fragment 2). Both clones are predicted to produce in-frame fusions with either the glutathione-S-transferase protein (PGEX vector) or the maltose binding protein (pMAL vector). Recombinant clones were isolated, and confirmed by restriction digestion, using standard recombinant molecular biology techniques. [Sambrook et al., *Molecular Cloning, A Laboratory Manual* (1989), and designated pGA30-660 and pMA660-1100, respectively (see FIG. 6 for description of the clone designations).]

Fragment 3 was cloned from a genomic library of size selected PstI digested *C. difficile* genomic DNA, using standard molecular biology techniques (Sambrook et al.). Given that the fragment 3 internal PstI site is protected from cleavage in *C. difficile* genomic DNA [Price et al., Curr. Microbiol., 16:55–60 (1987)], a 4.7 kb fragment from PstI restricted *C. difficile* genomic DNA was gel purified, and ligated to PstI restricted, phosphatase treated pUC9 DNA. The resulting genomic library was screened with a oligonucleotide primer specific to fragment 3, and multiple independent clones were isolated. The presence of fragment 3 in several of these clones was confirmed by restriction digestion, and a clone of the indicated orientation (FIG. 6) was restricted with BamHI/HindIII, the released fragment purified by gel electrophoresis, and ligated into similarly restricted pET23c expression vector DNA (Novagen). Recombinant clones were isolated, and confirmed by restriction digestion. This construct is predicted to create both a predicted in frame fusion with the pET protein leader sequence, as well as a predicted C-terminal poly-histidine affinity tag, and is designated pPA1100-2680 (see FIG. 6 for the clone designation).

b) Expression Of Large Fragments Of Toxin A In *E. coli*

Figure 7:
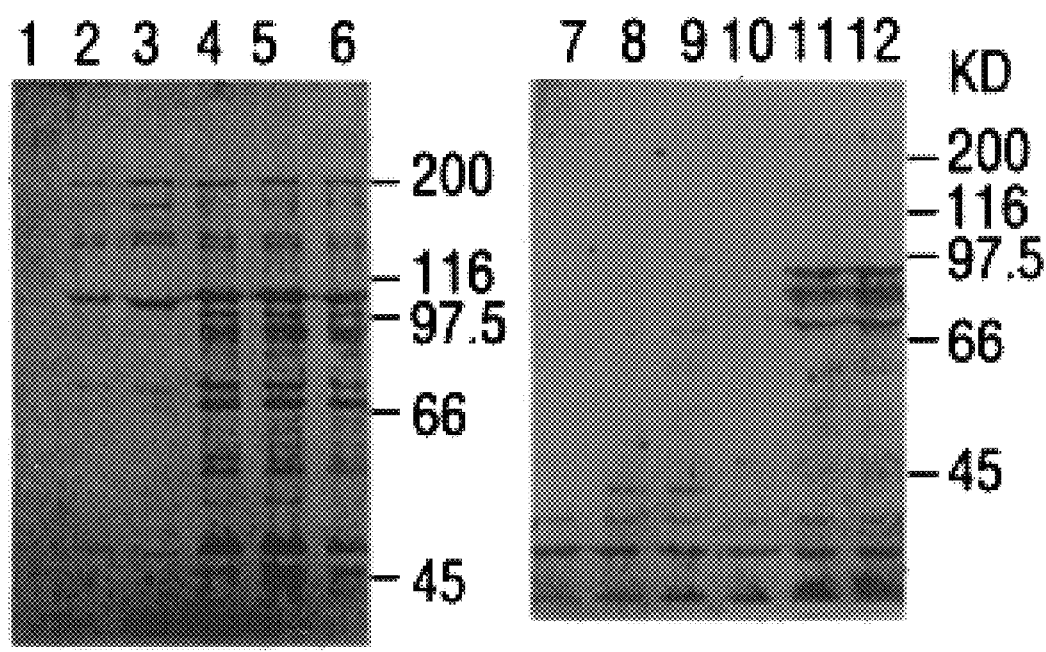
FIG. 7 is a Western blot of *C. difficile* toxin A reactive protein.

Protein expression from the three expression constructs made in (a) was induced, and analyzed by Western blot analysis with an affinity purified, goat polyclonal antiserum directed against the toxin A toxoid (Tech Lab). The procedures utilized for protein induction, SDS-PAGE, and Western blot analysis are described in detail in Williams et al (1994), supra. In brief, 5 ml 2×YT (16 g tryptone, 10 g yeast extract, 5 g NaCl per liter, pH 7.5+100 µg/ml ampicillin were added to cultures of bacteria (BL21 for pMAl and pGEX plasmids, and BL21(DE3)LysS for pET plasmids) containing the appropriate recombinant clone which were induced to express recombinant protein by addition of IPTG to 1 mM. Cultures were grown at 37° C., and induced when the cell density Teached 0.5 $OD_{600}$. Induced protein was allowed to accumulate for two hrs after induction. Protein samples were prepared by pelleting 1 ml aliquots of bacteria by centrifugation (1 min in a microfuge), and resuspension of the pelleted bacteria in 150 µl of 2×SDS-PAGE sample buffer [Williams et al. (1994), supra]. The samples were heated to 95° C. for 5 min, the cooled and 5 or 10 µl aliquots loaded on 7.5% SDS-PAGE gels. BioRad high molecular weight protein markers were also loaded, to allow estimation of the MW of identified fusion proteins. After electrophoresis, protein was detected either generally by staining gels with Coomassie blue, or specifically, by blotting to nitrocellulose for Western blot detection of specific immunoreactive protein. Western blots, (performed as described in Example 3) which detect toxin A reactive protein in cell lysates of induced protein from the three expression constructs are shown in FIG. 7. In this figure, lanes 1–3 contain cell lysates prepared from *E. coli* strains containing pPA1100-2860 in B121(DE3)lysE cells; lanes 4–6 contain cell lysates prepared from *E. coli* strains containing pPA1100-2860 in B 121 (DE3)lysS cells; lanes 7–9 contain cell lysates prepared from *E. coli* strains containing pMA30-660; lanes 10–12 contain cell lysates prepared from *E. coli* strains containing pMA660-1100. The lanes were probed with an affinity purified goat antitoxin A polyclonal antibody (Tech Lab). Control lysates from uninduced cells (lanes 1, 7, and 10) contain very little immunoreactive material compared to the induced samples in the remaining lanes. The highest molecular weight band observed for each clone is consistent with the predicted size of the full length fusion protein.

Figure 8:
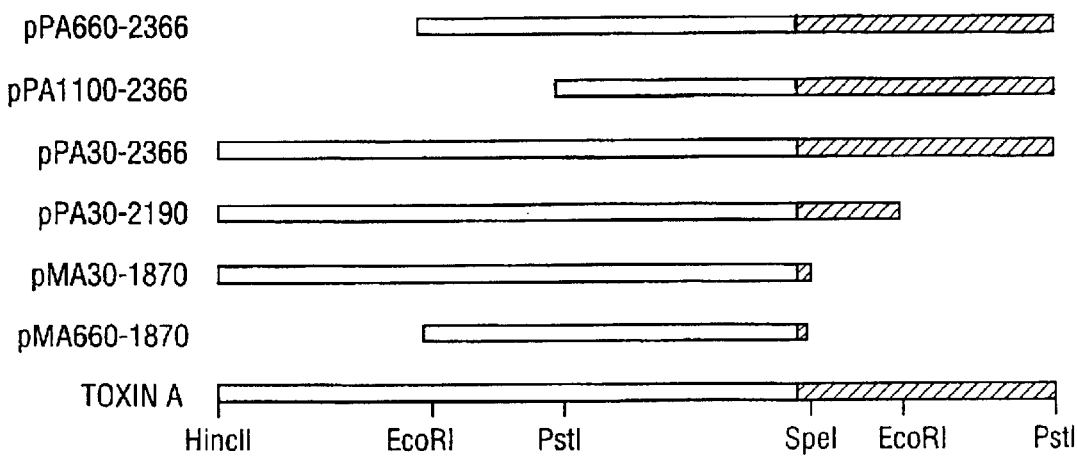
FIG. 8 shows *C. difficile* toxin A expression constructs.

Each construct directs expression of high molecular weight (HMW) protein that is reactive with the toxin A antibody. The size of the largest immunoreactive bands from each sample is consistent with predictions of the estimated MW of the intact fusion proteins. This demonstrates that the three fusions are in-frame, and that none of the clones contain cloning artifacts that disrupt the integrity of the encoded fusion protein. However, the Western blot demonstrates that fusion protein from the two larger constructs (pGA30-660 and pPA1100-2680) are highly degraded. Also, expression levels of toxin A proteins from these two constructs are low, since induced protein bands are not visible by Coomassie staining (not shown). Several other expression constructs that fuse large sub-regions of the toxin A gene to either pMALc or pET23a–c expression vectors, were constructed and tested for protein induction. These constructs were made by mixing gel purified restriction fragments, derived from the expression constructs shown in FIG. 6, with appropriately cleaved expression vectors, ligating, and selecting recombinant clones in which the toxin A restriction fragments had ligated together and into the expression vector as predicted for in-frame fusions. The expressed toxin A interval within these constructs are shown in FIG. 8, as well as the internal restriction sites utilized to make these constructs.

As used herein, the term "interval" refers to any portion (i.e., any segment of the toxin which is less than the whole toxin molecule) of a clostridial toxin. In a preferred embodiment, "interval" refers to portions of *C. difficile* toxins such as toxin A or toxin B. It is also contemplated that these intervals will correspond to epitopes of immunologic importance, such as antigens or immunogens against which a neutralizing antibody response is effected. It is not intended that the present invention be limited to the particular intervals or sequences described in these Examples. It is also contemplated that sub-portions of intervals (e.g., an epitope contained within one interval or which bridges multiple intervals) be used as compositions and in the methods of the present invention.

In all cases, Western blot analysis of each of these constructs with goat antitoxin A antibody (Tech Lab) detected HMW fusion protein of the predicted size (not shown). This confirms that the reading frame of each of these clones is not prematurely terminated, and is fused in the correct frame with the fusion partner. However, the Western blot analysis revealed that in all cases, the induced protein is highly degraded, and, as assessed by the absence of identifiable induced protein bands by Coomassie Blue staining, are expressed only at low levels. These results suggest that expression of high levels of intact toxin A recombinant protein is not possible when large regions of the toxin A gene are expressed in *E. coli* using these expression vectors.

c) High Level Expression Of Small Toxin A Protein Fusions In *E. coli*

Figure 9:
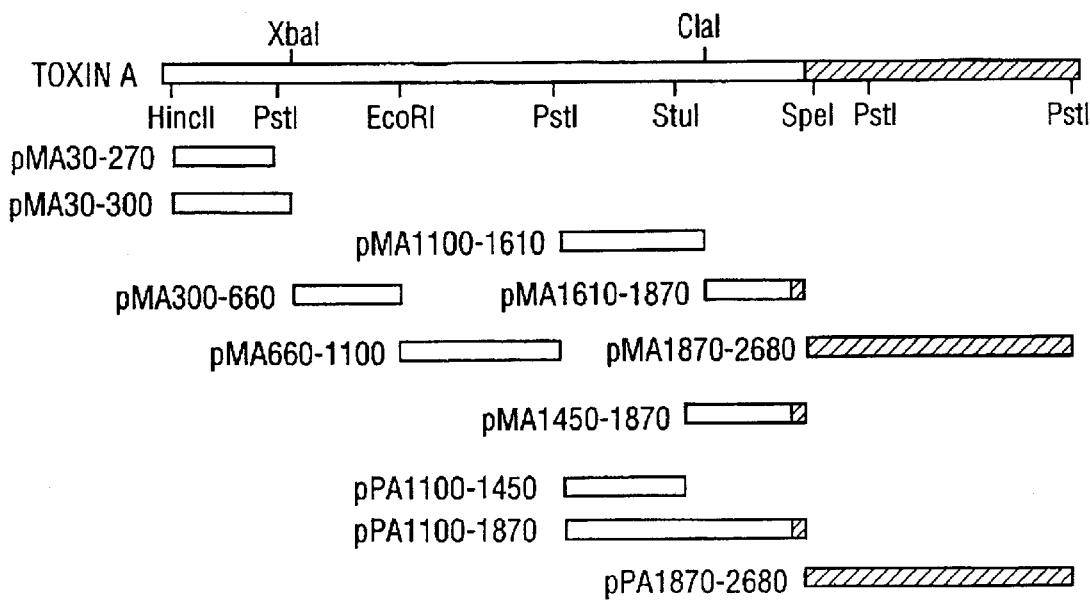
FIG. 9 shows *C. difficile* toxin A expression constructs.

Experience indicates that expression difficulties are often encountered when large (greater than 100 kd) fragments are expressed in *E. coli*. A number of expression constructs containing smaller fragments of the toxin A gene were constructed, to determine if small regions of the gene can be expressed to high levels without extensive protein degradation. A summary of these expression constructs are shown in FIG. 9. All were constructed by in-frame fusions of convenient toxin A restriction fragments to either the pMALc or pET23a–c vectors. Protein preparations from induced cultures of each of these constructs were analyzed by both Coomassie Blue staining and Western analysis as in (b) above. In all cases, higher levels of intact, full length fusion proteins were observed than with the larger recombinants from section (b).

d) Purification Of Recombinant Toxin A Protein

Figure 10:
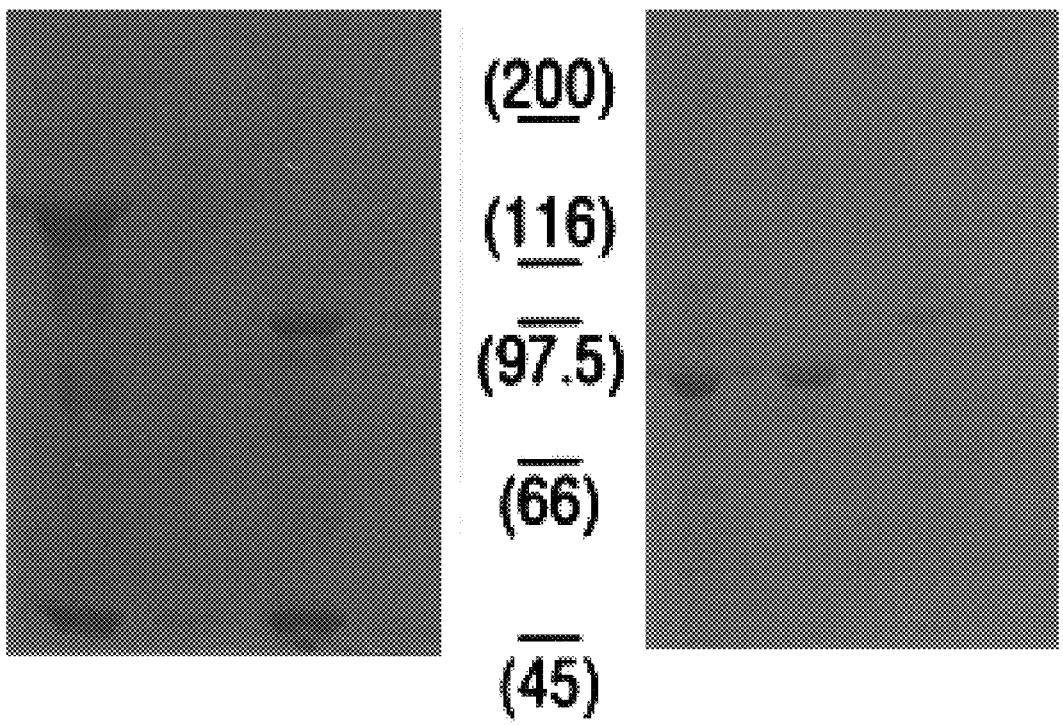
FIG. 10 shows the purification of recombinant *C. difficile* toxin A.

Large scale (500 ml) cultures of each recombinant from (c) were grown, induced, and soluble and insoluble protein fractions were isolated. The soluble protein extracts were affinity chromatographed to isolate recombinant fiusion protein, as described [Williams et al. (1994), supra]. In brief, extracts containing tagged pET fusions were chromatographed on a nickel chelate column, and eluted using imidazole salts as described by the distributor (Novagen). Extracts containing soluble pMAL fusion protein were prepared and chromatographed in column buffer (10 mM $NaPO_4$, 0.5M NaCl, 10 mM β-mercaptoethanol, pH 7.2) over an amylose resin column (New England Biolabs), and eluted with column buffer containing 10 mM maltose as described [Williams et al. (1994), supra]. When the expressed protein was found to be predominantly insoluble, insoluble protein extracts were prepared by the method described in Example 17, infra. The results are summarized in Table 16. FIG. 10 shows the sample purifications of recombinant toxin A protein. In this figure, lanes 1 and 2 contain MBP fusion protein purified by affinity purification of soluble protein.

TABLE 16

Purification Of Recombinant Toxin A Protein

| Clone[a] | Protein Solubility | Yield Affinity Purified Soluble Protein[b] | % Intact Soluble Fusion Protein [c] | Yield Intact Insoluble Fusion Protein |
|---|---|---|---|---|
| pMA30-270 | Soluble | 4 mg/500 mls | 10% | NA |
| PMA30-300 | Soluble | 4 mg/500 mls | 5–10% | NA |
| pMA300-660 | Insoluble | — | NA | 10 mg/500 ml |
| pMA660-1100 | Soluble | 4.5 mg/500 mls | 50% | NA |
| pMA1100-1610 | Soluble | 18 mg/500 mls | 10% | NA |
| pMA1610-1870 | Both | 22 mg/500 mls | 90% | 20 mg/500 ml |
| pMA1450-1870 | Insoluble | — | NA | 0.2 mg/500 ml |
| pPA1100-1450 | Soluble | 0.1 mg/500 mls | 90% | NA |
| pPA1100-1870 | Soluble | 0.02 mg/500 mls | 90% | NA |
| pMA1870-2680 | Both | 12 mg/500 mls | 80% | NA |
| pPA1870-2680 | Insoluble | — | NA | 10 mg/500 ml |

[a]pP = pET23 vector, pM = pMALc vector, A = toxin A.
[b]Based on 1.5 $OD_{280}$ = 1 mg/ml (extinction coefficient of MBP).
[c]Estimated by Coomassie staining of SDS-PAGE gels.

Lanes 3 and 4 contain MBP fusion protein purified by solubilization of insoluble inclusion bodies. The purified fusion protein samples are pMA1870-2680 (lane 1), pMA660-1100 (lane 2), pMA300-600 (lane 3) and pMA1450-1870 (lane 4).

Poor yields of affinity purified protein were obtained when poly-histidine tagged pET vectors were used to drive expression (pPA1100-1450, pP1100-1870). However, significant protein yields were obtained from pMAL expression constructs spanning the entire toxin A gene, and yields of full-length soluble fusion protein ranged from an estimated 200–400 μg/500 ml culture (pMA30-300) to greater than 20 mg/500 ml culture (pMA1610-1870). Only one interval was expressed to high levels as strictly insoluble protein (pMA300-660). Thus, although high level expression was not observed when using large expression constructs from the toxin A gene, usable levels of recombinant protein spanning the entire toxin A gene were obtainable by isolating induced protein from a series of smaller pMAL expression constructs that span the entire toxin A gene. This is the first demonstration of the feasibility of expressing recombinant toxin A protein to high levels in *E. coli.* e) Hemagglutination Assay Using The Toxin A Recombinant Proteins

The carboxy terminal end consisting of the repeating units contains the hemagglutination activity or binding domain of *C. difficile* toxin A. To determine whether the expressed toxin A recombinants retain functional activity, hemagglutination assays were performed. Two toxin A recombinant proteins, one containing the binding domain as either soluble affinity purified protein (pMA1870-2680) or SDS solubilized inclusion body protein (pPA1870-2680) and soluble protein from one region outside that domain (pMA 1100-1610) were tested using a described procedure. [H. C. Krivan et. al., Infect. Immun., 53:573 (1986).] Citrated rabbit red blood cells (RRBC)(Cocalico) were washed several times with Tris-buffer (0.1M Tris and 50 mM NaCl) by centrifugation at 450×g for 10 minutes at 4° C. A 1% RRBC suspension was made from the packed cells and resuspended in Tris-buffer. Dilutions of the recombinant proteins and native toxin A (Tech Labs) were made in the Tris-buffer and added in duplicate to a round-bottomed 96-well microtiter plate in a final volume of 100 μl. To each well, 50 μl of the 1% RRBC suspension was added, mixed by gentle tapping, and incubated at 4° C. for 3–4 hours. Significant hemagglutination occurred only in the recombinant proteins containing the binding domain (pMA 1870-2680) and native toxin A. The recombinant protein outside the binding domain (pMA 1100-1610) displayed no hemagglutination activity. Using equivalent protein concentrations, the hemagglutination titer for toxin A was 1:256, while titers for the soluble and insoluble recombinant proteins of the binding domain were 1:256 and about 1:5000. Clearly, the recombinant proteins tested retained functional activity and were able to bind RRBC's.

EXAMPLE 12

Functional Activity Of IgY Reactive Against Toxin A Recombinants

The expression of recombinant toxin A protein as multiple fragments in *E. coli* has demonstrated the feasibility of generating toxin A antigen through use of recombinant methodologies (Example 11). The isolation of these recombinant proteins allows the immunoreactivity of each individual subregion of the toxin A protein to be determined (i.e., in a antibody pool directed against the native toxin A protein). This identifies the regions (if any) for which little or no antibody response is elicited when the whole protein is used as a immunogen. Antibodies directed against specific fragments of the toxin A protein can be purified by affinity chromatography against recombinant toxin A protein, and tested for neutralization ability. This identifies any toxin A subregions that are essential for producing neutralizing antibodies. Comparison with the levels of immune response directed against these intervals when native toxin is used as an immunogen predicts whether potentially higher titers of neutralizing antibodies can be produced by using recombinant protein directed against a individual region, rather than the entire protein. Finally, since it is unknown whether antibodies reactive to the recombinant toxin A proteins produced in Example 11 neutralize toxin A as effectively as antibodies raised against native toxin A (Examples 9 and 10), the protective ability of a pool of antibodies affinity purified against recombinant toxin A fragments was assessed for its ability to neutralize toxin A.

This Example involved (a) epitope mapping of the toxin A protein to determine the titre of specific antibodies directed against individual subregions of the toxin A protein when native toxin A protein is used as an immunogen, (b) affinity purification of IgY reactive against recombinant proteins spanning the toxin A gene, (c) toxin A neutralization assays with affinity purified IgY reactive to recombinant toxin A protein to identify subregions of the toxin A protein that induce the production of neutralizing antibodies, and determination of whether complete neutralization of toxin A can be elicited with a mixture of antibodies reactive to recombinant toxin A protein.

a) Epitope Mapping Of The Toxin A Gene

The affinity purification of recombinant toxin A protein specific to defined intervals of the toxin A protein allows epitope mapping of antibody pools directed against native toxin A. This has not previously been possible, since previous expression of toxin A recombinants has been assessed only by Western blot analysis, without knowledge of the expression levels of the protein [e.g., von Eichel-Streiber et al, J. Gen. Microbiol., 135:55–64 (1989)]. Thus, high or low reactivity of recombinant toxin A protein on Western blots may reflect protein expression level differences, not immunoreactivity differences. Given that the purified recombinant protein generated in Example 11 have been quantitated, the issue of relative immunoreactivity of individual regions of the toxin A protein was precisely addressed.

For the purposes of this Example, the toxin A protein was subdivided into 6 intervals (1–6), numbered from the amino (interval 1) to the carboxyl (interval 6) termini.

The recombinant proteins corresponding to these intervals were from expression clones (see Example 11(d) for clone designations) pMA30-300 (interval 1), pMA300-660 (interval 2), pMA660-1100 (interval 3), pPA1100-1450 (interval 4), pMA1450-1870 (interval 5) and pMA1870-2680 (interval 6). These 6 clones were selected because they span the entire protein from amino acids numbered 30 through 2680, and subdivide the protein into 6 small intervals. Also, the carbohydrate binding repeat interval is contained specifically in one interval (interval 6), allowing evaluation of the immune response specifically directed against this region. Western blots of 7.5% SDS-PAGE gels, loaded and electrophoresed with defined quantities of each recombinant protein, were probed with either goat antitoxin A polyclonal antibody (Tech Lab) or chicken antitoxin A polyclonal antibody [PCTA IgY, Example 8(c)]. The blots were prepared and developed with alkaline phosphatase as previously described [Williams et al. (1994), supra]. At least 90% of all reactivity, in either goat or chicken antibody pools, was found to be directed against the ligand binding domain (interval 6). The remaining immunoreactivity was directed against all five remaining intervals, and was similar in both antibody pools, except that the chicken antibody showed a much lower reactivity against interval 2 than the goat antibody.

This clearly demonstrates that when native toxin A is used as an immunogen in goats or chickens, the bulk of the immune response is directed against the ligand binding domain of the protein, with the remaining response distributed throughout the remaining ⅔ of the protein.

b) Affinity Purification Of IgY Reactive Against Recombinant Toxin A Protein

Affinity columns, containing recombinant toxin A protein from the 6 defined intervals in (a) above, were made and used to (i) affinity purify antibodies reactive to each individual interval from the CTA IgY preparation [Example 8(c)], and (ii) deplete interval specific antibodies from the CTA IgY preparation. Affinity columns were made by coupling 1 ml of PBS-washed Actigel resin (Sterogene) with region specific protein and ⅒ final volume of Ald-coupling solution (1M sodium cyanoborohydride). The total region specific protein added to each reaction mixture was 2.7 mg (interval 1), 3 mg (intervals 2 and 3), 0.1 mg (interval 4), 0.2 mg (interval 5) and 4 mg (interval 6). Protein for intervals 1, 3, and 6 was affinity purified pMAl fusion protein in column buffer (see Example 11). Interval 4 was affinity purified poly-histidine containing pET fusion in PBS; intervals 2 and 5 were from inclusion body preparations of insoluble pMAL fusion protein, dialyzed extensively in PBS. Aliquots of the supernatants from the coupling reactions, before and after coupling, were assessed by Coomassie staining of 7.5% SDS-PAGE gels. Based on protein band intensities, in all cases greater than 50% coupling efficiencies were estimated. The resins were poured into 5 ml BioRad columns, washed extensively with PBS, and stored at 4° C.

Aliquots of the CTA IgY polyclonal antibody preparation were depleted for each individual region as described below. A 20 ml sample of the CTA IgY preparation [Example 8(c)] was dialyzed extensively against 3 changes of PBS (1 liter for each dialysis), quantitated by absorbance at $OD_{280}$, and stored at 4° C. Six 1 ml aliquots of the dialyzed IgY preparation were removed, and depleted individually for each of the six intervals. Each 1 ml aliquot was passed over the appropriate affinity column, and the eluate twice reapplied to the column. The eluate was collected, and pooled with a 1 ml PBS wash. Bound antibody was eluted from the column by washing with 5 column volumes of 4 M Guanidine-HCl (in 10 mM Tris-HCl, pH 8.0). The column was reequilibrated in PBS, and the depleted antibody stock reapplied as described above. The eluate was collected, pooled with a 1 ml PBS wash, quantitated by absorbance at $OD_{280}$, and stored at 4° C. In this manner, 6 aliquots of the CTA IgY preparation were individually depleted for each of the 6 toxin A intervals, by two rounds of affinity depletion. The specificity of each depleted stock was tested by Western blot analysis. Multiple 7.5% SDS-PAGE gels were loaded with protein samples corresponding to all 6 toxin A subregions. After electrophoresis, the gels were blotted, and protein transfer confirmed by Ponceau S staining [protocols described in Williams et al. (1994), supra]. After blocking the blots 1 hr at 20° C. in PBS+0.1% Tween 20 (PBST) containing 5% milk (as a blocking buffer), 4 ml of either a ⅟₅₀₀ dilution of the dialyzed CTA IgY preparation in blocking buffer, or an equivalent amount of the six depleted antibody stocks (using $OD_{280}$ to standardize antibody concentration) were added and the blots incubated a further 1 hr at room temperature. The blots were washed and developed with alkaline phosphatase (using a rabbit anti-chicken alkaline phosphate conjugate as a secondary antibody) as previously described [Williams et al. (1994), supra]. In all cases, only the target interval was depleted for antibody reactivity, and at least 90% of the reactivity to the target intervals was specifically depleted.

Region specific antibody pools were isolated by affinity chromatography as described below. Ten mls of the dialyzed CTA IgY preparation were applied sequentially to each affinity column, such that a single 10 ml aliquot was used to isolate region specific antibodies specific to each of the six subregions. The columns were sequentially washed with 10 volumes of PBS, 6 volumes of BBS-Tween, 10 volumes of TBS, and eluted with 4 ml Actisep elution media (Sterogene). The eluate was dialyzed extensively against several changes of PBS, and the affinity purified antibody collected and stored at 4° C. The volumes of the eluate increased to greater than 10 mls during dialysis in each case, due to the high viscosity of the Actisep elution media. Aliquots of each sample were 20×concentrated using Centricon 30 microconcentrators (Amicon) and stored at 4° C. The specificity of each region specific antibody pool was tested, relative to the dialyzed CTA IgY preparation, by Western blot analysis, exactly as described above, except that 4 ml samples of blocking buffer containing 100 µl region specific antibody (unconcentrated) were used instead of the depleted CTA IgY preparations. Each affinity purified antibody preparation was specific to the defined interval, except that samples purified against intervals 1–5 also reacted with interval 6. This may be due to non-specific binding to the interval 6 protein, since this protein contains the repetitive ligand binding domain which has been shown to bind antibodies nonspecifically. [Lyerly et al., Curr. Microbiol., 19:303–306 (1989).]

The reactivity of each affinity purified antibody preparation to the corresponding proteins was approximately the same as the reactivity of the $\frac{1}{500}$ diluted dialyzed CTA IgY preparation standard. Given that the specific antibody stocks were diluted $\frac{1}{40}$, this would indicate that the unconcentrated affinity purified antibody stocks contain $\frac{1}{10}$–$\frac{1}{20}$ the concentration of specific antibodies relative to the starting CTA IgY preparation.

c) Toxin A Neutralization Assay Using Antibodies Reactive Toward Recombinant Toxin A Protein The CHO toxin neutralization assay [Example 8(d)] was used to assess the ability of the depleted or enriched samples generated in (b) above to neutralize the cytotoxicity of toxin A. The general ability of affinity purified antibodies to neutralize toxin A was assessed by mixing together aliquots of all 6 concentrated stocks of the 6 affinity purified samples generated in (b) above, and testing the ability of this mixture to neutralize a toxin A concentration of 0.1 µg/ml. The results, shown in FIG. 11, demonstrate almost complete neutralization of toxin A using the affinity purified (AP) mix. Some epitopes within the recombinant proteins utilized for affinity purification were probably lost when the proteins were denatured before affinity purification [by Guanidine-HCl treatment in (b) above]. Thus, the neutralization ability of antibodies directed against recombinant protein is probably underestimated using these affinity purified antibody pools. This experiment demonstrates that antibodies reactive to recombinant toxin A can neutralize cytotoxicity, suggesting that neutralizing antibodies may be generated by using recombinant toxin A protein as immunogen.

In view of the observation that the recombinant expression clones of the toxin A gene divide the protein into 6 subregions, the neutralizing ability of antibodies directed against each individual region was assessed. The neutralizing ability of antibodies directed against the ligand binding domain of toxin A was determined first.

Figure 11:
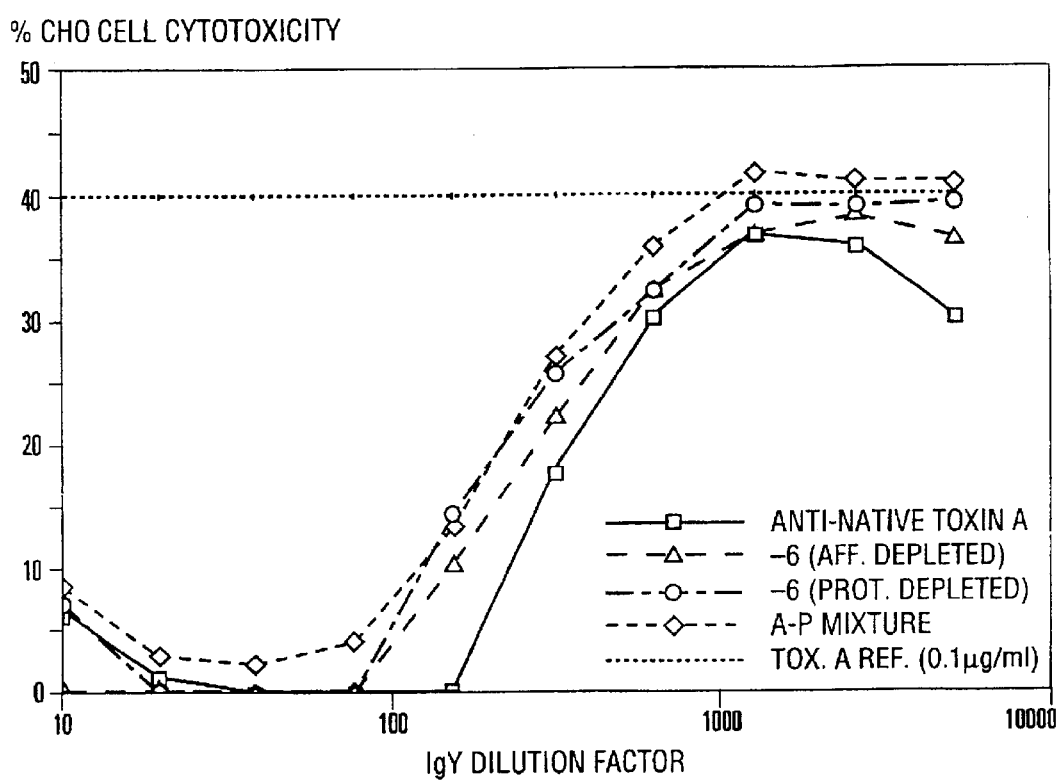
FIG. 11 shows the results of *C. difficile* toxin A neutralization assays with antibodies reactive to recombinant toxin A.

In the toxin neutralization experiment shown in FIG. 11, interval 6 specific antibodies (interval 6 contains the ligand binding domain) were depleted from the dialyzed PEG preparation, and the effect on toxin neutralization assayed. Interval 6 antibodies were depleted either by utilizing the interval 6 depleted CTA IgY preparation from (b) above ("–6 aff. depleted" in FIG. 11), or by addition of interval 6 protein to the CTA IgY preparation (estimated to be a 10 fold molar excess over anti-interval 6 immunoglobulin present in this preparation) to competitively compete for interval 6 protein ("–6 prot depleted" in FIG. 11). In both instances, removal of interval 6 specific antibodies reduces the neutralization efficiency relative to the starting CTA IgY preparation. This demonstrates that antibodies directed against interval 6 contribute to toxin neutralization. Since interval 6 corresponds to the ligand binding domain of the protein, these results demonstrate that antibodies directed against this region in the PEG preparation contribute to the neutralization of toxin A in this assay. However, it is significant that after removal of these antibodies, the PEG preparation retains significant ability to neutralize toxin A (FIG. 11). This neutralization is probably due to the action of antibodies specific to other regions of the toxin A protein, since at least 90% of the ligand binding region reactive antibodies were removed in the depleted sample prepared in (b) above. This conclusion was supported by comparison of the toxin neutralization of the affinity purified (AP) mix compared to affinity purified interval 6 antibody alone. Although some neutralization ability was observed with AP interval 6 antibodies alone, the neutralization was significantly less than that observed with the mixture of all 6 AP antibody stocks (not shown).

Figure 12:
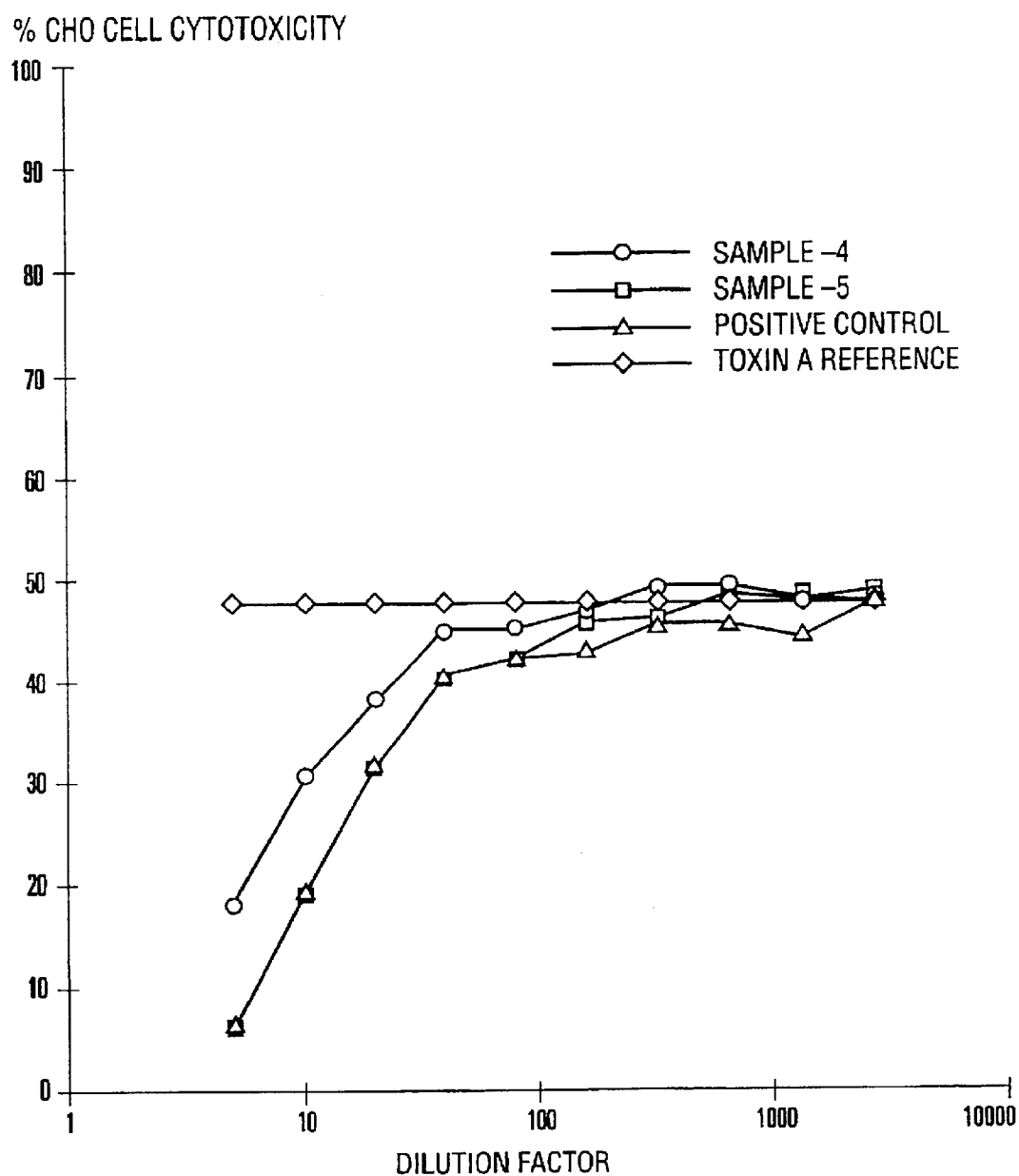
FIG. 12 shows the results for a *C. difficile* toxin A neutralization plate.

Given that the mix of all six affinity purified samples almost completely neutralized the cytotoxicity of toxin A (FIG. 11), the relative importance of antibodies directed against toxin A intervals 1–5 within the mixture was determined. This was assessed in two ways. First, samples containing affinity purified antibodies representing 5 of the 6 intervals were prepared, such that each individual region was depleted from one sample. FIG. 12 demonstrates a sample neutralization curve, comparing the neutralization ability of affinity purified antibody mixes without interval 4 (–4) or 5 (–5) specific antibodies, relative to the mix of all 6 affinity purified antibody stocks (positive control). While the removal of interval 5 specific antibodies had no effect on toxin neutralization (or intervals 1–3, not shown), the loss of interval 4 specific antibodies significantly reduced toxin neutralization (FIG. 12).

Figure 13:
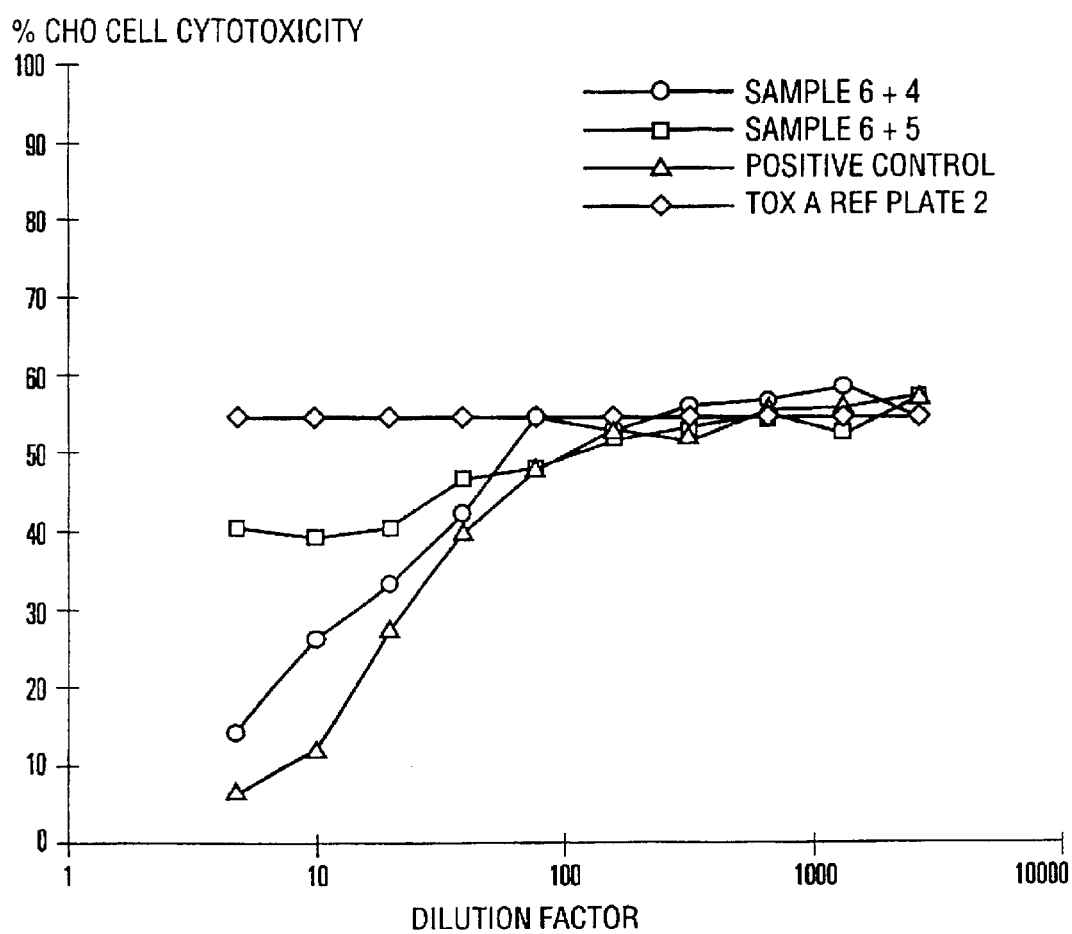
FIG. 13 shows the results for a *C. difficile* toxin A neutralization plate.

Similar results were seen in a second experiment, in which affinity purified antibodies, directed against a single region, were added to interval 6 specific antibodies, and the effects on toxin neutralization assessed. Only interval 4 specific antibodies significantly enhanced neutralization when added to interval 6 specific antibodies (FIG. 13). These results demonstrate that antibodies directed against interval 4 (corresponding to clone pPA1100-1450 in FIG. 9) are important for neutralization of cytotoxicity in this assay. Epitope mapping has shown that only low levels of antibodies reactive to this region are generated when native toxin A is used as an immunogen [Example 12(a)]. It is hypothesized that immunization with recombinant protein specific to this interval will elicit higher titers of neutralizing antibodies. In summary, this analysis has identified two critical regions of the toxin A protein against which neutralizing antibodies are produced, as assayed by the CHO neutralization assay.

EXAMPLE 13

Production And Evaluation Of Avian Antitoxin Against *C. difficile* Recombinant Toxin A Polypeptide In Example 12, we demonstrated neutralization of toxin A mediated cytotoxicity by affinity purified antibodies reactive to recombinant toxin A protein. To determine whether antibodies raised against a recombinant polypeptide fragment of *C. difficile* toxin A may be effective in treating clostridial diseases, antibodies to recombinant toxin A protein representing the binding domain were generated. Two toxin A binding domain recombinant polypeptides, expressing the binding domain in either the pMALc (pMA1870-2680) or pET 23(pPA1870-2680) vector, were used as immunogens. The pMAL protein was affinity purified as a soluble product [Example 12(d)] and the pET protein was isolated as insoluble inclusion bodies [Example 12(d)] and solubilized to an immunologically active protein using a proprietary method described in a pending patent application (U.S. patent application Ser. No. 08/129,027). This Example involves (a) immunization, (b) antitoxin collection, (c) determination of antitoxin antibody titer, (d) anti-recombinant toxin A neutralization of toxin A hemagglutination activity in vitro, and (e) assay of in vitro toxin A neutralizing activity.

a) Immunization

The soluble and the inclusion body preparations each were used separately to immunize hens. Both purified toxin A polypeptides were diluted in PBS and emulsified with approximately equal volumes of CFA for the initial immunization or IFA for subsequent booster immunizations. On day zero, for each of the recombinant preparations, two egg laying white Leghorn hens (obtained from local breeder) were each injected at multiple sites (intramuscular and subcutaneous) with 1 ml of recombinant adjuvant mixture containing approximately 0.5 to 1.5 mgs of recombinant toxin A. Booster immunizations of 1.0 mg were given on days 14 and day 28.

b) Antitoxin Collection

Total yolk immune IgY was extracted as described in the standard PEG protocol (as in Example 1) and the final IgY pellet was dissolved in sterile PBS at the original yolk volume. This material is designated "immune recombinant IgY" or "immune IgY."

c) Antitoxin Antibody Titer

To determine if the recombinant toxin A protein was sufficiently immunogenic to raise antibodies in hens, the antibody titer of a recombinant toxin A polypeptide was determined by ELISA. Eggs from both hens were collected on day 32, the yolks pooled and the antibody was isolated using PEG as described. The immune recombinant IgY antibody titer was determined for the soluble recombinant protein containing the maltose binding protein fusion generated in p-Mal (pMA1870-2680). Ninety-six well Falcon Pro-bind plates were coated overnight at 4° C. with 100 $\mu$l/well of toxin A recombinant at 2.5 $\mu$g/$\mu$l in PBS containing 0.05% thimerosal. Another plate was also coated with maltose binding protein (MBP) at the same concentration, to permit comparison of antibody reactivity to the fusion partner. The next day, the wells were blocked with PBS containing 1% bovine serum albumin (BSA) for 1 hour at 37° C. IgY isolated from immune or preimmune eggs was diluted in antibody diluent (PBS containing 1% BSA and 0.05% Tween-20), and added to the blocked wells and incubated for 1 hour at 37° C. The plates were washed three times with PBS with 0.05% Tween-20, then three times with PBS. Alkaline phosphatase conjugated rabbit anti-chicken IgG (Sigma) diluted 1:1000 in antibody diluent was added to the plate, and incubated for 1 hour at 37° C. The plates were washed as before and substrate was added, [p-nitrophenyl phosphate (Sigma)] at 1 mg/ml in 0.05M $Na_2CO_3$, pH 9.5 and 10 mM $MgCl_2$. The plates were evaluated quantitatively on a Dynatech MR 300 Micro EPA plate reader at 410 nm about 10 minutes after the addition of substrate.

Based on these ELISA results, high antibody titers were raised in chickens immunized with the toxin A recombinant polypeptide. The recombinant appeared to be highly immunogenic, as it was able to generate high antibody titers relatively quickly with few immunizations. Immune IgY titer directed specifically to the toxin A portion of the recombinant was higher than the immune IgY titer to its fusion partner, the maltose binding protein, and significantly higher than the preimmune IgY. ELISA titers (reciprocal of the highest dilution of IgY generating a signal) in the preimmune IgY to the MBP or the recombinant was <1:30 while the immune IgY titers to MBP and the toxin A recombinant were 1:18750 and >1:93750 respectively. Importantly, the anti-recombinant antibody titers generated in the hens against the recombinant polypeptide is much higher, compared to antibodies to that region raised using native toxin A. The recombinant antibody titer to region 1870-2680 in the CTA antibody preparation is at least five-fold lower compared to the recombinant generated antibodies (1:18750 versus >1:93750). Thus, it appears a better immune response can be generated against a specific recombinant using that recombinant as the immunogen compared to the native toxin A.

This observation is significant, as it shows that because recombinant portions stimulate the production of antibodies, it is not necessary to use native toxin molecules to produce antitoxin preparations. Thus, the problems associated with the toxicity of the native toxin are avoided and large-scale antitoxin production is facilitated.

d) Anti-Recombinant Toxin A Neutralization Of Toxin A Hemagglutination Activity In Vitro Toxin A has hemagglutinating activity besides cytotoxic and enterotoxin properties. Specifically, toxin A agglutinates rabbit erythrocytes by binding to a trisaccharide (gal 1-3B1-4GlcNAc) on the cell surface. [H. Krivan et al., Infect. Immun., 53:573–581 (1986).] We examined whether the anti-recombinant toxin A (immune IgY, antibodies raised against the insoluble product expressed in pET) can neutralize the hemagglutination activity of toxin A in vitro. The hemagglutination assay procedure used was described by H. C. Krivan et al. Polyethylene glycol-fractionated immune or preimmune IgY were pre-absorbed with citrated rabbit erythrocytes prior to performing the hemagglutination assay because we have found that IgY alone can agglutinate red blood cells. Citrated rabbit red blood cells (RRBC's) (Cocalico) were washed twice by centrifugation at 450×g with isotonic buffer (0.1 M Tris-HCl, 0.05 M NaCl, pH 7.2). RRBC-reactive antibodies in the IgY were removed by preparing a 10% RRBC suspension (made by adding packed cells to immune or preimmune IgY) and incubating the mixture for 1 hour at 37° C. The RRBCs were then removed by centrifugation. Neutralization of the hemagglutination activity of toxin A by antibody was tested in round-bottomed 96-well microtiter plates. Twenty-five $\mu$l of toxin A (36 $\mu$g/ml) (Tech Lab) in isotonic buffer was mixed with an equal volume of different dilutions of immune or preimmune IgY in isotonic buffer, and incubated for 15 minutes at room temperature. Then, 50 $\mu$l of a 1% RRBC suspension in isotonic buffer was added and the mixture was incubated for 3 hours at 4° C. Positive control wells containing the final concentration of 9 $\mu$g/ml of toxin A after dilution without IgY were also included. Hemagglutination activity was assessed visually, with a diffuse matrix of RRBC's coating the bottom of the well representing a positive hemagglutination reaction and a tight button of RRBC's at the bottom of the well representing a negative reaction. The anti-recombinant immune IgY neutralized toxin A hemagglutination activity, giving a neutralization titer of 1:8. However, preimmune IgY was unable to neutralize the hemagglutination ability of toxin A.

e) Assay Of In Vitro Toxin A Neutralizing Activity

Figure 14:
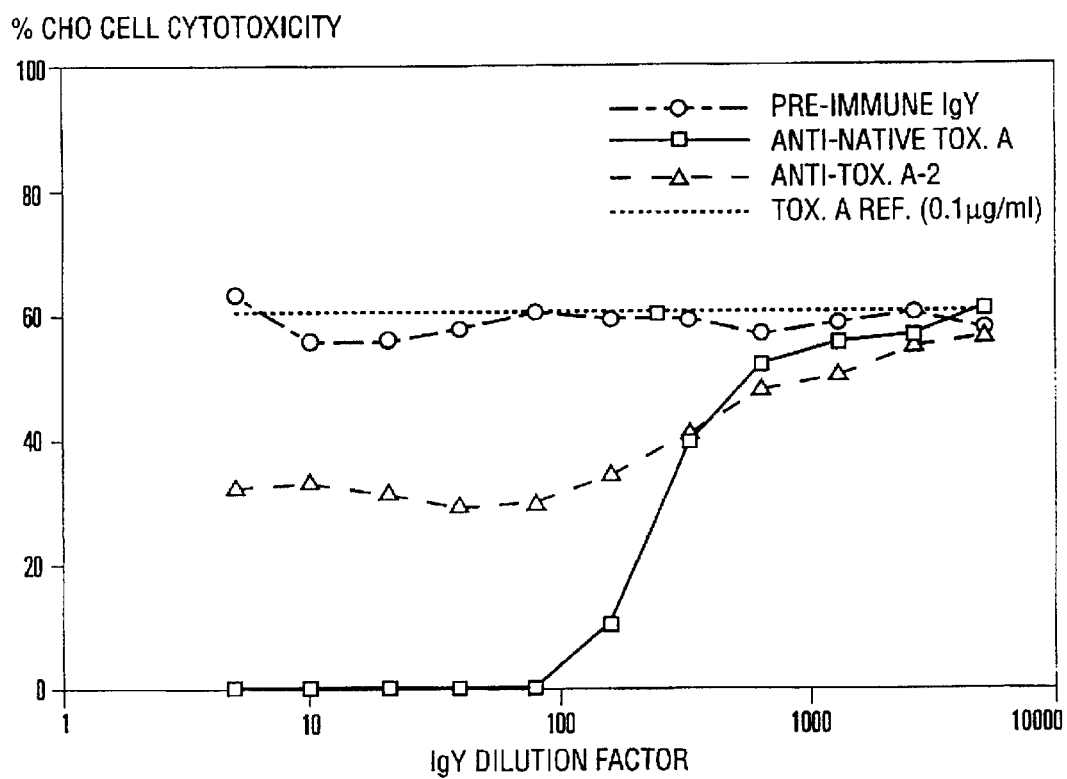
FIG. 14 shows the results of recombinant *C. difficile* toxin A neutralization assays.

The ability of the anti-recombinant toxin A IgY (immune IgY antibodies raised against pMA1870-2680, the soluble recombinant binding domain protein expressed in pMAL, designated as Anti-tox. A-2 in FIG. 14, and referred to as recombinant region 6) and pre-immune IgY, prepared as described in Example 8(c) above, to neutralize the cytotoxic activity of toxin A was assessed in vitro using the CHO cell cytotoxicity assay, and toxin A (Tech Lab) at a concentration of 0.1ug/ml, as described in Example 8(d) above. As additional controls, the anti-native toxin A IgY (CTA) and pre-immune IgY preparations described in Example 8(c) above were also tested. The results are shown in FIG. 14.

The anti-recombinant toxin A IgY demonstrated only partial neutralization of the cytotoxic activity of toxin A, while the pre-immune IgY did not demonstrate any significant neutralizing activity.

EXAMPLE 14

In vivo Neutralization Of *C. difficile* Toxin A

The ability of avian antibodies (IgY) raised against recombinant toxin A binding domain to neutralize the enterotoxin activity of *C. difficile* toxin A was evaluated in vivo using Golden Syrian hamsters. The Example involved:

(a) preparation of the avian anti-recombinant toxin A IgY for oral administration;

(b) in vivo protection of hamsters from *C. difficile* toxin A enterotoxicity by treatment of toxin A with avian anti-recombinant toxin A IgY; and (c) histologic evaluation of hamster ceca.

a) Preparation Of The Avian Anti-Recombinant Toxin A IgY For Oral Administration Eggs were collected from hens which had been immunized with the recombinant *C. difficile* toxin A fragment pMA1870-2680 (described in Example 13, above). A second group of eggs purchased at a local supermarket was used as a pre-immune (negative) control. Egg yolk immunoglobulin (IgY) was extracted by PEG from the two groups of eggs as described in Example 8(c), and the final IgY pellets were solubilized in one-fourth the original yolk volume using 0.1M carbonate buffer (mixture of $NaHCO_3$ and $Na_2CO_3$), pH 9.5. The basic carbonate buffer was used in order to protect the toxin A from the acidic pH of the stomach environment.

b) In vivo Protection Of Hamsters Against *C. difficile* Toxin A Enterotoxicity By Treatment Of Toxin A With Avian Anti-recombinant Toxin A IgY In order to assess the ability of the avian anti-recombinant toxin A IgY, prepared in section (a) above to neutralize the in vivo enterotoxin activity of toxin A, an in vivo toxin neutralization model was developed using Golden Syrian hamsters. This model was based on published values for the minimum amount of toxin A required to elicit diarrhea (0.08 mg toxin A/Kg body wt.) and death (0.16 mg toxin A/Kg body wt.) in hamsters when administered orally (Lyerly et al. Infect. Immun., 47:349–352 (1985).

For the study, four separate experimental groups were used, with each group consisting of 7 female Golden Syrian hamsters (Charles River), approx. three and one-half weeks old, weighing approx. 50 gms each. The animals were housed as groups of 3 and 4, and were offered food and water ad libitum through the entire length of the study.

For each animal, a mixture containing either 10 µg of toxin A (0.2 mg/Kg) or 30 µg of toxin A (0.6 mg/Kg) (*C. difficile* toxin A was obtained from Tech Lab and 1 ml of either the anti-recombinant toxin A IgY or pre-immune IgY (from section (a) above) was prepared. These mixtures were incubated at 37° C. for 60 min. and were then administered to the animals by the oral route. The animals were then observed for the onset of diarrhea and death for a period of 24 hrs. following the administration of the toxin A+IgY mixtures, at the end of which time, the following results were tabulated and shown in Table 17:

TABLE 17

Study Outcome At 24 Hours

| Experimental Group | Study Outcome at 24 Hours | | |
|---|---|---|---|
| | Healthy[1] | Diarrhea[2] | Dead[3] |
| 10 µg Toxin A + Antitoxin Against Interval 6 | 7 | 0 | 0 |
| 30 µg Toxin A + Antitoxin Against Interval 6 | 7 | 0 | 0 |
| 10 µg Toxin A + Pre-Immune Serum | 0 | 5 | 2 |
| 30 µg Toxin A + Pre-Immune | 0 | 5 | 2 |

[1]Animals remained healthy through the entire 24 hour study period.
[2]Animals developed diarrhea, but did not die.
[3]Animals developed diarrhea, and subsequently died.

Pretreatment of toxin A at both doses tested, using the anti-recombinant toxin A IgY, prevented all overt symptoms of disease in hamsters. Therefore, pretreatment of *C. difficile* toxin A, using the anti-recombinant toxin A IgY, neutralized the in vivo enterotoxin activity of the toxin A. In contrast, all animals from the two groups which received toxin A which had been pretreated using pre-immune IgY developed disease symptoms which ranged from diarrhea to death. The diarrhea which developed in the 5 animals which did not die in each of the two pre-immune groups, spontaneously resolved by the end of the 24 hr. study period.

c) Histologic Evaluation Of Hamster Ceca

In order to further assess the ability of anti-recombinant toxin A IgY to protect hamsters from the enterotoxin activity of toxin A, histologic evaluations were performed on the ceca of hamsters from the study described in section (b) above.

Three groups of animals were sacrificed in order to prepare histological specimens. The first group consisted of a single representative animal taken from each of the 4 groups of surviving hamsters at the conclusion of the study described in section (b) above. These animals represented the 24 hr. timepoint of the study.

The second group consisted of two animals which were not part of the study described above, but were separately treated with the same toxin A+pre-immune IgY mixtures as described for the animals in section (b) above. Both of these hamsters developed diarrhea, and were sacrificed 8 hrs. after the time of administration of the toxin A+pre-immune IgY mixtures. At the time of sacrifice, both animals were presenting symptoms of diarrhea. These animals represented the acute phase of the study.

The final group consisted of a single untreated hamster from the same shipment of animals as those used for the two previous groups. This animal served as the normal control.

Samples of cecal tissue were removed from the 7 animals described above, and were fixed overnight at 4° C. using 10% buffered formalin. The fixed tissues were paraffin-embedded, sectioned, and mounted on glass microscope slides. The tissue sections were then stained using hematoxylin and eosin (H and E stain), and were examined by light microscopy.

The tissues obtained from the two 24 hr. animals which received mixtures containing either 10 μg or 30 μg of toxin A and anti-recombinant toxin A IgY were indistinguishable from the normal control, both in terms of gross pathology, as well as at the microscopic level. These observations provide further evidence for the ability of anti-recombinant toxin A IgY to effectively neutralize the in vivo enterotoxin activity of C. difficile toxin A, and thus its ability to prevent acute or lasting toxin A-induced pathology.

In contrast, the tissues from the two 24 hr. animals which received the toxin A+pre-immune IgY mixtures demonstrated significant pathology. In both of these groups, the mucosal layer was observed to be less organized than in the normal control tissue. The cytoplasm of the epithelial cells had a vacuolated appearance, and gaps were present between the epithelium and the underlying cell layers. The lamina propria was largely absent. Intestinal villi and crypts were significantly diminished, and appeared to have been overgrown by a planar layer of epithelial cells and fibroblasts. Therefore, although these animals overtly appeared to recover from the acute symptoms of toxin A intoxication, lasting pathologic alterations to the cecal mucosa had occurred.

The tissues obtained from the two acute animals which received mixtures of toxin A and pre-immune IgY demonstrated the most significant pathology. At the gross pathological level, both animals were observed to have severely distended ceca which were filled with watery, diarrhea-like material. At the microscopic level, the animal that was given the mixture containing 10 μg of toxin A and pre-immune IgY was found to have a mucosal layer which had a ragged, damaged appearance, and a disorganized, compacted quality. The crypts were largely absent, and numerous breaks in the epithelium had occurred. There was also an influx of erythrocytes into spaces between the epithelial layer and the underlying tissue. The animal which had received the mixture containing 30 μg of toxin A and pre-immune IgY demonstrated the most severe pathology. The cecal tissue of this animal had an appearance very similar to that observed in animals which had died from C. difficile disease. Widespread destruction of the mucosa was noted, and the epithelial layer had sloughed. Hemorrhagic areas containing large numbers of erythrocytes were very prevalent. All semblance of normal tissue architecture was absent from this specimen. In terms of the presentation of pathologic events, this in vivo hamster model of toxin A-intoxication correlates very closely with the pathologic consequences of C. difficile disease in hamsters. The results presented in this Example demonstrate that while anti-recombinant toxin A (Interval 6) IgY is capable of only partially neutralizing the cytotoxic activity of C. difficile toxin A, the same antibody effectively neutralizes 100% of the in vivo enterotoxin activity of the toxin. While it is not intended that this invention be limited to this mechanism, this may be due to the cytotoxicity and enterotoxicity of C. difficile Toxin A as two separate and distinct biological functions.

EXAMPLE 15

In Vivo Neutralization Of C. Difficile Toxin A By Antibodies Against Recombinant Toxin A Polypeptides The ability of avian antibodies directed against the recombinant C. difficile toxin A fragment 1870-2680 (as expressed by pMA1870-2680; see Example 13) to neutralize the enterotoxic activity of toxin A was demonstrated in Example 14. The ability of avian antibodies (IgYs) directed against other recombinant toxin A epitopes to neutralize native toxin A in vivo was next evaluated. This example involved: (a) the preparation of IgYs against recombinant toxin A polypeptides; (b) in vivo protection of hamsters against toxin A by treatment with anti-recombinant toxin A IgYs and (c) quantification of specific antibody concentration in CTA and Interval 6 IgY PEG preparations.

The nucleotide sequence of the coding region of the entire toxin A protein is listed in SEQ ID NO:5. The amino acid sequence of the entire toxin A protein is listed in SEQ ID NO:6. The amino acid sequence consisting of amino acid residues 1870 through 2680 of toxin A is listed in SEQ ID NO:7. The amino acid sequence consisting of amino acid residues 1870 through 1960 of toxin A is listed in SEQ ID NO:8. The amino acid sequence of residues 1873 through 2684 of toxin A is listed in SEQ ID NO:29.

a) Preparation Of IgY's Against Recombinant Toxin A Polypeptides

Figure 15A:
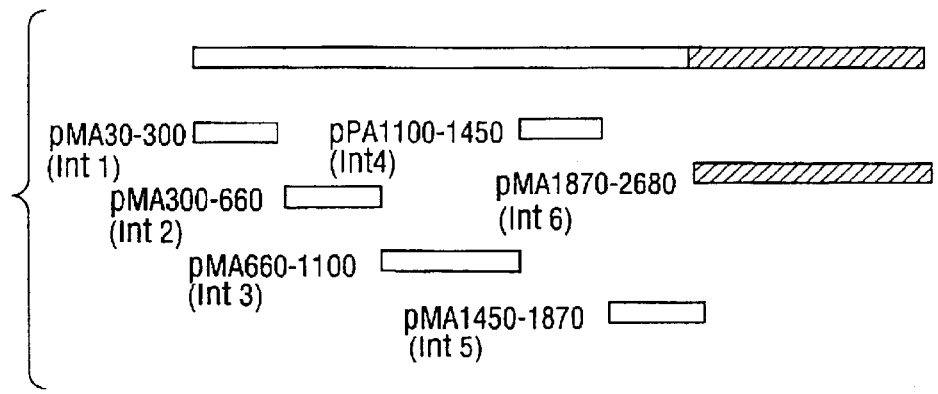
FIG. 15 shows *C. difficile* toxin A expression constructs.

Eggs were collected from Leghorn hens which have been immunized with recombinant C. difficile toxin A polypeptide fragments encompassing the entire toxin A protein. The polypeptide fragments used as immunogens were: 1) pMA 1870-2680 (Interval 6), 2) pPA 1100-1450 (Interval 4), and 3) a mixture of fragments consisting of pMA 30-300 (Interval 1), pMA 300-660 (Interval 2), pMA 660-1100 (Interval 3) and pMA 1450-1870 (Interval 5). This mixture of immunogens is referred to as Interval 1235. The location of each interval within the toxin A molecule is shown in FIG. 15A. In FIG. 15A, the following abbreviations are used: pP refers to the pET23 vector (New England BioLabs); pM refers to the pMAL™-c vector (New England BioLabs); A refers to toxin A; the numbers refer to the amino acid interval expressed in the clone. (For example, the designation pMA30-300 indicates that the recombinant clone encodes amino acids 30–300 of toxin A and the vector used was pMAL™-c).

The recombinant proteins were generated as described in Example 11. The IgYs were extracted and solubilized in 0.1M carbonate buffer pH 9.5 for oral administration as described in Example 14(a). The IgY reactivities against each individual recombinant interval was evaluated by ELISA as described in Example 13(c).

b) In Vivo Protection Of Hamsters Against Toxin A By Treatment With Anti-Recombinant Toxin A Antibodies The ability of antibodies raised against recombinant toxin A polypeptides to provide in vivo protection against the enterotoxic activity of toxin A was examined in the hamster model system. This assay was performed as described in Example 14(b). Briefly, for each 40–50 gram female Golden Syrian hamster (Charles River), 1 ml of IgY 4× (i.e., resuspended in ¼ of the original yolk volume) PEG prep against Interval 6, Interval 4 or Interval 1235 was mixed with 30 µg ($LD_{100}$ oral dose) of *C. difficile* toxin A (Tech Lab). Preimmune IgY mixed with toxin A served as a negative control. Antibodies raised against *C. difficile* toxoid A (Example 8) mixed with toxin A (CTA) served as a positive control. The mixture was incubated for 1 hour at 37° C. then orally administered to lightly etherized hamsters using an 18G feeding needle. The animals were then observed for the onset of diarrhea and death for a period of approximately 24 hours. The results are shown in Table 18.

TABLE 18

Study Outcome After 24 Hours

| Treatment Group | Healthy[1] | Diarrhea[2] | Dead[3] |
|---|---|---|---|
| Preimmune | 0 | 0 | 7 |
| CTA | 5 | 0 | 0 |
| Interval 6 | 6 | 1 | 0 |
| Interval 4 | 0 | 1 | 6 |
| Interval 1235 | 0 | 0 | 7 |

[1]Animal shows no sign of illness.
[2]Animal developed diarrhea, but did not die.
[3]Animal developed diarrhea and died.

Figure 16:
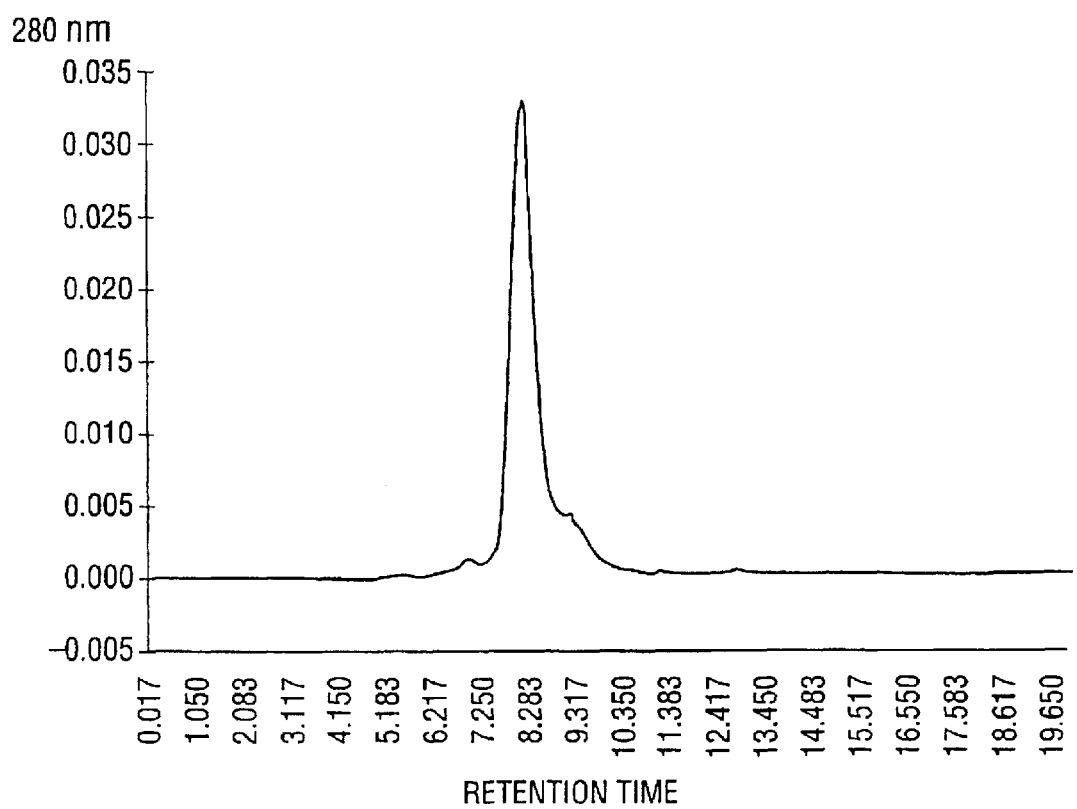
FIG. 16 shows a chromatograph plotting absorbance at 280 nm against retention time for a pMA1870-680 IgY PEG preparation.

Pre-treatment of toxin A with IgYs against Interval 6 prevented diarrhea in 6 of 7 hamsters and completely prevented death in all 7. In contrast, as with preimmune IgY, IgYs against Interval 4 and Interval 1235 had no effect on the onset of diarrhea and death in the hamsters.

c) Quantification Of Specific Antibody Concentration In CTA And Interval 6 IgY PEG Preparations To determine the purity of IgY PEG preparations, an aliquot of a pMA1870-2680 (Interval 6) IgY PEG preparation was chromatographed using HPLC and a KW-803 sizing column (Shodex). The resulting profile of absorbance at 280 nm is shown in FIG. 16. The single large peak corresponds to the predicted MW of IgY. Integration of the area under the single large peak showed that greater than 95% of the protein eluted from the column was present in this single peak. This result demonstrated that the majority (>95%) of the material absorbing at 280 nm in the PEG preparation corresponds to IgY. Therefore, absorbance at 280 rn can be used to determine the total antibody concentration in PEG preparations.

Figure 15B:
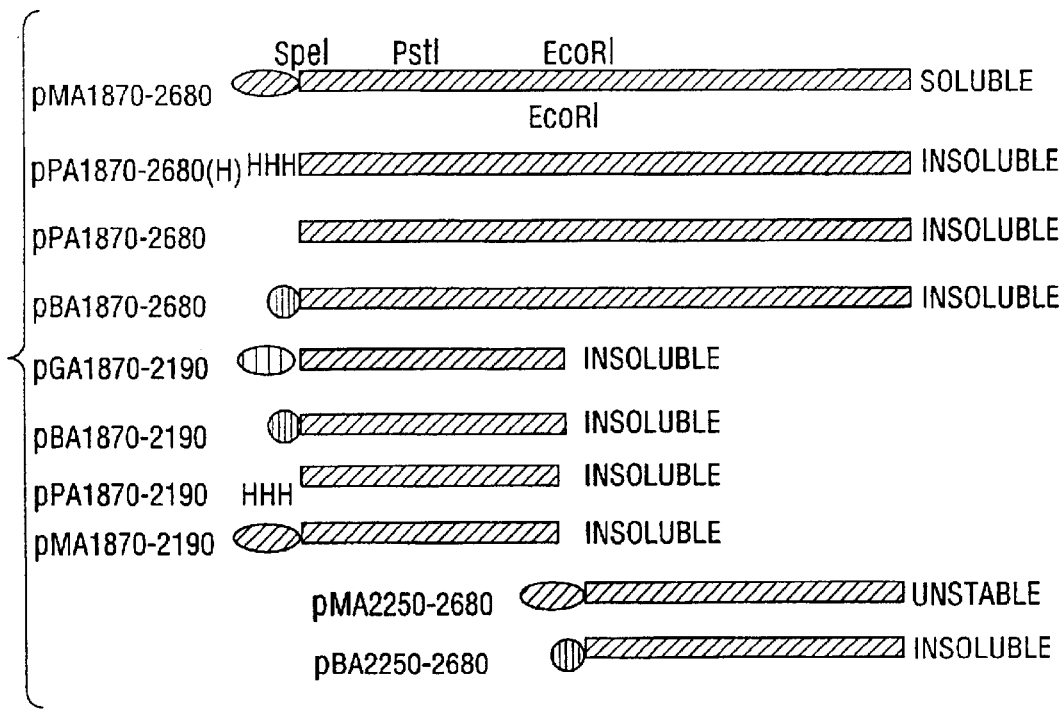

To determine the concentration of Interval 6-specific antibodies (expressed as percent of total antibody) within the CTA and pMA1870-2680 (Interval 6) PEG preparations, defined quantities of these antibody preparations were affinity purified on a pPA1870-2680(H) (shown schematically in FIG. 15B) affinity column and the specific antibodies were quantified. In FIG. 15B the following abbreviations are used: pP refers to the pET23 vector (New England BioLabs); pM refers to the pMAL™-c vector (New England BioLabs); pG refers to the pGEX vector (Pharmacia); pB refers to the PinPoint™ Xa vector (Promega); A refers to toxin A; the numbers refer to the amino acid interval expressed in the clone. The solid black ovals represent the MBP; the hatched ovals represent glutathione S-transferase; the hatched circles represent the biotin tag; and HHH represents the polyhistidine tag.

An affinity column containing recombinant toxin A repeat protein was made as follows. Four ml of PBS-washed Actigel resin (Sterogene) was coupled with 5–10 mg of pPA1870–2680 inclusion body protein [prepared as described in Example (17) and dialyzed into PBS] in a 15 ml tube (Falcon) containing ¹⁄₁₀ final volume Ald-coupling solution (1 M sodium cyanoborohydride). Aliquots of the supernatant from the coupling reactions, before and after coupling, were assessed by Coomassie staining of 7.5% SDS-PAGE gels. Based upon protein band intensities, greater than 6 mg of recombinant protein was coupled to the resin. The resin was poured into a 10 ml column (BioRad), washed extensively with PBS, pre-eluted with 4 M guanidine-HCl (in 10 mM Tris-HCl, pH 8.0; 0.005% thimerosal) and re-equilibrated with PBS. The column was stored at 4° C.

Aliquots of a pMA1870-2680 (Interval 6) or a CTA IgY polyclonal antibody preparation (PEG prep) were affinity purified on the above affinity column as follows. The column was attached to an UV monitor (ISCO) and washed with PBS. For pMA1870-2680 IgY purification, a 2×PEG prep (filter sterilized using a 0.45µ filter; approximately 500 mg total IgY) was applied. The column was washed with PBS until the baseline was re-established (the column flow-through was saved), washed with BBSTween to elute non-specifically binding antibodies and re-equilibrated with PBS. Bound antibody was eluted from the column in 4 M guanidine-HCl (in 10 mM Tris-HCl, pH 8.0; 0.005% thimerosal). The entire elution peak was collected in a 15 ml tube (Falcon). The column was re-equilibrated and the column eluate was re-chromatographed as described above. The antibody preparation was quantified by UV absorbance (the elution buffer was used to zero the spectrophotometer). Total purified antibody was approximately 9 mg and 1 mg from the first and second chromatography passes, respectively. The low yield from the second pass indicated that most specific antibodies were removed by the first round of chromatography. The estimated percentage of Interval 6 specific antibodies in the pMA1870-2680 PEG prep is approximately 2%.

The percentage of Interval 6 specific antibodies in the CTA PEG prep was determined (utilizing the same column and methodology described above) to be approximately 0.5% of total IgY.

A 4×PEG prep contains approximately 20 mg/ml IgY. Thus in b) above, approximately 400 µg specific antibody in the Interval 6 PEG prep neutralized 30 µg toxin A in vivo.

EXAMPLE 16

In Vivo Treatment Of *C. difficile* Disease In Hamsters By Recombinant Interval 6 Antibodies The ability of antibodies directed against recombinant Interval 6 of toxin A to protect hamsters in vivo from *C. difficile* disease was examined. This example involved: (a) prophylactic treatment of *C. difficile* disease and (b) therapeutic treatment of *C. difficile* disease.

a) Prophylactic Treatment Of *C. difficile* Disease

This experiment was performed as described in Example 9(b). Three groups each consisting of 7 female 100 gram Syrian hamsters (Charles River) were prophylactically treated with either preimmune IgYs, IgYs against native toxin A and B [CTAB; see Example 8 (a) and (b)] or IgYs against Interval 6. IgYs were prepared as 4×PEG preparations as described in Example 9(a).

The animals were orally dosed 3 times daily, roughly at 4 hour intervals, for 12 days with 1 ml antibody preparations diluted in Ensure®. Using estimates of specific antibody concentration from Example 15(c), each dose of the Interval 6 antibody prep contained approximately 400 µg of specific antibody. On day 2 each hamster was predisposed to *C. difficile* infection by the oral administration of 3.0 mg of Clindamycin-HCl (Sigma) in 1 ml of water. On day 3 the hamsters were orally challenged with 1 ml of *C. difficile* inoculum strain ATCC 43596 in sterile saline containing approximately 100 organisms. The animals were then observed for the onset of diarrhea and subsequent death during the treatment period. The results are shown in Table 19.

TABLE 19

Lethality After 12 Days Of Treatment

| Treatment Group | Number Animals Alive | Number Animals Dead |
|---|---|---|
| Preimmune | 0 | 7 |
| CTAB | 6 | 1 |
| Interval 6 | 7 | 0 |

Treatment of hamsters with orally-administered IgYs against Interval 6 successfully protected 7 out of 7 (100%) of the animals from C. difficile disease. One of the hamsters in this group presented with diarrhea which subsequently resolved during the course of treatment. As shown previously in Example 9, antibodies to native toxin A and toxin B were highly protective. In this Example, 6 out of 7 animals survived in the CTAB treatment group. All of the hamsters treated with preimmune sera came down with diarrhea and died. The survivors in both the CTAB and Interval 6 groups remained healthy throughout a 12 day post-treatment period. In particular, 6 out of 7 Interval 6-treated hamsters survived at least 2 weeks after termination of treatment which suggests that these antibodies provide a long-lasting cure. These results represent the first demonstration that antibodies generated against a recombinant region of toxin A can prevent CDAD when administered passively to animals. These results also indicate that antibodies raised against Interval 6 alone may be sufficient to protect animals from C. difficile disease when administered prophylactically.

Figure 17:
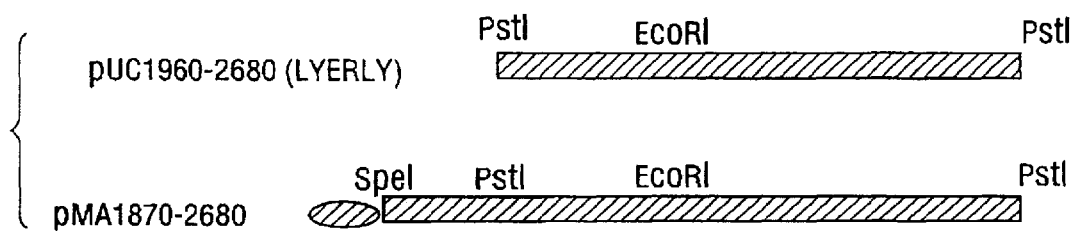
FIG. 17 shows two recombinant *C. difficile* toxin B expression constructs.

Previously others had raised antibodies against toxin A by actively immunizing hamsters against a recombinant polypeptide located within the Interval 6 region [Lyerly, D. M., et al. (1990) Curr. Microbiol. 21:29]. FIG. 17 shows schematically the location of the Lyerly, et al. intra-Interval 6 recombinant protein (cloned into the pUC vector) in comparison with the complete Interval 6 construct (pMA1870-2680) used herein to generate neutralizing antibodies directed against toxin A. In FIG. 17, the solid black oval represents the MBP which is fused to the toxin A Interval 6 in pMA1870-2680.

The Lyerly, et al. antibodies (intra-Interval 6) were only able to partially protect hamsters against C. difficile infection in terms of survival (4 out of 8 animals survived) and furthermore, these antibodies did not prevent diarrhea in any of the animals. Additionally, animals treated with the intra-Interval 6 antibodies [Lyerly, et al. (1990), supra] died when treatment was removed.

In contrast, the experiment shown above demonstrates that passive administration of anti-Interval 6 antibodies prevented diarrhea in 6 out of 7 animals and completely prevented death due to CDAD. Furthermore, as discussed above, passive administration of the anti-Interval 6 antibodies provides a long lasting cure (i.e., treatment could be withdrawn without incident).

b) Therapeutic Treatment Of C. difficile Disease: In Vivo Treatment Of An Established C. difficile Infection In Hamsters With Recombinant Interval 6 Antibodies The ability of antibodies against recombinant interval 6 of toxin A to therapeutically treat C. difficile disease was examined. The experiment was performed essentially as described in Example 10(b). Three groups, each containing seven to eight female Golden Syrian hamsters (100 g each;

Charles River) were treated with either preimmune IgY, IgYs against native toxin A and toxin B (CTAB) and IgYs against Interval 6. The antibodies were prepared as described above as 4×PEG preparations.

The hamsters were first predisposed to C. difficile infection with a 3 mg dose of Clindamycin-HCl (Sigma) administered orally in 1 ml of water. Approximately 24 hrs later, the animals were orally challenged with 1 ml of C. difficile strain ATCC 43596 in sterile saline containing approximately 200 organisms. One day after infection, the presence of toxin A and B was determined in the feces of the hamsters using a commercial immunoassay kit (Cytoclone A+B EPA, Cambridge Biotech) to verify establishment of infection. Four members of each group were randomly selected and tested. Feces from an uninfected hamster was tested as a negative control. All infected animals tested positive for the presence of toxin according to the manufacturer's procedure. The initiation of treatment then started approximately 24 hr post-infection.

The animals were dosed daily at roughly 4 hr intervals with 1 ml antibody preparation diluted in Ensure® (Ross Labs). The amount of specific antibodies given per dose (determined by affinity purification) was estimated to be about 400 $\mu$g of anti-Interval 6 IgY (for animals in the Interval 6 group) and 100 $\mu$g and 70 $\mu$g of anti-toxin A (Interval 6-specific) and anti-toxin B (Interval 3-specific; see Example 19), respectively, for the CTAB preparation. The animals were treated for 9 days and then observed for an additional 4 days for the presence of diarrhea and death. The results indicating the number of survivors and the number of dead 4 days post-infection are shown in Table 20.

TABLE 20

In vivo Therapeutic Treatment With Interval 6 Antibodies

| Treatment Group | Number Animals Alive | Number Animals Dead |
|---|---|---|
| Preimmune | 4 | 3 |
| CTAB | 8 | 0 |
| Interval 6 | 8 | 0 |

Antibodies directed against both Interval 6 and CTAB successfully prevented death from C. difficile when therapeutically administered 24 hr after infection. This result is significant since many investigators begin therapeutic treatment of hamsters with existing drugs (e.g., vancomycin, phenelfamycins, tiacumicins, etc.) 8 hr post-infection [Swanson, et al. (1991) Antimicrobial Agents and Chemotherapy 35:1108 and (1989) J. Antibiotics 42:94].

Forty-two percent of hamsters treated with preimmune IgY died from CDAD. While the anti-Interval 6 antibodies prevented death in the treated hamsters, they did not eliminate all symptoms of CDAD as 3 animals presented with slight diarrhea. In addition, one CTAB-treated and one preimmune-treated animal also had diarrhea 14 days post-infection. These results indicate that anti-Interval 6 antibodies provide an effective means of therapy for CDAD.

EXAMPLE 17

Induction Of Toxin A Neutralizing Antibodies Requires Soluble Interval 6 Protein As shown in Examples 11(d) and 15, expression of recombinant proteins in E. coli may result in the production of either soluble or insoluble protein. If insoluble protein is produced, the recombinant protein is solubilized prior to immunization of animals. To determine whether, one or both of the soluble or insoluble recombinant proteins could be used to generate neutralizing antibodies to toxin A, the following experiment was performed. This example involved a) expression of the toxin A repeats and subfragments of these repeats in *E. coli* using a variety of expression vectors; b) identification of recombinant toxin A repeats and sub-regions to which neutralizing antibodies bind; and c) determination of the neutralization ability of antibodies raised against soluble and insoluble toxin A repeat immunogen.

a) Expression Of The Toxin A Repeats And Subfragments Of These Repeats In *E. coli* Using A Variety Of Expression Vectors The Interval 6 immunogen utilized in Examples 15 and 16 was the pMA1870-2680 protein, in which the toxin A repeats are expressed as a soluble fusion protein with the MBP (described in Example 11). Interestingly, expression of this region (from the SpeI site to the end of the repeats, see FIG. 15B) in three other expression constructs, as either native (pPA1870-2680), poly-His tagged [pPA1870-2680 (H)] or biotin-tagged (pBA1870-2680) proteins resulted in completely insoluble protein upon induction of the bacterial host (see FIG. 15B). The host strain BL21 (Novagen) was used for expression of pBA1870-2680 and host strain BL21 (DE3) (Novagen) was used for expression of pPA1870-2680 and pPA1870-2680(H). These insoluble proteins accumulated to high levels in inclusion bodies. Expression of recombinant plasmids in *E. coli* host cells grown in 2×YT medium was performed as described [Williams, et al. (1994), supra].

As summarized in FIG. 15B, expression of fragments of the toxin A repeats (as either N-terminal SpeI-EcoRI fragments, or C-terminal EcoRI-end fragments) also yielded high levels of insoluble protein using pGEX (pGA1870-2190), PinPoint™-Xa (pBA1870-2190 and pBA2250-2680) and pET expression systems (pPA1870-2190). The pGEX and pET expression systems are described in Example 11. The PinPoint™-Xa expression system drives the expression of fusion proteins in *E. coli*. Fusion proteins from PinPoint™-Xa vectors contain a biotin tag at the amino-terminal end and can be affinity purified SoftLink™ Soft Release avidin resin (Promega) under mild denaturing conditions (5 mM biotin).

The solubility of expressed proteins from the pPG1870-2190 and pPA1870-2190 expression constructs was determined after induction of recombinant protein expression under conditions reported to enhance protein solubility [These conditions comprise growth of the host at reduced temperature (30° C.) and the utilization of high (1 mM IPTG) or low (0.1 mM IPTG) concentrations of inducer [Williams et al. (1994), supra]. All expressed recombinant toxin A protein was insoluble under these conditions. Thus, expression of these fragments of the toxin A repeats in pET and pGEX expression vectors results in the production of insoluble recombinant protein even when the host cells are grown at reduced temperature and using lower concentrations of the inducer. Although expression of these fragments in pMal vectors yielded affinity purifiable soluble fusion protein, the protein was either predominantly insoluble (pMA1870-2190) or unstable (pMA2250-2650). Attempts to solubilize expressed protein from the pMA1870-2190 expression construct using reduced temperature or lower inducer concentration (as described above) did not improve fusion protein solubility.

Collectively, these results demonstrate that expression of the toxin A repeat region in *E. coli* results in the production of insoluble recombinant protein, when expressed as either large (aa 1870-2680) or small (aa 1870-2190 or aa 2250-2680) fragments, in a variety of expression vectors (native or poly-his tagged pET, pGEX or PinPoin™-Xa vectors), utilizing growth conditions shown to enhance protein solubility. The exception to this rule were fusions with the MBP, which enhanced protein solubility, either partially (pMA1870-2190) or fully (pMA1870-2680).

b) Identification Of Recombinant Toxin A Repeats And Sub-Regions To Which Neutralizing Antibodies Bind Toxin A repeat regions to which neutralizing antibodies bind were identified by utilizing recombinant toxin A repeat region proteins expressed as soluble or insoluble proteins to deplete protective antibodies from a polyclonal pool of antibodies against native *C. difficile* toxin A. An in vivo assay was developed to evaluate proteins for the ability to bind neutralizing antibodies.

The rational for this assay is as follows. Recombinant proteins were first pre-mixed with antibodies against native toxin A (CTA antibody; generated in Example 8) and allowed to react. Subsequently, *C. difficile* toxin A was added at a concentration lethal to hamsters and the mixture was administered to hamsters via IP injection. If the recombinant protein contains neutralizing epitopes, the CTA antibodies would lose their ability to bind toxin A resulting in diarrhea and/or death of the hamsters.

The assay was performed as follows. The lethal dose of toxin A when delivered orally to nine 40 to 50 g Golden Syrian hamsters (Sasco) was determined to be 10 to 30 µg. The PEG-purified CTA antibody preparation was diluted to 0.5×concentration (i.e., the antibodies were diluted at twice the original yolk volume) in 0.1 M carbonate buffer, pH 9.5. The antibodies were diluted in carbonate buffer to protect them from acid degradation in the stomach. The concentration of 0.5× was used because it was found to be the lowest effective concentration against toxin A. The concentration of Interval 6-specific antibodies in the 0.5× CTA prep was estimated to be 10–15 µg/ml (estimated using the method described in Example 15).

The inclusion body preparation [insoluble Interval 6 protein; pPA1870-2680(H)] and the soluble Interval 6 protein [pMA1870-2680; see FIG. 15] were both compared for their ability to bind to neutralizing antibodies against *C. difficile* toxin A (CTA). Specifically, 1 to 2 mg of recombinant protein was mixed with 5 ml of a 0.5× CTA antibody prep (estimated to contain 60–70 µg of Interval 6-specific antibody). After incubation for 1 hr at 37° C., CTA (Tech Lab) at a final concentration of 30 µg/ml was added and incubated for another 1 hr at 37° C. One ml of this mixture containing 30 µg of toxin A (and 10–15 µg of Interval 6-specific antibody) was administered orally to 40–50 g Golden Syrian hamsters (Sasco). Recombinant proteins that result in the loss of neutralizing capacity of the CTA antibody would indicate that those proteins contain neutralizing epitopes. Preimmune and CTA antibodies (both at 0.5×) without the addition of any recombinant protein served as negative and positive controls, respectively.

Two other inclusion body preparations, both expressed as insoluble products in the pET vector, were tested; one containing a different insert (toxin B fragment) other than Interval 6 called pPB1850-2070 (see FIG. 18) which serves as a control for insoluble Interval 6, the other was a truncated version of the Interval 6 region called pPA1870-2190 (see FIG. 15B). The results of this experiment are shown in Table 21.

TABLE 21

Binding Of Neutralizing Antibodies By Soluble
Interval 6 Protein Study Outcome After 24 Hours

| Treatment Group | Healthy[2] | Diarrhea[3] | Dead[4] |
|---|---|---|---|
| Preimmune Ab | 0 | 3 | 2 |
| CTA Ab | 4 | 1 | 0 |
| CTA Ab + Int 6 (soluble) | 1 | 2 | 2 |
| CTA Ab + Int 6 (insoluble) | 5 | 0 | 0 |
| CTA Ab + pPB1850-2070 | 5 | 0 | 0 |
| CTA Ab + pPA1870-2190 | 5 | 0 | 0 |

[1]*C. difficile* toxin A (CTA) was added to each group.
[2]Animals showed no signs of illness.
[3]Animals developed diarrhea but did not die.
[4]Animals developed diarrhea and died.

Preimmune antibody was ineffective against toxin A, while anti-CTA antibodies at a dilute 0.5×concentration almost completely protected the hamsters against the enterotoxic effects of CTA. The addition of recombinant proteins pPB1850-2070 or pPA1870-2190 to the anti-CTA antibody had no effect upon its protective ability, indicating that these recombinant proteins do not bind to neutralizing antibodies. On the other hand, recombinant Interval 6 protein was able to bind to neutralizing anti-CTA antibodies and neutralized the in vivo protective effect of the anti-CTA antibodies. Four out of five animals in the group treated with anti-CTA antibodies mixed with soluble Interval 6 protein exhibited toxin associated toxicity (diarrhea and death). Moreover, the results showed that Interval 6 protein must be expressed as a soluble product in order for it to bind to neutralizing anti-CTA antibodies since the addition of insoluble Interval 6 protein had no effect on the neutralizing capacity of the CTA antibody prep.

c) Determination Of Neutralization Ability Of Antibodies Raised Against Soluble And Insoluble Toxin A Repeat Immunogen To determine if neutralizing antibodies are induced against solubilized inclusion bodies, insoluble toxin A repeat protein was solubilized and specific antibodies were raised in chickens. Insoluble pPA1870-2680 protein was solubilized using the method described in Williams et al. (1994), supra. Briefly, induced cultures (500 ml) were pelleted by centrifugation at 3,000×g for 10 min at 4° C. The cell pellets were resuspended thoroughly in 10 ml of inclusion body sonication buffer (25 mM HEPES pH 7.7, 100 mM KCl, 12.5 mM $MgCl_2$, 20% glycerol, 0.1% (v/v) Nonidet P-40, 1 mM DTT). The suspension was transferred to a 30 ml non-glass centrifuge tube. Five hundred pl of 10 mg/ml lysozyme was added and the tubes were incubated on ice for 30 min. The suspension was then frozen at −70° C. for at least 1 hr. The suspension was thawed rapidly in a water bath at room temperature and then placed on ice. The suspension was then sonicated using at least eight 15 sec bursts of the microprobe (Branson Sonicator Model No. 450) with intermittent cooling on ice.

The sonicated suspension was transferred to a 35 ml Oakridge tube and centrifuged at 6,000×g for 10 min at 4° C. to pellet the inclusion bodies. The pellet was washed 2 times by pipetting or vortexing in fresh, ice-cold RIPA buffer [0.1% SDS, 1% Triton X-100, 1% sodium deoxycholate in TBS (25 mM Tris-Cl pH 7.5, 150 mM NaCl)]. The inclusion bodies were recentrifuged after each wash. The inclusion bodies were dried and transferred using a small metal spatula to a 15 ml tube (Falcon). One ml of 10% SDS was added and the pellet was solubilized by gently pipetting the solution up and down using a 1 ml micropipettor. The solubilization was facilitated by heating the sample to 95° C. when necessary.

Once the inclusion bodies were in solution, the samples were diluted with 9 volumes of PBS. The protein solutions were dialyzed overnight against a 100-fold volume of PBS containing 0.05% SDS at room temperature. The dialysis buffer was then changed to PBS containing 0.01% SDS and the samples were dialyzed for several hours to overnight at room temperature. The samples were stored at 4° C. until used. Prior to further use, the samples were warmed to room temperature to allow any precipitated SDS to go back into solution.

The inclusion body preparation was used to immunize hens. The protein was dialyzed into PBS and emulsified with approximately equal volumes of CFA for the initial immunization or IFA for subsequent booster immunizations. On day zero, for each of the recombinant recombinant preparations, two egg laying white Leghorn hens were each injected at multiple sites (IM and SC) with 1 ml of recombinant protein-adjuvant mixture containing approximately 0.5–1.5 mg of recombinant protein. Booster immunizations of 1.0 mg were given of days 14 and day 28. Eggs were collected on day 32 and the antibody isolated using PEG as described in Example 14(a). High titers of toxin A specific antibodies were present (as assayed by ELISA, using the method described in Example 13). Titers were determined for both antibodies against recombinant polypeptides pPA1870-2680 and pMA1870-2680 and were found to be comparable at >1:62,500.

Antibodies against soluble Interval 6 (pMA1870-2680) and insoluble Interval 6 [(inclusion body), pPA1870-2680] were tested for neutralizing ability against toxin A using the in vivo assay described in Example 15(b). Preimmune antibodies and antibodies against toxin A (CTA) served as negative and positive controls, respectively. The results are shown in Table 22.

TABLE 22

Neutralization Of Toxin A By Antibodies Against
Soluble Interval 6 Protein Study Outcome After 24 Hours

| Antibody Treatment Group | Healthy[1] | Diarrhea[2] | Dead[3] |
|---|---|---|---|
| Preimmune | 1 | 0 | 4 |
| CTA | 5 | 0 | 0 |
| Interval 6 (Soluble)[4] | 5 | 0 | 0 |
| Interval 6 (Insoluble) | 0 | 2 | 3 |

[1]Animals showed no sign of illness.
[2]Animal developed diarrhea but did not die.
[3]Animal developed diarrhea and died.
[4]400 µg/ml.

Antibodies raised against native toxin A were protective while preimmune antibodies had little effect. As found using the in vitro CHO assay [described in Example 8(d)] where antibodies raised against the soluble Interval 6 could partially neutralize the effects of toxin A, here they were able to completely neutralize toxin A in vivo. In contrast, the antibodies raised against the insoluble Interval 6 was unable to neutralize the effects of toxin A in vivo as shown above (Table 22) and in vitro as shown in the CHO assay [described in Example 8(d)].

These results demonstrate that soluble toxin A repeat immunogen is necessary to induce the production of neutralizing antibodies in chickens, and that the generation of such soluble immunogen is obtained only with a specific expression vector (Mal) containing the toxin A region spanning aa 1870-2680. That is to say, insoluble protein that is subsequently solubilized does not result in a toxin A antigen that will elicit a neutralizing antibody.

EXAMPLE 18

Cloning And Expression Of The *C. difficile* Toxin B Gene

The toxin B gene has been cloned and sequenced; the amino acid sequence deduced from the cloned nucleotide sequence predicts a MW of 269.7 kD for toxin B [Barroso et al., Nucl. Acids Res. 18:4004 (1990)]. The nucleotide sequence of the coding region of the entire toxin B gene is listed in SEQ ID NO:9. The amino acid sequence of the entire toxin B protein is listed in SEQ ID NO:10. The amino acid sequence consisting of amino acid residues 1850 through 2360 of toxin B is listed in SEQ ID NO:11. The amino acid sequence consisting of amino acid residues 1750 through 2360 of toxin B is listed in SEQ ID NO:12. The amino acid sequence consisting of amino acid residues 1754 through 2362 of toxin B is listed in SEQ ID NO:30.

Given the expense and difficulty of isolating native toxin B protein, it would be advantageous to use simple and inexpensive procaryotic expression systems to produce and purify high levels of recombinant toxin B protein for immunization purposes. Ideally, the isolated recombinant protein would be soluble in order to preserve native antigenicity, since solubilized inclusion body proteins often do not fold into native conformations. Indeed as shown in Example 17, neutralizing antibodies against recombinant toxin A were only obtained when soluble recombinant toxin A polypeptides were used as the immunogen. To allow ease of purification, the recombinant protein should be expressed to levels greater than 1 mg/liter of *E. coli* culture.

To determine whether high levels of recombinant toxin B protein could be produced in *E. coli*, fragments of the toxin B gene were cloned into various prokaryotic expression vectors, and assessed for the ability to express recombinant toxin B protein in *E. coli*. This Example involved (a) cloning of the toxin B gene and (b) expression of the toxin B gene in *E. coli*.

a) Cloning Of The Toxin B Gene

The toxin B gene was cloned using PCR amplification from *C. difficile* genomic DNA. Initially, the gene was cloned in two overlapping fragments, using primer pairs P5/P6 and P7/P8. The location of these primers along the toxin B gene is shown schematically in FIG. 18. The sequence of each of these primers is: P5: 5' TAGAAAAAATGGCAAATGT 3' (SEQ ID NO: 1); P6: 5' TTTCATCTTGTA GAGTCAAAG 3' (SEQ ID NO:12); P7: 5' GATGCCACAAGATGATTTAGTG 3' (SEQ ID NO:13); and P8: 5' CTAATTGAGCTGTATCAGGATC 3' (SEQ ID NO:14).

Figure 18:
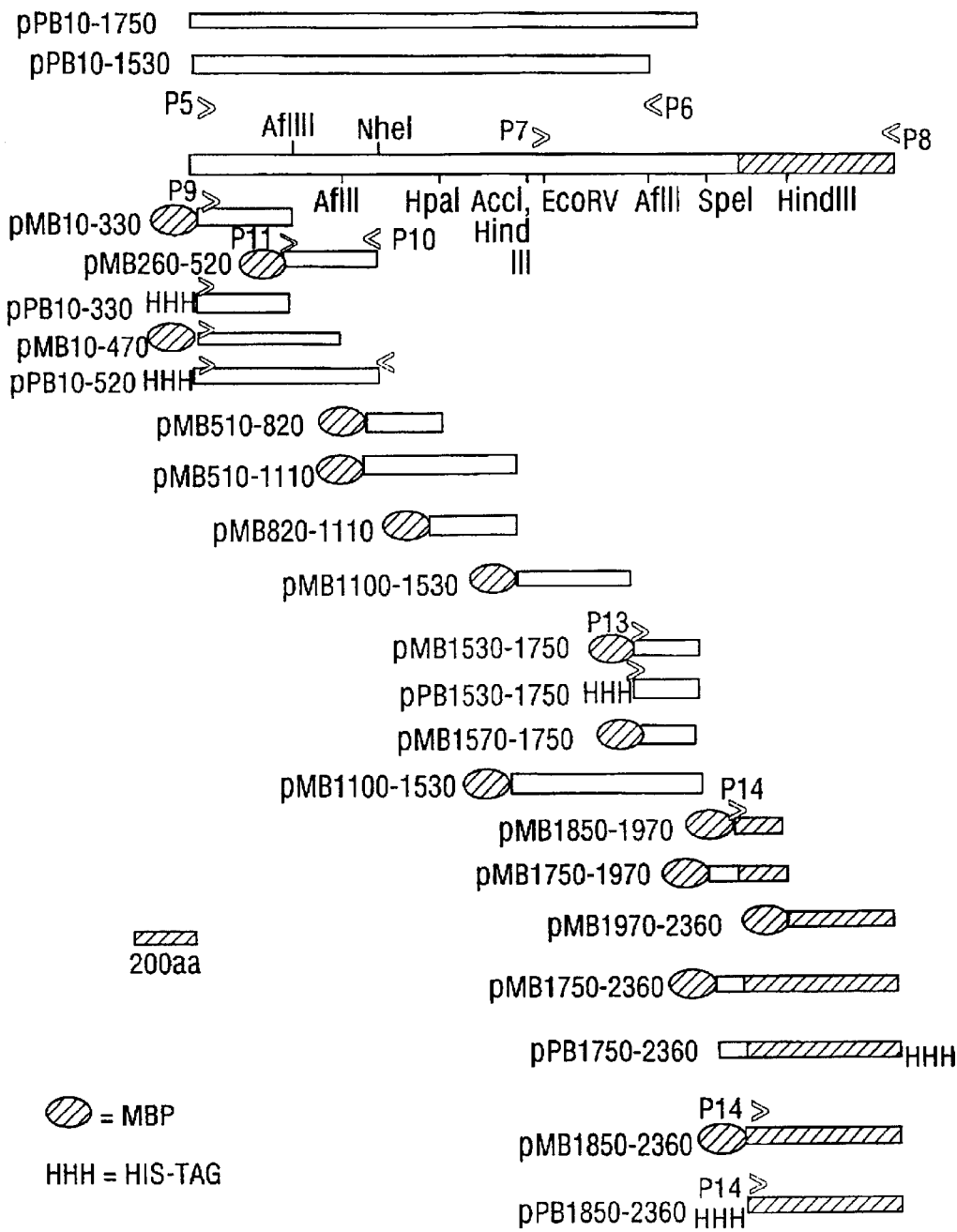
FIG. 18 shows *C. difficile* toxin B expression constructs.

FIG. 18 also shows the location of the following primers along the toxin B gene: P9 which consists of the sequence 5' CGGAATTCCTAGAAAAAATGGCAAATG 3' (SEQ ID NO:15); P10 which consists of the sequence 5' GCTCTAGAATGA CCATAAGCTAGCCA 3' (SEQ ID NO:16); P11 which consists of the sequence 5' CGGAATTCGAGTTGGTAGAAAGGTGGA 3' (SEQ ID NO:17); P13 which consists of the sequence 5' CGGAATTCGGTTATTATCTTAAGGATG 3' (SEQ ID NO:18); and P14 which consists of the sequence 5' CGGAATTCTTGATAACTGGAT TTGTGAC 3' (SEQ ID NO:19). The amino acid sequence consisting of amino acid residues 1852 through 2362 of toxin B is listed in SEQ ID NO:20. The amino acid sequence consisting of amino acid residues 1755 through 2362 of toxin B is listed in SEQ ID NO:21. The amino acid sequence consisting of amino acid residues 1754 through 2362 of toxin B is listed in SEQ ID NO:30.

*Clostridium difficile* VPI strain 10463 was obtained from the American Type Culture Collection (ATCC 43255) and grown under anaerobic conditions in brain-heart infusion medium (Becton Dickinson). High molecular-weight *C. difficile* DNA was isolated essentially as described [Wren and Tabaqchali (1987) J. Clin. Microbiol., 25:2402], except 1) 100 μg/ml proteinase K in 0.5% SDS was used to disrupt the bacteria and 2) cetytrimethylammonium bromide (CTAB) precipitation [as described by Ausubel et al., Eds., *Current Protocols in Molecular Biology*, Vol. 2 (1989) Current Protocols] was used to remove carbohydrates from the cleared lysate. Briefly, after disruption of the bacteria with proteinase K and SDS, the solution is adjusted to approximately 0.7 M NaCl by the addition of a ⅐ volume of 5M NaCl. A ⅒ volume of CTAB/NaCl (10% CTAB in 0.7 M NaCl) solution was added and the solution was mixed thoroughly and incubated 10 min at 65° C. An equal volume of chloroform/isoamyl alcohol (24:1) was added and the phases were thoroughly mixed. The organic and aqueous phases were separated by centrifugation in a microfuge for 5 min. The aqueous supernatant was removed and extracted with phenol/chloroform/isoamyl alcohol (25:24:1). The phases were separated by centrifugation in a microfuge for 5 min. The supernatant was transferred to a fresh tube and the DNA was precipitated with isopropanol. The DNA precipitate was pelleted by brief centrifugation in a microfuge. The DNA pellet was washed with 70% ethanol to remove residual CTAB. The DNA pellet was then dried and redissolved in TE buffer (10 mM Tris-HCl pH8.0, 1 mM EDTA). The integrity and yield of genomic DNA was assessed by comparison with a serial dilution of uncut lambda DNA after electrophoresis on an agarose gel.

Toxin B fragments were cloned by PCR utilizing a proofreading thermostable DNA polymerase [native Pfu polymerase (Stratagene)]. The high fidelity of this polymerase reduces the mutation problems associated with amplification by error prone polymerases (e.g., Taq polymerase). PCR amplification was performed using the PCR primer pairs P5 (SEQ ID NO:11) with P6 (SEQ ID NO:12) and P7 (SEQ ID NO:13) with P8 (SEQ ID NO:14) in 50 μl reactions containing 10 mM Tris-HCl pH8.3, 50 mM KCl, 1.5 mM MgCl$_2$, 200 μM of each dNTP, 0.2 μM each primer, and 50 ng *C. difficile* genomic DNA. Reactions were overlaid with 100 μl mineral oil, heated to 94° C. for 4 min, 0.5 μl native Pfu polymerase (Stratagene) was added, and the reactions were cycled 30 times at 94° C. for 1 min, 50° C. for 1 min, 72° C. (2 min for each kb sequence to be amplified), followed by 10 min at 72° C. Duplicate reactions were pooled, chloroform extracted, and ethanol precipitated. After washing in 70% ethanol, the pellets were resuspended in 50 μl TE buffer (10 mM Tris-HCl pH8.0, 1 mM EDTA).

The P5/P6 amplification product was cloned into pUC19 as outlined below. 10 μl aliquots of DNA were gel purified using the Prep-a-Gene kit (BioRad), and ligated to SmaI restricted pUC19 vector. Recombinant clones were isolated and confirmed by restriction digestion using standard recombinant molecular biology techniques (Sambrook et al., 1989). Inserts from two independent isolates were identified in which the toxin B insert was oriented such that the vector BamHI and SacI sites were 5' and 3' oriented, respectively (pUCB10-1530). The insert-containing BamHI/SacI fragment was cloned into similarly cut pET23a–c vector DNA, and protein expression was induced in small scale cultures (5 ml) of identified clones.

Total protein extracts were isolated, resolved on SDS-PAGE gels, and toxin B protein identified by Western analysis utilizing a goat anti-toxin B affinity purified antibody (Tech Lab). Procedures for protein induction, SDS-PAGE, and Western blot analysis were performed as described in Williams et al. (1994), supra. In brief, 5 ml cultures of bacteria grown in 2×YT containing 100 μg/ml ampicillin containing the appropriate recombinant clone were induced to express recombinant protein by addition of IPTG to 1 mM. The *E. coli* hosts used were: BL21(DE3) or BL21(DE3)LysS (Novagen) for pET plasmids.

Cultures were induced by the addition of IPTG to a final concentration of 1.0 mM when the cell density reached 0.5 $OD_{600}$, and induced protein was allowed to accumulate for two hrs after induction. Protein samples were prepared by pelleting 1 ml aliquots of bacteria by centrifugation (1 min in microfuge), and resuspension of the pelleted bacteria in 150 μl of 2×SDS-PAGE sample buffer (0.125 mM Tris-HCl pH 6.8, 2 mM EDTA, 6% SDS, 20% glycerol, 0.025% bromophenol blue; β-mercaptoethanol is added to 5% before use). The samples were heated to 95° C. for 5 min, then cooled and 5 or 10 μls loaded on 7.5% SDS-PAGE gels. High molecular weight protein markers (BioRad) were also loaded, to allow estimation of the MW of identified fusion proteins. After electrophoresis, protein was detected either generally by staining the gels with Coomassie Blue, or specifically, by blotting to nitrocellulose for Western blot detection of specific immunoreactive protein. The MW of induced toxin B reactive protein allowed the integrity of the toxin B reading frame to be determined.

Figure 21:
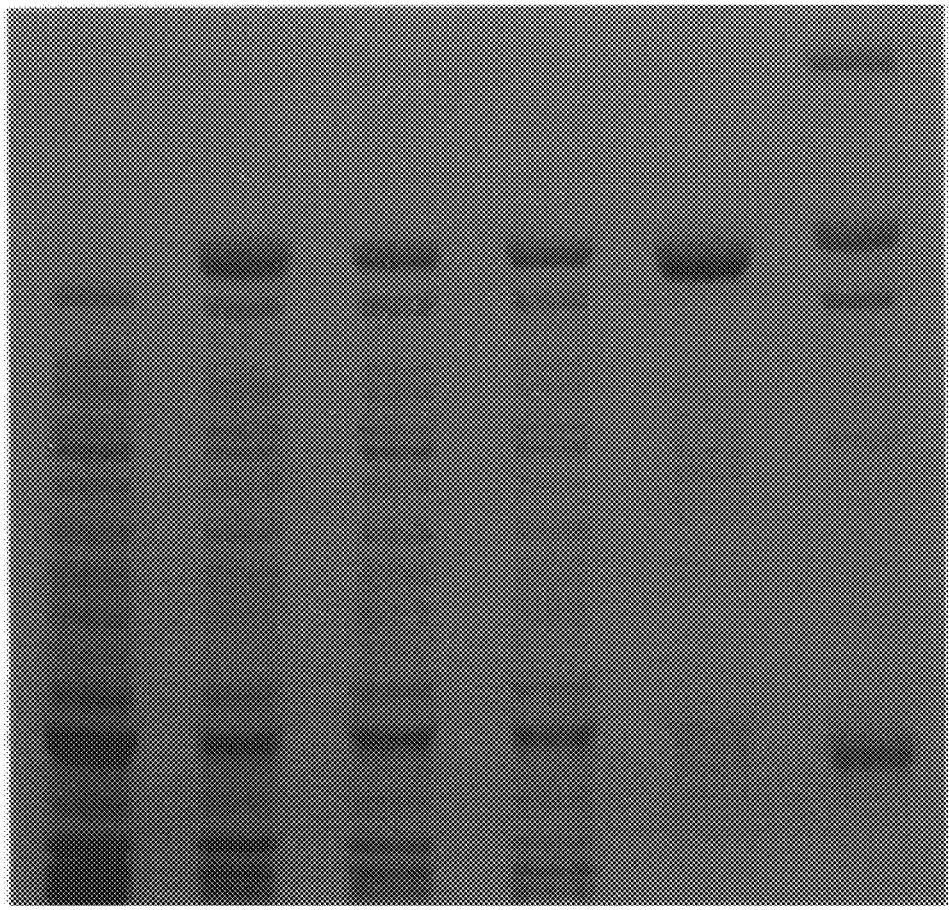
FIG. 21 is an SDS-PAGE gel showing the purification of recombinant *C. difficile* toxin B fusion protein.
Figure 22:
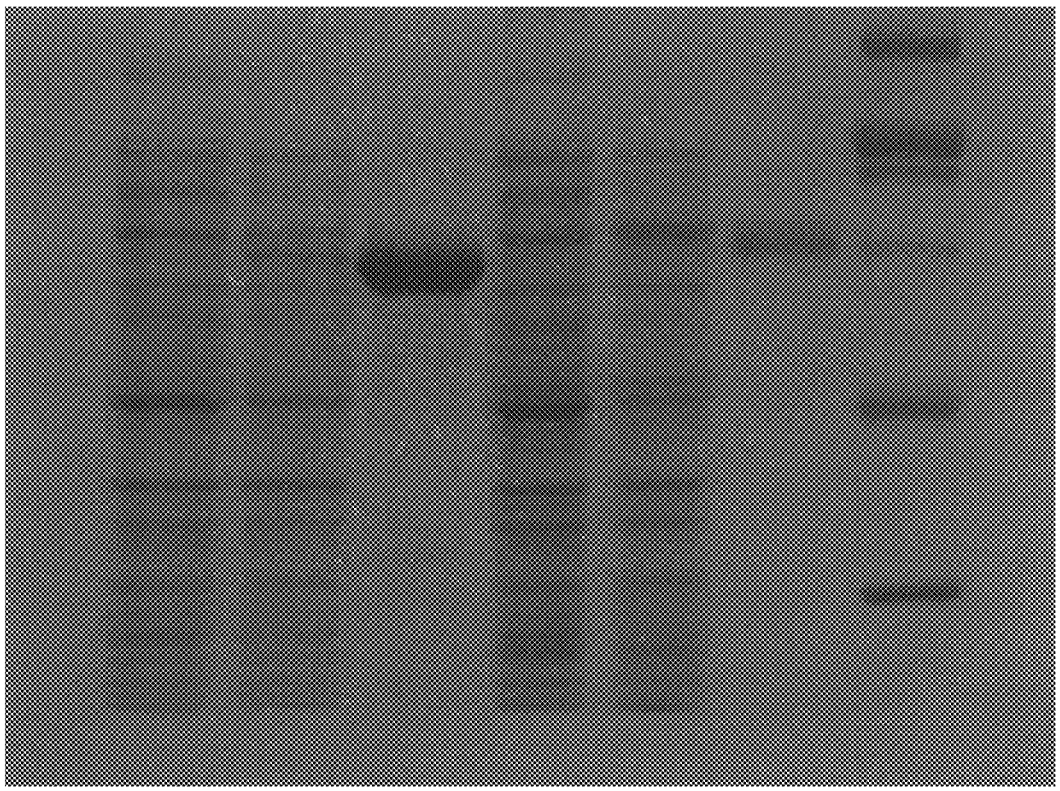
FIG. 22 is an SDS-PAGE gel showing the purification of two histidine-tagged recombinant *C. difficile* toxin B proteins.

The pET23b recombinant (pPB10-1530) expressed high MW recombinant toxin B reactive protein, consistent with predicted values. This confirmed that frame terminating errors had not occurred during PCR amplification. A pET23b expression clone containing the 10-1750aa interval of the toxin B gene was constructed, by fusion of the EcoRV-SpeI fragment of the P7/P8 amplification product to the P5-EcoRV interval of the P5/P6 amplification product (see FIG. 18) in pPB10-1530. The integrity of this clone (pPB10-1750) was confirmed by restriction mapping, and Western blot detection of expressed recombinant toxin B protein. Levels of induced protein from both pPB10-1530 and pPB10-1750 were too low to facilitate purification of usable amounts of recombinant toxin B protein. The remaining 1750-2360 aa interval was directly cloned into pMAL or pET expression vectors from the P7/P8 amplification product as described below.

b) Expression Of The Toxin B Gene i) Overview Of Expression Methodologies

Fragments of the toxin B gene were expressed as either native or fusion proteins in *E. coli*. Native proteins were expressed in either the pET23a–c or pET16b expression vectors (Novagen). The pET23 vectors contain an extensive polylinker sequence in all three reading frames (a–c vectors) followed by a C-terminal poly-histidine repeat. The pET16b vector contains a N-terminal poly-histidine sequence immediately 5' to a small polylinker. The poly-histidine sequence binds to Ni-Chelate columns and allows affinity purification of tagged target proteins [Williams et al. (1994), supra]. These affinity tags are small (10 aa for pET16b, 6 aa for pET23) allowing the expression and affinity purification of native proteins with only limited amounts of foreign sequences.

An N-terminal histidine-tagged derivative of pET16b containing an extensive cloning cassette was constructed to facilitate cloning of N-terminal poly-histidine tagged toxin B expressing constructs. This was accomplished by replacement of the promoter region of the pET23a and b vectors with that of the pET16b expression vector. Each vector was restricted with BglII and NdeI, and the reactions resolved on a 1.2% agarose gel. The pET16b promoter region (contained in a 200 bp BglII-NdeI fragment) and the promoter-less pET23 a or b vectors were cut from the gel, mixed and Prep-A-Gene (BioRad) purified. The eluted DNA was ligated, and transformants screened for promoter replacement by NcoI digestion of purified plasmid DNA (the pET16b promoter contains this site, the pET23 promoter does not). These clones (denoted pETHisa or b) contain the pET16b promoter (consisting of a pT7-lac promoter, ribosome binding site and poly-histidine (10 aa) sequence) fused at the NdeI site to the extensive pET23 polylinker.

All MBP fusion proteins were constructed and expressed in the pMAL™-c or pMAL™-p2 vectors (New England Biolabs) in which the protein of interest is expressed as a C-terminal fusion with MBP. All pET plasmids were expressed in either the BL21(DE3) or BL21(DE3)LysS expression hosts, while pMal plasmids were expressed in the BL21 host.

Large scale (500 mls to 1 liter) cultures of each recombinant were grown in 2×YT broth, induced, and soluble protein fractions were isolated as described [Williams, et al. (1994), supra]. The soluble protein extracts were affinity chromatographed to isolate recombinant fusion protein, as described [Williams et al., (1994) supra]. In brief, extracts containing tagged pET fusions were chromatographed on a nickel chelate column, and eluted using imidazole salts or low pH (pH 4.0) as described by the distributor (Novagen or Qiagen). Extracts containing soluble pMAL fusion protein were prepared and chromatographed in PBS buffer over an amylose resin (New England Biolabs) column, and eluted with PBS containing 10 mM maltose as described [Williams et al. (1994), supra].

ii) Overview Of Toxin B Expression

In both large expression constructs described in (a) above, only low level (i.e., less than 1 mg/liter of intact or nondegraded recombinant protein) expression of recombinant protein was detected. A number of expression constructs containing smaller fragments of the toxin B gene were then constructed, to determine if small regions of the gene can be expressed to high levels (i.e., greater than 1 mg/liter intact protein) without extensive protein degradation. All were constructed by in frame fusions of convenient toxin B restriction fragments to either the pMAL-c, pET23a–c, pET16b or pETHisa-b expression vectors, or by engineering restriction sites at specific locations using PCR amplification [using the same conditions described in (a) above]. In all cases, clones were verified by restriction mapping, and, where indicated, DNA sequencing.

Protein preparations from induced cultures of each of these constructs were analyzed, by SDS-PAGE, to estimate protein stability (Coomassie Blue staining) and immunoreactivity against anti-toxin B specific antiserum (Western analysis). Higher levels of intact (i.e., nondegraded), full length fusion proteins were observed with the smaller constructs as compared with the larger recombinants, and a series of expression constructs spanning the entire toxin B gene were constructed (FIGS. 18, 19 and 20 and Table 23).

Constructs that expressed significant levels of recombinant toxin B protein (greater than 1 mg/liter intact recombinant protein) in *E. coli* were identified and a series of these clones that spans the toxin B gene are shown in FIG. 19 and summarized in Table 23. These clones were utilized to isolate pure toxin B recombinant protein from the entire toxin B gene. Significant protein yields were obtained from pMAL expression constructs spanning the entire toxin B gene, and yields of full length soluble fusion protein ranged from an estimated 1 mg/liter culture (pMB1100-1530) to greater than 20 mg/liter culture (pMB1750-2360).

Representative purifications of MBP and poly-histidine-tagged toxin B recombinants are shown in FIGS. 21 and 22.

FIG. 21 shows a Coomassie Blue stained 7.5% SDS-PAGE gel on which various protein samples extracted from bacteria harboring pMB1850-2360 were electrophoresed. Samples were loaded as follows: Lane 1: protein extracted from uninduced culture; Lane 2: induced culture protein; Lane 3: total protein from induced culture after sonication; Lane 4: soluble protein; and Lane 5: eluted affinity purified protein. FIG. 22 depicts the purification of recombinant proteins expressed in bacteria harboring either pPB1850-2360 (Lanes 1–3) or pPB1750-2360 (Lanes 4–6). Samples were loaded as follows: uninduced total protein (Lanes 1 and 4); induced total protein (Lanes 2 and 5); and eluted affinity purified protein (Lanes 3 and 6). The broad range molecular weight protein markers (BioRad) are shown in Lane 7.

Thus, although high level expression was not attained using large expression constructs from the toxin B gene, usable levels of recombinant protein were obtained by isolating induced protein from a series of smaller pMAL expression constructs that span the entire toxin B gene.

These results represent the first demonstration of the feasibility of expressing recombinant toxin B protein to high levels in *E. coli*. As well, expression of small regions of the putative ligand binding domain (repeat region) of toxin B as native protein yielded insoluble protein, while large constructs, or fusions to MBP were soluble (FIG. 19), demonstrating that specific methodologies are necessary to produce soluble fusion protein from this interval.

iii) Clone Construction And Expression Details

A portion of the toxin B gene containing the toxin B repeat region [amino acid residues 1852–2362 of toxin B (SEQ ID NO:20)] was isolated by PCR amplification of this interval of the toxin B gene from *C. difficile* genomic DNA. The sequence, and location within the toxin B gene, of the two PCR primers [P7 (SEQ ID NO:13) and P8 (SEQ ID NO:14)] used to amplify this region are shown in FIG. 18.

DNA from the PCR amplification was purified by chloroform extraction and ethanol precipitation as described above. The DNA was restricted with SpeI, and the cleaved DNA was resolved by agarose gel electrophoresis. The restriction digestion with SpeI cleaved the 3.6 kb amplification product into a 1.8 kb doublet band. This doublet band was cut from the gel and mixed with appropriately cut, gel purified pMALc or pET23b vector. These vectors were prepared by digestion with HindIII, filling in the overhanging ends using the Klenow enzyme, and cleaving with XbaI (pMALc) or NheI (pET23b). The gel purified DNA fragments were purified using the Prep-A-Gene kit (BioRad) and the DNA was ligated, transformed and putative recombinant clones analyzed by restriction mapping.

pET and pMal clones containing the toxin B repeat insert (aa interval 1750-2360 of toxin B) were verified by restriction mapping, using enzymes that cleaved specific sites within the toxin B region. In both cases fusion of the toxin B SpeI site with either the compatible XbaI site (pMal) or compatible NheI site (pET) is predicted to create an in frame fusion. This was confirmed in the case of the pMB1750-2360 clone by DNA sequencing of the clone junction and 5' end of the toxin B insert using a MBP specific primer (New England Biolabs). In the case of the pET construct, the fusion of the blunt ended toxin B 3' end to the filled HindIII site should create an in-frame fusion with the C-terminal poly-histidine sequence in this vector. The pPB1750-2360 clone selected had lost, as predicted, the HindIII site at this clone junction; this eliminated the possibility that an additional adenosine residue was added to the 3' end of the PCR product by a terminal transferase activity of the Pfu polymerase, since fusion of this adenosine residue to the filled HindIII site would regenerate the restriction site (and was observed in several clones).

One liter cultures of each expression construct were grown, and fusion protein purified by affinity chromatography on either an amylose resin column (pMAL constructs; resin supplied by New England Biolabs) or Ni-chelate column (pET constructs; resin supplied by Qiagen or Novagen) as described [Williams et al. (1994), supra]. The integrity and purity of the fusion proteins were determined by Coomassie staining of SDS-PAGE protein gels as well as Western blot analysis with either an affinity purified goat polyclonal antiserum (Tech Lab), or a chicken polyclonal PEG prep, raised against the toxin B protein (CTB) as described above in Example 8. In both cases, affinity purification resulted in yields in excess of 20 mg protein per liter culture, of which greater than 90% was estimated to be full-length recombinant protein. It should be noted that the poly-histidine affinity tagged protein was released from the Qiagen Ni-NTA resin at low imidazole concentration (60 mM), necessitating the use of a 40 mM imidazole rather than a 60 mM imidazole wash step during purification.

A periplasmically secreted version of pMB1750-2360 was constructed by replacement of the promoter and MBP coding region of this construct with that from a related vector (pMAL™-p2; New England Biolabs) in which a signal sequence is present at the N-terminus of the MBP, such that fusion protein is exported. This was accomplished by substituting a BglII-EcoRV promoter fragment from pMAL-p2 into pMB1750-2360. The yields of secreted, affinity purified protein (recovered from osmotic shock extracts as described by Riggs in *Current Protocols in Molecular Biology*, Vol. 2, Ausubel, et al., Eds. (1989), Current Protocols, pp. 16.6.1–16.6.14] from this vector (pMBp1750-2360) were 6.5 mg/liter culture, of which 50% was estimated to be full-length fusion protein.

The interval was also expressed in two non-overlapping fragments. pMB1750-1970 was constructed by introduction of a frameshift into pMB1750-2360, by restriction with HindIII, filling in the overhanging ends and religation of the plasmid. Recombinant clones were selected by loss of the HindIII site, and further restriction map analysis. Recombinant protein expression from this vector was more than 20 mg/liter of greater than 90% pure protein.

The complementary region was expressed in pMB1970-2360. This construct was created by removal of the 1750-1970 interval of pMB1750-2360. This was accomplished by restriction of this plasmid with EcoRI (in the pMalc polylinker 5' to the insert) and III, filling in the overhanging ends, and religation of the plasmid. The resultant plasmid, pMB1970-2360, was made using both intracellularly and secreted versions of the pMB1750-2360 vector.

No fusion protein was secreted in the pMB1970-2360 version, perhaps due to a conformational constraint that prevents export of the fusion protein. However, the intracellularly expressed vector produced greater than 40 mg/liter of greater than 90% full-length fusion protein.

Constructs to precisely express the toxin B repeats in either pMalc (pMB1850-2360) or pET16b (pPB1850-2360) were constructed as follows. The DNA interval including the toxin B repeats was PCR amplified as described above utilizing PCR primers P14 (SEQ ID NO:19) and P8 (SEQ ID NO:14). Primer P14 adds a EcoRI site immediately flanking the start of the toxin B repeats.

The amplified fragment was cloned into the pT7 Blue T-vector (Novagen) and recombinant clones in which single copies of the PCR fragment were inserted in either orientation were selected (pT71850-2360) and confirmed by restriction mapping. The insert was excised from two appropriately oriented independently isolated pT71850-2360 plasmids, with EcoRI (5' end of repeats) and PstI (in the flanking polylinker of the vector), and cloned into EcoRI/PstI cleaved pMalc vector. The resulting construct (pMB1850-2360) was confirmed by restriction analysis, and yielded 20 mg/l of soluble fusion protein [greater than 90% intact (i.e., nondegraded)] after affinity chromatography. Restriction of this plasmid with HindIII and religation of the vector resulted in the removal of the 1970-2360 interval. The resultant construct (pMB1850-1970) expressed greater than 70 mg/liter of 90% full length fusion protein.

The pPB1850-2360 construct was made by cloning a EcoRI (filled with Klenow)-BamHI fragment from a pT71850-2360 vector (opposite orientation to that used in the pMB1850-2360 construction) into NdeI (filled)/BamHI cleaved pET16b vector. Yields of affinity purified soluble fusion protein were 15 mg/liter, of greater than 90% full length fusion protein.

Figure 19:
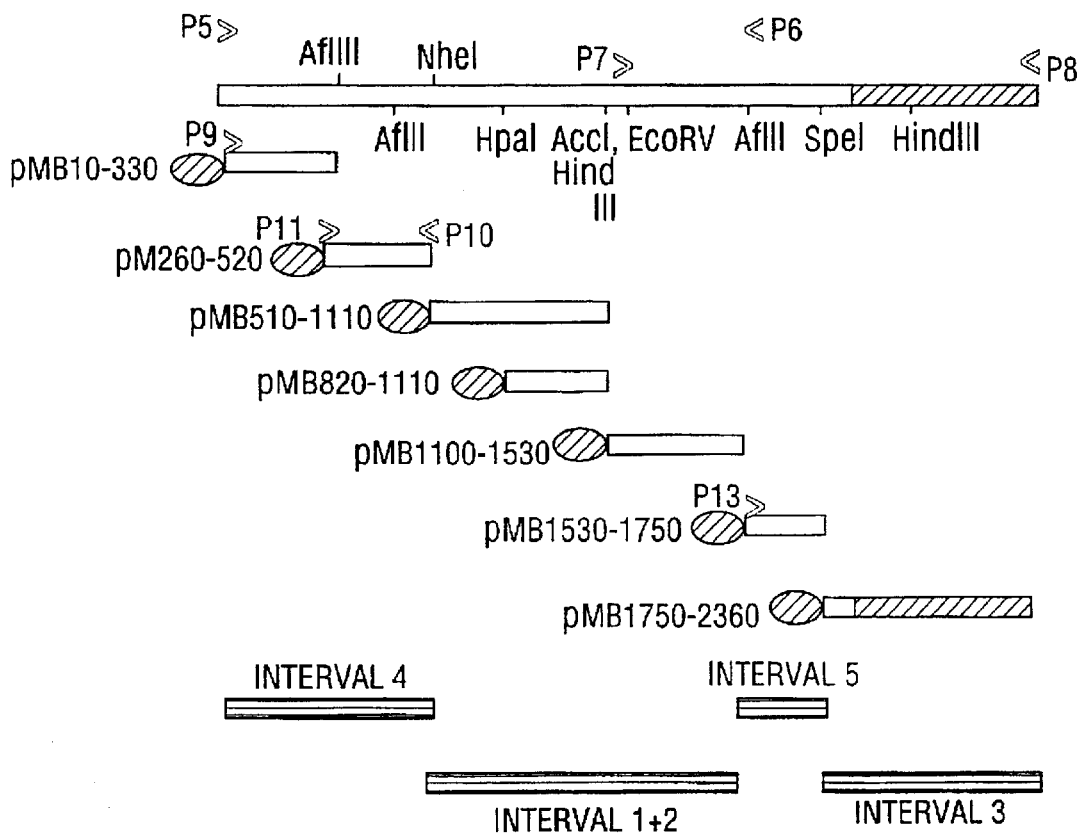
FIG. 19 shows *C. difficile* toxin B expression constructs.
Figure 20:
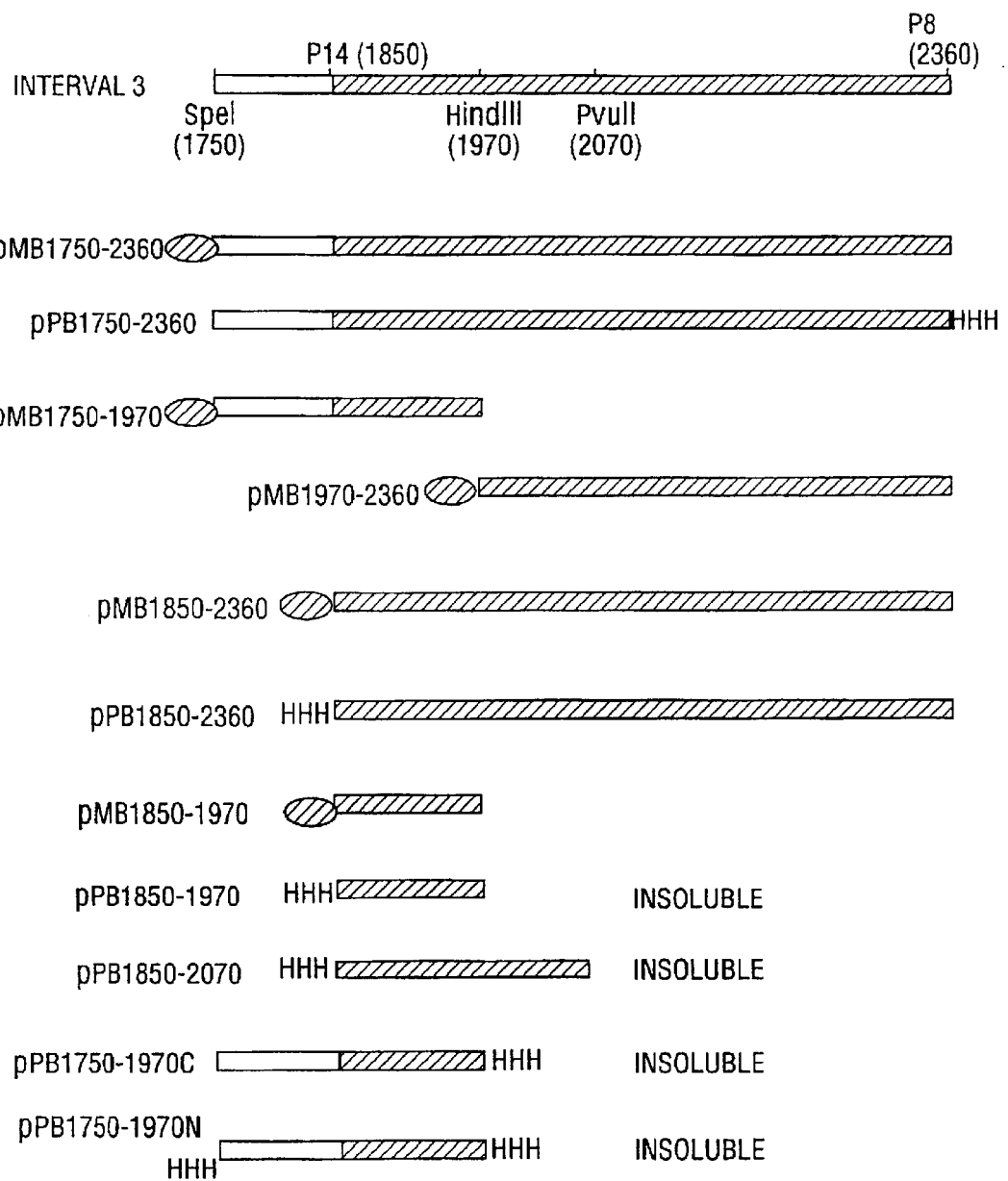
FIG. 20 shows *C. difficile* toxin B expression constructs.

Several smaller expression constructs from the 1750-2070 interval were also constructed in His-tagged pET vectors, but expression of these plasmids in the BL21 (DE3) host resulted in the production of high levels of mostly insoluble protein (see Table 23 and FIG. 19). These constructs were made as follows.

pPB1850-1970 was constructed by cloning a BglII-HindIII fragment of pPB1850-2360 into BglII/HindIII cleaved pET23b vector. pPB1850-2070 was constructed by cloning a BglII-PvuII fragment of pPB1850-2360 into BglII/HincII cleaved pET23b vector. pPB1750-1970(c) was constructed by removal of the internal HindIII fragment of a pPB1750-2360 vector in which the vector HindIII site was regenerated during cloning (presumably by the addition of an A residue to the amplified PCR product by terminal transferase activity of Pfu polymerase). The pPB1750-1970 (n) construct was made by insertion of the insert containing the NdeI-HindIII fragment of pPB1750-2360 into identically cleaved pETHisb vector. All constructs were confirmed by restriction digestion.

An expression construct that directs expression of the 10-470 aa interval of toxin B was constructed in the pMalc vector as follows. A NheI (a site 5' to the insert in the pET23 vector)-AflII (filled) fragment of the toxin B gene from pPB-10-1530 was cloned into XbaI (compatible with NheI)/HindIII (filled) pMalc vector. The integrity of the construct (pMB10-470) was verified by restriction mapping and DNA sequencing of the 5' clone junction using a MBP specific DNA primer (New England Biolabs). However, all expressed protein was degraded to the MBP monomer MW.

A second construct spanning this interval (aa 10-470) was constructed by cloning the PCR amplification product from a reaction containing the P9 (SEQ ID NO:15) and P10 (SEQ ID NO:16) primers (FIG. 18) into the pETHisa vector. This was accomplished by cloning the PCR product as an EcoRI-blunt fragment into EcoRI-HincII restricted vector DNA; recombinant clones were verified by restriction mapping. Although this construct (pPB10-520) allowed expression and purification (utilizing the N-terminal polyhistidine affinity tag) of intact fusion protein, yields were estimated at less than 500 $\mu$g per liter culture.

Higher yield of recombinant protein from this interval (aa 10-520) were obtained by expression of the interval in two overlapping clones. The 10-330aa interval was cloned in both pETHisa and pMalc vectors, using the BamHI-AflIII (filled) DNA fragment from pPB10-520. This fragment was cloned into BamHI-HindIII (filled) restricted pMalc or BamHI-HincII restricted pETHisa vector. Recombinant clones were verified by restriction mapping. High level expression of either insoluble (pET) or soluble (pMal) fusion protein was obtained. Total yields of fusion protein from the pMB10-330 construct (FIG. 18) were 20 mg/liter culture, of which 10% was estimated to be full-length fusion protein. Although yields of this interval were higher and >90% full-length recombinant protein produced when expressed from the pET construct, the pMal fusion was utilized since the expressed protein was soluble and thus more likely to have the native conformation.

The pMB260-520 clone was constructed by cloning EcoRI-XbaI cleaved amplified DNA from a PCR reaction containing the P11 (SEQ ID NO:17) and P10 (SEQ ID NO:16) DNA primers (FIG. 18) into similarly restricted pMalc vector. Yields of affinity purified protein were 10 mg/liter, of which approximately 50% was estimated to be full-length recombinant protein.

The aa510-1110 interval was expressed as described below. This entire interval was expressed as a pMal fusion by cloning the NheI-HindIII fragment of pUCB10-1530 into XbaI-HindIII cleaved pMalc vector. The integrity of the construct (pMB510-1110) was verified by restriction mapping and DNA sequencing of the 5' clone junction using a MBP specific DNA primer. The yield of affinity purified protein was 25 mg/liter culture, of which 5% was estimated to be full-length fusion protein (1 mg/liter).

To attempt to obtain higher yields, this region was expressed in two fragments (aa510-820, and 820-1110) in the pMalc vector. The pMB510-820 clone was constructed by insertion of a SacI (in the pMalc polylinker 5' to the insert)-HpaI DNA fragment from pMB510-1110 into SacI/StuI restricted pMalc vector. The pMB820-1110 vector was constructed by insertion of the HpaI-HindIII fragment of pUCB10-1530 into BamHI (filled)/HindIII cleaved pMalc vector. The integrity of these constructs were verified by restriction mapping and DNA sequencing of the 5' clone junction using a MBP specific DNA primer.

Recombinant protein expressed from the pMB510-820 vector was highly unstable. However, high levels (20 mg/liter) of >90% full-length fusion protein were obtained from the pMB820-1105 construct. The combination of partially degraded pMB510-1110 protein (enriched for the 510-820 interval) with the pMB820-1110 protein provides usable amounts of recombinant antigen from this interval.

The aa1100-1750 interval was expressed as described below. The entire interval was expressed in the pMalc vector from a construct in which the AccI(filled)-SpeI fragment of pPB10-1750 was inserted into StuI/XbaI (XbaI is compatible with SpeI; StuI and filled AccI sites are both blunt ended) restricted pMalc. The integrity of this construct (pMB1100-1750) was verified by restriction mapping and DNA sequencing of the clone junction using a MBP specific DNA primer. Although 15 mg/liter of affinity purified protein was isolated from cells harboring this construct, the protein was greater than 99% degraded to MBP monomer size.

A smaller derivative of pMB1100-1750 was constructed by restriction of pMB1100-1750 with AflII and SalI (in the pMalc polylinker 3' to the insert), filling in the overhanging ends, and religating the plasmid. The resultant clone (verified by restriction digestion and DNA sequencing) has deleted the aa1530-1750 interval, was designated pMB1100-1530. pMB1100-1530 expressed recombinant protein at a yield of greater than 40 mg/liter, of which 5% was estimated to be full-length fusion protein.

Three constructs were made to express the remaining interval. Initially, a BspHI (filled)-SpeI fragment from pPB10-1750 was cloned into EcoRI(filled)/XbaI cleaved pmalc vector. The integrity of this construct (pMB1570-1750) was verified by restriction mapping and DNA sequencing of the 5' clone junction using a MBP specific DNA primer. Expression of recombinant protein from this plasmid was very low, approximately 3 mg affinity purified protein per liter, and most was degraded to MBP monomer size. This region was subsequently expressed from a PCR amplified DNA fragment. A PCR reaction utilizing primers P13 [SEQ ID NO:18; P13 was engineered to introduce an EcoRI site 5' to amplified toxin B sequences] and P8 (SEQ ID NO:14) was performed on C. difficile genomic DNA as described above. The amplified fragment was cleaved with EcoRI and SpeI, and cloned into EcoRI/XbaI cleaved pMalc vector. The resultant clone (pMB1530-1750) was verified by restriction map analysis, and recombinant protein was expressed and purified. The yield was greater than 20 mg protein per liter culture and it was estimated that 25% was full-length fusion protein; this was a significantly higher yield than the original pMB1570-1750 clone. The insert of pMB1530-1750 (in a EcoRI-SalI fragment) was transferred to the pETHisa vector (EcoRI/XhoI cleaved, XhoI and SalI ends are compatible). No detectable fusion protein was purified on Ni-Chelate columns from soluble lysates of cells induced to express fuision protein from this construct.

animals would first be immunized with recombinant proteins and anti-recombinant antibodies are generated. These anti-recombinant protein antibodies are then tested for neutralizing ability in vivo or in vitro. Depending on the immunogenic nature of the recombinant polypeptide, the generation of high-titer antibodies against that protein may take several months. To accelerate this process and identify which recombinant polypeptide(s) may be the best candidate to generate neutralizing antibodies, depletion studies were performed. Specifically, recombinant toxin B polypeptide were pre-screened by testing whether they have the ability to bind to protective antibodies from a CTB antibody preparation and hence deplete those antibodies of their neutralizing capacity. Those recombinant polypeptides found to bind CTB, were then utilized to generate neutralizing antibodies. This Example involved: a) identification of recombinant sub-regions within toxin B to which neutralizing antibodies bind; b) identification of toxin B sub-region specific antibodies that neutralize toxin B in vivo; and c) generation and evaluation of antibodies reactive to recombinant toxin B polypeptides.

a) Identification Of Recombinant Sub-Regions Within Toxin B To Which Neutralizing Antibodies Bind Sub-regions within toxin B to which neutralizing antibodies bind were identified by utilizing recombinant toxin B

TABLE 23

Summary Of Toxin B Expression Constructs[a]

| Clone | Affinity Tag | Yield (mg/liter) | % Full Length |
|---|---|---|---|
| pPB10-1750 | none | low (estimated from Western blot hyb.) | ? |
| pPB10-1530 | none | low (as above) | ? |
| pMB10-470 | MBP | 15 mg/l | 0% |
| pPB10-520 | poly-his | 0.5 mg/l | 20% |
| pPB10-330 | poly-his | >20 mg/l (insoluble) | 90% |
| *pMB10-330* | MBP | 20 mg/l | 10% |
| *pMB260-520* | MBP | 10 mg/l | 50% |
| *pMB510-1110* | MBP | 25 mg/l | 5% |
| pMB510-820 | MBP | degraded (by Western blot hyb) | |
| *pMB820-1110* | MBP | 20 mg/l | 90% |
| pMB1100-1750 | MBP | 15 mg/l | 0% |
| *pMB1100-1530* | MBP | 40 mg/l | 5% |
| pMB1570-1750 | MBP | 3 mg/l | <5% |
| pPB1530-1750 | poly-his | no purified protein detected | ? |
| *pMB1530-1750* | MBP | 20 mg/l | 25% |
| *pMB1750-2360* | MBP | >20 mg/l | >90% |
| pMB1750-2360 | MBP | 6.5 mg/l (secreted) | 50% |
| pPBp1750-2360 | poly-his | >20 mg/l | >90% |
| pMB1750-1970 | MBP | >20 mg/l | >90% |
| pMB1970-2360 | MBP | 40 mg/l | >90% |
| pMBp1970-2360 | MBP | (no secretion) | NA |
| pMB1850-2360 | MBP | 20 mg/l | >90% |
| pPB1850-2360 | poly-his | 15 mg/l | >90% |
| pMB1850-1970 | MBP | 70 mg/l | >90% |
| pPB1850-1970 | poly-his | >10 mg/l (insoluble) | >90% |
| pPB1850-2070 | poly-his | >10 mg/l (insoluble) | >90% |
| pPB1750-1970(c) | poly-his | >10 mg/l (insoluble) | >90% |
| pPB1750-1970(n) | poly-his | >10 mg/l (insoluble) | >90% |

[a]Clones in italics are clones currently utilized to purify recombinant protein from each selected interval.

EXAMPLE 19

Identification, Purification And Induction Of Neutralizing Antibodies Against Recombinant C. difficile Toxin B Protein To determine whether recombinant toxin B polypeptide fragments can generate neutralizing antibodies, typically proteins to deplete protective antibodies from a polyclonal pool of antibodies against native C. difficile toxin B. An in vivo assay was developed to evaluate protein preparations for the ability to bind neutralizing antibodies. Recombinant proteins were first pre-mixed with antibodies directed against native toxin B (CTB antibody; see Example 8) and allowed to react for one hour at 37° C. Subsequently, C.

*difficile* toxin B (CTB; Tech Lab) was added at a concentration lethal to hamsters and incubated for another hour at 37° C. After incubation this mixture was injected intraperitoneally (IP) into hamsters. If the recombinant polypeptide contains neutralizing epitopes, the CTB antibodies will lose its ability to protect the hamsters against death from CTB. If partial or complete protection occurs with the CTB antibody-recombinant mixture, that recombinant contains only weak or non-neutralizing epitopes of toxin B. This assay was performed as follows.

Antibodies against CTB were generated in egg laying Leghorn hens as described in Example 8. The lethal dosage ($LD_{100}$) of *C. difficile* toxin B when delivered I.P. into 40 g female Golden Syrian hamsters (Charles River) was determined to be 2.5 to 5 μg. Antibodies generated against CTB and purified by PEG precipitation could completely protect the hamsters at the I.P. dosage determined above. The minimal amount of CTB antibody needed to afford good protection against 5 μg of CTB when injected I.P. into hamsters was also determined (1×PEG prep). These experiments defined the parameters needed to test whether a given recombinant protein could deplete protective CTB antibodies.

The cloned regions tested for neutralizing ability cover the entire toxin B gene and were designated as Intervals (INT) 1 through 5 (see FIG. 19). Approximately equivalent final concentrations of each recombinant polypeptide were tested. The following recombinant polypeptides were used: 1) a mixture of intervals 1 and 2 (INT-1, 2); 2) a mixture of Intervals 4 and 5 (INT-4, 5) and 3) Interval 3 (INT-3). Recombinant proteins (each at about 1 mg total protein) were first preincubated with a final CTB antibody concentration of 1× [i.e., pellet dissolved in original yolk volume as described in Example 1(c)] in a final volume of 5 mls for 1 hour at 37° C. Twenty-five μg of CTB (at a concentration of 5 μg/ml), enough CTB to kill 5 hamsters, was then added and the mixture was then incubated for 1 hour at 37° C. Five, 40 g female hamsters (Charles River) in each treatment group were then each given 1 ml of the mixture I.P. using a tuberculin syringe with a 27 gauge needle. The results of this experiment are shown in Table 24.

TABLE 24

Binding Of Neutralizing Antibodies By INT 3 Proteins

| Treatment Group[1] | Number Of Animals Alive | Number Of Animals Dead |
|---|---|---|
| CTB antibodies | 3 | 2 |
| CTB antibodies + INT 1, 2 | 3 | 2 |
| CTB antibodies + INT 4, 5 | 3 | 2 |
| CTB antibodies + INT 3 | 0 | 5 |

[1]*C. difficile* toxin B (CTB) was added to each group.

As shown in Table 24, the addition of recombinant proteins from INT-1, 2 or INT-4, 5 had no effect on the in vivo protective ability of the CTB antibody preparation compared to the CTB antibody preparation alone. In contrast, INT-3 recombinant polypeptide was able to remove all of the toxin B neutralizing ability of the CTB antibodies as demonstrated by the death of all the hamsters in that group.

The above experiment was repeated, using two smaller expressed fragments (pMB 1750-1970 and pMB 1970-2360, see FIG. 19) comprising the INT-3 domain to determine if that domain could be further subdivided into smaller neutralizing epitopes. In addition, full-length INT-3 polypeptide expressed as a nickel tagged protein (pPB1750-2360) was tested for neutralizing ability and compared to the original INT-3 expressed MBP fusion (pMB1750-2360). The results are shown in Table 25.

TABLE 25

Removal Of Neutralizing Antibodies By Repeat Containing Proteins

| Treatment Group[1] | Number Of Animals Alive | Number Of Animals Dead |
|---|---|---|
| CTB antibodies | 5 | 0 |
| CTB antibodies + pPB1750-2360 | 0 | 5 |
| CTB antibodies + pMB1750-2360 | 0 | 5 |
| CTB antibodies + pMB1970-2360 | 3 | 2 |
| CTB antibodies + pMB1750-1970 | 2 | 3 |

[1]*C. difficile* toxin B (CTB) was added to each group.

The results summarized in Table 25 indicate that the smaller polypeptide fragments within the INT-3 domain, pMB1750-1970 and pMB1970-2360, partially lose the ability to bind to and remove neutralizing antibodies from the CTB antibody pool. These results demonstrate that the full length INT-3 polypeptide is required to completely deplete the CTB antibody pool of neutralizing antibodies. This experiment also shows that the neutralization epitope of INT-3 can be expressed in alternative vector systems and the results are independent of the vector utilized or the accompanying fusion partner.

Other Interval 3 specific proteins were subsequently tested for the ability to remove neutralizing antibodies within the CTB antibody pool as described above. The Interval 3 specific proteins used in these studies are summarized in FIG. 23. In FIG. 23 the following abbreviations are used: pP refers to the pET23 vector; pM refers to the pMALc vector; B refers to toxin B; the numbers refer to the amino acid interval expressed in the clone. The solid black ovals represent the MBP; and HHH represents the polyhistidine tag.

Only recombinant proteins comprising the entire toxin B repeat domain (pMB1750-2360, pPB1750-2360 and pPB1850-2360) can bind and completely remove neutralizing antibodies from the CTB antibody pool. Recombinant proteins comprising only a portion of the toxin B repeat domain were not capable of completely removing neutralizing antibodies from the CTB antibody pool (pMB1750-1970 and pMB1970-2360 could partially remove neutralizing antibodies while pMB1850-1970 and pPB1850-2070 failed to remove any neutralizing antibodies from the CTB antibody pool).

The above results demonstrate that only the complete ligand binding domain (repeat region) of the toxin B gene can bind and completely remove neutralizing antibodies from the CTB antibody pool. These results demonstrate that antibodies directed against the entire toxin B repeat region are necessary for in vivo toxin neutralization (see FIG. 23; only the recombinant proteins expressed by the pMB1750-2360, pPB1750-2360 and pPB1850-2360 vectors are capable of completely removing the neutralizing antibodies from the CTB antibody pool).

These results represent the first indication that the entire repeat region of toxin B would be necessary for the generation of antibodies capable of neutralizing toxin B, and that sub-regions may not be sufficient to generate maximal titers of neutralizing antibodies.

b) Identification Of Toxin B Sub-Region Specific Antibodies That Neutralize Toxin B In Vivo To determine if antibodies directed against the toxin B repeat region are sufficient for neutralization, region specific antibodies within the CTB antibody preparation were affinity purified, and tested for in vivo neutralization. Affinity columns containing recombinant toxin B repeat proteins were made as described below. A separate affinity column was prepared using each of the following recombinant toxin B repeat proteins: pPB1750-2360, pPB1850-2360, pMB1750-1970 and pMB1970-2360.

For each affinity column to be made, four ml of PBS-washed Actigel resin (Sterogene) was coupled overnight at room temperature with 5–10 mg of affinity purified recombinant protein (first extensively dialyzed into PBS) in 15 ml tubes (Falcon) containing a 1/10 final volume Ald-coupling solution (1 M sodium cyanoborohydride). Aliquots of the supernatants from the coupling reactions, before and after coupling, were assessed by Coomassie staining of 7.5% SDS-PAGE gels. Based on protein band intensities, in all cases greater than 30% coupling efficiencies were estimated. The resins were poured into 10 ml columns (BioRad), washed extensively with PBS, pre-eluted with 4 M guanidine-HCl (in 10 mM Tris-HCl, pH 8.0) and reequilibrated in PBS. The columns were stored at 4° C.

Aliquots of a CTB IgY polyclonal antibody preparation (PEG prep) were =affinity purified on each of the four columns as described below. The columns were hooked to a UV monitor (ISCO), washed with PBS and 40 ml aliquots of a 2×PEG prep (filter sterilized using a 0.45μ filter) were applied. The columns were washed with PBS until the baseline value was re-established. The columns were then washed with BBStween to elute nonspecifically binding antibodies, and reequilibrated with PBS. Bound antibody was eluted from the column in 4M guanidine-HCl (in 10 mM Tris-HCl, pH8.0). The eluted antibody was immediately dialyzed against a 100-fold excess of PBS at 4° C. for 2 hrs. The samples were then dialyzed extensively against at least 2 changes of PBS, and affinity purified antibody was collected and stored at 4° C. The antibody preparations were quantified by UV absorbance. The elution volumes were in the range of 4–8 ml. All affinity purified stocks contained similar total antibody concentrations, ranging from 0.25–0.35% of the total protein applied to the columns.

The ability of the affinity purified antibody preparations to neutralize toxin B in vivo was determined using the assay outlined in a) above. Affinity purified antibody was diluted 1:1 in PBS before testing. The results are shown in Table 26.

In all cases similar levels of toxin neutralization was observed, such that lethality was delayed in all groups relative to preimmune controls. This result demonstrates that antibodies reactive to the repeat region of the toxin B gene are sufficient to neutralize toxin B in vivo. The hamsters will eventually die in all groups, but this death is maximally delayed with the CTB PEG prep antibodies. Thus neutralization with the affinity purified (AP) antibodies is not as complete as that observed with the CTB prep before affinity chromatography. This result may be due to loss of activity during guanidine denaturation (during the elution of the antibodies from the affinity column) or the presence of antibodies specific to other regions of the toxin B gene that can contribute to toxin neutralization (present in the CTB PEG prep).

TABLE 26

Neutralization Of Toxin B By Affinity Purified Antibodies

| Treatment group[a] | Number Animals Alive[b] | Number Animals Dead[b] |
|---|---|---|
| Preimmune[1] | 0 | 5 |
| CTB[1]; 400 μg | 5 | 0 |
| CTB (AP on pPB1750-2360);[2] 875 μg | 5 | 0 |
| CTB (AP on PMB1750-1970);[2] 875 μg | 5 | 0 |
| CTB (AP on pMB1970-2360);[2] 500 μg | 5 | 0 |

[a]*C. difficile* toxin B (CTB) (Tech Lab; at 5 μg/ml, 25 μg total) at lethal concentration to hamsters is added to antibody and incubated for one hour at 37° C.. After incubation this mixture is injected intraperitoneally (IP) into hamsters. Each treatment group received toxin premixed with antibody raised against the indicated protein, as either: [1]4× antibody PEG prep or [2]affinity purified (AP) antibody (from CTB PEG prep, on indicated columns). The amount of specific antibody in each prep is indicated; the amount is directly determined for affinity purified preps and is estimated for the 4× CTB as described in Example 15.
[b]The numbers in each group represent numbers of hamsters dead or alive, 2 hr post IP administration of toxin/antibody mixture.

The observation that antibodies affinity purified against the non-overlapping pMB1750-1970 and pMB1970-2360 proteins neutralized toxin B raised the possibility that either 1) antibodies specific to repeat sub-regions are sufficient to neutralize toxin B or 2) sub-region specific proteins can bind most or all repeat specific antibodies present in the CTB polyclonal pool. This would likely be due to conformational similarities between repeats, since homology in the primary amino acid sequences between different repeats is in the range of only 25–75% [Eichel-Streiber, et al. (1992) Molec. Gen. Genetics 233:260]. These possibilities were tested by affinity chromatography.

The CTB PEG prep was sequentially depleted 2× on the pMB1750-1970 column; only a small elution peak was observed after the second chromatography, indicating that most reactive antibodies were removed. This interval depleted CTB preparation was then chromatographed on the pPB1850-2360 column; no antibody bound to the column. The reactivity of the CTB and CTB (pMB1750-1970 depleted) preps to pPB1750-2360, pPB1850-2360, pMB1750-1970 and pMB1970-2360 proteins was then determined by ELISA using the protocol described in Example 13(c). Briefly, 96-well microtiter plates (Falcon, Pro-Bind Assay Plates) were coated with recombinant protein by adding 100 μl volumes of protein at 1–2 μg/ml in PBS containing 0.005% thimerosal to each well and incubating overnight at 4° C. The next morning, the coating suspensions were decanted and the wells were washed three times using PBS. In order to block non-specific binding sites, 100 μl of 1.0% BSA (Sigma) in PBS (blocking solution) was then added to each well, and the plates were incubated for 1 hr. at 37° C. The blocking solution was decanted and duplicate samples of 150 μl of diluted antibody was added to the first well of a dilution series. The initial testing serum dilution was (1/200 for CTB prep, (the concentration of depleted CTB was standardized by $OD_{280}$) in blocking solution containing 0.5% Tween 20, followed by 5-fold serial dilutions into this solution. This was accomplished by serially transferring 30 μl aliquots to 120 μl buffer, mixing, and repeating the dilution into a fresh well. After the final dilution, 30 μl was removed from the well such that all wells contained 120 μl final volume. A total of 5 such dilutions were performed (4 wells total). The plates were incubated for 1 hr at 37° C. Following this incubation, the serially diluted samples were decanted and the wells were washed three times using PBS containing 0.5% Tween 20 (PBST), followed by two 5 min washes using BBS-Tween and a final three washes using PBST. To each well, 100 μl of 1/1000 diluted secondary antibody [rabbit anti-chicken IgG alkaline phosphatase (Sigma) diluted in blocking solution containing 0.5% Tween 20] was added, and the plate was incubated 1 hr at 37° C. The conjugate solutions were decanted and the plates were washed 6 times in PBST, then once in 50 mM $Na_2CO_3$, 10 mM $MgCl_2$, pH 9.5. The plates were developed by the addition of 100 μl of a solution containing 1 mg/ml para-nitro phenyl phosphate (Sigma) dissolved in 50 mM $Na_2CO_3$, 10 mM $MgCl_2$, pH 9.5 to each well. The plates were then incubated at room temperature in the dark for 5–45 min. The absorbency of each well was measured at 410 nm using a Dynatech MR 700 plate reader.

As predicted by the affinity chromatography results, depletion of the CTB prep on the pMB1750-1970 column removed all detectable reactivity to the pMB1970-2360 protein. The reciprocal purification of a CTB prep that was depleted on the pMB1970-2360 column yielded no bound antibody when chromatographed on the pMB1750-1970 column. These results demonstrate that all repeat reactive antibodies in the CTB polyclonal pool recognize a conserved structure that is present in non-overlapping repeats. Although it is possible that this conserved structure represents rare conserved linear epitopes, it appears more likely that the neutralizing antibodies recognize a specific protein conformation. This conclusion was also suggested by the results of Western blot hybridization analysis of CTB reactivity to these recombinant proteins.

Western blots of 7.5% SDS-PAGE gels, loaded and electrophoresed with defined quantities of each recombinant protein, were probed with the CTB polyclonal antibody preparation. The blots were prepared and developed with alkaline phosphatase as described in Example 3. The results are shown in FIG. 24.

FIG. 24 depicts a comparison of immunoreactivity of IgY antibody raised against either native or recombinant toxin B antigen. Equal amounts of pMB1750-1970 (lane 1), pMB1970-2360 (lane 2), pPB1850-2360 (lane 3) as well as a serial dilution of pPB1750-2360 (lanes 4–6 comprising 1×, 1/10× and 1/100× amounts, respectively) proteins were loaded in duplicate and resolved on a 7.5% SDS-PAGE gel. The gel was blotted and each half was hybridized with PEG prep IgY antibodies from chickens immunized with either native CTB or pPB1750-2360 protein. Note that the full-length pMB1750-1970 protein was identified only by antibodies reactive to the recombinant protein (arrows).

Although the CTB prep reacts with the pPB1750-2360, pPB1850-2360, and pMB1970-2360 proteins, no reactivity to the pMB1750-1970 protein was observed (FIG. 24). Given that all repeat reactive antibodies can be bound by this protein during affinity chromatography, this result indicates that the protein cannot fold properly on Western blots. Since this eliminates all antibody reactivity, it is unlikely pthat the repeat reactive antibodies in the CTB prep recognize linear epitopes. This may indicate that in order to induce protective antibodies, recombinant toxin B protein will need to be properly folded.

c) Generation And Evaluation Of Antibodies Reactive To Recombinant Toxin B Polypeptides i) Generation Of Antibodies Reactive To Recombinant Toxin B Proteins Antibodies against recombinant proteins were generated in egg laying Leghorn hens as described in Example 13. Antibodies were raised [using Freund's adjuvant (Gibco) unless otherwise indicated] against the following recombinant proteins: 1) a mixture of Interval 1+2 proteins (see FIG. 18); 2) a mixture of interval 4 and 5 proteins (see FIG. 18); 3) pMB1970-2360 protein; 4) pPB1750-2360 protein; 5) pMB1750-2360; 6) pMB1750-2360 [Titermax adjuvant (Vaxcell)]; 7) pMB1750-2360 [Gerbu adjuvant (Biotech)]; 8) pMBp1750-2360 protein; 9) pPB1850-2360; and 10) pMB1850-2360.

Chickens were boosted at least 3 times with recombinant protein until ELISA reactivity [using the protocol described in b) above with the exception that the plates were coated with pPB1750-2360 protein] of polyclonal PEG preps was at least equal to that of the CTB polyclonal antibody PEG prep. ELISA titers were determined for the PEG preps from all of the above immunogens and were found to be comparable ranging from 1:12500 to 1:62500. High titers were achieved in all cases except in 6) pMB1750-2360 in which strong titers were not observed using the Titermax adjuvant, and this preparation was not tested further.

ii) Evaluation Of Antibodies Reactive To Recombinant Proteins By Western Blot Hybridization Western blots of 7.5% SDS-PAGE gels, loaded and electrophoresed with defined quantities of recombinant protein (pMB1750-1970, pPB1850-2360, and pMB1970-2360 proteins and a serial dilution of the pPB1750-2360 to allow quantification of reactivity), were probed with the CTB, pPB1750-2360, pMB1750-2360 and pMB1970-2360 polyclonal antibody preparations (from chickens immunized using Freund's adjuvant). The blots were prepared and developed with alkaline phosphatase as described above in b).

As shown in FIG. 24, the CTB and pMB1970-2360 preps reacted strongly with the pPB1750-2360, pPB1850-2360, and pMB1970-2360 proteins while the pPB1750-2360 and pMB1970-2360 (Gerbu) preparations reacted strongly with all four proteins. The Western blot reactivity of the pPB1750-2360 and pMB1970-2360 (Gerbu) preparations were equivalent to that of the CTB preparation, while reactivity of the pMB1970-2360 preparation was <10% that of the CTB prep. Despite equivalent ELISA reactivities only weak reactivity (approximately 1%) to the recombinant proteins were observed in PEG preps from two independent groups immunized with the pMB1750-2360 protein and one group immunized with the pMB1750-2360 preparation using Freund's adjuvant.

Affinity purification was utilized to determine if this difference in immunoreactivity by Western blot analysis reflects differing antibody titers. Fifty ml 2×PEG preparations from chickens immunized with either pMB1750-2360 or pMB1970-2360 protein were chromatographed on the pPB1750-2360 affinity column from b) above, as described. The yield of affinity purified antibody (% total protein in preparation) was equivalent to the yield obtained from a CTB PEG preparation in b) above. Thus, differences in Western reactivity reflect a qualitative difference in the antibody pools, rather than quantitative differences., These results demonstrate that certain recombinant proteins are more effective at generating high affinity antibodies (as assayed by Western blot hybridization).

iii) In Vivo Neutralization Of Toxin B Using Antibodies Reactive To Recombinant Protein The in vivo hamster model [described in Examples 9 and 14(b)] was utilized to assess the neutralizing ability of antibodies raised against recombinant toxin B proteins. The results from three experiments are shown below in Tables 27–29.

The ability of each immunogen to neutralize toxin B in vivo has been compiled and is shown in Table 30. As predicted from the recombinant protein-CTB premix studies (Table 24) only antibodies to Interval 3 (1750-2366) and not the other regions of toxin B (i.e., intervals 1–5) are protective. Unexpectedly, antibodies generated to INT-3 region expressed in pMAL vector (pMB1750-2360 and pMB1750-2360) using Freund's adjuvant were non-neutralizing. This observation is reproducible, since no neutralization was observed in two independent immunizations with pMB1750-2360 and one immunization with pMpB1750-2360. The fact that 5× quantities of affinity purified toxin B repeat specific antibodies from pMB1750-2360 PEG preps cannot neutralize toxin B while 1× quantities of affinity purified anti-CTB antibodies can (Table 28) demonstrates that the differential ability of CTB antibodies to neutralize toxin B is due to qualitative rather than quantitative differences in these antibody preparations. Only when this region was expressed in an alternative vector (pPB1750-2360) or using an alternative adjuvant with the pMB1750-2360 protein were neutralizing antibodies generated. Importantly, antibodies raised using Freund's adjuvant to pPB1850-2360, which contains a fragment that is only 100 amino acids smaller than recombinant pPB1750-2360, are unable to neutralize toxin B in vivo (Table 27); note also that the same vector is used for both pPB1850-2360 and pPB1750-2360.

TABLE 27

In Vivo Neutralization Of Toxin B

| Treatment Group[a] | Number Animals Alive[b] | Number Animals Dead[b] |
|---|---|---|
| Preimmune | 0 | 5 |
| CTB | 5 | 0 |
| INT 1 + 2 | 0 | 5 |
| INT 4 + 5 | 0 | 5 |
| pMB1750-2360 | 0 | 5 |
| pMB1970-2360 | 0 | 5 |
| pPB1750-2360 | 5 | 0 |

[a]*C. difficile* toxin B (CTB) (at 5 μg/ml; 25 μg total; Tech Lab) at lethal concentration to hamsters is added to antibody and incubated for one hour at 37° C. After incubation this mixture is injected intraperitoneally (IP) into hamsters. Each treatment group received toxin premixed with antibody raised against the indicated protein, as a 4X antibody PEG prep.
[b]The numbers in each group represent numbers of hamsters dead or alive, 2 hours post IP administration of toxin/antiboy mixture.

TABLE 28

In Vivo Neutralization Of Toxin B Using Affinity Purified Antibodies

| Treatment Group[a] | Number Animals Alive[b] | Number Animals Dead[b] |
|---|---|---|
| Preimmune(1) | 0 | 5 |
| CTB(1) | 5 | 0 |
| pPB1750-2360(1) | 5 | 0 |
| 1.5 mg anti-PMB1750-2360(2) | 1 | 4 |
| 1.5 mg anti-pMB1970-2360(2) | 0 | 5 |
| 300 μg anti-CTB(2) | 5 | 0 |

[a]*C. difficile* toxin B (CTB) (at 5 μg/ml; 25 μg total; Tech Lab) at lethal concentration to hamsters is added to antibody and incubated for one hour at 37° C.. After incubation, 1 ml of this mixture is injected intraperitoneally (IP) into hamsters. Each treatment group received toxin premixed with antibody raised against the indicated protein, as either (1) 4× antibody PEG prep or (2) affinity purified antibody (on a pPB1750-2360 resin), either 1.5 mg/group (anti-pMB1750-2360 and anti-pMB1970-2360; used undiluted affinity purified antibody) or 350 μg/group (anti-CTB, repeat specific; used 1/5 diluted anti-CTB antibody).
[b]The numbers in each group represent numbers of hamsters dead or alive, 2 hr post-IP administration of toxin/antibody mixture.

TABLE 29

Generation Of Neutralizing Antibodies Utilizing The Gerbu Adjuvant

| Treatment Group[a] | Number Animals Alive[b] | Number Animals Dead[b] |
|---|---|---|
| Preimmune | 0 | 5 |
| CTB | 5 | 0 |
| pMB1970-2360 | 0 | 5 |
| pMB1850-2360 | 0 | 5 |
| pPB1850-2360 | 0 | 5 |
| pMB1750-2360 (Gerbu adj) | 5 | 0 |

[a]*C. difficile* toxin B (CTB) (Tech Lab) at lethal concentration to hamsters is added to antibody and incubated for one hour at 37° C. After incubation this mixture is injected intraperitoneally (IP) into hamsters. Each treatment group received toxin premixed with antibody raised against the indicated protein, as a 4× antibody PEG prep.
[b]The numbers in each group represent numbers of hamsters dead or alive, 2 hrs post IP administration of toxin/antibody mixture.

TABLE 30

In Vivo Neutralization Of Toxin B

| Immunogen | Adjuvant | Tested Preparation[a] | Antigen Utilized For AP | In vivo Neutralization[b] |
|---|---|---|---|---|
| Preimmune | NA[1] | PEG | NA | no |
| CTB (native) | Titermax | PEG | NA | yes |
| CTB (native) | Titermax | AP | pPB1750-2360 | yes |
| CTB (native) | Titermax | AP | pPB1850-2360 | yes |
| CTB (native) | Titermax | AP | pPB1750-1970 | yes |
| CTB (native) | Titermax | AP | pPB1970-2360 | yes |
| pMB1750-2360 | Freunds | PEG | NA | no |
| pMB1750-2360 | Freunds | AP | pPB1750-2360 | no |
| pMB1750-2360 | Gerbu | PEG | NA | yes |
| pMB1970-2360 | Freunds | PEG | NA | no |
| pMB1970-2360 | Freunds | AP | pPB1750-2360 | no |
| pPB1750-2360 | Freunds | PEG | NA | yes |
| pPB1850-2360 | Freunds | PEG | NA | no |
| pMB1850-2360 | Freunds | PEG | NA | no |
| INT 1 + 2 | Freunds | PEG | NA | no |
| INT 4 + 5 | Freunds | PEG | NA | no |

[a]Either PEG preparation (PEG) or affinity purified antibodies (AP).
[b]'Yes' denotes complete neutralization (0/5 dead) while 'no' denotes no neutralization (5/5 dead) of toxin B, 2 hours post-administration of mixture.
[a]'NA' denotes not applicable.

The pPB1750-2360 antibody pool confers significant in vivo protection, equivalent to that obtained with the affinity purified CTB antibodies. This correlates with the observed high affinity of this antibody pool (relative to the pMB1750-2360 or pMB1970-2360 pools) as assayed by Western blot analysis (FIG. 24). These results provide the first demonstration that in vivo neutralizing antibodies can be induced using recombinant toxin B protein as immunogen.

The failure of high concentrations of antibodies raised against the pMB1750-2360 protein (using Freunds adjuvant) to neutralize, while the use of Gerbu adjuvant and pMB1750-2360 protein generates a neutralizing response, demonstrates that conformation or presentation of this protein is essential for the induction of neutralizing antibodies. These results are consistent with the observation that the neutralizing antibodies produced when native CTB is used as an immunogen appear to recognize conformational epitopes [see section b) above]. This is the first demonstration that the conformation or presentation of recombinant toxin B protein is essential to generate high titers of neutralizing antibodies.

EXAMPLE 20

Determination Of Quantitative And Qualitative Differences Between pMB1750-2360, pMB1750-2360 (Gerbu) Or pPB1750-2360 IgY Polyclonal Antibody Preparations In Example 19, it was demonstrated that toxin B neutralizing antibodies could be generated using specific recombinant toxin B proteins (pPB1750-2360) or specific adjuvants. Antibodies raised against pMB1750-2360 were capable of neutralizing the enterotoxin effect of toxin B when the recombinant protein was used to immunize hens in conjunction with the Gerbu adjuvant, but not when Freunds adjuvant was used. To determine the basis for these antigen and adjuvant restrictions, toxin B-specific antibodies present in the neutralizing and non-neutralizing PEG preparations were isolated by affinity chromatography and tested for qualitative or quantitative differences. The example involved a) purification of anti-toxin B specific antibodies from pMB1750-2360 and pPB1750-2360 PEG preparations and b) in vivo neutralization of toxin B using the affinity purified antibody.

a) Purification Of specific Antibodies From pMB1750-2360 And pPB1750-2360 PEG Preparations To purify and determine the concentration of specific antibodies (expressed as the percent of total antibody) within the pPB1750-2360 (Freunds and Gerbu) and pPB1750-2360 PEG preparations, defined quantities of these antibody preparations were chromatographed on an affinity column containing the entire toxin B repeat region (pPB1750-2360). The amount of affinity purified antibody was then quantified.

An affinity column containing the recombinant toxin B repeat protein, pPB1750-2360, was made as follows. Four ml of PBS-washed Actigel resin (Sterogene) was coupled with 5 mg of pPB1750-2360 affinity purified protein (dialyzed into PBS; estimated to be greater than 95% full length fusion protein) in a 15 ml tube (Falcon) containing ¹/₁₀ final volume Ald-coupling solution (1M sodium cyanoborohydride). Aliquots of the supernatant from the coupling reactions, before and after coupling, were assessed by Coomassie staining of 7.5% SDS-PAGE gels. Based on protein band intensities, greater than 95% (approximately 5 mg) of recombinant protein was coupled to the resin. The coupled resin was poured into a 10 ml column (BioRad), washed extensively with PBS, pre-eluted with 4M guanidine-HCl (in 10 mM Tris-HCL, pH 8.0; 0.005% thimerosal) and re-equilibrated in PBS and stored at 4° C.

Aliquots of pMB1750-2360, pMB1750-2360 (Gerbu) or pPB1750-2360 IgY polyclonal antibody preparations (PEG preps) were affinity purified on the above column as follows. The column was attached to an UV monitor (ISCO), and washed with PBS. Forty ml aliquots of 2×PEG preps (filter sterilized using a 0.45μ filter and quantified by $OD_{280}$ before chromatography) was applied. The column was washed with PBS until the baseline was re-established (the column flow-through was saved), washed with BBSTween to elute non-specifically binding antibodies and re-equilibrated with PBS. Bound antibody was eluted from the column in 4M guanidine-HCl (in 10 mM Tris-HCL, pH 8.0, 0.005% thimerosal) and the entire elution peak collected in a 15 ml tube (Falcon). The column was re-equilibrated, and the column eluate re-chromatographed as described above. The antibody preparations were quantified by UV absorbance (the elution buffer was used to zero the spectrophotometer). Approximately 10 fold higher concentrations of total purified antibody was obtained upon elution of the first chromatography pass relative to the second pass. The low yield from the second chromatography pass indicated that most of the specific antibodies were removed by the first round of chromatography.

Pools of affinity purified specific antibodies were prepared by dialysis of the column elutes after the first column chromatography pass for the pMB1750-2360, pMB1750-2360 (Gerbu) or pPB1750-2360 IgY polyclonal antibody preparations. The elutes were collected on ice and immediately dialyzed against a 100-fold volume of PBS at 4° C. for 2 hrs. The samples were then dialyzed against 3 changes of a 65-fold volume of PBS at 4° C. Dialysis was performed for a minimum of 8 hrs per change of PBS. The dialyzed samples were collected, centrifuged to remove insoluble debris, quantified by $OD_{280}$, and stored at 4° C.

The percentage of toxin B repeat-specific antibodies present in each preparation was determined using the quantifications of antibody yields from the first column pass (amount of specific antibody recovered after first pass/total protein loaded). The yield of repeat-specific affinity purified antibody (expressed as the percent of total protein in the preparation) in: 1) the pMB1750-2360 PEG prep was approximately 0.5%, 2) the pMB1750-2360 (Gerbu) prep was approximately 2.3%, and 3) the pPB1750-2360 prep was approximately 0.4%. Purification of a CTB IgY polyclonal antibody preparation on the same column demonstrated that the concentration of toxin B repeat specific antibodies in the CTB preparation was 0.35%.

These results demonstrate that 1) the use of Gerbu adjuvant enhanced the titer of specific antibody produced against the pMB1750-2360 protein 5-fold relative to immunization using Freunds adjuvant, and 2) the differences seen in the in vivo neutralization ability of the pMB1750-2360 (not neutralizing) and pPB1750-2360 (neutralizing) and CTB (neutralizing) PEG preps seen in Example 19 was not due to differences in the titers of repeat-specific antibodies in the three preparations because the titer of repeat-specific antibody was similar for all three preps; therefore the differing ability of the three antibody preparations to neutralize toxin B must reflect qualitative differences in the induced toxin B repeat-specific antibodies. To confirm that qualitative differences exist between antibodies raised in hens immunized with different recombinant proteins and/or different adjuvants, the same amount of affinity purified anti-toxin B repeat (aa 1870-2360 of toxin B) antibodies from the different preparations was administered to hamsters using the in vivo hamster model as described below.

b) In vivo Neutralization Of Toxin B Using Affinity Purified Antibody

The in vivo hamster model was utilized to assess the neutralizing ability of the affinity purified antibodies raised against recombinant toxin B proteins purified in (a) above. As well, a 4×IgY PEG preparation from a second independent immunization utilizing the pPB1750-2360 antigen with Freunds adjuvant was tested for in vivo neutralization. The results are shown in Table 31.

The results shown in Table 31 demonstrate that:
1) as shown in Example 19 and reproduced here, 1.5 mg of affinity purified antibody from pMB1750-2360 immunized hens using Freunds adjuvant does not neutralize toxin B in vivo. However, 300 µg of affinity purified antibody from similarly immunized hens utilizing Gerbu adjuvant demonstrated complete neutralization of toxin B in vivo. This demonstrates that Gerbu adjuvant, in addition to enhancing the titer of antibodies reactive to the pMB1750-2360 antigen relative to Freunds adjuvant (demonstrated in (a) above), also enhances the yield of neutralizing antibodies to this antigen, greater than 5 fold.

2) Complete in vivo neutralization of toxin B was observed with 1.5 mg of affinity purified antibody from hens immunized with pPB1750-2360

TABLE 31

In vivo Neutralization Of Toxin B Using Affinity Purified Antibodies

| Treatment Group[a] | Number Animals Alive[b] | Number Animals Dead[b] |
|---|---|---|
| Preimmune[1] | 0 | 5 |
| CTB (300 µg)[2] | 5 | 0 |
| CTB (100 µg)[2] | 1 | 4 |
| pMB1750-2360 (G) (5 mg)[2] | 5 | 0 |
| pMB1750-2360 (G) (1.5 mg)[2] | 5 | 0 |
| pMB1750-2360 (G) (300 µg)[2] | 5 | 0 |
| pMB1750-2360 (F) (1.5 mg)[2] | 0 | 5 |
| pPB1750-2360 (F) (1.5 mg)[2] | 5 | 0 |
| pPB1750-2360 (F) (300 µg)[2] | 1 | 4 |
| CTB (100 µg)[3] | 2 | 3 |
| pPB1750-2360 (F) (500 µg)[1] | 5 | 0 |

[a]*C. difficile* toxin B (CTB) (Tech Lab) at lethal concentration to hamsters (25 µg) was added to the antibody (amount of specific antibody is indicated) and incubated for one hour at 37° C.. After incubation, this mixture was injected IP into hamsters (1/5 total mix injected per hamster). Each treatment group received toxin premixed with antibody raised against the indicated protein (G = gerbu adjuvant, F = Freunds adjuvant). [1]indicates the antibody was a 4× IgY PEG prep; [2]indicates the antibody was affinity purified on a pPB1850-2360 resin; and [3]indicates that the antibody was a 1× IgY PEG prep.
[b]The numbers in each group represent numbers of hamsters dead or alive, 2 hrs post IP administration of toxin/antibody mixture.

antigen, but not with pMB1750-2360 antigen, when Freunds adjuvant was used. This demonstrates, using standardized toxin B repeat-specific antibody concentrations, that neutralizing antibodies were induced when pPB1750-2360 but not pMB1750-2360 was used as the antigen with Freunds adjuvant.

3) Complete in vivo neutralization was observed with 300 µg of pMB1750-2360 (Gerbu) antibody, but not with 300 µg of pPB1750-2360 (Freunds) antibody. Thus the pMB1750-2360 (Gerbu) antibody has a higher titer of neutralizing antibodies than the pPB1750-2360 (Freunds) antibody.

4) Complete neutralization of toxin B was observed using 300 µg of CTB antibody [affinity purified (AP)] but not 100 µg CTB antibody (AP or PEG prep). This demonstrates that greater than 100 µg of toxin B repeat-specific antibody (anti-CTB) is necessary to neutralize 25 µg toxin B in vivo in this assay, and that affinity purified antibodies specific to the toxin B repeat interval neutralize toxin B as effectively as the PEP prep of IgY raised against the entire CTB protein (shown in this assay).

5) As was observed with the initial pPB1750-2360 (IgY) PEG preparation (Example 19), complete neutralization was observed with a IgY PEG preparation isolated from a second independent group of pPB1750-2360 (Freunds) immunized hens. This demonstrates that neutralizing antibodies are reproducibly produced when hens are immunized with pPB1750-2360 protein utilizing Freund's adjuvant.

EXAMPLE 21

Diagnostic Enzyme Immunoassays For *C. difficile* Toxins A And B

The ability of the recombinant toxin proteins and antibodies raised against these recombinant proteins (described in the above examples) to form the basis of diagnostic assays for the detection of clostridial toxin in a sample was examined. Two immunoassay formats were tested to quantitatively detect *C. difficile* toxin A and toxin B from a biological specimen. The first format involved a competitive assay in which a fixed amount of recombinant toxin A or B was immobilized on a solid support (e.g., microtiter plate wells) followed by the addition of a toxin-containing biological specimen mixed with affinity-purified or PEG fractionated antibodies against recombinant toxin A or B. If toxin is present in a specimen, this toxin will compete with the immobilized recombinant toxin protein for binding to the anti-recombinant antibody thereby reducing the signal obtained following the addition of a reporter reagent. The reporter reagent detects the presence of antibody bound to the immobilized toxin protein.

In the second format, a sandwich immunoassay was developed using affinity-purified antibodies to recombinant toxin A and B. The affinity-purified antibodies to recombinant toxin A and B were used to coat microtiter wells instead of the recombinant polypeptides (as was done in the competitive assay format). Biological samples containing toxin A or B were then added to the wells followed by the addition of a reporter reagent to detect the presence of bound toxin in the well.

a) Competitive Immunoassay For The Detection Of *C. difficile* Toxin

Recombinant toxin A or B was attached to a solid support by coating 96 well microtiter plates with the toxin protein at a concentration of 1 µg/ml in PBS. The plates were incubated overnight at 2–8° C. The following morning, the coating solutions were removed and the remaining protein binding sites on the wells were blocked by filling each well with a PBS solution containing 0.5% BSA and 0.05% Tween-20. Native *C. difficile* toxin A or B (Tech Lab) was diluted to 4 tig/ml in stool extracts from healthy Syrian hamsters (Sasco). The stool extracts were made by placing fecal pellets in a 15 ml centrifuge tube; PBS was added at 2 ml/pellet and the tube was vortexed to create a uniform suspension. The tube was then centrifuged at 2000 rpm for 5 min at room temperature. The supernatant was removed; this comprises the stool extract. Fifty µl of the hamster stool extract was pipetted into each well of the microtiter plates to serve as the diluent for serial dilutions of the 4 µg/ml toxin samples. One hundred gl of the toxin samples at 4 µg/ml was pipetted into the first row of wells in the microtiter plate, and 50 µl aliquots were removed and diluted serially down the plate in duplicate. An equal volume of affinity purified anti-recombinant toxin antibodies [1 ng/well of anti-pMA1870-2680 antibody was used for the detection of toxin A; 0.5 ng/well of anti-pMB1750-2360(Gerbu) was used for the detection of toxin B] were added to appropriate wells, and the plates were incubated at room temperature for 2 hours with gentle agitation. Wells serving as negative control contained antibody but no native toxin to compete for binding.

Unbound toxin and antibody were removed by washing the plates 3 to 5 times with PBS containing 0.05% Tween-20. Following the wash step, 100 µl of rabbit anti-chicken IgG antibody conjugated to alkaline phosphatase (Sigma) was added to each well and the plates were incubated for 2 hours at room temperature. The plates were then washed as before to remove unbound secondary antibody. Freshly prepared alkaline phosphatase substrate (1 mg/ml p-nitrophenyl phosphate (Sigma) in 50 mM $Na_2CO_3$, pH 9.5; 10 mM $MgCl_2$) was added to each well. Once sufficient color developed, the plates were read on a Dynatech MR700 microtiter plate reader using a 410 nm filter.

The results are summarized in Tables 32 and 33. For the results shown in Table 32, the wells were coated with recombinant toxin A protein (pMA1870-2680). The amount of native toxin A added (present as an addition to solubilized hamster stool) to a given well is indicated (0 to 200 ng). Antibody raised against the recombinant toxin A protein, pMA1870-2680, was affinity purified on the an affinity column containing pPA1870-2680 (described in Example 20). As shown in Table 32, the recombinant toxin A protein and affinity-purified antitoxin can be used for the basis of a competitive immunoassay for the detection of toxin A in biological samples.

Similar results were obtained using the recombinant toxin B, pPB1750-2360, and antibodies raised against pMB1750-2360(Gerbu). For the results shown in Table 33, the wells were coated with recombinant toxin B protein (pPB1750-2360). The amount of native toxin B added (present as an addition to solubilized hamster stool) to a given well is indicated (0 to 200 ng). Antibody raised against the recombinant toxin B protein, pMB1750-2360(Gerbu), was affinity purified on the an affinity column containing pPB1850-2360 (described in Example 20). As shown in Table 33, the recombinant toxin B protein and affinity-purified antitoxin can be used for the basis of a competitive immunoassay for the detection of toxin B in biological sample.

In this competetiton assay, the reduction is considered significant over the background level at all points; therefore the assay can be used to detect samples containing less than 12.5 ng toxin A/well and as little as 50–100 ng toxin B/well.

TABLE 32

Competitive Inhibition Of Anti-*C. difficile* Toxin A By Native Toxin A

| ng Toxin A/Well | $OD_{410}$ Readout |
| --- | --- |
| 200 | 0.176 |
| 100 | 0.253 |
| 50 | 0.240 |
| 25 | 0.259 |
| 12.5 | 0.309 |
| 6.25 | 0.367 |
| 3.125 | 0.417 |
| 0 | 0.590 |

TABLE 33

Competitive Inhibition Of Anti-*C. difficile* Toxin B By Native Toxin B

| ng Toxin B/Well | $OD_{410}$ Readout |
| --- | --- |
| 200 | 0.392 |
| 100 | 0.566 |
| 50 | 0.607 |
| 25 | 0.778 |
| 12.5 | 0.970 |
| 6.25 | 0.902 |
| 3.125 | 1.040 |
| 0 | 1.055 |

These competitive inhibition assays demonstrate that native *C. difgicile* toxins and recombinant *C. difficile* toxin proteins can compete for binding to antibodies raised agaomst recombinant *C. difficile* toxins demonstrating that these anti-recombinant toxin antibodies provide effective diagnostic reagents.

b) Sandwich Immunoassay For The Detection Of *C. difficile* Toxin

Affinity-purified antibodies against recombinant toxin A or toxin B were immobilized to 96 well microtiter plates as follows. The wells were passively coated overnight at 4° C.

affinity purified antibodies raised against either pMA1870-2680 (toxin A) or pMB1750-2360(Oerbu) (toxin B). The antibodies were affinity purified as described in Example 20. The antibodies were used at a concentration of 39g/ml and 100 μl was added to each microtiter well. The wells were then blocked with 200 μl of 0.5% BSA in PBS for 2 hours at room temperature and the blocking solution was then decanted. Stool samples from healthy Syrian hamsters were resuspended in PBS, pH 7.4 (2 ml PBS/stool pellet was used to resuspend the pellets and the sample was centrifuged as described above). The stool suspension was then spiked with native C. difficile toxin A or B (Tech Lab) at 4 μg/ml. The stool suspensions containing toxin (either toxin A or toxin B) were then serially diluted two-fold in stool suspension without toxin and 50 μl was added in duplicate to the coated microtiter wells. Wells containing stool suspension without toxin served as the negative control.

The plates were incubated for 2 hours at room temperature and then were washed three times with PBS. One hundred μl of either goat anti-native toxin A or goat anti-native toxin B (Tech Lab) diluted 1:1000 in PBS containing 1% BSA and 0.05% Tween 20 was added to each well. The plates were incubated for another 2 hours at room temperature. The plates were then washed as before and 100 μl of alkaline phosphatase-conjugated rabbit anti-goat IgG (Cappel, Durham, N.C.) was added at a dilution of 1:1000. The plates were incubated for another 2 hours at room temperature. The plates were washed as before then developed by the addition of 100 μl/well of a substrate solution containing 1 mg/ml p-nitrophenyl phosphate (Sigma) in 50 mM $Na_2CO_3$, pH 9.5; 10 mM $MgCl_2$. The absorbance of each well was measured using a plate reader (Dynatech) at 410 nm. The assay results are shown in Tables 34 and 35.

TABLE 34

C. difficile Toxin A Detection In Stool
Using Affinity-Purified Antibodies Against Toxin A

| ng Toxin A/Well | $OD_{410}$ Readout |
|---|---|
| 200 | 0.9 |
| 100 | 0.8 |
| 50 | 0.73 |
| 25 | 0.71 |
| 12.5 | 0.59 |
| 6.25 | 0.421 |
| 0 | 0 |

TABLE 35

C. difficile Toxin B Detection In Stool
Using Affinity-Purified Antibodies Against Toxin B

| ng Toxin B/Well | $OD_{410}$ Readout |
|---|---|
| 200 | 1.2 |
| 100 | 0.973 |
| 50 | 0.887 |
| 25 | 0.846 |
| 12.5 | 0.651 |
| 6.25 | 0.431 |
| 0 | 0.004 |

The results shown in Tables 34 and 35 show that antibodies raised against recombinant toxin A toxin B fragments can be used to detect the presence of C. difficile toxin in stool samples. These antibodies form the basis for a sensitive sandwich immunoassay which is capable of detecting as little as 6.25 ng of either toxin A or B in a 50 μl stool sample. As shown above in Tables 34 and 35, the background for this sandwich immunoassay is extremely low; therefore, the sensitivity of this assay is much lower than 6.25 ng toxin/well. It is likely that toxin levels of 0.5 to 1.0 pg/well could be detected by this assay.

The results shown above in Tables 32–35 demonstrate clear utility of the recombinant reagents in C. difficile toxin detection systems.

EXAMPLE 22

Construction And Expression Of C. botulinum C Fragment Fusion Proteins

The C. botulinum type A neurotoxin gene has been cloned and sequenced [Thompson, et al., Eur. J. Biochem. 189:73 (1990)]. The nucleotide sequence of the toxin gene is available from the EMBL/GenBank sequence data banks under the accession number X52066; the nucleotide sequence of the coding region is listed in SEQ ID NO:27. The amino acid sequence of the C. botulinum type A neurotoxin is listed in SEQ ID NO:28. The type A neurotoxin gene is synthesized as a single polypeptide chain which is processed to form a dimer composed of a light and a heavy chain linked via disulfide bonds. The 50 kD carboxy-terminal portion of the heavy chain is referred to as the C fragment or the $H_C$ domain.

Previous attempts by others to express polypeptides comprising the C fragment of C. botulinum type A toxin as a native polypeptide (e.g., not as a fusion protein) in E. coli have been unsuccessful [H. F. LaPenotiere, et al. in Botulinum and Tetanus Neurotoxins, DasGupta, Ed., Plenum Press, New York (1993), pp. 463–466]. Expression of the C fragment as a fusion with the E. coli MBP was reported to result in the production of insoluble protein (H. F. LaPenotiere, et al., supra).

In order to produce soluble recombinant C fragment proteins in E. coli, fusion proteins comprising a synthetic C fragment gene derived from the C. botulinum type A toxin and either a portion of the C. difficile toxin protein or the MBP were constructed. This example involved a) the construction of plasmids encoding C fragment fusion proteins and b) expression of C. botulinum C fragment fusion proteins in E. coli.

a) Construction Of Plasmids Encoding C Fragment Fusion Proteins

In Example 11, it was demonstrated that the C. difficile toxin A repeat domain can be efficiently expressed and purified in E. coli as either native (expressed in the pET 23a vector in clone pPA1870-2680) or fusion (expressed in the pMALc vector as a fusion with the E. coli MBP in clone pMA1870-2680) proteins. Fusion proteins comprising a fusion between the MBP, portions of the C. difficile toxin A repeat domain (shown to be expressed as a soluble fusion protein) and the C fragment of the C. botulinum type A toxin were constructed. A fusion protein comprising the C fragment of the C. botulinum type A toxin and the MBP was also constructed.

Figure 25:
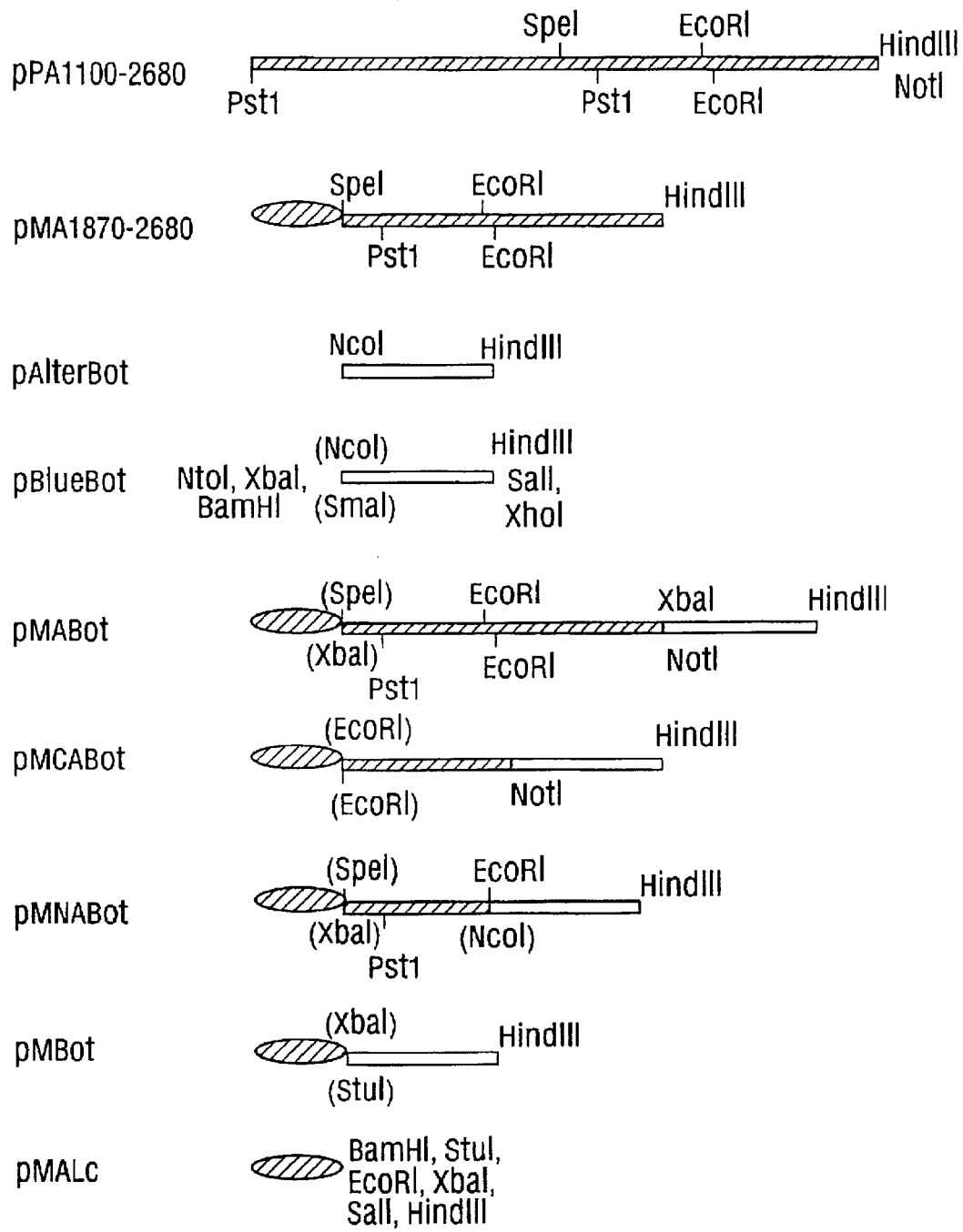
FIG. 25 shows *C. botulinum* type A toxin expression constructs; constructs used to provide *C. botulinum* or *C. difficile* sequences are also shown.

FIG. 25 provides a schematic representation of the botulinal fusion proteins along with the donor constructs containing the C. difficile toxin A sequences or C. botulinum C fragment sequences which were used to generate the botulinal fusion proteins. In FIG. 25, the solid boxes represent C. difficile toxin A gene sequences, the open boxes represent C. botulinum C fragment sequences and the solid black ovals represent the E. coli MBP. When the name for a restriction enzyme appears inside parenthesis, this indicates that the restriction site was destroyed during construction. An asterisk appearing with the name for a restriction enzyme indicates that this restriction site was recreated at the cloning junction.

In FIG. 25, a restriction map of the pMA1870-2680 and pPA1100-2680 constructs (described in Example 11) which contain sequences derived from the *C. difficile* toxin A repeat domain are shown, these constructs were used as the source of *C. difficile* toxin A gene sequences for the construction of plasmids encoding fusions between the *C. botulinum* C fragment gene and the *C. difficile* toxin A gene. The pMA 1870-2680 expression construct expresses high levels of soluble, intact fusion protein (20 mg/liter culture) which can be affinity purified on an amylose column (purification described in Example 11d).

The pAlterBot construct (FIG. 25) was used as the source of *C. botulinum* C fragment gene sequences for the botulinal fusion proteins. pAlterBot was obtained from J. Middlebrook and R. Lemley at the U.S. Department of Defense. pAlterBot contains a synthetic *C. botulinum* C fragment inserted in to the pALTER-1® vector (Promega). This synthetic C fragment gene encodes the same amino acids as does the naturally occurring C fragment gene. The naturally occurring C fragment sequences, like most clostridial genes, are extremely A/T rich (Thompson et al., supra). This high A/T content creates expression difficulties in *E. coli* and yeast due to altered codon usage frequency and fortuitous polyadenylation sites, respectively. In order to improve the expression of C fragment proteins in *E. coli*, a synthetic version of the gene was created in which the non-preferred codons were replaced with preferred codons.

The nucleotide sequence of the *C. botulinum* C fragment gene sequences contained within pAlterBot is listed in SEQ ID NO:22. The first six nucleotides (ATGGCT) encode a methionine and alanine residue, respectively. These two amino acids result from the insertion of the *C. botulinum* C fragment sequences into the pALTER® vector and provide the initiator methionine residue. The amino acid sequence of the *C. botulinum* C fragment encoded by the sequences contained within pAlterBot is listed in SEQ ID NO:23. The first two amino acids (Met Ala) are encoded by vector-derived sequences. From the third amino acid residue onward (Arg), the amino acid sequence is identical to that found in the *C. botulinum* type A toxin gene.

The pMA1870-2680, pPA1100-2680 and pAlterBot constructs were used as progenitor plasmids to make expression constructs in which fragments of the *C. difficile* toxin A repeat domain were expressed as genetic fusions with the *C. botulinum* C fragment gene using the pMAL-c expression vector (New England BioLabs). The pMAL-c expression vector generates fusion proteins which contain the MBP at the amino-terminal end of the protein. A construct, pMBot, in which the *C. botulinum* C fragment gene was expressed as a fusion with only the MBP was constructed (FIG. 25). Fusion protein expression was induced from *E. coli* strains harboring the above plasmids, and induced protein was affinity purified on an amylose resin column.

i) Construction Of pBlueBot

In order to facilitate the cloning of the *C. botulinum* C fragment gene sequences into a number of desired constructs, the botulinal gene sequences were removed from pAlterBot and were inserted into the pBluescript plasmid (Stratagene) to generate pBlueBot (FIG. 25). pBlueBot was constructed as follows. Bacteria containing the pAlterBot plasmid were grown in medium containing tetracycline and plasmid DNA was isolated using the QIAprep-spin Plasmid Kit (Qiagen). One microgram of pAlterBot DNA was digested with NcoI and the resulting 3' recessed sticky end was made blunt using the Klenow fragment of DNA polymerase I (here after the Klenow fragment). The pAlterBot DNA was then digested with HindIII to release the botulinal gene sequences (the Bot insert) as a blunt (filled NcoI site)-HindIII fragment. pBluescript vector DNA was prepared by digesting 200 ng of pBluescript DNA with SmaI and HindIII. The digestion products from both plasmids were resolved on an agarose gel. The appropriate fragments were removed from the gel, mixed and purified utilizing the Prep-a-Gene kit (BioRad). The eluted DNA was then ligated using T4 DNA ligase and used to transform competent DH5α cells (Gibco-BRL). Host cells were made competent for transformation using the calcium chloride protocol of Sambrook et al., supra at 1.82–1.83. Recombinant clones were isolated and confirmed by restriction digestion using standard recombinant molecular biology techniques (Sambrook et al, supra). The resultant clone, pBlueBot, contains several useful unique restriction sites flanking the Bot insert (i.e., the *C. botulinum* C fragment sequences derived from pAlterBot) as shown in FIG. 25.

ii) Construction Of *C. difficile*/*C. botulinum*/MBP Fusion Proteins

Constructs encoding fusions between the *C. difficile* toxin A gene and the *C. botulinum* C fragment gene and the MBP were made utilizing the same recombinant DNA methodology outlined above; these fusion proteins contained varying amounts of the *C. difficile* toxin A repeat domain.

The pMABot clone contains a 2.4 kb insert derived from the *C. difficile* toxin A gene fused to the Bot insert (i.e, the *C. botulinum* C fragment sequences derived from pAlterBot). pMABot (FIG. 25) was constructed by mixing gel-purified DNA from NotI/HindIII digested pBlueBot (the 1.2 kb Bot fragment), SpeI/NotI digested pPA1100-2680 (the 2.4 kb *C. difficile* toxin A repeat fragment) and XbaI/HindIII digested pMAL-c vector. Recombinant clones were isolated, confirmed by restriction digestion and purified using the QIAprep-spin Plasmid Kit (Qiagen). This clone expresses the toxin A repeats and the botulinal C fragment protein sequences as an in-frame fusion with the MBP.

The pMCABot construct contains a 1.0 kb insert derived from the *C. difficile* toxin A gene fused to the Bot insert (i.e, the *C. botulinum* C fragment sequences derived from pAlterBot). pMCABot was constructed by digesting the pMABot clone with EcoRI to remove the 5' end of the *C. difficile* toxin A repeat (see FIG. 25, the pMAL-c vector contains a EcoRI site 5' to the *C. difficile* insert in the pMABot clone). The restriction sites were filled and religated together after gel purification. The resultant clone (pMCABot, FIG. 25) generated an in-frame fusion between the MBP and the remaining 3' portion of the *C. difficile* toxin A repeat domain fused to the Bot gene.

The pMNABot clone contains the 1 kb SpeI/EcoRI (filled) fragment from the *C. difficile* toxin A repeat domain (derived from clone pPA1100-2680) and the 1.2 kb *C. botulinum* C fragment gene as a NcoI (filled)/HindIII fragment (derived from pAlterBot). These two fragments were inserted into the pMAL-c vector digested with XbaI/HindIII. The two insert fragments were generated by digestion of the appropriate plasmid with EcoRI (PPA1100-2680) or NcoI (pAlterBot) followed by treatment with the Klenow fragment. After treatment with the Klenow fragment, the plasmids were digested with the second enzyme (either SpeI or HindIII). All three fragments were gel purified, mixed and Prep-a-Gene purified prior to ligation. Following ligation and transformation, putative recombinants were analyzed by restriction analysis; the EcoRI site was found to be regenerated at the fusion junction, as was predicted for a fusion between the filled EcoRI and NcoI sites.

A construct encoding a fusion protein between the botulinal C fragment gene and the MBP gene was constructed (i.e., this fusion lacks any *C. difficile* toxin A gene sequences) and termed pMBot. The pMBot construct was made by removal of the *C. difficile* toxin A sequences from the pMABot construct and fusing the C fragment gene sequences to the MBP. This was accomplished by digestion of pMABot DNA with StuI (located in the pMALc polylinker 5' to the XbaI site) and XbaI (located 3' to the NotI site at the toxA-Bot fusion junction), filling in the XbaI site using the Klenow fragment, gel purifying the desired restriction fragment, and ligating the blunt ends to circularize the plasmid. Following ligation and transformation, putative recombinants were analyzed by restriction mapping of the Bot insert (i.e, the *C. botulinum* C fragment sequences).

b) Expression Of *C. botulinum* C Fragment Fusion Proteins In *E. coli*

Large scale (1 liter) cultures of the pMAL-c vector, and each recombinant construct described above in (a) were grown, induced, and soluble protein fractions were isolated as described in Example 18. The soluble protein extracts were chromatographed on amylose affinity columns to isolate recombinant fusion protein. The purified recombinant fusion proteins were analyzed by running samples on SDS-PAGE gels followed by Coomassie staining and by Western blot analysis as described [Williams et al, (1994) supra]. In brief, extracts were prepared and chromatographed in column buffer (10 mM NaPO$_4$, 0.5 M NaCl, 10 mM β-mercaptoethanol, pH 7.2) over an amylose resin (New England Biolabs) column, and eluted with column buffer containing 10 mM maltose as described [Williams, et al. (1994), supra]. An SDS-PAGE gel containing the purified protein samples stained with Coomassie blue is shown in FIG. 26.

Figure 26:
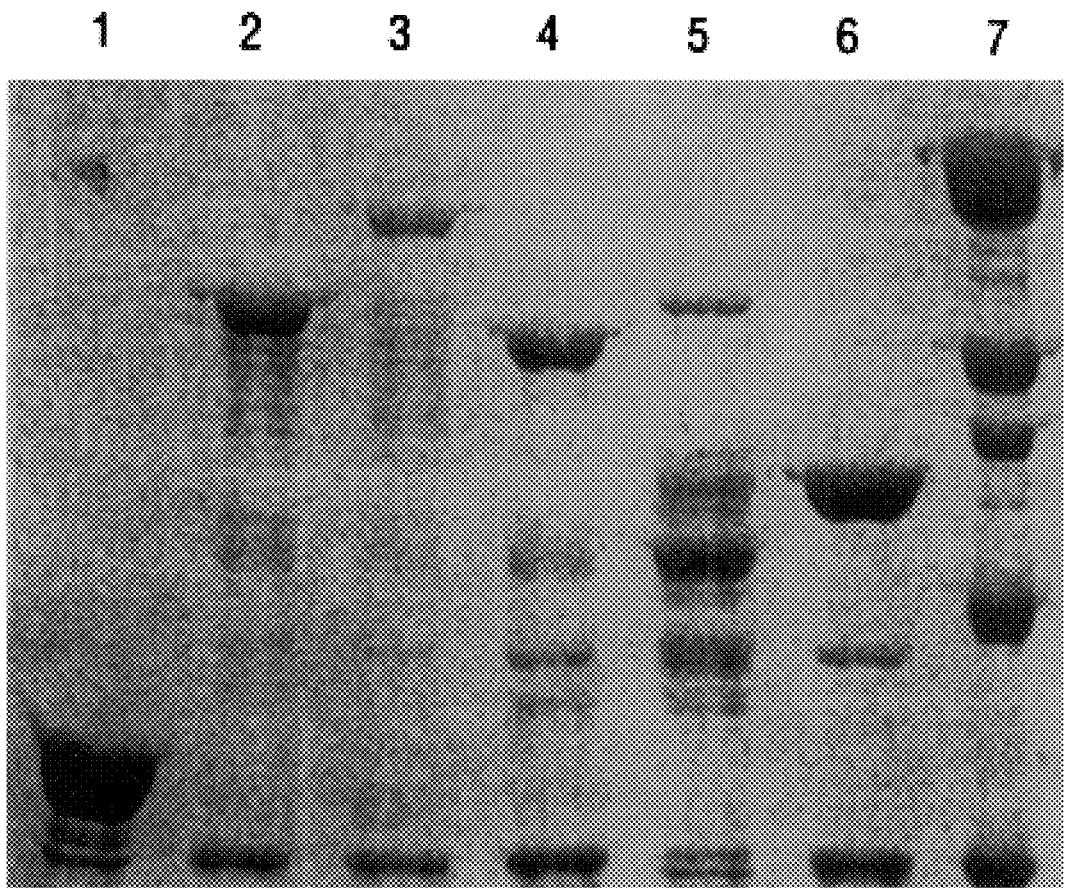
FIG. 26 is an SDS-PAGE gel stained with Coomaisse blue showing the purification of recombinant *C. botulinum* type A toxin fusion proteins.

In FIG. 26, the following samples were loaded. Lanes 1–6 contain protein purified from *E. coli* containing the pMAL-c, pPA1870-2680, pMABot, pMNABot, pMCABot and pMBot plasmids, respectively. Lane 7 contains broad range molecular weight protein markers (BioRad).

The protein samples were prepared for electrophoresis by mixing 5 μl of eluted protein with 5 μl of 2×SDS-PAGE sample buffer (0.125 mM Tris-HCl, pH 6.8, 2 mM EDTA, 6% SDS, 20% glycerol, 0.025% bromophenol blue; β-mercaptoethanol is added to 5% before use). The samples were heated to 95° C. for 5 min, then cooled and loaded on a 7.5% agarose SDS-PAGE gel. Broad range molecular weight protein markers were also loaded to allow estimation of the MW of identified fusion proteins. After electrophoresis, protein was detected generally by staining the gel with Coomassie blue.

In all cases the yields were in excess of 20 mg fusion protein per liter culture (see Table 36) and, with the exception of the pMCABot protein, a high percentage (i.e., greater than 20–50% of total eluted protein) of the eluted fusion protein was of a MW predicted for the full length fusion protein (FIG. 26). It was estimated (by visual inspection) that less than 10% of the pMCABot fusion protein was expressed as the full length fusion protein.

TABLE 36

Yield Of Affinity Purified *C. botulinum* C Fragment/MBP Fusion Proteins

| Construct | Yield (mg/liter of Culture) | Percentage Of Total Soluble Protein |
|---|---|---|
| pMABot | 24 | 5.0 |
| pMCABot | 34 | 5.0 |
| pMNABot | 40 | 5.5 |
| pMBot | 22 | 5.0 |
| pMA1870-2680 | 40 | 4.8 |

These results demonstrate that high level expression of intact *C. botulinum* C fragment/*C. difficile* toxin A fusion proteins in *E. coli* is feasible using the pMAL-c expression system. These results are in contrast to those reported by H. F. LaPenotiere, et al. (1993), supra. In addition, these results show that it is not necessary to fuse the botulinal C fragment gene to the *C. difficile* toxin A gene in order to produce a soluble fusion protein using the pMAL-c system in *E. coli*.

In order to determine whether the above-described botulinal fusion proteins were recognized by anti-*C. botulinum* toxin A antibodies, Western blots were performed. Samples containing affinity-purified proteins from *E. coli* containing the pMABot, pMCABot, pMNABot, pMBot, pMA1870-2680 or pMALc plasmids were analyzed. SDS-PAGE gels (7.5% acrylamide) were loaded with protein samples purified from each expression construct. After electrophoresis, the gels were blotted and protein transfer was confirmed by Ponceau S staining (as described in Example 12b).

Following protein transfer, the blots were blocked by incubation for 1 hr at 20° C. in blocking buffer [PBST (PBS containing 0.1% Tween 20 and 5% dry milk)]. The blots were then incubated in 10 ml of a solution containing the primary antibody; this solution comprised a 1/500 dilution of an anti-*C. botulinum* toxin A IgY PEG prep (described in Example 3) in blocking buffer. The blots were incubated for 1 hr at room temperature in the presence of the primary antibody. The blots were washed and developed using a rabbit anti-chicken alkaline phosphatase conjugate (Boehringer Mannheim) as the secondary antibody as follows. The rabbit anti-chicken antibody was diluted to 1 μg/ml in blocking buffer (10 ml final volume per blot) and the blots were incubated at room temperature for 1 hour in the presence of the secondary antibody. The blots were then washed successively with PBST, BBS-Tween and 50 mM Na2CO$_3$, pH 9.5. The blots were then developed in freshly-prepared alkaline phosphatase substrate buffer (100 μg/ml nitro blue tetrazolium, 50 μg/ml 5-bromo-chloro-indolylphosphate, 5 mM MgCl$_2$ in 50 mM Na$_2$CO$_3$, pH 9.5). Development was stopped by flooding the blots with distilled water and the blots were air dried.

This Western blot analysis detected anti-*C. botulinum* toxin reactive proteins in the pMABot, pMCABot, pMNABot and pMBot protein samples (corresponding to the predicted full length proteins identified above by Coomassie staining in FIG. 26), but not in the pMA1100-2680 or pMALc protein samples.

These results demonstrate that the relevant fusion proteins purified on an amylose resin as described above in section a) contained immunoreactive *C. botulinum* C fragment protein as predicted.

EXAMPLE 23

Generation Of Neutralizing Antibodies By Nasal Administration Of pMBot Protein

The ability of the recombinant botulinal toxin proteins produced in Example 22 to stimulate a systemic immune response against botulinal toxin epitopes was assessed. This example involved: a) the evaluation of the induction of serum IgG titers produced by nasal or oral administration of botulinal toxin-containing *C. difficile* toxin A fusion proteins and b) the in vivo neutralization of *C. botulinum* type A neurotoxin by anti-recombinant *C. botulinum* C fragment antibodies.

a) Evaluation Of The Induction Of Serum IgG Titers Produced By Nasal Or Oral Administration Of Botulinal Toxin-Containing *C. difficile* Toxin A Fusion Proteins Six groups containing five 6 week old CF female rats (Charles River) per group were immunized nasally or orally with one of the following three combinations using protein prepared in Example 22: (1) 250 µg pMBot protein per rat (nasal and oral); 2) 250 µg pMABot protein per rat (nasal and oral); 3) 125 µg pMBot admixed with 125 µg pMA1870-2680 per rat (nasal and oral). A second set of 5 groups containing 3 CF female rats/group were immunized nasally or orally with one of the following combinations (4) 250 µg pMNABot protein per rat (nasal and oral) or 5) 250 µg pMAL-c protein per rat (nasal and oral).

The fusion proteins were prepared for immunization as follows. The proteins (in column buffer containing 10 mM maltose) were diluted in 0.1 M carbonate buffer, pH 9.5 and administered orally or nasally in a 200 µl volume. The rats were lightly sedated with ether prior to administration. The oral dosing was accomplished using a 20 gauge feeding needle. The nasal dosing was performed using a P-200 micro-pipettor (Gilson). The rats were boosted 14 days after the primary immunization using the techniques described above and were bled 7 days later. Rats from each group were lightly etherized and bled from the tail. The blood was allowed to clot at 37° C. for 1 hr and the serum was collected.

The serum from individual rats was analyzed using an ELISA to determine the anti-*C. botulinum* type A toxin IgG serum titer. The ELISA protocol used is a modification of that described in Example 13c. Briefly, 96-well microtiter plates (Falcon, Pro-Bind Assay Plates) were coated with *C. botulinum* type A toxoid (prepared as described in Example 3a) by placing 100 µl volumes of *C. botulinum* type A toxoid at 2.5 µg/ml in PBS containing 0.005% thimerosal in each well and incubating overnight at 4° C. The next morning, the coating suspensions were decanted and all wells were washed three times using PBS.

In order to block non-specific binding sites, 100 µl of blocking solution [0.5% BSA in PBS] was then added to each well and the plates were incubated for 1 hr at 37° C. The blocking solution was decanted and duplicate samples of 150 µl of diluted rat serum added to the first well of a dilution series. The initial testing serum dilution was 1:30 in blocking solution containing 0.5% Tween 20 followed by 5-fold dilutions into this solution. This was accomplished by serially transferring 30 µl aliquots to 120 µl blocking solution containing 0.5% Tween 20, mixing, and repeating the dilution into a fresh well. After the final dilution, 30 µl was removed from the well such that all wells contained 120 µl final volume. A total of 3 such dilutions were performed (4 wells total). The plates were incubated 1 hr at 37° C. Following this incubation, the serially diluted samples were decanted and the wells were washed six times using PBS containing 0.5% Tween 20 (PBST). To each well, 100 µl of a rabbit anti-Rat IgG alkaline phosphatase (Sigma) diluted (¹⁄₁₀₀₀) in blocking buffer containing 0.5% Tween 20 was added and the plate was incubated for 1 hr at 37° C. The conjugate solutions were decanted and the plates were washed as described above, substituting 50 mM $Na_2CO_3$, pH 9.5 for the PBST in the final wash. The plates were developed by the addition of 100 µl of a solution containing 1 mg/ml para-nitro phenyl phosphate (Sigma) dissolved in 50 mM $Na_2CO_3$, 10 mM $MgCl_2$, pH 9.5 to each well, and incubating the plates at room temperature in the dark for 5–45 min. The absorbency of each well was measured at 410 nm using a Dynatech MR 700 plate reader. The results are summarized in Tables 37 and 38 and represent mean serum reactivities of individual mice.

TABLE 37

Determination Of Anti-*C. botulinum* Type A Toxin Serum IgG Titers
Following Immunization With *C. botulinum* C Fragment-Containing Fusion Proteins

| Route of Immunization | | Nasal | | | Oral | | |
|---|---|---|---|---|---|---|---|
| Immunogen | PRE-IMMUNE | pMBot | pMBot & pMA1870-2680 | pMABot | pMBot | pMBot & pMA1870-2680 | pMABot |
| Dilution | | | | | | | |
| 1:30 | 0.080 | 1.040 | 1.030 | 0.060 | 0.190 | 0.080 | 0.120 |
| 1:150 | 0.017 | 0.580 | 0.540 | 0.022 | 0.070 | 0.020 | 0.027 |
| 1:750 | 0.009 | 0.280 | 0.260 | 0.010 | 0.020 | 0.010 | 0.014 |
| 1:3750 | 0.007 | 0.084 | 0.090 | 0.009 | 0.009 | 0.010 | 0.007 |
| # Rats Tested | | 5 | 5 | 5 | 5 | 2 | 2 |

*Numbers represent the average values obtained from two ELISA plates, standardized utilizing the preimmune control.

TABLE 38

Determination Of Anti-*C. botulinum* Type A
Toxin Serum IgG Titers Following Immunization
With *C. botulinum* C Fragment-Containing Fusion Proteins

| Route of immunization | | Nasal | | Oral | |
|---|---|---|---|---|---|
| Immunogen | PRE-IMMUNE | pMBot | pMAbot | pMNABot | pMNABot |
| Dilution | | | | | |
| 1:30 | 0.040 | 0.557 | 0.010 | 0.015 | 0.010 |
| 1:150 | 0.009 | 0.383 | 0.001 | 0.003 | 0.002 |
| 1:750 | 0.001 | 0.140 | 0.000 | 0.000 | 0.000 |
| 1:3750 | 0.000 | 0.040 | 0.000 | 0.000 | 0.000 |
| # Rats Tested | | 1 | 1 | 3 | 3 |

The above ELISA results demonstrate that reactivity against the botulinal fusion proteins was strongest when the route of administration was nasal; only weak responses were stimulated when the botulinal fusion proteins were given orally. Nasally delivered pMbot and pMBot admixed with pMA1870-2680 invoked the greatest serum IgG response. These results show that only the pMBot protein is necessary to induce this response, since the addition of the pMA1870-2680 protein did not enhance antibody response (Table 37). Placement of the *C. difficile* toxin A fragment between the MBP and the *C. botulinum* C fragment protein dramatically reduced anti-bot IgG titer (see results using pMABot, pMCABot and pMNABot proteins).

This study demonstrates that the pMBot protein induces a strong serum IgG response directed against *C. botulinum* type A toxin when nasally administered.

b) In Vivo Neutralization Of *C. botulinum* Type A Neurotoxin By Anti- Recombinant *C. botulinum* C Fragment Antibodies The ability of the anti-*C. botulinum* type A toxin antibodies generated by nasal administration of recombinant botulinal fusion proteins (Example 22) to neutralize *C. botulinum* type A toxin was tested in a mouse neutralization model. The mouse model is the art accepted method for detection of botulinal toxins in body fluids and for the evaluation of anti-botulinal antibodies [E. J. Schantz and D. A. Kautter, J. Assoc. Off. Anal. Chem. 61:96 (1990) and Investigational New Drug (BB-IND-3703) application by the Surgeon General of the Department of the Army to the Federal Food and Drug Administration]. The anti-*C. botulinum* type A toxin antibodies were prepared as follows.

Rats from the group given pMBot protein by nasal administration were boosted a second time with 250 μg pMBot protein per rat and serum was collected 7 days later. Serum from one rat from this group and from a preimmune rat was tested for anti-*C. botulinum* type A toxin neutralizing activity in the mouse neutralization model described below.

The $LD_{50}$ of a solution of purified *C. botulinum* type A toxin complex, obtained from Dr. Eric Johnson (University of Wisconsin Madison), was determined using the intraperitoneal (IP) method of Schantz and Kautter [J. Assoc. Off. Anal. Chem. 61:96 (1978)] using 18–22 gram female ICR mice and was found to be 3500 $LD_{50}$/ml. The determination of the $LD_{50}$ was performed as follows. A Type A toxin standard was prepared by dissolving purified type A toxin complex in 25 mM sodium phosphate buffer, pH 6.8 to yield a stock toxin solution of $3.15 \times 10^7$ $LD_{50}$/mg. The $OD_{278}$ of the solution was determined and the concentration was adjusted to 10–20 μg/ml. The toxin solution was then diluted 1:100 in gel-phosphate (30 mM phosphate, pH 6.4; 0.2% gelatin). Further dilutions of the toxin solution were made as shown below in Table 39. Two mice were injected IP with 0.5 ml of each dilution shown and the mice were observed for symptoms of botulism for a period of 72 hours.

TABLE 39

Determination Of The $LD_{50}$ Of Purified *C. botulinum*
Type A Toxin Complex

| Dilution | Number Dead At 72 hr. |
|---|---|
| 1:320 | 2/2 |
| 1:640 | 2/2 |
| 1:1280 | 2/2 |
| 1:2560 | 0/2 (sick after 72 hr) |
| 1:5120 | 0/2 (no symptoms) |

From the results shown in Table 39, the toxin titer was assumed to be between 2560$LD_{50}$/ml and 1520 $LD_{50}$/ml (or about 3840 $LD_{50}$/ml). This value was rounded to 3500 $LD_{50}$/ml for the sake of calculation.

The amount of neutralizing antibodies present in the serum of rats immunized nasally with pMBot protein was then determined. Serum from two rats boosted with pMBot protein as described above and preimmune serum from one rat was tested as follows. The toxin standard was diluted 1:100 in gel-phosphate to a final concentration of 350 $LD_{50}$/ml. One milliliter of the diluted toxin standard was mixed with 25 μl of serum from each of the three rats and 0.2 ml of gel-phosphate. The mixtures were incubated at room temperature for 30 min with occasional mixing. Each of two mice were injected with IP with 0.5 ml of the mixtures. The mice were observed for signs of botulism for 72 hr. Mice receiving serum from rats immunized with pMBot protein neutralized this challenge dose. Mice receiving preimmune rat serum died in less than 24 hr.

The amount of neutralizing anti-toxin antibodies present in the serum of rats immunized with pMBot protein was then quantitated. Serum antibody titrations were performed by mixing 0.1 ml of each of the antibody dilutions (see Table 40) with 0.1 ml of a 1:10 dilution of stock toxin solution ($3.5 \times 10^4$ $LD_{50}$/ml) with 1.0 ml of gel-phosphate and injecting 0.5 ml IP into 2 mice per dilution. The mice were then observed for signs of botulism for 3 days (72 hr). The results are tabulated in Table 39.

As shown in Table 40 pMBot serum neutralized *C. botulinum* type A toxin complex when used at a dilution of 1:320 or less. A mean neutralizing value of 168 IU/ml was obtained for the pMBot serum (an IU is defined as 10,000 mouse $LD_{50}$). This value translates to a circulating serum titer of about 3.7 IU/mg of serum protein. This neutralizing titer is comparable to the commercially available bottled concentrated (Connaught Laboratories, Ltd.) horse anti-*C. botulinum* antiserum. A 10 ml vial of Connaught antiserum contains about 200 mg/ml of protein; each ml can neutralize 750

TABLE 40

Quantitation Of Neutralizing Antibodies In pMBot Sera

| Dilution | pMBot[a] | |
|---|---|---|
| | Rat 1 | Rat 2 |
| 1:20 | 2/2 | 2/2 |
| 1:40 | 2/2 | 2/2 |
| 1:80 | 2/2 | 2/2 |
| 1:160 | 2/2 | 2/2 |
| 1:320 | 2/2[b] | 2/2[b] |
| 1:640 | 0/2 | 0/2 |
| 1:1280 | 0/2 | 0/2 |
| 1:2560 | 0/2 | 0/2 |

[a]Numbers represent the number of mice surviving at 72 hours which received serum taken from rats immunized with the pMBot protein.
[b]These mice survived but were sick after 72 hr.

IU of *C. botulinum* type A toxin. After administration of one vial to a human, the circulating serum titer of the Connaught preparation would be approximately 25 IU/ml assuming an average serum volume of 3 liters). Thus, the circulating anti-*C. botulinum* titer seen in rats nasally immunized with pMBot protein (168 lU/mi) is 6.7 time higher than the necessary circulation titer of anti-*C. botulinum* antibody needed to be protective in humans.

These results demonstrate that antibodies capable of neutralizing *C. botulinum* type A toxin are induced when recombinant *C. botulinum* C fragment fusion protein produced in *E. coli* is used as an immunogen.

EXAMPLE 24

Production Of Soluble *C. botulinum* C Fragment Protein Substantially Free Of Endotoxin Contamination Example 23 demonstrated that neutralizing antibodies are generated by immunization with the pMBot protein expressed in *E. coli*. These results showed that the pMBot fusion protein is a good vaccine candidate. However, immunogens suitable for use as vaccines should be pyrogen-free in addition to having the capability of inducing neutralizing antibodies. Expression clones and conditions that facilitate the production of *C. botulinum* C fragment protein for utilization as a vaccine were developed.

The example involved: (a) determination of pyrogen content of the pMBot protein; (b) generation of *C. botulinum* C fragment protein free of the MBP; (c) expression of *C. botulinum* C fragment protein using various expression vectors; and (d) purification of soluble *C. botulinum* C fragment protein substantially free of significant endotoxin contamination.

a) Determination Of The Pyrogen Content Of The pMBot Protein

In order to use a recombinant antigen as a vaccine in humans or other animals, the antigen preparation must be shown to be free of pyrogens. The most significant pyrogen present in preparations of recombinant proteins produced in gram-negative bacteria, such as *E. coli*, is endotoxin [F. C. Pearson, *Pyrogens: endotoxins, LAL testing and depyrogentaion*, (1985) Marcel Dekker, New York, pp. 23–56]. To evaluate the utility of the pMBot protein as a vaccine candidate, the endotoxin content in MBP fusion proteins was determined.

The endotoxin content of recombinant protein samples was assayed utilizing the Limulus assay (LAL kit; Associates of Cape Cod ) according to the manufacturer's instructions. Samples of affinity-purified pMal-c protein and pMA1870-2680 were found to contain high levels of endotoxin [>50,000 EU/mg protein; EU (endotoxin unit)]. This suggested that MBP- or toxin A repeat-containing fusions with the botulinal C fragment should also contain high levels of endotoxin. Accordingly, removal of endotoxin from affinity-purified pMal-c and pMBot protein preparations was attempted as follows.

Samples of pMal-c and pMBot protein were depyrogenated with polymyxin to determine if the endotoxin could be easily removed. The following amount of protein was treated: 29 ml at 4.8 $OD_{280}$/ml for pMal-c and 19 mls at 1.44 $OD_{280}$/ml for pMBot. The protein samples were dialyzed extensively against PBS and mixed in a 50 ml tube (Falcon) with 0.5 ml PBS-equilibrated polymyxin B (Affi-Prep Polymyxin, BioRad). The samples were allowed to mix by rotating the tubes overnight at 4° C. The polymyxin was pelleted by centrifugation for 30 min in a bench top centrifuge at maximum speed (approximately 2000×g) and the supernatant was removed. The recovered protein (in the supernatant) was quantified by $OD_{280}$, and the endotoxin activity was assayed by LAL. In both cases only approximately ⅓ of the input protein was recovered and the polymyxin-treated protein retained significant endotoxin contamination (approximately 7000 EU/mg of pMBot).

The depyrogenation experiment was repeated using an independently purified pMal-c protein preparation and similar results were obtained. From these studies it was concluded that significant levels of endotoxin copurifies with these MBP fusion proteins using the amylose resin. Furthermore, this endotoxin cannot be easily removed by polymyxin treatment.

These results suggest that the presence of the MBP sequences on the fusion protein complicated the removal of endotoxin from preparations of the pMBot protein.

b) Generation Of *C. botulinum* C Fragment Protein Free Of The MBP

It was demonstrated that the pMBot fusion protein could not be easily purified from contaminating endotoxin in section a) above. The ability to produce a pyrogen-free (e.g., endotoxin-free) preparation of soluble botulinal C fragment protein free of the MBP tag was next investigated. The pMBot expression construct was designed to facilitate purification of the botulinal C fragment from the MBP tag by cleavage of the fusion protein by utilizing an engineered Factor Xa cleavage site present between the MBP and the botulinal C fragment. The Factor Xa cleavage was performed as follows.

Factor Xa (New England Biolabs) was added to the pMBot protein (using a 0.1–1.0% Factor Xa/pMBot protein ratio) in a variety of buffer conditions [e.g., PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP-40, PBS-C containing either 0.1 or 0.5% Triton X-100, PBS-C containing 0.1% sodium deoxycholate, PBS-C containing 0.1% SDS]. The Factor Xa digestions were incubated for 12–72 hrs at room temperature.

The extent of cleavage was assessed by Western blot or Coomassie blue staining of proteins following electrophoresis on denaturing SDS-PAGE gels, as described in Example 22. Cleavage reactions (and control samples of uncleaved pMBot protein) were centrifuged for 2 min in a microfuge to remove insoluble protein prior to loading the samples on the gel. The Factor Xa treated samples were compared with uncleaved, uncentrifuged pMBot samples on the same gel. The results of this analysis is summarized below.

1) Most (about 90%) pMBot protein could be removed by centrifugation, even when uncleaved control samples were utilized. This indicated that the pMBot fusion protein was not fully soluble (i.e., it exists as a suspension rather than as a solution). [This result was consistent with the observation that most affinity-purified pMBot protein precipitates after long term storage (>2 weeks) at 4° C. Additionally, the majority (i.e., 75%) of induced pMBot protein remains in the pellet after sonication and clarification of the induced *E. coli*. Resuspension of these insoluble pellets in PBS followed by sonication results in partial solubilization of the insoluble pMBot protein in the pellets.]

2) The portion of pMBot protein that is fully in solution (about 10% of pMBot protein) is completely cleaved by Factor Xa, but the cleaved (released) botulinal C fragment is relatively insoluble such that only the cleaved MBP remains fully in solution.

3) None of the above reaction conditions enhanced solubility without also reducing effective cleavage. Conditions that effectively solubilized the cleaved botulinal C fragment were not identified.

4) The use of 0.1% SDS in the buffer used for Factor Xa cleavage enhanced the solubility of the pMBot protein (all of pMBot protein was soluble). However, the presence of the SDS prevented any cleavage of the fusion protein with Factor Xa.

5) Analysis of pelleted protein from the cleavage reactions indicated that both full length pMBot (i.e., uncleaved) and cleaved botulinal C fragment protein precipitated during incubation.

These results demonstrate that purification of soluble botulinal C fragment protein after cleavage of the pMBot fusion protein is complicated by the insolubility of both the pMBot protein and the cleaved botulinal C fragment protein.

c) Expression Of *C. botulinum* C Fragment Using Various Expression Vectors

In order to determine if the solubility of the botulinal C fragment was enhanced by expressing the C fragment protein as a native protein, an N-terminal His-tagged protein or as a fusion with glutathione-S-transferase (GST), alternative expression plasmids were constructed. These expression constructs were generated utilizing the methodologies described in Example 22. FIG. 27 provides a schematic representation of the vectors described below.

In FIG. 27, the following abbreviations are used. pP refers to the pET23 vector. pHIS refers to the pETHisa vector. pBlue refers to the pBluescript vector. pM refers to the pMAL-c vector and pG refers to the pGEX3T vector (described in Example 11). The solid black lines represent *C. botulinum* C fragment gene sequences; the solid black ovals represent the MBP; the hatched ovals represent GST; "HHHHH" represents the poly-histidine tag. In FIG. 27, when the name for a restriction enzyme appears inside parenthesis, this indicates that the restriction site was destroyed during construction. An asterisk appearing with the name for a restriction enzyme indicates that this restriction site was recreated at a cloning junction.

i) Construction Of pPBot

In order to express the *C. botulinum* C fragment as a native (i.e., non-fused) protein, the pPBot plasmid (shown schematically in FIG. 27) was constructed as follows. The C fragment sequences present in pAlterBot (Example 22) were removed by digestion of pAlterBot with NcoI and HindIII. The NcoI/HindIII C fragment insert was ligated to pETHisa vector (described in Example 18b) which was digested with NcoI and HindIII. This ligation creates an expression construct in which the NcoI-encoded methionine of the botulinal C fragment is the initiator codon and directs expression of the native botulinal C fragment. The ligation products were used to transform competent BL21(DE3)pLysS cells (Novagen). Recombinant clones were identified by restriction mapping.

ii) Construction Of pHisBot

In order to express the *C. botulinum* C fragment containing a poly-histidine tag at the amino-terminus of the recombinant protein, the pHisBot plasmid (shown schematically in FIG. 27) was constructed as follows. The NcoI/HindIII botulinal C fragment insert from pAlterbot was ligated into the pETHisa vector which was digested with NheI and HindIII. The NcoI (on the C fragment insert) and NheI (on the pETHisa vector) sites were filled in using the Klenow fragment prior to ligation; these sites were then blunt end ligated (the NdeI site was regenerated at the clone junction as predicted). The ligation products were used to transform competent BL21(DE3)pLysS cells and recombinant clones were identified by restriction mapping.

The resulting pHisBot clone expresses the botulinal C fragment protein with a histidine-tagged N-terminal extension having the following sequence: MetGlyHisHisHisHisHisHisHisHisHisHisHisSerSerGlyHisIleGluGlyArgHis MetAla, (SEQ ID NO:24); the amino acids encoded by the botulinal C fragment gene are underlined and the vector encoded amino acids are presented in plain type. The nucleotide sequence present in the pETHisa vector which encodes the pHisBot fusion protein is listed in SEQ ID NO:25. The amino acid sequence of the pHisBot protein is listed in SEQ ID NO:26.

iii) Construction Of pGBot

The botulinal C fragment protein was expressed as a fusion with the glutathione-S-transferase protein by constructing the pGBot plasmid (shown schematically in FIG. 27). This expression construct was created by cloning the NotI/SalI C fragment insert present in pBlueBot (Example 22) into the pGEX3T vector which was digested with SmaI and XhoI. The NotI site (present on the botulinal fragment) was made blunt prior to ligation using the Klenow fragment. The ligation products were used to transform competent BL21 cells.

Each of the above expression constructs were tested by restriction digestion to confirm the integrity of the constructs.

Large scale (1 liter) cultures of pPBot [BL21(DE3)pLysS host], pHisBot [BL21(DE3)pLysS host] and pGBot (BL21 host) were grown in 2X YT medium and induced (using IPTG to 0.8–1.0 mM) for 3 hrs as described in Example 22. Total, soluble and insoluble protein preparations were prepared from 1 ml aliquots of each large scale culture [Williams et al. (1994), supra] and analyzed by SDS-PAGE. No obvious induced band was detectable in the pPBot or pHisBot samples by Coomassie staining, while a prominent insoluble band of the anticipated MW was detected in the pGBot sample. Soluble lysates of the pGBot large scale (resuspended in PBS) or pHisBot large scale [resuspended in Novagen 1×binding buffer (5 mM imidazole, 0.5 M NaCl, 20 mM Tris-HCl, pH 7.9)] cultures were prepared and used to affinity purify soluble affinity-tagged protein as follows.

The pGBot lysate was affinity purified on a glutathione-agarose resin (Pharmacia) exactly as described in Smith and Corcoran [Current Protocols in Molecular Biology, Supplement 28 (1994), pp. 16.7.1–16.7.7]. The pHisBot protein was purified on the His-Bind resin (Novagen) utilizing the His-bind buffer kit (Novagen) exactly as described by manufacturer.

Samples from the purification of both the pGBot and pHisBot proteins (including uninduced, induced, total, soluble, and affinity-purified eluted protein) were resolved on SDS-PAGE gels. Following electrophoresis, proteins were analyzed by Coomassie staining or by Western blot detection utilizing a chicken anti-C. botulinum Type A toxoid antibody (as described in Example 22).

These studies showed that the pGBot protein was almost entirely insoluble under the utilized conditions, while the pHisBot protein was soluble. Affinity purification of the pHisBot protein on this first attempt was inefficient, both in terms of yield (most of the immunoreactive botulinal protein did not bind to the His-bind resin) and purity (the botulinal protein was estimated to comprise approximately 20% of the total eluted protein).

d) Purification Of Soluble C. botulinum C Fragment Protein Substantially Free Of Endotoxin Contamination The above studies showed that the pHisBot protein was expressed in E. coli as a soluble protein. However, the affinity purification of this protein on the His-bind resin was very inefficient. In order to improve the affinity purification of the soluble pHisBot protein (in terms of both yield and purity), an alternative poly-histidine binding affinity resin (Ni-NTA resin; Qiagen) was utilized. The Ni-NTA resin was reported to have a superior binding affinity ($K_d=1\times10^{-13}$ at pH 8.0; Qiagen user manual) relative to the His-bind resin.

A soluble lysate (in Novagen 1×binding buffer) from an induced 1 liter 2×YT culture was prepared as described above. Briefly, the culture of pHisBot [B121(DE3)pLysS host] was grown at 37° C. to an $OD_{600}$ of 0.7 in 1 liter of 2×YT medium containing 100 µg/ml ampicillin, 34 µg/ml chloramphenicol and 0.2% glucose. Protein expression was induced by the addition of IPTG to 1 mM. Three hours after the addition of the IPTG, the cells were cooled for 15 min in a ice water bath and then centrifuged 10 min at 5000 rpm in a JA10 rotor (Beckman) at 4° C. The pellets were resuspended in a total volume of 40 mls Novagen 1× binding buffer (5 mM imidazole, 0.5 M NaCl, 20 mM Tris-HCl, pH 7.9), transferred to two 35 ml Oakridge tubes and frozen at −70° C. for at least 1 hr. The tubes were thawed and the cells were lysed by sonication (4×20 second bursts using a Branson Sonifier 450 with a power setting of 6–7) on ice. The suspension was clarified by centrifugation for 20 min at 9,000 rpm (10,000×g) in a JA-17 rotor (Beckman).

The soluble lysate was brought to 0.1% NP40 and then was batch absorbed to 7 ml of a 1:1 slurry of Ni-NTA resin:binding buffer by stirring for 1 hr at 4° C. The slurry was poured into a column having an internal diameter of 1 or 2.5 cm (BioRad). The column was then washed sequentially with 15 mls of Novagen 1×binding buffer containing 0.1% NP40, 15 ml of Novagen 1×binding buffer, 15 ml wash buffer (60 mM imidazole, 0.5 M NaCl, 20 mM Tris-HCl, pH 7.9) and 15 ml $NaHPO_4$ wash buffer (50 mM $NaHPO_4$, pH 7.0, 0.3 M NaCl, 10% glycerol). The bound protein was eluted by protonation of the resin using elution buffer (50 mM $NaHPO_4$, pH 4.0, 0.3 M NaCl, 10% glycerol). The eluted protein was stored at 4° C.

Figure 28:
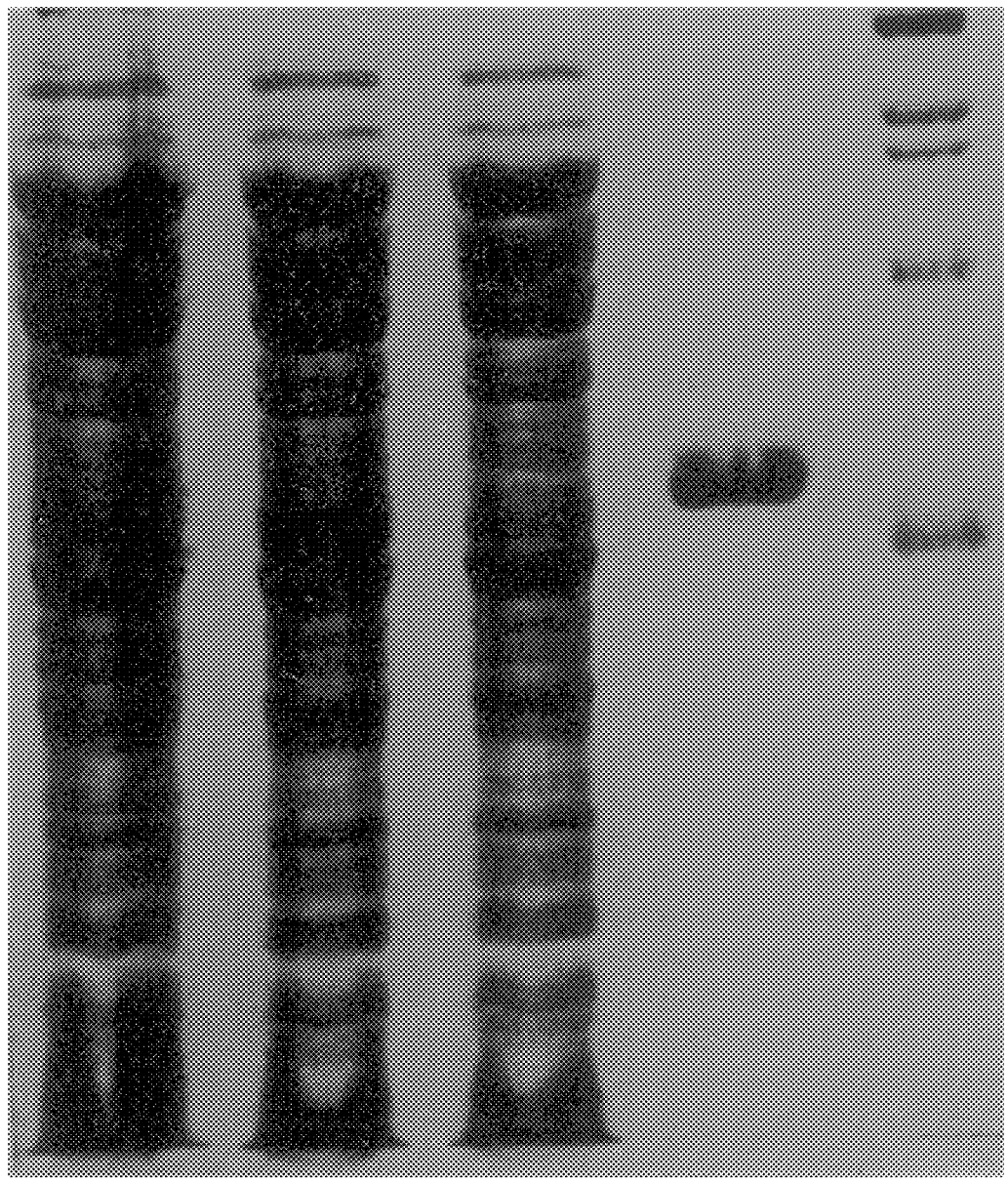
FIG. 28 is an SDS-PAGE gel stained with Coomaisse blue showing the purification of pHisBot protein using the Ni-NTA resin.
Figure 29:
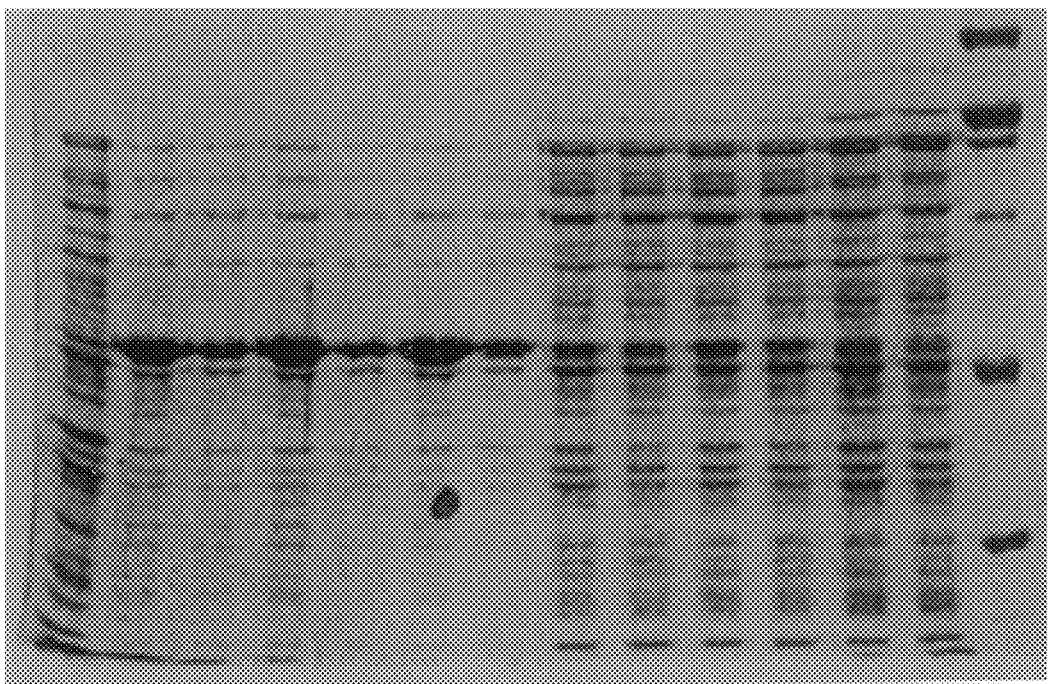
FIG. 29 is an SDS-PAGE gel stained with Coomaisse blue showing the expression of pHisBot protein in BL21(DE3) and BL21(DE3)pLysS host cells.
Figure 30:
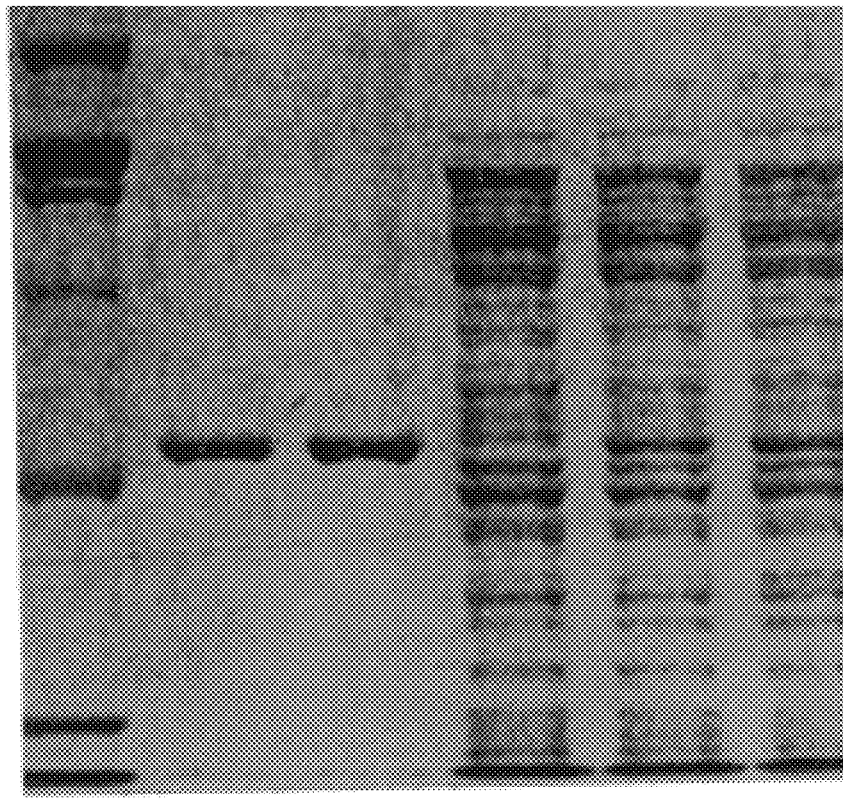
FIG. 30 is an SDS-PAGE gel stained with Coomaisse blue showing the purification of pHisBot protein using a batch absorption procedure.

Samples of total, soluble and eluted protein were resolved by SDS-PAGE. Protein samples were prepared for electrophoresis as described in Example 22b. Duplicate gels were stained with Coomassie blue to visualize the resolved proteins and C. botulinum type A toxin-reactive protein was detected by Western blot analysis as described in Example 22b. A representative Coomassie stained gel is shown in FIG. 28. In FIG. 28, the following samples were loaded on the 12.5% acrylamide gel. Lanes 1–4 contain respectively total protein, soluble protein, soluble protein present in the flow-through of the Ni-NTA column and affinity-purified pHisBot protein (i.e., protein released from the Ni-NTA resin by protonation). Lane 5 contains high molecular weight protein markers (BioRad).

The purification of pHisBot protein resulted in a yield of 7 mg of affinity purified protein from a 1 liter starting culture of BL21(DE3)pLysS cells harboring the pHisBot plasmid. The yield of purified pHisBot protein represented approximately 0.4% of the total soluble protein in the induced culture. Analysis of the purified pHisBot protein by SDS-PAGE revealed that at least 90–95% of the protein was present as a single band (FIG. 28) of the predicted MW (50 kD). This 50 kD protein band was immunoreactive with anti-C. botulinum type A toxin antibodies. The extinction coefficient of the protein preparation was determined to be 1.4 (using the Pierce BCA assay) or 1.45 (using the Lowry assay) $OD_{280}$ per 1 mg/ml solution.

Samples of pH neutralized eluted pHisBot protein were resolved on a KB 803 HPLC column (Shodex). Although His-tagged proteins are retained by this sizing column (perhaps due to the inherent metal binding ability of the proteins), the relative mobility of the pHisBot protein was consistent with that expected for a non-aggregated protein in solution. Most of the induced pHisBot protein was determined to be soluble under the growth and solubilization conditions utilized above (i.e., greater than 90% of the pHisBot protein was found to be soluble as judged by comparison of the levels of pHisBot protein seen in total and soluble protein samples prepared from BL21(DE3)pLysS cells containing the pHisBot plasmid). SDS-PAGE analysis of samples obtained after centrifugation, extended storage at −20° C., and at least 2 cycles of freezing and thawing detected no protein loss (due to precipitation), indicating that the pHisBot protein is soluble in the elution buffer (i.e., 50 mM $NaHPO_4$, pH 4.0, 0.3 M NaCl, 10% glycerol).

Determination of endotoxin contamination in the affinity purified pHisBot preparation (after pH neutralization) using the LAL assay (Associates of Cape Cod) detected no significant endotoxin contamination. The assay was performed using the endpoint chromogenic method (without diazo-coupling) according to the manufacturer's instructions. This method can detect concentrations of endotoxin greater than or equal to 0.03 EU/ml (EU refers to endotoxin units). The LAL assay was run using 0.5 ml of a solution comprising 0.5 mg pHisBot protein in 50 mM $NaHPO_4$, pH 7.0, 0.3 M NaCl, 10% glycerol; 30–60 EU were detected in the 0.5 ml sample. Therefore, the affinity purified pHisBot preparation contains 60–120 EU/mg of protein. FDA Guidelines for the administration of parenteral drugs require that a composition to be administered to a human contain less than 5 EU/kg body weight (The average human body weight is 70 kg; therefore up to 349 EU units can be delivered in a parental dose.). Because very small amount of protein are administered in a vaccine preparation (generally in the range of 10–500 µg of protein), administration of affinity purified pHisBot containing 60–120 EU/mg protein would result in delivery of only a small percentage of the permissible endotoxin load. For example, administration of 10–500 µg of purified pHisBot to a 70 kg human, where the protein preparation contains 60 EU/mg protein, results in the introduction of only 0.6 to 30 EU [i.e., 0.2 to 8.6% of the maximum allowable endotoxin burden per parenteral dose (less than 5 EU/kg body weight)].

The above results demonstrate that endotoxin (LPS) does not copurify with the pHisBot protein using the above purification scheme. Preparations of recombinantly produced pHisBot protein containing lower levels of endotoxin (less than or equal to 2 EU/mg recombinant protein) may be produced by washing the Ni-NTA column with wash buffer until the $OD_{280}$ returns to baseline levels (i.e., until no more UV-absorbing material comes off of the column).

The above results illustrate a method for the production and purification of soluble, botulinal C fragment protein substantially free of endotoxin.

EXAMPLE 25

Optimization Of The Expression And Purification Of pHisBot Protein

The results shown in Example 24d demonstrated that the pHisBot protein is an excellent candidate for use as a vaccine as it could be produced as a soluble protein in *E. coli* and could be purified free of pyrogen activity. In order to optimize the expression and purification of the pHisBot protein, a variety of growth and purification conditions were tested.

a) Growth Parameters i) Host Strains

The influence of the host strain utilized upon the production of soluble pHisBot protein was investigated. A large scale purification of pHisBot was performed [as described in Example 24d above] using the BL21(DE3) host (Novagen) rather than the BL21(DE3)pLysS host. The deletion of the pLysS plasmid in the BL21(DE3) host yielded higher levels of expression due to de-repression of the plasmid's T7-lac promoter. However, the yield of affinity-purified soluble recombinant protein was very low (approximately 600 μg/liter culture) when purified under conditions identical to those described in Example 24d above. This result was due to the fact that expression in the BL21(DE3) host yielded very high level expression of the pHisBot protein as insoluble inclusion bodies as shown by SDS-PAGE analysis of protein prepared from induced BL21(DE3) cultures (FIG. 29, lanes 1–7, described below). These results demonstrate that the pHisBot protein is not inherently toxic to *E. coli* cells and can be expressed to high levels using the appropriate promoter/host combination.

FIG. 29 shows a Coomassie blue stained SDS-PAGE gel (12.5% acrylamide) onto which extracts prepared from BL21(DE3) cells containing the pHisBot plasmid were loaded. Each lane was loaded with 2.5 gl protein sample mixed with 2.5 μl of 2×SDS sample buffer. The samples were handled as described in Example 22b. The following samples were applied to the gel. Lanes 1–7 contain protein isolated from the BL21(DE3) host. Lanes 8–14 contain proteins isolated from the BL21(DE3)pLysS host. Total protein was loaded in lanes 1, 2, 4, 6, 8, 10 and 12. Soluble protein was loaded in Lanes 3, 5, 7, 9, 11 and 13. Lane 1 contains protein from uninduced host cells. Lanes 2–13 contain protein from host cells induced for 3 hours. IPTG was added to a final concentration of 0.1 mM (Lanes 6–7), 0.3 mM (Lanes 4–5) or 1.0 mM (Lanes 2, 3, 8–13). The cultures were grown in LB broth (Lanes 8–9), 2×YT broth (Lanes 10–11) or terrific broth (Lanes 1–7, 12–13). The pHisBot protein seen in Lanes 3, 5 and 7 is insoluble protein which spilled over from Lanes 2, 4 and 6, respectively. High molecular weight protein markers (BioRad) were loaded in Lane 14.

A variety of expression conditions were tested to determine if the BL21(DE3) host could be utilized to express soluble pHisBot protein at suitably high levels (i.e., about 10 mg/ml). The conditions altered were temperature (growth at 37 or 30° C.), culture medium (2×YT, LB or Terrific broth) and inducer levels (0.1, 0.3 or 1.0 mM IPTG). All combinations of these variables were tested and the induction levels and solubility was then assessed by SDS-PAGE analysis of total and soluble extracts [prepared from 1 ml samples as described in Williams et al., (1994), supra].

All cultures were grown in 15 ml tubes (Falcon #2057). All culture medium was prewarmed overnight at the appropriate temperature and were supplemented with 100 μg/ml ampicillin and 0.2% glucose. Terrific broth contains 12 g/l bacto-tryptone, 24 g/l bacto-yeast extract and 100 ml/l of a solution comprising 0.17 M $KH_2PO_4$, 0.72 M $K_2HPO_4$. Cultures were grown in a incubator on a rotating wheel (to ensure aeration) to an $OD_{600}$ of approximately 0.4, and induced by the addition of IPTG. In all cases, high level expression of insoluble pHisBot protein was observed, regardless of temperature, medium or inducer concentration.

The effect of varying the concentration of IPTG upon 2×YT cultures grown at 23° C. was then investigated. IPTG was added to a final concentration of either 1 mM, 0.1 mM, 0.05 mM or 0.01 mM. At this temperature, similar levels of pHis Bot protein was induced in the presence of either 1 or 0.1 mM IPTG; these levels of expression was lower than that observed at higher temperatures. Induced protein levels were reduced at 0.05 mM IPTG and absent at 0.01 mM IPTG (relative to 1.0 and 0.1 mM IPTG inductions at 23° C.). However, no conditions were observed in which the induced pHisBot protein was soluble in this host. Thus, although expression levels are superior in the BL21(DE3) host (as compared to the BL21(DE3)pLysS host), conditions that facilitate the production of soluble protein in this host could not be identified.

These results demonstrate that production of soluble pHisBot protein was achieved using the BL21(DE3)pLysS host in conjunction with the T7-lac promoter.

ii) Effect Of Varying Temperature, Medium And IPTG Concentration And Length Of Induction The effect growing the host cells in various mediums upon the expression of recombinant botulinal protein from the pHisBot expression construct [in the BL21(DE3)pLysS host] was investigated. BL21(DE3)pLysS cells containing the pHisBot plasmid were grown in either LB, 2×YT or Terrific broth at 37° C. The cells were induced using 1 mM IPTG for a 3 hr induction period. Expression of pHisBot protein was found to be the highest when the cells were grown in 2×YT broth (see FIG. 29, lanes 8–13).

The cells were then grown at 30° C. in 2×YT broth and the concentration of IPTG was varied from 1.0, 0.3 or 0.1 mM and the length of induction was either 3 or 5 hours. Expression of pHisBot protein was similar at all 3 inducer concentrations utilized and the levels of induced protein were higher after a 5 hr induction as compared to a 3 hr induction.

Using the conditions found to be optimal for the expression of pHisBot protein, a large scale culture was grown in order to provide sufficient material for a large scale purification of the pHisBot protein. Three 1 liter cultures were grown in 2×YT medium containing 100 μg/ml ampicillin, 34 μg/ml chloramphenicol and 0.2% glucose. The cultures were grown at 30° C. and were induced with 1.0 mM IPTG for a 5 hr period. The cultures were harvested and a soluble lysate were prepared as described in Example 18. A large scale purification was performed as described in Example 24d with the exception that except the soluble lysate was batch absorbed for 3 hours rather than for 1 hour. The final yield was 13 mg pHisBot protein/liter culture. The pHisBot protein represented 0.75% of the total soluble protein.

The above results demonstrate growth conditions under which soluble pHisBot protein is produced (i.e., use of the BL21(DE3)pLysS host, 2×YT medium, 30° C., 1.0 mM IPTG for 5 hours).

b) Optimization Of Purification Parameters

For optimization of purification conditions, large scale cultures (3×1 liter) were grown at 30° C. and induced with 1 mM IPTG for 5 hours as described above. The cultures were pooled, distributed to centrifuge bottles, cooled and pelleted as described in Example 24d. The cell pellets were frozen at −70° C. until used. Each cell pellet represented ⅓ of a liter starting culture and individual bottles were utilized for each optimization experiment described below. This standardized the input bacteria used for each experiment, such that the yields of affinity purified pHisBot protein could be compared between different optimization experiments.

i) Binding Specificity (pH Protonation)

A lysate of pHisBot culture was prepared in PBS (pH 8.0) and applied to a 3 ml Ni-NTA column equilibrated in PBS (pH 8.0) using a flow rate of 0.2 ml/min (3–4 column volumes/hr) using an Econo chromatography system (BioRad). The column was washed with PBS (pH 8.0) until the absorbance ($OD_{280}$) of the elute was at baseline levels. The flow rate was then increased to 2 ml/min and the column was equilibrated in PBS (pH 7.0). A pH gradient (pH 7.0 to 4.0 in PBS) was applied in order to elute the bound pHisBot protein from the column. Fractions were collected and aliquots were resolved on SDS-PAGE gels. The PAGE gels were subjected to Western blotting and the pHisBot protein was detected using a chicken anti-*C. botulinum* Type A toxoid antibody as described in Example 22.

From the Western blot analysis it was determined that the pHisBot protein begins to elute from the Ni-NTA column at pH 6.0. This is consistent with the predicted elution of a His-tagged protein monomer at pH 5.9.

These results demonstrate that the pH at which the pHisBot protein is protonated (released) from Ni-NTA resin in PBS buffer is pH 6.0.

ii) Binding Specificity (Imidazole Competition)

In order to define purification conditions under which the native *E. coli* proteins could be removed from the Ni-NTA column while leaving the pHisBot protein bound to the column, the following experiment was performed. A lysate of pHisBot culture was prepared in 50 mM $NaHPO_4$, 0.5 M NaCl, 8 mM imidazole (pH 7.0). This lysate was applied to a 3 ml Ni-NTA column equilibrated in 50 mM $NaHPO_4$, 0.5 M NaCl (pH 7.0) using an Econo chromatography system (BioRad). A flow rate of 0.2 ml/min (3–4 column volumes/hr) was utilized. The column was washed with 50 mM $NaHPO_4$, 0.5 M NaCl (pH 7.0) until the absorbance of the elute returned to baseline. The flow rate was then increased to 2 ml/min.

The column was eluted using an imidazole step gradient [in 50 mM $NaHPO_4$, 0.5 M NaCl (pH 7.0)]. Elution steps were 20 mM, 40 mM, 60 mM, 80 mM, 100 mM, 200 mM, 1.0 M imidazole, followed by a wash using 0.1 mM EDTA (to strip the nickel from the column and remove any remaining protein). In each step, the wash was continued until the $OD_{280}$ returned to baseline. Fractions were resolved on SDS-PAGE gels, Western blotted, and pHisBot protein detected using a chicken anti-*C. botulinum* Type A toxoid antibody as described in Example 22. Duplicate gels were stained with Coomassie blue to detect eluted protein in each fraction.

The results of the PAGE analysis showed that most of the non-specifically binding bacterial protein was removed by the 20 mM imidiazole wash, with the remaining bacterial proteins being removed in the 40 and 60 mM imidazole washes. The pHisBot protein began to elute at 100 mM imidazole and was quantitatively eluted in 200 mM imidazole.

These results precisely defined the window of imidazole wash stringency that optimally removes *E. coli* proteins from the column while specifically retaining the pHisBot protein in this buffer. These results provided conditions under which the pHisBot protein can be purified free of contaminating host proteins.

iii) Purification Buffers And Optimized Purification Protocols

A variety of purification parameters were tested during the development of an optimized protocol for batch purification of soluble pHisBot protein. The results of these analyses are summarized below.

Batch purifications were performed (as described in Example 24d) using several buffers to determine if alternative buffers could be utilized for binding of the pHisBot protein to the Ni-NTA column. It was determined that quantitative binding of pHisBot protein to the Ni-NTA resin was achieved in either Tris-HCl (pH 7.9) or $NaHPO_4$ (pH 8.0) buffers. Binding of the pHisBot protein in $NaHP0_4$ buffer was not inhibited using 5 mM, 8 mM or 60 mM imidazole. Quantitative elution of bound pHisBot protein was obtained in buffers containing 50 mM $NaHPO_4$, 0.3 M NaCl (pH 3.5–4.0), with or without 10% glycerol. However, quantitation of soluble affinity purified pHisBot protein before and after a freeze thaw (following several weeks storage of the affinity purified elute at −20° C.) revealed that 94% of the protein was recovered using the glycerol-containing buffer, but only 68% of the protein was recovered when the buffer lacking glycerol was employed. This demonstrates that glycerol enhanced the solubility of the pHisBot protein in this low pH buffer when the eluted protein was stored at freezing temperatures (e.g., −20° C.). Neutralization of pH by addition of $NaH_2PO_4$ buffer did not result in obvious protein precipitation.

It was determined that quantitative binding of pHisBot protein using the batch format occurred after 3 hrs (FIG. 30), but not after 1 hr of binding at 4° C. (the resin was stirred during binding). FIG. 30 depicts a Coomaisse blue stained SDS-PAGE gel (7.5% acrylamide) containing samples of proteins isolated during the purification of pHisBot protein from lysate prepared from the BL21(DE3)pLysS host. Each lane was loaded with 5 μl of protein sample mixed with 5 μl of 2×sample buffer and processed as described in Example 22b. Lane 1 contains high molecular weight protein markers (BioRad). Lanes 2 and 3 contain protein eluted from the Ni-NTA resin. Lane 4 contains soluble protein after a 3 hr batch incubation with the Ni-NTA resin. Lanes 5 and 6 contain soluble and total protein, respectively. FIG. 30 demonstrates that the pHisBot protein is completely soluble [compare Lanes 5 and 6 which show that a similar amount of the 50 kD pHisBot protein is seen in both; if a substantial amount (greater than 20%) of the pHisBot protein were partially insoluble in the host cell, more pHisBot protein would be seen in lane 6 (total protein) as compared to lane 5 (soluble protein)]. FIG. 30 also demonstrates that the pHisBot protein is completely removed from the lysate after batch absorption with the Ni-NTA resin for 3 hours (compare Lanes 4 and 5).

The reported high affinity interaction of the Ni-NTA resin with His-tagged proteins ($K_d$=1×$10^{-13}$ at pH 8.0) suggested that it should be possible to manipulate the resin-protein complexes without significant release of the bound protein. Indeed, it was determined that after the recombinant protein was bound to the Ni-NTA resin, the resin-pHisBot protein complex was highly stable and remained bound following repeated rounds of centriftigation of the resin for 2 min at 1600×g. When this centrifugation step was performed in a 50 ml tube (Falcon), a tight resin pellet formed. This allowed the removal of spent soluble lysate by pouring off the supernatant followed by resuspension of the pellet in wash buffer. Further washes can be performed by centrifugation. The ability to perform additional washes permits the development of protocols for batch absorption of large volumes of lysate with removal of the lysate being performed simply by centrifugation following binding of the recombinant protein to the resin.

A simplified, integrated purification protocol was developed as follows. A soluble lysate was made by resuspending the induced cell pellet in binding buffer [50 mM $NaHPO_4$, 0.5 M NaCl, 60 mM imidazole (pH 8.0)], sonicating 4×20 sec and centrifuging for 20 min at 10,000×g. NP-40 was added to 0.1% and Ni-NTA resin (equilibrated in binding buffer) was added. Eight milliliters of a 1:1 slurry (resin:binding buffer) was used per liter of starting culture. The mixture was stirred for 3 hrs at 4° C. The slurry was poured into a column having a 1 cm internal diameter (BioRad), washed with binding buffer containing 0.1% NP40, then binding buffer until baseline was established (these steps may alternatively be performed by centrifugation of the resin, resuspension in binding buffer containing NP40 followed by centrifuigation and resuspension in binding buffer). Imidazole was removed by washing the resin with 50 mM $NaHPO_4$, 0.3M NaCl (pH 7.0). Protein bound to the resin was eluted using the same buffer (50 mM $NaHPO_4$, 0.3M NaCl) having a reduced pH (pH 3.5–4.0).

A pilot purification was performed following this protocol and yielded 18 mg/liter affinity-purified pHisBot. The pHisBot protein was greater than 90% pure as estimated by Coomassie staining of an SDS-PAGE gel. This represents the highest observed yield of soluble affinity-purified pHisBot protein and this protocol eliminates the need for separate imidazole-containing binding and wash buffers. In addition to providing a simplified and efficient protocol for the affinity purification of recombinant pHisBot protein, the above results provide a variety of purification conditions under which pHisBot protein can be isolated.

EXAMPLE 26

The pHisBot Protein Is An Effective Immunogen

In Example 23 it was demonstrated that neutralizing antibodies are generated in mouse serum after nasal immunization with the pMBot protein. However, the pMBot protein was found to copurify with significant amounts of endotoxin which could not be easily removed. The pHisBot protein, in contrast, could be isolated free of significant endotoxin contamination making pHisBot a superior candidate for vaccine production. To further assess the suitability of pHisBot as a vaccine, the immunogenicity of the pHisBot protein was determined and a comparison of the relative immunogenicity of pMBot and pHisBot proteins in mice was performed as follows.

Two groups of eight BALBc mice were immunized with either pMBot protein or pHisBot protein using Gerbu GMDP adjuvant (CC Biotech). pMBot protein (in PBS containing 10 mM maltose) or pHisBot protein (in 50 mM $NaHPO_4$, 0.3 M NaCl, 10% glycerol, pH 4.0) was mixed with Gerbu adjuvant and used to immunize mice. Each mouse received an IP injection of 100 µl antigen/adjuvant mix (50 µg antigen pluy 1 µg adjuvant) on day 0. Mice were boosted as described above with the exception that the route of administration was IM on day 14 and 28. The mice were bled on day 77 and anti-*C. botulinum* Type A toxoid titers were determined using serum collected from individual mice in each group (as described in Example 23). The results are shown in Table 40.

TABLE 40

Anti-*C. botulinum* Type A Toxoid Serum IgG Titers In Individual Mice Immunized With pMBot or pHisBot Protein

| Mouse # | Preimmune[1] Sample Dilution | | | | pMBot[2] Sample Dilution | | | | pHisBot[2] Sample Dilution | | | |
|---|---|---|---|---|---|---|---|---|---|---|---|---|
| | 1:50 | 1:250 | 1:1250 | 1:6250 | 1:50 | 1:250 | 1:1250 | 1:6250 | 1:50 | 1:250 | 1:1250 | 1:620 |
| 1 | | | | | 0.678 | 0.190 | 0.055 | 0.007 | 1.574 | 0.799 | 0.320 | 0.093 |
| 2 | | | | | 1.161 | 0.931 | 0.254 | 0.075 | 1.513 | 0.829 | 0.409 | 0.134 |
| 3 | | | | | 1.364 | 0.458 | 0.195 | 0.041 | 1.596 | 1.028 | 0.453 | 0.122 |
| 4 | | | | | 1.622 | 1.189 | 0.334 | 0.067 | 1.552 | 0.840 | 0.348 | 0.090 |
| 5 | | | | | 1.612 | 1.030 | 0.289 | 0.067 | 1.629 | 1.580 | 0.895 | 0.233 |
| 6 | | | | | 0.913 | 0.242 | 0.069 | 0.013 | 1.485 | 0.952 | 0.477 | 0.145 |
| 7 | | | | | 0.910 | 0.235 | 0.058 | 0.014 | 1.524 | 0.725 | 0.269 | 0.069 |
| 8 | | | | | 0.747 | 0.234 | 0.058 | 0.014 | 1.274 | 0.427 | 0.116 | 0.029 |
| Mean Titer | 0.048 | 0.021 | 0.011 | 0.002 | 1.133 | 0.564 | 0.164 | 0.037 | 1.518 | 0.896 | 0.411 | 0.114 |

[1]The preimmune sample represents the average from 2 sets of duplicate wells containing serum from a individual mouse immunized with recombinant Staphylococcus enterotoxin B (SEB) antigen. This antigen is immunologically unrelated to *C. botulinum* toxin and provides a control serum.
[2]Average of duplicate wells.

The results shown above in Table 40 demonstrate that both the pMBot and pHisBot proteins are immunogenic in mice as 100% of the mice (8/8) in each group serconverted from non-immune to immune status. The results also show that the average titer of anti-*C. botulinum* Type A toxoid IgG is 2–3 fold higher after immunization with the pHisBot protein relative to immunization with the pMBot protein. This suggests that the pHisBot protein may be a superior immunogen to the pMBot protein.

EXAMPLE 27

Immunization With The Recombinant pHisBot Protein Generates Neutralizing Antibodies The results shown in Example 26 demonstrated that both the pHisBot and pMBot proteins were capable of inducing high titers of anti-*C. botulinum* type A toxoid-reactive antibodies in immunized hosts. The ability of the immune sera from mice immunized with either the pHisBot or pMBot proteins to neutralize *C. botulinum* type A toxoid in vivo was determined using the. mouse neutralization assay described in Example 23b.

The two groups of eight BALBc mice immunized with either pMBot protein or pHisBot protein in Example 26 were boosted again one week after the bleeding on day 77. The boost was performed by mixing pMBot protein (in PBS containing 10 mM maltose) or pHisBot protein (in 50 mM $NaHPO_4$, 0.3 M NaCl, 10% glycerol, pH 4.0) with Gerbu adjuvant as described in Example 26. Each mouse received an IP injection of 100 μl antigen/adjuvant mix (50 μg antigen plus 1 μg adjuvant). The mice were bled 6 days after this boost and the serum from mice within a group was pooled. Serum from preimmune mice was also collected (this serum is the same serum described in the footnote to Table 40).

The presence of neutralizing antibodies in the pooled or preimmune serum was detected by challenging mice with 5 $LD_{50}$ units of type A toxin mixed with 100 μl of pooled serum. The challenge was performed by mixing (per mouse to be injected) 100 μl of serum from each pool with 100 μl of purified type A toxin standard (50 $LD_{50}$/ml prepared as described in Example 23b) and 500 μl of gel-phosphate. The mixtures were incubated for 30 min at room temperature with occasional mixing. Each of four mice were injected IP with the mixtures (0.7 ml/mouse). The mice were observed for signs of botulism for 72 hours. Mice receiving toxin mixed with serum from mice immunized with either the pHisBot or pMBot proteins showed no signs of botulism intoxication. In contrast, mice receiving preimmune serum died in less than 24 hours.

These results demonstrate that antibodies capable of neutralizing *C. botulinum* type A toxin are induced when either of the recombinant *C. botulinum* C fragment proteins pHisBot or pMBot are used as immunogens.

EXAMPLE 28

Expression and Purification of Recombinant *C. difficile* Toxin A Proteins Containing the 1870-2680, 1870-2190 and 1960-2680 Interval Previously others had raised antibodies against *C. difficile* toxin A by actively immunizing hamsters against a recombinant polypeptide located within the Interval 6 region [Lyerly, D. M., et al. (1990) Curr. Microbiol. 21:29]. The structure of the recombinant clone used by Lyerly et al. [(1990) Curr. Microbiol. 21:29] is shown schematically in FIG. 31 as pUC1960-2680.

Figure 31:
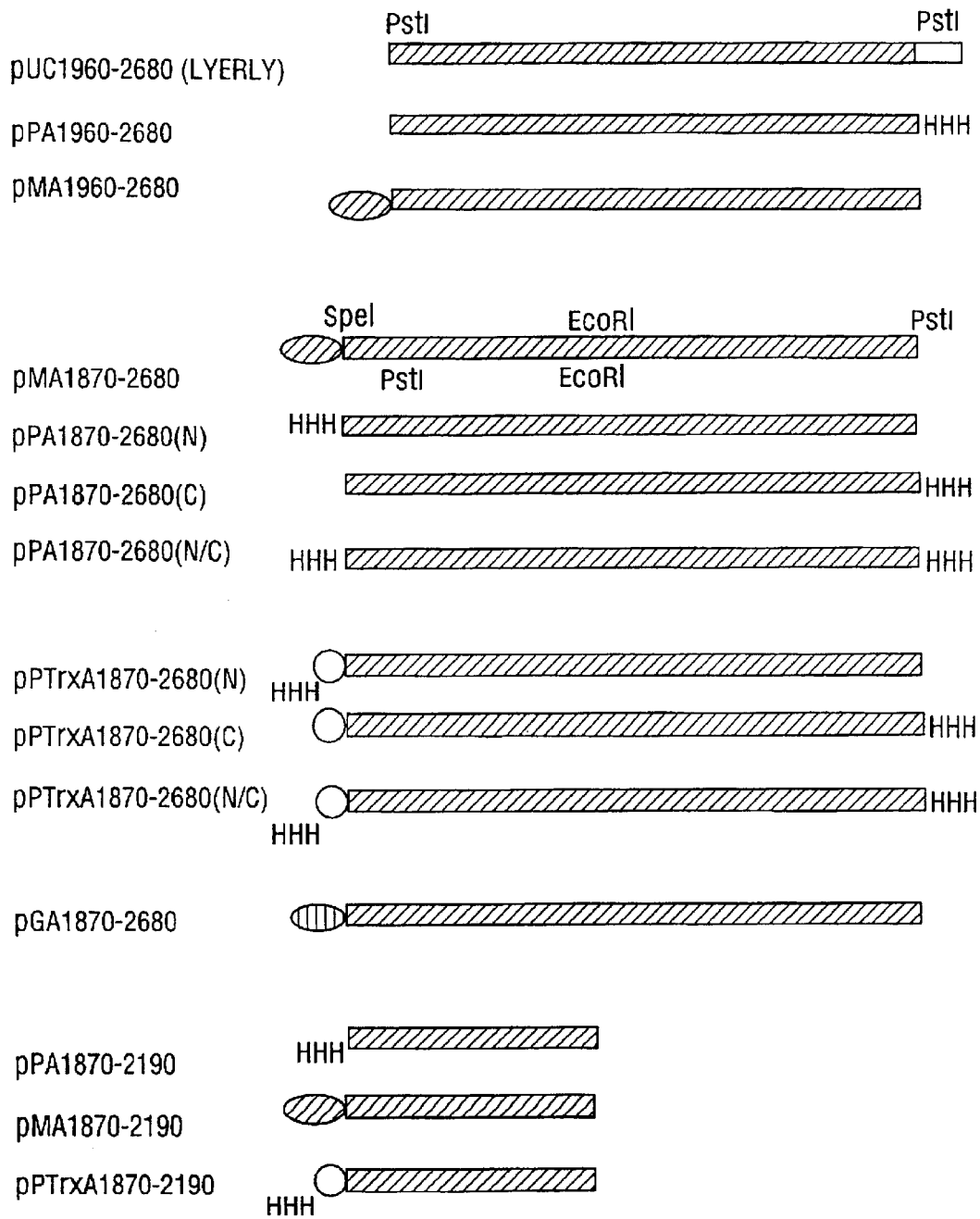
FIG. 31 shows *C. difficile* toxin A expression constructs.

In FIG. 31, the following abbreviations are used. pP refers to the pET23 vector; pM refers to the pMal-c vector; pGEX refers to the pGEX vector; Trx refers to thioredoxin; pUC refers to the pUC9 vector; A refers to *C. difficile* toxin A. The numbers refer to the amino acid interval expressed in a given construct. The solid black boxes represent coding regions; the open box at the 3' end of the pUC1960-2680 construct represents a portion of α-peptide of the lacZ gene which is encoded by vector sequences. The solid ovals represent the MBP. "HHH" represents the poly-histidine tract. The open circles represent thioredoxin. The hatched ovals represent GST.

Using a hamster model of *C. difficile* associated disease (CDAD) where antibodies are given prophylactically, the Lyerly, et al. antibodies (intra-Interval 6; pUC1960-2680) were only able to partially protect hamsters against *C. difficile* infection in terms of survival (4 out of 8 animals survived) and furthermore, these antibodies did not prevent diarrhea in any of the animals. Additionally, animals treated with the intra-Interval 6 antibodies [Lyerly, et al. (1990), supra] died when treatment was removed. In contrast, Example 16 demonstrated that passive administration of anti-Interval 6 antibodies (anti-pMA1870-2680) prevented diarrhea in 6 out of 7 animals and completely prevented death due to CDAD in the prophylactic treatment model system. Furthermore passive administration of the anti-Interval 6 antibodies provided a long lasting cure (i.e., treatment could be withdrawn without incident).

While the antibodies of Lyerly, et al. were reported to provide some protection against CDAD, the integrity and purity of the recombinant protein expressed from the pUC1960-2680 construct was not reported. The pUC1960-2680 construct potentially expresses the 1960-2680 aa interval of *C. difficile* toxin A in the pUC9 vector; this interval is nested within the pMA1870-2680 clone (see FIG. 31).

This example involved: (a) construction of pUC1960-2680 and characterization of the expressed protein by Western blot analysis; (b) cloning and expression of the 1960-2680 interval as an affinity tagged protein in pET and pMal vectors and (c) affinity purification and characterization of soluble MBP tagged proteins from clones expressing the 1870-2680, 1870-2190 or 1960-2680 intervals.

a) Construction of pUC1960-2680 and Characterization of Expressed Protein by Western Blot Analysis The pUC1960-2680 construct contains a 2.1 kb *C. difficile* toxin A gene fragment encoding 33 of the 38 repeat units; this construct was generated to provide the same recombinant protein utilized by Lyerly et al. [(1990) Curr. Microbiol. 21:29] for the generation of anti-*C. difficile* toxin A antibodies. pUC1960-2680 was constructed as follows. Briefly, the 2.1 kb PstI fragment containing the *C. difficile* toxin A repeats was removed from pPA1100-2680 (Example 11) and was cloned into pUC9 which had been digested with PstI and dephosphorylated. The dephosphoryation reaction was performed using calf intestinal alkaline phosphatase (CIP) according to the manufacturers instructions (New England Biolabs). Following restriction digestion and CIP-treatment, the reaction products were resolved on an agarose gel, and the appropriate fragments were excised, mixed, and purified utilizing the Prep-a-Gene kit (BioRad). The eluted DNA was ligated, transformed into JM109 competent cells and recombinant clones isolated, and confirmed by restriction digestion using standard techniques of molecular biology. Plasmid DNA was isolated using the QIA-prep spin plasmid kit (Qiagen).

JM109 containing the pUC1960-2680 construct were grown, induced and total and soluble extracts were prepared as described [Lyerly et al.(1990) *Curr. Microbiol.* 21:29]. Briefly, a 500 ml culture of Terrific broth was inoculated with pUC1960-2680 (in JM109) and grown at 37° C. to early stationary phase (0.8 $OD_{600}$). IPTG was added to a final concentration of 1 mM and the culture was induced for 2 hrs. A 1 ml aliquot of the culture was withdrawn prior to the addition of IPTG and served as the uninduced sample. Following growth in the presence of the IPTG for 2 hr, another 1 ml aliquot of the culture was withdrawn and served as the induced sample. These 1 ml uninduced and induced samples were treated as follows. The bacteria were pelleted by centrifugation. The cell pellets were resuspended in 100 μl 2×sample buffer (0.125 mM Tris-HCl, pH 6.8, 2 mM EDTA 6% SDS, 20% glycerol, 0.25% bromophenol blue; β-mercaptoethanol was added to 5% before use).

The remaining culture was then processed to prepare total and soluble extracts for analysis. The culture was distributed into 500 ml centrifuge bottles. The bottles were cooled for 15 min in a ice water bath and the cells were pelleted by centrifugation at 5,000 rpm in a Beckman JA10 rotor. The cell pellet was resuspended in 1/10 initial culture volume (i.e., 50 ml) of TBS (0.05 M Tris-HCl, 0.15 M NaCl, pH.7.5) and distributed to two 35 ml Oakridge tubes. One and one forth milliliters of a 10 mg/ml solution of lysozyme (in TBS) was added to each tube and the mixtures were incubated on ice for 20 min. The two tubes were stored at −70° C. overnight. One of the two tubes from the induced culture was then thawed and sonicated in ice water using four twenty second bursts (Branson Sonifier Model 450 set at level 5–6). The sample was clarified by centrifugation for 20 min at 9000 rpm (Beckman J2–21 rotor), and the soluble lysate filter sterilized through a 0.45 µm filter. Total (before centrifugation) and soluble (after filter sterilization) extracts were prepared for electrophoresis by mixing 4 µl extract with 16 µl PBS and 20 µl 2×sample buffer.

The protein samples were resolved by electrophoresis on a 12.5% SDS-PAGE gel and the proteins detected either by Coomassie blue staining (detects all proteins) and Western blot analysis (detects specific proteins) utilizing a goat anti-toxin A specific antibody (TechLabs) as follows. The 12.5% SDS-PAGE gels were loaded with the protein samples. After electrophoresis, the gel was bisected. One half was stained with Coomassie blue and the proteins on the other half were transferred to a solid support for Western blot analysis. Protein transfer was confirmed by Ponceau S staining (as described in Example 12b). The blot was then incubated for 1 hr at 20° C. in PBS containing 0.1% Tween 20 (PBST) and 5% milk (blocking buffer). Then 10 ml of a solution comprising a 1/1000 dilution of an affinity purified goat anti-*C. difficile* toxin A antibody (Tech Labs) in blocking buffer was added and the blot was incubated for 1 hr at room temperature. The blot was then washed and the presence of the bound anti-*C. difficile* antibody was detected using a rabbit anti-goat alkaline phosphatase conjugate as secondary antibody as described in Example 3. The resulting Coomassie blue-stained gel and developed Western blot are shown in FIG. 32.

Figure 32:
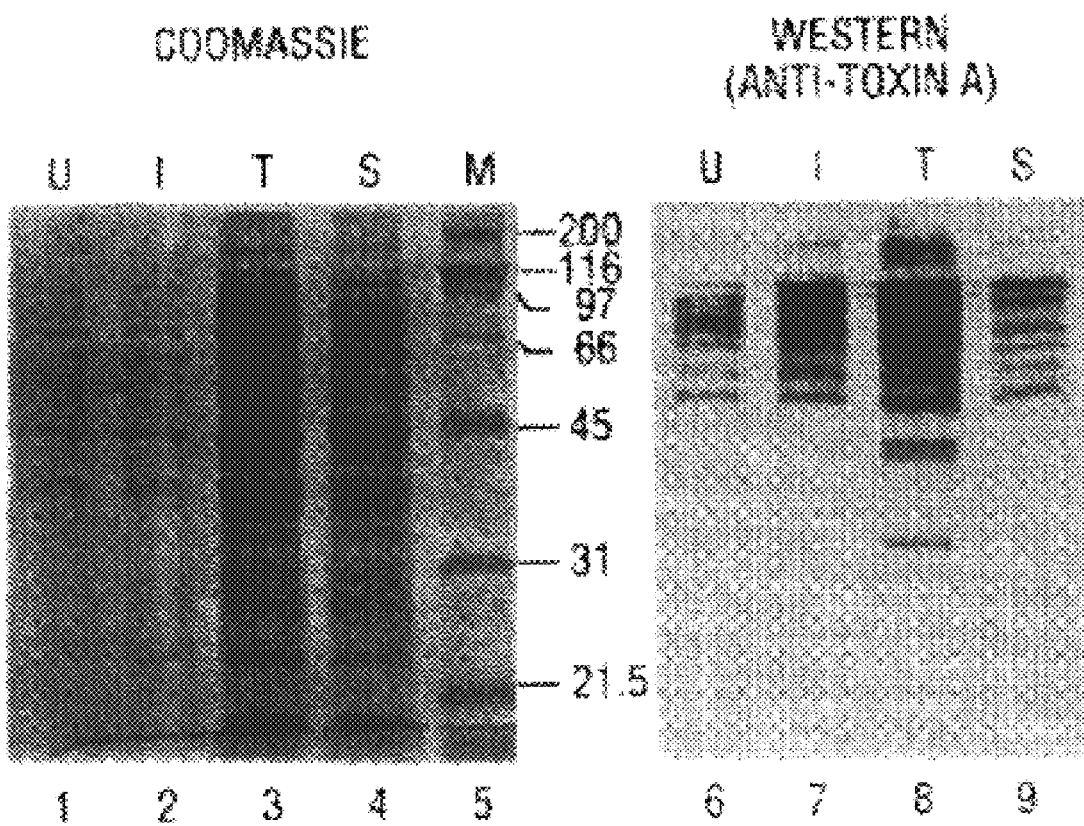
FIG. 32 shows an SDS-PAGE gel stained with Coomaisse blue and a Western blot showing the expression of the pUC1960-2680 in *E. coli* host cells.

In FIG. 32, the Coomassie blue-stained gel is shown on the left (lanes 1–5) and the Western blot is shown on the right (lanes 6–9). The following abbreviations are used: uninduced (U), induced (I), total (T), soluble (S) and broad range molecular weight markers (M; BioRad). The size of the MW markers is indicated by the numbers to the right of lane 5. FIG. 32 shows that no induced bands corresponding to the size expected for the recombinant pUC1960-2680 protein were detectable by Coomassie blue staining. However, Western blot detection of *C. difficile* toxin A-reactive material revealed a predominant, inducible protein species of the predicted MW for the full length recombinant *C. difficile* toxin A protein. Although some induced protein is soluble, the majority of the protein is insoluble [compare the amount of protein reactive with the antibody present in lanes 8 (total) and 9 (soluble)]. The recombinant protein produced by pUC1960-2680 was also clearly unstable, since breakdown products were detected even in the uninduced (lane 6) or induced (lane 7) culture samples.

b) Cloning and Expression of the 1960-2680 Interval as an Affinity Tagged Protein in pET and pMal Vectors As shown above, the protein produced by the pUC1960-2680 construct was unstable (i.e., prone to proteolytic degradation) and furthermore, it lacks an affinity tag. The instability of the pUC1960-2680 protein may be due to the presence of the a-peptide of the lacZ gene at the C terminus of the fusion protein; the presence of these sequences on a fusion protein is known to results in the production of an unstable protein. In order to determine whether soluble, stable, affinity purified fusion protein representing the pUC1960-2680 interval could be isolated, the following two constructs were made. The pPA1960-2680 construct contains the 1960-2680 interval of *C. difficile* toxin A in the pET23c vector (Novagen). The pET23 series of vectors permits the expression of inserted genes as a fusion protein containing a poly-histidine tag or tract at either the C- or N-terminus of the fusion protein; the pPA1960-2680 construct expresses the *C. difficile* toxin A repeat region as a fusion protein containing a C-terminal poly-histidine tract. The pMA1960-2680 construct contains the 1960-2680 interval of *C. difficile* toxin A in the pMal-c vector (New England BioLabs) and expresses a fusion protein comprising the MBP at the N-terminus of the fusion protein.

The pPA1960-2680 construct was made as follows. A pUC1960-2680 clone in which the 2.1 kb PstI fragment was in the opposite transcriptional orientation (relative to the direction of transcription through the LacZ sequences on the vector) was isolated using the methods described in section a). The *C. difficile* toxin A insert was excised by digestion with BamHI and HindIII and the insert was cloned into the pET23c vector (Novagen) digested with BamHI and HindIII as described in section a).

The pMA1960-2680 construct was created by cloning the *C. difficile* toxin A repeat region of pPA1960-2680 as an NheI-HindIII fragment into the pMal-c vector cleaved with XbaI (XbaI ends are compatible with NheI ends) and HindIII.

Expression of recombinant protein from these two plasmids was assessed in small scale cultures grown at 30° C., utilizing the BL21(DE3) pLysS (pPA1960-2680) or BL2lpLysS (pMA1960-2680) hosts. The following conditions were varied: culture broth (2×YT, LB, Terrific broth) and inducer levels (0.1, 0.3 or 1.0 mM IPTG). All combinations of these variables were tested [except in Terrific broth, in which a single concentration (1 mM) of IPTG was tested]. The level of recombinant protein expressed upon induction and the solubility of the recombinant protein was assessed by SDS-PAGE analysis of total and soluble extracts (prepared from 1 ml samples as described in Example 25). All cultures were grown in 15 ml tubes (Falcon 2057); all culture medium was prewarmed overnight at the appropriate temperature, and supplemented with 100 µg/ml ampicillin and glucose to 0.2%. Cultures were grown in a incubator on a rotating wheel (to ensure aeration) to an $OD_{600}$ of approximately 0.5–0.7 and induced with the indicated concentration of IPTG.

In all cases, high level expression of insoluble pPA1960-2680 protein was observed, regardless of the broth or inducer concentration employed. The pMA1960-2680 protein was partially soluble under all tested conditions, with maximal levels of soluble protein produced in 2×YT media at the lower inducer concentrations (i.e., 0.1 and 0.3 mM IPTG).

These results demonstrate that the expression of the 1960-2680 interval of *C. difficile* toxin A in the pPA1960-2680 construct results in the production of insoluble recombinant protein under the conditions tested. The expression of this interval in the pMA1960-2680 construct permitted the expression of some soluble recombinant protein.

c) Affinity Purification and Characterization of Soluble MBP-Tagged Proteins From Constructs Expressing the 1870-2680, 1870-2190 or 1960-2680 Intervals of *C. difficile* Toxin A Large scale (1 liter) cultures of the pMal-c vector (i.e., vector lacking an insert), and each of the following recombinant constructs were grown, induced, and soluble protein fractions isolated: pMA1870-2190 (Example 17), pMA1960-2680 (Example 28b) and pMA1870-2680 [Example 11; Interval 6; Interval 6 contains amino acid residues 1873 through 2684 (SEQ ID NO:29) of the *C. difficile* toxin A protein]. The large scale cultures were grown at 32° C. in 2×YT broth and recombinant protein expression was induced by the addition of IPTG to 0.3 mM at $OD_{600}$ of 0.6. The cultures were induced for 4–5 hrs and then the cells were harvested. Soluble protein extracts were prepared and subjected to affinity chromatography to isolate recombinant fusion protein (Example 11d), and analyzed by Coomassie staining and Western analysis as described (Example 11b).

Briefly, soluble extracts were prepared and applied in PBS to an amylose resin (New England Biolabs) column. The column was eluted with PBS containing 10 mM maltose. Protein yields were 40 mg per 1 liter starting volume (i.e., 1 liter cultures) for each recombinant. Protein samples were analyzed by electrophoresis on 7.5% SDS-PAGE gels followed by staining with Coomassie blue and Western blot analysis as described in section a). Protein samples were prepared for electrophoresis by mixing 1 µl total (T) or soluble (S) protein with 4 µl PBS and 5 µl 2×sample buffer, or 5 µl eluted (E) protein and 5 µl 2×sample buffer or 0.5 µl eluted protein, 4.5 µl PBS and 5 µl 2×sample buffer (1/10E). Samples of pMA1870-2680 and pPA1870-2680 (inclusion body preparations described in Example 11) were also resolved on the gel. The samples were heated to 95° C. for 5 min, then cooled and loaded on a 7.5% SDS-PAGE gel. Broad range molecular weight protein markers (BioRad) were also loaded to allow estimation of the MW of identified fusion proteins.

After electrophoresis, protein was detected by staining the gel with Coomassie blue or the proteins were subjected to Western blotting using a goat anti-toxin A antibody (Tech Labs) as described in section a) above. The resulting gel and Western blot are shown in FIG. 33.

Figure 33:
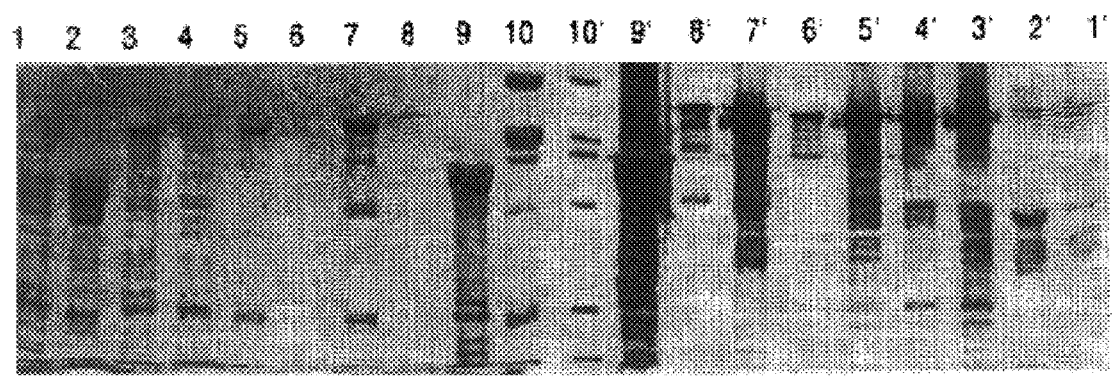
FIG. 33 shows an SDS-PAGE gel stained with Coomaisse blue and a Western blot showing the expression of the several recombinant *C. difficile* toxin A fusion proteins in *E. coli* host cells.

In FIG. 33, the Coomaisse blue-stained gel is shown on the left (lanes 1–10) and the Western blot is shown on the right (lanes 1'–10'). Lanes 1–10 and 1'–10' are mirror images of one another and contain the following samples: lanes 1 and 1' contain pMA1870-2190 (T); lanes 2 and 2' contain pMA1870-2190 (E); lanes 3 and 3' contain pMA1960-2680 (T); lanes 4 and 4' contain pMA1960-2680 (S); lanes 5 and 5' contain pMA1960-2680 (E); lanes 6 and 6' contain pMA1960-2680 (1/10E); lanes 7 and 7' contain pMA1870-2680 (E); lanes 8 and 8' contain pMA1870-2680 (1/10E); lanes 9 and 9' contain pPA1870-2680(N/C) (E) [pPA1870-2680(N/C) is described in Examples 15 and 29d]; and lanes 10 and 10' contain molecular weight markers.

The results shown in FIG. 33 demonstrate:

1) That the pMA1870-2190 protein was unstable but was at least partially soluble under the growth conditions utilized. The affinity purified pMA1870-2190 preparation does however contain significant concentrations of full length fusion protein (FIG. 33, lane 2).

2) The pMA1960-2680 protein was partially soluble (compare lanes 3' and 4' in FIG. 33) and the integrity of the affinity purified protein (FIG. 33, lanes 5' and 6') was comparable to that of the pMA1870-2680 preparation (FIG. 33, lane 2).

3) The full-length pMA1960-2680, pMA1870-2680 and pPA1870-2680 proteins bind the anti-*C. difficile* toxin A antibody, while the full-length pMA1870-2190 protein does not (however, smaller breakdown products of the pMA1870-2190 protein do bind to the antibody as shown in FIG. 33, lanes 1' and 2'). This implies that either the epitopes identified by the antibody are present only in the C terminal end of the repeats, or that the antibodies recognize a conformation that cannot form with the N terminal fragment represented in pMA1870-2190. This observation is similar to the lack of reactivity of N-terminal fragments of the C. dlficile toxin B gene (pMB1750-1970) with anti-toxin B antibody (Tech Labs) on Western blots seen in Example 19b (FIG. 24).

The results shown above provide a method for the production of affinity purified recombinant *C. difficile* toxin A protein from the 1870-2190 and 1960-2680 intervals. These results are in contrast to those obtained when using the pUC1960-2680 construct, which was prepared according to the description of Lyerly et al. [(1990) Curr. Microbiol. 21:29]. The protein expressed by the pUC1960-2680 construct was mainly insoluble and could not be affinity purified due to the absence of an affinity tag on the recombinant protein.

EXAMPLE 29

Purification of Soluble, Substantially Endotoxin-Free pPA1870-2680(N/C) Protein

For potential utilization as a human vaccine (i.e., to induce active immunity) or as an antigen in a host animal to induce protective antibodies (i.e., antitoxin) for passive immunization of humans, a protein antigen should be 1) easily purified, 2) well characterized and of a high purity, 3) pyrogen poor (when used as a human vaccine), 4) immunogenic and 5) capable of inducing a protective immune response. In the case of the *C. difficile* toxin A repeat antigen, the protein must be soluble and capable of assuming a conformation which will induce a protective response. As was shown in Example 17, when pPA1870-2680(N/C) protein, which was expressed as insoluble protein inside inclusion bodies, was solubilized with SDS and then used to immunize chickens, no protective anti-toxin A antibodies were produced.

In this example, the recombinant *C. difficile* toxin A proteins were expressed and evaluated as vaccine candidates using the criteria stated above. This example involved a) evaluation of the utility of affinity purified pMA1870-2680 protein as a vaccine antigen, b) construction, purification and evaluation of the pGA1870-2680 protein, c) development of a protocol for production of soluble pPA1870-2680, d) construction of pPA1870-2680(N) and large scale purification of N, C and N/C his-tagged 1870-2680 protein, e) construction of pPTrxA1870-2680(N) (C) and (N/C), and large scale purification of N, C and N/C his-tagged Trx 1870-2680 proteins, f) large scale affinity purification of pPA1870-2680 and pPB1750-2360 proteins and determination of endotoxin levels and g) construction, large scale affinity purification of pPB1750-2360(N/C) and determination of endotoxin levels.

a) Evaluation of the Utility of Affinity Purified pMA1870-2680 Protein as a Vaccine Antigen Although the pMA1870-2680 protein (Example 11) was shown to be easily purified, immunogenic and capable of inducing a protective response (Example 17), the ability to use this protein as a vaccine is limited by the poor purity of the affinity purified protein (see FIG. 33, lanes 7' and 8'). It was estimated that only 50% of the affinity purified protein represents full-length fusion protein. The remainder of the proteins in the affinity purified preparation was found to be primarily MBP alone and contaminating *E. coli* proteins.

In order to assess whether affinity purified pMA1870-2680 protein could be used as a vaccine candidate, the endotoxin content in two independently affinity purified preparations of pMA1870-2680 protein was determined. Pyrogen content in the samples was assayed utilizing the Limulus assay (LAL kit; Associates of Cape Cod) as described in Example 24d. Both samples of affinity purified pMA1870-2680 were found to contain high levels of endotoxin (>50,000 EU/mg purified recombinant protein). As seen in Examples 24a and b, high endotoxin load was determined to be a general feature of affinity purified MBP fusion proteins, or MBP alone. The above results indicate that, using current purification protocols, affinity purified MBP-*C. difficile* toxin A fusion proteins are not suitable for use as vaccine antigens.

The pMA1870-2680 expression construct was designed to facilitate purification of the toxin A protein from the MBP tag by cleavage of the fusion protein at the engineered Factor Xa cleavage site located between the MBP and toxin A protein domains. The feasibility of obtaining substantially endotoxin-free, soluble recombinant *C. difficile* toxin A protein by purification of cleaved *C. difficile* toxin A protein from the MBP-toxin A fusion protein was assessed. Factor Xa (New England Biolabs) was added to the affinity purified pMA1870-2680 protein (0, 0.2, 0.5, 1.0 and 2.5% Factor Xa/pMA1870-2680 protein ratio) in PBS containing 10 mM maltose and the mixtures were incubated for 5.5 and 20 hrs at room temperature. The extent of cleavage was assessed by Coomassie blue staining proteins after electrophoresis on SDS-PAGE gels.

The results demonstrated that some cleavage was observed in the 2.5% Factor Xa sample after 20 hrs, but cleavage was only partial. This indicates that cleavage of pMA1870-2680 is not an efficient purification strategy to obtain soluble endotoxin-free *C. difficile* toxin A repeat protein using the above tested reaction conditions.

b) Construction, Purification and Evaluation of pG1870-2680 Protein

In order to facilitate evaluation of the GST-containing proteins as a means of large scale production of antigens, the *C. difficile* toxin A repeats were expressed as a fusion with GST. The *C. difficile* toxin A repeats were isolated by cleavage of pPA 1100-2680 (Example 11) with SpeI followed by treatment with the Klenow fragment to fill in the ends; the DNA was then digested with XhoI. The SpeI (Klenow filled)-XhoI fragment was cloned into EcoRI (Klenow filled)-XhoI cleaved pGEX3T vector (Pharmacia) to yield the pGA1870-2680 expression construct.

A large scale (1 liter) 2×YT culture of pGA1870-2680 [in BL21 host cells (Novagen)] was grown in 2×YT medium containing 50 μg/ml ampicillin and induced (using IPTG to 1.0 mM) for 3 hrs at 30° C. as described in Example 28. A soluble lysate of the pGA1870-2680 large scale culture (resuspended in PBS) was prepared, and used to affinity purify soluble affinity tagged protein. The pGA1870-2680 lysate was affinity purified on Glutathione-agarose resin (Pharmacia) as described in [Smith and Corcoran, Current Protocols in Molecular Biology, Suppl. 28 (1994) pp. 16.7.1–16.7.7] with the exception that binding of protein to resin was for 1 hr at 4° C. Briefly, following induction of the 1 liter culture for 3 hrs, the cells were collected by centrifugation for 10 min at 5,000×g at room temperature. The cell pellet was resuspended in 10 ml ice-cold PBS. The cells were then disrupted by sonication as described in Example 24d. Triton X-100 was added to a final concentration of 1% and the sample was well mixed. Insoluble debris was removed by centrifugation of the sample for 5 min at 10,000×g at 4° C. The supernatant was carefully removed and added to 1 ml of 50% slurry of glutathione-agarose beads (Pharmacia). The mixture was allowed incubate for 1 hr at 4° C. to allow the GST-tagged fusion protein to bind to the resin. The glutathione-agarose beads were then washed by adding 50 ml of ice-cold PBS, mixing and centrifuging for 10 sec at 500×g at room temperature. The wash step was repeated twice (for a total of 3 washes). The resin was resuspended in 1 ml of ice-cold PBS and transferred to a 1.5 ml microcentrifuge tube. The resin was pelleted by centrifugation for 10 sec at 500×g at room temperature. The supernatant was removed and the fusion protein was eluted from the washed resin by adding 1 ml of 50 mM Tris-HCl (pH 8.0) and 5 mM reduced glutathione. The tube was mixed gently for 2 min then centrifuged for 10 sec at 500×g at room temperature. The elution was repeated twice and the supernatants were pooled. The pooled supernatant, containing the eluted fusion protein, was stored in a solution containing 50 mM Tris-HCl (pH 8.0), 5 mM reduced glutathione and 10% glycerol. Endotoxin content of the purified fusion protein was determined using the LAL kit as described in Example 24d.

Samples from the growth, induction and purification steps (uninduced, induced, total, soluble, and affinity purified elution) were resolved on SDS-PAGE gels, and proteins detected by staining with Coomassie blue (as described in Example 28). The fusion protein was found to be partially soluble (i.e., most protein remained in the pellet) and approximately 0.5 mg/liter starting culture of mostly full length protein was affinity purified. The affinity purified preparation contained approximately 5000 EU/mg of affinity purified fusion protein. These results demonstrate that under the above conditions, the pGEX expression system did not facilitate high level production of recombinant *C. difficile* toxin A fusion protein, and that the recovered protein contained significant endotoxin contamination.

c) Development of a Protocol for Production of Soluble pPA1870-2680

In Example 11 it was shown that, when produced by growth at 37° C., induced pPA1870-2680 protein is almost entirely insoluble. To determine if expression at a lower temperature could enhance solubility, a culture of pPA1870-2680(N/C) was grown at 30° C. and the level of soluble affinity purifiable protein determined. A soluble lysate (in Novagen 1X binding buffer) from an induced 1 liter 2×YT culture was prepared as described below.

Briefly, a culture of pPA1870-2680(N/C) [in the BL21 (DE3)pLysS host] was grown at 30° C. to an $OD_{600}$ of 0.9 in 1 liter of 2×YT medium containing 100 μg/ml ampicillin, 34 μg/ml chloramphenicol and 0.2% glucose. Protein expression was induced by the addition of IPTG to 1 mM. After a 5 hr induction, the cells were cooled 15 min in a ice water bath and then centrifuged 10 min at 5,000 rpm in a JA10 rotor (Beckman) at 4° C. The pellets were resuspended in a total volume of 40 mls Novagen 1×binding buffer (5 mM imidazole, 0.5 M NaCl, 20 mM Tris-HCl, pH 7.9), transferred to two 35 ml Oakridge tubes and frozen at −70° C. for at least 1 hr. The tubes were thawed and the cells were lysed by sonication (4×20 second bursts) on ice using a Branson Sonifier 450 with a power setting of 6–7. The suspension was clarified by centrifugation for 20 min at 9,000 rpm (10,000×g) in a JA-17 rotor. The soluble lysate (after addition of NP40 to 0.1%) was batch absorbed to 7 ml of a 1:1 slurry of NiNTA resin (Qiagen): binding buffer [50 mM $NaHPO_4$, 0.5 M NaCl, 60 mM imidazole (pH 8.0)] by stirring the mixture for 3 hr at 4° C. The slurry was poured into a column having an internal diameter of 1 cm (BioRad), and washed with the following solutions in succession: 15 mls binding buffer containing 0.1%NP40, 15 ml binding buffer, 15 ml wash buffer (40 mM imidazole, 0.5 M NaCl, 20 mM Tris-HCl, pH 7.9). The bound protein was eluted in 200 mM imidazole, 0.5 M NaCl, 20 mM Tris-HCl, pH 7.9.

Samples of total, soluble, and eluted protein were resolved by SDS-PAGE. Total protein was detected by staining the gel with Coomassie blue. The purification resulted in a yield of 34 mg of affinity purified protein from a 1 liter starting culture (3.2% of the total soluble extract), of which at least 90–95% of the protein was found to migrated as a single band of the predicted MW (90 kd) for the recombinant *C. difficile* toxin A fusion protein [i.e., the pPA1870-2680(N/C) protein].

These results provide a method, utilizing reduced growth temperature, that facilitates the efficient purification of high levels of soluble recombinant *C. difficile* toxin A protein utilizing the pPA1870-2680(N/C) expression plasmid.

d) Construction of pPA1870-2680(N) and Large Scale Purification of N, C and N/C His-Tagged 1870-2680 Protein Expression plasmids that facilitated expression of the 1870-2680 interval of *C. difficile* toxin A with either a N-terminal his-tag [pPA1870-2680 (N)], a C terminal his-tag [pPA1870-2680(C)] or with both N- and C-terminal his-tags [pPA1870-2680(N/C)] were evaluated for large scale production and affinity purification of *C. difficile* toxin A repeat protein.

The features of the pPA1870-2680(C) and pPA1870-2680 (N/C) expression vectors was described in Examples 11 and 15. In Example 11, pPA1870-2680(C) was termed pPA1870-2680 and in Example 15, pPA1870-2680(N/C) was termed pPA1870-2680(H). In order to more clearly identify the location of the poly-histidine tract (his-tag) the plasmids are hereinafter referred to with the (C), (N) and (N/C) suffixes. These three expression plasmids were constructed as follows. pPA1870-2680(C) was constructed by insertion of the *C. difficile* toxin A repeat containing SpeI-HindIII fragment from pPA1000-2680 (Example 11a) into the pET23b vector (Novagen) cleaved with NheI and HindIII.

The pPA1870-2680(N/C) plasmid was constructed by replacement of the pPA1870-2680(C) promoter region, contained on a BglII-NdeI fragment, with the corresponding BglII-NdeI fragment from the pET16b vector (Novagen).

The pPA1870-2680(N) vector was created by digestion of pPA1870-2680(N/C) at the C-terminal HindIII site followed by treatment with the Klenow enzyme to fill-in the cut ends. The blunted plasmid was then circularized by ligation to create pPA1870-2680(N).

Large scale cultures of pPA1870-2680(N) and pPA1870-2680(C) were grown (using the BL21(DE3)pLysS host), induced and soluble protein was affinity purified and eluted as described in section c) above. In each case 10–20 mg affinity purified protein was recovered and the purified protein was found to be greater than 50% full length fusion protein as estimated by SDS-PAGE analysis. However, the bulk of the pPA1860-2680(C) protein eluted in the 40 mM wash buffer. In an attempt to identify wash conditions which did not result in the elution of significant amounts of the pPA1860-2680(C) protein, the following experiment was performed.

A one liter culture of pPA1870-2680(C) was grown as described above and purified utilizing a phosphate buffer based binding, wash and elution buffers. Cells were resuspended in phosphate binding buffer (50 mM NaPO$_4$, 0.5 M NaCl, 5 mM imidazole, pH 8.0) and sequentially washed in phosphate binding buffer containing either 20, 40, or 200 mM imidazole. Recombinant protein eluted in all three washes (5.5 mg, 12.5 mg and 12 mg total protein, respectively) indicating that the C-terminal his-tagged protein is not retained by the resin at 40 mM imidazole concentrations in either buffer system utilized.

The above results demonstrated that soluble, affinity purified *C. difficile* toxin A protein was isolated using any of the pPA1870-2680 (N), (C), or (N/C) expression plasmids.

e) Construction of pPTrxA1870-2680(N) (C) and (N/C) and Large Scale Purification of N, C and N/C His-Tagged Trx 1870-2680 Proteins The thioredoxin (Trx) expression system (Invitrogen) has been developed to facilitate soluble expression of normally insoluble or difficult to express proteins. Genes are cloned into the pTrxFus vector and expressed as fusions with the *E. coli* thioredoxin protein; this linkage often confers the solubility properties of thioredoxin to the fusion protein [La Vallie, et al. (1993) Bio/Technology 11:187]. However, the pTrxFus vector has several undesirable properties for an expression vector. All plasmids must be grown in specific strains and growth media since fusion protein expression in this system is inducible by tryptophan. As well, the promoter is not stringently controlled, such that low level expression of fusion protein occurs at reduced temperatures (i.e., 30° C.). Finally, the expression vector does not contain an affinity tag to facilitate high level affinity purification of soluble fusion protein.

To facilitate construction of IPTG-inducible, affinity tagged Trx fusion proteins, the pETHisTrx vector was constructed. The thioredoxin gene of pTrxFus (Invitrogen) was excised as an NdeI-BamHI DNA fragment and was cloned into NdeI-BamHI digested pETHisb vector (Example 18) to created the pETHisTrx vector.

In the pETHisTrx vector, the Trx gene is expressed from the pET16b promoter and contains the pET16b N-terminal leader and his-tag sequence upstream of Trx, and the pET23b polylinker (from the BamHI site) downstream of the Trx gene for construction of C-terminal genetic fusions. Three expression constructs which facilitate expression of a Trx-toxin A 1870-2680 interval fusion, as N, C or N/C terminal his-tags were constructed as follows.

The pPTrxA1870-2680(N/C) construct was constructed by ligation of the NdeI-BamHI (filled) Trx gene (isolated from the pTrxFus vector) and a SpeI (filled)-XhoI fragment containing the *C. difficile* toxin A 1870-2680 gene [isolated from pPA1100-2680 construct (Example 11)] into the NdeI-XhoI cleaved pETHisb vector (the filled BamHI and SpeI sites blunt end ligate together and create an in-frame Trx-*C. difficile* toxin A fusion).

The above Trx-*C. difficile* toxin A fusion was excised as an NdeI-HindIII fragment and inserted into NdeI-HindIII cleaved pET23a vector (Novagen) to create pPTrxA1870-2680(C).

The HindIII site of pPTrxA1870-2680(N/C) was cleaved, filled-in by treatment with the Klenow enzyme and religated to create pPTrxA1870-2680(N).

The above constructions were carried using standard techniques of molecular biology as described in Example 29.

Large scale cultures of all three TrxA1870-2680 fusions [i.e., pPTrxA1870-2680(C), pPTrxA1870-2680(N) and pPTrxA1870-2680(N/C)] were grown and soluble affinity purified protein was isolated as described in section c) above. In all cases, affinity purified Trx fusion protein yields were similar in terms of solubility, mg/liter culture yields, and purity to the parallel pPA1870-2680 N, C, or N/C constructs described in section d) above.

f) Large Scale Affinity Purification of pPA1870-2680 and pPB1750-2360 Proteins and Determination of Endotoxin Levels Preparations of affinity purified pPA1870-2680(N/C) (Example 15) and pPB1750-2360 (Example 15b) protein were generated to determine the endotoxin levels in the purified samples. All buffers were filter sterilized and gloves were worn through the preparation of the buffers to reduce buffer-mediated endotoxin contamination of the purified recombinant protein samples. Large scale purifications of pPA1870-2680(N/C) and pPB1750-2360 proteins were performed as follows.

Briefly, cultures of pPA1870-2680(N/C) and pPB1750-2360 [in the BL21(DE3)pLysS host] was grown at 30° C. to an OD$_{600}$ of 1.0 in 1 liter of 2×YT medium containing 100 μg/ml ampicillin, 34 μg/ml chloramphenicol and 0.2% glucose. Expression of the recombinant proteins was induced by the addition of IPTG to 0.3 mM. After 5–6 hrs of induction, the cells were for cooled 15 min in a ice water bath and then centrifuged 10 min at 5,000 rpm in a JA10 rotor (Beckman) at 4° C. The cell pellets were frozen at −70° C. overnight and then thawed and resuspended in a total volume of 40 mls binding buffer (5 mM imidazole, 0.5 M NaCl, 50 mM NaPO$_4$, pH 8.0) and transferred to two 35 ml Oakridge tubes. The cells lysed by sonication (8×20 second bursts) on ice using as described in Example 29c. The suspension was clarified by centrifugation for 30 min at 9,000 rpm (10,000×g) in a JA-17 rotor (Beckman). The supernatant was removed (this constitutes the soluble lysate) and NP40 was added to a final concentration of 1%. The soluble lysate (after addition of NP40 to 0.1%) was batch absorbed to 8 ml of a 1:1 slurry of NiNTA resin (Qiagen): binding buffer by stirring for 3 hr at 4° C. The slurry was centrifuged for 1 min at 500×g in 50 ml tube (Falcon), resuspended in 5 mls binding buffer containing 0.1% NP40 and poured into a 2.5 cm diameter column (BioRad). The resin was then washed with 20 mls binding buffer containing 0.1% NP40. The column was attached to a UV monitor (ISCO) and was washed with binding buffer until the baseline was established. Following establishment of the baseline absorbance, the column was washed with wash buffer [20 mM (pPB1750-2360) or 40 mM (pPA1870-2680) imidazole, 0.5 M NaCl, 50 mM NaPO$_4$, pH 8.0] until baseline was reestablished. Imidazole was removed by washing the column with 50 mM NaPO$_4$, 0.3 M NaCl, 10% glycerol, pH 7.0, and the bound proteins were eluted in 50 mM NaPO$_4$, 0.3 M NaCl, 10% glycerol, pH 3.5–4.0. Proteins samples from various stages in the purification process were resolved by electrophoresis on an SDS-PAGE gel;the resulting gel is shown in FIG. 34.

Figure 34:
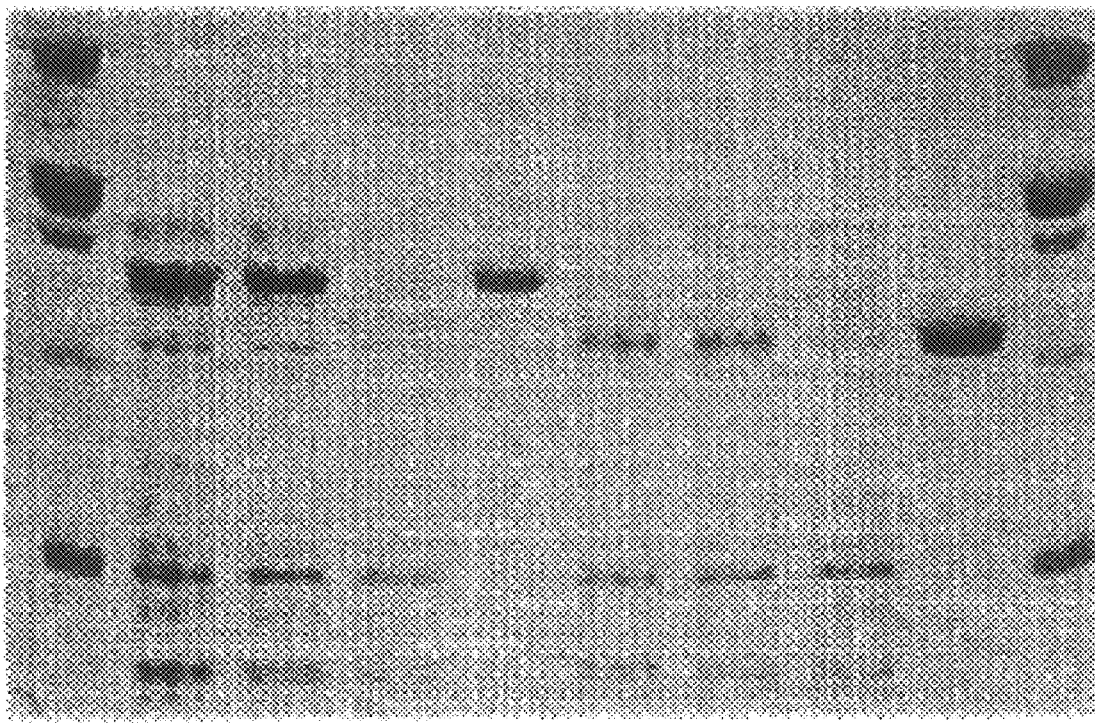
FIG. 34 is an SDS-PAGE gel stained with Coomaisse blue showing the purification of recombinant *C. difficile* toxin A and B fusion proteins.

FIG. 34 shows a Coomassie blue-stained gel showing the steps of the purification. Protein samples were prepared for electrophoresis by mixing 1 μl total (T) or soluble (S) or soluble protein after binding to NiNTA resin and centrifugation (A) protein with 4 μl PBS and 5 μl 2×SDS-PAGE sample buffer, or 5 μl eluted (E) protein and 5 μl 2×sample buffer. The samples were heated to 95° C. for 5 min, then cooled and loaded onto a 7.5% SDS-PAGE gel. Broad range molecular weight protein markers (M; BioRad) were also loaded, to allow the estimation of the MW of identified fusion proteins. After electrophoresis, protein was detected generally by staining the gel with Coomassie blue. In FIG. 34, lanes 1–4 contain protein from the purification of the pPA1870-2680 protein and lanes 5–8 contain protein from the purification of the pPB 1750-2360 protein.

The purification resulted in a yield of approximately 30 mg/liter of affinity purified protein from 1 liter starting cultures (2–2.5% of the total soluble extract) for both proteins, of which at least 90–95% of the protein migrated as a single band of the predicted MW (90 kD) for the recombinant C. difficile toxin A protein. In both cases, most (i.e, greater than 90%) of the induced protein was soluble, and bound the resin quantitatively under the purification conditions utilized.

The endotoxin levels of the purified recombinant proteins was determined using the LAL kit (Example 24d) and was found to be less than 1.0 EU/mg purified protein for pPA1870-2680(N/C), and greater than 250 EU/mg purified protein for pPB1750-2360. The difference in endotoxin levels between these two purified recombinant proteins may reflect the lower stringency wash utilized during the purification of the pPB1750-2360 protein.

g) Construction, Large Scale Affinity Purification of pPB1750-2360(N/C) and Determination of Endotoxin Levels As shown above, the affinity purified pPB1750-2360 protein contained higher levels of endotoxin than did the purified pPA1870-2680(N/C) protein. The pPB1750-2360 protein contains a poly-histidine tract at the carboxy-terminus while pPA1870-2680(N/C) contains a poly-histidine tract at both the amino- and carboxy-termini. The presence of a poly-histidine tract at both ends of the fusion protein permitted higher stringency wash conditions to be employed during the affinity purification of pPA1870-2680 (N/C) as compared to pPB1750-2360 (40 mM imidazole versus 20 mM imidazole, respectively).

In order to produce a fusion protein comprising the 1750-2360 interval of C. difficile toxin B containing poly-histidine tracts at both the amino- and carboxy-termini, pPB1750-2360(N/C) was constructed as follows. pPB1750-2360 (Example 15b) was digested with NdeI and XhoI and the 1.5 kb NdeI/XhoI fragment was isolated and inserted into pETHisb vector (Example 18) digested with NdeI and XhoI. Routine procedures were employed for this construction as described in the preceding Examples.

Large scale purification of pPB1750-2360(N/C) was conducted as described above in section f) for the purification of pPB1750-2360 with the exception that the wash buffer contained 40 mM imidazole, 0.5 M NaCl, 50 mM NaPO$_4$, pH 8.0. Following the wash step, imidazole was removed by washing the column with 50 mM NaPO$_4$, 0.3 M NaCl, 10% glycerol, pH 7.0. The column was then washed with 50 mM NaPO$_4$, 0.3 M NaCl, 10% glycerol, pH 3.0 in an attempt to elute the bound protein. No pPB1750-2360(N/C) was eluted under these conditions.

The large scale purification was then repeated as described above with the exception that following the wash step using the wash buffer containing 40 mM imidazole, 0.5 M NaCl, 50 mM NaPO$_4$, pH 8.0, the bound protein was eluted using a solution containing 200 mM imidazole, 0.5 M NaCl, 50 mM NaPO$_4$, pH 8.0. The imidazole was removed from the eluted protein by dialysis against PBS.

Analysis of the eluted pPB1750-2360(N/C) on SDS-PAGE gels stained with Coomassie blue revealed a single band of the MW expected for the full-length fusion protein.

The endotoxin levels of the purified pPB1750-2360(N/C) protein was determined using the LAL kit (Example 24d). Three separate determinations were conducted and the endotoxin level was found to be 80, 300 or 450 EU/mg of purified recombinant protein. While not limited to any particular mechanism, it is believed that the inconsistent LAL assay results seen with pPB1750-2360(N/C) and the high reading obtained with pPB1750-2360 (see section f) are due to non-specific agglutination of the LAL components by carbohydrate binding moieties present on the C. difficile toxin B sequences present on these proteins. Regardless of whether the actual endotoxin level is 80 or 450 EU/mg purified protein, the affinity purified pPB1750-2360(N/C) preparation represents a substantially endotoxin-free preparation of recombinant protein (Administration of 10 to 500 μg of purified pPB1750-2360(N/C) would result in the introduction of only 4.5 to 225 EU; in a 70 μg human this amount of endotoxin is 1.3 to 64.5% of the maximum permissible dose).

The above results provide a protocol for the affinity purification of substantially endotoxin-free preparations of recombinant C. difficile toxin A and B repeat proteins in high yields.

EXAMPLE 30

Purification of Soluble pPA1870-2680(N/C), pPA1960-2680 and pPA1870-2190 Proteins In Example 29, methods for the production of soluble, substantially endotoxin-free samples of pPA1870-2680(N), (C) or (N/C) were provided which produced proteins that met the initial criteria set for antigen production, that is the proteins were 1) easily purified 2) well characterized and of a high purity and 3) substantially endotoxin-free. In this example, the ability to produce similarly pure antigen from the pPA1870-2190 or pPA1960-2680 expression constructs was examined. This example involved a) large scale purification of soluble pPA1870-2190 and pPA1960-2680 proteins and b) construction of the pPTrxA1870-2190 vector and large scale purification of soluble pPTrxA1870-2190 protein.

a) Large Scale Purification of Soluble pPA1870-2190 and pPA1960-2680 Proteins

Previous attempts to produce soluble affinity purified protein utilizing the pPA1870-2190 (Example 17a) or pPA1960-2680 (Example 28) vectors were unsuccessful, as assessed by analysis of total and soluble protein produced in small scale cultures. However, the solubility properties of a protein determined utilizing small scale or minicultures may not translate to large scale cultures, due to differences in buffers, sonication conditions, etc. Indeed, the successfull expression of soluble, substantially endotoxin-free *C. difficile* toxin A repeat protein utilizing the pPA1870-2680 N, C or N/C constructs suggested that the conditions utilized to solubilize these proteins might also enhance solubility of the pPA1870-2190 and pPA1960-2680 proteins. This hypothesis was tested as follows.

Large scale cultures of pPA1870-2190 and pPA1960-2680 were grown and soluble protein affinity purified on Ni-NTA resin as described in Example 29c. Both the BL21(DE3) and BL21(DE3)pLysS hosts for pPA1960-2680, and the BL21 (DE3)pLysS host for pPA1870-2190 were utilized. The culture of pPA1870-2680(N/C) [in the BL21(DE3)pLysS host] was grown at 30° C. to an $OD_{600}$ of 0.9 in 1 liter of 2×YT medium containing 100 pg/ml ampicillin and 0.2% glucose; when the host utilized harbored the pLysS plasmid, 34 µg/ml chloramphenicol was added to the above medium. Protein expression was induced by addition of IPTG to 1 mM. After 5 hrs of induction, the cells were cooled for 15 min in a ice water bath and then centrifuged for 10 min at 5,000 rpm in a JA10 rotor (Beckman) at 4° C. The pellets were resuspended in a total volume of 40 mls Novagen 1×binding buffer (5 mM imidazole, 0.5 M NaCl, 20 mM Tris-HCl, pH 7.9), transferred to two 35 ml Oakridge tubes and frozen at −70° C. for at least 1 hr. The tubes were thawed and the cells were lysed by sonication (4×20 second bursts using a Branson Sonifer 450 with a power setting of 6-7) on ice. The suspension was clarified by centrifugation for 20 min at 9,000 rpm (10,000×g) in a JA-17 rotor (Beckman) at 4° C. The soluble lysate (after addition of NP40 to 0.1%) was batch absorbed to 7 ml of a 1:1 slurry of NiNTA resin (Qiagen): Novagen 1×binding buffer by stirring for 3 hr at 4° C. The slurry was poured into a 1 cm internal diameter column (BioRad), and washed with the following solutions in succession: 15 mls Novagen 1×binding buffer containing 0.1%NP40, 15 ml Novagen 1×binding buffer, 15 ml wash buffer (40 mM imidazole, 0.5 M NaCl, 20 mM Tris-HCl, pH 7.9). The bound protein was eluted in 200 mM imidazole, 0.5 M NaCl, 20 mM Tris-HCl, pH 7.9.

Samples of total, soluble, and eluted protein (both the 40 mM and 200 mM wash and elution buffers) were resolved by SDS-PAGE. Total protein was detected by Coomassie staining, and *C. difficile* toxin A-reactive protein (in the case of pPA1960-2680) detected by Western blot detection, utilizing affinity purified goat anti-toxin A antibody as described in Example 28.

The results of these analyses showed that for the pPA1870-2190 protein, only 600 µg protein/liter culture was purified in the 200 mM imidazole elution. The *C. difficile* toxin A protein was expressed to high levels with this construct, but most of the induced protein was insoluble. As well, the pPA1870-2190 protein represented less than 10% of the total eluted protein. For the pPA1960-2680 construct, total yields of soluble affinity purified protein was either 1 mg [B121(DE3)pLysS host] or 200 µg [BL21(DE3) host] in the 200 mM elution fraction. Coomassie and Western analysis demonstrated that the pPA1960-2680 protein was expressed to high levels, but that most of the induced protein was insoluble, and that eluted protein preparations contained only approximately 20% *C. difficile* toxin A-reactive protein.

The above results demonstrate that the conditions utilized to solubilize the pPA1870-2680 protein were not successful in generating solubilized *C. difficile* toxin A repeat protein expressed by either the pPA1960-2680 or pPA1870-2190 constructs.

b) Construction of the pPTrxA1870-2190 Plasmid and Large Scale Purification of Soluble Protein To determine if the solubility of recombinant proteins comprising 1870-2680 interval of *C. difficile* toxin A could be enhanced by utilizing the solubilizing properties of the Trx protein, a fusion construct in which the 1870-2680 interval was expressed as a fusion to thioredoxin (Trx) was constructed.

The pPTrxA1870-2190 construct was made in two steps. First, the 1870-2190 interval was cloned into the pTrxFus vector (Invitrogen). This was accomplished by ligating the KpnI-SalI fragment from pMA1870-2190 which contains the 1870-2190 interval of *C. difficile* toxin A into the KpnI-SalI cleaved pTrxFus vector. A recombinant clone containing the appropriate DNA fragments was selected and the sequences encoding the Trx-*C. difficile* toxin A fusion protein were excised utilizing NdeI and SalI, and cloned into the pETHisb vector (Example 18) cleaved with NdeI and XhoI. The resultant construct, pPTrxA1870-2190, contains an N-terminal his-tagged Trx-*C. difficile* toxin A fusion driven by the pET16b promoter.

Purification of soluble affinity purified Trx-*C. difficile* toxin A protein from the pPTrxA1870-2190 construct was performed from a large scale culture as described in section a) above. Total, soluble and elution samples were resolved on a 12.5% SDS-PAGE gel and protein was detected by staining with Coomassie blue.

The results of this analysis revealed that the total yield of affinity purified recombinant protein was 2 mg of greater than 50% pure protein in the 200 mM imidazole elution. This yield of 1 mg specific protein (50% of 2 mg total purified protein) represents a ten fold increase over the yield obtained with the pPA1870-2190 construct (10% of 600 jig, or less than 100 µg specific protein) and demonstrates the solubilizing property of the Trx protein. However, the majority of induced protein was insoluble with both constructs (i.e., pPTrxA1870-2190 and pPA1870-2190) and the overall affinity purifiable protein yield with the pPTrxA1870-2190 vector was still less than 20 fold lower that obtained with the pPA1870-2680 constructs.

EXAMPLE 31

Protection of Hamsters Against *C. difficile* Disease with Avian Antibodies (IgY) Against Recombinant *C. difficile* Toxin A and Toxin B In this example, experiments were performed to determine if orally administered IgY against a recombinant fragment of *C. difficile* toxin A and/or recombinant *C. difficile* toxin B can effectively prevent hamsters against *C. difficile* disease. This example involved a) the immunization of hens with recombinant *C. difficile* toxin A or B protein, b) purification, detection and quantification of anti-recombinant *C. difficile* toxin A and toxin B IgY and c) in vivo protection infection study using either anti-recombinant *C. difficile* toxin A IgY or a mixture of anti-recombinant *C. difficile* toxin A IgY and anti-recombinant *C. difficile* toxin B IgY.

a) Immunization of Hens with Recombinant *C. difficile* Toxin A or B Proteins

Egg-laying Leghorn hens were each immunized with *C. difficile* toxin A recombinant protein pMA1870-2680 (the 1870-2680 interval of *C. difficile* toxin A is referred to as Interval A-6) or *C. difficile* toxin B recombinant pPB1750-2360 (the 1750-2360 interval of *C. difficile* toxin B is referred to as Interval B-3). Both recombinant proteins were expressed as soluble products and purified as described in Example 28 (pMA1870-2680) and Example 29 (pPB1750-2360). About 1 mg of each recombinant protein was mixed with complete Freund's adjuvant (prepared as described in Example 1) and subcutaneously administered to the hens at multiple sites. The hens were immunized ten times. The first four immunizations were given on Day 1, 14, 21 and 35. The remaining immunizations were then given at 4 week intervals.

b) Purification, Detection and Quantification of Anti-Recombinant *C difficile* Toxin A and Toxin B IgY Eggs were collected about 1 week after the last boost and IgYs were extracted using PEG as described in Example 1. The anti-recombinant *C. difficile* toxin A and B IgYs were resuspended as a 4×PEG concentrate (i.e., resuspended in ¼ of the original yolk volume) in 0.1 M carbonate buffer, pH 9.5. The total protein concentration of both of the 4×IgY concentrates was 20 mg/ml as judged by absorbance at 280 nm. The relative levels of IgY specific for reactivity with the immunogens were detected by ELISA as follows.

Microtiter plates were coated at 100 µl/well with either 0.05 µg/ml of the recombinant *C. difficile* toxin A protein, pPA1870-2680 (Example 11) or 1 µg/ml of the recombinant *C. difficile* toxin B, pPB1750-2360 (Example 18b). The ELISA was performed as described in Example 13c. The results of this analysis revealed that the antibody titers were both greater than 1:125,000. (Antibody titer is defined as the reciprocal of the highest antibody dilution that gives an ELISA signal that is at least 3-fold over pre-immune IgY.) The amount of specific anti-recombinant toxin A and anti-recombinant toxin B IgY was determined by affinity purification as described in Example 15c. The amount of specific anti-recombinant *C. difficile* toxin A and B antibodies present in the anti-pMA1870-2680 and anti-pPB1750-2360 preparations was determined to be about 160 µg/ml and 200 µg/ml, respectively.

c) In Vivo Protection Infection Study Using Either Anti-Recombinant *C. difficile* Toxin A IgY or a Mixture of Anti-Recombinant *C. difficile* Toxin A IgY and Anti-Recombinant *C. difficile* Toxin B IgY An in vivo protection study using antibodies raised against pMA1870-2680 (Example 15) and pPB1750-2360 (Example 18b) was performed using the *C. difficile* -hamster model. This study employed a hamster model which was modified from that used in Example 9, as follows.

Hamsters were predisposed to infection with *C. difficile* by I.P. administration of 1 mg/100 gm body weight of Clindamycin phosphate (Biomol) in 1 ml of sterile water. The Clindamycin was administered I.P. using a 1 ml tuberculin syringe (Terumo). About 20–24 hours later, the hamsters were each infected orally with 1 ml of saline containing 1×10$^4$ *C. difficile* (ATCC 43596). The *C. difficile* was grown for about 48 hours on CCFA (*C. difficile* selective agar) plates (BBL) prior to infection.

Using the above modifications in the hamster model, the time course of infection (in particular, the time of onset of disease) in the hamsters was much more consistent and rapid as compared to the results obtained using the conditions described in Example 9. For the present study, 3 groups of hamsters (Sasco), 8 per group were treated with 2 mls of a 4× concentrate of preimmune or anti-recombinant *C. difficile* toxin A IgY containing 40 mg of total IgY; the amount of specific anti-recombinant *C. difficile* toxin A was approximately 400 µg. The third group was treated with 2 mls of an equal mixture of 4×concentration of IgYs to both recombinant *C. difficile* toxin A and B giving a final specific concentration to each of 2× (the amount of specific anti-recombinant toxin A and B IgY was approximately 200 µg each). The third group, therefore has one-half the amount of specific antibodies to the recombinant *C. difficile* toxin A compared to the anti-recombinant *C. difficile* toxin A only treatment.

Hamsters were treated 3 times daily at roughly 4 hour intervals starting 24-hours prior to infection. The hamsters were treated for 5 days. This was about 1 week less than the treatment period employed in Example 9. The outcome of the present prophylactic treatment study is shown in FIG. 35.

Figure 35:
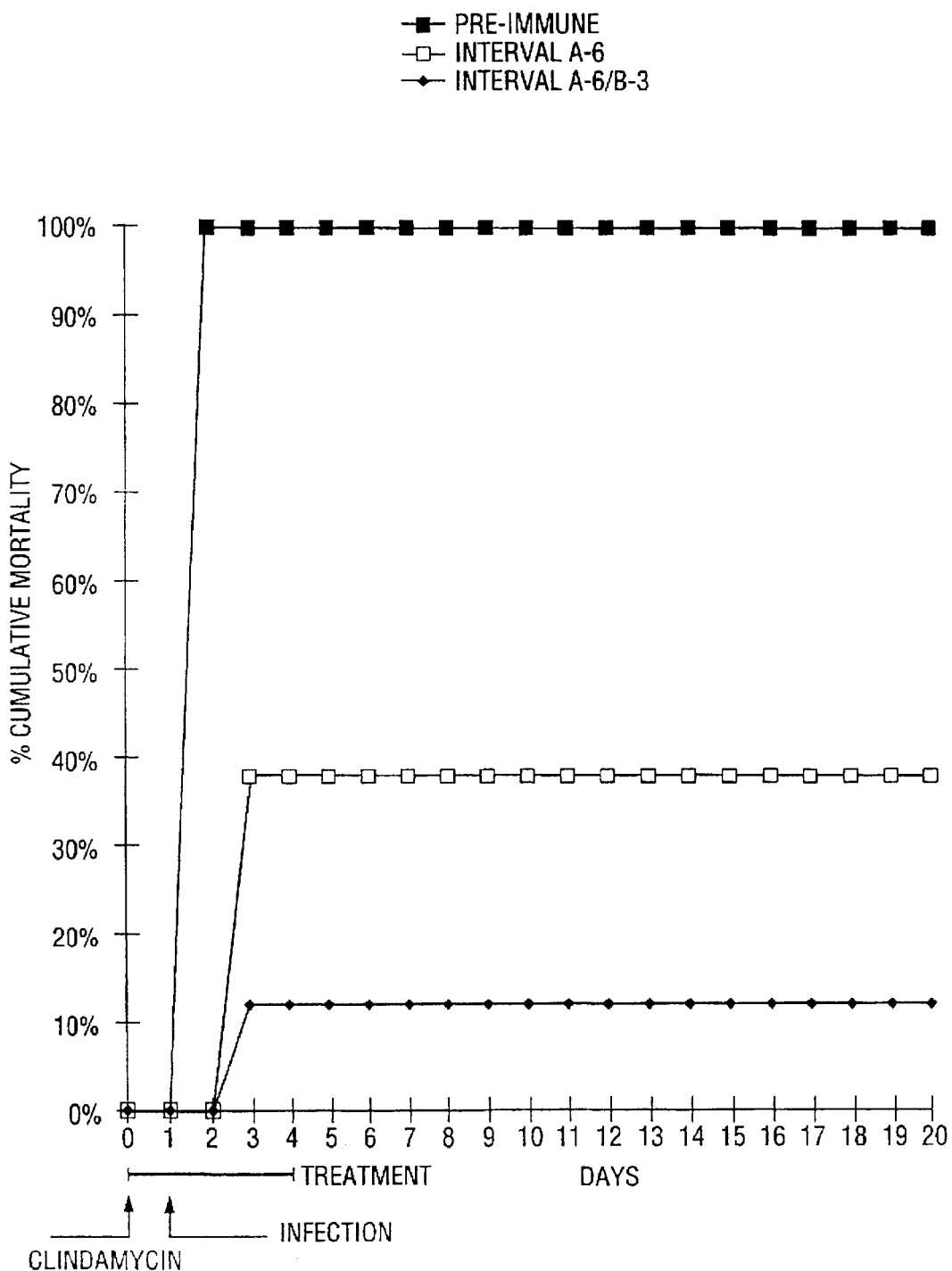
FIG. 35 shows the results of a prophylactic treatment study in hamsters.

In FIG. 35, the percentage cumulative mortality is displayed along the ordinate and the time (in days) is displayed along the abscissa. The treatment period is indicated by the use of the bar between days 0 and 4. The administration of Clindamycin and the inoculation with *C. difficile* (marked as "Infection" in FIG. 35) is indicated. The solid black squares represent hamsters which received pre-immune IgY; the open squares represent hamsters which received anti-recombinant *C. difficile* toxin A IgY (anti-Interval A-6) and the solid black diamonds represent hamsters which received a mixture of anti-recombinant *C. difficile* toxins A and B IgY (anti-Interval A-6/B-3).

The results shown in FIG. 35 demonstrate that under these model conditions, all of the hamsters treated with pre-immune IgY developed diarrhea less than 24-hours post inoculation. One day post inoculation all of the animals were dead in that group. In contrast, using the conditions employed in Example 9, the group treated with pre-immune IgY took several days before the onset of illness was apparent and often not all of the members died from the disease.

As shown in FIG. 35, the hamsters treated with either the anti-recombinant *C. difficile* toxin A IgY (anti-pMA1870-2680) or anti-recombinant *C. difficile* toxin A (anti-pMA1870-2680) and toxin B (anti-pPB1750-2360) mixture were protected from death; 62% and 88% survived from each group, respectively. Chi-squared analysis of the results in the anti-recombinant *C. difficile* toxin A and the mixture treated groups was significant compared to the pre-immune treated group, with P values of less than 0.05 and less than 0.005, respectively. Although the results comparing death as an endpoint between two test groups was not significant (P <0.75), diarrhea in the animals receiving the anti-recombinant *C. difficile* toxin A and B IgY mix was less severe than that seen in the pre-immune control group.

The above results, using a highly aggressive hamster model of CDAD, show that IgYs against a recombinant *C. difficile* toxin A protein (pMA1870-2680) was protective, but the addition of antibodies against the recombinant C. difficile toxin B (pPB1750-2360) provided additional protection (i.e., a lessening of the severity of the disease symptoms).

EXAMPLE 32

Treatment of Hamsters with an Established C. difficile Infection with Avian Antibodies (IgY) Against Recombinant C. difficile Toxin A and Toxin B In order to determine if orally administered IgY against a recombinant C. difficile toxin A protein and /or recombinant C. difficile toxin B can effectively treat hamsters infected with C. difficile, the following experiments were performed. The example involved a) the immunization of hens with recombinant C. difficile toxin A or B proteins b) purification and detection of anti-recombinant C. difficile toxin A and B chicken IgYs c) an in vivo infection study where hamsters were treated with IgYs against either recombinant C. difficile toxin A or recombinant toxin B (Infection study #1). In addition, a mixture of IgY, containing both anti-recombinant toxin A and B was also used to treat hamsters after infection with C. difficile (Infection study #2). The conditions used in infection study #2 were repeated to yield Infection study #3.
a) Immunization of Hens with Recombinant C. difficile Toxin A or B proteins Egg-laying Leghorn hens were each immunized with the recombinant C. difficile toxin A recombinant protein pMA1870-2680 (Interval A-6) or the C. difficile toxin B recombinant pPB1750-2360 (Interval B-3). Each recombinant comprises the repeat regions of C. difficile toxin A and toxin B. Both recombinant proteins were expressed as soluble proteins utilizing the pMal vector for the toxin A recombinant (Example 15) and pET for the toxin B recombinant (Example 18b).

About 1 mg of each recombinant protein was mixed with 500 pg of Fowl adjuvant (RIBI Immunochemical Research) for the C. difficile toxin A recombinant and or Freund's adjuvant (prepared as described in Example 1) for the C. difficile toxin B recombinant. Each hen was subcutaneously immunized about 7 times at roughly two to four week intervals.
b) Purification and Detection of Anti-Recombinant C. difficile Toxin A and B Chicken IgYs Eggs were collected about 1 week after the last boost and antibodies were extracted using PEG as described (Example 1). The IgYs were resuspended as a 8× or 4×concentrate (i.e., resuspension at ⅛ or ¼ yolk volume in 0.1 M carbonate buffer, pH 9.5). The relative levels of specific antibodies to the recombinant immunogens was detected by ELISA as described in Example 13c with the following modifications. The 96-well microtiter plate was coated with 0.05 μg/ml of recombinant toxin A protein pPTrxA1870-2680N/C (Example 29e) or 1 μg/ml of toxin B recombinant pPB1750-2360 (Example 18b) at 100 μl/well. The standard ELISA format to detect anti-recombinant C. difficile toxin A or B was performed (Example 13c). Antibody titers by ELISA were both determined to be greater than 1:125,000.
c) In vivo Infection Study Three Infection Studies, #1, #2 and #3 Were Performed Using the Hamster Model Described in Example 31.

i) Infection Study #1

In the infection study #1, three separate experimental groups, each consisting of 12 Golden Syrian hamsters (Sasco) weighing approximately 80–90 grams each were used. The animals were housed at 3 per cage and were offered food and water ad libitum throughout the study. The hamster model was conducted as described in Example 31. At the start of the study, each hamster was predisposed to infection by the intra-peritoneal administration of Clindamycin-phosphate (Biomol) at 1 mg/100 gm body weight in 1 ml of water using a 1 ml tuberculin syringe (27 gauge needle). Approximately 24 hours later, each animal was orally challenged, using an 18 gauge feeding needle, with 1 ml of C. difficile, (strain ATCC 43596) with approximately $10^3$ to $10^4$ organisms in sterile saline. The organisms were grown for 48 hours on CCFA plates (BBL) prior to infection.

Three hours after inoculation (Day 1), treatment was initiated for both groups. The groups were each orally treated using an 18 gauge feeding needle to administer 2 mls of a 4× concentrate of either pre-immune IgY or specific immune IgY against either the recombinant C. difficile toxin A (pMA1870-2680; Interval A-6) or toxin B (pPB1750-2360; Interval B-3). On Day 1, the hamsters were treated additionally two more times at 2 hour intervals. On Day 2, through 4 the hamsters were each treated with 2 mls of the respective antibody preparations 3 times daily roughly at 4 hour intervals. Each 2 ml dose contained about 40 mg of IgY of which about 400 μg is specific IgY (determined by affinity purification as described in Example 15c) to the recombinant toxin protein or about 1200 μg of specific anti-C. difficile toxin protein per day. All animals were observed for the onset of diarrhea and death during and after the treatment period. The results are shown in FIG. 36.

Figure 36:
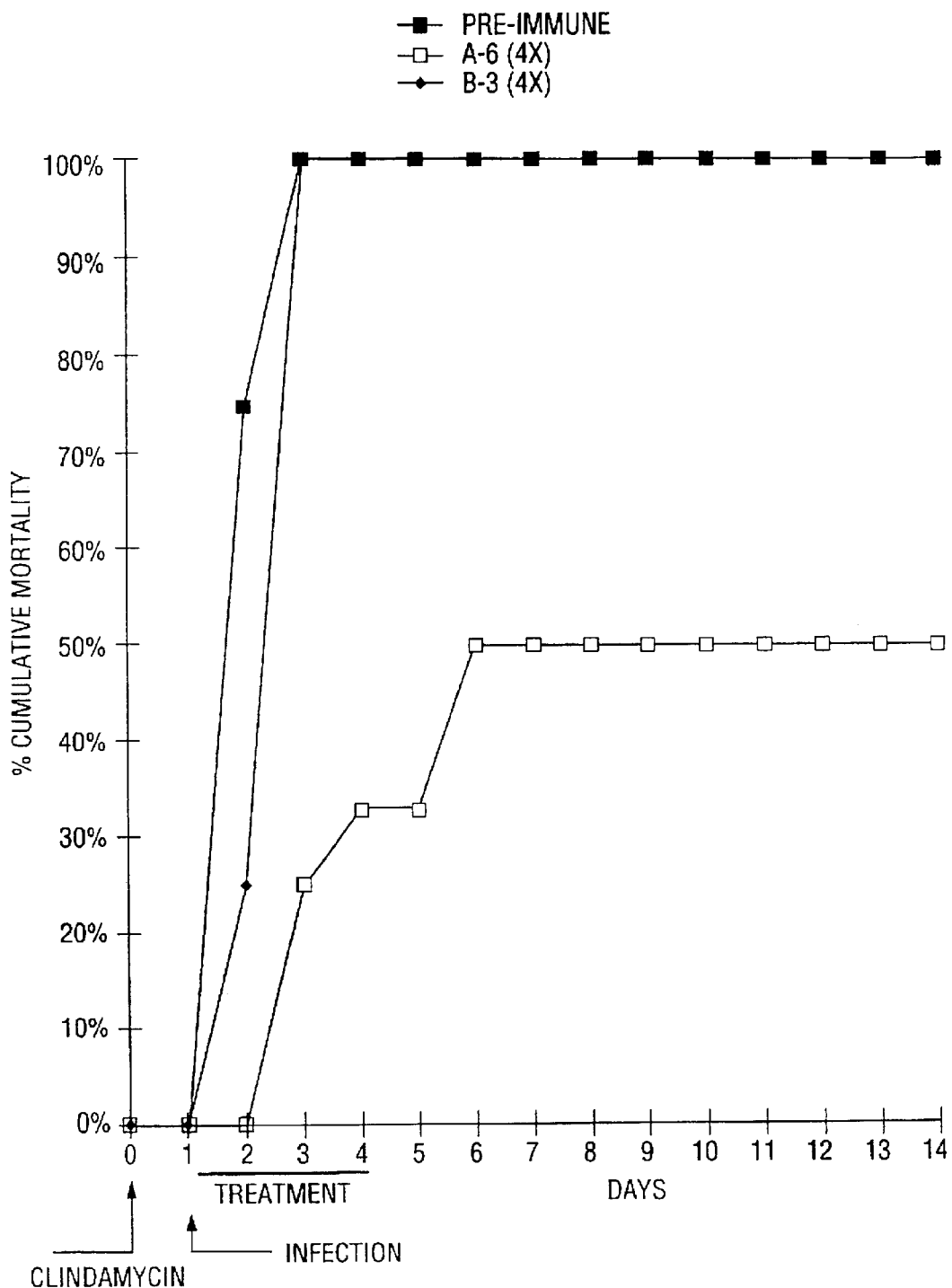
FIG. 36 shows the results of a therapeutic treatment study in hamsters.

In FIG. 36, the percentage cumulative mortality is displayed along the ordinate and the time (in days) is displayed along the abscissa. The treatment period is indicated by the use of the bar between days 1 and 4. The administration of Clindamycin and C. difficile organisms ("Infection") is indicated. The solid black squares represent hamsters which received pre-immune IgY; the open squares represent hamsters which received a 4× preparation of anti-recombinant C. difficile toxin A IgY (anti-Interval A-6) and the solid black diamonds represent hamsters which received a 4× preparation of anti-recombinant C. difficile toxin B IgY (anti-Interval B-3).

The results shown in FIG. 36 demonstrate that half of the hamsters (6/12) treated after infection with antibodies against the C. difficile toxin A recombinant were protected from death from CDAD. The degree of protection in the anti-recombinant C. difficile toxin A group was statistically significant at P<0.025 using Chi-square analysis. Most of the hamsters (10/12) in that group presented with diarrhea. It appeared that at the concentration tested, antibodies against the C. difficile toxin A recombinant was unable to prevent diarrhea in the hamsters. In contrast, all of the pre-immune and anti-recombinant C. difficile toxin B treated hamsters developed diarrhea and died shortly afterward.

The above results demonstrated that IgYs raised against a recombinant C. difficile toxin A protein (pMA1870-2680) can protect the hamsters from death due to CDAD.

ii) Infection Study #2

A second experiment was conducted basically as described above with the exception that a mixture of antibodies to both recombinant C. difficile toxins A and B w a s tested for the ability to protect hamsters from CDAD. Equal volumes of an 8× concentration of IgYs to both recombinants (pMA1870-2680 and pPB1750-2360) were mixed to give a final concentration to each recombinant equal to 4×. Each dose (2 ml) contained approximately 80 mg/ml protein containing about 400 μg of specific IgY (1% specific anti-C. difficile toxin protein as compared to the total) to each recombinant. The amount of specific anti-recombinant IgY to each toxin recombinant was determined by affinity purification using the respective recombinant protein. The resulting preparation therefore contains the same final concentration of anti-recombinant toxin A used in the previous experiment (section c(i) above) except it contains twice the amount of protein. Because of this difference, an additional test group was set-up and treated with equal volumes of two 8× concentration of anti-recombinant *C. difficile* toxin A and pre-immune IgY. As a control, a third group of hamsters were treated with an 8× concentrate of only pre-immune IgY. Nine hamsters per group were infected with 1×10⁴ *C. difficile* organisms (ATCC 43596) and then were treated 4 hours later with 2 mls of either preimmune IgY, anti-recombinant *C. difficile* toxin A IgY mixed with preimmune IgY or a mixture of anti-recombinant *C. difficile* toxin A and B IgYs. The animals were treated as described (section c(i) above) at 3 times a day for 4 days. The outcome of this experiment is shown in FIG. 37.

Figure 37:
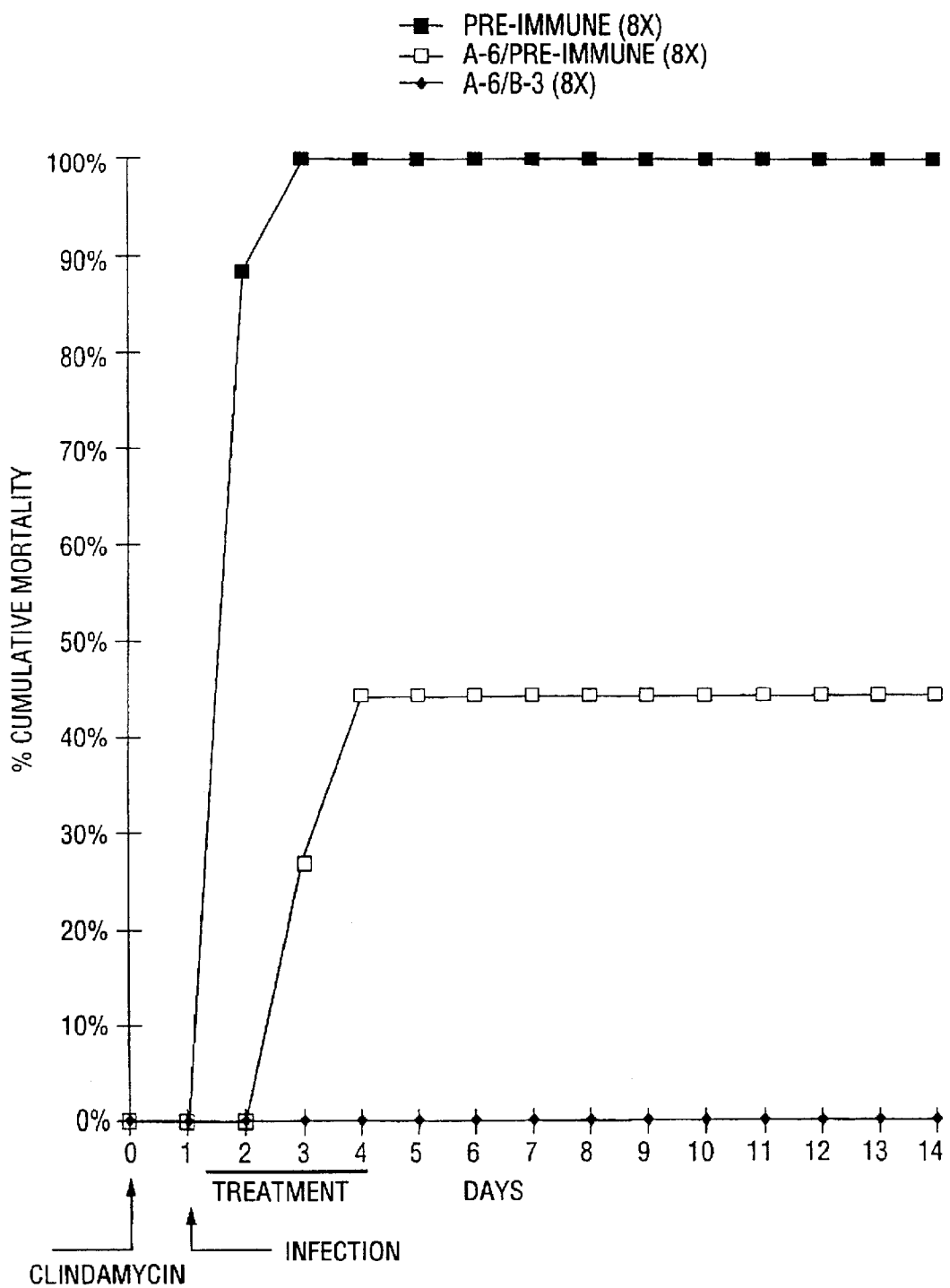
FIG. 37 shows the results of a therapeutic treatment study in hamsters.

In FIG. 37, the percentage cumulative mortality is displayed along the ordinate and the time (in days) is displayed along the abscissa. The treatment period is indicated by the use of the bar between days 1 and 4. The administration of Clindamycin and *C. difficile* organisms ("Infection") is indicated. The solid black squares represent hamsters which received an 8× preparation of pre-immune IgY; the open squares represent hamsters which received a mixture of 8X preparations of pre-immune sera and anti-recombinant *C. difficile* toxin A IgY (anti-Interval A-6) and the solid black diamonds represent hamsters which received a mixture of 8× preparations of anti-recombinant *C. difficile* toxins A and B IgY (anti-Interval A-6 and B-3).

The results shown in FIG. 37 demonstrate that a mixture of IgYs to both recombinant *C. difficile* toxin A and B (pMA1870-2680 and pPB1750-2360) completely protected all the hamsters from death from CDAD. Only ⅓ (3 out of 9) of the animals treated with the mixture of anti *C. difficile* toxin A and B antibodies exhibited diarrhea (one had a very mild case). Hamsters treated with a mixture of anti-recombinant *C. difficile* toxin A antibodies (anti-Interval A-6) and pre-immune IgY were partially protected with a 56% survival rate. All except one hamster in the anti-Interval A-6/pre-imrnmune IgY group presented with diarrhea. The survival rate in this group, was comparable to the rate seen in infection study #1 (50%) using only anti-recombinant *C. difficile* toxin A IgY without the addition of pre-immune IgY. This indicated that the addition of preimmune IgY probably had little or no effect (in terms of non-specific protection from proteases in the GI tract) on the effectiveness of the anti-recombinant *C. difficile* toxin A IgY. As usual, treatment of animals with pre-immune antibodies alone did not protect the hamsters from *C. difficile* infection and all the hamsters died within 2 days post-infection. The survival rates seen due to administration of the anti-recombinant *C. difficile* toxin A IgY and the anti-recombinant *C. difficile* toxins A and B were both statistically significant compared to pre-immune IgY with P values of less than 0.05 and 0.001, respectively. The P-value comparing both recombinant treated groups was less than 0.10.

The survivors in both infection studies #1 and #2 survived lived long-term (i.e., for a period of greater than or equal to 30 days after withdrawal of treatment; animals were euthanized about one month after withdrawal of treatment when the experiment was terminated). Furthermore, no relapse was observed in these animals (relapse is commonly seen in animals, including humans, treated with drugs such as vancomycin or metronidazole to combat *C. difficile* infection). These results represent the first time antibodies raised against recombinants proteins derived from *C. difficile* toxins A and B have been shown to be completely effective in animals given a lethal infection with *C. difficile*.

iii) Infection Study #3

After several more immunizations of the hens with the recombinant *C. difficile* toxin A alone (pMA1870-2680) and *C. difficile* toxin A/B recombinants (a mixture of pMA1870-2680 and pPB1750-2360), the in vivo therapeutic study described above (infection study #2) using the mixture of both antibodies was repeated (infection study #3). Three groups of hamsters, each group consisting of 10 members were treated 4 hours post-infection with either pre-immune IgY, anti-recombinant *C. difficile* toxin A or a mixture of anti-recombinant *C. difficile* toxin A and B IgYs at the same dosages and times outlined above. The results of this study is shown in FIG. 38.

Figure 38:
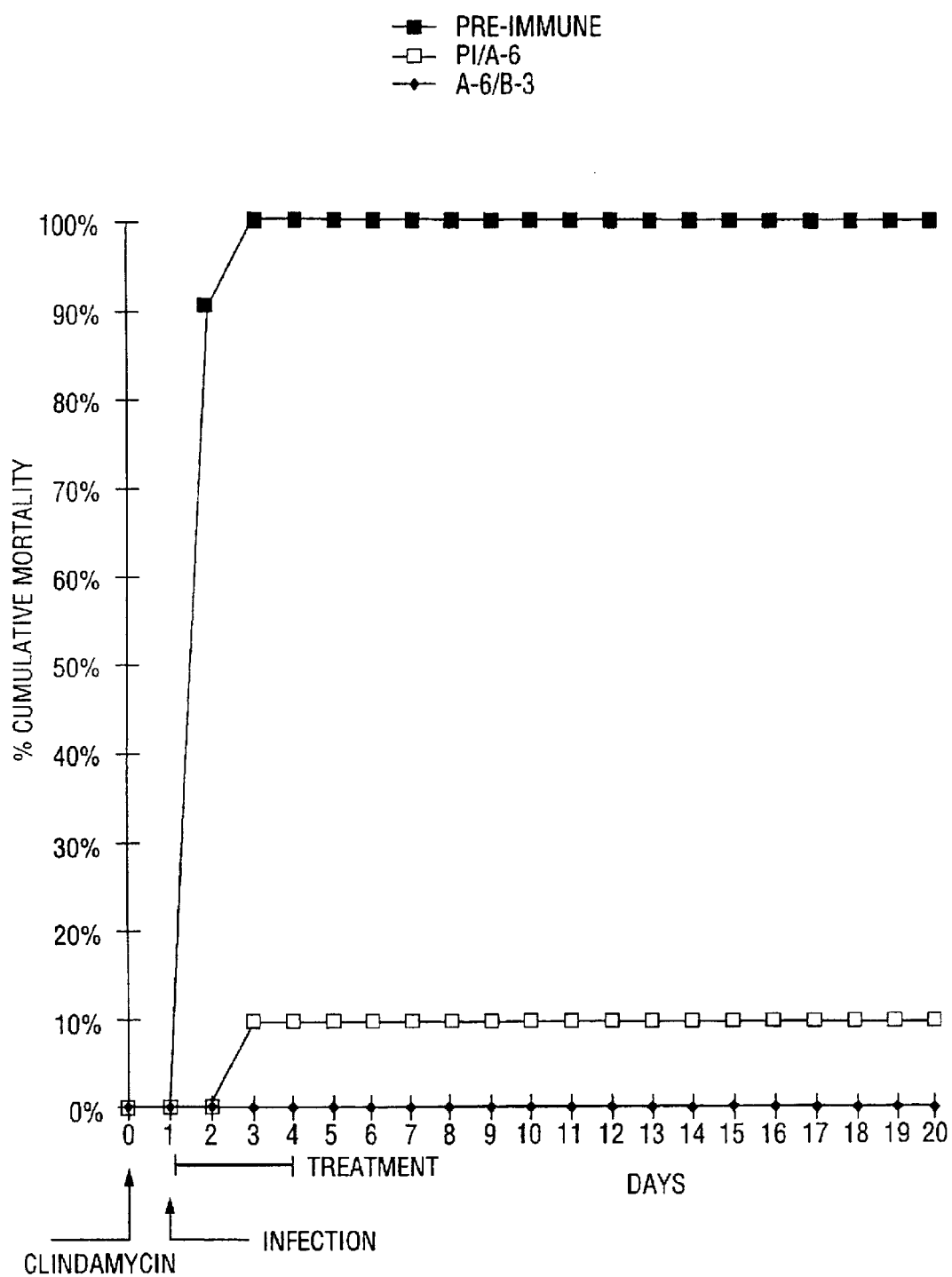
FIG. 38 shows the results of a therapeutic treatment study in hamsters.

In FIG. 38, the percentage cumulative mortality is displayed along the ordinate and the time (in days) is displayed along the abscissa. The treatment period is indicated by the use of the bar between days 1 and 4. The administration of Clindamycin and *C. difficile* organisms ("Infection") is indicated. The solid black squares represent hamsters which received an 8× preparation of pre-immune IgY; the open squares represent hamsters which received a mixture of 8× preparations of pre-immune sera and anti-recombinant *C. difficile* toxin A IgY (anti-Interval A-6) and the solid black diamonds represent hamsters which received a mixture of 8× preparations of anti-recombinant *C. difficile* toxins A and B IgY (anti-Interval A-6 and B-3).

As shown in FIG. 38, the hamsters treated with the antibody mixture to both recombinant *C. difficile* toxins A and B were completely protected from death as shown in the previous experiment (infection study #2) but in addition none of the treated (anti-recombinant toxins A and B) animals presented with diarrhea. While hamsters treated with anti-recombinant *C. difficile* toxin A were also protected from mortality (only one of ten died) all but one (90%) had diarrhea. All hamsters treated with preimmune IgY developed diarrhea and died within 48-hours of infection.

Prevention against mortality using antibodies to recombinant *C. difficile* toxin A and both *C. difficile* toxins A and B was statistically significant (P<0.001), compared to the results obtained using pre-immune antibody. Also, was shown in previous Examples (16 and sections i and ii above), all the treated hamsters survived long-term with no signs of relapse. The prevention of morbidity in the hamsters, which includes presence of diarrhea and weight loss, by treating with anti-recombinant A and B IgY is shown in Table 41.

TABLE 41

Interval A-6 and B-3 Antibodies Reduce CDAD Morbidity

| Treatment Group | % Animals with Diarrhea | P | % Weight loss [a] | P |
|---|---|---|---|---|
| Pre-Immune | 100 | | NA[b] | |
| pmA1870-2680 (A-6) | 90 | NS[c] | 16 | <0.001 |
| pmA1870-2680 plus pPB1750-2360 (A-6/B-3) | 0 | <0.001 | 1 | NS |

[a]Weight loss of survivors calculated as the difference between the starting weight and that at termination of treatment.
[b]NA, not applicable.
[c]NS, not significant.

As shown in Table 41, the percent weight loss in the survivors treated with the anti-recombinant *C. difficile* toxin A IgY alone (pMA1870-2680; A-6) compared to the mean weight before infection was about 16%. The hamsters treated with both antibodies to both recombinants (pMA1870-2680 and pPB1750-2360; A-6/B-3) only lost 1% of their mean starting weight. These results demonstrate that the antibodies raised against the *C. difficile* toxin A recombinant protected the hamsters from the fatal stage of CDAD but the addition of antibodies to the *C. difficile* toxin B recombinant was necessary for the prevention of the diarrheal stage associated with CDAD.

EXAMPLE 33

Relapse During In Vivo Treatment of Hamsters Infected with *C. difficile* Using Vancomycin Therapy To determine if relapse of *C. difficile* disease occurs after vancomycin treatment under conditions used in the previous treatment studies, the following experiment was performed.

The conditions employed for the hamster model were identical to the conditions used in Example 32. Three groups of hamsters (Sasco), each group containing 6 members, were treated with 0.2, 1 or 5 mg/kg of vancomycin (Vancomycin HCl, Lilly) in one ml of sterile water. Animals were dosed once per day for 5 days. An additional untreated group was tested as a control. Hamsters were each orally infected with $1 \times 10^3$ *C. difficile* organisms (ATCC 43596) and then vancomycin treatment was begun 3 hours post-infection. The outcome of the experiment, twenty days after infection, is shown in FIG. 39.

Figure 39:
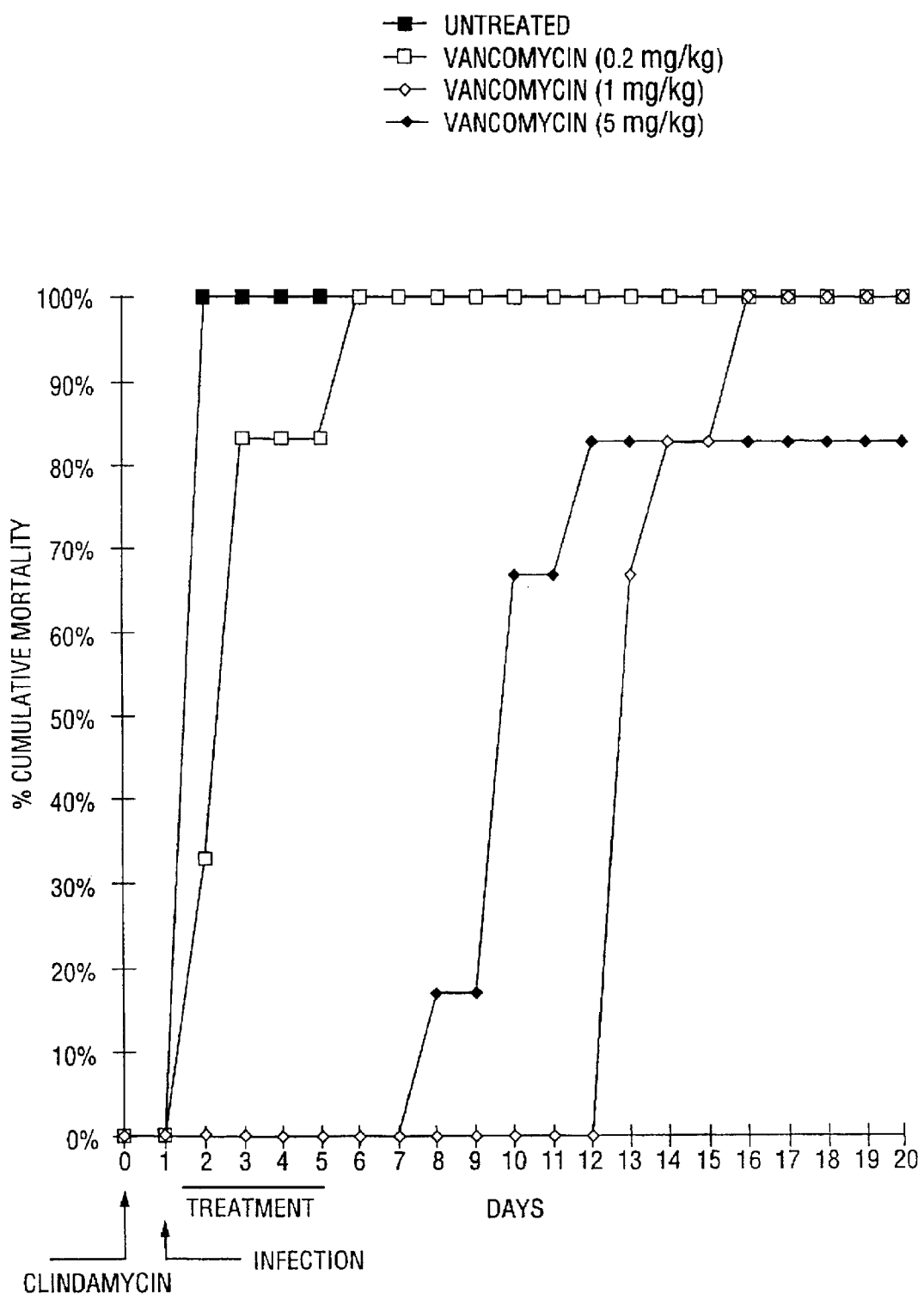
FIG. 39 shows the results of administration of vancomycin to hamsters having an established *C. difficile* infection.

In FIG. 39, the percentage cumulative mortality is displayed along the ordinate and the time (in days) is displayed along the abscissa. The treatment period is indicated by the use of the bar between days 1 and 5. The administration of Clindamycin and the inoculation with *C. difficile* organisms (marked as "Infection" in FIG. 39) is indicated. The solid black squares represent hamsters which received no treatment (untreated); the open squares represent hamsters which received 0.2 mg/kg vancomycin; the solid black diamonds represent hamsters which received 1.0 mg/kg vancomycin; and the open diamonds represent hamsters which received 5.0 mg/kg vancomycin.

The results shown in FIG. 39 demonstrate that the hamsters treated with 0.2 mg/kg of vancomycin all died during the course of treatment. Hamsters treated with 1 mg/kg or 5 mg/kg of vancomycin were protected during the period of treatment, but quickly relapsed and most died shortly after the termination of treatment. All of the treated hamsters developed diarrhea and 83% (5/6) of the hamsters treated with 1 mg/kg vancomycin or 100% (6/6) of the hamsters treated with 5 mg/kg vancomycin died 7 days or 9 days after withdrawal of treatment.

This relapse effect using vancomycin as illustrated here or using metronidazole to treat *C. difficile* infections in the hamster model or in humans is a common occurrence that has been reported frequently. Up to 100% of hamsters and about 25% of humans treated with either of these two drugs relapse. This relapse effect is in marked contrast to the effect shown in the present invention when treating hamsters infected with *C. difficile* with IgYs raised against either native or recombinant *C. difficile* toxin A or B. Relapse rarely or never occurs when animals are treated with anti-*C. difficile* toxin IgY. Thus, the prevention of relapse by the administration of anti-*C. difficile* toxin IgY represents an important therapeutic advantage over conventional antibiotic treatments.

EXAMPLE 34

Comparison of *C. difficile* Toxin A Neutralization In Vivo Using IgYs Against Three Different *C. difficile* Toxin A Repeat-Containing Recombinant Proteins Three *C. difficile* toxin A recombinants proteins from the repeat region of *C. difficile* toxin A were expressed in the pMal-c vector. Antibodies against each were generated and compared for their ability to neutralize *C. difficile* toxin A in hamsters. The example involved a) immunization of hens, b) purification and detection of anti-recombinant toxin A IgYs and c) *C. difficile* toxin A neutralization study in hamsters using anti-recombinant toxin A IgYs.

a) Immunization of Hens

Three groups of egg-laying Leghorn hens were immunized with different toxin A recombinants proteins produced in the pMal vector. All were expressed as MBP fusions. They were pMA1870-2190 (Example 17), pMA1960-2680 (Example 28) and pMA1870-2680 (Example 11). The first two recombinants proteins comprise overlapping subfragments within the interval contained in the recombinant pMA1870-2680.

Approximately 1 mg of each recombinant protein was given with Freund's adjuvant to each hen. The standard immunization procedure using this adjuvant was performed as described Example 1. The hens were immunized four times at multiple sites using the time intervals described in Example 32a.

b) Purification and Detection of Anti-Recombinant *C. difficile* Toxin A IgYs

Antibodies were extracted using PEG from eggs collected after at least one week after the last boost. Anti-*C. difficile* toxin A (CTA) and pre-immune IgYs were also prepared as a controls (as described in Examples and 1, respectively). The IgYs were resuspended in 0.1 M carbonate buffer (pH 9.5) at 4× concentration (¼ the original yolk volume). The levels of specific antibodies from each group was determined by ELISA. Reactivity was determined against the soluble recombinant toxin A protein pPTrx1870-2680. The pPTrx1870-2680 protein does not contain the MBP as do the other 3 immunogens and therefore the ELISA reactivity is specific to only the toxin A recombinant. The standard ELISA protocol was employed (Example 13c). From the ELISA results, all four of the anti-recombinant *C. difficile* toxin A IgYs were shown to have very similar titers at greater than 1:31,250 compared to the pre-immune IgY.

c) *C. difficile* Toxin A Neutralization Study in Hamsters Using Anti-Recombinant Toxin A IgYs The ability of the above recombinant toxin A IgYs (ie., pMA1870-2190, pMA1960-2680 and pMA1870-2680) to provide protection against *C. difficile* toxin A was determined in the hamster model. Two groups of hamsters received the anti-pMA1870-2680 IgYs; therefore a total of 6 treatment groups were examined. The assay was performed as described in Example 14.

One ml of IgY was mixed and preincubated for 1 hour with 30 µg of *C. difficile* toxin A (Tech Labs) then administered orally to 30–40 gm Golden Syrian hamsters (Charles River). Preimmune and CTA IgY (Example 8) served as negative and positive controls, respectively. The animals were observed for 24 hours and the number dead in each group was tallied. The results of the experiment is shown in Table 42.

TABLE 42

Generation of Toxin A Neutralizing Antibodies
Against Different Toxin A Recombinant Fragments

| Treatment Group | Alive[1] | Dead[1] |
| --- | --- | --- |
| Preimmune | 0 | 5 |
| CTA | 5 | 0 |
| pMA 1870-2190 | 0 | 5 |
| pMA 1960-2680 | 5 | 0 |
| pMA 1870-2680 a | 5 | 0 |
| pMA 1870-2680 b | 3 | 2 |

[1]Study outcome after 24 hours.

As shown in Table 42, pre-treatment of *C. difficile* toxin A with IgY against pMA1870-2680 prevented death in all 5 treated hamsters in the treatment group designated "pMA1870-2680 a" and 3 out of 5 in the treatment group designated "pMA1870-2680 b." Antibodies raised against pMA1870-2680 and the slightly smaller, carboxy-terminal polypeptide, pMA1960-2680, both prevented death in all 5 animals. In contrast, as with preimmune IgY, IgYs raised against the amino-terminal polypeptide pMA1870-2190 had no effect on the prevention of death. As expected, hamsters treated with CTA IgYs were completely protected from the enterotoxic effects of *C. difficile* toxin A.

EXAMPLE 35

Identification of Adjuvants that Optimally Induce Neutralizing Antibodies Against Native *C. difficile* Toxin A In Vivo In order to compare the ability of different adjuvants to invoke neutralizing antibodies against *C. difficile* toxin A in hens using a recombinant *C. difficile* toxin A protein as the immunogen, the following experiments were performed. The example involved a) immunization of hens with a recombinant *C. difficile* toxin A protein using four different adjuvants; b) determination of anti-recombinant *C. difficile* toxin A IgY titers by ELISA and c) testing the neutralizing ability of the anti-recombinant *C. difficile* toxin A IgYs against *C. difficile* toxin A in vivo.

a) Immunization of Hens with a Recombinant *C. difficile* Toxin A Protein Using Four Different Adjuvants Eight groups of egg-laying Leghorn hens, each group containing 4 hens, were immunized with either 100 µg or 1 mg of recombinant toxin A protein (pMA1870-2680; Example 11) in combination with four different adjuvants. The four adjuvants tested were: Freund's (GIBCO), Fowl adjuvant LES-STM (here after referred to as the RIBI adjuvant; RIBI Immunochemical Research, Inc.), Gerbu (Biotech) and Quil A (Accurate Chemical). Each adjuvant was tested at both concentrations of antigen. The procedures for preparation and administration for each of the adjuvants were those provided by each manufacturers' protocol. The adjuvant dose in hens was also determined according to manufacturers recommendation if specified.

For immunization with Freund's adjuvant, the standard protocol was used (Example 1). Briefly, 1 volume of antigen were emulsified in 1.2 volumes of either complete Freund's adjuvant for the first immunization or incomplete Freund's for the subsequent boosts. One milliliter of the antigen/Freund's mixture was administered to each hen at four sites. Since Freund's adjuvant contains an oil, the mixing of Freund's adjuvant with the immunogen required vigorous emulsification of the material until solidification using two syringes connected together by a barrel connector. The other three adjuvants (RIBI, Gerbu and Quil A) are aqueous in composition and uniform mixing with the recombinant antigen was far easier as compared to Freund's. Only gentle vortexing was required for mixing the three aqueous adjuvants. The final mixture using these aqueous adjuvants also remained a homogenous liquid allowing easier administration into the hens as compared to using Freund's.

Using the RIBI adjuvant, each hen received 500 µl of the antigen/adjuvant mixture at one site containing 100 µg of adjuvant. The recommended Quil-A dose for guinea pigs and rabbits was 50 µg and 100 µg, respectively. By extrapolating by weight, the hens were each given 75 µg of the Quil A adjuvant at one site in an antigen/adjuvant volume of 500 µl. Using Gerbu material, each hen received 5 µg of adjuvant in 500 µl antigen mixture at one site. The hens were all immunized subcutaneously for 4 times at roughly two-week intervals.

b) Determination of Anti-Recombinant *C. difficile* Toxin A IgY Titers by ELISA

Anti-recombinant toxin A antibody levels generated using the different adjuvants were compared by ELISA. About 1 week after the last boost, at least 3 eggs from each of the 8 groups along with pre-immune eggs were collected, yolks pooled within the group and IgYs were extracted by PEG as described in Example 1. The purified anti-recombinant toxin A IgYs were then resuspended in PBS at 1× yolk volume. The protein concentration of each of the preparations, determined by absorbance at 280 nm, were all similar at about 4 to 5 mg/ml. The IgY reactivity and titer of each of the individual antibody preparations against pMA1870-2680 were determined by ELISA against a soluble (pPTrxA1870-2680N/C; Example 29) and an insoluble (pPA1870-2190; Example 17a) analog of the *C. difficile* toxin A 1870-2680 interval. These recombinant *C. difficile* toxin A analogs were used to coat the microtiter plates for ELISA instead of the recombinant used in the immunization (pMA1870-2680) as both pPTrxA1870-2680N/C and pPA1870-2680 were not expressed as fusions with the MBP as was the pMA1870-2680 immunogen. This was done in order to determine antibody reactivity against the toxin portion of the *C. difficile* toxin A recombinant specifically rather than to the MBP portion of the fusion protein.

The soluble analog pPTrxA1870-2680N/C used to coat the microtiter plate was expressed as a fusion with thioredoxin which aids in solubility and the resulting fusion protein probably exists in a native conformation. The insoluble analog pPA1870-2190, which presumably contains denatured epitopes, was also used to coat microtiter plates. The ELISA reactivity of each IgY to both the soluble and insoluble analogs was tested to determine if there was any preferential reactivity to one or the other analogs when different adjuvants were used for the generation of the IgY.

The standard ELISA protocol described in Example 13c was used with the exception that 20 to 40 fold-less pPTrxA1870-2680N/C protein was used than normal to coat the 96-well microtiter plates (Falcon, Pro-Bind Assay plates) to reduce background. One-hundred µl/well were coated overnight at 4° C. with the soluble pPTrxA1870-2680N/C protein at 0.05 µg/ml or the insoluble protein pPA1870-2680 at 1 µg/ml. The results are shown in FIG. 40.

Figure 40:
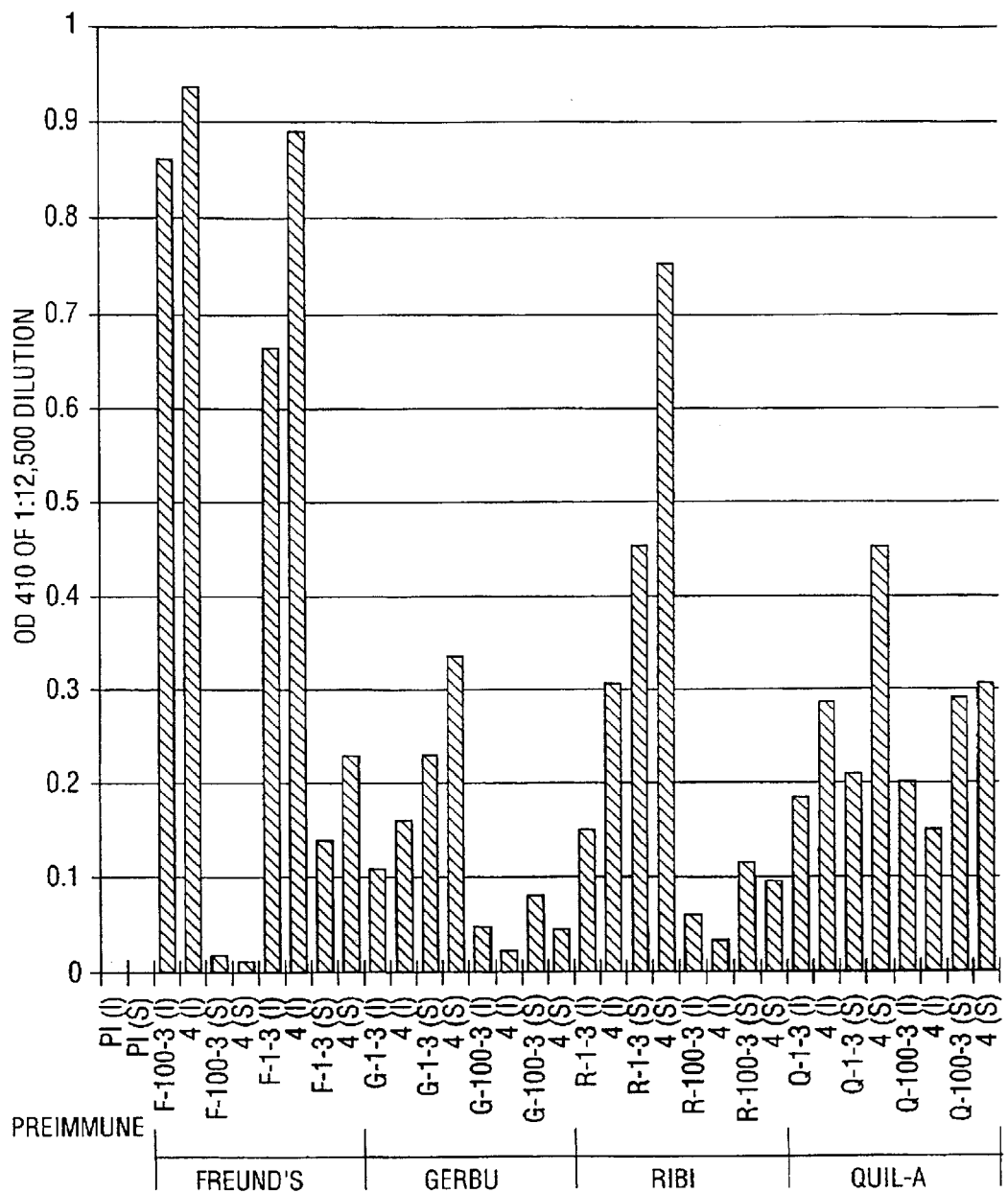
FIG. 40 shows the results of an ELISA analysis of IgY isolated from hens immunized with the recombinant *C. difficile* toxin A protein pMA1870-2680 and four different adjuvants.

In FIG. 40, the results of the ELISA reactivity comparing the antibody titer of each of the adjuvant/antigen combinations to either the insoluble (I) or the soluble (S) *C. difficile* toxin A recombinant is shown. The following abbreviations were utilized: PI (pre-immune); adjuvants were designated as F, R, Q and G for Freund's, RIBI, Quil-A and Gerbu respectively at either 1 mg (1) or 100 µg (100).

In addition, the antibody titer in each group was compared after 3 or 4 immunizations to determine if antibody response has plateaued (indicated by the use of −3 or −4 in FIG. 40). All four adjuvants were able to elicit antibody responses in the hens to varying degrees, but their antibody responses to the soluble or native antigen and insoluble or denatured antigen differed. Freund's adjuvant generated a greater antibody response to the insoluble analog as compared to the soluble one. Almost no reactivity was seen using Freund's adjuvant with 100 μg of antigen to the soluble analog. There was also no difference in response using Freund's to the insoluble analog at either concentration (100 μg or 1 mg) of immunogen while an increase in reactivity to the soluble analog was seen in the higher concentration compared to the lower concentration. In contrast, the antibody reactivity to the soluble analog was generally greater than the insoluble analog using the three other aqueous adjuvants. Antibody reactivities in the ELISA to the soluble analog were about 2-fold higher compared to the insoluble analog. The antibody response improved in the Gerbu, RIBI and Quil-A groups using the increased dose of antigen (1 mg versus 100 μg, and was more pronounced against the soluble analog compared to the insoluble one. The antibody levels to both the insoluble and soluble analog in most of the groups increased after an additional boosting when comparing the 3rd and 4th immunizations.

The results shown in FIG. 40 demonstrate that the immunization of chickens with Freund's adjuvant using a soluble recombinant *C. difficile* toxin A immunogen elicits antibodies primarily against the insoluble analog. This finding is important if conformational antibodies are required to confer protection in vivo. If conformational antibodies are required, the alternative adjuvants such as Gerbu or RIBI used here would be preferred. The soluble antigen may become denatured during the harsh emulsification process required when using Freund's adjuvant as compared with the other adjuvants. The resulting denatured antigen would then presumably invoke antibodies primarily against an insoluble or non-conformational analog. This effect using Freund's may be overcome by using more antigen for immunization because less of the total is being denatured and a greater amount of native antigen is present. Indeed, there was an increase in soluble analog antibody reactivity at the higher immunogen concentration while there is no difference in insoluble antibody reactivity at both immunogen concentrations.

c) Testing the Neutralizing Ability of the Anti-Recombinant *C. difficile* Toxin A IgYs Against *C. difficile* Toxin A In Vivo The ability of the antibodies raised against the pMA1870-2680 protein generated above using the different adjuvants to neutralize toxin A was compared in vivo. PEG-purified IgYs from eggs from hens immunized with each of the four adjuvants at the 1 mg immunogen concentration were diluted at 0.5x yolk volume in 0.1 M carbonate buffer, pH 9.5. This antibody concentration (0.5x) was chosen because it would illustrate the best differentiation in IgY neutralizing capability using the different adjuvants. Pre-immune antibodies also at 0.5x concentration in carbonate were prepared as controls. The antibodies were diluted in carbonate buffer so they could be orally administered with acid less degradation in the stomach.

The IgY protein concentration by absorbance at 280 nm of all of the 0.5x preparations was 2.4–2.5 mg/ml of which 25 to 50 μg/ml was specific antibody against the *C. difficile* toxin A recombinant protein. An in vivo protection study of hamsters against *C. difficile* toxin A using the five IgY preps was preformed as described in Example 14(c). Five groups, each consisting of 4 male 30–40 gms Golden Syrian hamsters (Charles River). Each hamster was given a mixture of 30 μg of *C. difficile* toxin A (Tech Labs) in 1 ml of anti-recombinant *C. difficile* toxin A IgYs or pre-immune IgY. This mixture was first allowed to preincubate for one hour at 37° C. prior to oral administration. The animals were then observed for 24 hours after administration for the presence of diarrhea and death. The results were tabulated and shown in Table 43.

TABLE 43

Generation of Toxin A Neutralizing Antibodies Using Different Adjuvants with pMA 1870-2680

| Treatment Group | Healthy[a] | Diarrhea[a] | Dead[a] |
|---|---|---|---|
| Preimmune | 0 | 1 | 3 |
| Freund's | 0 | 0 | 4 |
| Gerbu | 4 | 0 | 0 |
| RIBI | 4 | 0 | 0 |
| Quil A | 4 | 0 | 0 |

[a]Study outcome after 24 hours.

The results shown in Table 43 demonstrate that premixture of *C. difficile* toxin A with 0.5x anti-recombinant *C. difficile* toxin A IgYs generated using the Gerbu, RIBI and Quil A adjuvants before administration prevented all overt symptoms and death from the disease in the hamsters. In contrast, all the animals treated with anti-recombinant *C. difficile* toxin A IgY generated by use of Freund's adjuvant (as a 0.5x antibody preparation) mixed with *C. difficile* toxin A failed to protect and the hamsters developed diarrhea and died within 24 hours. Three out of four hamsters treated with pre-immune IgY died and the lone survivor had severe diarrhea. These results showed that the anti-recombinant *C. difficile* toxin A IgYs generated using Gerbu, RIBI and Quil A were able to neutralize the *C. difficile* toxin A activity in vivo while the Freund's-generated IgY at the same concentration could not. The inability to neutralize *C. difficile* toxin A by the Freund's-generated anti-recombinant *C. difficile* toxin A IgY correlates with its low ELISA reactivity against the soluble toxin A analog. In contrast, all of the other adjuvants invoked high antibody levels to the soluble analog and were neutralizing. These results indicated that the neutralizing potential of the antibodies correlated well with their reactivity to the soluble, but not the insoluble analog. The results also indicated that the maintenance of a soluble or conformational *C. difficile* toxin A immunogen was important in generating neutralizing antibodies. Thus, the choice of an adjuvants such as RIBI or Gerbu was important to retain the conformation of the immunogen which was important in generating anti-*C. difficile* toxin A antibodies which were protective in vivo.

EXAMPLE 36

In Vivo Neutralization of Toxin A Using Antibodies Against the Recombinant pPA1870-2680 Protein To determine if the immunization of hens with the *C. difficile* toxin A recombinant pPA1870-2680(N/C) induced neutralizing antibodies, the following experiment was performed. The example involved a) immunization of hens with the *C. difficile* toxin A recombinant pPA1870-2680(N/C) using four different adjuvants; b) purification and detection of anti-recombinant IgY; and c) in vivo neutralization study in hamsters using the anti-pPA1870-2680 antibodies incubated with toxin A.

a) Immunization of Hens with the *C. difficile* Toxin A Recombinant pPA1870-2680 Using Four Different Adjuvants Egg-laying Leghorn hens were each immunized with the C. difficile toxin A recombinant pPA1870-2680(N/C) (Example 29d). This recombinant protein is expressed in the pET vector and was shown to be capable of isolation in a highly pure form which contained very low levels of endotoxin as compared to the same region expressed in other vectors such as pMal-c (Example 11). These results showed that the pPA1870-2680 recombinant protein would be compatible for use in a vaccine. Accordingly, the ability of pPA1870-2680 to stimulate an antibody response was tested.

Four groups of hens (2 hens/group) were immunized with 100 g of pPA1870-2680(N/C) (purified as described in Example 29d) using 4 different adjuvants. The adjuvants used were: Freund's (GIBCO), Fowl (RIBI) adjuvant (RIBI Immunochemical), Gerbu (Biotech) and Quil A (Accurate Chemical). The amount of each adjuvant used with the recombinant was described in Example 35. The hens were all immunized 4 times at 2 week intervals.

b) Purification and Detection of Anti-Recombinant IgY

The anti-recombinant pPA1870-2680(N/C) levels using the different adjuvants were compared by ELISA. About one week after the last boost, standard PEG preps were prepared from eggs from each group and resuspended at a 4× concentration (all contained about 20 mg/ml IgY) in 0.1 M carbonate buffer, pH. 9.5. The standard ELISA protocol (Example 13c) was followed to determine specific antibody reactivity to soluble immunogen pPA1870-2680. The ELISA results are shown in FIG. 41.

Figure 41:
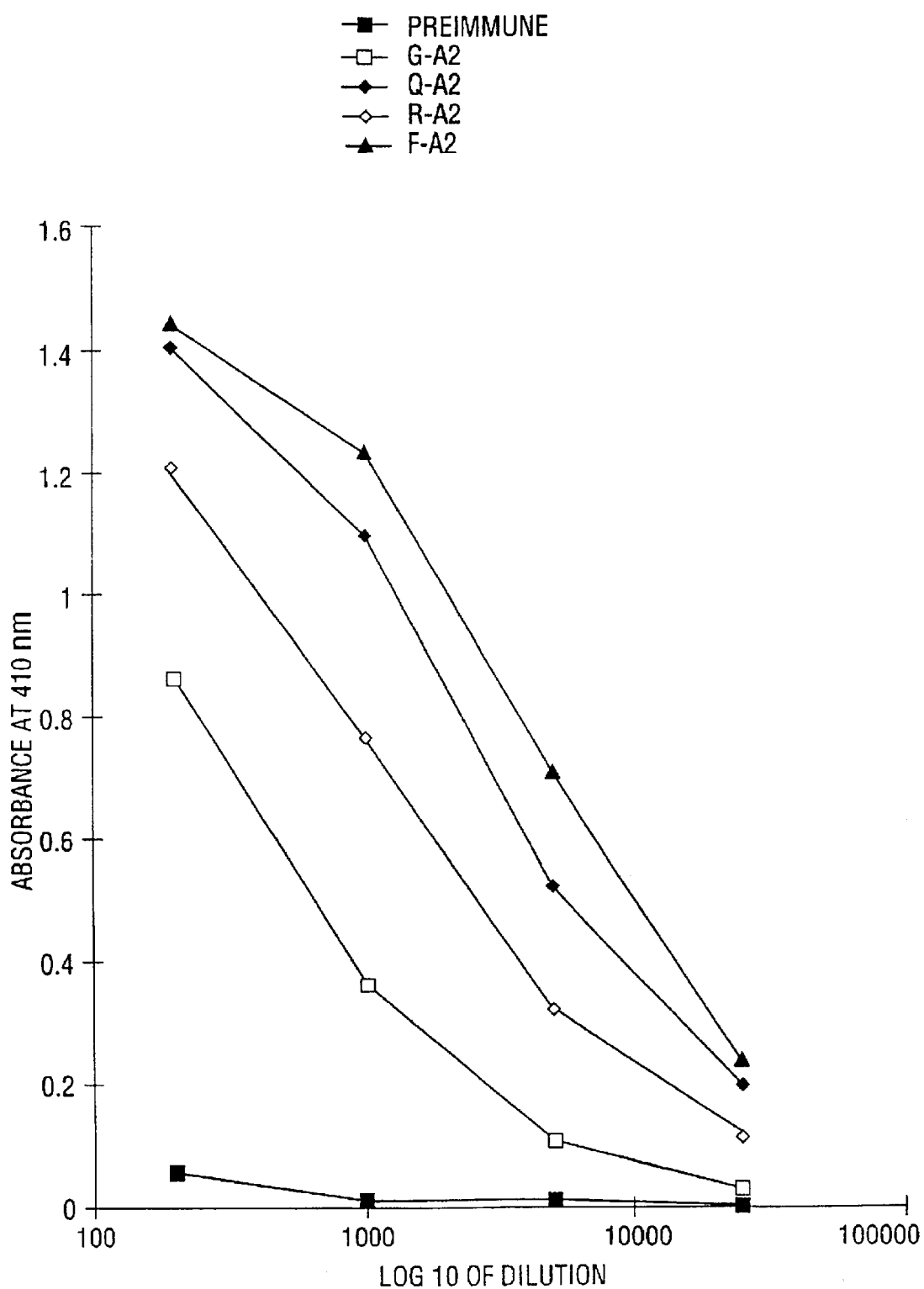
FIG. 41 shows the results of an ELISA analysis of IgY isolated from hens immunized with the recombinant *C. difficile* toxin A protein pPA1870–2680(N/C) and four different adjuvants.

In FIG. 41, the absorbance at 410 nm is plotted against the $\log_{10}$ of the dilution of each antibody tested. The solid black squares represent the results of the ELISA using the preimmune IgY; the open squares, black diamonds, open diamonds and black triangles represent the results of the ELISA using antibodies generated using pPA1870-2680(N/C) (Interval A2) and the following adjuvants: Gerbu (G-A2); Quil A (Q-A2); RIBI (R-A2) and Freund's (F-A2), respectively.

After 4 immunizations, all the hens generated a specific IgY response against the C. difficile toxin A recombinant expressed in the pET vector [i.e., pPA1870-2680N/C)]. The response generated by using Freund's, Fowl (RIBI) adjuvant and Quil A were comparable as shown in FIG. 41. A lower antibody response was seen in the Gerbu immunized hens. Interestingly, using the Freund's adjuvant with pPA1870-2680(N/C) gave the highest anti-recombinant activity, whereas in the previous example (Example 35) using the same recombinant region expressed in pMal-c (pMA1870-2680), Freund's adjuvant generated the weakest response. The other adjuvants invoked similar antibody responses comparing both recombinants. These result indicated that the level of antibody response using Freund's adjuvant may depend on what type of antigen is used.

c) In Vivo Neutralization Study in Hamsters Using the Anti-pPA1870-2680(N/C) Antibodies Incubated with C. difficile Toxin A The ability of antibodies to neutralize C. difficile toxin A in vivo was compared using antibodies raised against pPA1870-2680(N/C) protein generated using the RIBI and Freund's adjuvants. This assay was preformed as described in Example 35c with the exception that the antibodies were diluted to a 2× concentration containing 10 mg/ml of IgY protein. C. difficile toxin A (Tech Labs) was mixed with antibodies generated using Freund's and Fowl (RIBI) adjuvant and orally administered to hamsters. Hamsters treated with pre-immune IgY served as the control. The number of hamsters which were healthy, had diarrhea or were dead 24 hours after administration of the IgYs is shown in Table 44.

TABLE 44

Generation of C. difficile Toxin A Neutralizing Antibodies Using Different Adjuvants with pMA 1870-2680

| Treatment Group | Healthy | Diarrhea | Dead |
|---|---|---|---|
| Preimmune | 0 | 0 | 4 |
| Freund's | 4 | 0 | 0 |
| RIBI | 4 | 0 | 0 |

As shown in Table 44, both the Freund's and RIBI adjuvants used in conjunction with pPA1870-2680(N/C) were able to elicit in vivo neutralizing antibodies against C. difficile toxin A as compared to pre-immune IgY. The ability of the antibodies to neutralize C. difficile toxin A shown in this example and in Example 35 appears to correlate well with their ELISA reactivity to a soluble (native) recombinant protein. These results show that the C. difficile toxin A recombinant, pPA1870-2680(N/C), was immunogenic in hens and was capable of generating in vivo neutralizing antibodies; therefore, the pPA1870-2680(N/C) protein is an excellent vaccine candidate.

EXAMPLE 37

Enteric Coating of IgY Raised Against Recombinant C. difficile Toxin A For Oral Delivery To determine if the avian antibodies (IgYs) raised against recombinant C. difficile toxin A could be enterically-coated and potentially retain in vivo protective abilities, the following experiment was conducted. The example involved a) enteric coating of anti-recombinant C. difficile toxin A antibodies, b) dissolution studies to determine the disintegration kinetics of the enteric-coated IgYs as a function of pH and c) determination of the stability of the antibody reactivity after coating and dissolution by ELISA.

a) Enteric Coating of Anti-Recombinant C. difficile Toxin A Antibodies

Preliminary studies were performed to determine an effective enteric coating process. Enterically-coated avian antibodies should be more resistant to degradation in the stomach compared to antibodies delivered in solution when the route of administration is oral. Intestinal enteric coatings would remain intact at the low pH ranges found in the stomach and therefore the coated IgYs would be able to pass the through stomach undegraded but dissolve at the higher pHs (about 6.0) and release the IgYs in the intestines. An additional property of the enteric films selected for testing is that they are compatible in aqueous solutions instead of organic solvents during the coating process. This property of the enteric film should probably preserve conformation and integrity of the IgY antibody during the coating process. Since the intestines are the site of C. difficile disease, enteric coating of the anti-C. difficile toxin IgY' should concentrate the amount of antibodies available at the site of infection to improve efficacy and reduce the effective dose required as compared to the use of uncoated IgYs.

The anti-C. difficile toxin A antibodies were coated as follows. Sixty grams of lyophilized antibodies against the recombinant C. difficile toxin A protein pMA1870-2680 (Example 11) were prepared. IgYs from eggs collected from hens immunized with the recombinant protein were purified by PEG-precipitation. The IgY pellets after purification were resuspended in 0.1× PBS, pH 7.4 at about ¼ starting yolk volume (4×) and from 200 to 250 ml volumes were transferred to 600 ml lyophilizing flasks (Labconco). The IgY solutions were flash frozen in the flasks by rotation in an reagent alcohol bath containing dry ice. The frozen antibodies were lyophilized on a Labconco Freeze Dry System/Lyph Lock 4.5 unit operated according to manufacturer's instruction. About 250 mls of the 4×IgY prep yielded about 10 grams of dry material after lyophilization.

The lyophilized IgY was sent to The Coating Place Inc. (Verona, Wis.) for enteric coating. The antibodies were encapsulated using a Wurster coating chamber which is well-suited for coating materials efficiently and uniformly at a small scale in a single operation. Encapsulated IgYs were prepared using two different coating processes. Either a single step direct process or a two-step process using a non-pariel (i.e., a sugar particle of 40–60 mesh size). The lyophilized IgY was either overcoated directly with the film coatings or a two-step method was performed where first the IgY itself was used to overcoat the non-pariel. Then the IgY-coated sugar particle was then overcoated with the enteric film. The use of the sugar particle provides extra bulk necessary to maintain the antibodies in the coating chamber and can aid in a more uniform application of the enteric film.

Two different aqueous enteric films were selected and used with each coating process. The lyophilized IgY was either overcoated with Aquateric (FMC Corp.) or Eudragit® L30D (Röhm Tech Inc). Both of these coatings are water-soluble enteric film coatings that dissolve at pH 6.5 or 5.5, respectively. Both of these enteric films were selected because they fuilfill the selection criteria suitable for the needs as described above. Each of the different coating procedures using both enteric films yielded enterically-coated antibodies product. The two-step process using the sugar particle made the entire overcoating procedure in Wurster apparatus technically easier with less loss of material and subsequent greater yields of final product. An enteric coating of approximately a 27–30% by weight was applied to the IgY using the direct method. About 70% of the remaining weight of this enteric-coated material was IgY. About a 32–33% by weight of the enteric coating was achieved in the IgY-overcoated sugar particle. The remaining 67% by weight of the enteric particle was comprised of about 40–50% due to the sugar particle and about 20% the IgY.

b) Dissolution Studies to Determine the Disintegration Kinetics of the Enteric-coated IgYs as a Function of pH The performance of each of the enterically-coated IgY were tested by determining their dissolution profile. Properly coated IgY particles with intestinal enteric films should remain intact in a gastric solution of pH 1 to 2, but dissolve and release the IgYs into an intestinal solution of pH 7.5. Simulated gastric fluid at about pH 1.2 and simulated intestinal fluid at pH 7.5 were prepared according to USP guidelines except the digestive enzymes were omitted [United States Pharmacopeia, Vol. XXII (1990) United States Pharmacopeial Convention, Rockville, Md., pp. 1788–1789]. Ten milligrams of each enteric coated preparation (i.e., Aquateric and Eudragit® coatings) was added per 1 ml of the simulated gastric and intestinal fluids and mixed gently for 1–2 hours at room temperature. An aliquot of the solution was taken at different time points and checked for the presence of protein released in solution. Protein amounts in solution were determined either by absorbance at 280 nm or using a BCA protein assay (Pierce).

Figure 42:
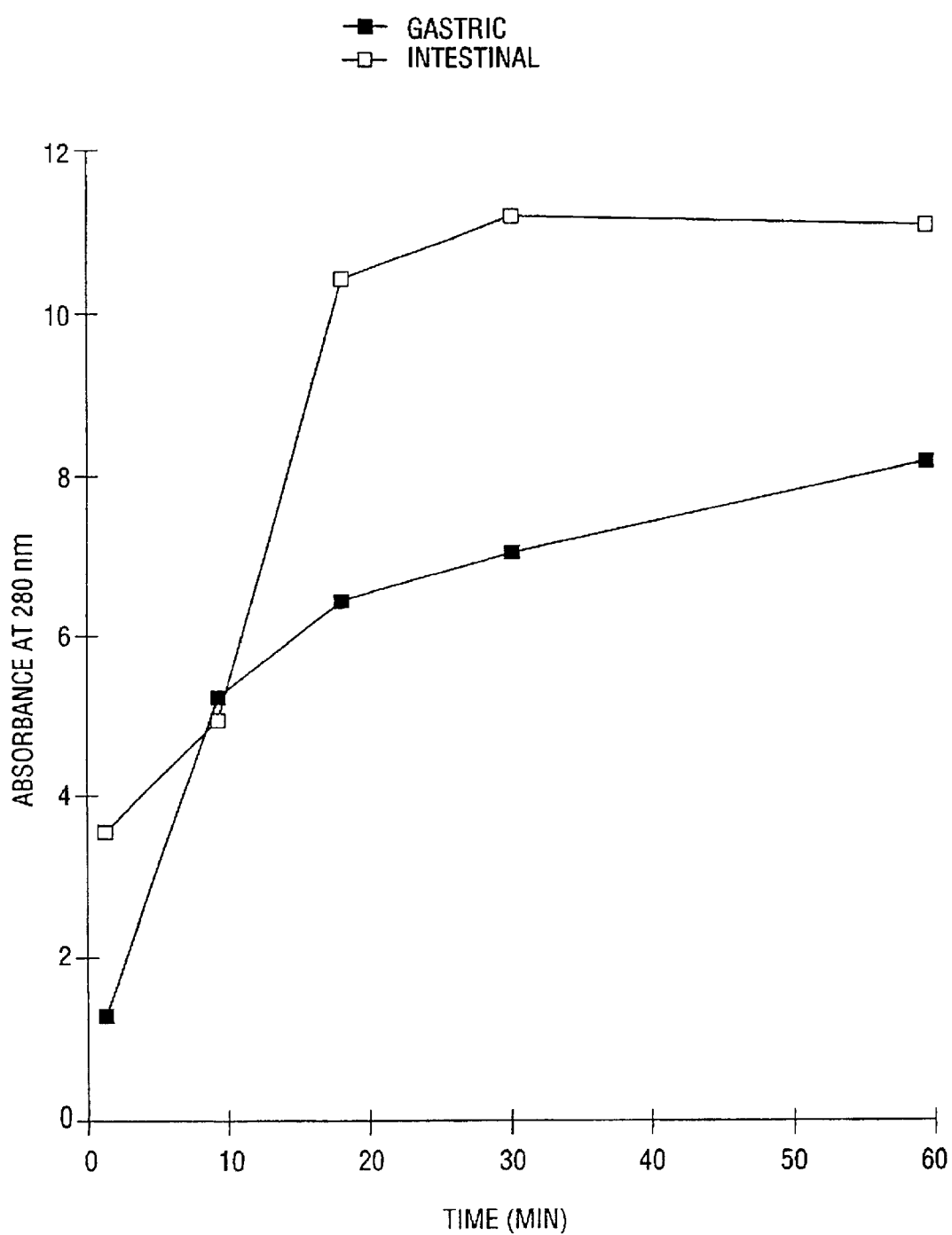
FIG. 42 shows dissolution profiles for Aquateric-coated IgY.
Figure 43:
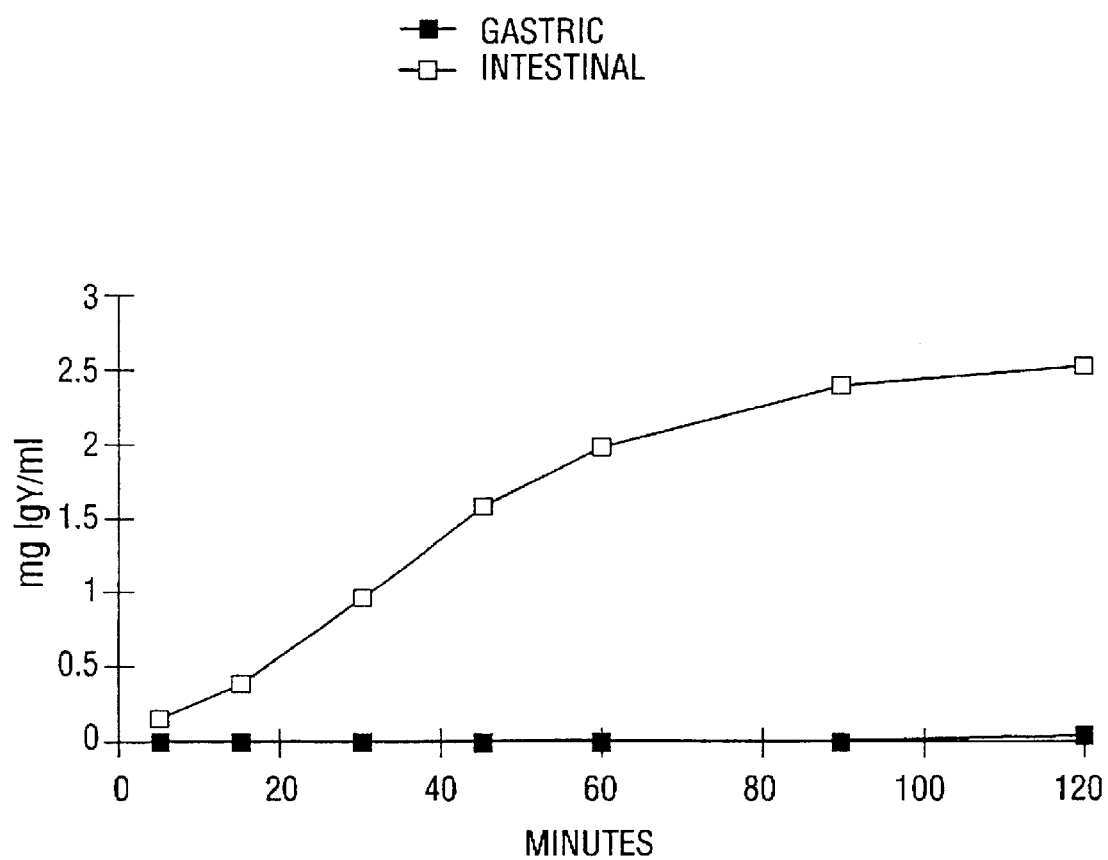
FIG. 43 shows dissolution profiles for Eugragit®-coated IgY.

The studies demonstrated that the IgY directly coated with both the Aquateric and Eudragit® coatings and the Aquateric-overcoated IgY sugar-particles failed to perform adequately in the dissolution studies. IgYs at both pH 1.2 and 7.5 were released in the solution within minutes after addition of these particles. The dissolution profile for the Aquateric-overcoated IgY sugar particle monitored by absorbance is shown in FIG. 42. The dissolution profile for the Eudragit®-overcoated IgY sugar particle is shown in FIG. 43.

In FIG. 42 the absorbance at 280 nm is plotted against time in minutes. The release of the IgY from the Aquateric-overcoated particle in simulated gastric fluid is shown by the solid black squares; release of the IgY from the coated particle in simulated intestinal fluid is shown by the open black squares. Because the Aquateric film itself absorbs UV at a similar wavelength as protein (275–276 nm), UV absorbance at 280 nm cannot be used to accurately quantitate the amount of IgY in solution. Thus, protein at 1 hour (60 min) dissolution was quantitated using the BCA method in order to obtain an accurate determination of the protein concentration.

As shown in FIG. 42, the amount of specific IgY found after dissolution of the Aquateric-overcoated IgY in the two fluids were similar; 4 mg/ml at pH 1.2 and 4.9 mg/ml at pH 7.5. The difference in absorbance shown in FIG. 42 between the gastric and intestinal solutions is due to the presence of more Aquateric film being dissolved in the intestinal solution.

In contrast to the performance of the failed coatings, the Eudragit®-overcoated IgY sugar particle properly opened and released IgY into the solution in the simulated intestinal fluid in a time-dependant manner, while it remained intact in the gastric fluid. The dissolution profile in the gastric and intestinal solutions of the Eudragit®-overcoated IgY sugar particle as a function of time is shown in FIG. 43.

In FIG. 43, the absorbance at 280 nm is plotted against time in minutes. The release of the IgY from the Eudragit®-overcoated particle in simulated gastric fluid is shown by the solid black squares; release of the IgY from the coated particle in simulated intestinal fluid is shown by the open black squares. Since Eudragit® does not absorb UV at the amounts found in the coatings, absorbance values at 280 nm can be directly converted to protein concentration.

As shown in FIG. 43, little or no protein was released in the gastric solution while protein was continually released into the intestinal solution at a linear rate reaching a maximal dissolution after about 2 hours. Ten mg/ml of Eudragit®-overcoated particles yielded from 2 to 2.5 mg/ml of IgY after dissolution. The Eudragit®-overcoated particles in the gastric solution remained intact for long periods of time, even after further incubation at 4° C. for an additional week.

The dissolution profile Eudragit®-overcoated IgY sugar particles was determined under conditions that mimic normal physiological conditions (i.e., simulated travel through the GI tract). The particle was first placed in the gastric solution for 120 minutes followed by an 180 minute incubation in the intestinal solution. Both of these incubations took place with gentle mixing at 37° C. Under these conditions (i.e., incubation in gastric fluid followed by incubation in intestinal fluid), IgY from the Eudragit®-overcoated sugar particle was not released into the gastric solution protein as found in FIG. 42 (i.e., incubation in gastric fluid only), but was only released and detected in the intestinal solution at similar levels found in FIG. 42 (from 2 to 2.5 mg/ml protein released after about 2 hours).

The dissolution studies discussed above demonstrated that the anti-recombinant *C. difficile* toxin A IgYs were successfully enterically-coated using Eudragit® and a non-pariel.

c) Determination of the Stability of the Antibody Reactivity after Coating and Dissolution by ELISA The stability of the anti-recombinant C. difficile toxin A IgYs after the overcoating process was determined. This was tested by comparing the ELISA reactivity of the antibodies before coating then after the coating process followed by dissolution at pH 1.2 then pH 7.5. Pre-immune IgY, lyophilized anti-recombinant toxin A IgY starting material and anti-recombinant toxin A IgY obtained from the Eudragit®-overcoated IgY sugar particle after dissolution were first all quantitated for protein and normalized at 2 mg/ml in PBS (pH 7.4). An ELISA was performed detecting antibodies against the recombinant toxin A pPTrxA1870-2680N/C as described in Example 35b. The ELISA results are shown in Table 45.

TABLE 45

Comparison of Anti-Recombinant Toxin A
Titers by ELISA Before and After Enteric Coating

| Dilution | Preimmune IgY* | Pre-Coated Anti-Recombinant A* | Post Coated Anti-Recombinant A* |
| --- | --- | --- | --- |
| 1:50 | 0.017 | 1.4 | 1.2 |
| 1:250 | 0.005 | 0.59 | 0.38 |
| 1:1,250 | 0.004 | 0.15 | 0.10 |
| 1:6,250 | 0.005 | 0.037 | 0.026 |
| 1:31,250 | 0.007 | 0.015 | 0.009 |
| 1:156,250 | 0.009 | 0.009 | 0.007 |

*Average A280 readings.

The results shown in Table 45 demonstrate that the reactivity of the anti-recombinant C. dfficile toxin A IgYs before and after Eudragit®-coating to the recombinant C. difficile toxin A protein was very similar. These results indicated that the coating process was not harmful to the IgY and that the IgY remain reactive and finctional after dissolution under physiological conditions.

The results shown above demonstrate that enterically-coated IgY that remained stable and active was generated.

EXAMPLE 38

Vaccination of Hamsters Against C. difficile Infection with Recombinant C. difficile Toxin A Proteins To determine if hamsters vaccinated with C. difficile toxin A recombinant proteins would elicit protective antibodies against C. difficile infection, the following experiment was conducted. Three different C. difficile toxin A recombinants, expressed in the pMal-c or pET vectors, were compared. The example involved a) immunization of hamsters, b) detection of humoral and mucosal anti-recombinant antibody responses by ELISA, and c) challenge study of hamsters with C. difficile.

a) Immunization of Hamsters

Three groups of 90–100 gram female Golden Syrian hamsters (Charles River), each group containing 9 to 11 members, were tested as follows. Hamsters from each group were individually tagged using an ear punch for identification. The animals from each group were housed together and were given food and water ad libitum throughout the course of the experiment. Hamsters were immunized with two different recombinant C. difficile toxin A protein repeats fragments produced the in pMal-c vector and expressed with a maltose binding protein (MBP) fusion and one recombinant C. difficile toxin A protein repeats fragment produced the in pET vector. The animals were immunized subcutaneously with 25 ×g of purified protein of either pPA1870-2680N/C (Example 15), pMA1870-2680, a subfragment of pMA1870-2680 called pMA1960-2680 or the MBP (pMal-c) alone as a control. All three recombinant pMal vectors were grown and protein was expressed and purified as described in Example 28c. Recombinant pPA1870-2680N/C was purified as described in Example 29f.

Mixtures comprising 200 µl of antigen and complete Freund's adjuvant (for the first injection) and incomplete Freund's adjuvant (for the subsequent injections) were given subcutaneously behind the neck. The vaccination was administered using a 1 ml 27 gauge tuberculin syringe after the animals were lightly etherized. The animals were vaccinated five times at roughly 2 week intervals.

b) Detection of Humoral and Mucosal Anti-Recombinant Antibody Responses by ELISA The detection of humoral and mucosal anti-recombinant C. difficile toxin A IgY titers in the hamsters was determined by ELISA. For the humoral response, serum from all members from each group was collected and assayed for anti-recombinant toxin A IgG levels. At least 1 week after the last boost, the hamsters were etherized, bled by cardiac puncture and serum was collected. Ninety-six well microtiter plates (Probind, Falcon) were coated overnight with the soluble C. difficile toxin A recombinant, pPTrxA1870-2680N/C (Example 29e) at 0.05 µg/ml in PBS (pH 7.4) at 100 µl per well. Standard ELISA procedure were followed as described in Example 35b. The secondary antibody used was goat anti-hamster IgG-alkaline phosphatase (Southern Biotech) at a dilution of 1/2000. The average absorbance at 410 nm from duplicate test wells of each serum sample diluted at 1/250 is shown in FIG. 44.

Figure 44:
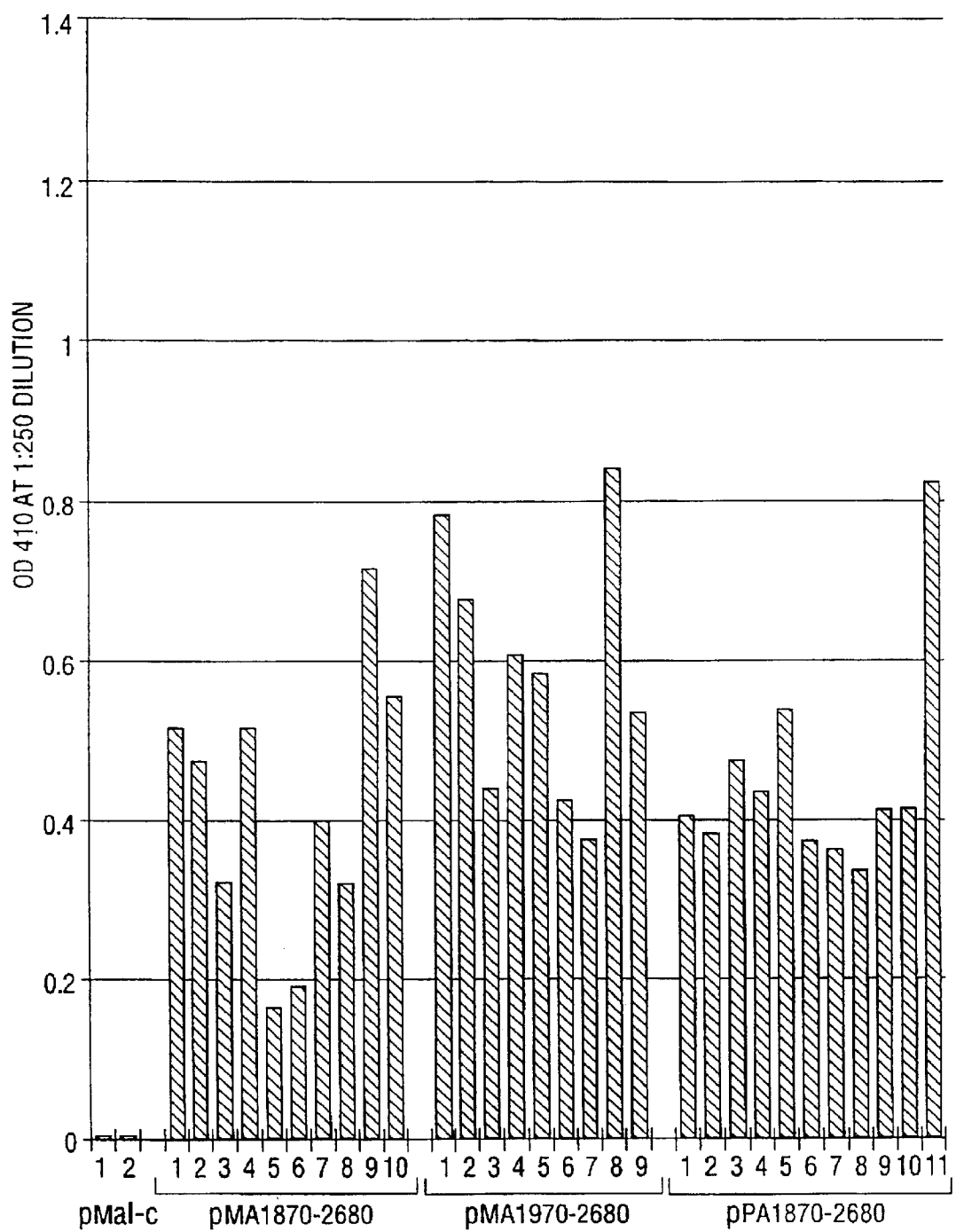
FIG. 44 shows the results of an ELISA analysis of IgY isolated from hamsters vaccinated with recombinant *C. difficile* toxin A proteins.

In FIG. 44, the $OD_{410}$ of a 1:250 dilution of serum taken from hamsters immunized with either pMal-c (the pMal-c vector lacking an insert), pMA1870-2680 (Example 28c), pMA1960-2680 (Example 28b) or pPA1870-2680 (Example 15). The numerals shown on the ordinate represent the number assigned to animals within a group.

The results shown in FIG. 44 demonstrate that all the hamsters immunized with the C. difficile toxin A recombinants responded by producing anti-recombinant C. difficile toxin A IgG in the serum. Some variability in the antibody response within the hamsters in a group existed although this difference was not greater than 4-fold. The average antibody response to pMA1960-2680 and pPA1870-2680 was uniformly higher than the response to pMA 1870-2680. The hamsters immunized with pMal protein did not produce an anti-serum IgG response to the C. difficile toxin A recombinant protein.

Whether a mucosal IgA response was elicited after immunization was also determined by ELISA. Freshly isolated feces from 4 members of each group were collected, weighed and resuspended by vortexing at 300 µl per 100 mg of stool in PBS, pH 7.4 containing 0.05% thimerosal. The fecal suspension was centrifuged for 5 minutes at 14,000 rpm in a microcentrifuge. Microtiter plates were coated with recombinant antigen as described above. Standard ELISA procedures were used with goat anti-mouse IgA-alkaline phosphatase (Southern Biotech) at 1/1000 as the secondary antibody. This conjugate was used instead of an anti-hamster IgA because the anti-hamster IgA is not commercially available and the anti-mouse antibody has been previously reported to cross-react with hamster IgA. In all samples of fecal extracts, mucosal IgA against recombinant toxin A was not detected by ELISA. These results confirm previous studies [Kim and Rolfe (1989) Microbial Ecology in Health and Disease 2:47] in which IgA against toxoid A was not detected in hamsters immunized with a toxoid prepared from C. difficile toxin A.

c) Challenge Study of Hamsters with *C. difficile*

The vaccinated hamsters (described in section a above) were challenged with *C. difficile* to determine if the anti-recombinant *C. difficile* toxin A antibodies were protective against *C. difficile* disease. Normal hamsters infected with a toxigenic strain of *C. difficile* develop a fatal disease beginning with diarrhea and eventually die from severe enterocolitis of the cecum (proximal colon) and ileum (as described in Example 9).

The four groups of vaccinated hamsters were first each predisposed with an intra-peritoneal dose of Clindamycin-phosphate (Biomol) in 1 ml of water at 1 mg per 100 gm body weight. About 24 hours later, the hamsters were orally challenged with $1 \times 10^6$ *C. difficile* in 1 ml of sterile saline using an 18 gauge feeding needle. The animals were lightly anethesized with ether prior to administration. The toxigenic strain of *C. difficile*, ATCC 43596, was used after 48-hours growth on CCFA plates (BBL). One hamster in the pMA1960-2680 immunized group died accidentally from ether overdose reducing the group number from 9 to 8. The results of the immunization study are shown in Table 46.

TABLE 46

Vaccination Against Lethal *C. difficile* Enterocolitis Using Recombinant Toxin A Fragments

| Vaccination Group | % Protection |
|---|---|
| pMal-c (MBP) | 10% (1/10) |
| pMA1960-2680 | 62% (5/8) |
| pMA1870-2680 | 30% (3/10) |
| pPA1870-2680 | 19% (2/11) |

The results shown in Table 46 demonstrate that protection against death occurred in some of the hamsters immunized with each of the recombinant toxin A proteins (i.e., pMA1960-2680 and pMA1870-2680). These results were not statistically significant compared to the fusion control (pMal-c which expresses only the MBP) at a P-value of 0.05 or less using Chi-squared analysis. Ninety percent mortality occurred in the fusion control immunized group (pMal-c). The percent mortality in the pMA1960-2680 immunized group was 38%. The percent mortality in the pMA1870-2680 immunized group was 70% and in the pPA1870-2680 immunized group was 81%. The time to death in recombinant *C. difficile* toxin A vaccinated group was not delayed compared to the control, occurring up to 3 days after infection. Necropsy of the dead hamsters revealed typical pathology such as severe megacecum.

The specific P-values of the test groups compared to the control group for pMA1960-2680, pMA1870-2680 and pPA1870-2680 groups were less than 0.10, less than 0.75 and less than 0.90, respectively. All of the hamsters except one in the pMA1870-2680 immunized group presented with diarrhea one to two days after infection. There appeared to be no correlation between anti-recombinant *C. difficile* toxin A antibody titers and the level of protection. For example, hamster number 6 in the pMA1960-2680 immunized group had a lower ELISA titer compared to hamster number 2 (see FIG. 44) yet number 6 survived and number 2 was not protected and died. From these results, hamsters vaccinated with either of the recombinant *C. difficile* toxin A repeats proteins were not protected against *C. difficile* -induced diarrhea and from 19 to 62% were protected from the lethal stage of the disease.

The above results correlate with previously published work [Lyerly et al. (1990) Curr. Microbiol. 21:29] which showed that hamsters vaccinated with the smaller *C. difficile* toxin A recombinant fragment (the 1960-2680 interval) expressed in pUC9 could also only partially protect against the lethal stage of disease and none of those hamsters were protected against diarrhea. Lyerly et al. [(1990) Curr. Microbiol. 21:29] stated that antibodies to the *C. difficile* toxin A recombinant protein tested did not prevent the diarrheal stage of the disease and the death in half of the hamsters was due to the varying levels of neutralizing serum antibodies to the toxin A recombinant. From the above results, differences in anti-recombinant *C. difficile* toxin A titers seen between hamsters in a group may not explain why protection did not occur in all of the animals. The above results indicate that possibly an additional component, possibly a toxin B recombinant protein, is necessary for a more effective vaccine against *C. difficile* disease.

EXAMPLE 39

Vaccination of Hamsters Against *C. difficile* Infection with *C. difficile* Toxin A and Toxin B Recombinant Proteins Hamsters were immunized with recombinant *C. difficile* toxin A or recombinant toxin B alone or in combination to test whether this would invoke a humoral response to the recombinant proteins. Furthermore, the ability of the antibodies produced by these vaccinations were tested for the ability to protect the hamsters from infection with *C. difficile*. Specifically, it was determined if antibodies raised against a recombinant *C. difficile* toxin B would provide any protection in vivo by itself or above that provided by vaccination with recombinant *C. difficile* toxin A alone. The example involved a) the immunization of hamsters, b) determination of humoral and mucosal antibody response by ELISA and c) in vivo challenge studies in vaccinated hamsters.

a) Immunization of Hamsters

The recombinant proteins used for vaccination were the *C. difficile* toxin A recombinant protein pPA1870-2680N/C (Examples 11 and 29) and the *C. difficile* toxin B recombinant protein pPB1750-2360 (Example 15b). The recombinant proteins were expressed in the pET vector instead of pMal-c vector used in Example 38 because the proteins expressed and isolated using the pET vector were found to be capable of purification at a higher level of purity with lower levels of endotoxin. Production of recombinant proteins in the pET vector is especially amenable for the potential utilization of the recombinant protein as a human vaccine which demands high purity and low levels of potentially harmful endotoxin.

For immunization, 100 μg of pPA1870-2680, 100 μg of pPB1750-2360 or 100 μg of each in combination (200 μg total) were mixed with 2 μg of Gerbu adjuvant (Biotech). The control group were immunized with 100 μg of bovine serum albumin (BSA) with the Gerbu adjuvant. Each group (four total) consisted of 9–10 members of 100 gm female Golden Syrian hamsters (Charles River). Animals were individually tagged to identify members. The hamsters were lightly anesthetized prior to injection sub-cutaneously behind the neck using 1 ml syringe with a 27 gauge needle. The hamsters were immunized 4 times at roughly 2 week intervals.

b) Determination of Humoral and Mucosal Antibody Response by ELISA

Serum from all individuals from each of the above groups were tested for anti-recombinant protein IgG levels by ELISA. At least one week after the last boost, all of the animals from each group were bled by cardiac puncture and serum was collected. Anti-recombinant C. difficile toxin A and anti-recombinant C. difficile toxin B from the serum samples were determined by ELISA. Ninety-six well microtiter plates (Probind, Falcon) were coated overnight at 4° C. with either pPA1870-2680 protein at 0.05 µg/ml or pPB1750-2360 protein at 1.0 µg/ml in PBS (pH 7.4) at 100 µl per well. Standard ELISA procedures were used exactly as described (Example 13c). The results are shown in FIGS. 45 and 46.

Figure 45:
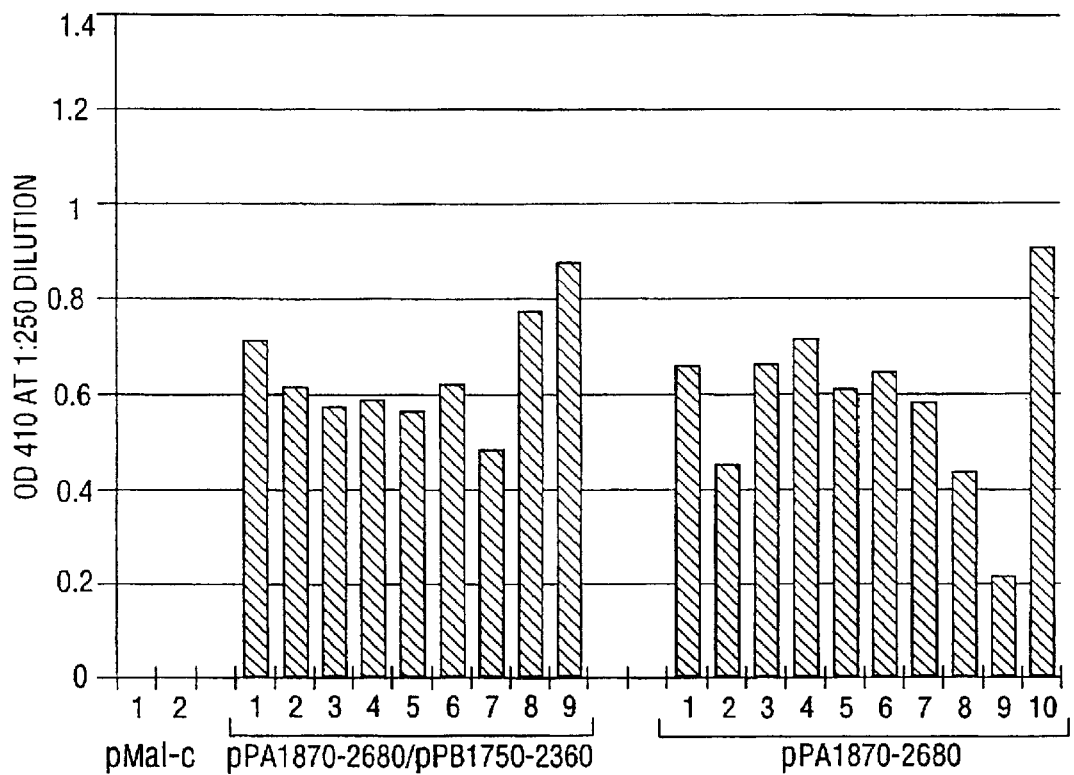
FIG. 45 shows the results of an ELISA analysis of IgY isolated from hamsters vaccinated with recombinant *C. difficile* toxin A and B proteins; reactivity to recombinant *C. difficile* toxin A is shown.
Figure 46:
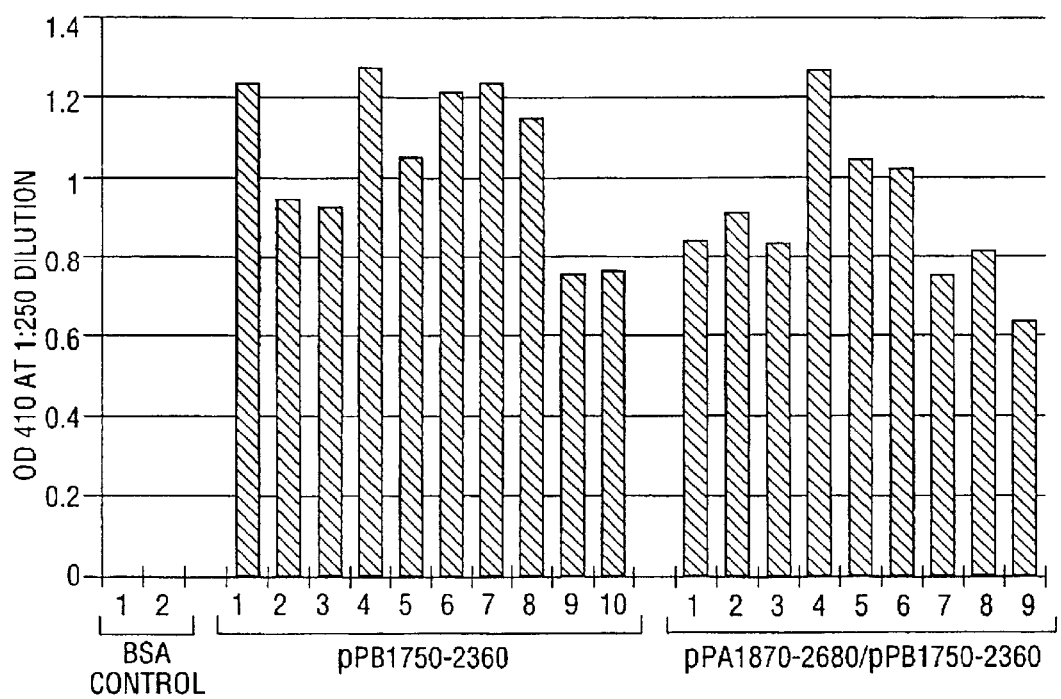
FIG. 46 shows the results of an ELISA analysis of IgY isolated from hamsters vaccinated with recombinant *C. difficile* toxin A and B proteins; reactivity to recombinant *C. difficile* toxin B is shown.

The average absorbance of each serum performed in duplicate and diluted at 1/250 is shown in FIGS. 45 and 46. FIG. 45 shows individual antibody reactivity to the C. difficile toxin A recombinant in the groups immunized with either the C. difficile toxin A recombinant (pPA 1870-2680) or a mixture of recombinant C. difficile toxins A and B (pPA1870-2680 and pPB1750-2360). FIG. 46 shows antibody reactivity to recombinant C. difficile toxin B in the groups immunized with either the C. difficile toxin B recombinant (pPB1750-2360) or a mixture of recombinant C. difficile toxins A and B (pPA1870-2680 and pPB1750-2360).

The results shown in FIGS. 45 and 46 demonstrate that in all cases each animal responded and produced a specific IgG antibody response to the immunogen. As expected, the hamsters immunized with BSA (negative control group) did not invoke any antibody response to the recombinant antigens. The anti-recombinant C. difficile toxin A or B response within members of the same group were similar.

The determination of a mucosal anti-recombinant C. difficile toxin A or recombinant C. difficile toxin B IgA response was elicited after immunization was also determined by ELISA. Freshly isolated feces from 4 members of each group were collected, weighed and processed as described in Example 21. Plates were coated with recombinant C. difficile toxin A or recombinant C. difficile toxin B antigen as described above for determination of serum IgG levels. Standard ELISA procedures (Example 13c) were used in conjunction with goat anti-mouse IgA-alkaline phosphatase (Southern Biotech, Birmingham, Ala.). In all samples of fecal extracts, IgA against recombinant toxin A or B was not detected. Again this result using different recombinants confirms that found in Example 38 and with previous studies [Kim and Rolfe (1989), supra].

c) In Vivo Challenge Studies in Vaccinated Hamsters

The vaccinated hamsters described above in section a) above were challenged with C. difficile to determine whether the serum antibody response to either recombinant C. difficile toxin A or B alone or in combination was protective against CDAD. The four groups of vaccinated hamsters were first each predisposed to CDAD with an intraperitoneal dose of Clindamycin-phosphate (Biomol) in 1 ml of water at 1 mg per 100 gm weight. About 24 hours later, the hamsters were orally challenged with 1×10$^6$ C. difficile organisms in 1 ml of sterile saline using an 18 gauge feeding needle. The animals were lightly anethesized with ether prior to administration. The toxigenic strain ATCC 43596 was used after 48-hours growth on CCFA plates (BBL). The results of the immunization study is shown in Table 47.

TABLE 47

Vaccination Against Lethal C. difficile Enterocolitis
Using Recombinant Toxin A and Toxin B Polypeptides

| Vaccination Group[a] | % Protection |
| --- | --- |
| BSA | 0% (0/10) |
| pPA1870-2680N/C | 20% (2/10) |

TABLE 47-continued

Vaccination Against Lethal C. difficile Enterocolitis
Using Recombinant Toxin A and Toxin B Polypeptides

| Vaccination Group[a] | % Protection |
| --- | --- |
| pPB1750-2360 | 0% (0/10) |
| pPA1870-2680N/C & pPB1750-2360 | 100% (9/9) |

[a]Vaccinated with 100 µg recombinant protein per hamster subcutaneously 4 times at 2 week intervals.

As shown in Table 47, one to three days after challenge with C. difficile, all of the hamsters immunized with either pPA1870-2680 or pB1750-2360 and the BSA control group developed diarrhea. All the hamsters in those three groups except two members immunized with pPA1870-2680, died from several hours to 48 hours after the detected onset of diarrhea. Necropsy revealed severe enterocolitis in the animals with inflamed and enlarged cecums characteristic of C. difficile disease. In contrast, hamsters immunized with the vaccine comprising the combination of pPA 1870-2680 or pB1750-2360 proteins showed no signs of illness such as diarrhea and remained healthy for the entire 14-day postinfection observation period. In fact, these animals have remained healthy for a period of at least 5 months postinfection; these results demonstrate that vaccination with the combination of pPA1870-2680 or pB1750-2360 proteins confers complete and long term protection on hamsters inoculated with C. difficile.

The protective effect seen with the combination vaccine was not due to differences in antibody titer in this group compared to the antibody titers in the hamsters vaccinated with only recombinant C. difficile toxin A or C. difficile toxin B. Protection of the hamsters immunized with the C. difficile toxin A/B combination (i.e., pPA1870-2680 and pB1750-2360) was statistically significant compared to the control; the P value was determined to be less than 0.001.

The above results demonstrate that recombinant C. difficile toxin A and toxin B proteins are both key components for an effective vaccine against C. difficile and that ellictation of antibodies against recombinant C. difficile toxins A or B alone was not sufficient to confer complete protection. Antibodies generated against a recombinant C. difficile toxin B in addition to recombinant C. difficile toxin A both confer protection and they both act synergistically to neutralize C. difficile-associated diarrhea and death. While the invention is not limited by any particular mechanism, the protection from the anti-C. difficile toxin serum antibodies may result from the leakage of the C. difficile toxin A and B neutralizing antibodies into tissues or the intestinal lumen during the inflammation that accompanies the early stages of C. difficile enterocolitis.

The results shown above (vaccination of hamsters with recombinant C. difficile toxins A and B) and in Example 32(c)(iii) (administration of antitoxin comprising a mixture of antibodies raised against both C. difficile toxins A and B) strongly support one another. Together they demonstrate that full protection from CDAD (i.e., protection from both morbidity and mortality) requires the use of recombinant proteins derived from both C. difficile toxins A and B for either active or passive immunization.

EXAMPLE 40

In Vivo Protection Against C. difficile Infection by the Parenteral Administration of Antibodies Against Recombinant C. difficile Toxin A and B Proteins The results shown in Example 39 demonstrated that vaccination of hamsters with recombinant C. difficile toxin A and B proteins generated neutralizing serum antibodies in the recipient animals which conferred complete protection (ie., protection from both morbidity and mortality) from the deleterious effects of infection with *C. difficile*. Example 38 demonstrated that vaccination of hamsters with recombinant *C. difficile* toxin A proteins produced neutralizing serum anti-toxin A antibodies (IgG) but undetectable levels of mucosal (IgA) anti-toxin A antibodies. Thus, the production of serum anti-toxin A and B antibodies is sufficient to confer protection from CDAD. In order to determine whether parenteral delivery of anti-recombinant toxin A and B IgYs is an effective way to treat *C. difficile* infection, the following experiment is conducted.

Six groups of 80–100 gram female Golden Syrian hamsters (Charles River), each group containing 9–10 members, are infected with *C. difficile* as described in Example 32c). The animals are housed three per cage and are offered food and water ad libitum throughout the study. At the start of the study, each hamster is predisposed to infection by the intra-peritoneal administration of Clindamycin-phosphate (Biomol) at 1 mg/100 gram body weight in 1 ml of water using a 1 ml tuberculin syringe (27 gauge needle). Approximately 24 hours later, each animal is orally challenged, using an 18 gauge feeding needle, with 1 ml of *C. difficile*, (strain ATCC 43596) with approximately $10^3$ to $10^4$ organisms in sterile saline. The organisms are grown for 48 hours on CCFA plates (BBL) prior to infection.

Three hours after infection (Day 1), treatment is initiated as follows. Each hamster receives 2 mls of a solution comprising either pre-immune IgY (as an 8× PEG preparation) or a mixture of anti-recombinant toxins A and B (e.g., antitoxin raised against pMA1870-2680 and pPB1750-2360). The 8× PEG preparations are prepared and mixed as described in 32(c)(ii) with the exception that the IgYs are resuspended in sterile saline rather than in carbonate buffer. The IgY preparations are delivered by intraperitoneal injection. The IgY preparations are administered either once, twice or three times a day for a period of 4 days (the treatment period).

The animals are observed for the onset of diarrhea and death during and after the treatment period. The level of protection afforded by each treatment dosage is ]calculated. If the lowest dose is protective in a significant number of hamsters, then lower doses are tested in subsequent experiments using the above conditions. For example, 1.0 and 0.5 ml of IgY preparation per animal per day for 4 days would be tested to determine the lowest intra-peritoneal dosage sufficient for protection. If only very small doses of IgY are needed to confer protection via intra-peritoneal injection, then the IgY would also be delivered via intra-vascular injection to determine whether intra-vascular delivery of the IgY PEG preparations confer protection from *C. difficile* infection.

EXAMPLE 41

Treatment of Hamsters Infected with *C. difficile* using Enteric-Coated IgYs Against a Recombinant *C. difficile* Toxin A Protein To determine whether the enterically-coated anti-recombinant toxin A IgY (Example 37a) is effective in treating *C. difficile* infection in hamsters at a lower dose required using the same IgY without an enteric coating, the following experiment is performed.

The hamster infection model is carried out exactly as described in Example 32c with the exception that enterically-coated antitoxin (Eudragit® L30D-coated pMA1870-2680 which had first be applied to a non-pariel) is used in place of the non-coated IgY in carbonate buffer. Briefly, three groups of hamsters (Sasco) containing 7 members per group are predisposition to infection with Clindamycin-phosphate (Biomol) at 1 mg/100 gram body weight. Twenty-four later, each animal is orally challenged, using an 18 gauge feeding needle, with 1 ml of *C. difficile* (ATCC 43596) containing approximately $1\times10^3$ organisms in sterile saline. The organisms are grown for 48 hours on CCFA plates (BBL) prior to infection.

Three hours after infection (Day 1), treatment is intimated by oral administration of various concentrations of Eudragit®-coated anti-toxin A IgY as follows. Each group receives 0 (the control group), 2, 20, 50, 100 or 600 mg of enterically-coated IgY once per day for a period of 4 days. The enterically-coated particles are administered orally to the hamsters by placing each dose in a microcentrifuge tube, resuspending the particles in a low pH buffer such as acetate, pH 4.0 (low pH buffers are used to prevent the release of the IgY from the enterically-coated particle prior to delivery to the hamster); the suspension is then orally administered using a 14 gauge feeding needle. The animals are observed for the onset of diarrhea and death during and after the treatment period. The percentage cumulative mortality (i.e., death) and morbidity (i.e., diarrhea) are calculated.

The results form the above experiment (administration of enterically-coated IgY) are compared to the results obtained in Example 32c. In Example 32c, the same infection conditions were employed but the anti-toxin A antibodies were delivered in carbonate buffer and they lacked an enteric coating. In Example 32c, 50% of the hamsters treated after infection with uncoated IgYs were protected from death from *C. difficile*. The amount of total IgY given per day in Example 32c was about 120 mg. Of that dose, the amount of specific antibody per day necessary achieve that level of protection (i.e., 50% survival) was about 1200 $\mu$g of specific IgY. In the present example, the hamsters are each given 2, 20, 50, 100 or 600 mg of enterically coated IgY. Since only ⅕ of the weight of the enterically-coated material is IgY, the actual amount of total IgY administered in the 2, 20, 50, 100 and 600 mg doses is about 0.40 mg, 4 mg, 10 mg, 20 mg and 120 mg, respectively. Of that about 1% is specific anti-recombinant toxin A IgY. The 600 mg dose of the enteric particle (i.e., the Eudragit®-coated anti-recombinant *C. difficile* toxin A IgY preparation) is roughly equivalent to the amount of antibody delivered in carbonate buffer in Example 32c which gave 50% protection. Comparison of the dose of the enteric particles required to give the same (i.e., 50%) level of protection indicates the degree of increased potency afforded by enterically-coating the IgY preparation. The results of the above experiment demonstrate whether enterically-coated anti-recombinant *C. difficile* toxin A IgY (Example 37a) is effective in treating *C. difficile* infection in hamsters at a lower dose as compared to non-coated anti-recombinant toxin A.

Accordingly, the recombinant *C. difficile* toxin B IgY (i.e., anti-pPB1750-2360) is also enterically-coated using the methods described in Example 37a. The enterically-coated anti-recombinant *C. difficile* toxin B IgY is tested in the hamster infection model described above alone or in combination with enterically-coated anti-recombinant *C. difficile* toxin A (i.e., the coated anti-pMA1870-2680 IgY preparation). The results of these experiments demonstrate whether enterically-coated anti-recombinant *C. difficile* toxin A and B IgYs (Example 37a) are effective in completely protecting animals from the morbidity and mortality associated with *C. difficile* infection at lower doses as compared to the use of non-coated anti-recombinant *C. difficile* toxin A and B IgYs.

EXAMPLE 42

Determination of the Minimum Effective Dose of Avian Antibodies in Carbonate Buffer Against Recombinant *C. difficile* Toxin A and Toxin B to Treat *C. difficile*-Infected Hamsters The minimum effective dose of avian antibodies (IgY) raised against recombinant toxin A protein and recombinant toxin B protein necessary to treat *C. difficile*-associated disease (CDAD) in hamsters was determined. The experiment involved an in vivo infection study in which hamsters were treated with different concentrations of IgYs raised against recombinant toxin A and recombinant toxin B.

Antibodies were generated against recombinant *C. difficile* toxin A (pMA1870-2680; Interval A-6) using RIBI adjuvant and against the recombinant *C. difficile* toxin B (pPB1750-2360; Interval B-3) using Freund's adjuvant. The immunization protocol used for each adjuvant was previously described in Example 35. Antibodies were PEG-purified and resuspended at an 8× concentration (all contained about 40 mg/ml IgY) in 0.1 M carbonate buffer, pH 9.5.

The infection study involved the testing of three experimental groups (Group I, Group II, and Group III). Group I animals received 2 mls pre-immune IgY. Group II animals received 1 ml of a mixture containing anti-*C. difficile* toxin A and anti-*C. difficile* toxin B IgY. Group III animals received 2 ml of the mixture given to Group II. Each group consisted of eight Golden Syrian hamsters (Sasco) weighing an average of 79+/−3.2 gm. The hamsters were housed two or three per cage and were given food and water ad libitum throughout the study. The infection study was performed using the protocol described in Example 3 1c.

Hamsters were predisposed to infection with *C. difficile* by I.P. administration of 1 mg/100 gm body weight of Clindamycin-phosphate (Biomol) in 1 ml of sterile water. The Clindamycin was administered I.P. using a 1 ml 27-gauge tuberculin syringe (Terumo). About 24 hours later, the hamsters were each infected orally with approximately 1 ml of sterile saline containing $1 \times 10^4$ *C. difficile* (strain ATCC 43596). The *C. difficile* were grown for about 48 hours on CCFA (cycloserine-cefoxitin-fructose-egg yolk agar, a *C. difficile* -selective and differential medium) plates (BBL) prior to inoculation.

Eight hours after inoculation (Day 1), treatment was initiated. The hamsters in each of the three groups orally received one of three treatments through an 18-gauge feeding needle (Popper). Group I received 2 ml of pre-immune IgY (as an 8× PEG preparation), Group II received 1 ml of immune IgY (i.e., a mixture of antibodies generated against pMA1870-2680 [Interval A-6] and pPB1750-2360 [Interval B-3]), and Group III received 2 ml of immune IgY.

The immune IgY mixture was prepared by mixing an equal volume of an 8× concentrate of IgY raised against pMA 1870-2680 and an equal volume of an 8× concentrate of IgY raised against pPB1750-2360; the resulting mixture was designated A-6/B-3 IgY. The amount of anti-toxin protein specific antibodies contained in this A-6/B-3 IgY mixture was about 1.2 mg/ml of anti-recombinant toxin A IgY and about 400 µg/ml of anti-recombinant toxin B IgY. These amounts were determined by affinity purification as previously described in Example 15c. The amounts of total IgY in the 2 ml IgY dose was about 80 mg, and about 40 mg in the 1 ml dose.

The hamsters were treated once each day for 3 days. [The dosing schedule in this treatment regimen differs from that used previous Examples (e.g., Example 32), where the hamsters were treated with 2 ml three times daily for 3 days.] All hamsters were observed for the onset of diarrhea and death during and after the treatment period. The results are shown in FIG. 47 and Table 48.

Figure 47:
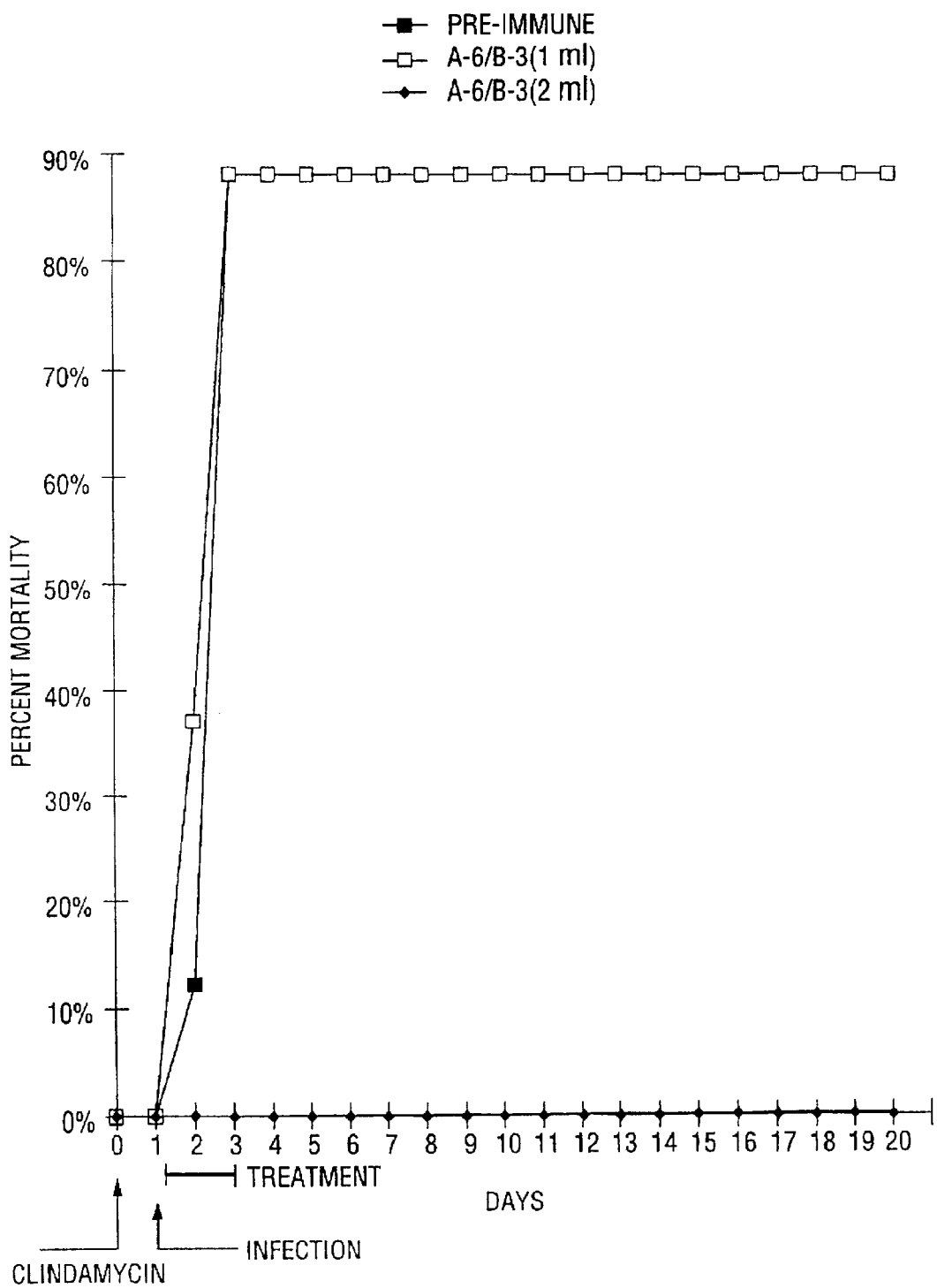
FIG. 47 results of a therapeutic treatment study in hamsters.

In FIG. 47, cumulative mortality (expressed as a percentage) is displayed along the ordinate and time (expressed in days) is displayed along the abscissa. The duration of the treatment period, indicated by the horizontal bar in FIG. 47, was 3 days. The administration of Clindamycin and the inoculation with *C. difficile* ("Infection") is indicated by arrows. The solid black squares represent the Group I hamsters (i.e., hamsters treated with 2 ml of pre-immune IgY). The open squares represent the Group II hamsters (i.e., hamsters treated with 1 ml of the A-6/B-3 IgY). The solid black diamonds represent the Group III hamsters (ie., hamsters treated with 2 ml of A-6/B-3 IgY).

The results shown in FIG. 47 demonstrate that all the hamsters (i.e., 8/8) in Group III were protected from death. In contrast, only 13% (i.e., 1/8) of the hamsters in both Groups I and II survived. The degree of protection in Group III was statistically significant at $P<0.005$, using Chi-square analysis.

The following table shows the results observed using A-6/B-3 IgY. The dose given in this table refers to the total (not specific) IgY concentration given to the animals in a 1 or 2 ml dose.

TABLE 48

Prevention of Morbidity In Vivo Using A-6/B-3 IgY

| Treatment Group | % Animals with Diarrhea | Mean Weight[1] |
|---|---|---|
| Pre-immune, 80 mg (Group I) | 110 | 67.3 ± 3.9 |
| A-6/B-3, 40 mg (Group II) | 100 | 69 ± 4.2 |
| A-6/B-3, 80 mg (Group III) | 0 | 81.6 ± 5.5 |

[1]Weight expressed in grams ± S.D.; mean starting weight of hamsters was 79 ± 3.2 gm. For the animals that died, weight was measured at the time of death. For survivors, the weight was measured after the end of treatment.

The results shown in Table 48 demonstrate that morbidity was also prevented when the hamsters were treated using 2 ml of A-6/B-3 IgY per day. Morbidity from CDAD was defined here as including diarrhea and weight loss. As shown in Table 48, none of the hamsters in Group III presented with diarrhea. In contrast, all of the hamsters treated with either 1 ml of A-6/B-3 IgY (Group II) or with 2 ml of pre-immune IgY (Group I) presented with diarrhea. Moreover, all but one of the hamsters in Groups I and II died about 48 hours after presenting with diarrhea. The prevention of diarrhea in Group III was statistically significant ($P<0.001$) in comparison to the other two treatment groups.

In addition, the results shown in Table 48 indicate that hamsters treated with either 2 ml of pre-immune IgY (Group I) or 1 ml of A-6/B-3 IgY (Group II) lost 14% of their mean starting weight prior to infection. In contrast, the animals treated with 2 ml of the A-6/B-3 IgY (Group III) gained about 2% of their mean starting weight at the end of the treatment period.

Based on the above results, the minimal effective therapeutic dose of specific IgY to both recombinant *C. difficile* toxins A and B (pMA1870-2680 and pPB1750-2360; Intervals A-6 and B-3, respectively) necessary to prevent mortality and morbidity of CDAD in hamsters under the conditions set forth above (i.e., in carbonate buffer) is about 2.4 mg of A-6 IgY and about 800 μg of B-3 IgY per day for 3 days.

EXAMPLE 43

Determination of Specific IgY in the Cecum of a Hamster Treated with Anti-Recombinant *C. difficile* Toxin A and Anti-Recombinant *C. difficile* Toxin B The amount of specific anti-*C. difficile* toxin IgY found in the cecum of a hamster treated with antibodies raised against the recombinant toxin A (pMA1870-2680; A-6) and the recombinant toxin B (pPB1750-2360; B-3) was determined. The results of this study provide an indication of the approximate therapeutic dose of anti-recombinant toxin A and anti-recombinant toxin B IgY (A-6/B-3 IgY) that must be present at the site of infection to protect an animal infected with *C. difficile*.

The example involved a) recovery of cecal contents from an untreated hamster and from a hamster treated with anti-recombinant *C. difficile* toxin A and anti-recombinant *C. difficile* toxin B IgY (i.e., A-6/B-3 IgY), b) direct determination by ELISA of the amount of specific A-6 IgY and B-3 IgY in the cecal contents, and c) direct determination by ELISA of total IgY in the cecum and indirect determination of specific IgY.

a) Recovery of Cecal Contents from an Untreated Hamster and from a Hamster Treated with Anti-Recombinant *C. difficile* Toxin A and Anti-Recombinant *C. difficile* Toxin B IgY (A-6/B-3 IgY)

A hamster was treated according to the protocol for Group III animals as described in Example 42 (i.e., a hamster that was successfully treated against CDAD using 2 ml of 8× A-6/B-3 IgY per day for 3 days). Four hours after the last dose of IgY was administered, the hamster was sacrificed using ether. A control hamster was treated with Clindamycin to predispose the animal to infection with *C. difficile*, but did not receive any IgY nor *C. difficile*, served as a negative control. The control hamster was sacrificed two days after administration of Clindamycin.

The ceca from both hamsters were removed and most of the cecal contents were collected in a 15 ml centrifuge tube. Each centrifuge tube contained several mls of cecal material. The contents in each tube were vortexed and a 1 ml aliquot from each tube was removed to a 1.5 ml microcentrifuge tube. The microcentrifuge tubes were centrifuged for 1 minute at 14,000 rpm. The resulting supernatant was collected and the specific IgY in the samples was quantitated by ELISA.

b) Direct Determination by ELISA of the Amount of Specific A-6 IgY and B-3 IgY in the Cecal Contents The levels of anti-recombinant toxin A and toxin B IgY present in the cecal contents were detected by ELISA using the protocol described in Example 13c with the following modifications. The 96-well microtiter plates were coated (100 μl/well) overnight at 4° C. with 0.05 μg/ml of recombinant *C. difficile* toxin A protein [pPA1870-2680 (N/C) (Example 29)] or with 1 μg/ml of recombinant *C. difficile* toxin B protein [pPB1750-2360 (Example 18b)] in PBS, pH 7.4. Cecal samples were initially diluted two-fold into PBS and placed in the wells. The diluted samples were then serially diluted 5-fold in the microtiter wells. All samples were tested in duplicate.

Quantitation of specific IgY levels in the cecal samples was determined by comparing the antibody reactivity directed against either recombinant toxin A or recombinant toxin B to the reactivity generated using known amounts of affinity-purified IgY in ELISA assays. IgY specific for recombinant *C. difficile* toxins A and B were affinity purified as described in Example 15c. Briefly, affinity-purified antibodies were isolated from PEG-purified IgYs from the eggs of hens immunized with either pMA1870-2680 (Interval A-6) or pPB1750-2360 (Interval B-3). The PEG-purified anti-pMA1870-2680 IgY was affinity-purified using a column comprising pMA1870-2680 bound to Actigel (Sterogene). The PEG-purified anti-pPB1750-2360 IgY was affinity purified using an Actigel column containing pPB1850-2360 (Example 15c), a recombinant *C. difficile* toxin B protein that is 100 amino acids smaller than pPB1750-2360.

The affinity-purified anti-pMA1870-2680 IgY (A-6) and the affinity-purified anti-pPB1750-2360 IgY (B-3) were quantitated by measuring the absorbance at 280 nm and each preparation was diluted to a concentration of 10 μg/ml in PBS. The affinity-purified IgYs were tested by ELISA starting with an initial concentration of 10 μg/ml and at serial 5-fold dilutions in the respective coated-microtiter plate along side the cecal extracts. Rabbit anti-chicken IgY conjugated with alkaline phosphatase (Sigma) was used as the secondary antibody at a dilution of 1:750 to detect the bound IgYs in the ELISA.

Comparison of the ELISA reactivity equivalence between the cecal extracts to the known concentrations of the affinity-purified IgY allowed the amount of specific anti-recombinant IgY present in the cecal extracts to be estimated. From the ELISA results the amount of specific anti-pMA1870-2680 IgY (A-6) was found to be about 12 μg/ml. The amount of specific anti-pPB1750-2360 IgY (B-3) was determined to be about 800 ng/ml. These concentrations of specific IgYs provide estimates of the effective therapeutic concentrations necessary to achieve protection at the site of infection. Since the amount of specific IgY given orally prior to collection of the cecal fluid was about 2400–2800 μgs against the toxin A recombinant and from 400–800 μgs against the toxin B recombinant, there was approximately a 200–233 fold reduction and 500–1000 fold reduction in the detectable amount of anti-recombinant toxin protein IgY found in the cecum directed against Interval A-6 and Interval B-3, respectively.

These results were obtained using antibodies present in carbonate buffer. If the orally administered anti-recombinant toxin IgY were properly protected from degradation during passage through the GI tract (i.e. through use of an enteric coating as described in Example 37) the effective therapeutic dose required for oral administration would be less than that specified in Example 42.

c) Indirect Determination of the Amount of Specific Anti-Recombinant *C. difficile* Toxin A and Toxin B IgY in the Cecal Contents by ELISA In order to confirm the values determined in Example 43(b) for the amount of anti-recombinant toxin IgY levels found in the cecum of a treated hamster, the following experiment was performed. The standard ELISA format was used (described in Example 13c) unless otherwise specified.

The cecal extracts from an untreated hamster (serving as the negative control) and one treated with both anti-recombinant toxin A and anti-recombinant toxin B IgY [described in section a) above] were used in this experiment. The total cecal IgY, not just the amount of cecal IgY specific for the recombinant *C. difficile* toxin proteins, was directly determined. Because the percent amounts of specific antibody contained within the IgY preparations was known, the determination of the total IgY level present in the cecal extracts allowed the amounts of specific antibody in the cecal extract to be calculated.

A sandwich ELISA assay was used to capture IgY in the cecal material as follows. Rabbit anti-chicken IgG (Cappel) at 0.1 Ig/ml in PBS was used to coat a microtiter plate (100 μl per well) overnight at 4° C. Both of the cecal extracts were tested at an initial dilution of 1:500 and at serial 5-fold dilutions to a final dilution of 1:312,500. All sample dilutions were tested in duplicate. Affinity-purified antibodies directed against recombinant toxin A (pPA1870-2680, Interval A-6) were diluted to 0.1 μg/ml and then further diluted serially by five-fold to a final concentration of 0.16 ng/ml, was also tested by ELISA for allow for quantitation by comparison. After incubation and washing, rabbit anti-chicken alkaline phosphatase IgG (Sigma) was added (at 1:1000 dilution) to the plates. The plates were then washed and substrate (p-nitrophenyl phosphate) was added and the plates were evaluated as described in Example 13c.

As described above in Example 43(b), the ELISA reactivity obtained using the affinity purified anti-recombinant toxin A IgY was matched to that ELISA activity generated in dilutions of cecal extract, to quantitate the amount of total IgY found in the cecum of the treated hamster.

From the results of the ELISA assay, the amount of total IgY in the cecum of the treated hamster was estimated to be 50 μg/ml. Affinity purification studies showed that total IgY preparations comprised about 7% or 3.5 μg/ml IgY specific for recombinant toxin A (anti-A-6 IgY) and about 1–2% or 500–1000 ng/ml IgY specific for anti-recombinant toxin B (anti-B-3 IgY). The concentrations of both of the specific IgYs detected here correlates fairly closely with the amounts detected above in Example 43(b), namely, 3.5 μg/ml versus 12 μg/ml for anti-Interval A-6 and 800 ng/ml versus 500–1000 ng/ml for anti-Interval B-3.

The results above and in section b) of this Example, both indicate that very low levels of specific anti-Interval A-6 and B-3 IgY's were detected at the site of the *C. difficile* infection. Since the hamster was protected from CDAD, this level of anti-recombinant toxin A and B is within the therapeutic range. These results also support the proposition that much lower levels of anti-recombinant toxin IgYs would need to be orally administered if they were delivered using means to prevent degradation in the GI tract (i.e., enteric coating of IgY).

EXAMPLE 44

Treatment of Diarrheic Hamsters Using Anti-Recombinant *C. difficile* Toxin A Protein IgY To determine whether hamsters presenting with diarrhea after infection with *C. difficile* could be effectively treated using the anti-recombinant *C. difficile* toxin A IgY alone or whether a combination of anti-recombinant toxin A and B IgY is required, the following experiment was performed.

Hamsters were given Clindamycin and infected with *C. difficile* essentially as described in Example 32c. The anti-recombinant toxin A IgY and anti-recombinant toxin B IgY were produced against pMA1870-2680 (Interval A-6) and pPB1750-2360 (Interval B-3), respectively.

Three groups of hamsters (Sasco) were predisposed to *C. difficile* infection by I.P. injection of 1 ml of Clindamycin-phosphate (Biomol) at 1 mg/100 g body weight. About 24-hours later, each hamster was challenged, using an 18 gauge feeding needle, with a 1 ml inoculum containing approximately $1'10^4$ *C. difficile* (ATCC 43596) organisms in sterile saline. The bacteria were grown for about 48 hours on CCFA agar (BBL) plates prior to infection.

The three groups, each containing nine to ten members, were given IgY preparations using a feeding needle. Group I received pre-immune IgY; Group II received anti-recombinant toxin A IgY (anti-A-6 IgY); Group III received a mixture of anti-recombinant toxin A IgY and anti-recombinant toxin B IgY (anti-A-6/B-3 IgY). Each IgY preparation comprised an 8× PEG prep in 0.1 M carbonate buffer, pH 9.5 and contained about 40 mg/ml of protein. To generate the anti-A-6/B-3 IgY mixture, equal volumes of the two 8× concentrates (i.e., anti-A-6 and anti-B-3) were mixed together. The amount of specific anti-recombinant *C. difficile* toxin A IgY in the anti-A-6 IgY preparation was about 2.8 mg/ml. The amount of specific anti-recombinant *C. difficile* toxin A IgY in the anti-A-6/B-3 IgY prep per ml was therefore half that of the A-6 IgY prep (i.e., 1.4 mg/ml). About 200–400 μg/ml of specific anti-recombinant *C. difficile* toxin B IgY was present in the anti-A-6/B-3 IgY preparation.

After the onset of diarrhea was detected in each individual hamster, that animal was dosed with 2 ml of their respective treatment preparations (i.e., either pre-immune, anti-A-6 IgY or anti-A-6/B-3 IgY). The onset of diarrhea was detected in the hamsters from 20 to 44 hours post-inoculation with *C. difficile*. The majority of the hamsters (82%) exhibited diarrhea within 24 hours post-inoculation with the organisms. The majority of the animals were given 3 doses of IgY per day at roughly 4 hour intervals for 2 days; however, some hamsters were only dosed once or twice on the first day of treatment due to a later onset of diarrhea.

The results of this experiment indicated that the anti-A-6 IgY was able to protect many of the hamsters from death, even if given after the onset of diarrhea. About half (55%) of the hamsters treated with anti-A-6 IgY survived for approximately one month, while only 11% of the hamsters treated with preimmune IgY and 20% of the hamsters treated with anti-A-6/B-3 IgY survived.

Because it appears that the anti-A-6 IgY is the most important component for prevention of death in the hamster model (e.g., Example 32(a)), the results obtained in hamsters treated with the anti-A-6/B-3 IgY (which contains half the amount of specific anti-A-6 IgY compared to the A-6 IgY alone preparation) was not unexpected (only 20% of the animals were protected from death). In this Example, anti-A-6 IgY alone could not prevent mortality in 50% of the hamsters, and anti B-3 IgY alone did not provide protection. In addition, the results obtained in previous studies (e.g., Example 32c) indicated that the anti-B-3 antibodies are more important in preventing the onset of diarrhea rather than in preventing death due to CDAD.

All of the animals that were successfully treated with the anti-A-6 IgY exhibited mild diarrhea before treatment was started. If diarrhea was severe and neurological symptoms were present before treatment was initiated, the hamsters could not be successfully treated with oral anti-A-6 IgY.

The above hamster treatment experiment was repeated, with the exception that only pre-immune or anti-A-6 IgY were administered. Ten to eleven hamsters per group were treated with 2 ml of 8×IgY concentrates after diarrhea has been detected in each individual hamster. The treatment schedule was as described above.

Diarrhea was detected in the hamsters from about 20 to 45 hours after inoculation with *C. difficile*. Eighty-five percent of the animals (17/20) presented with diarrhea about 28 hours after infection. The data from these two studies were combined and are shown in FIG. 48.

Figure 48:
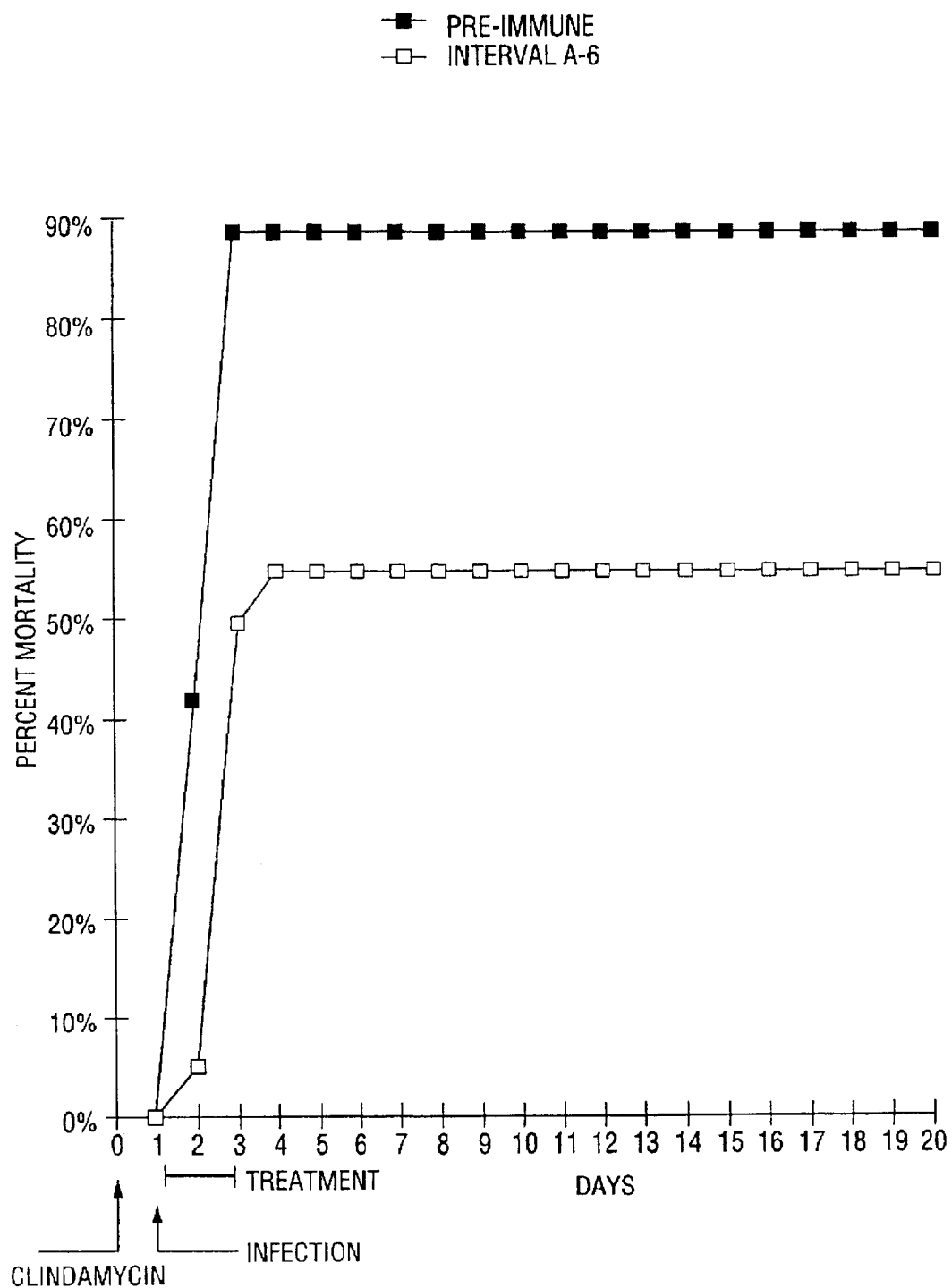
FIG. 48 results of a therapeutic treatment study in diarrhetic hamsters.

In FIG. 48, the percentage cumulative mortality is displayed along the ordinate and the time (in days) is displayed along the abscissa. The treatment period is indicated by the use of the bar between days 2 and 3. The administration of Clindamycin and the inoculation with *C. difficile* organisms (marked as "Infection" in FIG. 48) is indicated by the arrows. The solid black squares represent hamsters which received pre-immune IgY and the open squares represent hamsters which received anti-A-6 IgY.

The data shown in FIG. 48 demonstrates that 45% of the hamsters treated with anti-A-6 IgY post-diarrhea survived after treatment (diarrhea resolved itself in most of these hamsters). The results obtained using anti-A-6 IgY as compared to the results obtained using pre-immune IgY was statistically significant at P<0.05. All of the hamsters treated with anti-A-6 IgY survived long term (>1 month after treatment until the termination of the experiment).

These results provide the first description of a treatment regime which can be used to treat hamsters after the onset of diarrhea due to infection with *C. difficile*. Furthermore, these results demonstrate that the anti-recombinant *C. difficile* toxin A IgY is an effective therapeutic even when administered at the late stages of CDAD, (i.e.,after the onset of diarrhea).

EXAMPLE 45

Treatment of Established *C. difficile* Infection Using Anti-Recombinant *C. difficile* Toxin A Protein and Toxin B Protein IgYs Generated Using Two Different Adjuvants.

The ability of recombinant toxin A and toxin B proteins produced using the pET vector to elicit neutralizing IgY in the hens capable of protecting hamsters against *C. difficile* infection was examined. In previous studies (Example 32 or Example 44), the IgYs were generated against recombinant *C. difficile* toxin A proteins expressed using the pMal vector (pMA1870-2680, Interval A-6). Because recombinant proteins expressed using the pET system could be isolated in a more highly purified form, as compared to proteins expressed using the pMal vector, production of antibodies against the toxin A recombinant produced in pET (pPA1870-2680, A-6) was preferred.

The anti-pPA1870-2680 IgYs were tested in the hamster model along with antibodies raised against the toxin B protein also expressed using the pET vector (pPB1750-2360, Interval B-3). The use of a common expression system to produce both recombinant toxins has definite manufacturing advantages. For example, the same affinity-purification columns and protocols can be used for both recombinants and both antigens should be of comparable purity and yield.

A further objective of this example was to generate antibodies against both pET produced A-6 and B-3 toxin proteins using the same adjuvant. In previous examples (Example 32 or Example 44), the IgYs tested were generated against either A-6 or B-3 recombinants using different adjuvants (the RIBI adjuvant was used for the anti-recombinant toxin A IgY and Freund's adjuvant was used for the recombinant toxin B IgY).

The example involved a) the immunization of hens with recombinant *C. diffcile* toxin proteins expressed using the pET vector and 2 different adjuvants and the determination of anti-recombinant protein IgY titers by ELISA and b) treatment of *C. difficile*-infected hamsters using a mixture of Gerbu or Quil A-generated anti-recombinant toxin A (A-6) and toxin B (B-3) IgY.

a) Immunization of Hens with Recombinant *C. difficile* Toxin Proteins Expressed Using the pET Vector and Two Different Adjuvants and the Determination of Anti-Recombinant Protein IgY Titers by ELISA Hens were immunized with recombinant proteins expressed using the pET vector; nickel column affinity-purified recombinant toxin A (pPA1870-2680) or the recombinant toxin B (pPB1750-2360) proteins were mixed with either the Quil A (Accurate Scientific) or Gerbu (CC Biotech) adjuvants. These two adjuvants were chosen on the basis of performance (shown in Example 35) and cost. The immunization protocol followed was basically that described in Example 35.

Briefly, hens were immunized with 100 µg of pPA1870-2680 for the first four immunizations followed by two immunizations using 1 mg of protein. Hens were immunized six times using 1 mg of pPB1750-2360 per immunization. Five hundred microliters of a solution containing either recombinant toxin protein and either 5 µg of Gerbu or 75 µg of Quil A was administered sub-cutaneously to each hen. About 1 week after the last boost, the eggs were collected and the IgYs in each group (four groups of hens, using both toxin recombinants with both adjuvants) were extracted using PEG as described in Example 1. IgY from preimmune eggs was also processed.

The IgYs were resuspended in 0.1 M carbonate buffer, pH 9.5 at 8× yolk concentration (about 40 mg/ml) and an ELISA was performed (as described in Example 35) to determine the anti-recombinant toxin A and anti-recombinant toxin B titers. The antibody titers generated against either the pPA1870-2680 (A-6) or pPB1750-2360 (B-3) proteins using either the Gerbu or Quil A adjuvants was found to be 1:62,500. By affinity purification, the amount of specific A-6 and B-3 IgY using Gerbu was 4.3% and 1.0% respectively. The amount of specific IgY using Quil A was 2.2% for A-6 and 1.9% for B-3.

b) Treatment of *C. difficile* -Infected Hamsters Using a Mixture of Gerbu or Quil A-Generated Anti-Recombinant Toxin A (A-6) and Toxin B (B-3) IgY Equal volumes of the anti-A-6 and anti-B-3 IgY PEG preps generated in section a) using the same adjuvant were mixed. These preparations were designated A-6/B-3 Gerbu and A-6/B-3 Quil A. The hamster treatment study was performed exactly as described in Example 42. Six hours after challenge with $10^4$ *C. difficile* organisms (ATCC strain 43596), the hamsters were treated with 2 ml of either pre-immune IgY or an immune IgY preparation (A-6/B-3 Gerbu and A-6/B-3 Quil A). The hamsters were treated with 2 ml of IgY for two more days, once per day.

Figure 49:
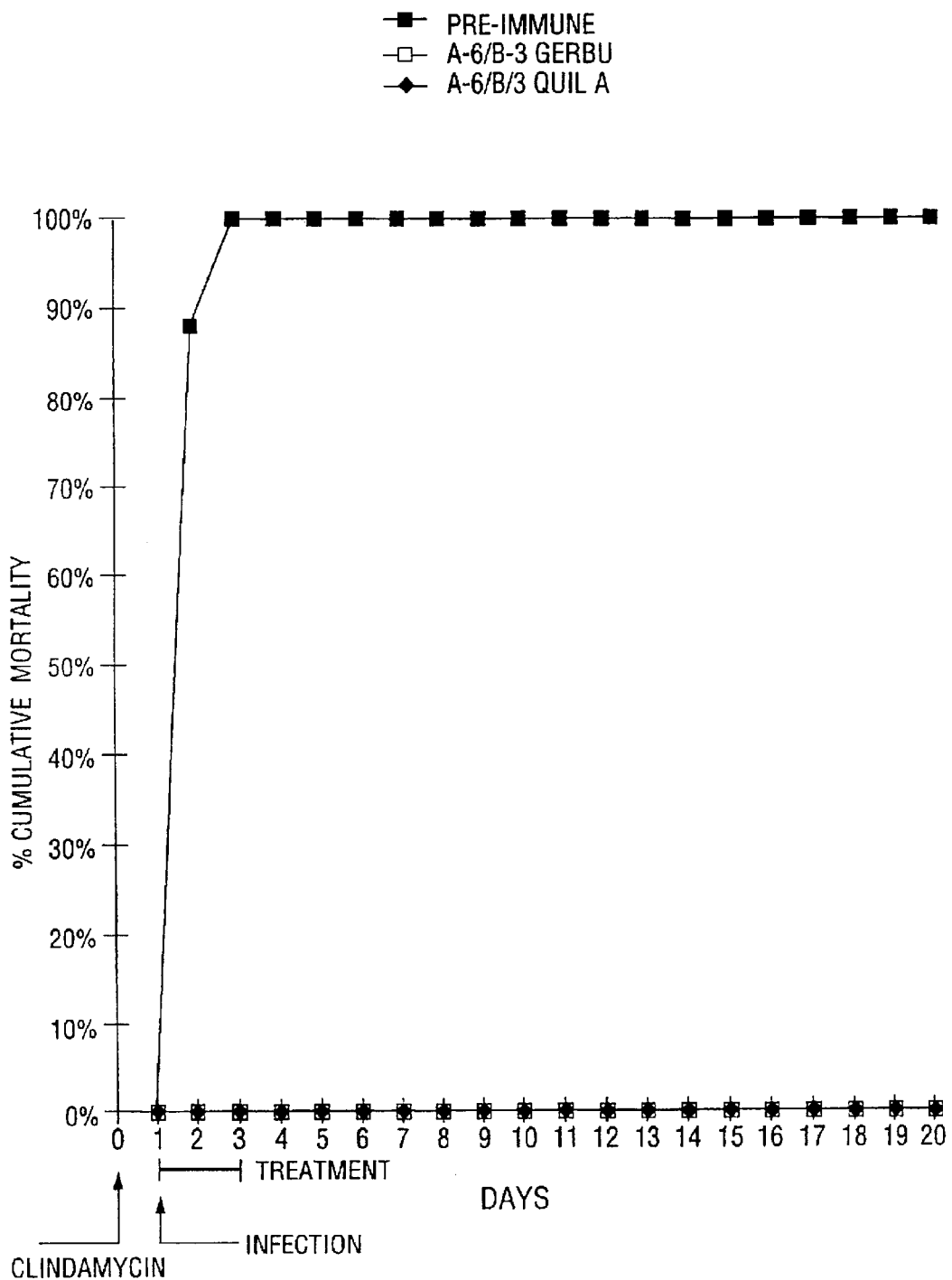
FIG. 49 results of a therapeutic treatment study in hamsters.
Figure 50:
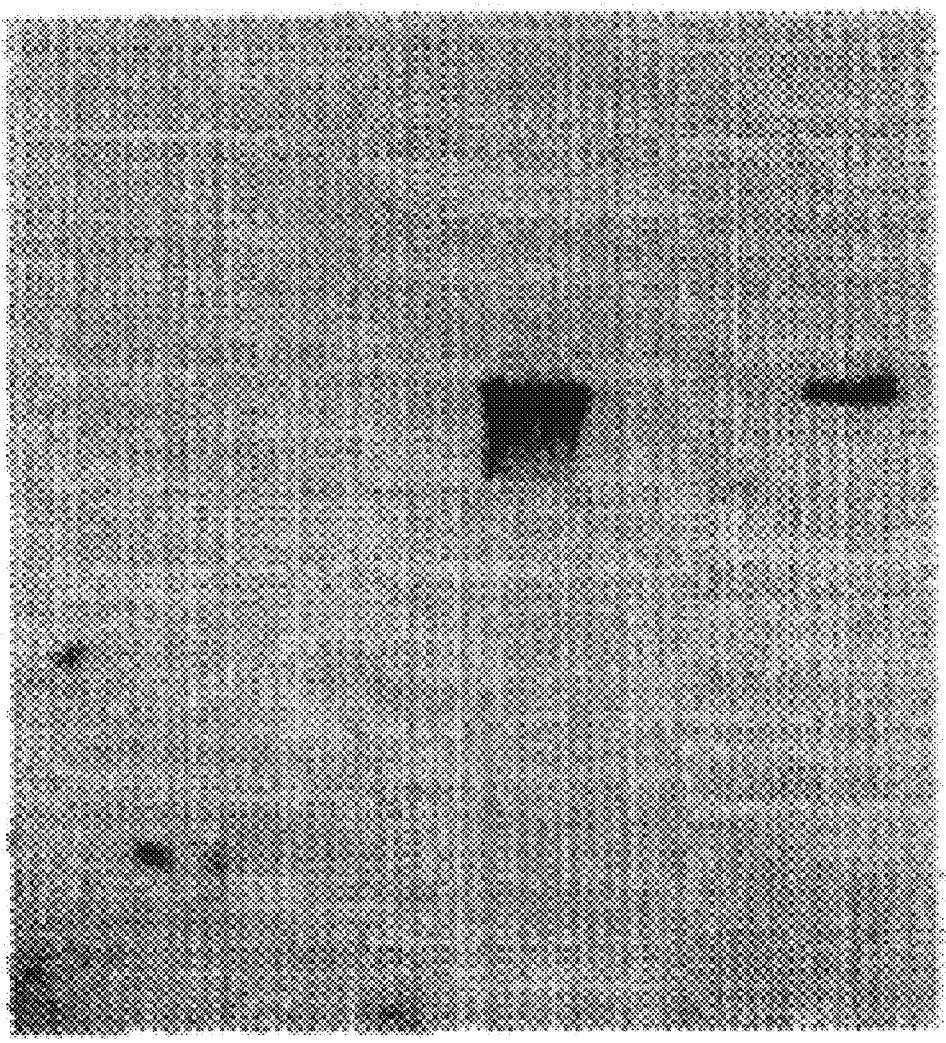
FIG. 50 shows a Western blot showing *C. difficile* toxin A levels in culture supernatant, column flow through and column eluate from an affinity purification column.

The results of this hamster treatment study are shown in FIG. 49. In FIG. 49, the percentage cumulative mortality is displayed along the ordinate and the time (in days) is displayed along the abscissa. The treatment period is indicated by the use of the bar between days 1 and 3. The administration of Clindamycin and the inoculation with *C. difficile* organisms (marked as "Infection" in FIG. 49) is indicated by the arrows. The solid black squares represent hamsters which received pre-immune IgY; the open squares represent hamsters which received anti-A-6/B-3 Gerbu IgY and the solid black diamonds represent hamsters which received anti-A-6/B-3 Quil A IgY. The results shown in FIG. 49 demonstrate that both immune IgY preparations (A-6/B-3 Gerbu and A-6/B-3 Quil A) completely protected the hamsters from death due to CDAD. Nine out of nine of the hamsters treated with either of the immune IgY preparations survived infection with *C. difficile*, while all nine of the hamsters treated with pre-immune IgY died. The survival rates seen using either the A-6/B-3 Gerbu or A-6/B-3 Quil A preparations were statistically significant compared to the result obtained using pre-immune IgY (P value of <0.001 using Chi-square analysis).

Three out of nine of the animals treated with A-6/B-3 Gerbu and one out of nine of the animals treated with A-6/B-3 Quil A presented with very slight diarrhea. The slight diarrhea seen in these treated hamsters (compared to the total absence of diarrhea seen in previous Examples, such as Example 32) may be due to the lower antibody titer of the preparations used here (1:62,500 versus 1:125,000). Additional booster immunizations should increase titers to the 1:125,000 range for hens immunized using either Gerbu or Quil A adjuvants, and thus increase therapeutic potency against diarrhea.

The above results indicate that the recombinant C. difficile toxin A and B proteins can be produced using the pET vector (in place of the pMal vector) without deleterious effects upon the production of neutralizing antitoxin. Furthermore, the same adjuvant can be used in conjunction with the pET-produced proteins to elicit in vivo neutralizing IgY. Moreover, the same adjuvant can be used with both recombinant toxin proteins to produce a therapeutic anti-recombinant IgY response in vivo.

EXAMPLE 46

Production of Antibodies Using a Mixture Containing Recombinant *C. difficile* Toxins A and B in Hens The ability to raise chicken antibodies directed against both a recombinant *C. difficile* toxin A and toxin B protein using a mixture of both proteins as a combined immunogen was investigated. The example involved a) immunization of hens with a mixture of recombinant *C. difficile* toxin A and B proteins and b) purification and detection of anti-recombinant *C. difficile* toxin A and toxin B IgY.

a) Immunization of Hens With a Mixture of Recombinant *C. difficile* Toxin A and B Proteins Egg-laying Leghorn hens were immunized with a mixture of recombinant toxin A (pPA1870-2680, Interval A-6) and recombinant toxin B (pPB1750-2360, Interval B-3) proteins; both recombinant proteins were expressed using the pET vector system. Two groups of hens (each containing 4 hens) were immunized with 500 μg of each recombinant protein mixed with either Quil A (Accurate Scientific) or Gerbu (CC Biotech) adjuvant. A total volume of 1 ml containing the recombinant proteins and either 5 μg Gerbu or 75 μg Quil A adjuvant was administered to each hen. The immunization protocol followed for each adjuvant was as described in Example 35. The hens were immunized twice 2 weeks apart.

b) Purification and Detection of Anti-Recombinant *C. difficile* Toxin A and Toxin B IgY About 1 week after the last boost, 3 eggs from each group were collected and IgY was extracted using PEG as described in Example 1. The IgYs were resuspended in PBS (pH 7.4) at a 4× concentration each containing about 20 mg/ml total protein. Preimmune IgY served as a negative control.

The amount of anti-recombinant toxin A (A-6 IgY) and anti-recombinant toxin B (B-3 IgY) antibodies present in the two immune IgY preparations was determined by ELISA essentially as described in Example 13c or Example 43b. Briefly, the wells of a microtiter plate were passively coated with either the toxin A recombinant (pPA1870-2680) or the toxin B recombinant (pPB1750-2360). The IgY samples were initially diluted 250-fold, then serially diluted 5-fold. All samples were tested in duplicate. Rabbit anti-chicken IgG alkaline phosphatase (Sigma) diluted 1:1000 was used to detect the specific IgY.

The results of these ELISA assays revealed that both recombinant toxin antigens were able to elicit an IgY response in the hen. The antibody titers are expressed as the reciprocal of the highest dilution that was found to be about 3-fold higher in ELISA reactivity compared to pre-immune (i.e., the negative control) at the same dilution. The titers for both the anti-A-6 IgY and anti-B-3 IgY generated using the Gerbu adjuvant were very low at about 1:250. The titer for the anti-A-6 IgY and anti-B-3 IgY generated using the Quil A adjuvant was from 5 and 25 fold-higher compared to the Gerbu adjuvant. Antibody titers generated using Quil A for the anti-A-6 IgY was greater than 1:6250 and greater than 1:1250 for the anti-B-3 IgY.

While the IgY titers against the recombinant toxins using Quil A are lower than the levels achieved previous Examples (e.g., Example 32) (mainly because these hens in this example have been immunized only twice; in comparison the hens in previous examples were immunized 5 to 10 or more times and the resulting anti-toxin protein titers reached 1:100,000 or more), the results indicated that both recombinant toxin proteins appear to be equally antigenic in the hens and the antibodies produced to each were present at comparable levels. The results also indicated that the level of the antibody response generated depends on the adjuvant used. It was found that the Quil A adjuvant invoked a higher anti-A-6 and anti-B-3 IgY response early during the immunization process in comparison to the results obtained using the Gerbu adjuvant.

EXAMPLE 47

Affinity Purification of Native *C. difficile* Toxin A Using Anti-Recombinant *C. difficile* Toxin A Antibodies Avian antibodies (IgY) raised against recombinant *C. difficile* toxin A protein were affinity purified using interval A-6 as the affinity ligand. The resulting specific antibodies were then immobilized on a solid support to purify native toxin A from *C. difficile* (ATCC #43255) organisms grown in dialysis bags submerged in BHI broth. The following example describes the a) affinity purification of avian antibodies directed against a recombinant fragment of toxin A and generation of a toxin A affinity column, b) growth of *C. difficile* organisms to produce toxin A and B in dialysis bag culture supernatants, c) affinity purification of toxin A, d) in vitro characterization of affinity purified *C. difficile* toxin A, e) investigation of an alternate strategy for coupling the anti-A-6 IgY to a solid support to affinity purify toxin A, f) affinity purification of *C. difficile* toxin A on affinity column generated by periodate oxidation of A-6 IgY and g) in vitro characterization of affinity purified *C. difficile* toxin A.

a) Affinity Purification of Avian Antibodies Directed Against a Recombinant Fragment of Toxin A and Generation of a Toxin A Affinity Column Antibodies specific for Interval A-6 (aa 1870-2680) of *C. difficile* toxin A were affinity purified to provide reagents for the generation of an affinity column to permit purification of *C. difficile* toxin A from liquid culture supernatants and to provide an immunoassay reagent to permit detection of *C. difficile* toxin A in culture supernatant and affinity purified *C. difficile* toxin A samples.

i) Affinity purification of A-6 IgY

Hyperimmune IgY from eggs containing antibodies to A-6 recombinant protein using Freund's adjuvant was extracted using the PEG fraction method (Example 1). The antibody-containing supernatant was applied to a A-6 affinity column, made by covalently coupling pPA1870-2680 protein (prepared in Example 29) to Actigel A affinity resin (Sterogene Biochemicals) according to manufacturer's instructions. Approximately 10.2 mg of pPA1870-268 (A-6) protein was coupled to 5 ml Actigel affinity resin. The anti-A-6 IgY was eluted with Actisep elution media (Sterogene Biochemicals) as described in Example 15c, and dialyzed against PBS for 24–48 hours at 2–8° C.

ii) Coupling of Affinity-Purified Anti-A-6 IgY to an Activated Affinity Resin to Make a *C. difficile* Toxin A Affinity Column An initial toxin A affinity column was prepared as described in Example 48a below, by coupling the anti-A-6 IgY to Actigel A affinity resin. By comparing the pre- and post-coupling absorbance values of the IgY at 280 nm, it was estimated that 58%, or about 7.6 mg, of the anti-A-6 IgY was coupled to the affinity resin.

b) Growth of *C. difficile* Organisms to Produce Toxins A and B in Dialysis Bag Culture

*C. difficile* strain #43255 was grown as described in Example 49b, sections iv and v, below. SDS-PAGE/Western blot analysis was conducted to evaluate the *C. difficile* dialysis bag culture supernatants for the presence of toxin A as follows.

The dialysis bag culture supernatant samples and a known toxin A sample purchased commercially were analyzed as described in Example 49b, section iv, with the exception that affinity purified A-6 IgY was used as the primary antibody for the western blot.

Following SDS-PAGE (5% polyacrylamide gel) the proteins were transferred to nitrocellulose using a Milliblot transfer apparatus (Millipore) according to the manufacturer's instructions. The blot was temporarily stained with 10% Ponceau S, and blocked overnight in PBS containing 1 mg/ml dry milk. The preimmune and anti-A-6 IgY primary antibodies were diluted to 1 tg/ml in PBS containing 1 mg/ml BSA, and the appropriate antibody was incubated with the corresponding blot for 2 hours at room temperature with gentle agitation. The strips were washed with PBS (10 mM sodium phosphate, 150 mM NaCl, pH 7.2), BBS-Tween (0.1 M boric acid, 0.025 M sodium borate, 1 M NaCl, 0.1% v/v Tween 20) and PBS to remove unbound primary antibody, and incubated with Rabbit anti-chicken IgG alkaline phosphatase conjugated secondary antibody (Sigma Chemical Co), diluted 1:2000 in PBS/BSA. The blots were washed to remove unbound secondary antibody, and the strips were developed in BCIP/NBT substrate solution (as described in Example 48 below).

Both culture supernatant samples analyzed appeared to contain immunoreactive *C. difficile* toxin A when analyzed by Western blot. This protein co-migrated with the commercial toxin A and was recognized by the affinity-purified anti-A-6 IgY. The culture supernatant samples were pooled prior to affinity purification of toxin A. The pooled culture supernatants were not concentrated prior to loading on the affinity column.

c) Affinity Purification of *C. difficile* Toxin A

The *C. difficile* toxin culture supernatant samples were affinity purified as described in Example 48c. The volume of the Actisep fraction following elution and dialysis was 42 ml, 15 ml of which were removed and concentrated to 3 ml prior to analysis. A Centricon 30 concentrator (Amicon) was used to concentrate the sample.

d) Analysis of *C. difficile* Culture Supernatant, Actisep-Eluted Fraction and Column Effluent for the Presence of Toxin A In order to determine the presence or absence of toxin A in the Actisep eluted sample and effluent from the affinity column, these samples were analyzed by SDS-PAGE and Western blot along with the culture supernatant starting material. These analyses were performed as described in section b above to evaluate the relative amount of toxin A in the samples and the efficiency of the affinity purification.

The resulting Western blot is shown in FIG. 50. In FIG. 50, lanes 1–3 were incubated with pre-immune IgY as the primary antibody and lanes 4–6 were incubated with anti-A-6 IgY as the primary antibody. Lanes 1 and 4 contain culture supernatant starting material; lanes 2 and 5 contain column flow-through and lanes 3 and 6 contain affinity purified toxin A.

The results shown in FIG. 50 demonstrated that immunoreactive toxin A was detected in the culture supernatant starting material and the Actisep fraction. Furthermore, no toxin A was observed in the column effluent sample, indicating most of the toxin was bound by the affinity column. There appeared to be significantly more toxin A in the starting material than in the Actisep fraction. Since the column effluent apparently contains no toxin A, the difference in toxin A amounts between the starting material and Actisep fraction suggested a significant amount of the toxin was still bound to column, even after Actisep elution. One possible explanation for the inability of the Actisep to elute all of the toxin A is the tendency for toxin A to bind nonspecifically to the carbohydrate region of molecules such as immunoglobulins. This is possible because the anti-A-6 IgY on the column is coupled via primary amines, which would allow for a subpopulation of the IgY to couple via the Fab region, leaving the carbohydrate-containing Fc region accessible for binding to toxin A.

e) Investigation of an Alternate Strategy for Coupling the Anti-A-6 IgY to a Solid Support to Affinity Purify Toxin A The possibility of coupling IgY to a solid support by periodate oxidation of the carbohydrate region was next examined. This method of coupling was predicted to accomplish the following: 1) couple the IgY to the support via the Fc region, leaving the Fab regions accessible for binding to *C. difficile* toxin, and 2) alter the carbohydrates enough to eliminate or reduce the nonspecific binding of *C. difficile* toxin A.

i) Oxidation of Anti-A-6 IgY with Sodium Periodate

The anti-A-6 IgY was oxidized using sodium periodate (Sigma Chemical Co) as follows. A sodium periodate stock solution was made by dissolving 25 mg of sodium periodate in 1.2 ml of distilled, deionized water. To six ml of A-6 IgY (at 2.7 mg/ml) in a 15 ml polystyrene tube 600 μl (0.1 volume) of the sodium periodate stock solution was added. The tube was then covered with aluminum foil and mixed gently at room temperature for 1 hour and 20 minutes. Glycerol was then added to a final concentration of 20 mM, and the tube was inverted for 10 more minutes. The solution was then dialyzed against 100 mM sodium acetate, 150 mM NaCl, pH 5.5 to remove the sodium periodate.

ii) Coupling of Oxidized IgG to Affi-Gel Hz Hydrazide Gel (BioRad)

Six ml of Affi-Gel resin was washed with coupling buffer (100 mM sodium acetate, pH 5.5 and 150 mM sodium chloride). The oxidized anti-A-6 IgY was filtered through a glass fiber syringe filter to remove the precipitate which had formed during the oxidation procedure, and a 100 μl aliquot was removed for $A_{280}$ analysis. The washed Affi-Gel resin was added to the oxidized IgY in a 15 ml polystyrene tube, and the tube was inverted overnight at room temperature (Total volume=12 ml).

iii) Determination of Coupling Efficiency

The anti-A-6 IgY-Affi-Gel affinity resin was poured into a BioRad Econo column and the unbound antibody was washed through the resin and saved for $A_{280}$ analysis. The resin was then washed with 1 bed volume of PBS (10 mM sodium phosphate, 0.5 M NaCl, pH 7.2). This wash was also collected and saved for $A_{280}$ analysis. The resin was then washed with several more volumes of PBS, and treated with the Actisep elution buffer (Sterogene Bioseparations) to ensure no unbound antibody remained in the resin. By comparing the pre-and post-coupling $A_{280}$ values of the A-6 IgY, it was estimated that 95%, or 8.4 mg, of the IgY was coupled to the resin.

f) Affinity Purification of C. difficile toxin A on Affinity Column Generated by Periodate Oxidation of Anti-A-6 IgY Two dialysis bag culture supernatants, grown as described in Example 48b, sections iv and v, were pooled and concentrated to about 10.5 ml using an Amicon centriprep concentrator. The pooled, concentrated supernatants were then applied to the anti-A-6 IgY Affi Gel affinity column and the column effluent was collected and reloaded several times to bind as much toxin as possible. The unbound protein was then removed by washing the column with several bed volumes of PBS and the bound toxin A was eluted with 2 bed volumes of Actisep elution media. The column effluent was saved for analysis to evaluate the efficiency of the affinity purification. The Actisep-eluted toxin was then dialyzed against TBS for 24–48 hours at 2–8° C., and concentrated from 53 to 3 ml using a Centriprep concentrator (Amicon).

g) In Vitro Characterization of Affinity Purified C. difficile Toxin A i) Protein Assay The purified toxin concentration was determined using a BCA protein assay (Pierce) and was found to be 70 μg/ml, or about 210 μg total from 37 ml of culture supernatant, indicating there was about 5.7 μg of toxin/ml of culture supernatant.

ii) Comparison of Toxin Purity and Retention Times by HPLC

HPLC analysis was used to compare both the purity and retention times of the affinity purified toxin A samples. Commercial and affinity purified toxin A samples were applied to a Shodex KW 803 HPLC column and eluted with PBS, using a Waters HPLC system. The toxin A retention times were approximately 7 minutes for both toxin samples, suggesting the toxins are identical. Furthermore, the purities of both toxins were similar.

iii) Western Blot Analysis of Culture Supernatant Starting Material, Affinity Purified Toxin A and Column Effluent (flow through)

In order to evaluate the efficiency of the affinity purification and immunochemically identify the affinity purified toxin A, the culture supernatant, affinity purified toxin A, and column effluent samples were electrophoresed by SDS-PAGE on a 5% gel under reducing conditions and transferred to nitrocellulose using standard methods. The blot was temporarily stained with 10% Ponceau S to allow the lanes to be marked and the remaining protein binding sites were blocked overnight at 2–8° C. with a PBS solution containing 1 mg/ml dry milk. The blot was cut into two halves, one of which was incubated with anti-A-6 IgY primary antibody, diluted to 1 μg/ml in PBS containing 1 mg/ml BSA, and the second half incubated with preimmune IgY diluted to 1 μg/ml in PBS/BSA. After a two hour incubation in the presence of the primary antibody (with gentle agitation), the unbound primary antibody was removed with successive washes of PBS, BBS-Tween and PBS. Rabbit anti-chicken IgY alkaline phosphatase conjugated secondary antibody, diluted 1:2000 in PBS containing 1 mg/ml BSA was then added to each blot. After two hours, the blots were washed to remove unbound secondary antibody and developed with BLIP/NBT (Kirkegaard and Perry) substrate solution. Color development was stopped by flooding the blots with water. The resulting Western blot is shown in FIG. 51.

Figure 51:
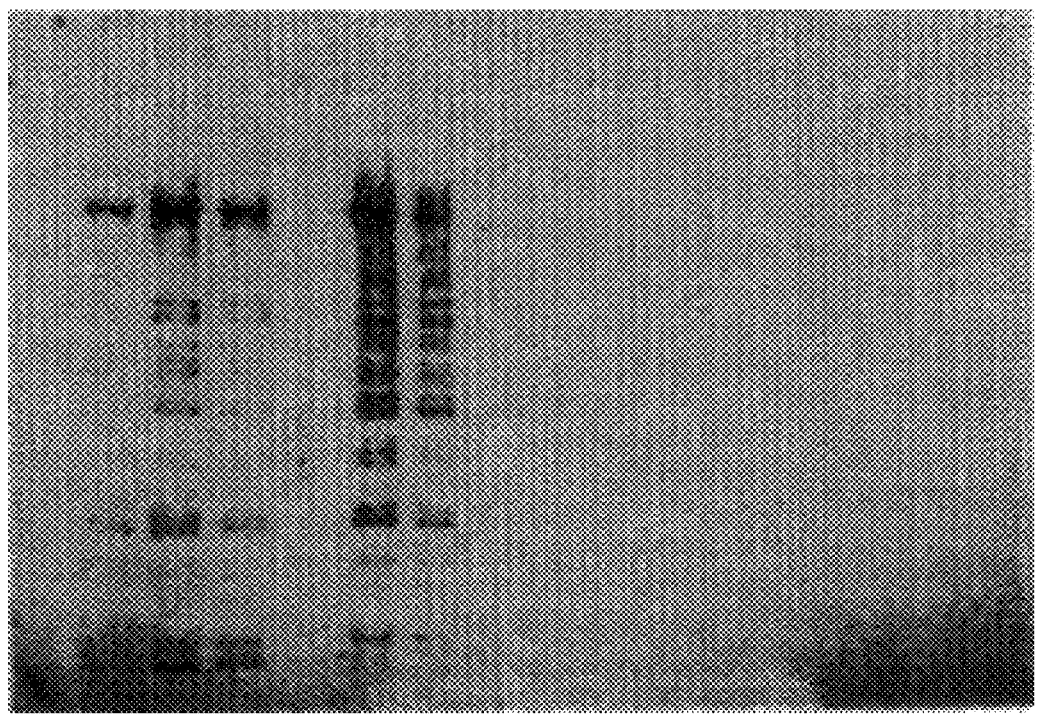
FIG. 51 shows a Western blot showing *C. difficile* toxin A levels in culture supernatant, column flow through and column eluate from an affinity purification column.
Figure 52:
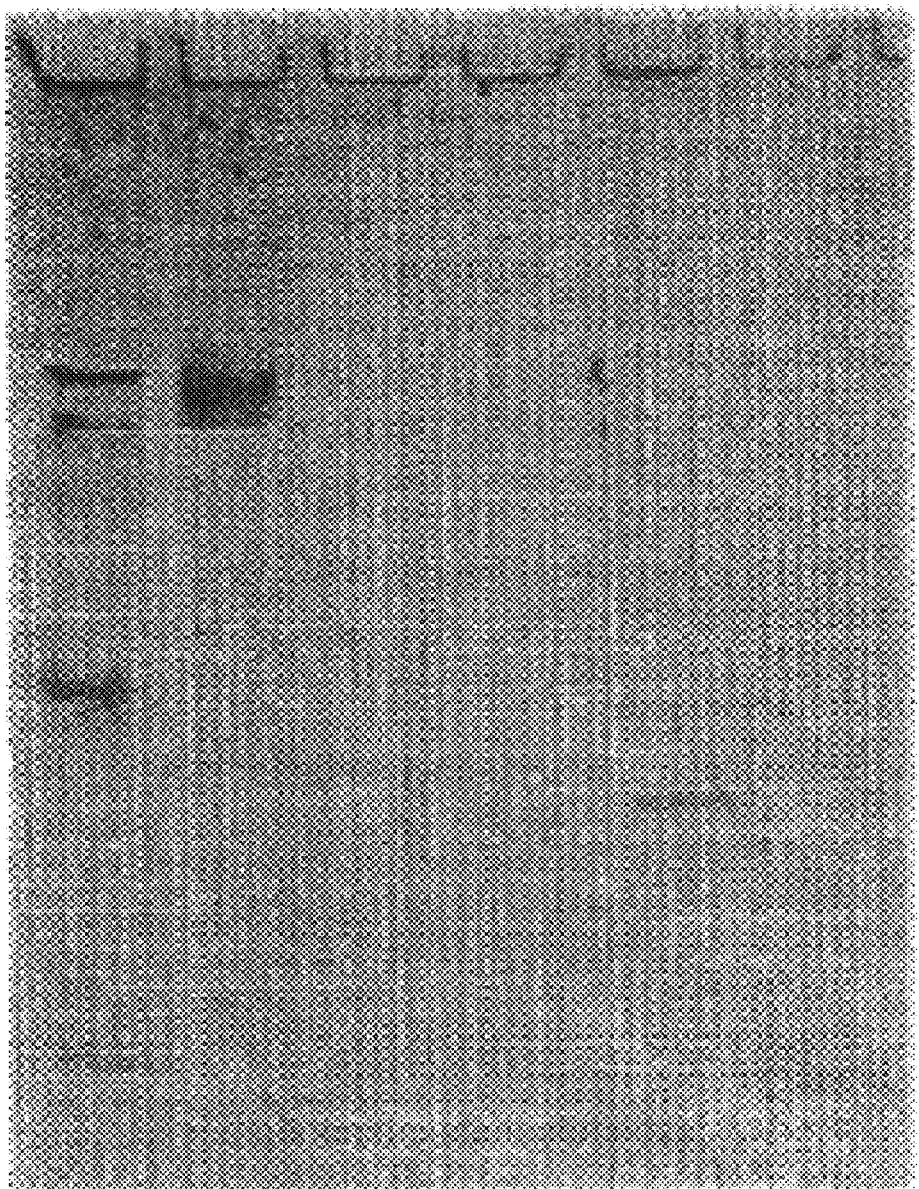
FIG. 52 is an native PAGE gel stained with Coomaisse blue showing *C. difficile* toxin B levels in liquid culture supernatant.

In FIG. 51, lanes 1–7 were incubated with anti-A-6 IgY as the primary antibody and lanes 8–15 were incubated with pre-immune IgY as the primary antibody. Lanes 1 and 9 contain broad range molecular weight markers (BioRad). Lanes 2 and 10 contain C. difficile culture supernatant #1. Lanes 3 and 11 contain C. difficile culture supernatant #2. Lanes 4 and 12 contain C. difficile culture supernatants #1 and #2 (pooled). Lanes 5 and 13 contain column flow-through. Lanes 6 and 14 contain affinity purified Toxin A (high load; i.e., 2× the load shown in lanes 7 and 15). Lanes 7 and 15 contain affinity purified Toxin A (low load). Lane 8 does not contain any sample material (blank).

The affinity purified toxin A sample (lane 7) was 3.5 fold more concentrated than the pooled starting material sample (lane 4); however, ⅓ the volume (5 μl vs 15 μl) of the affinity purified sample was loaded compared to the pooled starting material sample. Consequently, if most of the toxin A was recovered from the column,the toxin A levels detected on the Western blot should be similar. As shown in FIG. 51, the signals corresponding to the main high molecular weight bands are comparable. Therefore, the recovery of toxin A from the affinity column appeared to be quantitative.

EXAMPLE 48

Affinity Purification of Native C. difficile Toxin B Using Anti-Recombinant C. difficile Toxin B Antibodies Avian antibodies (IgY) raised against recombinant C. difficile toxin B protein (pPB 1750-2360; Interval B-3) were affinity purified using Interval B-3 (i.e., aa 1750-2360 of C. difficile toxin B) as the affinity ligand. The resulting purified anti-Interval B-3 specific antibodies were then immobilized on a solid support to facilitate purification of native toxin B derived from C. difficile organisms (ATCC #43255) grown under conditions favorable for toxin production.

The example involved a) affinity purification of avian antibodies directed against a recombinant fragment of C. difficile toxin B and generation of a C. difficile toxin B affinity column, b) growth of C. difficile organisms to produce toxins A and B in liquid culture and dialysis bag culture supernatants, c) affinity purification of C. difficile toxin B, and d) in vitro and in vivo characterization of affinity purified toxin B from C. difficile.

a) Affinity Purification of Avian Antibodies Directed Against a Recombinant Fragment of C. difficile Toxin B and Generation of a C. difficile Toxin B Affinity Column Antibodies specific for Interval B-3 of C. difficile toxin B protein were affinity purified to provide reagents for the generation of an affinity column to permit purification of C. difficile toxin B from liquid culture supernatants and to provide an immunoassay reagent to permit detection of C. difficile toxin B in culture supernatants and affinity-purified *C. difficile* toxin B samples.

i) Affinity Purification of Anti-Interval B-3 IgY

Hyperimmune IgY was extracted from eggs containing antibodies to the Interval B-3 recombinant protein (pPB 1750-2360) generated using Gerbu adjuvant (see Example 45) using the PEG fractionation method (Example 1). The antibody-containing supernatant was applied to an Interval B-3 affinity column, made by covalently coupling pPB 1750-2360 protein (prepared in Example 29) to Actigel A affinity resin (Sterogene) as described in Example 15c. This fragment was chosen because it contains the *C. difficile* toxin B repeat region and does not contain regions of homology with the *C. difficile* toxin A protein, therefore the resulting purified antibody should not cross-react with *C. difficile* toxin A. The anti-Interval B-3 antibodies (anti-B-3 IgY) were eluted from the column with 4 M guanidine HCl, pH 8.0 and dialyzed against PBS for 24 to 48 hours at 2–8° C.

ii) Coupling of Affinity-Purified Anti-B-3 IgY to an Activated Affinity Resin to Make a *C. difficile* Toxin B Affinity Column.

A *C. difficile* toxin B affinity column was made by coupling 11 mg of the affinity purified avian anti-B-3 antibodies prepared above to 5 ml of Actigel affinity resin (Sterogene). A coupling time of 30 minutes was used rather than the minimum 2 hours recommended by the manufacturer in order to minimize the number of sites where each antibody molecule is coupled to the resin, thereby making the antibody more accessible to the toxin. In addition, the column was only exposed to high salt buffers or the Actisep elution buffer (Sterogene); no guanidine solutions were utilized during the preparation of the affinity column in order to minimize denaturation of the anti-B-3 antibodies. Comparison of the pre- and post-coupling absorbance values of the IgY at 289 nm, revealed that approximately estimate 62%, or about 6.8 mg, of the anti-B-3 IgY was coupled to the resin.

b) Growth of *C. difficile* Organisms to Produce Toxins A and B in Liquid Culture and Dialysis Bag Culture Supernatants i) Liquid Culture of *C. difficile* in BHI Broth A frozen stock vial of *C. difficile* (ATCC #43255) was thawed and plated on CCFA plates (BBL) and grown for 36 to 48 hours at 37° C. in an anaerobic chamber. Colonies were harvested from the CCFA plates using a sterile swab. The harvested colonies were used to inoculate a 20 ml liquid culture of BHI broth (BBL). This culture was grown for approximately 24 hours in an anaerobic jar at 37° C. Ten milliliters of the overnight culture were used to inoculate a 500 ml liquid culture of BHI broth, and the culture was grown for approximately 72 hours at 37° C. in an anaerobic chamber.

ii) Harvest of Liquid Culture Supernatant

The 72 hour culture was centrifuged at 5000 rpm (4420×g) for 10 minutes in a Beckman J2-21 centrifuge to pellet the *C. difficile* organisms and the supernatant was filtered through a 0.45μ filter (Nalgene) and saved for toxin purification and analysis at 2–8° C.

iii) In Vitro Analysis of Culture Supernatant to Detect Presence of *C. difficile* Toxin B In order to determine whether *C. difficile* toxin B was present in the culture supernatant, the supernatant was analyzed by native PAGE and Western blotting as follows. The harvested culture supernatant was concentrated about 10-fold using a Centricon 30 concentrator (Amicon) prior to electrophoresis on native PAGE gels. The concentrated sample was then mixed with an equal volume of native gel sample buffer (50% sucrose, 0.1% bromophenol blue) and loaded on a 4–15% Tris-glycine gradient gel (Bio-Rad), along with a known sample of *C. difficile* toxin B, purchased from Techlab. The samples were electrophoresed for 3 hours at 150 volts, constant voltage, using a Hoefer power supply. Following electrophoresis, the gel was cut in half and one half was stained with Coomassie blue and destained with a solution comprising 10% glacial acetic acid/40% methanol to visualize any protein bands. The other half of the gel was blotted and probed using affinity purified anti-B-3 antibody (section i above).

The Coomassie blue stained gel is shown in FIG. 52. In FIG. 52, lane 1 contains broad range molecular weight markers. Lane 2 contains the commercial toxin B (Techlab); lane 3 contains BHI broth; lane 4 contains culture supernatant and lane 5 contains concentrated culture supernatant.

As shown in FIG. 52, the commercial toxin B was detectable on the Coomassie stained gel. The concentrated culture supernatant showed several relatively faint bands, however no detectable proteins in the supernatant samples co-migrated with the known *C. difficile* toxin B sample. Furthermore, western blot analysis did not detect any proteins in the culture supernatant that were recognized by the affinity purified anti-B-3 antibody. These results demonstrated that the above growth conditions did not appear to be optimal for toxin production.

iv) Production of *C. difficile* Toxin B in Dialysis Bag Culture

In order to identify growth conditions optimal for the production of *C. difficile* toxin B, the following experiment was conducted. A liquid culture of *C. difficile* #43255 was grown overnight as described above. The overnight culture was used to inoculate large scale cultures grown in dialysis bags containing PBS and submerged in BHI broth, as described by Meador and Tweten [Infection and Immunity, 56:7 (1988)]. Briefly, two 500 ml wide-mouth media bottles were filled with 400 ml of BHI broth. A dialysis bag having a molecular weight cut-off of 12–14,000 (Spectrapor) containing 25 ml of PBS was tied off at both ends and submerged in the BHI media in each 500 ml bottle. The bottles and dialysis bags were then autoclaved for 30 minutes to sterilize the broth and PBS. The bottles were then incubated for 1 hour at 37° C. under anaerobic conditions to cool the liquids and remove oxygen from the media.

The PBS in each dialysis bag was then inoculated with 10 ml of the overnight culture using a 10 cc syringe fitted with a 27 gauge needle to puncture the bags above the broth level. The bottles were then incubated for 48 to 72 hours at 37° C. under anaerobic conditions. Both bottles showed heavy growth inside the dialysis bags, however one of the bottles also showed turbidity in the BHI broth outside of the dialysis bag, suggesting the BHI was contaminated. Therefore, the contents of the two dialysis bags were kept separate until the contents could be analyzed separately. It was thought that the BHI growth in the contaminated bag was due to *C. difficile* which may have fallen from the needle during inoculation of the dialysis bag.

v) Harvest of Dialysis Bag Culture Supernatants

The dialysis bag contents were removed and centrifuged at 5000 rpm (3440×g) for 10 minutes to pellet the cells and the dialysis bag culture supernatants from each bag were handled separately; each was filtered through a 0.45μ syringe filter and concentrated using a Centriprep 30 concentrator (Amicon). The two samples were concentrated from 35 ml to 3 ml, and stored at 2–8° C.

The culture supernatants from the dialysis bag liquid cultures were analyzed by native PAGE and western blot analysis to evaluate the amount of toxin B produced in the dialysis bag culture supernatants.

vi) Native PAGE/Western Blot Analysis of *C. difficile* Dialysis Bag Culture Supernatants Aliquots of the concentrated dialysis bag culture supernatants and a known *C. difficile* toxin B sample were electrophoresed on a 4–15% Tris-glycine gel (Bio-Rad) as described above in section iii). One half of the gel was stained with Coomassie blue and the other half was transferred to a nitrocellulose membrane for western blot analysis using a semi-dry transfer apparatus (Millipore) and standard transfer conditions (12 volts, constant voltage, for 30 minutes). The remaining protein binding sites on the membrane were blocked overnight in PBS containing 1 mg/ml dry milk.

Figure 53:
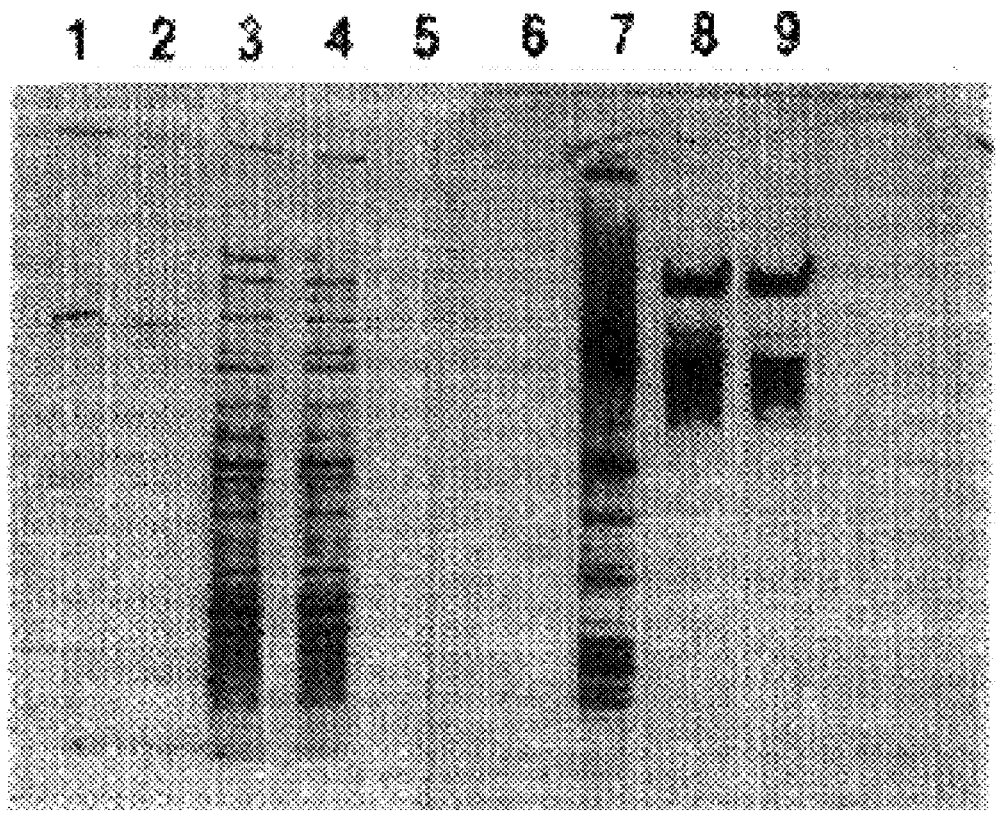
FIG. 53 is an native PAGE gel stained with Coomaisse blue and a Western blot showing *C. difficile* toxin B levels in dialysis bag cultures.

FIG. 53 shows the resulting Coomassie stained gel and Western blot. In FIG. 53, lanes 1–4 represent the Coomassie stained gel and lanes 6–9 represent the Western blot. Lanes 1 and 6 contain broad range molecular weight markers; lanes 2 and 7 contain commercial toin B (Techlab); lanes 3 and 8 contain dialysis bag culture supernatant from the culture having sterile BHI broth; lanes 4 and 9 contain dialysis bag culture supernatant from the culture having "contaminated" BHI broth; lane 5 is blank.

A shown in FIG. 53, the presence of C. difficile toxin B was detected by incubating the blot strips with affinity purified anti-B-3 IgY. After washing the blots to remove unbound anti-B-3 antibodies, bound anti-B-3 antibodies were detected by incubating the strips with a secondary antibody comprising rabbit anti-chicken Ig conjugated to alkaline phosphatase (Sigma). The blots were washed again to remove any unbound secondary antibody and the blots were developed in freshly prepared BLIP/NBT substrate solution. Development was stopped by flooding the blots with water once an adequate signal was obtained.

The results of the PAGE and Western blot analysis showed that the amount of toxin B present in the dialysis bag supernatant samples was too dilute to be detected by staining with Coomassie. However, both culture supernatant samples (one from the bottle with sterile BHI broth and one from the bottle with contaminated BHI broth) contained immunoreactive toxin B when analyzed by Western blotting. The only difference seen between the two culture supernatant samples appeared to be in the amount of toxin B produced. The sterile broth sample appeared to contain more toxin B than did the contaminated broth sample.

Comparison of the commercial toxin B sample to the toxin B produced in the dialysis bag culture supernatant samples revealed that the culture supernatant sample contained a higher percentage of intact toxin B protein (i.e., there was much less evidence of degradation in the form of minor immunoreactive bands present in the culture supernatant samples). Because both culture supernatant samples contained toxin B (although at different concentrations), they were pooled prior to affinity purification.

c) Affinity Purification of C. difficile Toxin B

The dialysis bag culture supernatant samples were pooled and applied to the toxin B affinity column [prepared in section a)]. Nonspecific proteins were removed by washing the column with PBS until the baseline OD was achieved. The bound protein was eluted using Actisep elution media (Sterogene) and was then dialyzed against Tris-buffered saline, pH 7.5 (50 mM Tris, 150 mM NaCl). Following dialysis, the affinity purified protein was concentrated from 40 ml to 4.5 ml using a Centricon 30 concentrator (Amicon).

d) In Vitro and In Vivo Characterization of Affinity Purified Toxin B From C. difficile In order to determine the presence or absence of C. difficile toxin B in the Actisep-eluted sample and effluent from the affinity column (i.e., the flow-through), these samples were analyzed by native PAGE and Western blotting along with the culture supernatant starting material. These analyses were performed to evaluate the relative amount of C. difficile toxin B in the culture supernatant and the efficiency of the affinity purification.

The affinity purified, culture supernatant, flow-through, and commercial C. difficile toxin B samples were each mixed with an equal volume native sample buffer and loaded on a 4–15% native Tris-glycine gradient gel (Bio-Rad). The sample were electrophoresed for approximately 2.5 hours at 200 volts, constant voltage, using a Hoefer power supply, and transferred to nitrocellulose using a semi-dry blotting apparatus (Millipore) according to manufacturer's instructions. The blot was blocked overnight using a solution containing 1% powdered milk in PBS. The blot was then incubated with affinity purified anti-B-3 IgY as the primary antibody and rabbit anti-chicken conjugated to alkaline phosphatase as the secondary antibody. The blots were handled as described in section b(vi) to permit visualization of the C. difficile toxin B protein.

Figure 54:
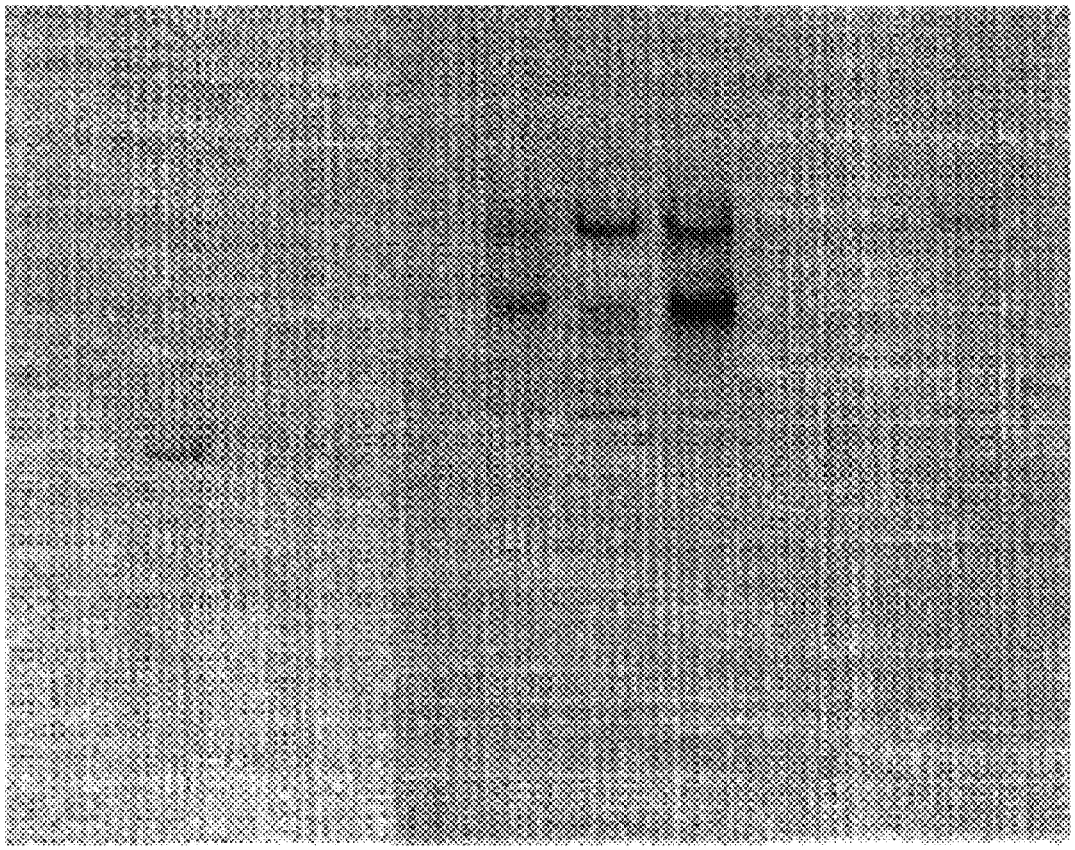
FIG. 54 is an native PAGE gel stained with Coomaisse blue and a Western blot showing *C. difficile* toxin B levels in a commercial toxin B preparation and column flow through and column eluate from an affinity purification column.

FIG. 54 shows the Coomassie stained gel and corresponding Western blots. In FIG. 54, lanes 1–3 were stained with Coomassie blue; lanes 5–10 were probed with anti-B-3 IgY and lanes 8–10 were probed with pre-immune IgY. Lanes 1, 5 and 8 contain affinity purified toxin B; lanes 2, 6 and 9 contain the column flow through; lanes 3, 7 and 10 contain commercial toxin B (Techlab). Lane 4 does not contain any protein (blank).

The following results were obtained upon western blot analysis. All three samples (culture supernatant, eluted protein and flow-through) contained immunoreactive toxin B. These results indicated that the affinity purification protocol was successful in purifying some toxin B. However, as the flow-through fraction was found to contain significant amounts of toxin B the following modifications would be examined for the ability to further optimize the purification process (e.g., coupling of B-3 IgY to Affigel hydrazide support (BioRad) via periodate oxidation of IgY).

ii) Yield of Affinity Purified C. diffwile Toxin B

The yield of affinity purified C. difficile toxin B was determined by BCA protein assay (Pierce), using BSA as the protein standard. This assay showed that the toxin B concentration was 73 $\mu$g/ml×4.5 ml (volume of affinity purified material)=365 $\mu$g of toxin B. Approximately 70 ml of dialysis bag culture supernatant was used as the starting material; therefore, about 5 $\mu$g toxin B was recovered per milliliter of culture. This yield was consistent with previously reported yields using this method of culturing C. difficile [7.8 $\mu$g toxin B/ml of culture supernatant; Meador and Tweten (1988), supra].

iii) Measurement of the In Vivo Activity of the Affinity Purified C. difficile Toxin B The in vivo activity of the affinity purified C. difficile toxin B was determined by injecting various amounts of the purified toxin B preparation (described below) into 30 to 40 gram female Syrian hamsters. Another group of hamsters was injected with various amounts of a commercial toxin B preparation (TechLabs) for comparison with results previously obtained. The $LD_{100}$ of the TechLabs preparation of C. difficile toxin B was found to be about 5 $\mu$g for 30–40 g hamsters when administered I.P. (Example 19). At this concentration (5 $\mu$g/30–40 g hamster), the hamsters died within about 3 hours post-I.P. injection.

The $LD_{100}$ concentration of the affinity purified toxin B was determined by I.P. injection of 1 ml of a solution containing either 5 or 50 $\mu$g of affinity purified toxin B diluted in saline. Two 30–40 gram hamsters were injected with each concentration of affinity purified toxin B. The hamsters injected with 50 $\mu$g of affinity purified material hamster died within 2 hours; the hamsters injected with 5 $\mu$g of affinity purified toxin B died within 4 hours. These results demonstrated that the toxicity of the affinity purified C. difficile toxin B preparation was comparable to the commercially available C. difficile toxin B.

EXAMPLE 49

Diagnostic Agglutination Assay for the Detection of C. difficile Toxin A and Toxin B In this example, a rapid agglutination assay designed to detect C. difficile toxin A and toxin B in either culture supernatants or biological specimens such as feces was developed. Affinity purified antibodies against recombinant *C. difficile* toxin A and toxin B from hens were used to passively coat small polystyrene particles. In principle, the particles coated with the specific avian antibodies (IgY) to toxin A and toxin B should form visible aggregates when they are mixed with a sample containing the toxins. This format should produce a specific, sensitive and rapid assay. Affinity purified IgY in this case confers specificity and sensitivity to *C. difficile* toxin, while ease of use and speed of the assay is conferred using an agglutination assay format. This example describes: a) initial development of the agglutination assay for the detection of *C. difficile* toxin A and toxin B; and b) evaluation and optimization of the agglutination assay.

a) Development of an Agglutination Assay for Detection of *C. difficile* Toxin A and Toxin B Antibodies were generated in hens using the toxin A recombinant (pMAL 1870-2680) and the toxin B recombinant (pPB1750-2360) using Freund's adjuvant as described in previous Examples. The recombinant toxin A antibodies (A-6 IgY) and the recombinant toxin B antibodies(B-3 IgY) were PEG fractionated the then affinity purified as described in Example 15c. The A-6 IgY was affinity purified against pPA1870-2680 and the B-3 IgY was affinity purified against pB1750-2369. The affinity-purified antibodies were then passively coated onto the polystyrene particles.

For each IgY preparation to be coated, 100 $\mu$l of a 5% bead suspension of 1$\mu$ beads (Spherotech Inc., Libertyville, Ill.) was removed and centrifuged for 2 minutes at 14,000×g in a Beckman microfuge to pellet the particles. The particles were then washed with TBS (10 mM Tris, 150 mM NaCl, pH 8) PBS-Tween (10 mM sodium phosphate, 150 mM NaCl, pH 7.2+0.05% Tween 20) and TBS. The particles were centrifuged for 2 minutes following each wash and the wash buffer was discarded. Following the last TBS wash, the particles were resuspended in 1 ml of the antibody coating solution; affinity purified avian A-6 or B-3 IgY at 100 $\mu$g/ml in TBS. PEG-fractionated preimmune IgY was also coated in the same manner to serve as a negative control in the agglutination assays. The particle suspensions were then inverted at room temperature for 18 to 24 hours to allow the IgY to coat the particles.

To remove the unbound antibody, the suspensions were centrifuged for 2 minutes, the antibody solution was discarded, and the particles were washed as before (TBS, PBS-Tween, TBS). After the last TBS wash, the IgY-coated particles were resuspended in 200 $\mu$l of TBS, giving a 2.5% particle suspension.

In order to demonstrate that the particles were coated with IgY, 10 $\mu$l of the particles were incubated with 5 $\mu$l of undiluted goat anti-chicken IgG (Fisher Biotech) in depression wells. Samples were then evaluated for macroscopic agglutination. Particles that had not been coated with IgY showed no agglutination in this procedure.

In order to demonstrate the feasibility of using affinity purified polyclonal avian IgY in this type of assay, the ability of A-6 IgY coated particles to agglutinate in the presence of various concentrations of toxin A was evaluated.

Commercial toxin A (Tech labs) was diluted 10-fold serially from a starting concentration of 0.29 mg/ml, using PBS containing BSA at 1 mg/ml as the diluent. Ten $\mu$l of each dilution was mixed with 10 $\mu$l of the coated beads in a depression-well slide, and the mixture was incubated for 20 minutes at 37° C. The slides were then analyzed macroscopically for evidence of agglutination.

Strong agglutination was observed with the 1:10 and 1:100 dilutions, and weak agglutination was observed in the 1:1000 dilution. The dilutions greater than 1:1000 showed no agglutination. The pre-immune coated particles did not agglutinate at any dilution tested. The 1:100 dilution of toxin A had a concentration of 2.9 $\mu$g/ml. Ten $\mu$l of the 2.9 $\mu$g/ml dilution contains 29 ng of toxin A, therefore the assay is sensitive to 29 ng of toxin A, or 2.9 $\mu$g/ml. The agglutination assay format appears to be suitable for detecting *C. difficile* toxins A and B.

Affinity purified polyclonal avian antibodies were most commonly used to coat the particles, however the use of PEG-fractionated and water-diluted IgY preparations was also investigated, in order to determine if it was possible to increase the sensitivity of the agglutination assay by using polyclonal antibodies which might contain a population of high affinity antibodies lost during affinity purification.

PEG-fractionated polyclonal A2 IgY was used to coat 1 p polystyrene particles under conditions identical to those described above, and the particles were evaluated for sensitivity in the *C. difficile* toxin A agglutination assay. These particles were less sensitive than particles coated with affinity purified IgY.

To investigate the possibility that residual PEG in the PEG-fractionated IgY may inhibit particle agglutination in the assay, A-2 IgY was extracted by the acidified water dilution method described by Akita and Nakai [J. of Food Science, 57:629 (1992)]. Polystyrene particles were then coated with water diluted IgY under conditions identical to those described above, and the particles were evaluated for sensitivity in the *C. difficile* toxin A agglutination assay.

It was determined that particles coated with water-diluted IgY preparations were less sensitive than particles coated with affinity purified IgY. Affinity purified IgY therefore appears superior to batch-fractionated IgY preparations in this assay format. In order to increase the sensitivity and maintain the specificity of the agglutination assays, we then evaluated the effect of several other variables on the assay performance.

b) Evaluation and Optimization of the *C. difficile* Toxin A and Toxin B Agglutination Assay A-6 and B-3 IgY-coated beads were evaluated for their agglutinability with lowest amount of toxin (i.e., sensitivity) and specificity. Instead of using PEG-fractionated preimmune IgY, affinity-purified IgY against an irrelevant antigen, *C. atrox* snake venom, was used to coat the particles as a negative control. Toxin A and toxin B were serially diluted in PBS from 1 $\mu$g/ml to 0.1 ng/ml. Ten $\mu$l of bead suspension was mixed with 20 $\mu$l sample in wells of glass agglutination plates, mixed well and rotated on nutator (Lab Quake) or manually for two minutes. Agglutination was read after two minutes. A completely uniform suspension was rated as "−," a slightly gritty appearance was rated as "±," and distinct agglutination was rated as "+" or "++," according to the size of the aggregates.

Various parameters which affect the sensitivity and/or specificity of the assay such as bead size, concentration of coating antibody, temperature of reaction, pH of coating buffer, antibodies generated using different adjuvants, final density of the beads (%, w/v) and sample diluents were evaluated. Four different bead sizes 0.39$\mu$, 0.81$\mu$, 1$\mu$, and 1.2$\mu$ were initially evaluated. The 1$\mu$ bead agglutinated very rapidly, resulting in large aggregates with little or no non-specific agglutination. Hence, 1$\mu$ bead size was chosen for further optimization studies. Samples were initially diluted in PBS. If the beads autoagglutinated in PBS, PBS with 1 mg/ml BSA or PBS with 0.01% Tween-20 was substituted. Both diluents prevented autoagglutination, but PBS with Tween-20 also inhibited the specific signal. Various other blocking agents such as sucrose, BSA at higher concentration and gelatin were evaluated as diluents. PBS containing 1 mg/ml BSA was found to be optimal at preventing autoagglutination without inhibiting specific signal.

The density of the beads in final suspension was also evaluated. In order to improve the sensitivity and specificity, A-6 or B-3 IgY-coated latex particles were tested for their agglutinability at 2.5%, 1.25%, 0.5%, and 0.25% suspensions. All the bead suspensions except 2.5% resulted in no or low signal. Antibodies generated using different adjuvants have different avidities and affinities, and hence agglutinate differently. It was known that antibodies with higher avidity and affinity form large and distinct aggregates. A-6 and B-3 IgY generated using Freund's and Gerbu as adjuvants were evaluated for their agglutinability at lowest concentration of toxin. Antibodies generated using Gerbu adjuvant were found to be better in giving distinct and large aggregates at 10-times lower concentrations of toxin A or toxin B, compared to antibodies generated with Freund's adjuvant.

The effect of antibody concentration/mg of beads with lower or higher incubation temperature was also tested. The polystyrene particles were coated with 20 µg IgY or 50 µg IgY/mg of beads, and incubated at room temperature, 37° C., or 56° C. There was a direct correlation between higher concentration of coating antibody and higher temperature with respect to increase in sensitivity. However, it was found that coating the particles at higher temperature also resulted in increased non-specific signal. High pH and low pH coating buffers were evaluated in order to optimize maximum sensitivity and specificity. The polystyrene particles coated in 50 mM sodium acetate, 150 mM sodium chloride, pH 5.5 (low pH buffer) agglutinated non-specifically, while beads coated using 50 mM sodium carbonate, pH 9.5 (high pH buffer) buffer increased sensitivity and specificity with A-6 IgY coated particles, but not for B-3 IgY coated particles. The sensitivity and specificity of A-6 or B-3 IgY sensitized particles using various methods is summarized in Table 49.

TABLE 49

Summary of Results

| | A-6 IgY-sensitized beads | | | | | | B-3 IgY-sensitized beads | | | | | |
|---|---|---|---|---|---|---|---|---|---|---|---|---|
| | Sensitivity | | | | Specificity | | Sensitivity | | | | Specificity | |
| Conditions | 100 ng/ml | 50 ng/ml | 10 ng/ml | neg control | Feces$^M$ | E. coli | 100 ng/ml | 10 ng/ml | 1 ng/ml | neg control | Feces$^M$ | E. coli |
| A. 100 µg/ml, 1µ, TBS, pH 7.5 (F/RT) | ++ | − | − | − | − | − | ++ | + | − | − | − | − |
| B. 100 µg/ml, 1µ, TBS, pH 7.5 (G/RT) | ++ | ± | − | − | ++ | ++ | ++ | ++ | ± | − | − | − |
| C. 100 µg/ml, 1µ, TBS, pH 7.5 (G/37° C.) | ++ | ++ | + | − | ++ | ++ | n/a | | | | | |
| D. 250 µg/ml, 1µ, TBS, pH 7.5 (G/RT) | ++ | + | − | − | ++ | ++ | n/a | | | | | |
| E. 250 µg/ml, 1µ, TBS, pH 7.5, (G/37° C.) | ++ | ++ | ++ | − | ++ | ++ | ++ | ++ | ++ | +* | ++ | ++ |
| F. 30 µg/mg of beads 0.81µ (Yamamoto, et al procedure) | ± | − | − | − | ++ | ++ | ± | − | − | − | − | ∓ |
| G. 30 µg/mg of beads 0.39µ (Yamamoto, et al procedure) | ± | − | − | − | ++ | ++ | ± | − | − | − | − | ∓ |
| H. 150 µg/ml, 1µ, TBS, pH 7.5 (G/RT) blocking procedure | ++ | ++ | + | − | ++ | ++ | + | ∓ | ∓ | ∓ | ++ | ++ |
| I. 150 µg/ml, 0.81µ, TBS, pH 7.5, (G/RT) blocking procedure | ++ | ± | − | − | ++ | + | + | ± | ∓ | ∓ | ++ | + |
| J. 100 µg/ml, 1µ, TBS, pH 7.5, (F/RT) | ++ | + | − | − | − | − | n/a | | | | | |
| K. 100 µg/ml, 1µ, TBS, pH 7.5 (G/RT) | ++ | ++ | ± | − | ++ | ++ | n/a | | | | | |
| L. 250 µg/ml, 1µ, TBS, pH 7.5 (F/RT) | ++ | ++ | ± | − | ± | ± | n/a | | | | | |
| M. 250 µg/ml, 1µ, Acetate, pH 5.5 (F/RT) | ++ | ++ | ± | − | ++ | ++ | n/a | | | | | |
| N. 250 µg/ml, 1µ, CO$_3$ buffer, pH 9.5, (F/RT) | ++ | ++ | − | − | − | − | | | | | | |
| O. 250 µg/ml, 1µ, CO$_3$ buffer, pH 9.5, (G/RT) | ++ | ++ | + | − | − | − | ++ | ± | − | − | − | − |
| P. 250 µg/ml, 1µ, Glycine saline buffer, pH 8.2 (F/56° C.) | ++ | ++ | ++ | + | ++ | ++ | n/a | | | | | |
| Q. 250 µg/ml, 1.2µ, pH 9.5, (F/RT) | ++ | ++ | ++ | − | ++ | + | ++ | ++ | + | + | ++ | + |
| R. same as Q except after overcoating w/BSA | ++ | ++ | ++ | − | ++ | + | ++ | ++ | + | + | + | + |

Explanation of conditions: coating concentration of IgY, bead size, coating solution, pH, adjuvant used, temperature during coating.
*No autoagglutination with sensitivity of 1 ng/ml in presence of PBS + BSA + 0.01% TW20, however nonspecific agglutination did occur with E. coli and M feces even with this diluent.

TABLE 49-continued

Summary of Results

| | A-6 IgY-sensitized beads | | | | | | B-3 IgY-sensitized beads | | | | | |
|---|---|---|---|---|---|---|---|---|---|---|---|---|
| | Sensitivity | | | Specificity | | | Sensitivity | | | Specificity | | |
| Conditions | 100 ng/ml | 50 ng/ml | 10 ng/ml | neg control | Feces$^M$ | E. coli | 100 ng/ml | 10 ng/ml | 1 ng/ml | neg control | Feces$^M$ | E. coli |

F = IgY generated using Freund's adjuvant
G = IgY generated using Gerbu adjuvant
E. coli = E. coli colony was picked from agar plate and resuspended in 500 μl diluent
Feces$^M$ = 50 mg mouse feces was suspended in 500 μL diluent vortexed and spun at 14,000 × g for 2 min. supernatant was used in the assay Based on the information from various parameters tested, the following bead coating protocols with A-6 and B-3 IgY were established:

i) A-6 IgY coated particles to detect toxin A directly from feces of human patients.

Five mg polystyrene particles (1μ, Spherotech Inc., Libertyville, Ill.) were added to a tube and washed with 1 ml of TBS, PBS-T, and TBS followed by another wash with 50 mM Na$_2$CO$_3$, pH 9.5 buffer. The beads were resuspended in the latter buffer to a total volume of 1 ml. A-6 IgY (affinity-purified, Gerbu-generated) was added to beads to a final concentration of 250 μg/ml and incubated at room temperature on a nutator overnight. The next day, IgY-sensitized particles were washed with TBS, PBS-T, and TBS and resuspended in TBS to a final concentration of 2.5%. These IgY-sensitized particles were stored at 4° C. until use.

ii) B-3 coated latex particles to detect toxin B directly from feces of human patients.

Five mg polystyrene particles (1μ, Spherotech Inc., Libertyville, Ill.) were added to a tube and washed with 1 ml of TBS, PBS-T, and TBS followed by another wash with 50 mM Na$_2$CO$_3$, pH 9.5 buffer. The beads were resuspended in the latter buffer to a total volume of 1 ml. B-3 IgY (affinity-purified, Gerbu-generated) was added to beads to a final concentration of 100 μg/ml and incubated at room temperature on a nutator overnight. The next day, IgY-sensitized latex particles were washed with TBS, PBS-T, and TBS and resuspended in TBS to a final concentration of 2.5%. These IgY-sensitized latex particles were stored at 4° C. until use.

The agglutination assay to detect toxin A and B from feces was compared with commercially available assays to detect toxin A and toxin B from human stool specimens. Cytoclone™ A+B EIA (Cambridge Biotech), which detects both toxins A and B, and Premier™ C. difficile Toxin A Test (Meridian Diagnostics Inc.), which detects only toxin A, were used for comparison. Normal human stool specimens were processed according to each of the manufacturer's instructions. Stool samples were spiked with 1 μg/ml of toxin A or toxin B and serially diluted 10-fold, to 0.01 ng/ml toxin A and 0.1 ng/ml toxin B. For agglutination assays, stool was diluted 5-fold with PBS containing 1 mg/ml BSA and centrifuged at 2500×g for 3 minutes. The supernatant was then used in the assay.

EIA's were performed according to the manufacturer's instructions, and results were read spectrophotometrically. Interpretation of results was made based on optical density values and the manufacturer's recommendations. For the agglutination assay, 10 μl suspension of A-6, B-3 IgY- or non-specific IgY-sensitized particles were placed in the wells of glass agglutination plates. Twenty μl samples were added to each well, mixed well, and rotated on a nutator. Agglutination was read visually after 2 minutes of rotation. Interpretation of results was made as described earlier. The summary of the results is presented in Table 50. The agglutination assay of the present invention detected toxin A at 1 ng/ml, while both the Cytoclone™ A+B EIA, and Premier™ C. difficile toxin A test detected toxins at 10-fold lower levels. Toxin B was detected at 1 ng/ml, using both agglutination and Cytoclone A+B EIA. The results show that agglutination assay of the invention, is simple, easy to perform, and very rapid, as the results can be obtained in 5 minutes.

TABLE 50

Comparison of results of three different methods to detect toxin A and toxin B spiked in normal human stool specimens

| Parameter | Cytoclone ™ A + B EIA Cambridge Biotech | Premier ™ C. difficile toxin A test Meridian Diagnostics | Agglutination assay for Toxin A & B Ophidian Pharmaceuticals |
|---|---|---|---|
| Stool spiked with Toxin A | | | |
| 100 ng/ml | ++ | ++ | ++ |
| 10 ng/ml | ++ | ++ | ++ |
| 1 ng/ml | ++ | ++ | + |
| 0.1 ng/ml | + | ++ | – |
| 0.01 ng/ml | – | ND$^a$ | ND |
| Stool spiked with Toxin B | | | |
| 100 ng/ml | ++ | N/A$^b$ | ++ |
| 10 ng/ml | ++ | | ++ |

TABLE 50-continued

Comparison of results of three different methods to detect toxin A and toxin B spiked in normal human human stool specimens

| Parameter | Cytoclone ™ A + B EIA Cambridge Biotech | Premier ™ C. difficile toxin A test Meridian Diagnostics | Agglutination assay for Toxin A & B Ophidian Pharmaceuticals |
|---|---|---|---|
| 1 ng/ml | ± | | ± |
| 0.1 ng/ml | − | | − |
| Total Time | 150 min | 150 min | 5 min |

[a]Not determined
[b]Not applicable

EXAMPLE 50

Characterization of Hamsters After Successful Treatment with Avian Antibodies Directed against Recombinant C. difficile Toxin A and Toxin B Proteins In order to investigate why hamsters treated with IgYs directed against recombinant toxin A (A-6 IgY) and recombinant toxin B (B-3 IgY) before or after challenge with C. difficile do not relapse and contract C. difficile associated disease CDAD) after the withdrawal of treatment, the following experiment was performed.

Relapse is commonly seen in hamsters (as demonstrated in Example 33) and in humans treated with drugs, such as vancomycin or metronidazole, to combat CDAD once drug treatment is terminated. In contrast, data presented in Examples 16 and 32 show that IgYs directed against recombinant C. difficile toxin A alone (given prophylactically) or a mixture containing IgYs directed against recombinant toxin A and B proteins (given therapeutically) can be used to successfully prevent or treat CDAD and also prevent relapse.

The example involved a) the detection of C. difficile organisms and toxins in the feces of hamsters treated with anti-A-6/B-3 IgY, b) the detection of anti-C. difficile toxin A and anti-C. difficile toxin B IgG in the serum of treated hamsters by ELISA, c) the detection of anti-C. difficile toxin A and anti-C. difficile toxin B IgA in the saliva of treated hamsters by ELISA and d) re-exposure of A-6/B-3 treated hamsters with antibiotics.

a) Detection of C. difficile Organisms and Toxins in the Feces of Hamsters Treated with A-6/B-3 IgY The 7 hamsters that were successfully treated with 2 ml per day of A-6/B-3 IgY and the lone surviving hamster treated with 1 ml per day of A-6/B-3 IgY (Example 42) were tested for the presence of C. difficile and toxin A and toxin B in fecal material after treatment was withdrawn. This determination was performed to investigate whether hamsters treated A-6/B-3 IgY were protected from relapse because the IgY treatment either reduced or completely eliminated C. difficile organisms and toxins from the GI tract of the treated hamsters.

Stools were collected from the 7 individual hamsters 4 days after termination of treatment with A-6/B-3 IgY. A suspension was made from the stool samples as follows. Fifty milligrams of feces were added to 100 µl of PBS (pH 7.4) and the mixture was suspended by vortexing the sample. An aliquot (50 µl) of each suspension was streaked unto a C. difficile selective agar plate (CCFA plates;BBL) and the plates were incubated for 48 hours under anaerobic conditions. The remaining suspension was tested for the presence of C. difficile toxin A and toxin B using the toxin agglutination assay described in Example 49.

The results obtained by culturing stool suspensions on the CCFA plates demonstrated that all of the hamsters successfully treated with A-6/B-3 IgY still harbored C. difficile organisms 4 days after treatment (ranging from approximately 6–100 colonies). Furthermore, C. difficile toxin A was detected in the feces from all nine treated hamsters using the agglutination assay (Example 49). Surprisingly, C. difficile toxin B was not detected in the feces of any of the hamsters.

Stool samples were collected from the same 7 hamsters again about 5 weeks after the termination of antibody treatment. Suspensions were prepared and plated onto CCFA plates as described above. After this prolonged period, the presence of C. difficile was only detected in the stool from one of the hamsters. Interestingly, the organisms were detected in the hamster that was treated with the lower (1 ml) dose of A-6/B-3 IgY. Only a low number of colonies (5 colonies) was detected in the stool of that animal. In control animals there were no organisms detected, as normally, only a very low percentage of hamsters have detectable levels of organisms.

These results indicate that although the A-6/B-3 treated hamsters have been successfully treated for CDAD and the disease does not relapse, they still shed C. difficile organisms and contain toxin A in their feces early after treatment. The anti-recombinant C. difficile toxin A and B antibodies (ie., A-6/B-3 IgY) apparently eliminate disease symptoms without completely eliminating C. difficile organisms or toxin A from the GI tract of the treated hamsters. While not limiting the invention to a particular theory of action, the avian IgYs may exert their therapeutic effects by lowering the level of toxin present and thus possibly reducing organism number enough to not only prevent CDAD but also prevent CDAD from re-occurring, as it is possible that toxin A may aid in the colonization of C. difficile.

Five weeks after treatment with the avian antitoxin preparation, C. difficile organisms were not detected in the feces of most (7/8) of the treated hamsters. These results indicate that long-term colonization of the GI tract by C. difficile does not occur following treatment with A-6/B-3 IgY.

b) Detection of Anti-C. difficile Toxin A and Anti-C. difficile Toxin B IgG in the Serum of Treated Hamsters by ELISA Serum was collected from hamsters following treatment with anti-A-6/B-3 IgY to determine if an endogenous serum IgG response directed against C. difficile toxins was elicited in the treated hamsters. The generation of an anti-toxin IgG response could account for the prevention of subsequent relapse in the animals.

Blood was collected by cardiac puncture in the seven hamsters that were still available after five weeks (described above) four days after termination of treatment. The blood was allowed to clot and serum was prepared by centrifugation of the clotted sample. Serum was also collected from an uninfected hamster and from a hamster vaccinated with a mixture of recombinant toxin A and toxin B proteins (Example 39) to serve as negative and positive controls, respectively. The ELISA was conducted using the protocol described in Example 1. Briefly, the wells of the microtiter plates were coated with 0.05 µg/ml of the toxin A recombinant pPA1870-2680 (A-6) or 1.0 µg/ml of toxin B recombinant pPB 1750-2360 (B-3) at 100 µl per well. Serum samples were tested at a starting dilution of 1:50 followed by 5-fold serial dilutions. Goat-anti-hamster IgG alkaline phosphatase (Southern Biotechnology Assoc.) was used at a dilution of 1:1000 as the secondary antibody. All antibody incubations were carried out at 37° C. for 2 hours. The plates were developed for 30 minutes using para-nitrophenyl phosphate (Sigma).

The results of the ELISA demonstrated that all of the serum samples from the test hamsters contained significantly lower levels of anti-toxin A and anti-toxin B IgG as compared to the positive control serum (serum from a hamster that generated a protective IgG response after active immunization with recombinant toxin A and B proteins). Antibody titers present in the serum from the 7 treated hamsters were comparable to those present in the negative control. These results demonstrated that the protection from CDAD relapse achieved by treatment of hamsters with the A-6/B-3 IgY is probably not due to the generation of an active serum IgG response in the hamsters following infection with *C. difficile* organisms.

c) Detection of an Anti-*C. difficile* Toxin A and Anti-*C. difficile* Toxin B IgA Response in the Saliva by ELISA in Treated Hamsters To investigate whether the protection from relapse from CDAD seen in the anti-A-6/B-3 IgY treated hamsters was due to the production of a mucosal IgA response in the animals, the following experiment was performed. Saliva was collected from 6 hamsters previously treatment with anti-A-6/B-3 IgY (Example 42; 2 ml) using pilocarpine (Sigma) which causes hyper-secretion of saliva. Hamsters were injected I.P. with a solution containing pilocarpine (1 mg/ml) in sterile water; 1 to 3 mgs pilocarpine was administered to the animals. Saliva was collected from 6 hamsters using a pipettor. As a negative control, saliva was collected from an mouse given 200 µg of pilocarpine. A mouse specimen was used as a negative control because the only anti-IgA conjugate commercially available is a goat anti-mouse IgA (this reagent has been reported to cross-react with hamster IgA).

The ELISA was performed as described above (b) with the following modifications. The saliva samples were tested at an initial 1:10 dilution followed by serial five-fold dilutions. Goat anti-mouse IgA (Southern Biotechnology Assoc.) was used as the secondary antibody at a 1:1000 dilution.

The results of the ELISA showed that saliva from only 2 out of the 6 treated hamsters contained levels of anti-toxin A and anti-toxin B IgA higher than that seen in the mouse negative control. The saliva of the two anti-toxin IgA-positive hamsters had fairly low titers (between 1:250 and 1:1250). Typical hyper-immune IgA titers normally range about 1:10,000 or greater. The remaining 4 hamsters did not have a significant anti-toxin IgA response to either toxin A or toxin B as compared to the negative control. Since all six of the hamsters were successfully treated against CDAD relapse and the majority (4/6) of the treated hamsters did not produce a significant anti-toxin IgA response, it is unlikely that the prevention of relapse was due to the generation of an anti-toxin A or anti-toxin B IgA response by the hamster.

The results shown in sections b) and c) indicate that the protection against relapse seen in hamsters successfully treated with IgY directed against *C. difficile* Intervals A-6 and B-3 is not due to the production of a anti-*C. difficile* toxin humoral response by the host. Thus, prevention of relapse is a function of the administration of the IgY preparations. This indicates that the host's immune status may not be relevant in terms of prediction of disease outcome (i.e., survival) or whether relapse will occur. This is important as many of the patients who would most benefit most from treatment with an A-6/B-3 IgY therapeutic are immunocompromised.

d) Re-exposure of A-6/B-3 Treated Hamsters with Antibiotics

As shown in section a) above, the treated hamsters still possess detectable levels of *C. difficile* organisms in their feces (4 days after termination of IgY treatment) and thus have the potential for developing CDAD. An experiment was performed to investigate whether re-exposure of these treated hamsters to Clindamycin would initiate onset of CDAD.

Four of the same hamsters used in the above experiments (e.g., in Example 42) that were successfully treated with A-6/B-3 IgY were again predisposed to *C. difficile* infection by administration of Clindamycin-phosphate. Seven days after termination of the initial antibody treatment, the hamsters were given another I.P. injection of Clindamycin-phosphate (Biomol) at 1 mg/100 g body weight. Twelve days post-Clindamycin predisposition (i.e., the second application of Clindamycin), none of the hamsters developed any signs of CDAD.

These results demonstrated that once the hamsters are successfully treated with the anti-A-6/B-3 IgY, they were resistant to developing CDAD even after another exposure to Clindamycin. To take this result another step further, the same hamsters were given another antibiotic, namely Cefoxitin (Sigma) which is also known to predispose the hamsters to *C. difficile* infection. This was done as it was possible that the prevention of CDAD in the hamsters after the Clindamycin re-treatment was due to the generation of Clindamycin-resistant normal flora which may have prevented colonization of the GI tract with *C. difficile*. The 4 hamsters were each given a subcutaneous injection of 10 mg of Cefoxitin in saline 11 days after (18 days post treatment with A-6/B-3 IgY). This dosage of Cefoxitin is known to predispose hamsters to CDAD.

Seven days post-Cefoxitin treatment, 1 of the 4 hamsters developed diarrhea and died. The remaining 3 hamsters remained healthy and have survived long-term (i.e., at least one month). The results obtained after treatment with Cefoxitin indicate that protection from the re-occurrence of CDAD in the treated hamsters is probably not due to the development of specific antibiotic resistance (i.e., resistance to Clindamycin) in the hamster flora.

Together the above results showed that hamsters treated for CDAD using anti-A-6/B-3 IgY contain viable *C. difficile* organisms and *C. difficile* toxin A in their GI tract early after the withdrawal of treatment and yet the hamsters do not relapse. Even more surprising was the finding that while the hamsters still harbor *C. difficile* in the gut, they were resistant to a subsequent challenge using antibiotics capable of predisposing hamsters to CDAD. As was shown above, 5 weeks after withdrawal of the avian antitoxin, the hamsters no longer shed organisms into feces and thus were probably no longer colonized by *C. difficile*. The results further indicate that oral administration of A-6/B-3 IgY to hamsters not only successfully treated CDAD, but also conferred resistance to relapse. Moreover, the A-6/B-3 IgY protected the hamsters against CDAD from repeated antibiotic predisposition using two different antibiotics.

From the above it is clear that the present invention provides antitoxins and vaccines for the treatment and prevention of *C. difficile* disease. Furthermore, these antitoxins prevent the relapse of *C. difficile* disease which is commonly seen using conventional treatment protocols. Additionally, the invention provides a rapid agglutination assay for the detection of *C. difficile* toxins A and B in samples.

What is claimed is:

1. A method of treating *Clostridium difficile* intoxication where an intoxicated subject ceases to exhibit symptoms and treatment can be terminated, comprising:
   a) providing:
      i) a subject exposed to *Clostridium difficile* exhibiting symptoms comprising diarrhea; and
      ii) avian antibody reactive with *Clostridium difficile* toxin, said antibody in a therapeutic amount that is administrable, and
   b) administering said antibody to said subject under conditions such that said subject ceases to exhibit diarrhea and treatment can be terminated.

2. The method of claim 1, wherein said subject exhibits long-term survival beyond the treatment period.

3. The method of claim 1, wherein said avian antibodies reacts with Toxin A of *Clostridium difficile*.

4. The method of claim 3, wherein said avian antibodies reacts with the A-6 interval of Toxin A.

5. The method of claim 1, wherein said avian antibodies react with Toxin B of *Clostridium difficile*.

6. The method of claim 5, wherein said avian antibodies react with the B-3 interval of Toxin B.

7. The method of claim 1, wherein said avian antibodies react with Toxin A and Toxin B.

8. A method of treating *Clostridium difficile* intoxication where an intoxicated subject ceases to exhibit symptoms and treatment can be terminated, consisting essentially of:
   a) providing:
      i) a subject exposed to *Clostridium difficile* exhibiting symptoms comprising diarrhea; and
      ii) avian antibody reactive with *Clostridium difficile* toxin, said antibody in a therapeutic amount that is administrable, and
   b) administering said antibody to said subject under conditions such that said subject ceases to exhibit diarrhea and treatment can be terminated.

9. The method of claim 8, wherein said subject exhibits long-term survival beyond the treatment period.

10. The method of claim 8, wherein said avian antibodies reacts with Toxin A of *Clostridium difficile*.

11. The method of claim 10, wherein said avian antibodies reacts with the A-6 interval of Toxin A.

12. The method of claim 8, wherein said avian antibodies react with Toxin B of *Clostridium difficile*.

13. The method of claim 12, wherein said avian antibodies react with the B-3 interval of Toxin B.

14. The method of claim 8, wherein said avian antibodies react with Toxin A and Toxin B.

* * * * *